United States Patent
Knowlton

(10) Patent No.: US 11,751,903 B2
(45) Date of Patent: *Sep. 12, 2023

(54) PIXEL ARRAY MEDICAL SYSTEMS, DEVICES AND METHODS

(71) Applicant: SRGI HOLDINGS, LLC, Henderson, NV (US)

(72) Inventor: Edward Knowlton, Henderson, NV (US)

(73) Assignee: SRGI HOLDINGS, LLC, Henderson, NV (US)

( * ) Notice: Subject to any disclaimer, the term of this patent is extended or adjusted under 35 U.S.C. 154(b) by 911 days.

This patent is subject to a terminal disclaimer.

(21) Appl. No.: 16/443,164

(22) Filed: Jun. 17, 2019

(65) Prior Publication Data

US 2020/0138464 A1 May 7, 2020

Related U.S. Application Data

(63) Continuation-in-part of application No. 16/403,377, filed on May 3, 2019, now Pat. No. 11,116,540, and (Continued)

(51) Int. Cl.
*A61B 18/14* (2006.01)
*A61B 17/3211* (2006.01)
(Continued)

(52) U.S. Cl.
CPC ............ *A61B 17/322* (2013.01); *A61B 17/24* (2013.01); *A61B 17/3211* (2013.01);
(Continued)

(58) Field of Classification Search
CPC ............ A61B 17/322; A61B 17/32053; A61B 2017/3225; A61B 2017/320064; A61B 2017/00792; A61M 35/003
See application file for complete search history.

(56) References Cited

U.S. PATENT DOCUMENTS

| 1,610,089 A | 12/1926 | Steven et al. |
| 3,613,242 A | 10/1971 | Hill et al. |
| (Continued) | | |

FOREIGN PATENT DOCUMENTS

| CN | 101530636 B | 2/2012 |
| KR | 200303833 Y1 | 8/2003 |
| (Continued) | | |

OTHER PUBLICATIONS

Sheridan R.L., et al., "Initial Experience with a Composite Autologous Skin Substitute," Burns, 2000, vol. 27 (5), pp. 421-424.

(Continued)

*Primary Examiner* — Anh T Dang
(74) *Attorney, Agent, or Firm* — BAKER DONELSON PC

(57) ABSTRACT

Embodiments include a method comprising determining histological factors at a target site of a subject, and determining parameters of a fractional resection based on the histological factors. The parameters include dimensionality of a fractional field, orientation of the fractional field, resection depth, and a vector of directed closure. The method includes configuring a cannula assembly for the fractional resection that includes a procedure to generate a fractional field at the target site by fractionally resecting tissue according to the parameters. The fractional resection includes applying a cannula array of the cannula assembly to the target site, and rotating at least one cannula of the cannula array to circumferentially incise and remove a plurality of skin plugs in the fractional field.

45 Claims, 300 Drawing Sheets

Related U.S. Application Data a continuation-in-part of application No. 16/378,336, filed on Apr. 8, 2019, now Pat. No. 11,490,952, and a continuation-in-part of application No. 16/280,303, filed on Feb. 20, 2019, and a continuation-in-part of application No. 16/203,130, filed on Nov. 28, 2018, now Pat. No. 11,229,452, and a continuation-in-part of application No. 16/203,138, filed on Nov. 28, 2018, and a continuation-in-part of application No. 16/132,575, filed on Sep. 17, 2018, now Pat. No. 11,051,844, and a continuation-in-part of application No. 15/997,316, filed on Jun. 4, 2018, now Pat. No. 11,090,473, and a continuation-in-part of application No. 15/977,865, filed on May 11, 2018, now Pat. No. 10,695,546, and a continuation-in-part of application No. 15/977,741, filed on May 11, 2018, now Pat. No. 10,905,865, and a continuation-in-part of application No. 15/977,934, filed on May 11, 2018, now Pat. No. 10,661,063, and a continuation-in-part of application No. 15/977,882, filed on May 11, 2018, now Pat. No. 10,716,924, and a continuation-in-part of application No. 15/977,912, filed on May 11, 2018, now Pat. No. 10,967,162, and a continuation-in-part of application No. 15/977,958, filed on May 11, 2018, now Pat. No. 10,702,684, and a continuation-in-part of application No. 15/890,046, filed on Feb. 6, 2018, now Pat. No. 11,612,410, and a continuation-in-part of application No. 15/890,064, filed on Feb. 6, 2018, now Pat. No. 10,772,658, and a continuation-in-part of application No. 15/890,052, filed on Feb. 6, 2018, now Pat. No. 10,856,900, and a continuation-in-part of application No. 15/890,068, filed on Feb. 6, 2018, now Pat. No. 11,278,309, and a continuation-in-part of application No. 15/890,074, filed on Feb. 6, 2018, now Pat. No. 11,000,310, and a continuation-in-part of application No. 15/821,325, filed on Nov. 22, 2017, now Pat. No. 10,335,191, and a continuation-in-part of application No. 15/821,258, filed on Nov. 22, 2017, and a continuation-in-part of application No. 15/812,952, filed on Nov. 14, 2017, now Pat. No. 10,773,064, and a continuation-in-part of application No. 15/585,701, filed on May 3, 2017, now abandoned, and a continuation-in-part of application No. 15/585,679, filed on May 3, 2017, now Pat. No. 10,335,190, and a continuation-in-part of application No. 15/585,732, filed on May 3, 2017, now Pat. No. 10,736,653, and a continuation-in-part of application No. 15/431,230, filed on Feb. 13, 2017, now Pat. No. 11,109,887, and a continuation-in-part of application No. 15/431,247, filed on Feb. 13, 2017, now Pat. No. 10,368,904, and a continuation-in-part of application No. 15/016,954, filed on Feb. 5, 2016, now Pat. No. 10,517,635, and a continuation-in-part of application No. 15/017,007, filed on Feb. 5, 2016, now abandoned, and a continuation-in-part of application No. 14/840,274, filed on Aug. 31, 2015, now Pat. No. 10,485,606, and a continuation-in-part of application No. 14/840,284, filed on Aug. 31, 2015, now Pat. No. 10,485,575, and a continuation-in-part of application No. 14/840,290, filed on Aug. 31, 2015, now Pat. No. 10,321,948, and a continuation-in-part of application No. 14/840,267, filed on Aug. 31, 2015, now Pat. No. 10,342,574.

(60) Provisional application No. 62/800,830, filed on Feb. 4, 2019, provisional application No. 62/750,084, filed on Oct. 24, 2018, provisional application No. 62/685,961, filed on Jun. 16, 2018.

(51) Int. Cl.
| | |
|---|---|
| A61B 17/322 | (2006.01) |
| A61B 17/24 | (2006.01) |
| A61B 17/3205 | (2006.01) |
| A61B 17/3209 | (2006.01) |
| A61B 17/32 | (2006.01) |
| A61B 17/00 | (2006.01) |
| A61B 18/00 | (2006.01) |

(52) U.S. Cl.
CPC ............... *A61B 17/32053* (2013.01); *A61B 17/320068* (2013.01); *A61B 17/32093* (2013.01); *A61B 18/1487* (2013.01); *A61B 2017/00199* (2013.01); *A61B 2017/00398* (2013.01); *A61B 2017/00477* (2013.01); *A61B 2017/00561* (2013.01); *A61B 2017/00752* (2013.01); *A61B 2017/00761* (2013.01); *A61B 2017/00769* (2013.01); *A61B 2017/00792* (2013.01); *A61B 2017/00796* (2013.01); *A61B 2017/00805* (2013.01); *A61B 2017/248* (2013.01); *A61B 2017/320064* (2013.01); *A61B 2018/0047* (2013.01); *A61B 2018/00458* (2013.01); *A61B 2018/00601* (2013.01); *A61B 2218/007* (2013.01)

(56) References Cited

U.S. PATENT DOCUMENTS

| | | | |
|---|---|---|---|
| 3,820,543 A | 6/1974 | Vanjushin et al. | |
| 3,867,942 A * | 2/1975 | Bellantoni | A61F 2/10 408/129 |
| 4,018,228 A | 4/1977 | Goosen | |
| 4,098,278 A | 7/1978 | Schwartz | |
| 4,160,453 A | 7/1979 | Miller | |
| 4,476,864 A * | 10/1984 | Tezel | A61B 17/32053 600/568 |
| 4,542,742 A | 9/1985 | Winkelman et al. | |
| 4,582,640 A | 4/1986 | Smestad et al. | |
| 4,803,075 A | 2/1989 | Wallace et al. | |
| 4,944,737 A | 7/1990 | Bloom | |
| 5,123,907 A | 6/1992 | Romaine | |
| 5,141,513 A | 8/1992 | Fortune et al. | |
| 5,209,755 A | 5/1993 | Abrahan et al. | |
| 5,415,182 A | 5/1995 | Chin et al. | |
| 5,417,683 A | 5/1995 | Shiao | |
| 5,570,700 A | 11/1996 | Vogeler | |
| 5,578,054 A | 11/1996 | Arnold | |
| 5,591,444 A | 1/1997 | Boss, Jr. | |
| 5,643,308 A | 7/1997 | Markman | |
| 5,665,372 A | 9/1997 | Boss, Jr. | |
| 5,693,064 A | 12/1997 | Arnold | |
| 5,827,297 A | 10/1998 | Boudjema | |
| 5,858,019 A | 1/1999 | Ashraf | |
| 5,871,495 A | 2/1999 | Mueller | |
| 5,879,326 A | 3/1999 | Godshall et al. | |
| 5,895,403 A | 4/1999 | Collinsworth | |
| 5,922,000 A | 7/1999 | Chodorow | |
| 5,928,162 A | 7/1999 | Giurtino et al. | |
| 5,964,729 A | 10/1999 | Choi et al. | |
| 5,970,709 A | 10/1999 | Tohji | |
| 5,989,278 A | 11/1999 | Mueller | |
| 6,027,512 A | 2/2000 | Bridges | |
| 6,059,807 A | 5/2000 | Boudjema | |
| 6,126,615 A | 10/2000 | Allen et al. | |
| 6,432,710 B1 | 8/2002 | Boss, Jr. et al. | |
| 6,471,712 B2 | 10/2002 | Burres | |
| 6,497,875 B1 | 12/2002 | Sorrell et al. | |
| 6,572,625 B1 | 6/2003 | Rassman | |
| 6,585,746 B2 | 7/2003 | Gildenberg | |
| 6,589,202 B1 | 7/2003 | Powell | |

(56) References Cited

U.S. PATENT DOCUMENTS

| | | |
|---|---|---|
| 6,626,865 B1 | 9/2003 | Prisell |
| 6,669,685 B1 | 12/2003 | Rizoiu et al. |
| 6,997,923 B2 | 2/2006 | Anderson et al. |
| 7,204,828 B2 | 4/2007 | Rosiello |
| 7,261,721 B2 | 8/2007 | Feller |
| 7,316,822 B2 | 1/2008 | Binette et al. |
| 7,331,953 B2 | 2/2008 | Manstein et al. |
| 7,354,423 B2 | 4/2008 | Zelickson et al. |
| 7,412,978 B1 | 8/2008 | Keller |
| 7,621,933 B2 | 11/2009 | Bodduluri et al. |
| 7,625,384 B2 | 12/2009 | Eriksson et al. |
| 7,708,746 B2 | 5/2010 | Eriksson et al. |
| 7,846,465 B1 | 12/2010 | Keller et al. |
| 7,942,153 B2 | 5/2011 | Manstein et al. |
| 7,962,192 B2 | 6/2011 | Bodduluri et al. |
| 7,993,310 B2 | 8/2011 | Rosiello |
| 8,062,322 B2 | 11/2011 | Rassman et al. |
| 8,202,279 B2 | 6/2012 | Cole |
| 8,211,134 B2 | 7/2012 | Oostman, Jr. |
| 8,317,804 B1 | 11/2012 | Rassman et al. |
| 8,486,155 B2 | 7/2013 | Mcalister et al. |
| 8,529,883 B2 | 9/2013 | Maslowski |
| 8,535,299 B2 | 9/2013 | Giovannoli |
| 8,540,731 B2 | 9/2013 | Kay et al. |
| 8,545,489 B2 | 10/2013 | Giovannoli |
| 8,690,863 B2 | 4/2014 | Chan et al. |
| 8,728,819 B2 | 5/2014 | Maslowski et al. |
| 8,765,121 B2 | 7/2014 | Maslowski |
| 8,900,181 B2 | 12/2014 | Knowlton |
| 8,986,324 B2 | 3/2015 | Bodduluri et al. |
| 9,005,218 B2 | 4/2015 | Harris |
| 9,060,803 B2 | 6/2015 | Anderson et al. |
| 9,095,368 B2 | 8/2015 | Umar et al. |
| 9,351,792 B2 | 5/2016 | Manstein et al. |
| 9,415,075 B2 | 8/2016 | Maslowski |
| 9,439,673 B2 | 9/2016 | Austen |
| 9,468,459 B2 | 10/2016 | Hall et al. |
| 9,743,949 B2 | 8/2017 | Guiles et al. |
| D797,286 S | 9/2017 | Ginggen et al. |
| 9,902,937 B2 | 2/2018 | Maslowski et al. |
| 10,098,914 B2 | 10/2018 | Maslowski |
| 10,117,721 B2 | 11/2018 | Tripathi et al. |
| 10,219,827 B2 | 3/2019 | Knowlton et al. |
| 10,251,792 B2 | 4/2019 | Levinson et al. |
| 10,335,190 B2 | 7/2019 | Knowlton |
| 10,368,904 B2 | 8/2019 | Knowlton |
| 2001/0053888 A1 | 12/2001 | Athanasiou et al. |
| 2002/0052619 A1 | 5/2002 | Transue |
| 2002/0088779 A1 | 7/2002 | Neev et al. |
| 2002/0111563 A1 | 8/2002 | Hall |
| 2002/0183688 A1 | 12/2002 | Lastovich et al. |
| 2003/0036770 A1 | 2/2003 | Markman |
| 2003/0069548 A1 | 4/2003 | Connelly et al. |
| 2003/0216719 A1 | 11/2003 | Debenedictis et al. |
| 2004/0082940 A1 | 4/2004 | Black et al. |
| 2004/0087893 A1 | 5/2004 | Kwon |
| 2004/0087992 A1 | 5/2004 | Gartstein et al. |
| 2004/0175690 A1 | 9/2004 | Mishra et al. |
| 2004/0210214 A1 | 10/2004 | Knowlton |
| 2005/0049582 A1 | 3/2005 | Debenedictis et al. |
| 2005/0154331 A1 | 7/2005 | Christie et al. |
| 2005/0154431 A1 | 7/2005 | Quistgaard et al. |
| 2005/0171504 A1 | 8/2005 | Miller |
| 2005/0267506 A1 | 12/2005 | Harris |
| 2005/0283141 A1* | 12/2005 | Giovannoli .......... A61B 18/203 606/9 |
| 2006/0051404 A1 | 3/2006 | Yeshurun et al. |
| 2006/0155266 A1 | 7/2006 | Manstein et al. |
| 2007/0038236 A1 | 2/2007 | Cohen |
| 2007/0073217 A1 | 3/2007 | James |
| 2007/0073327 A1 | 3/2007 | Giovannoli |
| 2007/0179481 A1 | 8/2007 | Frangineas et al. |
| 2007/0179516 A1 | 8/2007 | Mishra et al. |
| 2007/0207131 A1 | 9/2007 | Boss et al. |
| 2007/0224173 A1 | 9/2007 | Koullick et al. |
| 2007/0293884 A9 | 12/2007 | Cole et al. |
| 2008/0172047 A1 | 7/2008 | Altshuler et al. |
| 2008/0275378 A1 | 11/2008 | Herndon |
| 2009/0048558 A1 | 2/2009 | Del Vecchio |
| 2010/0114118 A1 | 5/2010 | Harris |
| 2010/0121307 A1 | 5/2010 | Lockard et al. |
| 2010/0204722 A1 | 8/2010 | Gilsdorf |
| 2010/0303770 A1 | 12/2010 | Maslowski et al. |
| 2011/0009860 A1 | 1/2011 | Chornenky et al. |
| 2011/0077664 A1 | 3/2011 | Schulz et al. |
| 2011/0177591 A1 | 7/2011 | Iwatschenko et al. |
| 2011/0208089 A1 | 8/2011 | Sundheimer et al. |
| 2011/0251602 A1 | 10/2011 | Anderson et al. |
| 2011/0257588 A1 | 10/2011 | Knowlton |
| 2011/0264115 A1 | 10/2011 | Asrani et al. |
| 2011/0282239 A1 | 11/2011 | Conlon et al. |
| 2011/0282382 A1 | 11/2011 | Mcalister et al. |
| 2011/0313429 A1 | 12/2011 | Anderson et al. |
| 2012/0022510 A1 | 1/2012 | Welches et al. |
| 2012/0035599 A1 | 2/2012 | Sabir et al. |
| 2012/0041430 A1 | 2/2012 | Anderson et al. |
| 2012/0041451 A1* | 2/2012 | Bodduluri ........ A61B 17/32053 606/133 |
| 2012/0219634 A1 | 8/2012 | Maslowski et al. |
| 2012/0226214 A1 | 9/2012 | Gurtner et al. |
| 2012/0271320 A1 | 10/2012 | Hall et al. |
| 2012/0323139 A1 | 12/2012 | Richardson |
| 2012/0323325 A1 | 12/2012 | Fulton |
| 2013/0006168 A1 | 1/2013 | Del Vecchio |
| 2013/0090669 A1 | 4/2013 | Bellomo et al. |
| 2013/0096600 A1 | 4/2013 | Wesley et al. |
| 2013/0204273 A1 | 8/2013 | Sabir et al. |
| 2013/0236427 A1 | 9/2013 | Pernock |
| 2013/0287286 A1 | 10/2013 | Zingaretti et al. |
| 2013/0295061 A1 | 11/2013 | Maslowski |
| 2013/0304090 A1 | 11/2013 | Dostman, Jr. et al. |
| 2013/0345721 A1 | 12/2013 | Menke et al. |
| 2014/0031801 A1 | 1/2014 | Giovannoli |
| 2014/0099383 A1 | 4/2014 | Maslowski et al. |
| 2014/0277055 A1 | 9/2014 | Austen, Jr. |
| 2014/0296741 A1 | 10/2014 | Austen |
| 2014/0303648 A1 | 10/2014 | Knowlton |
| 2014/0343575 A1 | 11/2014 | Andreani et al. |
| 2015/0018844 A1 | 1/2015 | Harris |
| 2015/0173991 A1 | 6/2015 | Anderson et al. |
| 2015/0201955 A1 | 7/2015 | Sabir et al. |
| 2015/0216545 A1 | 8/2015 | Anderson et al. |
| 2015/0230818 A1 | 8/2015 | Knowlton |
| 2015/0238214 A1 | 8/2015 | Anderson et al. |
| 2015/0250493 A1 | 9/2015 | Umar |
| 2015/0366719 A1 | 12/2015 | Levinson et al. |
| 2016/0008515 A1 | 1/2016 | Stilwell et al. |
| 2016/0095592 A1 | 4/2016 | Levinson et al. |
| 2016/0166272 A1 | 6/2016 | Shiao |
| 2016/0192961 A1 | 7/2016 | Ginggen et al. |
| 2016/0287281 A1 | 10/2016 | Knowlton |
| 2016/0310157 A1 | 10/2016 | Guiles et al. |
| 2016/0310158 A1 | 10/2016 | Guiles et al. |
| 2016/0310159 A1 | 10/2016 | Guiles et al. |
| 2016/0310444 A1 | 10/2016 | Dobak, III |
| 2016/0317170 A1 | 11/2016 | Knowlton |
| 2016/0317721 A1 | 11/2016 | Ginggen et al. |
| 2016/0340651 A1 | 11/2016 | Maslowski et al. |
| 2016/0367280 A1 | 12/2016 | Austen |
| 2017/0042561 A1 | 2/2017 | Hall et al. |
| 2017/0079824 A1 | 3/2017 | Thompson |
| 2017/0296214 A1 | 10/2017 | Knowlton |
| 2017/0333068 A1 | 11/2017 | Knowlton |
| 2017/0367729 A1 | 12/2017 | Ginggen et al. |
| 2018/0006300 A1 | 1/2018 | Jeong et al. |
| 2018/0036029 A1 | 2/2018 | Anderson et al. |
| 2018/0078278 A1 | 3/2018 | Levinson et al. |
| 2018/0161056 A1 | 6/2018 | Kim et al. |
| 2018/0325543 A1 | 11/2018 | Skog et al. |
| 2018/0346878 A1 | 12/2018 | Maslowski et al. |
| 2019/0015255 A1 | 1/2019 | Gurtner et al. |

(56) References Cited

U.S. PATENT DOCUMENTS

| | | | |
|---|---|---|---|
| 2019/0046777 | A1 | 2/2019 | Knowlton |
| 2019/0099199 | A1 | 4/2019 | Levinson et al. |

FOREIGN PATENT DOCUMENTS

| | | | |
|---|---|---|---|
| KR | 20080100795 | A | 11/2008 |
| WO | 0145566 | A1 | 6/2001 |
| WO | 2005072181 | A2 | 8/2005 |
| WO | 2008002064 | A1 | 1/2008 |
| WO | 2009146068 | A1 | 12/2009 |
| WO | 2012103483 | A2 | 8/2012 |
| WO | 2012136904 | A1 | 10/2012 |
| WO | 2013013196 | A1 | 1/2013 |
| WO | 2013013199 | A2 | 1/2013 |
| WO | 2014028626 | A1 | 2/2014 |
| WO | 2014089488 | A2 | 6/2014 |
| WO | 2015051164 | A2 | 4/2015 |

OTHER PUBLICATIONS

Shortliffe L.M., et al., "Treatment of Urinary Incontinence by the Periurethral Implantation of Glutaraldehyde Cross-Linked Collagen," The Journal of Urology, Mar. 1989, vol. 141 (3), pp. 538-541.
Sklar L.R., et al., "Use of Transcutaneous Ultrasound for Lipolysis and Skin Tightening: A Review," Aesthetic Plastic Surgery, 2014, vol. 38 (2), pp. 429-441.
Sukal S.A., et al., "Thermage: The Nonablative Radiofrequency for Rejuvenation," Clinics in Dermatology, 2008, vol. 26 (6), pp. 602-607.
Supplementary European Search Report for Application No. EP14850567 dated May 4, 2017, 4 pages.
Supplementary European Search Report for Application No. EP15836045 dated Jan. 8, 2018, 7 pages.
Supplementary European Search Report for Application No. EP17750972 dated Sep. 13, 2019, 8 pages.
Supplementary European Search Report for Application No. EP17793252 dated Nov. 22, 2019, 7 pages.
Supplementary European Search Report for Application No. EP13859972, dated Jun. 10, 2016, 6 pages.
Thourani V.H., et al., "Factors Affecting Success of Split-Thickness Skin Grafts in the Modern Burn Unit," The Journal of Trauma, Mar. 2003, vol. 54 (3), pp. 562-568.
Wells M.D., et al., "A New Method of Skin-Graft Stabilization: The Reston Technique," Annals of Plastic Surgery, 1995, vol. 34 (5), pp. 554-556.
Wendt J.R., et al., "Long-Term Survival of Human Skin Allografts in Patients with Immunosuppression," Plastic and Reconstructive Surgery, Apr. 2004, vol. 133 (5), pp. 1347-1354.
Williamson J. S., et al., "Cultured Epithelial Autograft: Five Years of Clinical Experience with Twenty-Eight Patients," The Journal of Trauma, Aug. 1995, vol. 39 (2), pp. 309-319.
Wood F.M., et al., "The Use of Cultured Epithelial Autograft in the Treatment of Major Burn Injuries: A Critical Review of the Literature," Burns, 2006, vol. 32 (4), pp. 395-401.
Zuber T.J., "Fusiform Exision," American Family Physician, Apr. 2003, vol. 67 (7), pp. 1539-1544.
Ablaza V.J., et al., "An Alternative Treatment for the Split Skin-Graft Donor Site," Aesthetic Plastic Surgery, 1997, vol. 21 (3), pp. 207-209.
Akan M., et al., "An Alternative Method to Minimize Pain in the Split-Thickness Skin Graft Donor Site," Plastic and Reconstructive Surgery, Aug. 2002, vol. 111 (7), pp. 2243-2249.
Alguire P.C. et al., "Skin Biopsy Techniques for the Internist," Journal of General Internal Medicine, Jan. 1998, vol. 13 (1), pp. 46-54.
Andreassi A., et al., "Classification and Pathophysiology of Skin Grafts," Clinics in Dermatology, 2005, vol. 23 (4), pp. 332-337.
Bello Y.M., et al., "Tissue-Engineered Skin, Current Status in Wound Healing," American Journal Clinical Dermatology, 2001, vol. 2 (5), pp. 305-313.
Branski L.K., et al., "A Porcine Model of Full-Thickness Burn, Excision, and Skin Autographing," Burns, 2008, vol. 34 (8), pp. 1119-1127.
Burns J.A., "Thermage: Monopolar Radiofrequency," Aesthetic Surgery Journal, Nov./Dec. 2005, vol. 25 (6), pp. 638-642.
Cirodde A., et al., "Cultured Epithelial Autografts in Massive Burns: A Single-Center Retrospective Study with 63 Patients," Burns, 2011, vol. 37 (6), pp. 964-972.
Clugston P.A., et al., "Cultured Epithelial Autografts: Three Years of Clinical Experience with Eighteen Patients," Journal of Burn Care and Rehabilitation, 1991, vol. 12 (6), pp. 533-539.
Cooperman L.S., et al., "Injectable Collagen: A Six-Year Clinical Investigation," Aesthetic Plastic Surgery, Jun. 1985, vol. 9 (2), pp. 145-151.
Dornseifer U., et al., "The Ideal Split-Thickness Skin Graft Donor Site Dressing: Rediscovery of Polyurethane Film," Annals of Plastic Surgery, Aug. 2009, vol. 63 (2), pp. 198-200.
Dornseifer U., et al., "The Ideal Split-Thickness Skin Graft Donor-Site Dressing: A Clinical Comparative Trial of a Modified Polyurethane Dressing and Aquacel," Plastic and Reconstructive Surgery, 2011, vol. 128 (4), pp. 918-924.
Elliot M., et al., "Initial Experience with Cultured Epithelial Autografts in Massively Burnt Patients," ANZ Journal of Surgery, 2002, vol. 72 (11), pp. 893-895.
Extended European Search Report for Application No. EP05027935 dated Jun. 12, 2009, 4 pages.
Fischer J.P., et al., "Complications in Body Contouring Procedures: An Analysis of 1797 Patients from the 2005 to 2010 American College of Surgeons National Surgical Quality Improvement Program Databases," Plastic and Reconstructive Surgery, 2013, vol. 132 (6), pp. 1411-1420.
Ford C.N., et al., "A Preliminary Study of Injectable Collagen in Human Vocal Fold Augmentation," Otolaryngology-Head and Neck Surgery, Jan. 1986, vol. 94 (1), pp. 104-112.
Ford C.N., et al., "Autologous Collagen Vocal Fold Injection: A Preliminary Clinical Study," Laryngoscope, Sep. 1995, vol. 105 (9 Pt 1), pp. 944-998.
Ford C.N., et al., "Clinical Experience with Injectable Collagen for Vocal Fold Augmentation," Larynscope, Aug. 1986, vol. 96 (8), pp. 863-869.
Ford C.N., et al., "Role of Injectable Collagen in the Treatment of Glottic Insufficiency: A Study of 119 Patients," The Annals of otology, Rhinology and Laryngology, Mar. 1992, vol. 101 (3), pp. 237-247.
Frey P., et al., "Subureteral Collagen Injection for the Endoscopic Treatment of Vesicoureteral Reflux in Children. Followup Study of 97 Treated Ureters and Histological Analysis of Collagen Implants," The Journal of Urology, Aug. 1992, vol. 148 (2 Pt 2), pp. 718-723.
Giordano A., et al., "From the Laboratory Bench to the Patient's Bedside: An Update on Clinical Trials with Mesenchymal Stem Cells," Department of Experimental Medicine of Biotechnology and Molecular Biology, Second University of Naples, Oct. 2006, 10 pages.
Greenwood J., et al., "Real-Time Demonstration of Split Skin Graft Inosculation and Integra Dermal Matrix Neovascularization Using Confocal Laser Scanning Microscopy," Journal of Plastic Surgery, Aug. 2009, vol. 9, pp. e33.
Hallock G.G., "The Cosmetic Split-Thickness Skin Graft Donor Site," Plastic and Reconstructive Surgery, 1999, vol. 104 (7), pp. 2286-2288.
Hansbrough W., et al., "Management of Skin-Grafted Burn Wounds with Xeroform and Layers of Dry Coarse-Mesh Gauze Dressing Results in Excellent Graft Take and Minimal Nursing Time," Journal of Burn Care and Rehabilitation, 1995, vol. 16(5), pp. 531-534.
Hazani R., et al., "Optimizing Aesthetic Results in Skin Grafting," The American Surgeon, Feb. 2012, vol. 78 (2), pp. 151-154.
International Search Report and Written Opinion for Application No. PCT/US2017/017683, dated Jul. 27, 2017, 10 pages.

(56) References Cited

OTHER PUBLICATIONS

International Search Report and Written Opinion for Application No. PCT/US2017/030840, dated Oct. 3, 2017, 15 pages.
International Search Report and Written Opinion for Application No. PCT/US2018/017100, dated Sep. 12, 2018, 18 pages.
International Search Report and Written Opinion for Application No. PCT/US2018/32387, dated Jan. 7, 2019, 15 pages.
International Search Report and Written Opinion for Application No. PCT/US2019/037484, dated Jan. 7, 2020, 15 pages.
International Search Report and Written Opinion for Application No. PCT/US2013/073678, dated May 27, 2014, 18 pages.
International Search Report and Written Opinion for Application No. PCT/US2014/058886, dated Mar. 3, 2015, 22 pages.
International Search Report and Written Opinion for Application No. PCT/US2015/047695, dated Jan. 28, 2016, 40 pages.
International Search Report and Written Opinion for Application No. PCT/US2015/047721, dated Feb. 3, 2016, 20 pages.
International Search Report and Written Opinion for Application No. PCT/US2016/016834, dated May 17, 2016, 11 pages.
To K., et al., "Biology of Fracture Healing," AO Principles of Fracture Management, AO Foundation Publishing, Jan. 2013, 5 pages.
Jones L.M., "The Biobrane Stent," Journal of Burn Care and Rehabilitation, 1998, vol. 19 (4), pp. 352-353.
Kaplan E.N., et al., "Clinical Utilization of Injectable Collagen," Annals of Plastic Surgery, Jun. 1983, vol. 10 (6), pp. 437-451.
Klein A.W., et al., "Implantation Technics for Injectable Collagen," Journal of the American Academy of Dermatology, Aug. 1983, vol. 9 (2), pp. 224-228.
Kogan L., et al., "Vertical (Two-Layer) Skin Grafting: New Reserves for Autologic Skin," Annals of Plastic Surgery, 2003, vol. 50 (5), pp. 514-516.
Lee H., et al., "Outcomes of Sprayed Cultured Epithelial Autografls for Full-Thickness Wounds: A Single-Centre Experience," Burns, 2012, vol. 38 (6), pp. 931-936.
Lindenblatt N., et al., "A New Model for Studying the Revascularization of Skin Grafts In Vivo: The Role of Angiogenesis," Plastic and Reconstructive Surgery, 2008, vol. 122 (6), pp. 1669-1680.
Matton G., et al., "The History of Injectable Biomaterials and the Biology of Collagen," Aesthetic Plastic Surgery, Jun. 1985, vol. 9 (2), pp. 133-140.
Mimoun M., et al., "The Scalp is an Advantageous Donor Site for Thin-Skin Grafts: A Report on 945 Harvested Samples," Plastic and Reconstructive Surgery, 2006, vol. 118 (2), pp. 369-373.
Mottura A.A., et al., "Open Frontal Lift: A Conservative Approach," Aesthetic Plastic Surgery, 2006, vol. 30 (4), pp. 381-389.
O'connor K.W., et al., "Endoscopic Placement of Collagen at the Lower Esophageal Sphincter to Inhibit Gastroesophageal Reftux: a Pilot Study of 10 Medically Intractable Patients," Gastrointestinal Endoscopy, 1988, vol. 34 (2), pp. 106-112.
Pallua N., et al.," The Lipo-Facelift: Merging the Face-Lift and Liposculpture: Eight Years Experience and a Preliminary Observational Study," Aesthetic Plastic Surgery, 2013, vol. 37 (6), pp. 1107-1113.
Penington A.J., et al., "Skin Graft Failure Is Predicted By Waist-Hip Ratio: Marker for Metabolic Syndrome," ANZ Journal of Surgery, 2007, vol. 77 (3), pp. 118-120.
Polder K.D., et al., "Radiofrequency: Thermage," Facial Plastic Surgery Clinics of North America, 2011, vol. 19 (2), pp. 347-359.
Russe E et al., "Micro-Fractional, Direction Skin Tightening: A Porcine Model," Lasers in Surgery and Medicine, Mar. 2016, vol. 48 (3), pp. 264-269.

\* cited by examiner

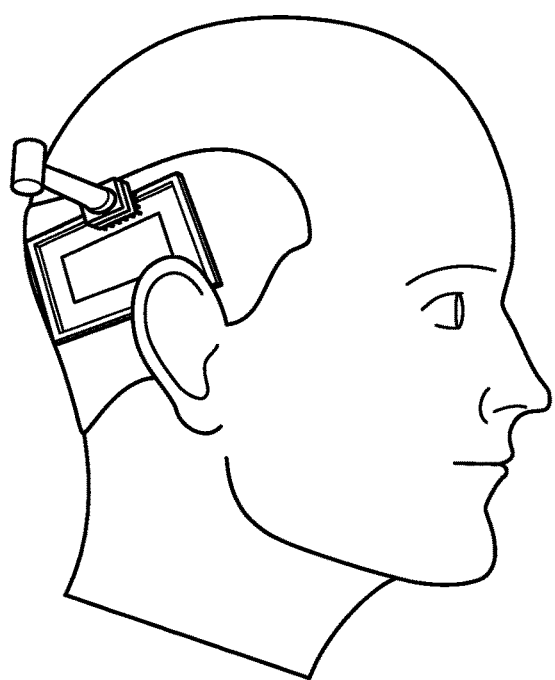 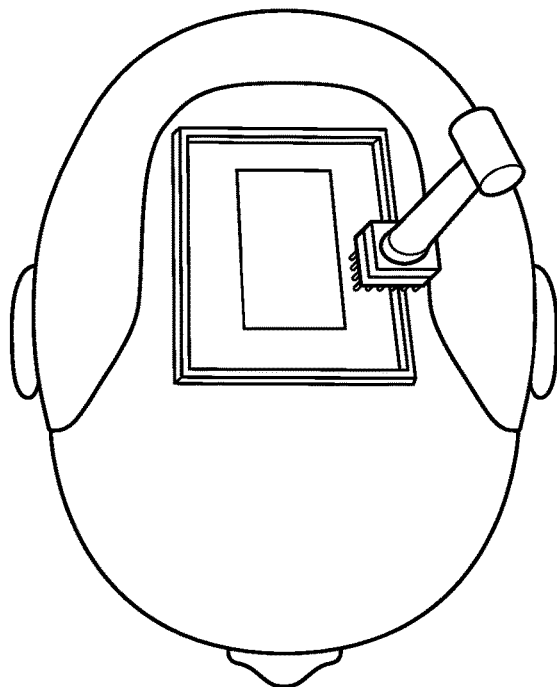
Donor Hair Transplant Site  Recipient Hair Transplant Site
FIG. 27  FIG. 28

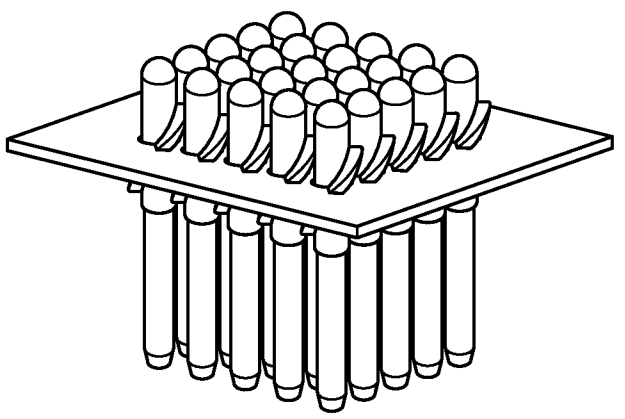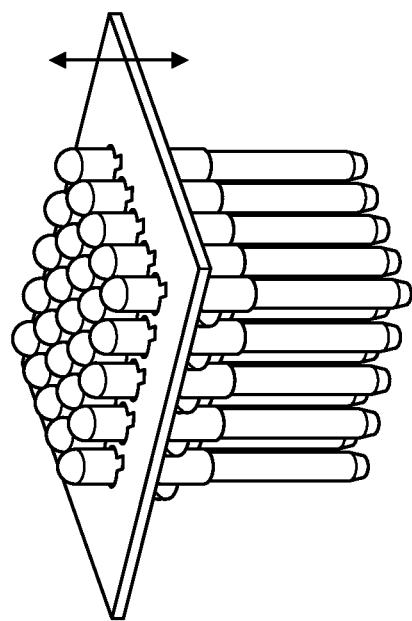
FIG. 55

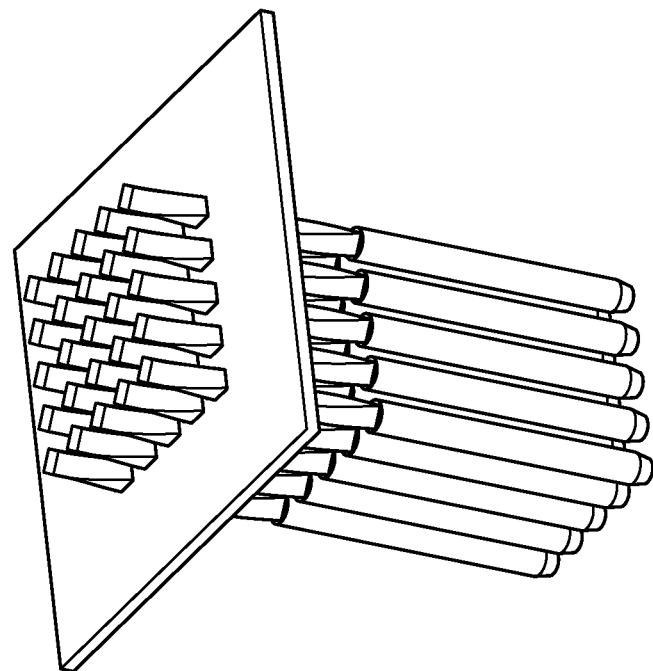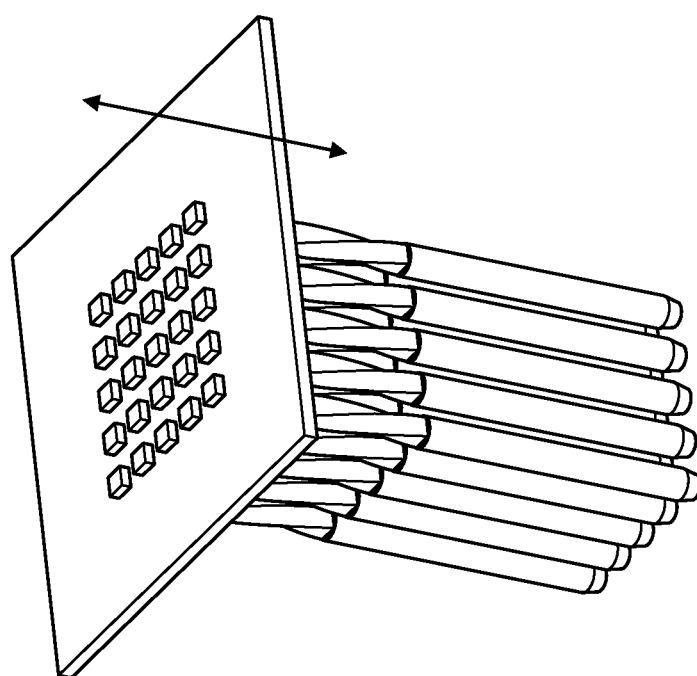
FIG. 57

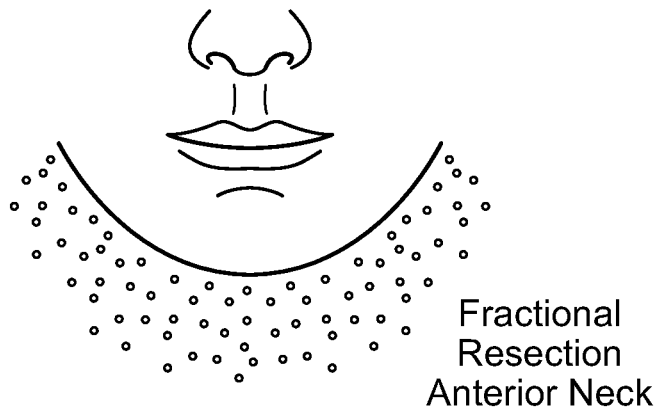
Fractional Resection Anterior Neck
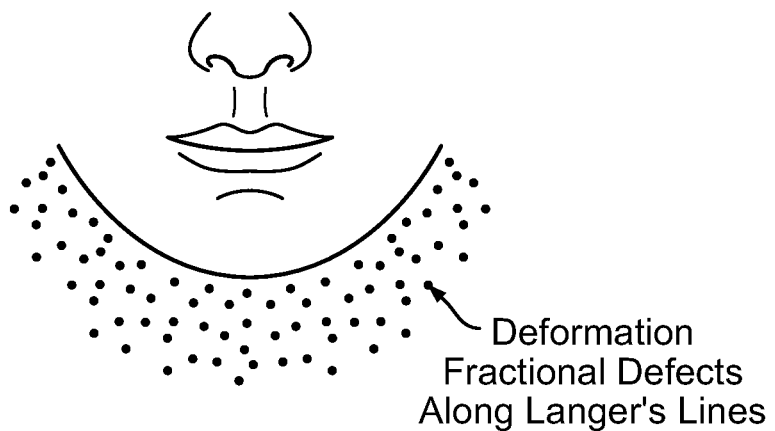
Deformation Fractional Defects Along Langer's Lines
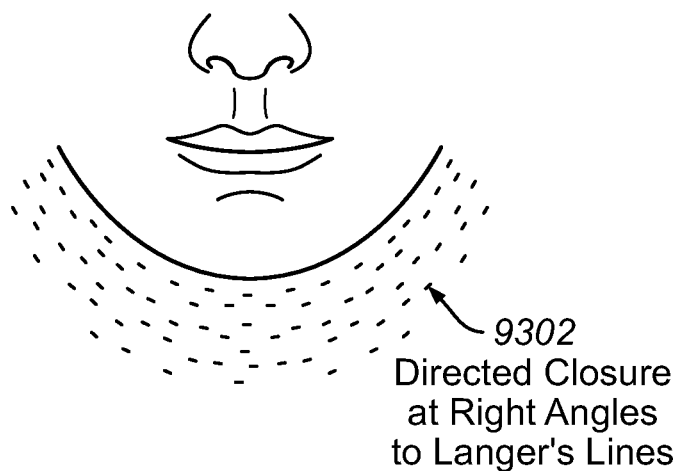
9302 Directed Closure at Right Angles to Langer's Lines
FIG. 93

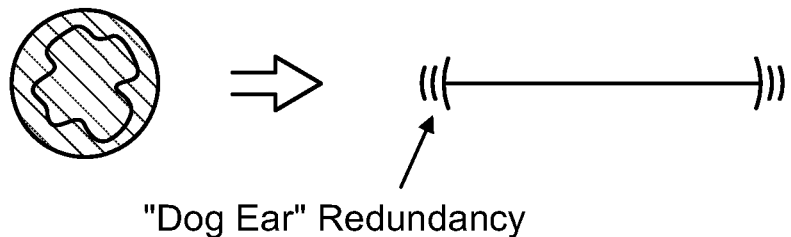
"Dog Ear" Redundancy
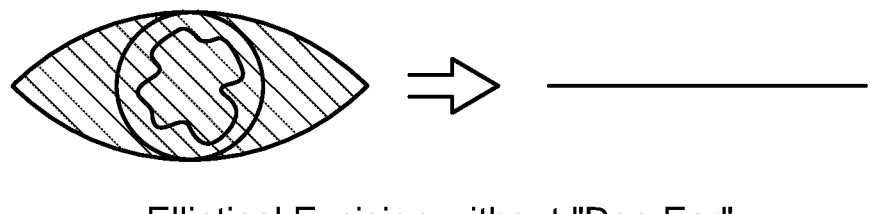
Elliptical Excision without "Dog Ear"
but length of incision is increased
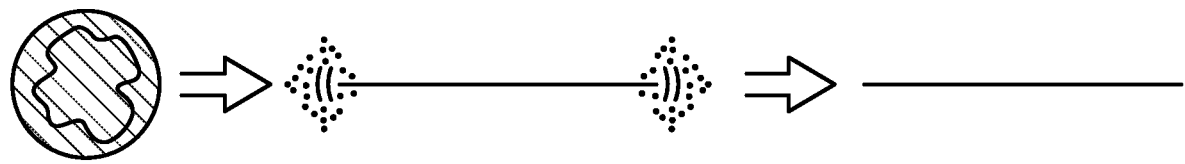
Fractional Resection of "Dog Ear"
Shorter incision without "Dog Ear"
FIG. 95

**Inferior View
(Looking Upward)
Submentum**

Elliptical Excision of Lesion
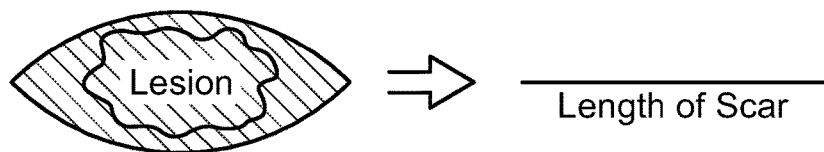
Excision of Lesion with FR
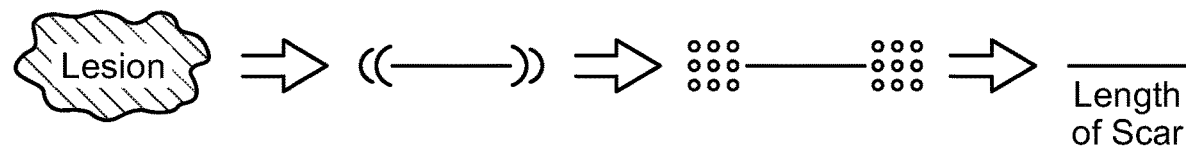
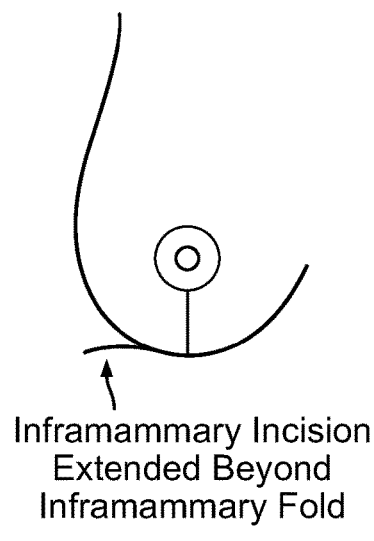
Inframammary Incision Extended Beyond Inframammary Fold
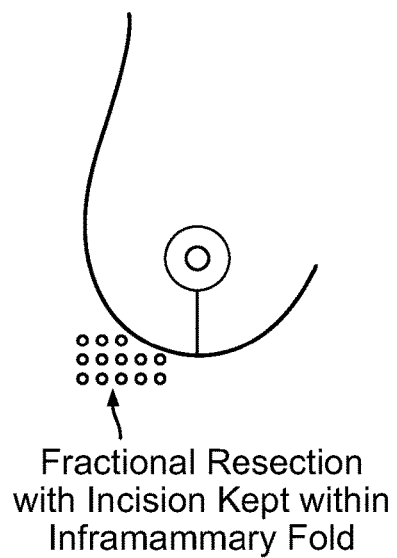
Fractional Resection with Incision Kept within Inframammary Fold
FIG. 133

Fractional Skin Graft Harvest
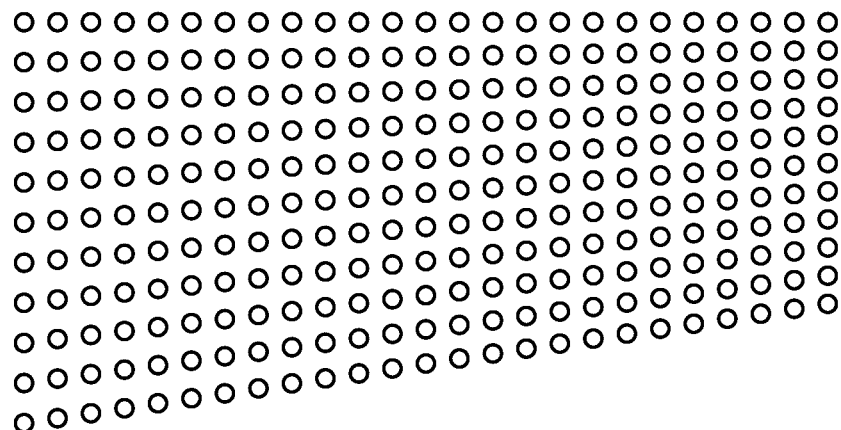
⇩ Directed Chose of Donor Site
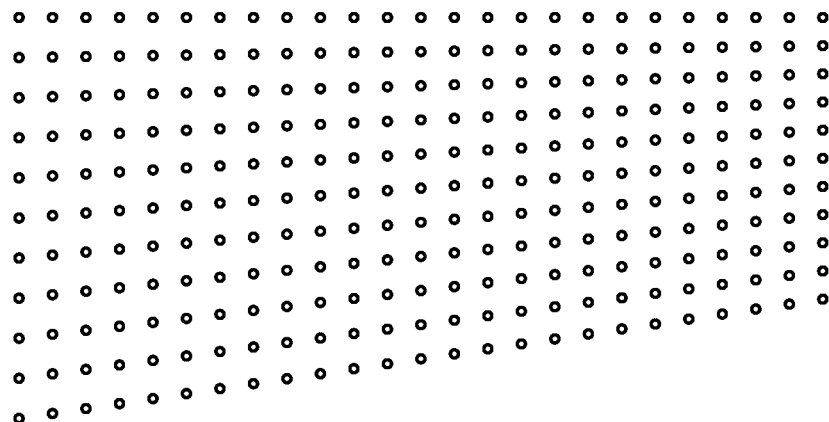
FIG. 135

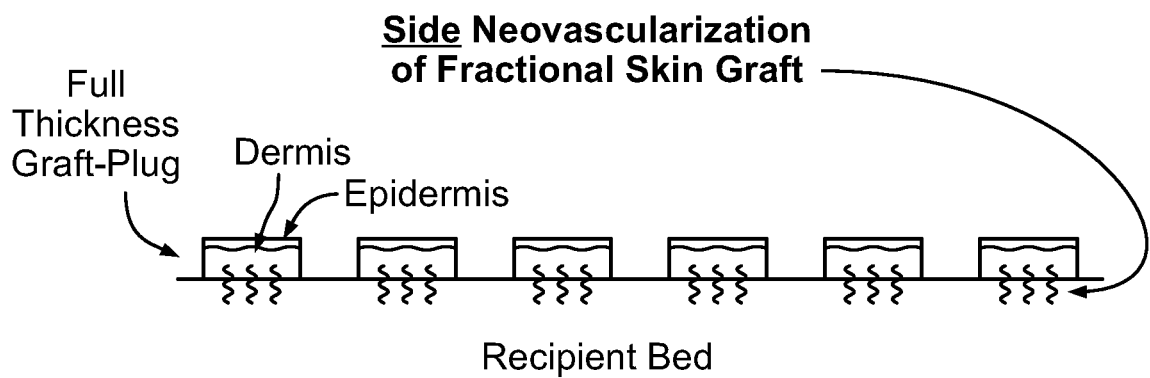
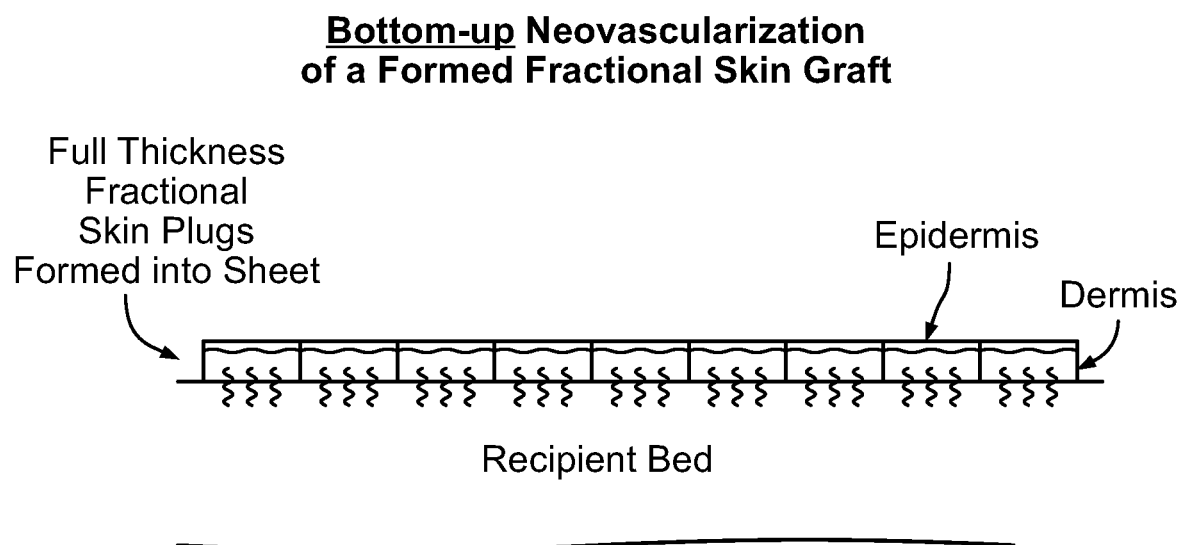
FIG. 136

1.5mm Scalpets
Design 1
- Skived
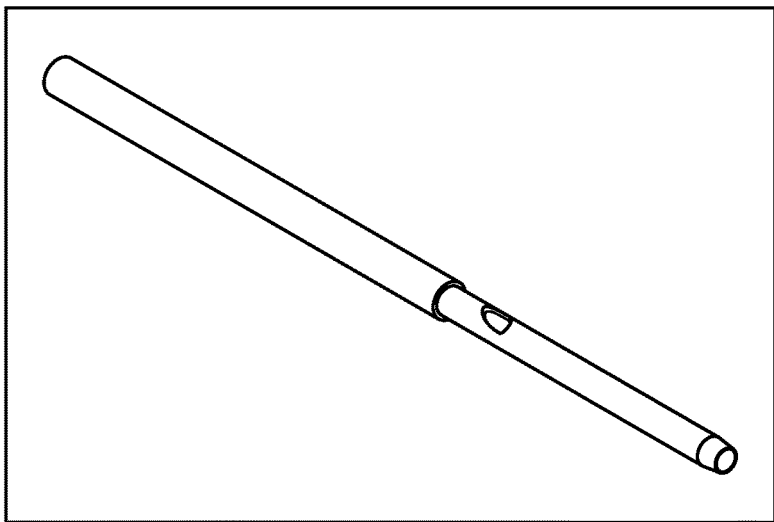
Design 2
- Skived
Distal Port
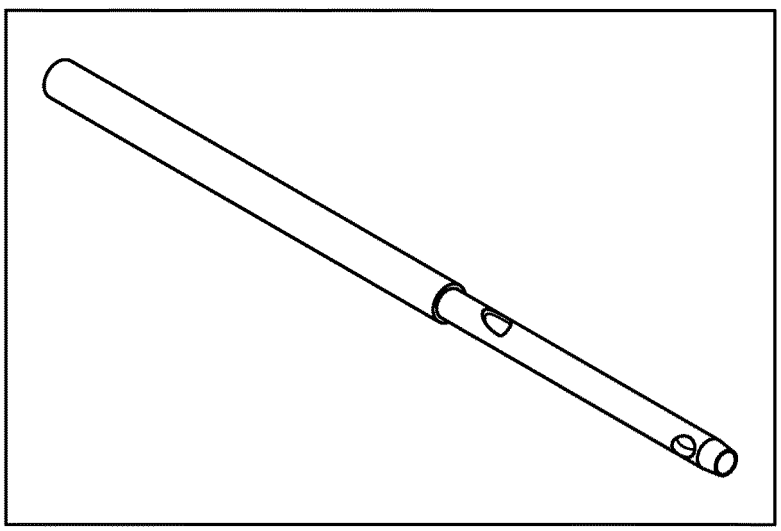
Design 3
- Blunt
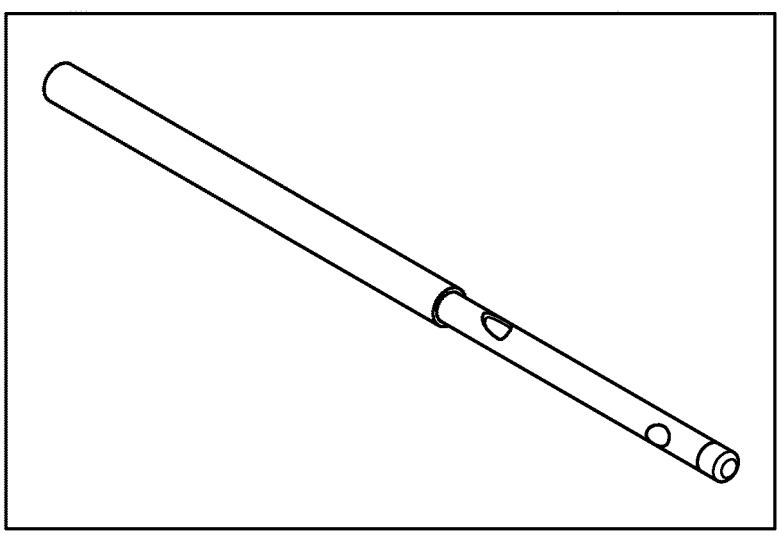
FIG. 139B

| Skin Defect | Mechanism of Action | Scalpet Diameter and Type | Stop guide (mm) | Suction Use | Directed Closure Technique and Recipient Site Dressing | Vector of Directed Closure | Pre-op and Intra-op Considerations | Post-Considerations | General Comments |
|---|---|---|---|---|---|---|---|---|---|
| Traumatic avulsive or full thickness abrasive loss | Cleaning and Debridement of the wound (Figs. 156A-B) with partial closure and immediate fractional skin graft. Delay in skin grafting to establish a granulation base may not be required due to the ability of the skin plugs to neovascularize with an uneven contour of the recipient site. | Standard surgical intruments and 2.00 Scalpet (Skived Non-slotted) or scalpet array | 3-4 | "wall suction" aspirator on lowest vacuum setting providing evacuation and canister harvest of the skin plugs. Fat resection is to be minimized | Flexzan/ Optifoam - Single or Double Mooring Technique at the donor site. The dressing at the recipient site will consist of Xeroform gauze, 4x4s and an ABD. Splint immobilization across a joint surface may be required. | The donor site fractional field is closed according to the deformation of the FR defects corresponding to Langer's lines | Photo & Video documentation Perioperatively The 4-to-1 rule (Fig. 157) applies to the size of the donor fractional harvest field. The canister of harvested full thickness skin plugs are directly applied and oriented at the recipient site. Either a vertical or side orientation is acceptable as neovascularization and vertical top down growth re-orientation of the plugs will occur with either type of initial plug application i.e., the recipient site acts as it's own biological docking station (Figs. 158A-B). | Flexzan dressing at the donor site is removed at 1 week to 10 days. The recipient site dressing is changed at 1 week.<br><br>Photo documentation of Flexzan removal and as per protocol | Vertical (FR) technique of skin plug harvest is used. The amount of fat resection is minimized. Both vertical and side neovascularization occurs at the recipient site. |

FIG. 155A

| Skin Defect | Mechanism of Action | Scalpet Diameter and Type | Stop guide (mm) | Suction Use | Directed Closure Technique and Recipient Site Dressing | Vector of Directed Closure | Pre-op and Intra-op Considerations | Post-Considerations | General Comments |
|---|---|---|---|---|---|---|---|---|---|
| 3rd Degree Burn | Debridement of the burn eshcar (Figs. 156A-B) may require multiple procedures. The delay required for granulation formation may be reduced with a fractional skin graft due to the ability of the skin plugs to neovascularize within an uneven contour of the recipient site. | Standard surgical intruments and 2.00 Scalpet (Skived Non-slotted) or scalpet array | 3-4 | "wall suction" aspirator on lowest vacuum setting providing evacuation and canister harvest of the skin plugs. Fat resection is to be minimized | Flexzan/ Optifoam - Single or Double Mooring Technique at the donor site. The dressing at the recipient site will consist of Xeroform gauze, 4x4s and an ABD. Splint immobilization across a joint surface may be required. | The donor site fractional field is closed according to the deformation of the FR defects corresponding to Langer's lines | Photo & Video documentation Perioperatively The 4-to-1 rule (Fig. 157) applies to the size of the donor fractional harvest field. The canister of harvested full thickness skin plugs are directly applied and oriented at the recipient site. Either a vertical or side orientation is acceptable as neovascularization and vertical top down growth re-orientation of the plugs will occur with either type of initial plug application i.e., the recipient site acts as it's own biological docking station (Figs. 158A-B). | Flexzan dressing at the donor site is removed at 1 week to 10 days. The recipient site dressing is changed at 1 week. Photo documentation of Flexzan removal and as per protocol | Vertical (FR) technique of skin plug harvest is used. The amount of fat resection is minimized. Both vertical and side neovascularization occurs at the recipient site. |

FIG. 155B

| Skin Defect | Mechanism of Action | Scalpet Diameter and Type | Stop guide (mm) | Suction Use | Directed Closure Technique and Recipient Site Dressing | Vector of Directed Closure | Pre-op and Intra-op Considerations | Post-Considerations | General Comments |
|---|---|---|---|---|---|---|---|---|---|
| Lower extremity | Repeated Debridement (Figs. 156A-B) of a vascular compromised recipient site may also require a vascular procedure to revascularize the lower extremity. The most common ulcers of the lower extremity are Venous stasis, ischemic and diabetic ulcers. The delay required for granulation base formation may be reduced with a fractional skin graft. Many of these patients require multiple skin grafts to achieve closure. The ability to serially harvest a skin graft from the same donor site will be a distinct advantage. | Standard surgical intruments and 2.00 Scalpet (Skived Non-slotted) or scalpet array | 3-4 | "wall suction" aspirator on lowest vacuum setting providing evacuation and canister harvest of the skin plugs. Fat resection is to be minimized | Flexzan/ Optifoam - Single or Double Mooring Technique at the donor site. The dressing at the recipient site will consist of Xeroform gauze, 4x4s and an ABD. Splint immobilization across a joint surface may be required. | The donor site fractional field is closed according to the deformation of the FR defects corresponding to Langer's lines | Photo & Video documentation Perioperatively The 4-to-1 rule (Fig. 157) applies to the size of the donor fractional harvest field. The canister of harvested full thickness skin plugs are directly applied and oriented at the recipient site. Either a vertical or side orientation is acceptable as neovascularization and vertical top down growth re-orientation of the plugs will occur with either type of initial plug application i.e., the recipient site acts as it's own biological docking station (Figs. 158A-B). | Flexzan dressing at the donor site is removed at 1 week to 10 days. The recipient site dressing is changed at 1 week. Photo documentation of Flexzan removal and as per protocol | Vertical (FR) technique of skin plug harvest is used. The amount of fat resection is minimized. Both vertical and side neovascularization occurs at the recipient site. |

FIG. 155C

| Skin Defect | Mechanism of Action | Scalpet Diameter and Type | Stop guide (mm) | Suction Use | Directed Closure Technique and Recipient Site Dressing | Vector of Directed Closure | Pre-op and Intra-op Considerations | Post-Considerations | General Comments |
|---|---|---|---|---|---|---|---|---|---|
| Excisional | Skin defects are created (Fig. 156B) from the lesion resection such as melanoma or large squamous cell carcinomas where skin grafting to close the defect is indicated. A fractional full thickness skin graft will provide durable coverage in areas requiring such coverage. The advantages to both the recipient site and donor site have been described. | Standard surgical intruments and 2.00 Scalpet (Skived Non-slotted) or scalpet array | 3-4 | "wall suction" aspirator on lowest vacuum setting providing evacuation and canister harvest of the skin plugs. Fat resection is to be minimized | Flexzan/Optifoam - Single or Double Mooring Technique at the donor site. The dressing at the recipient site will consist of Xeroform gauze, 4x4s and an ABD. Splint immobilization across a joint surface may be required. | The donor site fractional field is closed according to the deformation of the FR defects corresponding to Langer's lines | Photo & Video documentation Perioperatively The 4-to-1 rule (Fig. 157) applies to the size of the donor fractional harvest field. The canister of harvested full thickness skin plugs are directly applied and oriented at the recipient site. Either a vertical or side orientation is acceptable as neovascularization and vertical top down growth re-orientation of the plugs will occur with either type of initial plug application i.e., the recipient site acts as it's own biological docking station (Figs. 158A-B). | Flexzan dressing at the donor site is removed at 1 week to 10 days. The recipient site dressing is changed at 1 week. Photo documentation of Flexzan removal and as per protocol | Vertical (FR) technique of skin plug harvest is used. The amount of fat resection is minimized. Both vertical and side neovascularization occurs at the recipient site. |

FIG. 155D

| Treatment Area | Primary Purpose | Scalpet Diameter Length and Type | Stop guide (mm) | Suction Use | Directed Closure Technique | Vector of Directed Closure | Pre-op and Intra-op Considerations | Post-Considerations | General Comments |
|---|---|---|---|---|---|---|---|---|---|
| Anterior Neck | First Pass (Fractional Skin Resection of the entire demarcated treatment area) | 1.5 (Skived Non-slotted) | 4 | Yes "wall suction" aspirator on lower vacuum setting for evacuation of the skin plugs only | Flexzan/ Optifoam - Single or Double Mooring Technique | Horizontal (At right angles to lines indicated by Langer's lines. Fractional Defects Closed Vertically to accentuate the Cervical-Mandibular Angle) | Photo & Video documenation Perioperatively (Treatment areas demarcated and stencil applied preoperatively) | Use of compression garment for 2 weeks postoperatively Photo documentation with use of imageJ/NIH software for 6 months | Vertical (FR) technique is used with minimal amount of tissue resection |
| Submentum | Second Pass (Fractional Tissue Resection in topographically marked submentum) | 1.5/2.0 Skived and Slotted (Sharp and/or Blunt Tip) | 14 | Vacuum Assisted Tissue Resection (with scalpet manifold and "Wall Suction" aspirator on higher setting) (Techniques 1 and 2) | Flexzan/ Optifoam - Single Mooring Technique | Vertical (As indicated by Langer's lines. Fractional Defects closed horizontally to flatten contour of submentum) | Photo & Video documenation Perioperatively (Treatment areas demarcated and stencil applied preoperatively) | Use of compression garment for 2 weeks postoperatively Photo documentation with use of imageJ/NIH software for 6 months | Vertical and Horizontal tissue resection (TR) (Techniques 1 and 2) |

FIG. 159A

| Jowl | Second Pass (Fractional Tissue Resection in topographically marked submandibular jowl) | 1.5/2.0 Skived and Slotted (Sharp and/or Blunt Tip) | 14 | Vacuum Assisted Tissue Resection (with scalpet manifold and "Wall Suction" aspirator on higher setting) (Technique 2 only) | Flexzan/ Optifoam - Single Mooring Technique | Vertical (As indicated by Langer's lines. Fractional Defects closed horizontally to flatten contour of jowl) | Photo & Video documenation Perioperatively (Treatment areas demarcated and stencil applied preoperatively) | Use of compression garment for 1 week postoperatively Photo documentation with use of imageJ/NIH software for 6 months | Vertical tissue resection (TR) (Technique 2 only) |

FIG. 159B

| Scar Type | Mechanism of Action | Scalpet Diameter and Type | Stop guide (mm) | Suction Use | Directed Closure Technique | Vector of Directed Closure | Pre-op and Intra-op Considerations | Post-Considerations | General Comments |
|---|---|---|---|---|---|---|---|---|---|
| Linear | The scar is less visibly apparent by Fractional de-delineation of the scar/skin margins (Figs. 4,5,6,7) | 1.5 and 2.0 (Skived and Slotted)? (Figs. 1,2,3) | 3-4 | "wall suction" aspirator on lowest vacuum setting providing evacuation of the skin plugs. Fat resection is to be minimized | Flexzan/ Optifoam - Single or Double Mooring | Parallel to longitudinal axis of the scar FR defects are closed horizontally at right angles to the linear scar (Fig. 4) | Photo & Video documenation Perioperatively  A freehand interdigitating pattern of fractional scar margin resection will be employed (Figs. 4,5) | Flexzan dressing removed at 1 week to 10 days  Photo documentation of Flexzan removal and as per protocol | Vertical (FR) technique of skin and scar epithelium is used. The amount of fat resection is minimized |

FIG. 165A

| Scar Type | Mechanism of Action | Scalpet Diameter and Type | Stop guide (mm) | Suction Use | Directed Closure Technique | Vector of Directed Closure | Pre-op and Intra-op Considerations | Post-Considerations | General Comments |
|---|---|---|---|---|---|---|---|---|---|
| Wide (hypotrophic, hypertrophic and scar contracture - examples, post-tangential split dermal excision, cervical and axillary contractures) | Direct surgical excision of scar with shortening of scar revision incision by fractional "dog ear" resection (Figs. 8,9,10, 11,12,13,14) | Standard surgical instrumentation with 1.5 (Skived Non-slotted) and 2.0 (Skived and Slotted)? (Figs. 1,2,3) | 3-6 (14?) | "wall suction" aspirator on lowest vacuum setting providing evacuation of the skin plugs. Fat resection is to be minimized | Steristrip 1/2" or 1" using Single Mooring Technique | At Right angles to longitudinal axis of wound closure. The FR defects are closed longitudinally with long axis of the scar. | Photo & Video documenation Perioperatively  The 4-to-1 rule (Fig. 11) applies to the size of Fractional resection field and the dimensions of an elliptical excision of the "dog ear" | Steristrips removed and reapplied at 1 week to 10 days  Photo documentation of Steristrip removal and as per protocol | Vertical (FR) technique of skin (and fat?) is used for "dog ear" resection.  Layered linear would closure, V-Y advancement and Flap transfer techniques are to be standardized. (Figs. 8,9,10, 11,12,13,14) |

FIG. 165B

| Scar Type | Mechanism of Action | Scalpet Diameter and Type | Stop guide (mm) | Suction Use | Directed Closure Technique | Vector of Directed Closure | Pre-op and Intra-op Considerations | Post-Considerations | General Comments |
|---|---|---|---|---|---|---|---|---|---|
| Acne | Flattening of contour with a combined surgical (pit) scar resection and a fractional skin (fat?) resection of the adjacent skin | Standard surgical instrumentation including a 3.0/4.0 punch biopsy, microtome scalpel and 1.5/2.0 (Skived scalpet) | 2-4 | "wall suction" aspirator on lowest vacuum setting providing evacuation of the skin plugs. Fat resection is to be minimized at scar pit and the pit scar epithelium is removed surgically | Flexzan/Optifoam - Single or Double Mooring | As indicated by Langer's lines | Photo & Video documenation Perioperatively  Topographical marking of the pits and peaks is performed preoperatively with patient in a sitting position.  A microtome release of the base of the pit following punch biopsy excision of the scar epithelium. No fat resection at the base of the acne pit. Closure of the resected Pit defect is performed with a 6.0 nylon horizontal mattress suture. | Flexzan/Optifoam dressing removed at 4-6 days post-op  Photo documentation of Flexzan removal and as per protocol | Vertical (FR) technique of scar epithelium is used. The amount of fat resection is minimized in the acne pit. Fractional fat resection (?) with fractional skin resection at the peak to flatten contour |

FIG. 165C

| Scar Type | Mechanism of Action | Scalpet Diameter and Type | Stop guide (mm) | Suction Use | Directed Closure Technique | Vector of Directed Closure | Pre-op and Intra-op Considerations | Post-Considerations | General Comments |
|---|---|---|---|---|---|---|---|---|---|
| Incisional Scar from a primary excisional skin defects | Reduction in length of incisional scarring due to Fractions resection of "dog ear" skin redundancies (Figs. 8,9,10,11, 12,13,14) | Standard surgical instrumentation with 1.5/2.0 (Skived scalpet) and 2.0 (Skived and Slotted)? (Figs. 1,2,3) | 4-6 (14?) | "wall suction" aspirator on a vacuum setting providing evacuation of the skin (and fat) plugs. | Steristrip 1/2" or 1" using Single Mooring Technique | At Right angles to longitudinal axis of wound closure. The FR defects are closed longitudinally with long axis of the scar. | Photo & Video documenation Perioperatively<br><br>Either direct linear or V-Y advancement used to close the excisional defects (Figs. 14,15) or V-Y advancement at the perimeter of the excisional defect to reduce the size of a local flap closure.<br><br>Dog ear redundancies of the V-Y closures are then fractionally resected (Fig. 15) 4-to-1 rule applies (Fig. 11) | Steristrips removed at 1 week and reapplied as needed<br><br>Photo documentation of Steristrip removal and as per protocol | Vertical (FR) technique of skin (and fat) is used for "dog ear" resection.<br><br>Layered wound closure and flap transfer techniques are standardized (Figs. 14,15) |

FIG. 165D

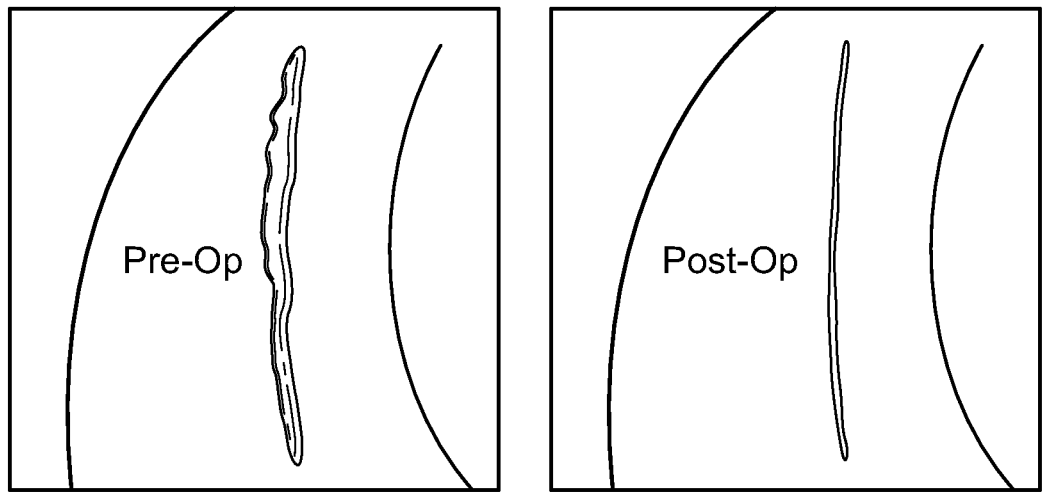
Preoperative and Postoperative (12 months)
Fractional Scar Revision
of Hypertrophic Scar Left Hip
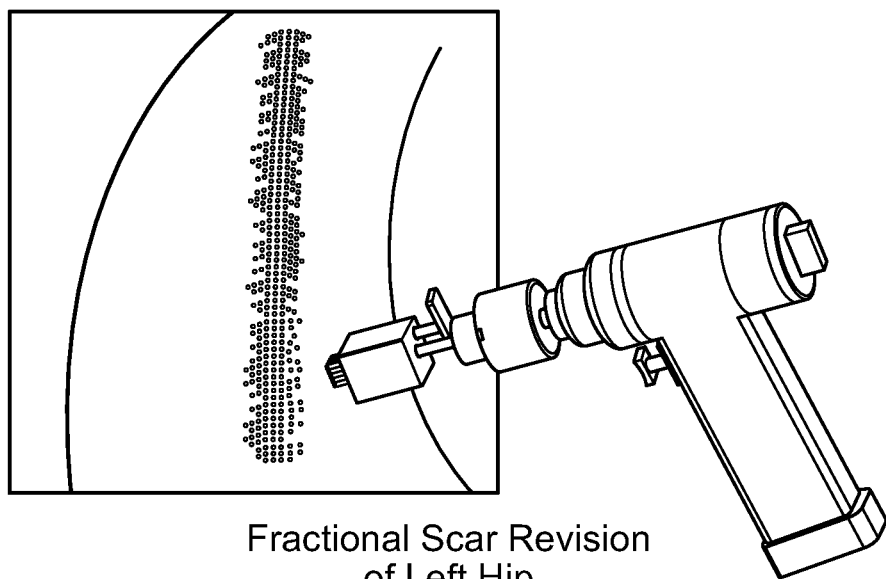
Fractional Scar Revision
of Left Hip
FIG. 168

Cervical Scar Contractures

Cervical Scar Contracture Release Pre-op

Cervical Scar Contracture Release Post-op

| Tattoo Type | Mechanism of Action | Scalpet Diameter and Type | Stop guide (mm) | Suction Use | Directed Closure Technique and Recipient Site Dressing | Vector of Directed Closure | Pre-op and Intra-op Considerations | Post-Considerations | General Comments |
|---|---|---|---|---|---|---|---|---|---|
| Solid | Enough Ink is removed that the pattern or presence of the tattoo is no longer visible apparent (Figs. 4,5,6) | 1.5 and 2.0 (Skived, Non-slotted) (Figs 1,2,3) | 2-4 | "wall suction" aspirator on a vacuum setting providing evacuation of the skin plugs. | Flexzan/ Optifoam - Single or Double Mooring | As indicated by Langer's lines to reduce visible scarring. The vector of closure is at right angles to the longitudinal deformation of the fractional skin defects. | Photo & Video documentation Perioperatively  A freehand resection of inked skin is employed where the margin of the tattoo includes non-tattooed skin. As most tattoos are created with impregnation of ink in the superficial dermis, an intradermal fractional resection will be performed. (Figs. 5,6) | Flexzan dressing removed at 1 week to 10 days  Photo documentation of Flexzan removal and as per protocol | The amount of fat resection is minimized and de-delineation of the pattern of the tattoo may be required with the fractional resection of non-tattooed skin |

FIG. 176A

| Tattoo Type | Mechanism of Action | Scalpet Diameter and Type | Stop guide (mm) | Suction Use | Directed Closure Technique and Recipient Site Dressing | Vector of Directed Closure | Pre-op and Intra-op Considerations | Post-Considerations | General Comments |
|---|---|---|---|---|---|---|---|---|---|
| Cursive or Non-Solid (Fig. 4) | Enough Ink is removed that the pattern or presence of the tattoo is no longer visible apparent (Figs. 4,5,6) | 1.5 and 2.0 (Skived, Non-slotted) (Figs 1,2,3) | 2-4 | "wall suction" aspirator on a vacuum setting providing evacuation of the skin plugs. | Flexzan/ Optifoam - Single or Double Mooring | As indicated by Langer's lines to reduce visible scarring. The vector of closure is at right angles to the longitudinal deformation of the fractional skin defects. | Photo & Video documentation Perioperatively  A freehand resection of inked skin is employed where the margin of the tattoo includes non-tattooed skin. As most tattoos are created with impregnation of ink in the superficial dermis, an intradermal fractional resection will be performed. (Figs. 5,6) | Flexzan dressing removed at 1 week to 10 days  Photo documentation of Flexzan removal and as per protocol | The amount of fat resection is minimized and de-delineation of the pattern of the tattoo may be required with the fractional resection of non-tattooed skin |

FIG. 176B

| Tattoo Type | Mechanism of Action | Scalpet Diameter and Type | Stop guide (mm) | Suction Use | Directed Closure Technique and Recipient Site Dressing | Vector of Directed Closure | Pre-op and Intra-op Considerations | Post-Considerations | General Comments |
|---|---|---|---|---|---|---|---|---|---|
| Large | Enough Ink is removed that the pattern or presence of the tattoo is no longer visible apparent (Figs. 4,5,6) | 1.5 and 2.0 (Skived, Non-slotted) (Figs 1,2,3) 3x3 Array | 2-4 | "wall suction" aspirator on a vacuum setting providing evacuation of the skin plugs. | Flexzan/ Optifoam -Single or Double Mooring | As indicated by Langer's lines to reduce visible scarring. The vector of closure is at right angles to the longitudinal deformation of the fractional skin defects. | Photo & Video documentation Perioperatively  A freehand resection of inked skin is employed where the margin of the tattoo includes non-tattooed skin. As most tattoos are created with impregnation of ink in the superficial dermis, an intradermal fractional resection will be performed. Large tattoos require the use of the array. (Figs. 5,6) | Flexzan dressing removed at 1 week to 10 days  Photo documentation of Flexzan removal and as per protocol | The amount of fat resection is minimized and de-delineation of the pattern of the tattoo may be required with the fractional resection of non-tattooed skin |

FIG. 176C

Vertically and horizontally aligned fractional fields with vertical and horizontal deformities Wider vertically aligned field
with more severe skin laxity Dependant horizontal curvilinear deformity with horizontally aligned fractional field Horizontal dependent curvilinear deformity with horizontally aligned vector of directed closure Vertical deformity of the submentum requiring lengthening in the vertical axis and tightening in the horizontal axis

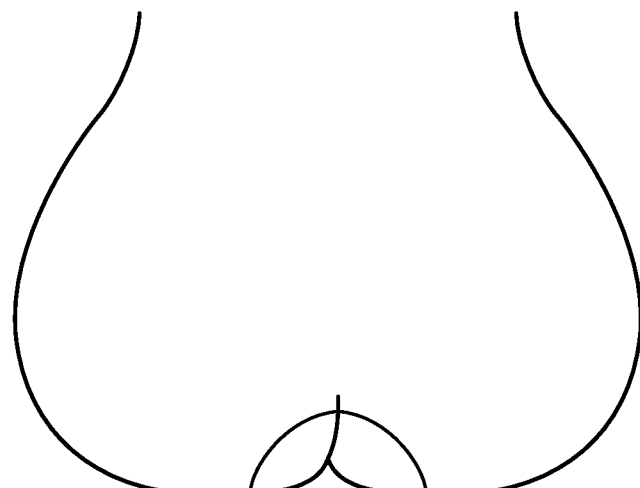
Oblique fractional field
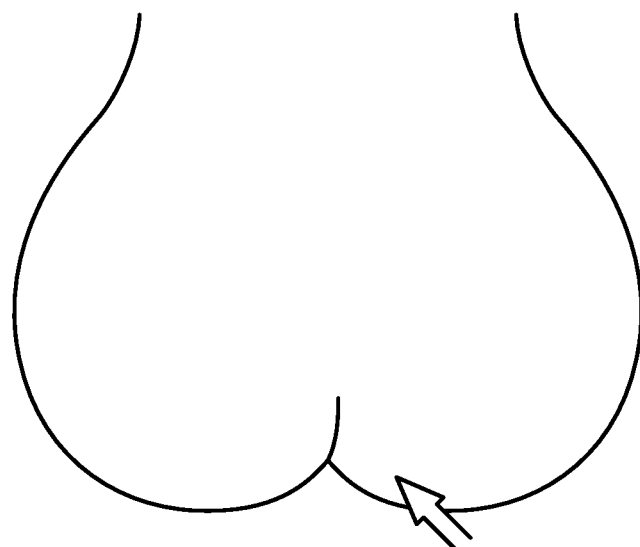
Vector obliquely aligned to longitudinal field axis
FIG. 188

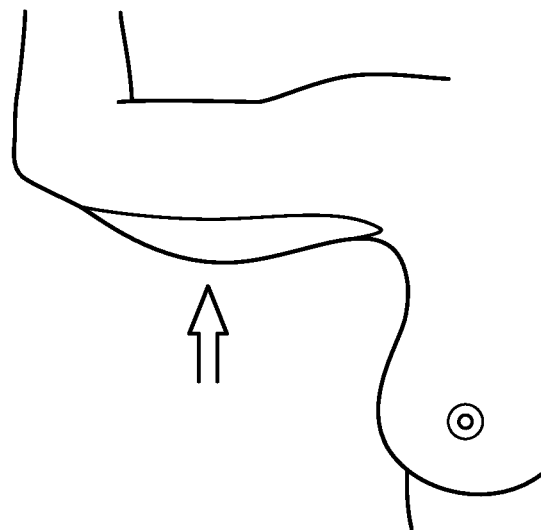
Vector at right angle to the longitudinal field axis
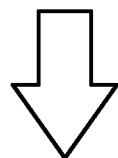
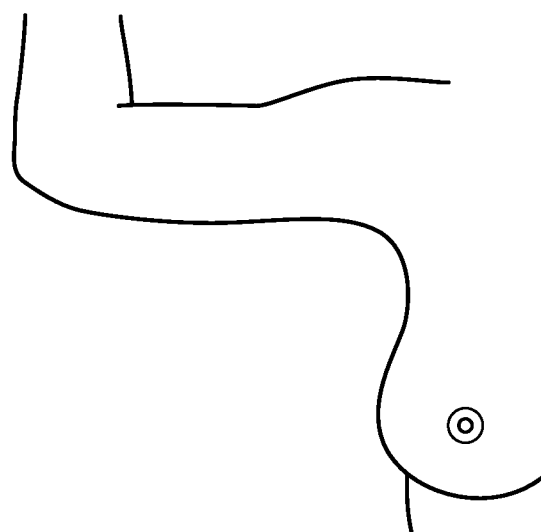
FIG. 189

Dependent curvilinear deformity
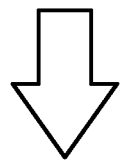
Horizontally aligned fractional field
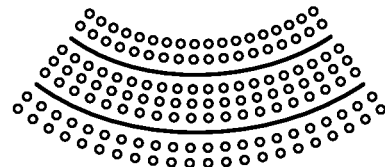
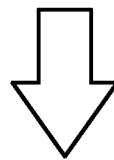
Horizontal vector with straightening
of margin
FIG. 190

**Fractionally Incised Field
(skin plugs insitu)**

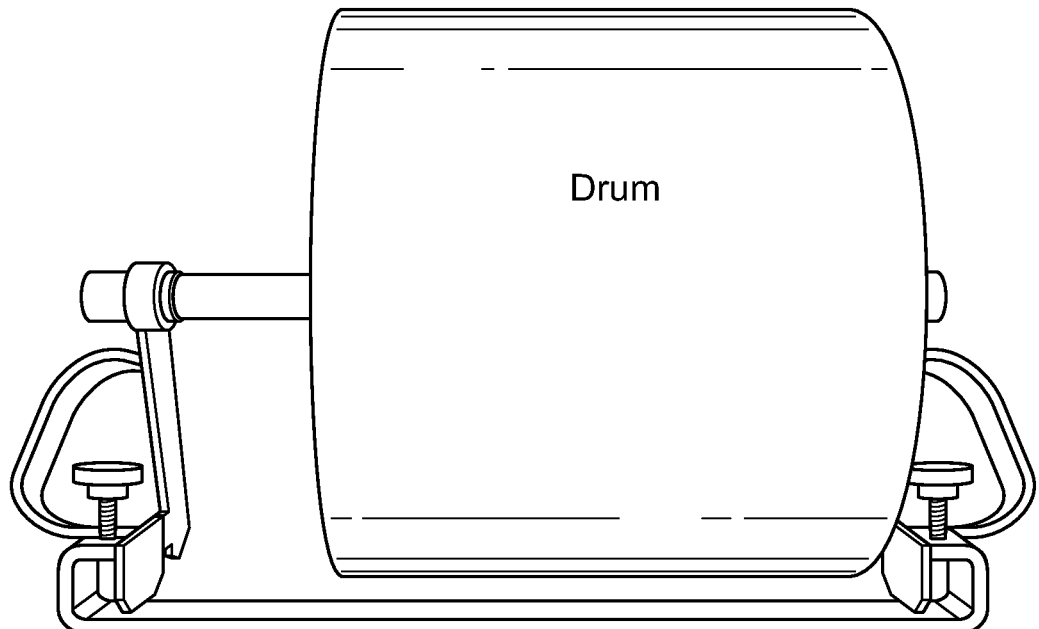
Adjustable Outrigger Blade
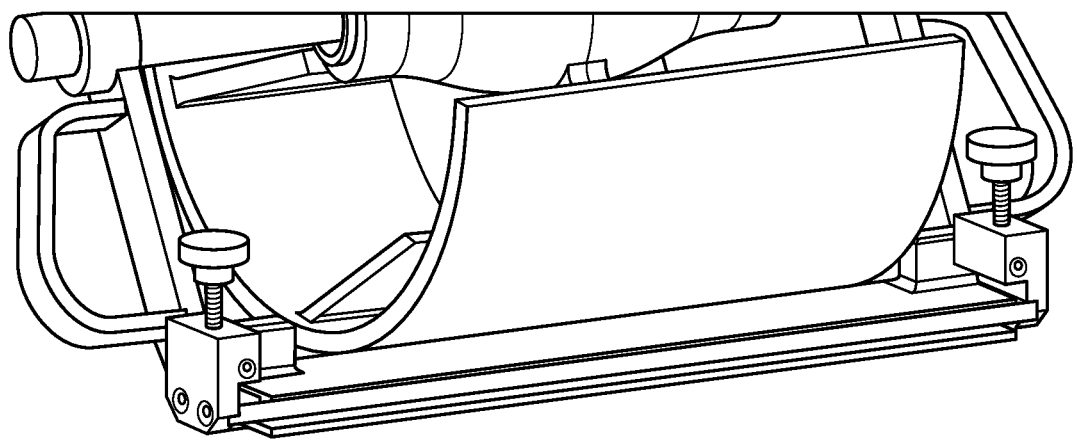
Adjustable Outrigger for Transection Blade
FIG. 194

Non-compressive Moreselizer

Millard Cleft Lip Repair
(Rotation Advancement)

Scalpets

PIXEL ARRAY MEDICAL SYSTEMS, DEVICES AND METHODS

RELATED APPLICATIONS

This application claims the benefit of U.S. Patent Application No. 62/685,961, filed Jun. 16, 2018.

This application claims the benefit of U.S. Patent Application No. 62/750,084, filed Oct. 24, 2018.

This application claims the benefit of U.S. Patent Application No. 62/800,830, filed Feb. 4, 2019.

This application is a continuation in part of U.S. patent application Ser. No. 15/585,679, filed May 3, 2017.

This application is a continuation in part of U.S. patent application Ser. No. 15/585,701, filed May 3, 2017.

This application is a continuation in part of U.S. patent application Ser. No. 15/585,732, filed May 3, 2017.

This application is a continuation in part of U.S. patent application Ser. No. 16/203,130, filed Nov. 28, 2018.

This application is a continuation in part of U.S. patent application Ser. No. 16/203,138, filed Nov. 28, 2018.

This application is a continuation in part of U.S. patent application Ser. No. 15/812,952, filed Nov. 14, 2017.

This application is a continuation in part of U.S. patent application Ser. No. 15/997,316, filed Jun. 4, 2018.

This application is a continuation in part of U.S. patent application Ser. No. 16/280,303, filed Feb. 20, 2019.

This application is a continuation in part of U.S. patent application Ser. No. 15/821,258, filed Nov. 22, 2017.

This application is a continuation in part of U.S. patent application Ser. No. 16/132,575, filed Sep. 17, 2018.

This application is a continuation in part of U.S. patent application Ser. No. 16/403,377, filed May 3, 2019.

This application is a continuation in part of U.S. patent application Ser. No. 15/821,325, filed Nov. 22, 2017.

This application is a continuation in part of U.S. patent application Ser. No. 14/840,274, filed Aug. 31, 2015.

This application is a continuation in part of U.S. patent application Ser. No. 14/840,284, filed Aug. 31, 2015.

This application is a continuation in part of U.S. patent application Ser. No. 14/840,267, filed Aug. 31, 2015.

This application is a continuation in part of U.S. patent application Ser. No. 14/840,290, filed Aug. 31, 2015.

This application is a continuation in part of U.S. patent application Ser. No. 16/378,336, filed Apr. 8, 2019.

This application is a continuation in part of U.S. patent application Ser. No. 15/016,954, filed Feb. 5, 2016.

This application is a continuation in part of U.S. patent application Ser. No. 15/017,007, filed Feb. 5, 2016.

This application is a continuation in part of U.S. patent application Ser. No. 15/431,230, filed Feb. 13, 2017.

This application is a continuation in part of U.S. patent application Ser. No. 15/431,247, filed Feb. 13, 2017.

This application is a continuation in part of U.S. patent application Ser. No. 15/890,046, filed Feb. 6, 2018.

This application is a continuation in part of U.S. patent application Ser. No. 15/890,052, filed Feb. 6, 2018.

This application is a continuation in part of U.S. patent application Ser. No. 15/890,064, filed Feb. 6, 2018.

This application is a continuation in part of U.S. patent application Ser. No. 15/890,068, filed Feb. 6, 2018.

This application is a continuation in part of U.S. patent application Ser. No. 15/890,074, filed Feb. 6, 2018.

This application is a continuation in part of U.S. patent application Ser. No. 15/977,741, filed May 11, 2018.

This application is a continuation in part of U.S. patent application Ser. No. 15/977,865, filed May 11, 2018.

This application is a continuation in part of U.S. patent application Ser. No. 15/977,882, filed May 11, 2018.

This application is a continuation in part of U.S. patent application Ser. No. 15/977,912, filed May 11, 2018.

This application is a continuation in part of U.S. patent application Ser. No. 15/977,934, filed May 11, 2018.

This application is a continuation in part of U.S. patent application Ser. No. 15/977,958, filed May 11, 2018.

TECHNICAL FIELD

The embodiments herein relate to medical systems, instruments or devices, and methods and, more particularly, to medical instrumentation and methods applied to the surgical management of burns, skin defects, and hair transplantation.

BACKGROUND

The aging process is most visibly depicted by the development of dependent skin laxity. This life long process may become evident as early as the third decade of life and will progressively worsen over subsequent decades. Histological research has shown that dependant stretching or age related laxity of the skin is due in part to progressive dermal atrophy associated with a reduction of skin tensile strength. When combined with the downward force of gravity, age related dermal atrophy will result in the two dimensional expansion of the skin envelope. The clinical manifestation of this physical-histological process is redundant skin laxity. The most affected areas are the head and neck, upper arms, thighs, breasts, lower abdomen and knee regions. The most visible of all areas are the head and neck. In this region, prominent "turkey gobbler" laxity of neck and "jowls" of the lower face are due to an unaesthetic dependency of skin in these areas.

Plastic surgery procedures have been developed to resect the redundant lax skin. These procedures must employ long incisions that are typically hidden around anatomical boundaries such as the ear and scalp for a facelift and the inframammary fold for a breast uplift (mastopexy). However, some areas of skin laxity resection are a poor tradeoff between the aesthetic enhancement of tighter skin and the visibility of the surgical incision. For this reason, skin redundancies of the upper arm, suprapatellar knees, thighs and buttocks are not routinely resected due to the visibility of the surgical scar.

The frequency and negative societal impact of this aesthetic deformity has prompted the development of the "Face Lift" surgical procedure. Other related plastic surgical procedures in different regions are the Abdominoplasty (Abdomen), the Mastopexy (Breasts), and the Brachioplasty (Upper Arms). Inherent adverse features of these surgical procedures are post-operative pain, scarring and the risk of surgical complications. Even though the aesthetic enhancement of these procedures is an acceptable tradeoff to the significant surgical incisions required, extensive permanent scarring is always an incumbent part of these procedures. For this reason, plastic surgeons design these procedures to hide the extensive scarring around anatomical borders such as the hairline (Facelift), the inframmary fold (Mastopexy), and the inguinal crease (Abdominoplasty). However, many of these incisions are hidden distant to the region of skin laxity, thereby limiting their effectiveness. Other skin laxity regions such as the Suprapatellar (upper-front) knee are not amendable to plastic surgical resections due to the poor tradeoff with a more visible surgical scar.

More recently, electromagnetic medical devices that create a reverse thermal gradient (i.e., Thermage) have attempted with variable success to tighten skin without surgery. At this time, these electromagnetic devices are best deployed in patients with a moderate amount of skin laxity. Because of the limitations of electromagnetic devices and potential side effects of surgery, a minimally invasive technology is needed to circumvent surgically related scarring and the clinical variability of electromagnetic heating of the skin. For many patients who have age related skin laxity (neck and face, arms, axillas, thighs, knees, buttocks, abdomen, bra line, ptosis of the breast), fractional resection of excess skin could augment a significant segment of traditional plastic surgery.

Even more significant than aesthetic modification of the skin envelope is the surgical management of burns and other trauma related skin defects. Significant burns are classified by the total body surface burned and by the depth of thermal destruction. First-degree and second-degree burns are generally managed in a non-surgical fashion with the application of topical creams and burn dressings. Deeper third-degree burns involve the full thickness thermal destruction of the skin. The surgical management of these serious injuries involves the debridement of the burn eschar and the application of split thickness grafts.

Any full thickness skin defect, most frequently created from burning, trauma, or the resection of a skin malignancy, can be closed with either skin flap transfers or skin grafts using current commercial instrumentation. Both surgical approaches require harvesting from a donor site. The use of a skin flap is further limited by the need of to include a pedicle blood supply and in most cases by the need to directly close the donor site.

The split thickness skin graft procedure, due to immunological constraints, requires the harvesting of autologous skin grafts, that is, from the same patient. Typically, the donor site on the burn patient is chosen in a non-burned area and a partial thickness sheet of skin is harvested from that area. Incumbent upon this procedure is the creation of a partial thickness skin defect at the donor site. This donor site defect is itself similar to a deep second-degree burn. Healing by re-epithelialization of this site is often painful and may be prolonged for several days. In addition, a visible donor site deformity is created that is permanently thinner and more de-pigmented than the surrounding skin. For patients who have burns over a significant surface area, the extensive harvesting of skin grafts may also be limited by the availability of non-burned areas.

For these reasons, there is a need in the rapidly expanding aesthetic market for instrumentation and procedures for aesthetic surgical skin tightening. There is also a need for systems, instruments or devices, and procedures that enable the repeated harvesting of skin grafts from the same donor site while eliminating donor site deformity.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE DRAWINGS

FIG. 1311 is a back view of the drum dermatome along with the scalpet plate, under an embodiment.

FIG. 27 shows harvesting of donor follicles, under an embodiment.

FIG. 28 shows preparation of the recipient site, under an embodiment.

FIG. 55 shows the helical scalpet array with the push plate, under an embodiment.

FIG. 57 shows the helical scalpet array with the drive plate, under an embodiment.

FIG. 93 depicts directed closure of a fractionally resected field, under an embodiment.

FIG. 95 depicts shortening of incisions through continuity fractional procedures, under an embodiment.

FIG. 96 is an example depiction of "dog ear" skin redundancies in breast reduction and abdominoplasty.

FIG. 97 is a sPAD including a skived single scalpet with depth control, under an embodiment.

FIG. 98 is a sPAD including a standard single scalpet, under an embodiment.

FIG. 99 is a sPAD including a pencil-style gear reducing handpiece, under an embodiment.

FIG. 100 is a sPAD including a 3×3 centerless array, under an embodiment.

FIG. 101 is a sPAD including a cordless surgical drill for large arrays, under an embodiment.

FIG. 102 is a sPAD comprising a drill mounted 5×5 centerless array, under an embodiment.

FIG. 103 is a sPAD including a vacuum assisted pneumatic resection sPAD, under an embodiment.

FIG. 104 is a VAPR sPAD coupled to a drill via a DAC, under an embodiment.

FIG. 105 depicts the VAPR sPAD in a ready state (left), and an extended treatment state (right), under an embodiment.

FIG. 106 depicts the SAVR sPAD in a ready state (left), and a retracted state (right), under an embodiment.

FIG. 107A is a cross-sectional side view of a carrier including a vacuum manifold, under an embodiment.

Figure 107A:
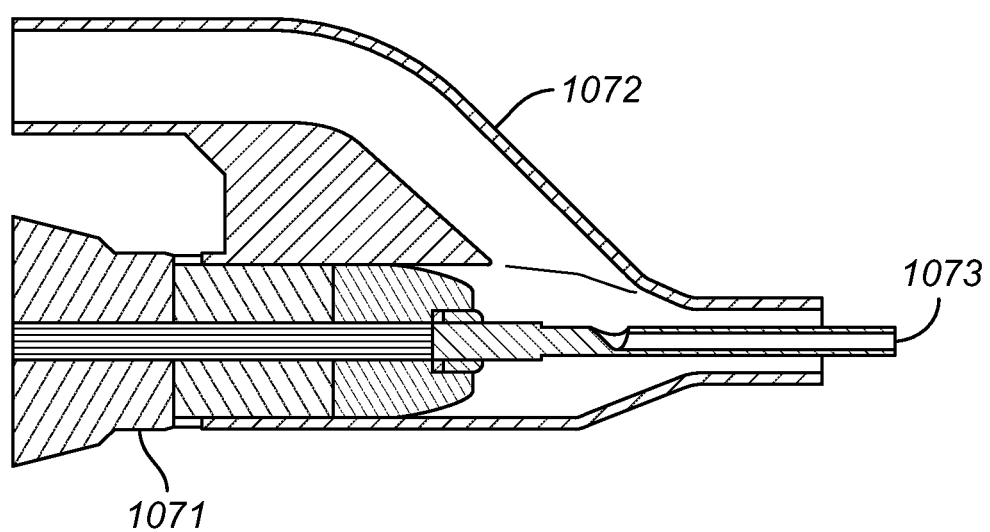
Figure 107B:
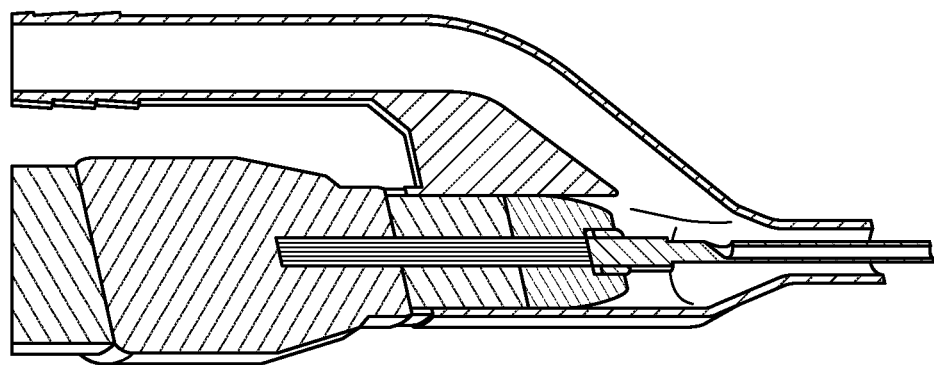

FIG. 107B is an isometric cross-sectional side view of the carrier including the vacuum manifold, under an embodiment.

Figure 107C:
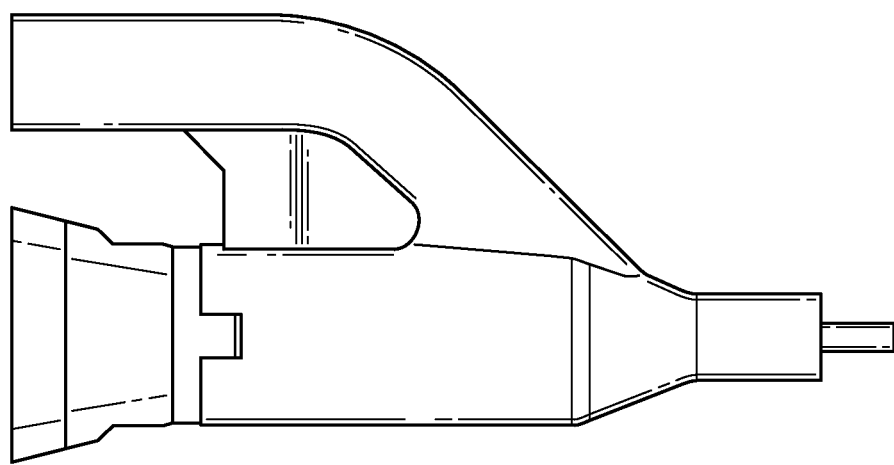

FIG. 107C is a side view of the carrier including the vacuum manifold, under an embodiment.

Figure 108:
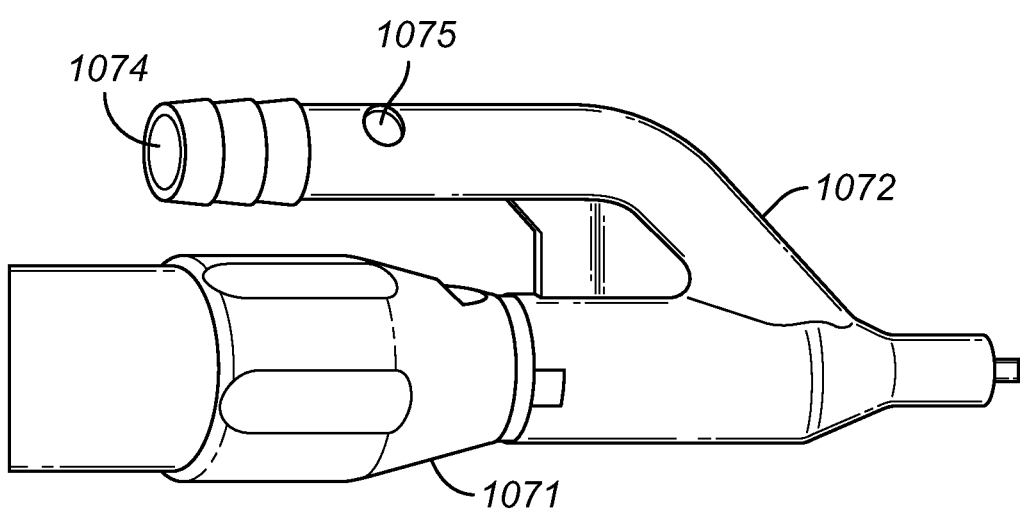

FIG. 108 is a solid side view of the carrier with the vacuum manifold configured for manual control via an aperture, under an embodiment.

Figure 109A:
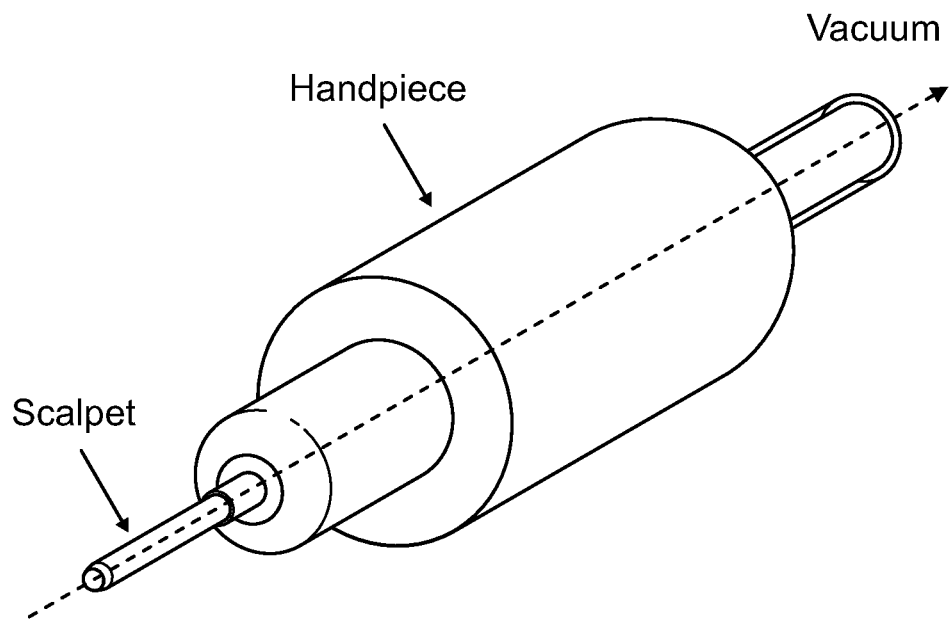

FIG. 109A is an isometric view of a handpiece configured to include or incorporate vacuum, under an embodiment.

Figure 109B:
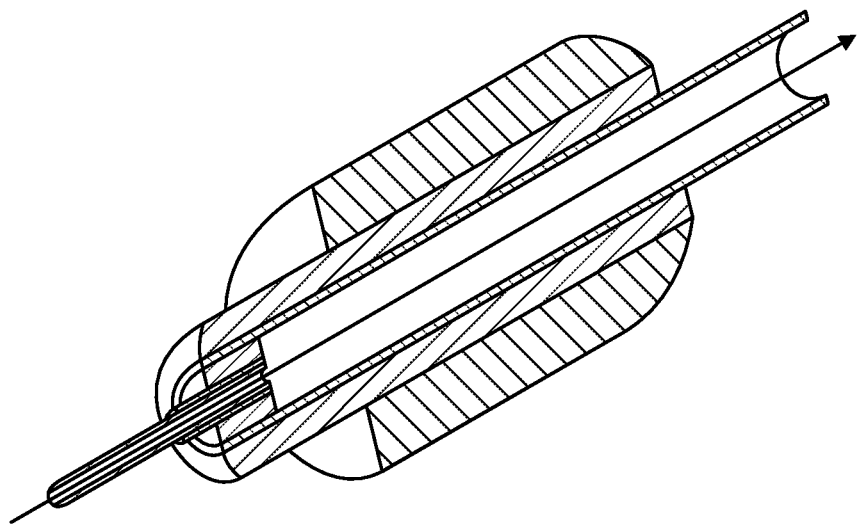

FIG. 109B is an isometric cutaway view of the handpiece configured to include or incorporate vacuum, under an embodiment.

Figure 110A:
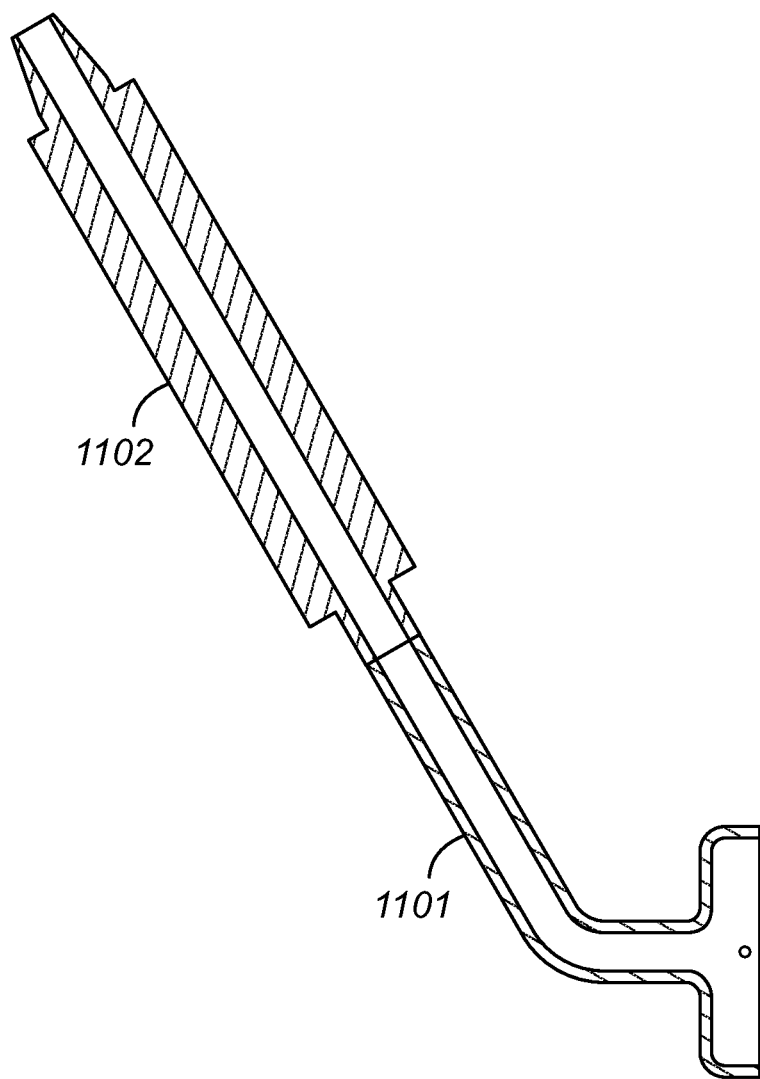

FIG. 110A is a cross-sectional side view of a vacuum manifold configured to be coupled or connected to an in-line vacuum component, under an embodiment.

Figure 110B:
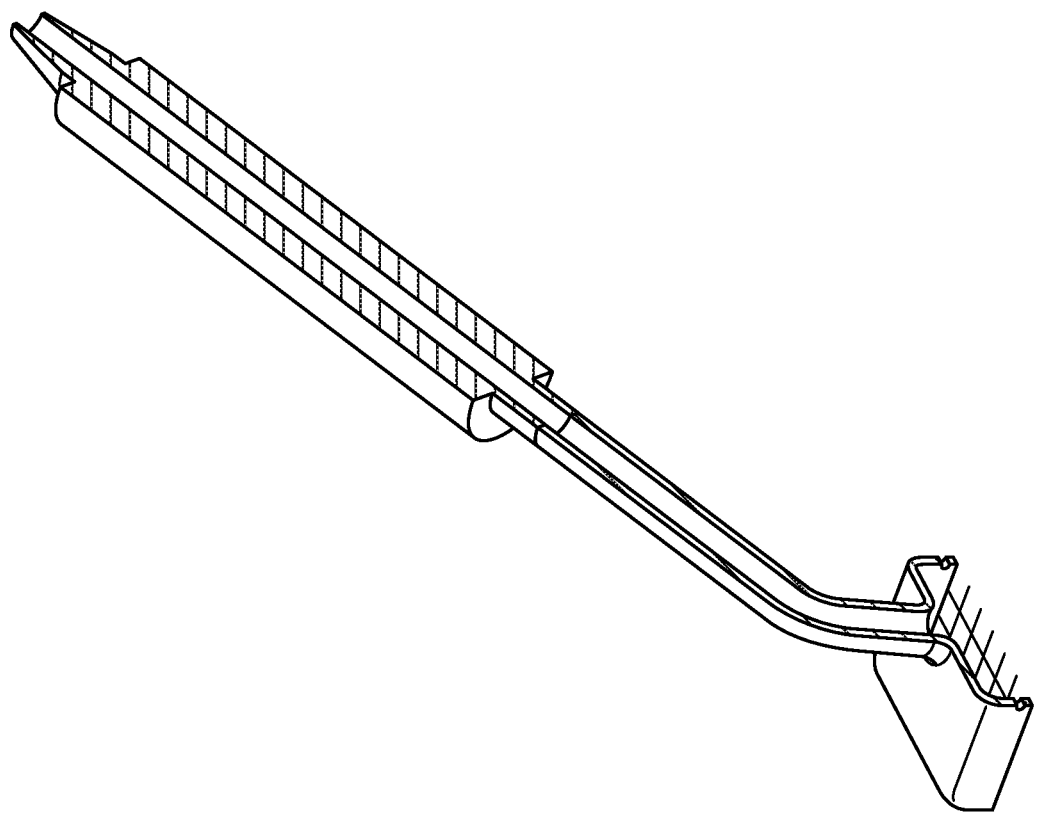

FIG. 110B is an isometric cross-sectional view of a vacuum manifold configured to be coupled or attached to an in-line vacuum component, under an embodiment.

Figure 110C:
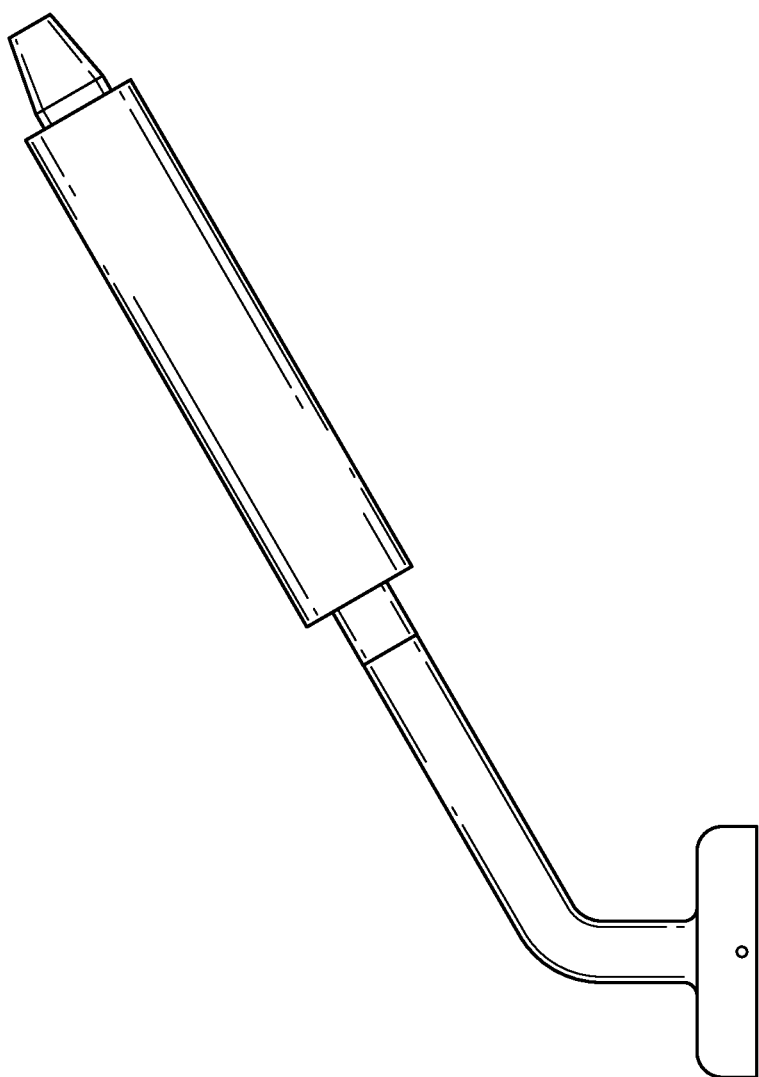

FIG. 110C is a solid side view of a vacuum manifold configured to be coupled or attached to an in-line vacuum component, under an embodiment.

Figure 111A:
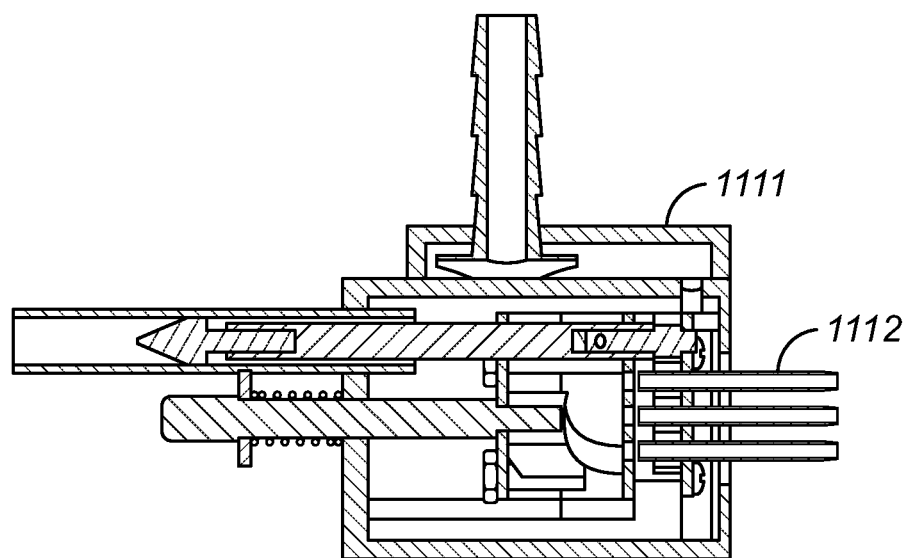

FIG. 111A is a cross-sectional side view of a scalpet array used with a vacuum aspirator, under an alternative embodiment.

Figure 111B:
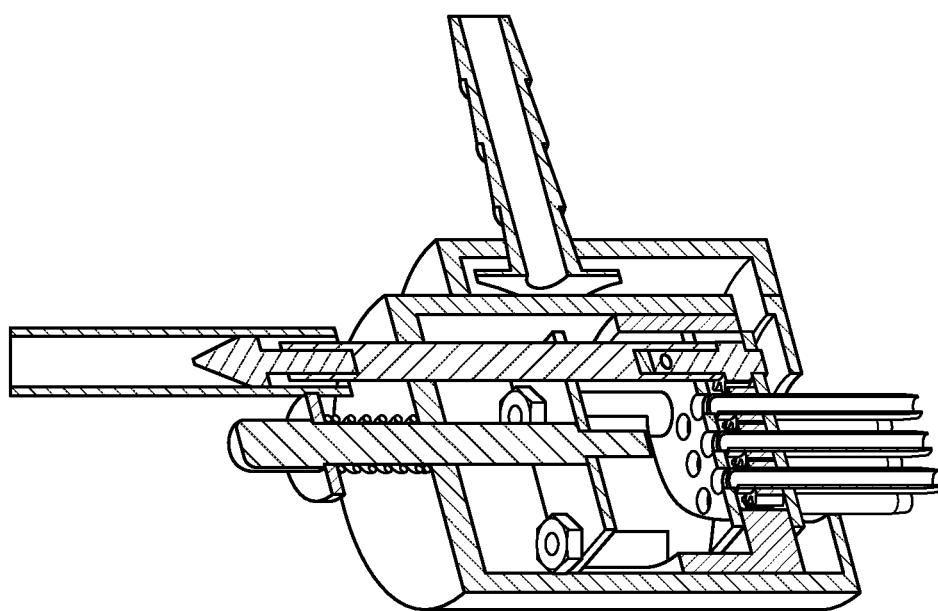

FIG. 111B is an isometric cross-sectional view of a scalpet array used with a vacuum aspirator, under an embodiment.

Figure 111C:
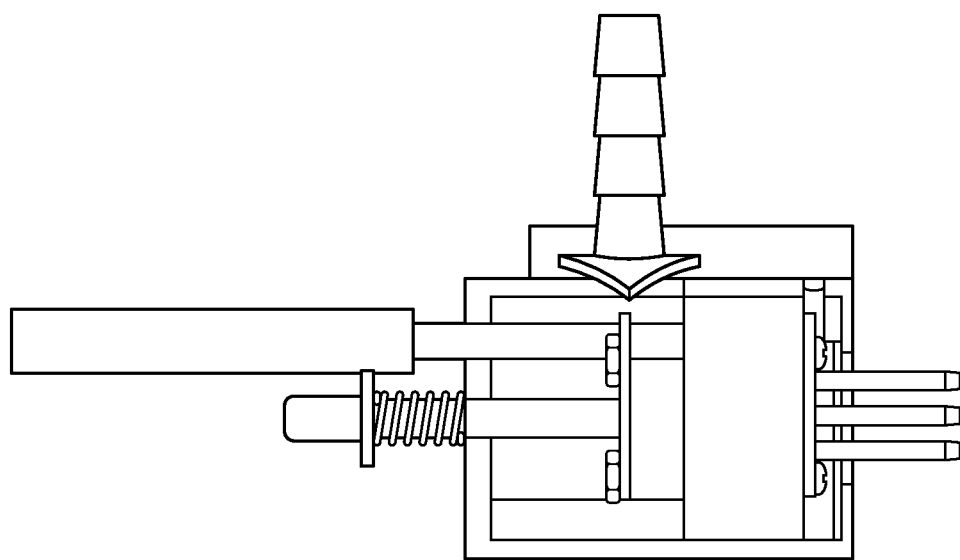

FIG. 111C is a side view of a scalpet array used with a vacuum aspirator, under an embodiment.

Figure 112:
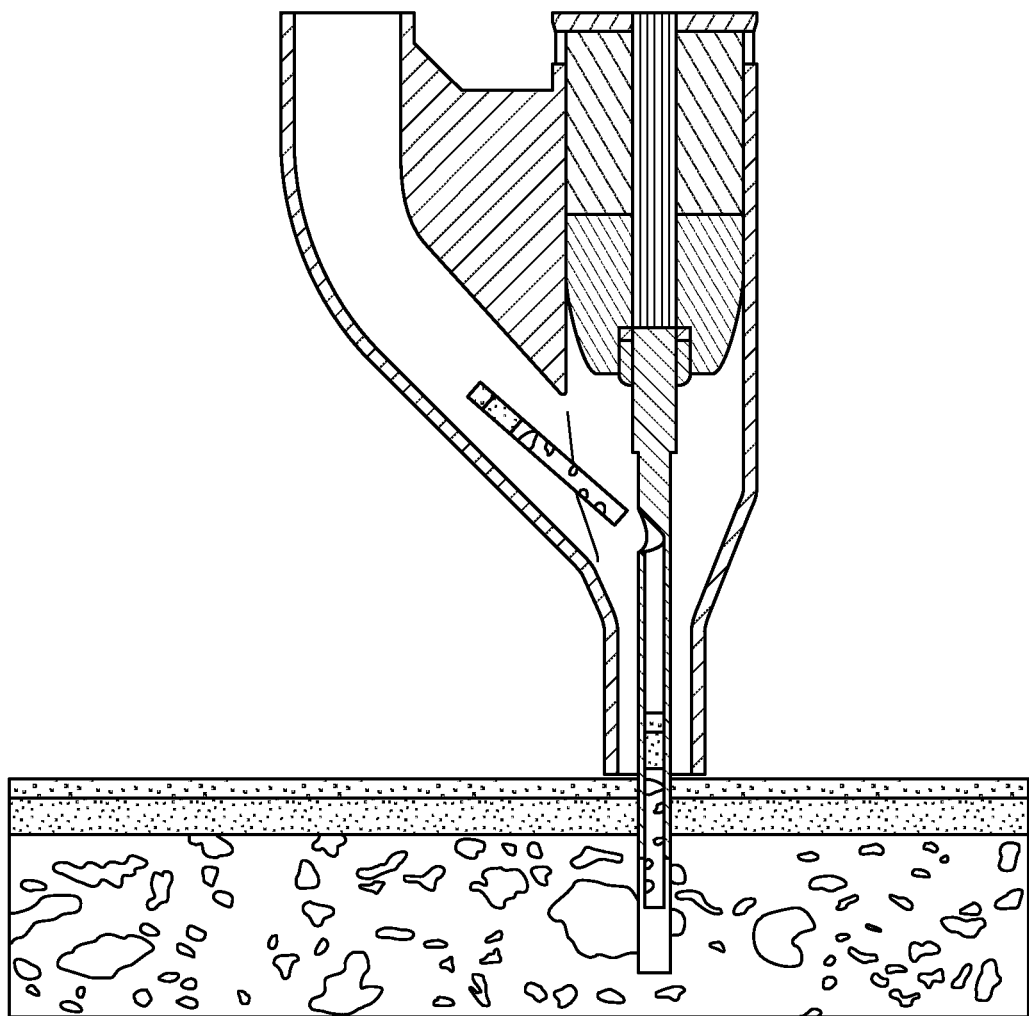

FIG. 112 is a cross-sectional side view of a single-scalpet device applied to a target tissue site, under an embodiment.

Figure 113:
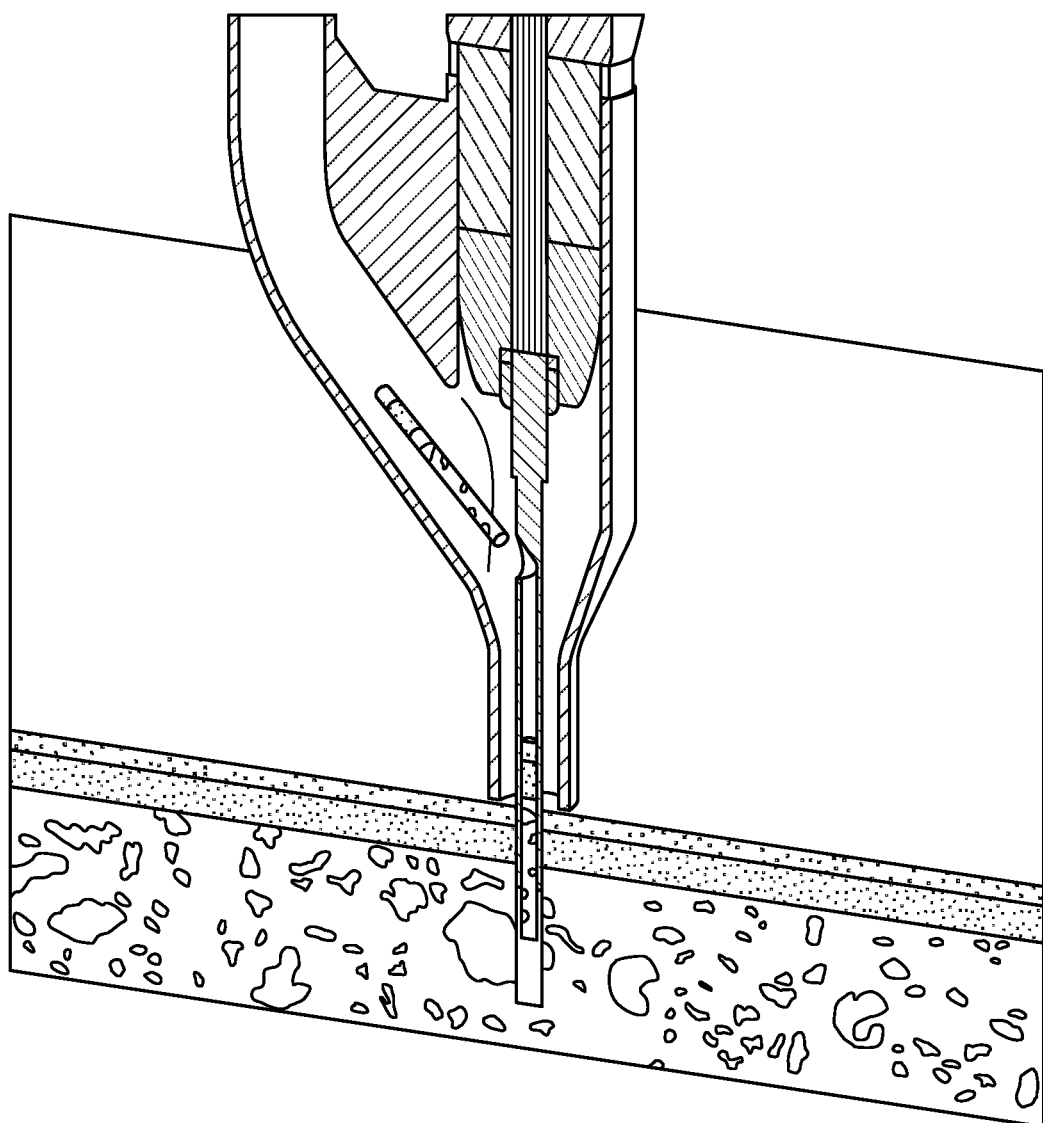

FIG. 113 is an isometric cross-sectional view of a single-scalpet device applied to a target tissue site, under an embodiment.

Figure 114A:
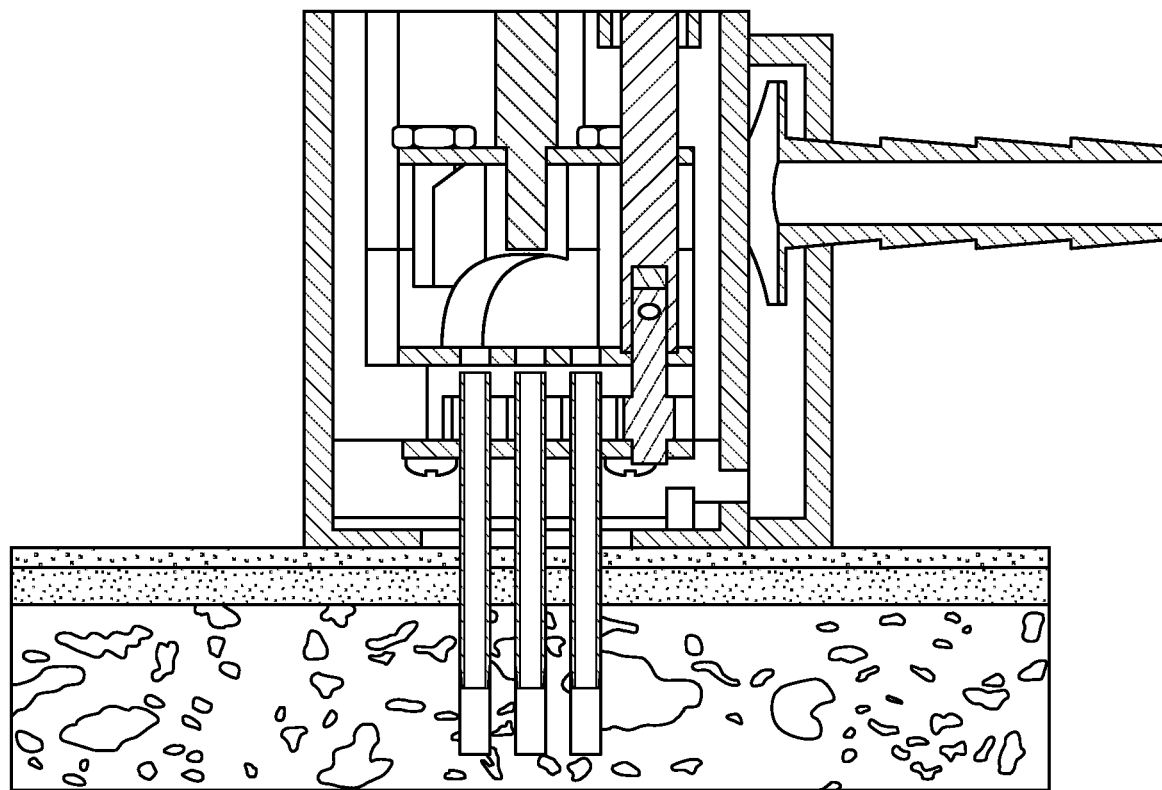

FIG. 114A is a cross-sectional side view of a multi-scalpet device applied to a target tissue site, under an embodiment.

Figure 114B:
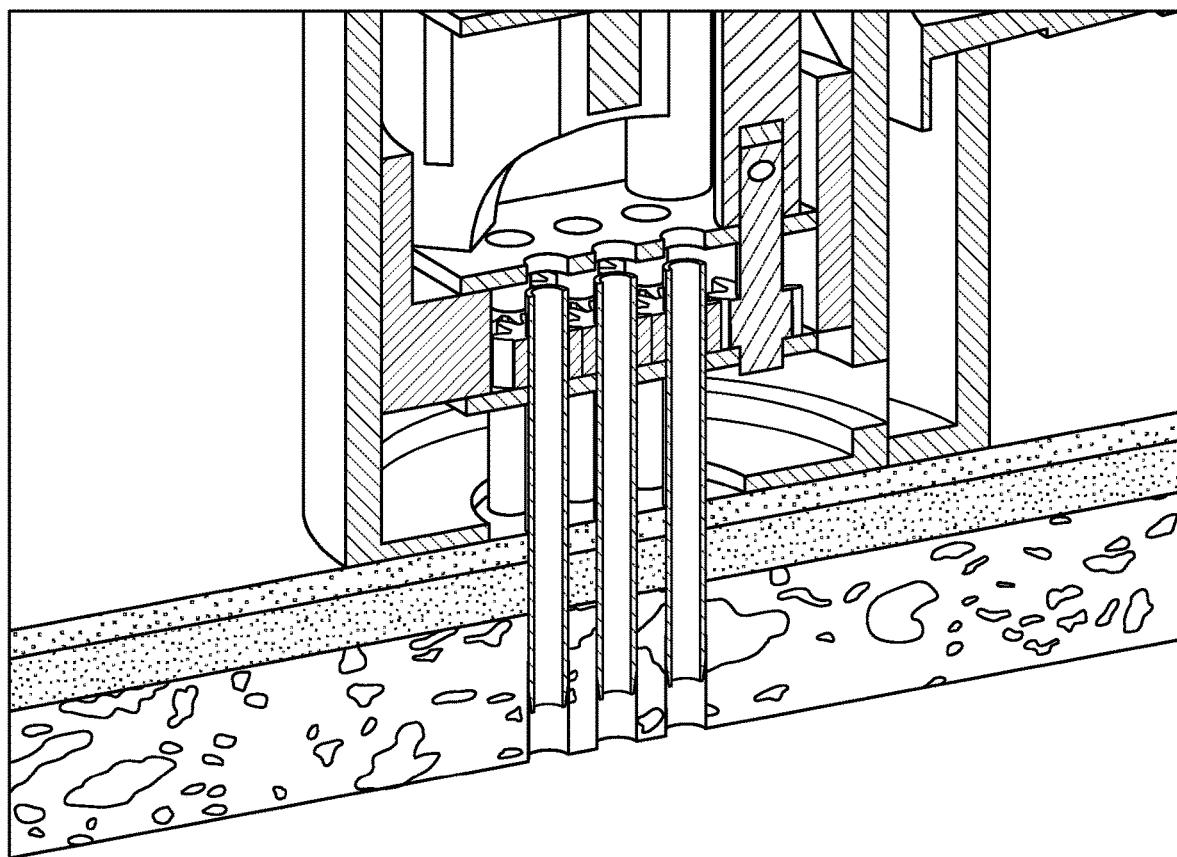

FIG. 114B is an isometric cross-sectional view of a multi-scalpet device applied to a target tissue site, under an embodiment.

Figure 115:
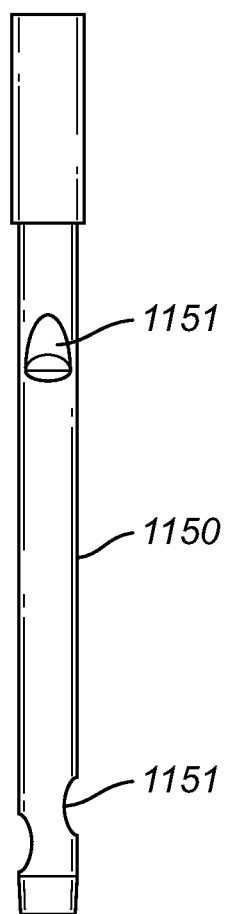

FIG. 115 is an example scalpet including apertures or slots, under an embodiment.

Figure 116:
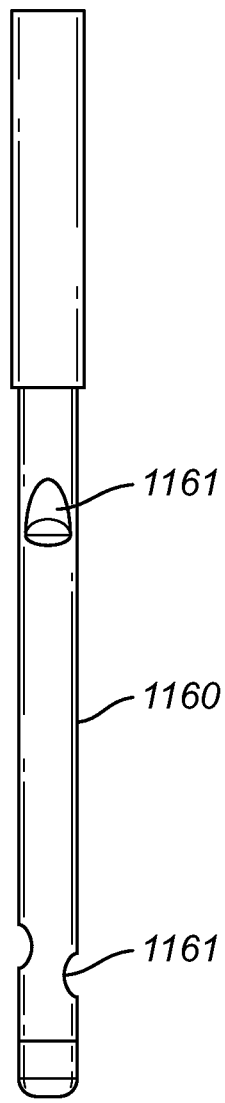

FIG. 116 is an example blunt micro-tip scalpet or cannula including apertures or slots, under an embodiment.

Figure 117:
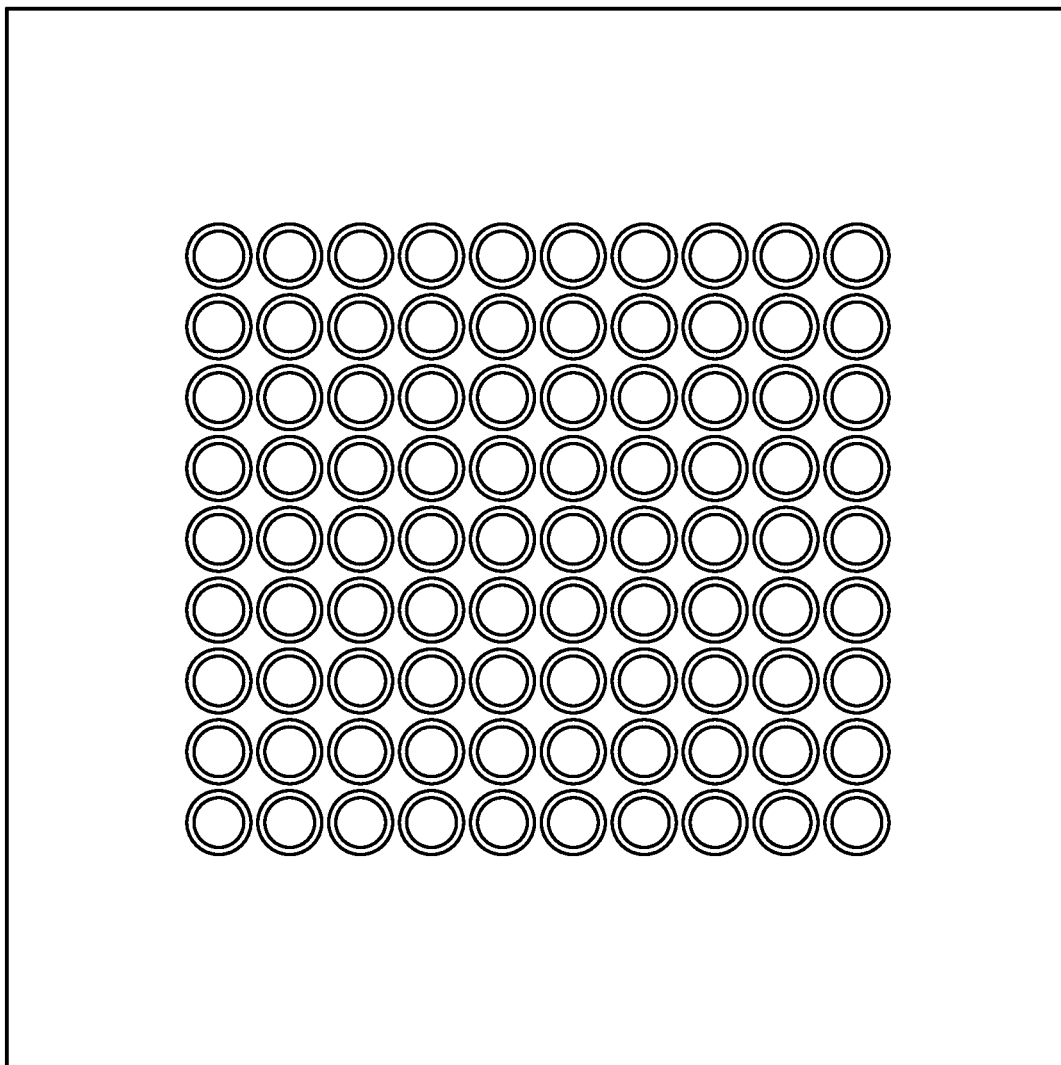

FIG. 117 is an example negative stencil marking system, under an embodiment.

Figure 118:
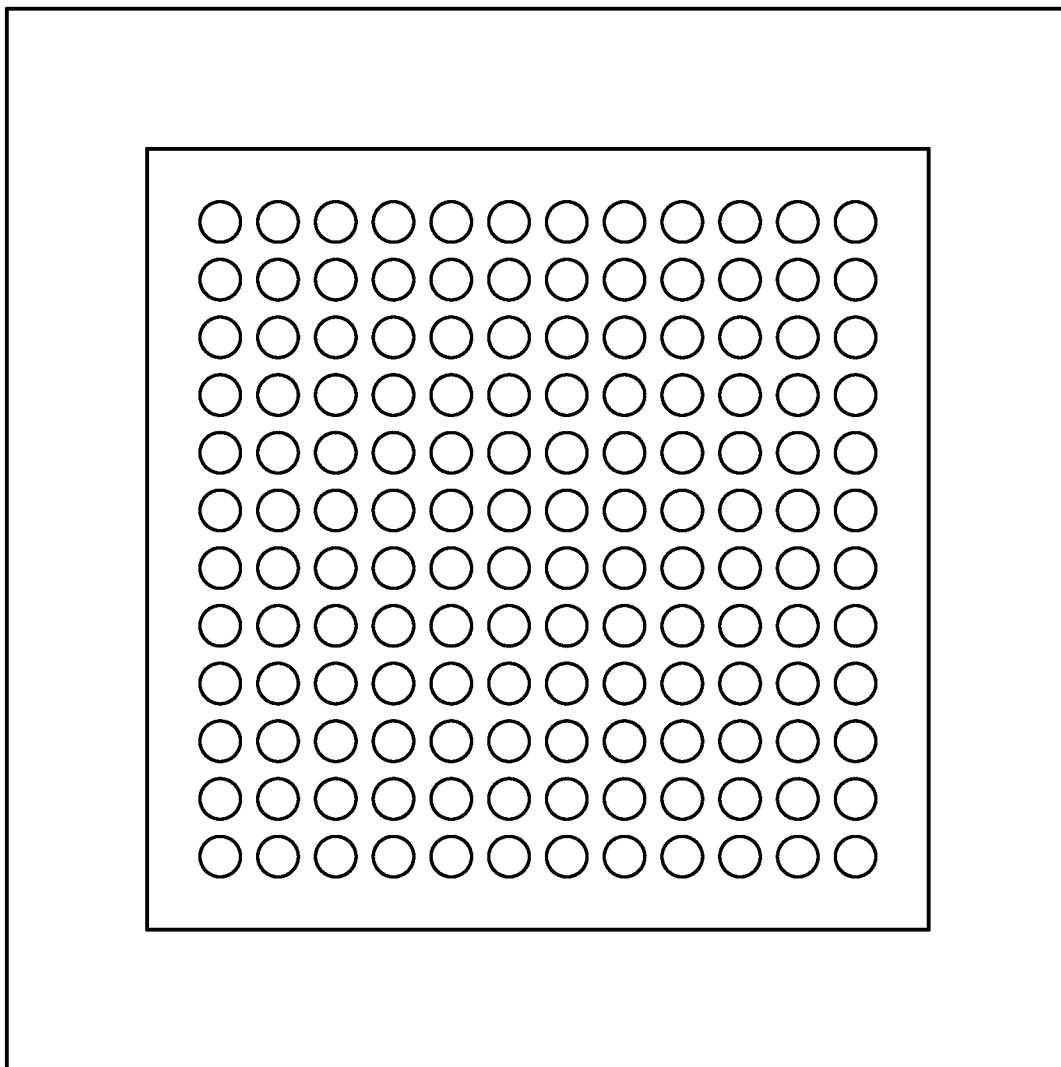

FIG. 118 is an example positive stencil marking system, under an embodiment.

Figure 119A:
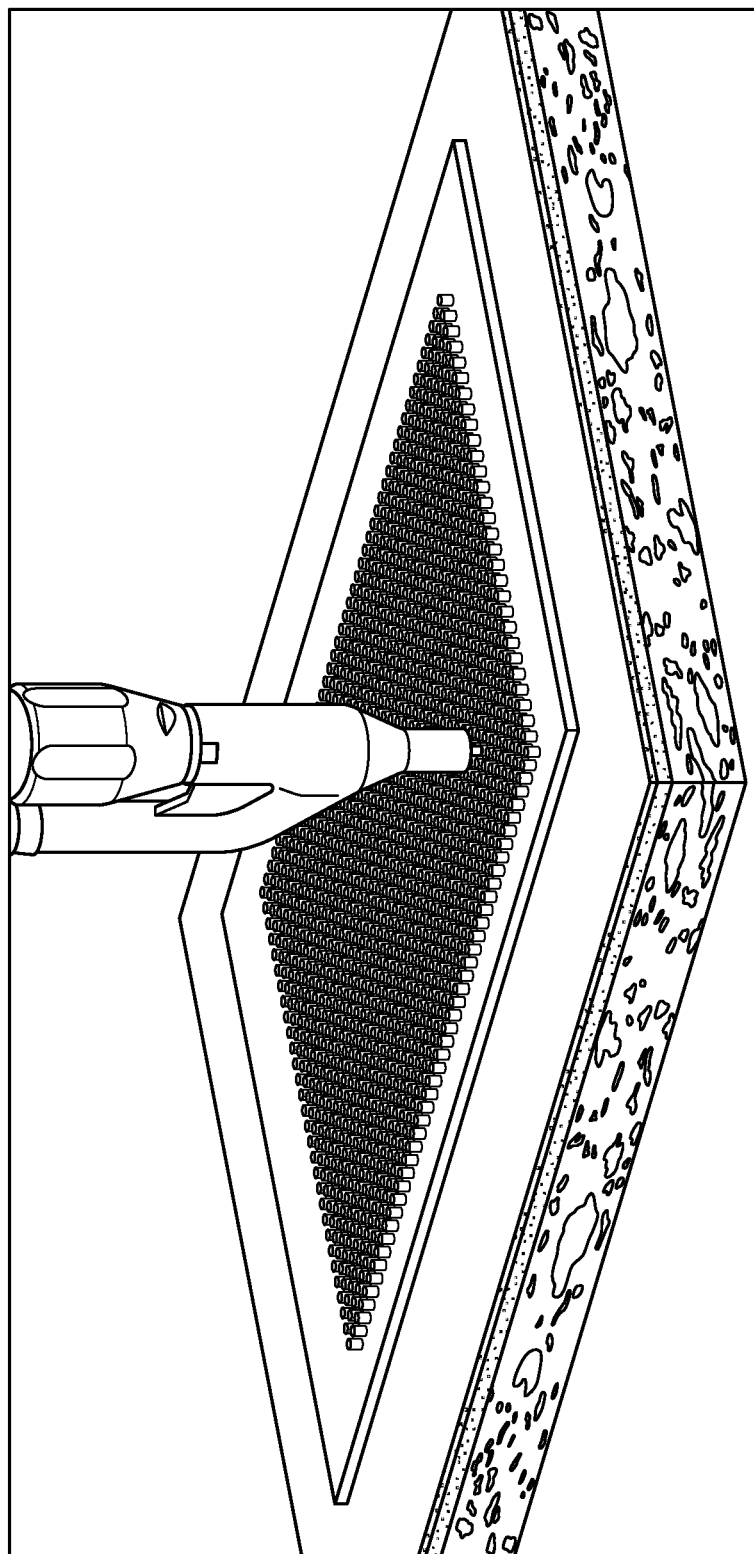

FIG. 119A shows a side view of the ASPPMP in use as a depth guide with the single-scalpet device, under an embodiment.

Figure 119B:
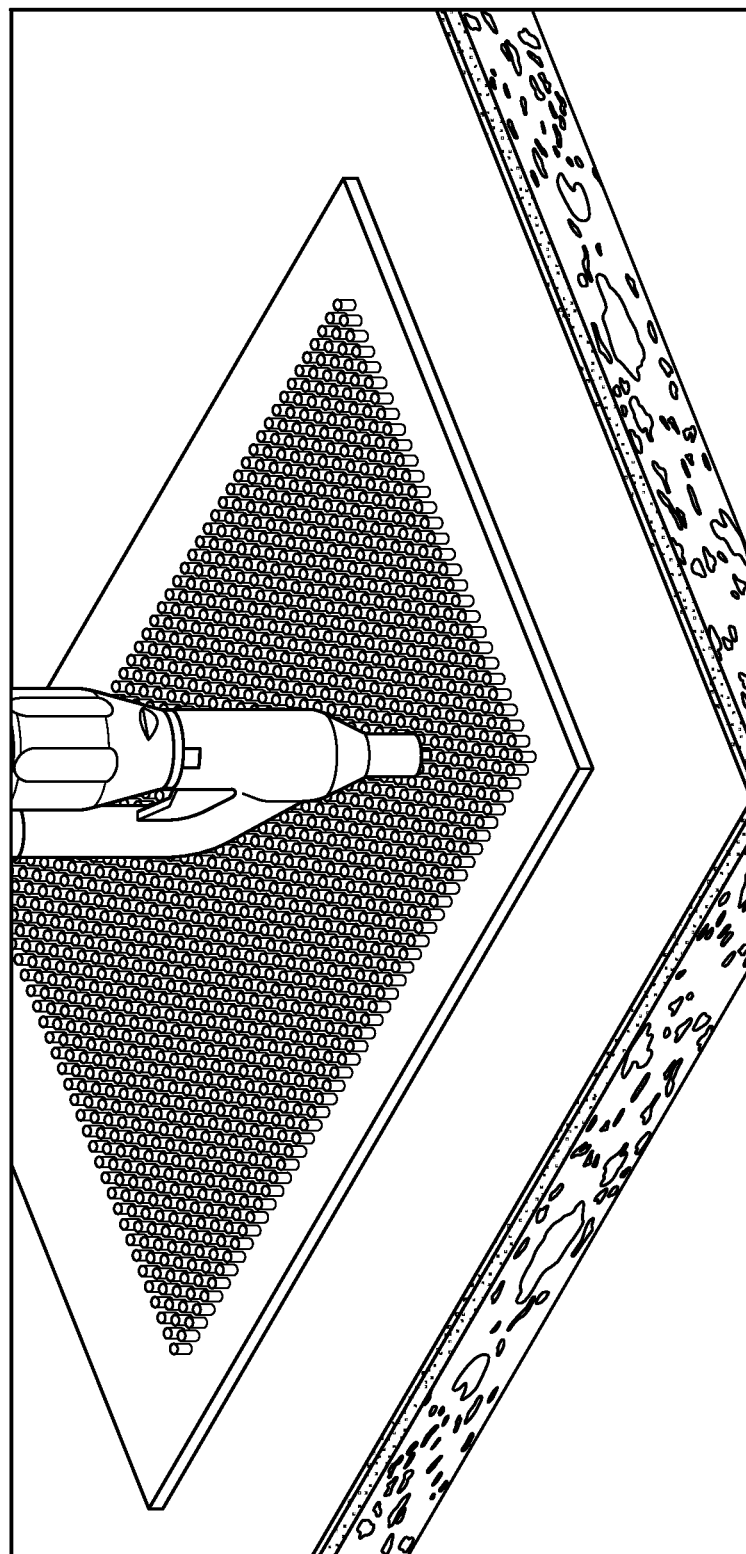

FIG. 119B shows a top isometric view of the ASPPMP in use as a depth guide with the single-scalpet device, under an embodiment.

Figure 120:
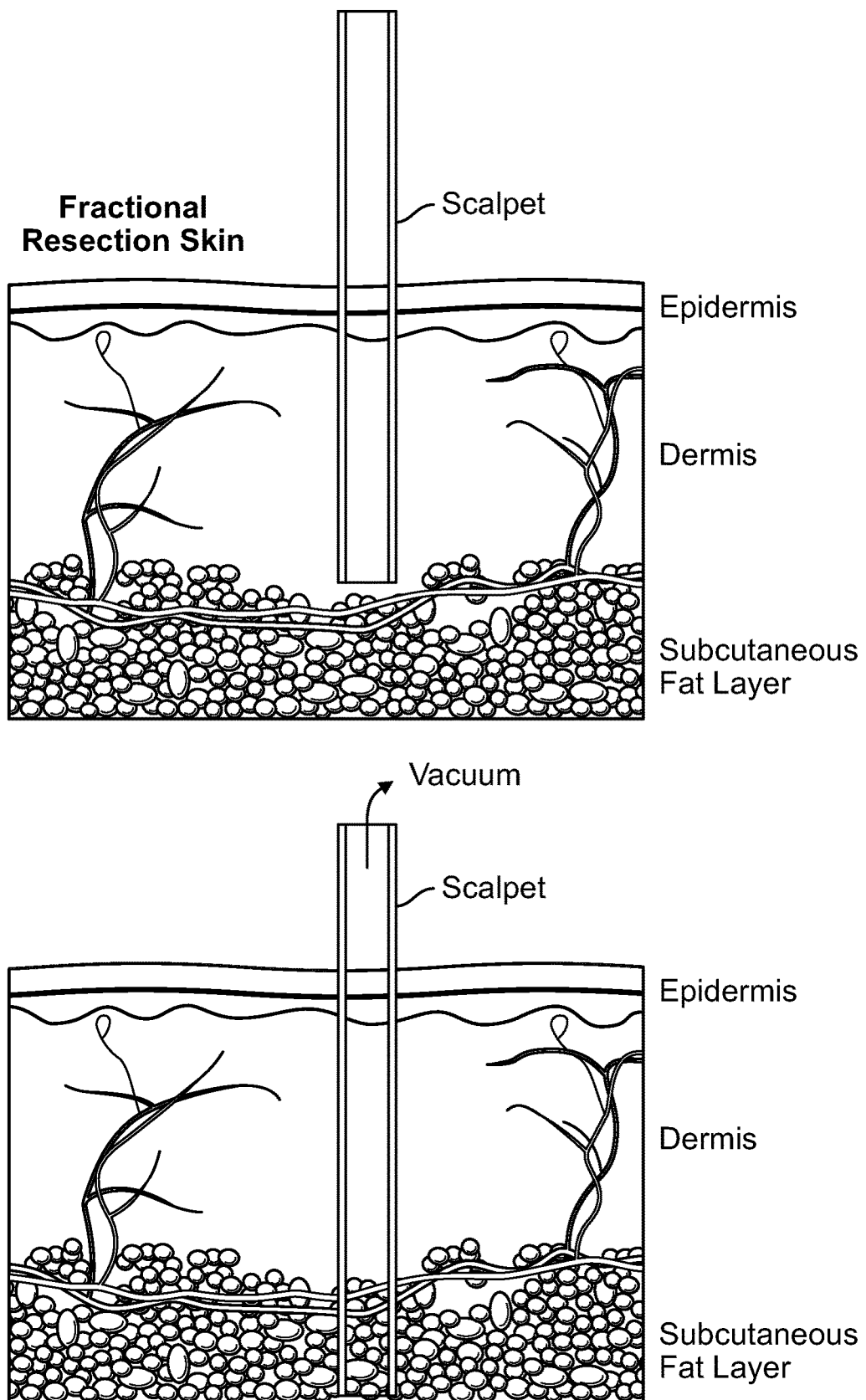

FIG. 120 shows fractional resection of skin and fractional subdermal/subcutaneous lipectomy, under an embodiment.

Figure 121:
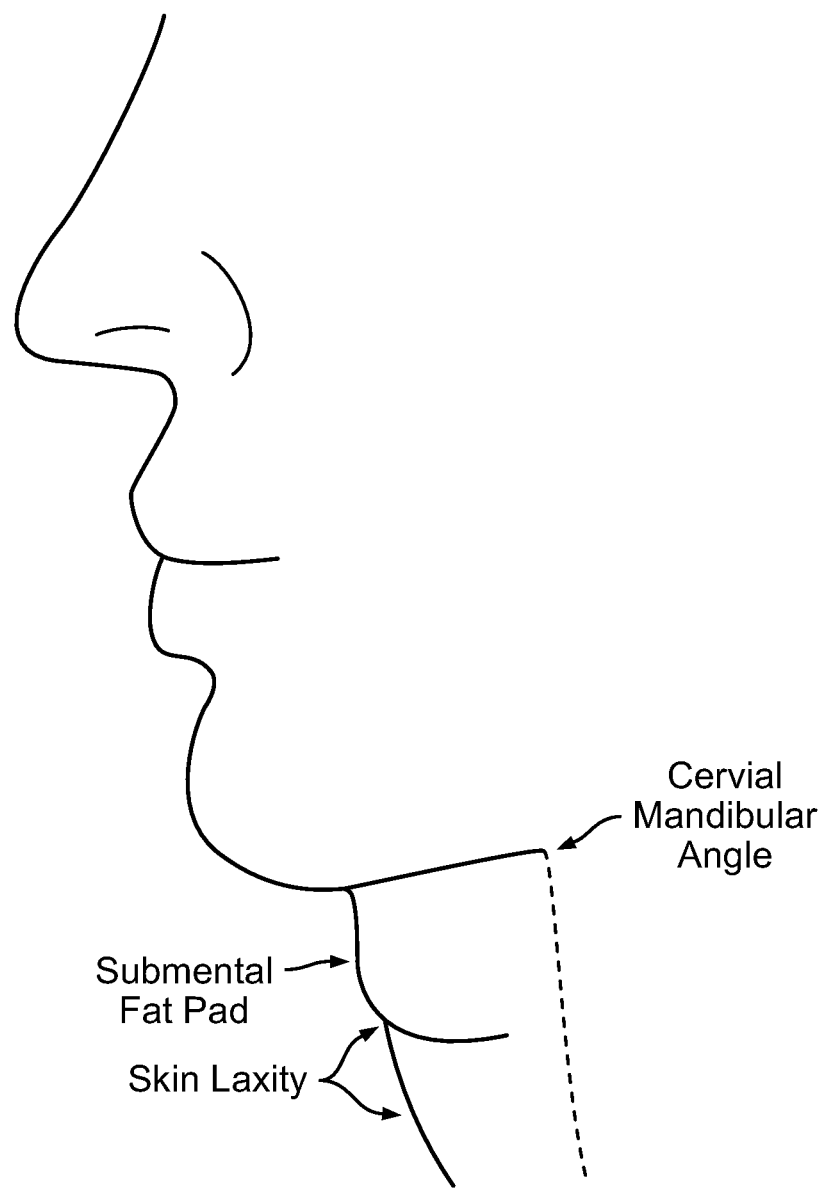

FIG. 121 shows a side view of the submentum as a target area for fractional resection of skin and fractional subdermal/subcutaneous lipectomy, under an embodiment.

Figure 122:
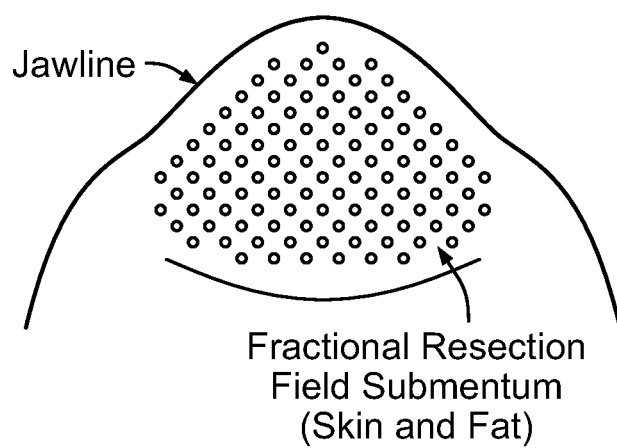

FIG. 122 shows an inferior view (looking upward) of the fractional resection field submentum as a target area for fractional resection of skin and fractional subdermal/subcutaneous lipectomy, under an embodiment.

Figure 123:
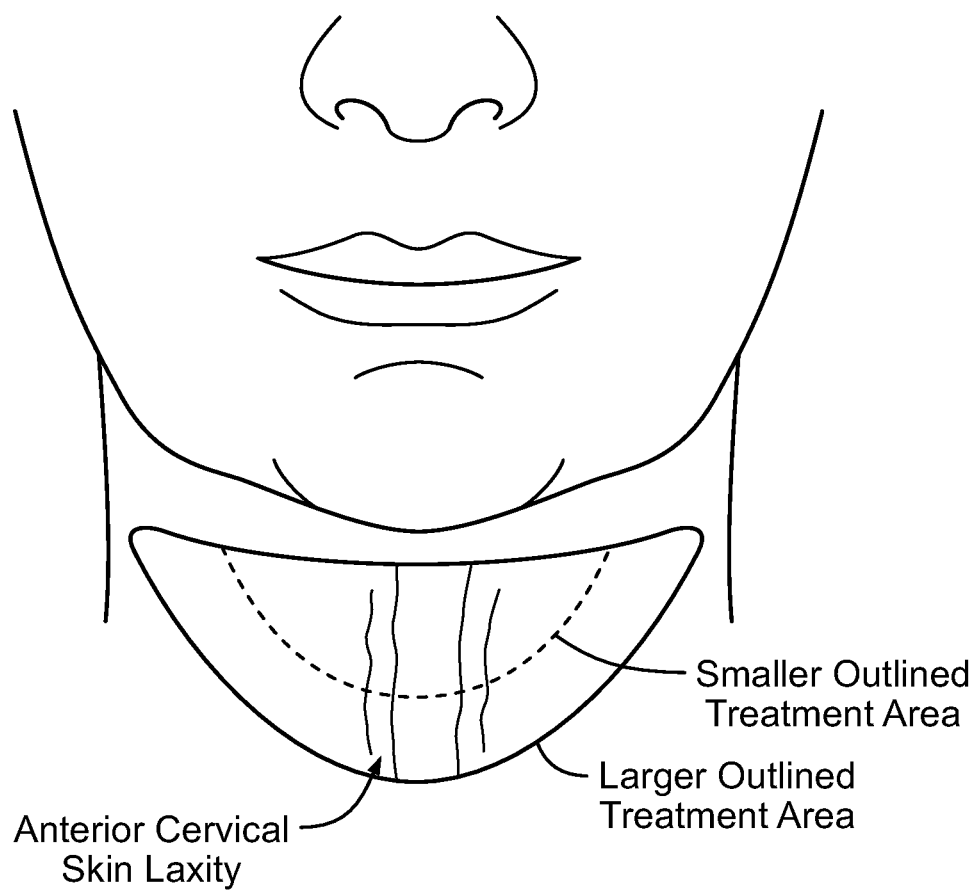

FIG. 123 shows a horizontally aligned treatment area in the submentum and lateral neck for severe skin laxity, under an embodiment.

Figure 124:
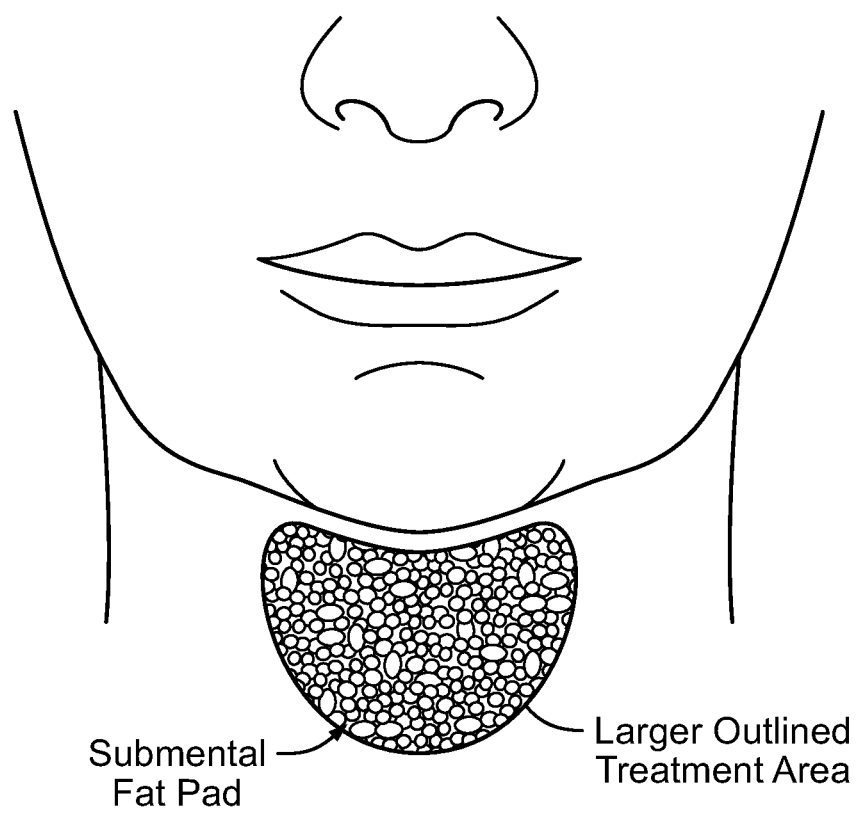

FIG. 124 shows broader fractional lipectomy in the submentum for severe lipodystrophy, under an embodiment.

Figure 125:
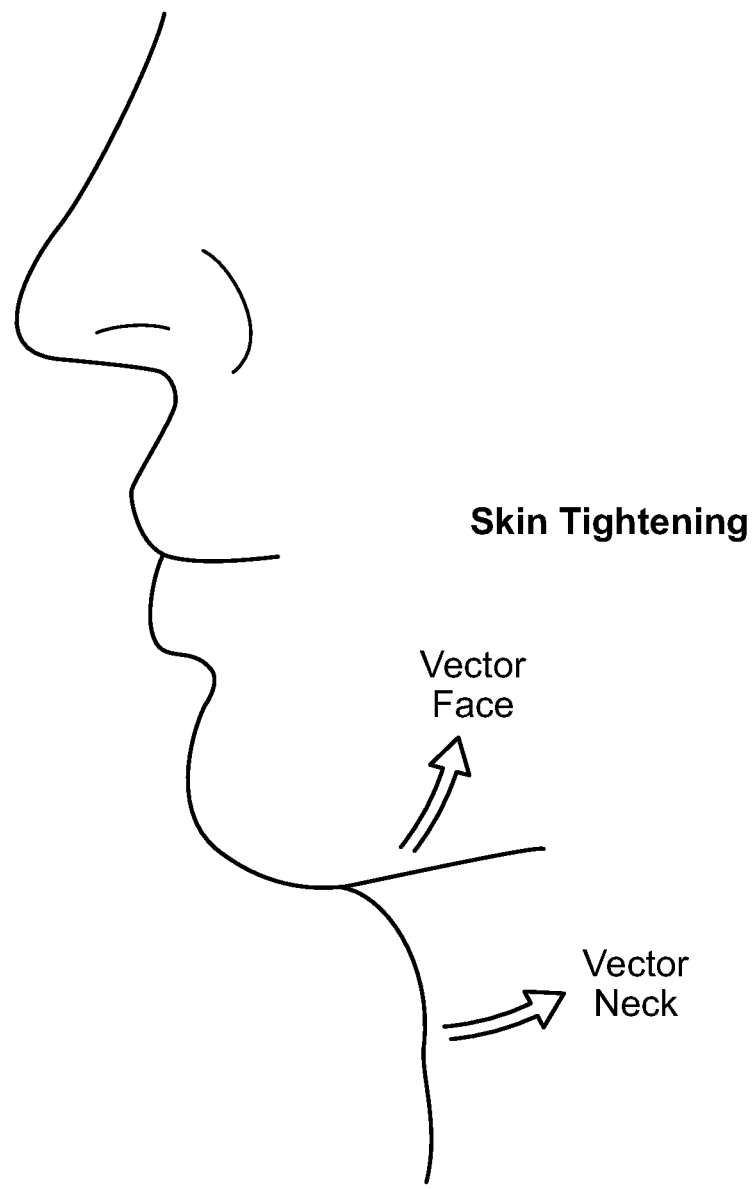

FIG. 125 shows example face vector and neck vector directed closures, under an embodiment.

Figure 126:
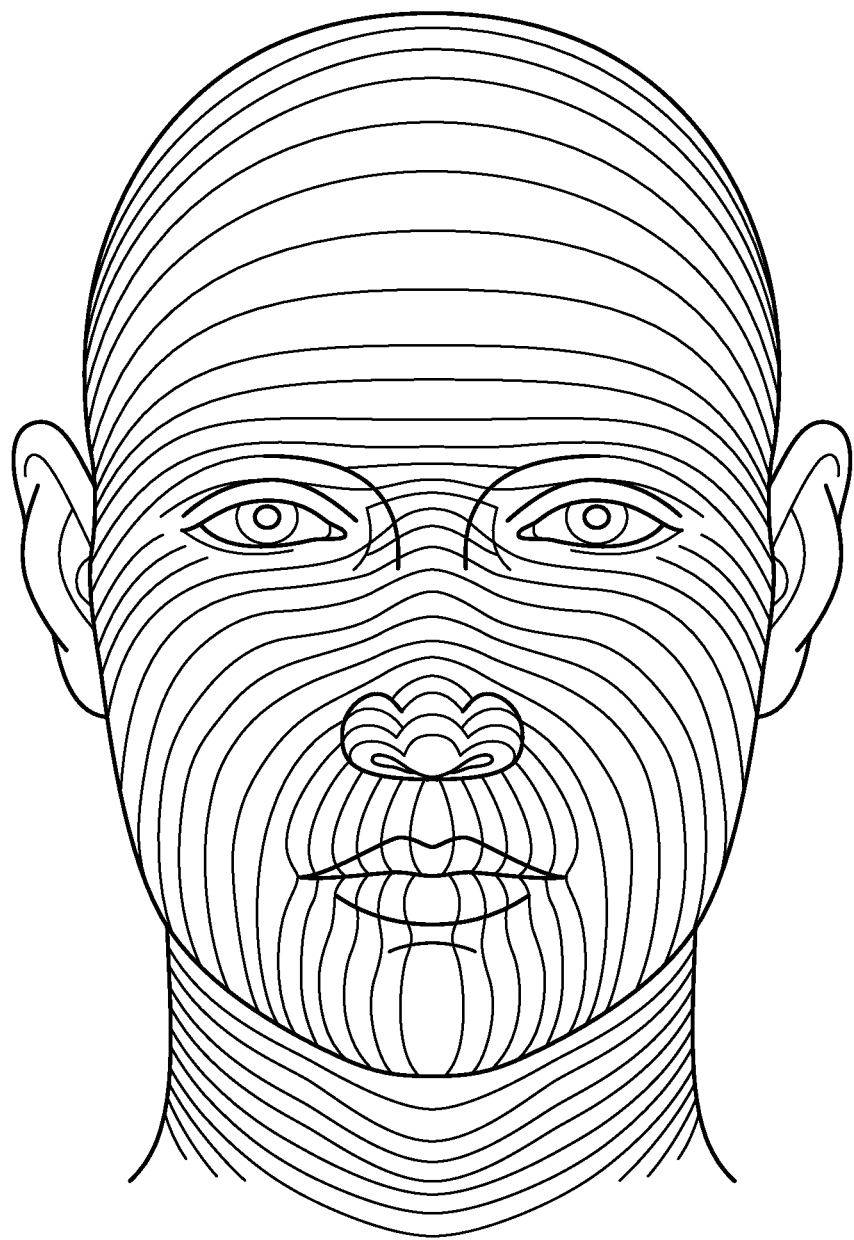

FIG. 126 shows Langer's lines of closure.

Figure 127:
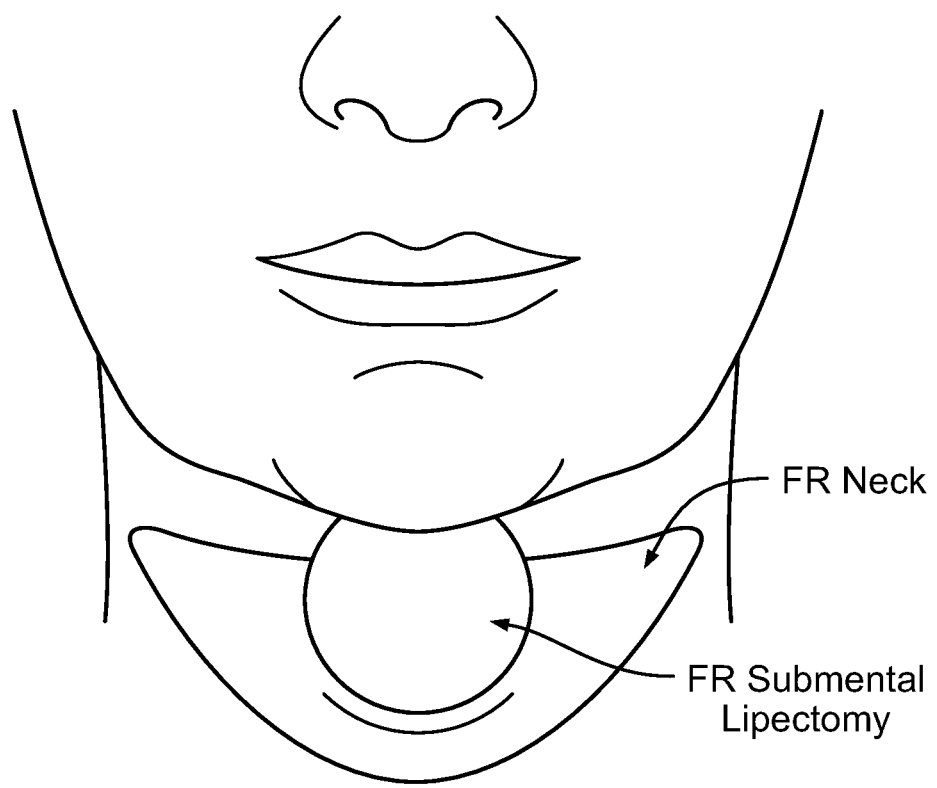

FIG. 127 shows marked target areas for fractional resection of neck and submental lipectomy, under an embodiment.

Figure 128:
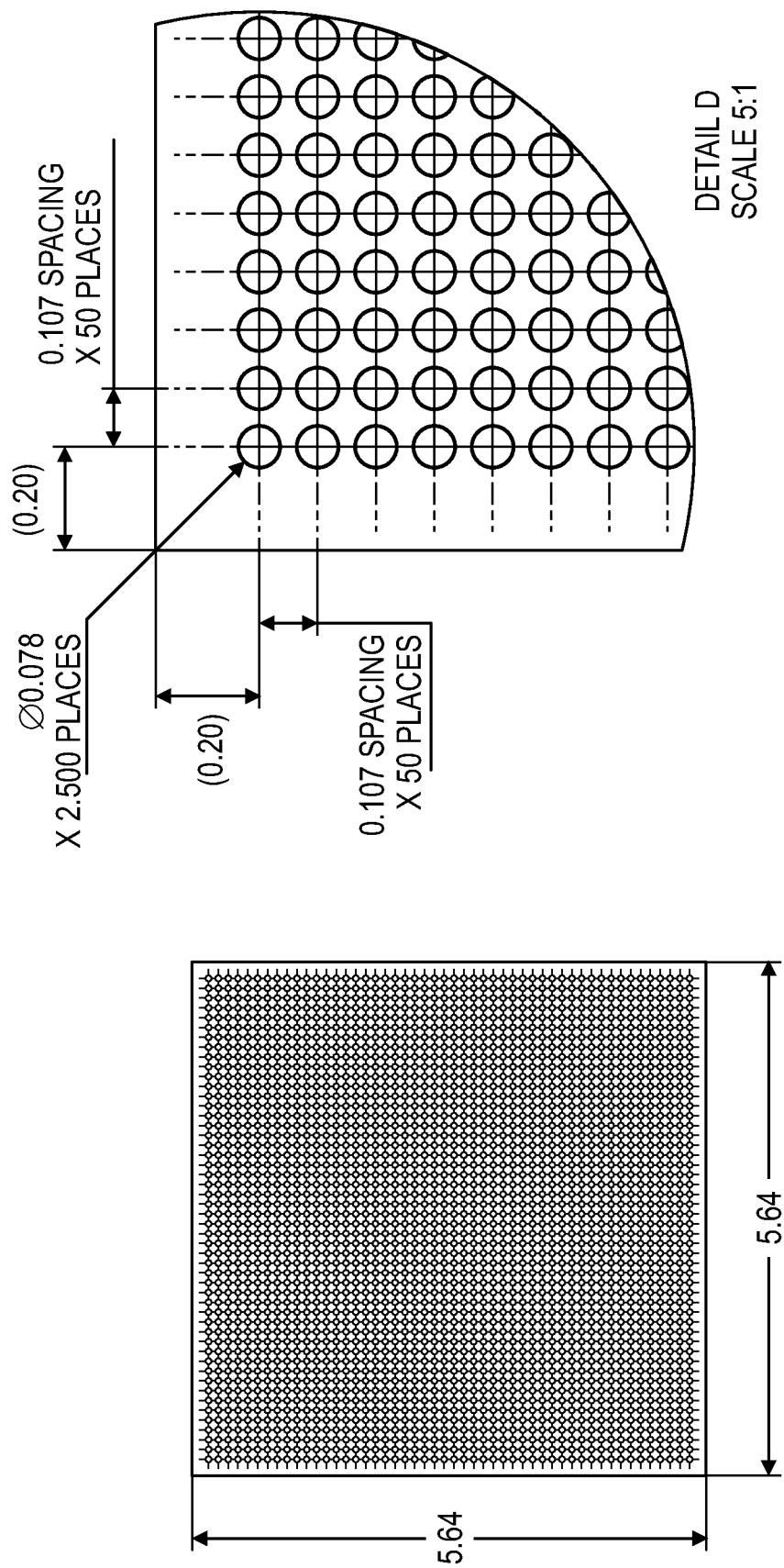

FIG. 128 shows an example stencil, under an embodiment.

Figure 129:
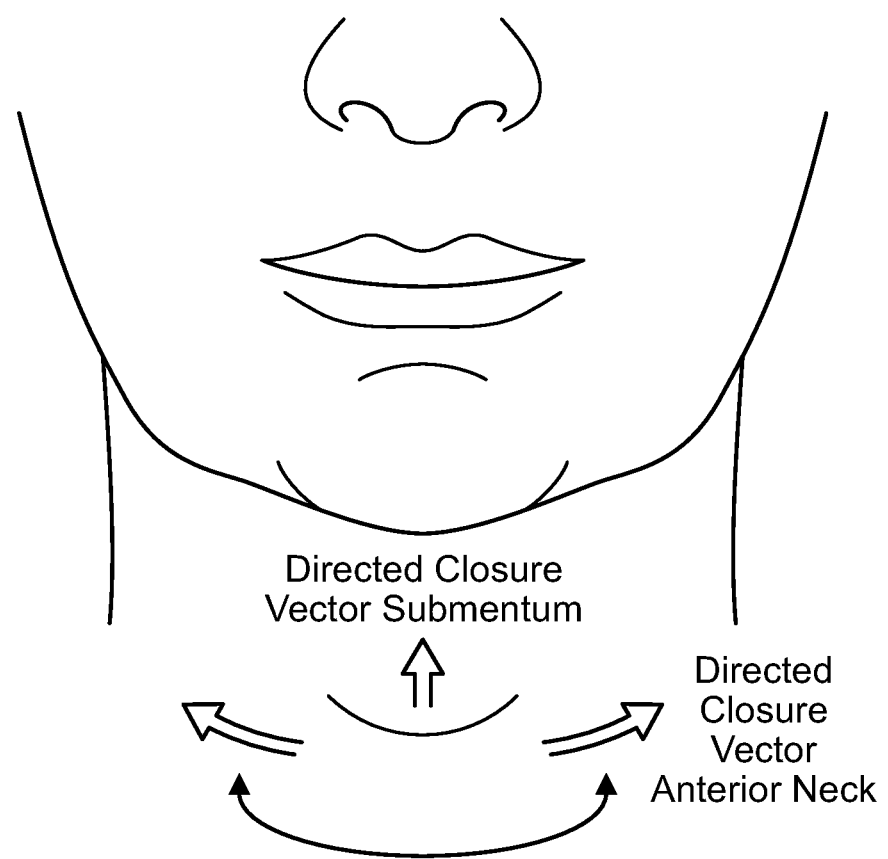

FIG. 129 shows example directed closure vectors of the submentum and anterior neck, under an embodiment.

Figure 130:
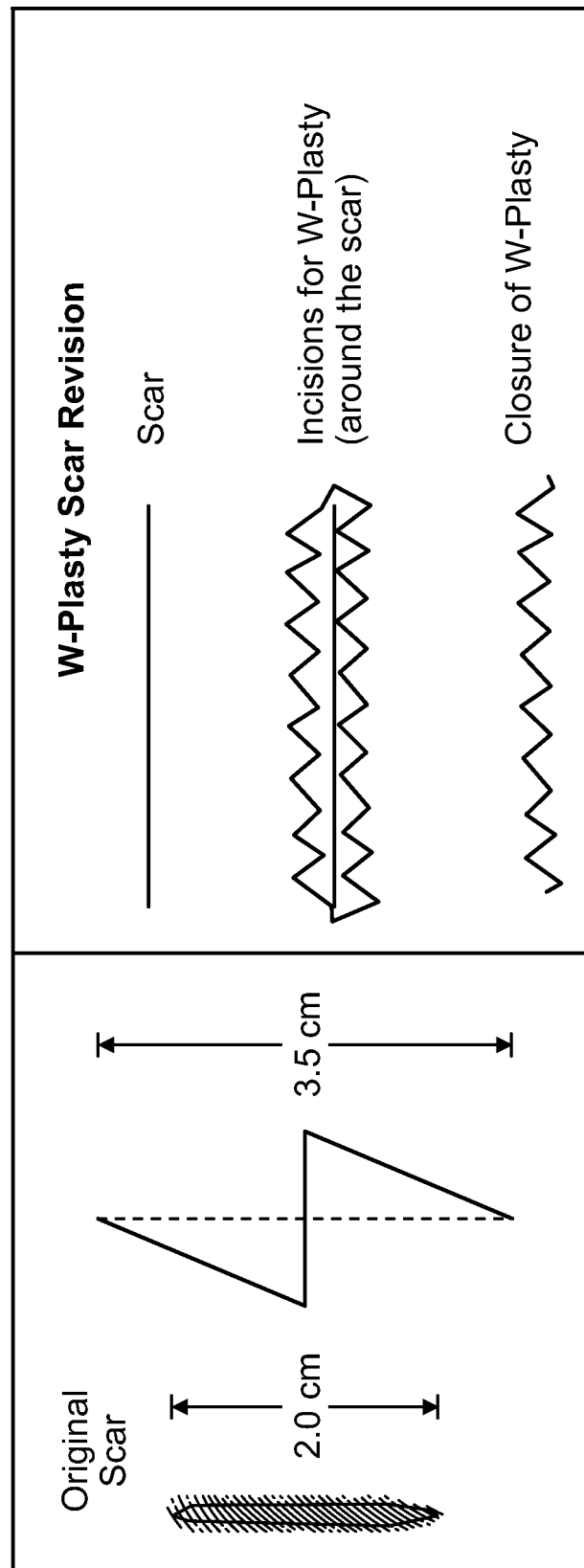

FIG. 130 depicts Z-plasty and W-plasty scar revision.

Figure 131:
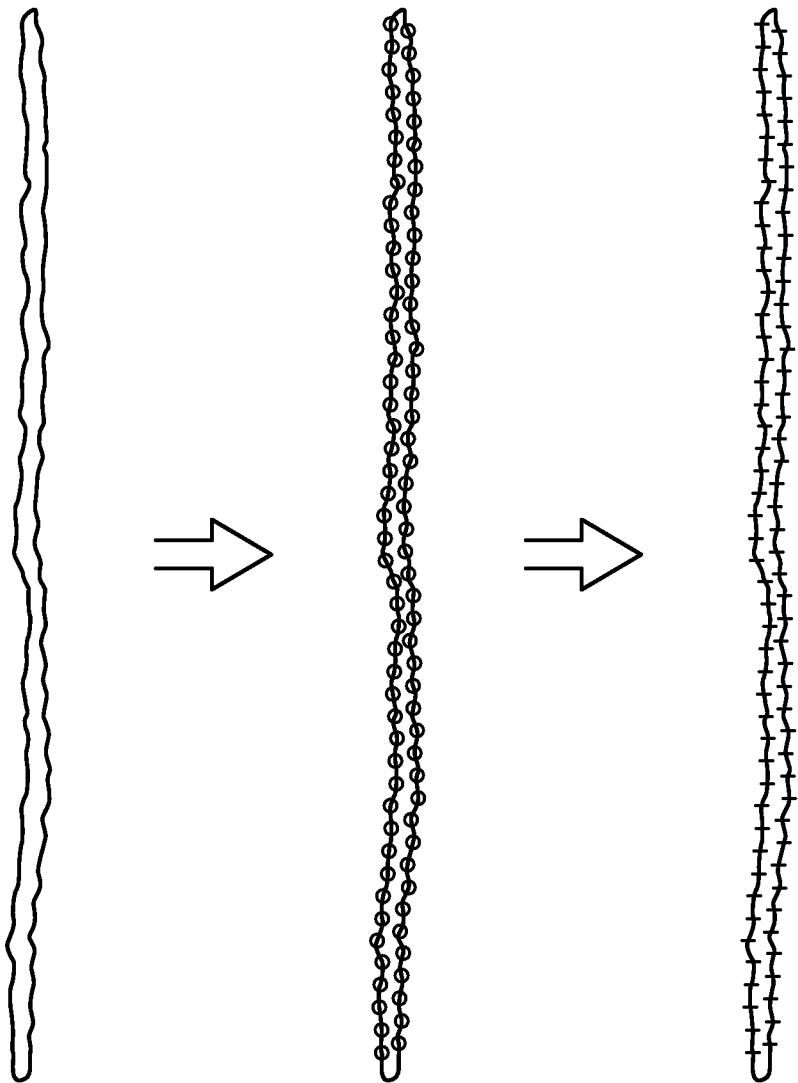

FIG. 131 shows an example of the fractional de-delineation technique of scar resection, under an embodiment.

Figure 132:
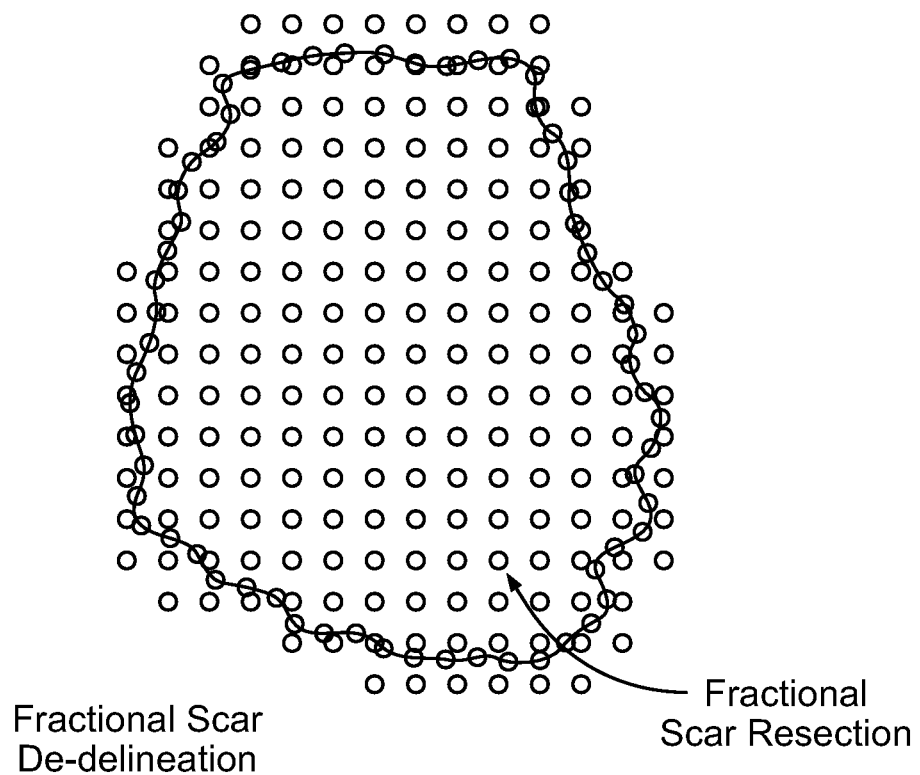

FIG. 132 shows an example of the fractional scar resection for broad hypotrophic scars, under an embodiment.

FIG. 133 shows an example comprising shortening of the inframmary incision as applied to breast reduction and/or breast repositioning, under an embodiment.

Figure 134:
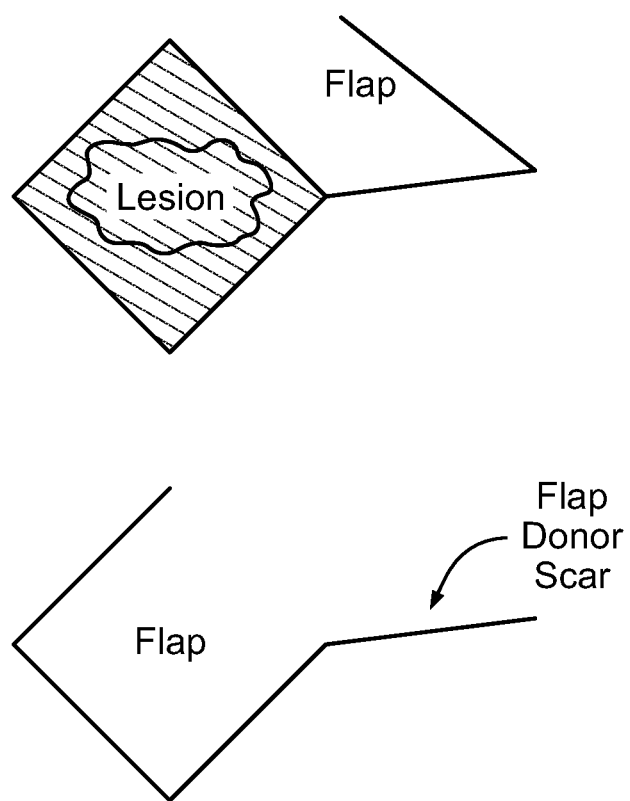

FIG. 134 shows an example flap closure.

FIG. 135 shows an example comprising fractional skin graft harvesting to be applied to a donor site, under an embodiment.

FIG. 136 shows an example comprising neovascularization of a fractional skin graft at a recipient site, under an embodiment.

Figure 137:
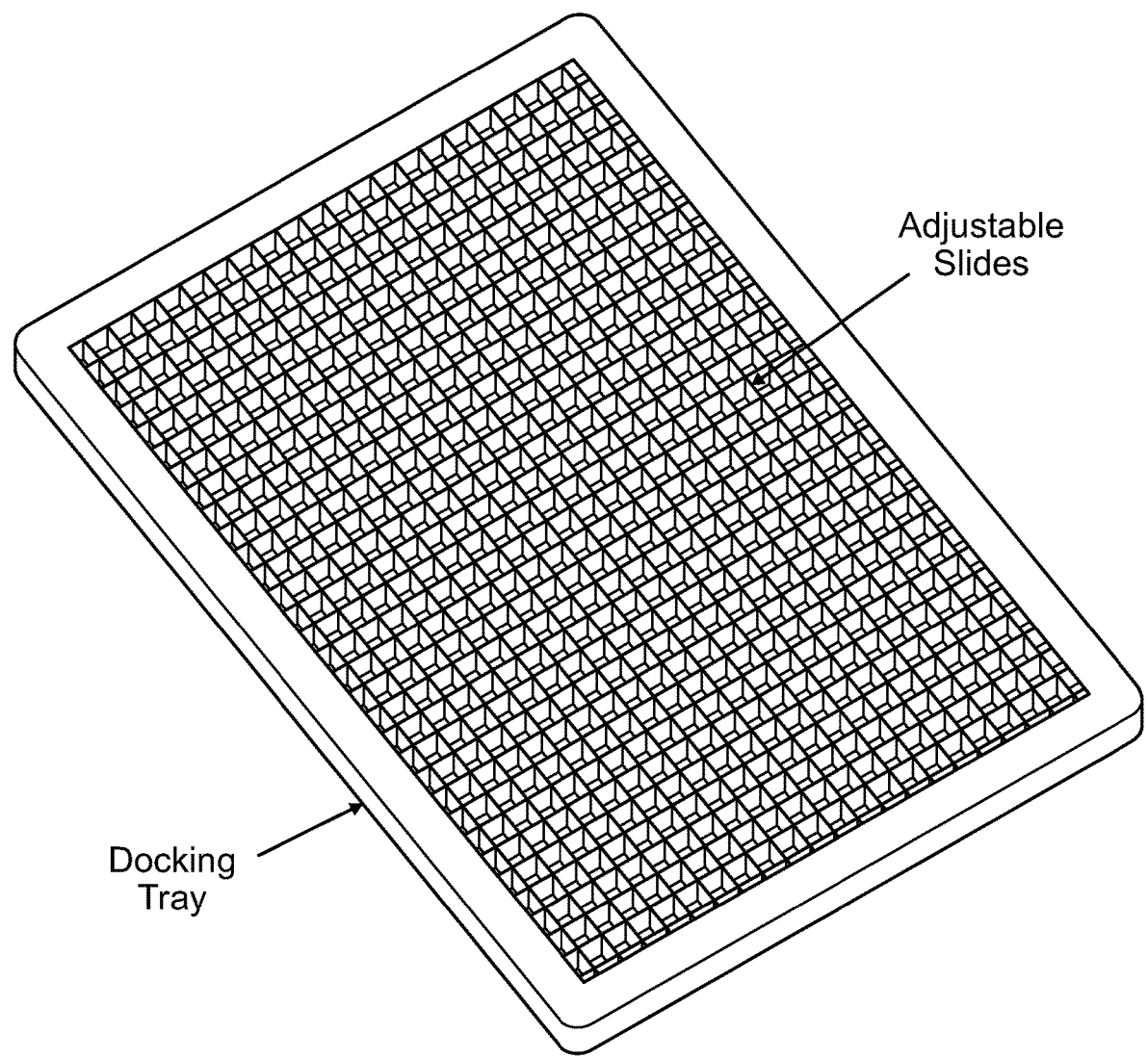

FIG. 137 shows an example docking station comprising a docking tray and adjustable slides, under an embodiment.

Figure 138:
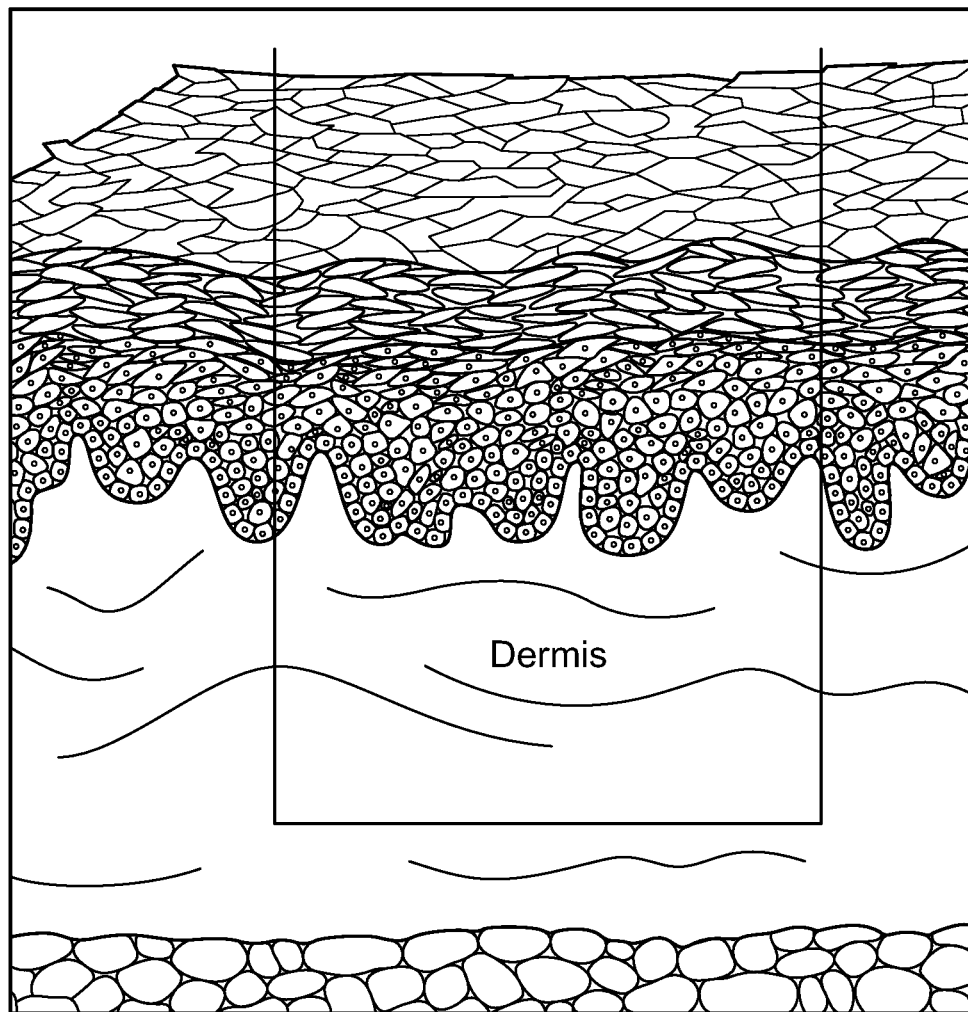

FIG. 138 shows the segment of skin removed in a fractional skin resection, under an embodiment.

Figure 139A:
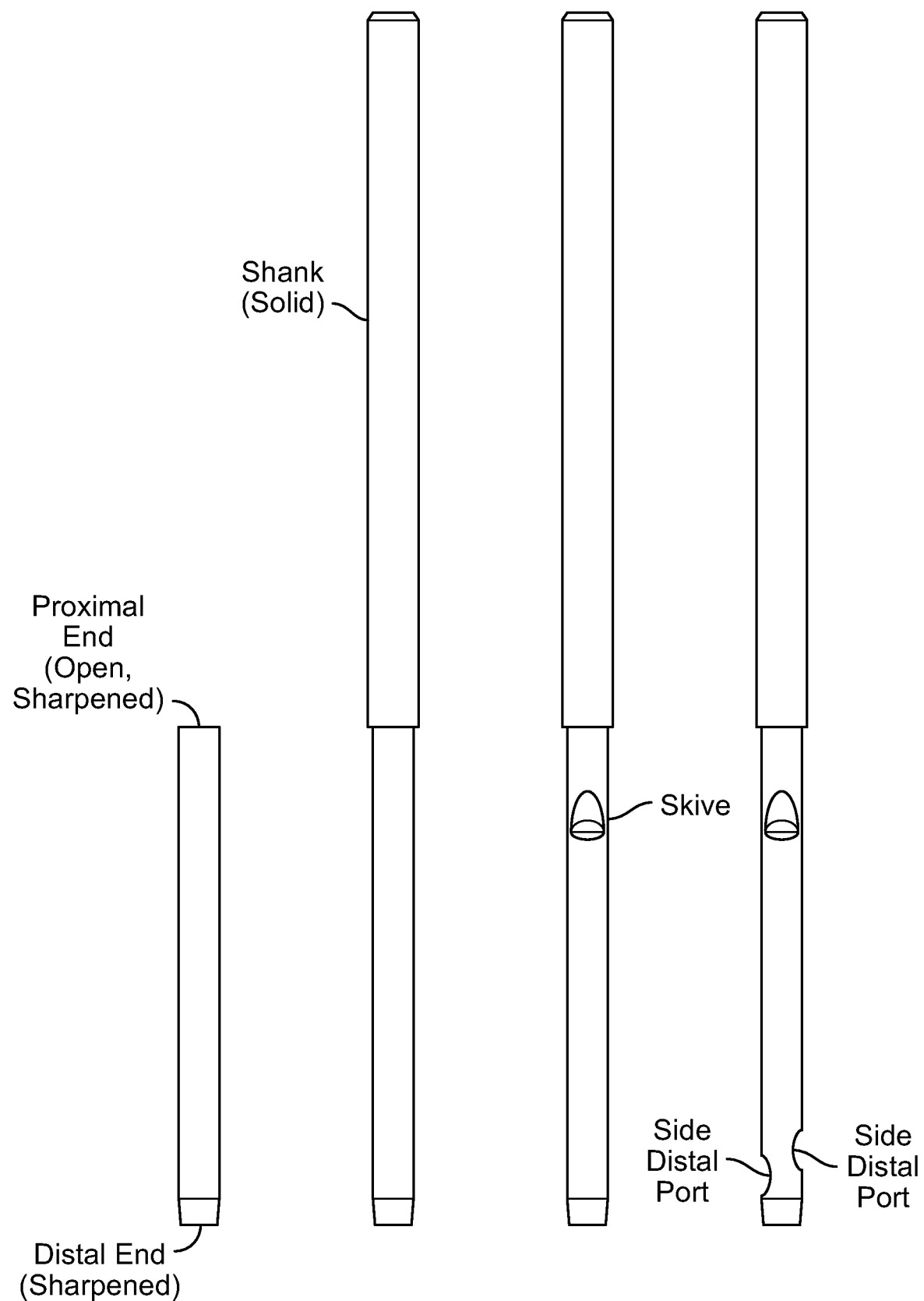
Figure 139C:
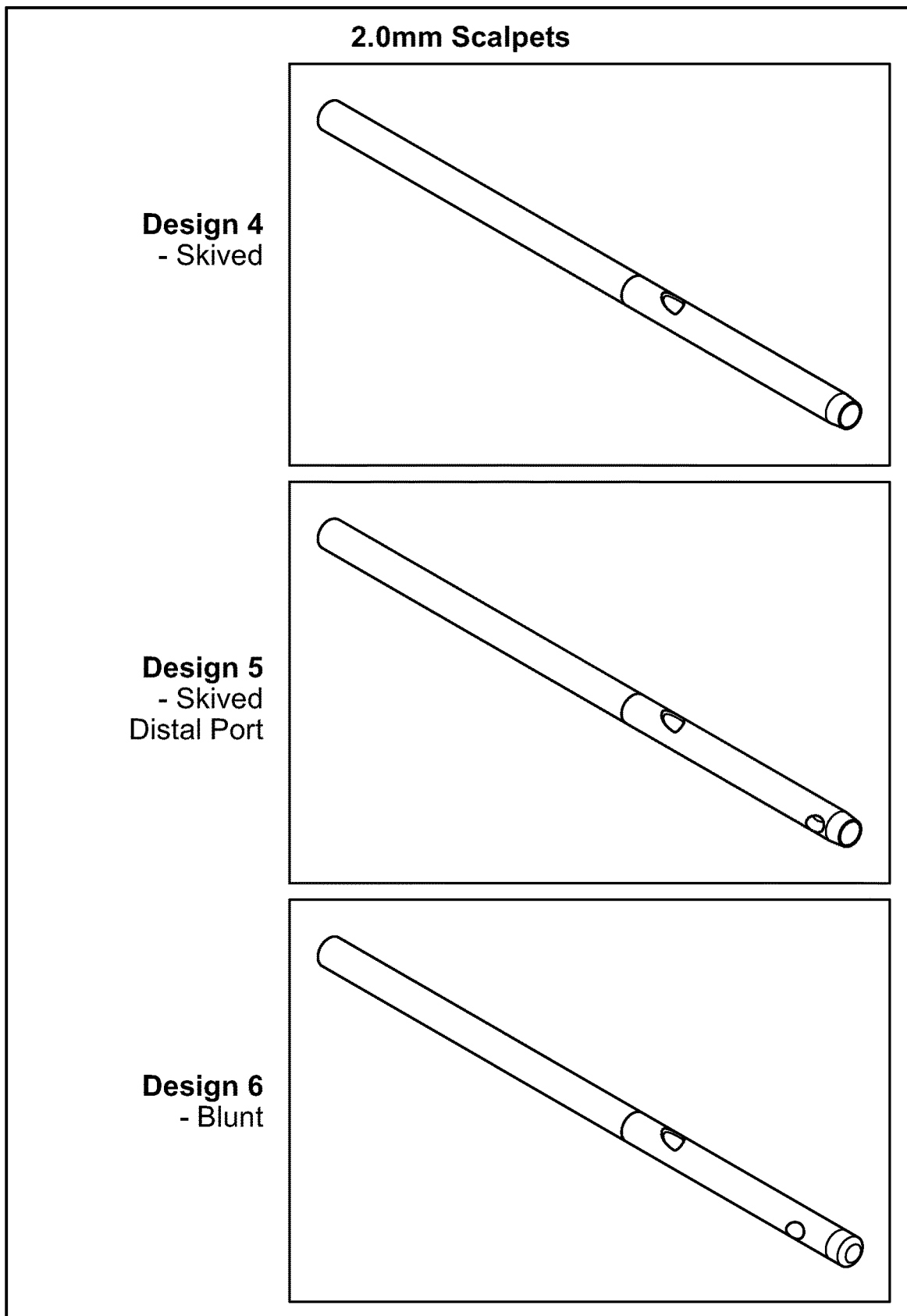

FIGS. 139A-139C show different scalpet configurations, under an embodiment.

Figure 140A:
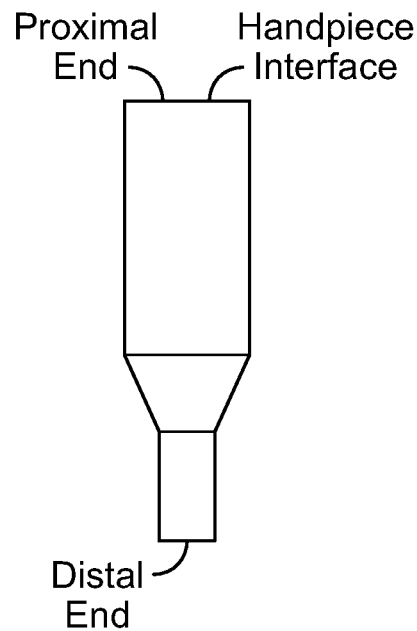

FIG. 140A shows a single scalpet depth guide configured for use without vacuum, under an embodiment.

Figure 140B:
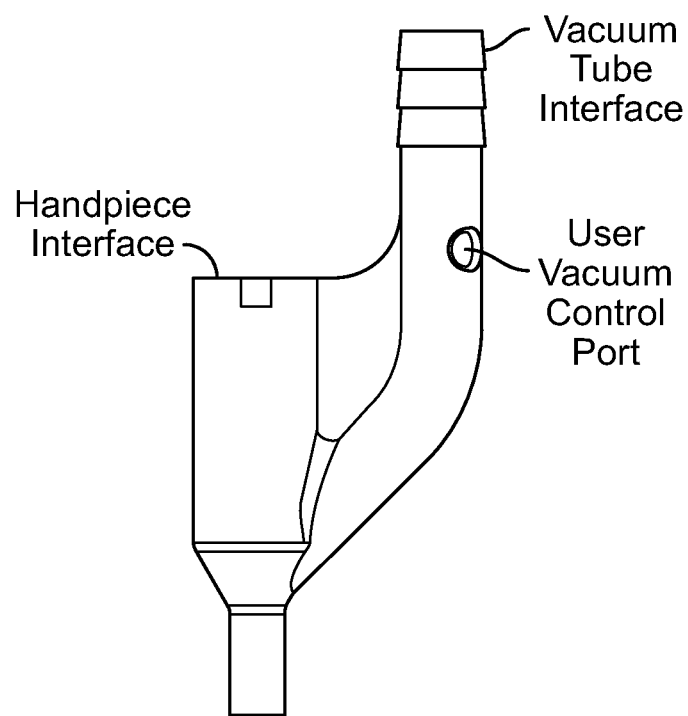

FIG. 140B shows a single scalpet depth guide configured for use with vacuum, under an embodiment.

Figures 141A, 141B:
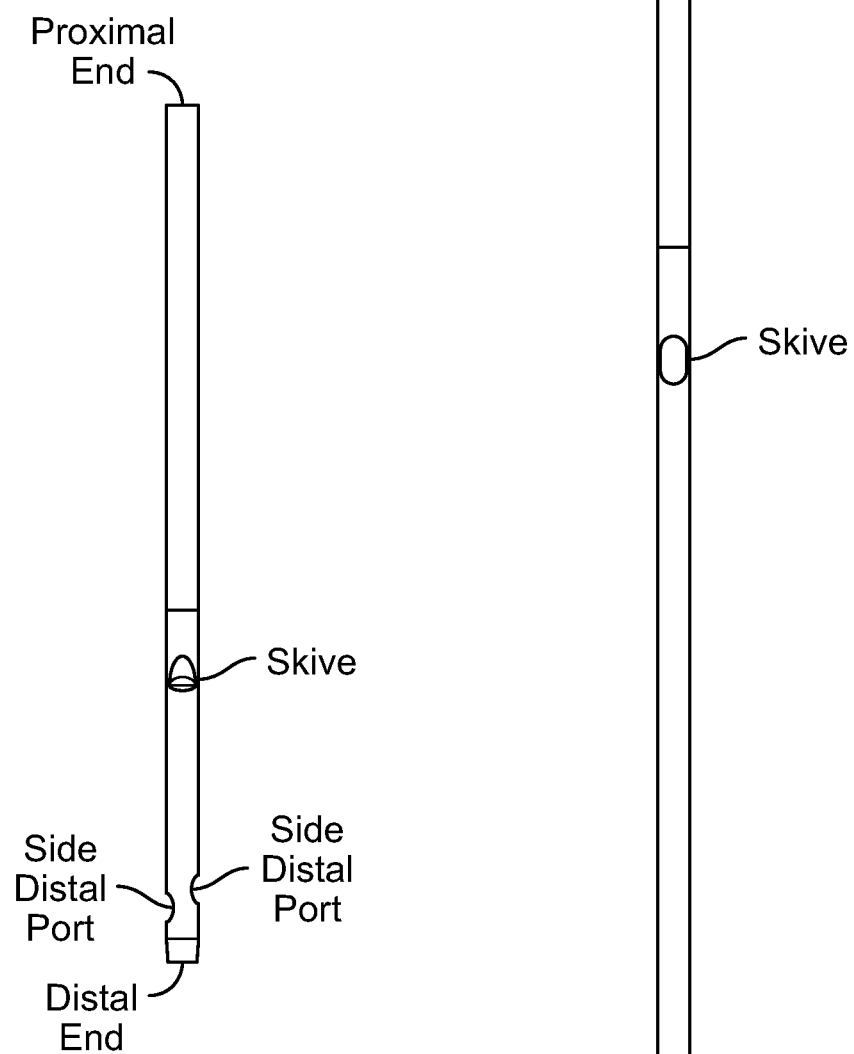

FIG. 141A shows a lipectomy cannula having first dimensions, under an embodiment.

FIG. 141B shows a lipectomy cannula having second dimensions, under an embodiment.

Figure 142:
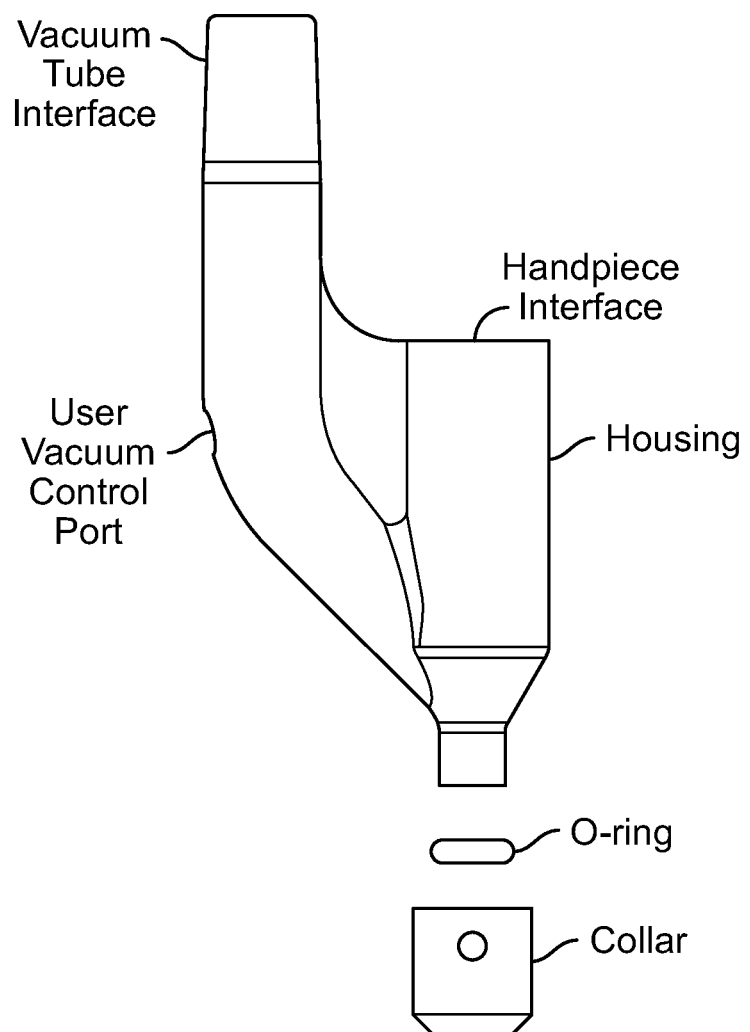

FIG. 142 shows a vacuum manifold, under an embodiment.

Figure 143:
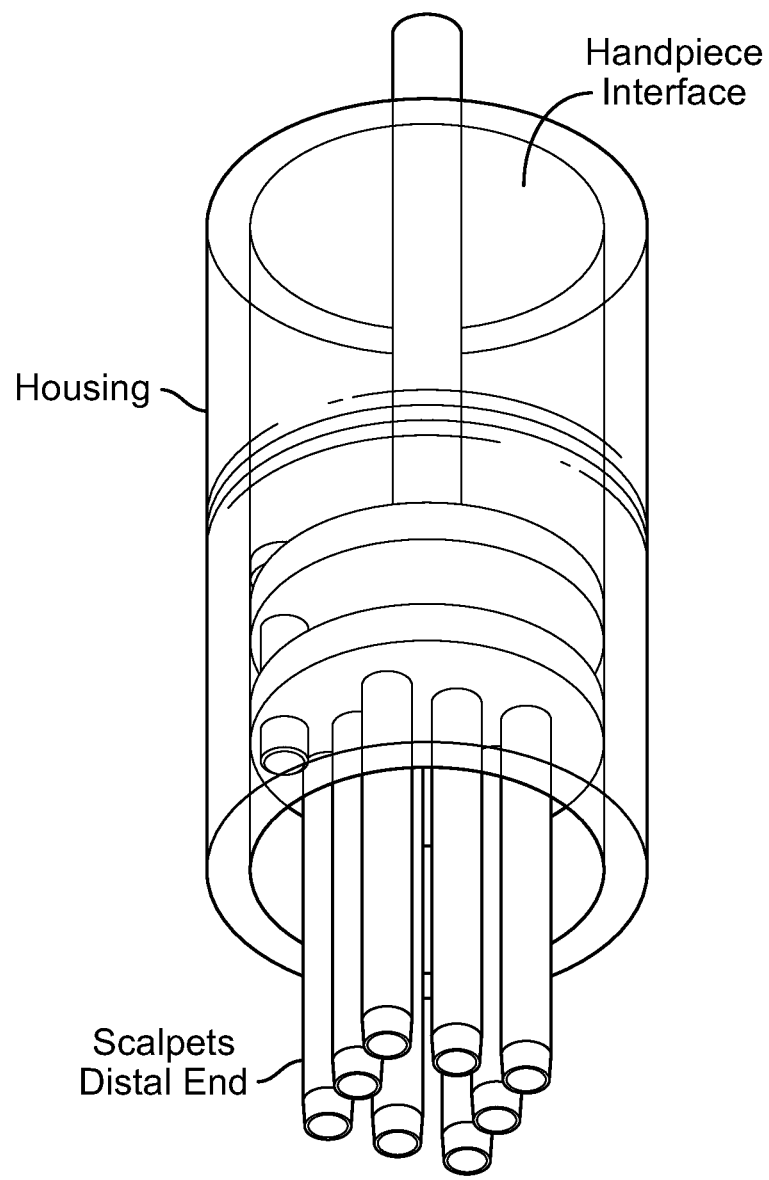

FIG. 143 shows a multi-scalpet array (MSA) (3×3 array) including a housing and a handpiece interface, under an embodiment.

Figure 144:
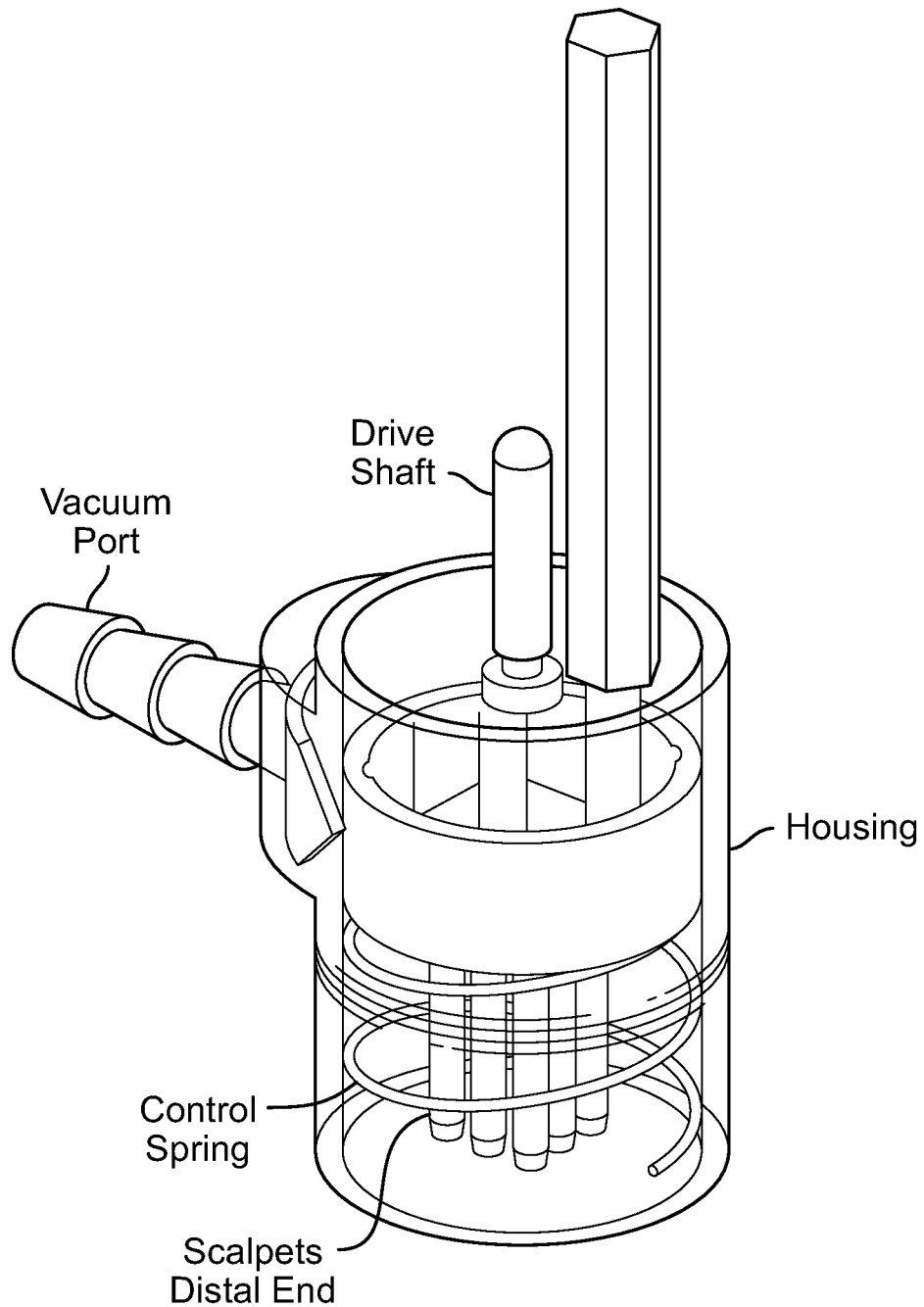

FIG. 144 shows a multi-scalpet array (3×3 array) in a housing, under an alternative embodiment.

Figure 145B:
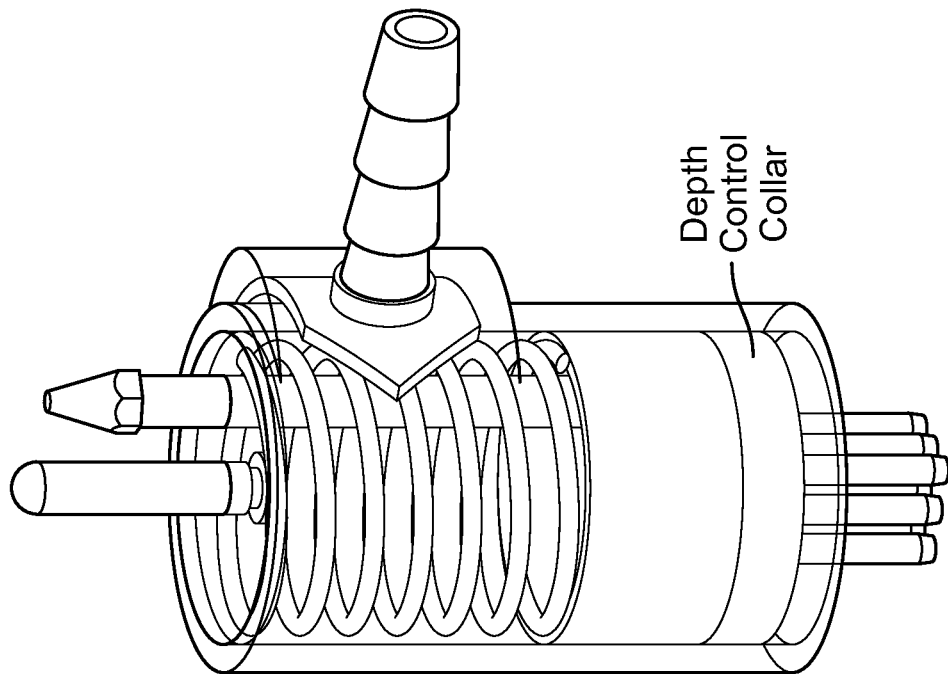
Figure 145A:
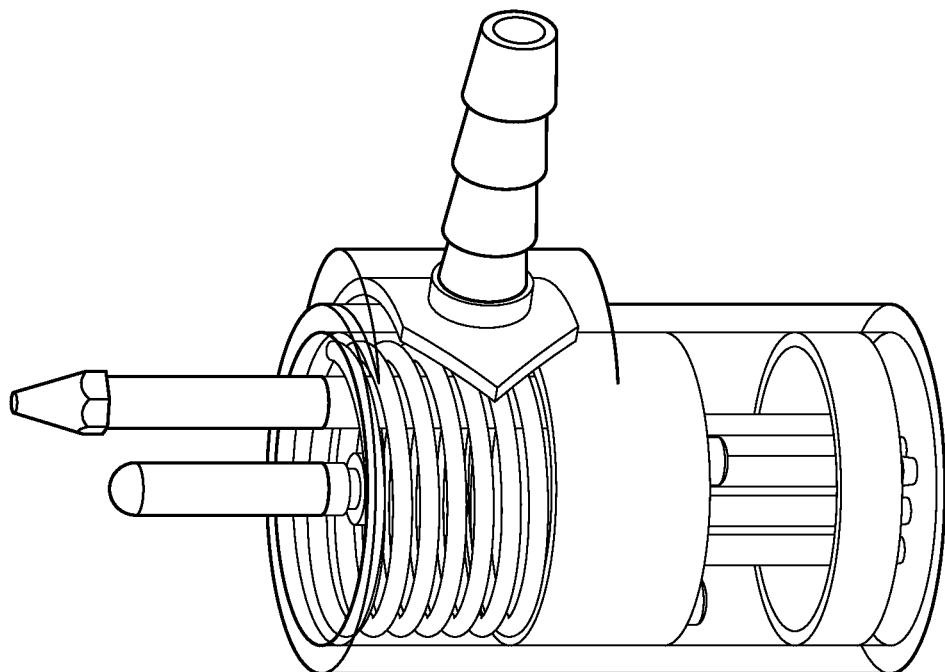

FIG. 145A shows a multi-scalpet array (3×3 array) in a retracted state, under an embodiment.

FIG. 145B shows a multi-scalpet array (3×3 array) in an extended state, under an embodiment.

Figure 146:
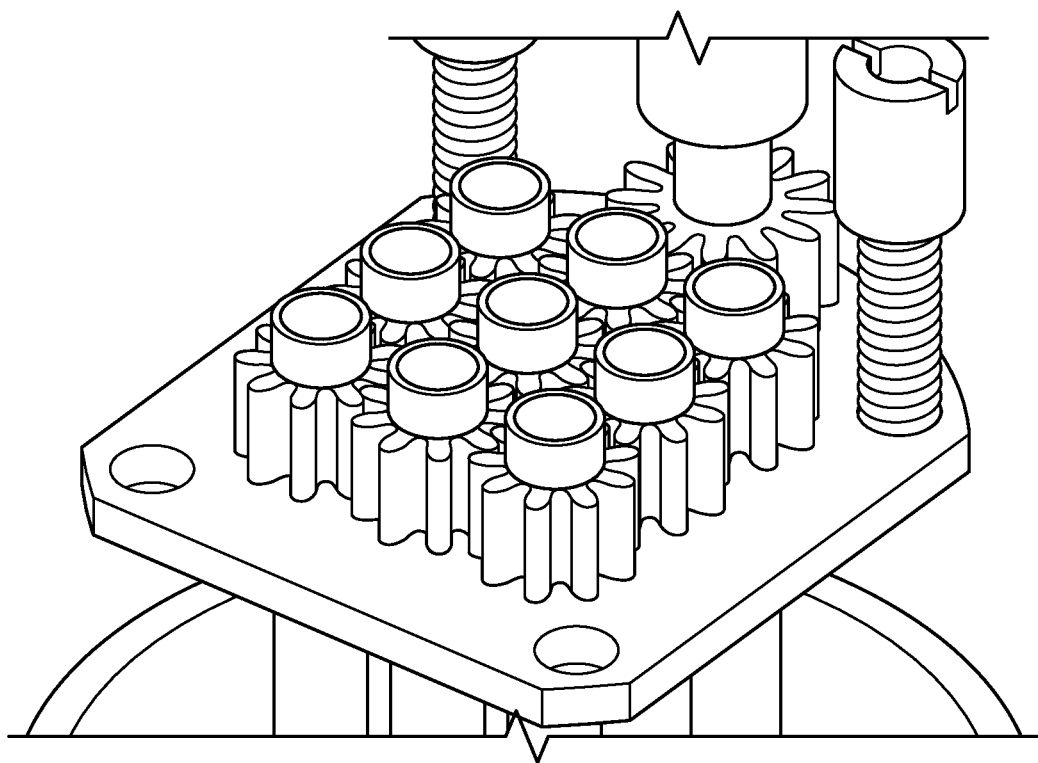

FIG. 146 shows a gear drive mechanism of the multi-scalpet array, under an embodiment.

Figure 147:
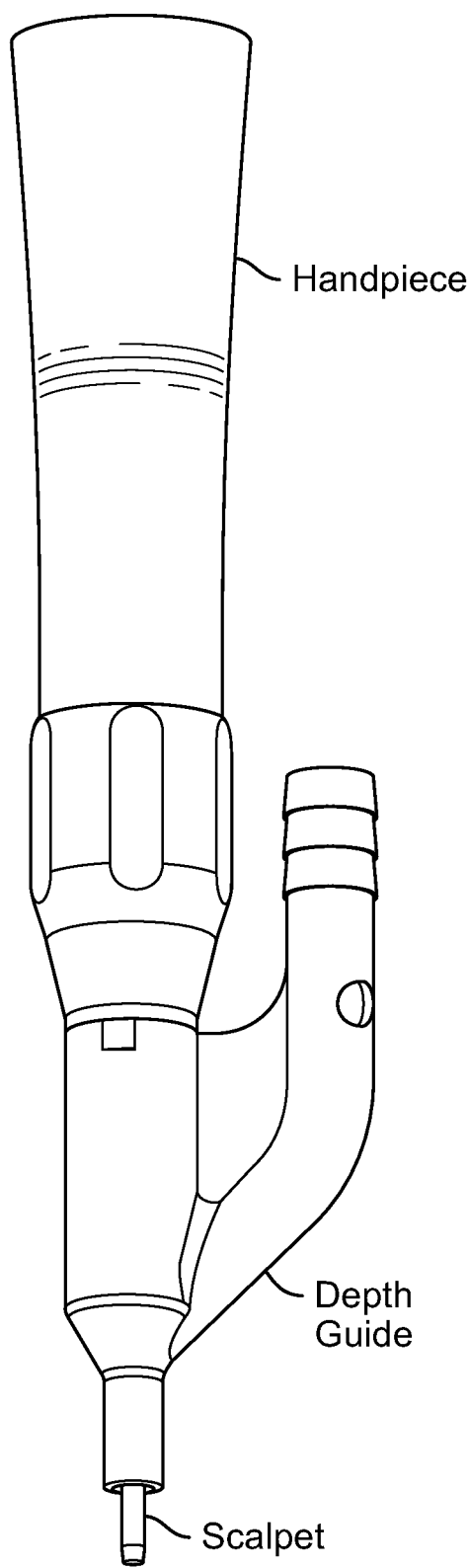

FIG. 147 shows a single scalpet device with vacuum configured for a fractional resection procedure, under an embodiment.

Figure 148:
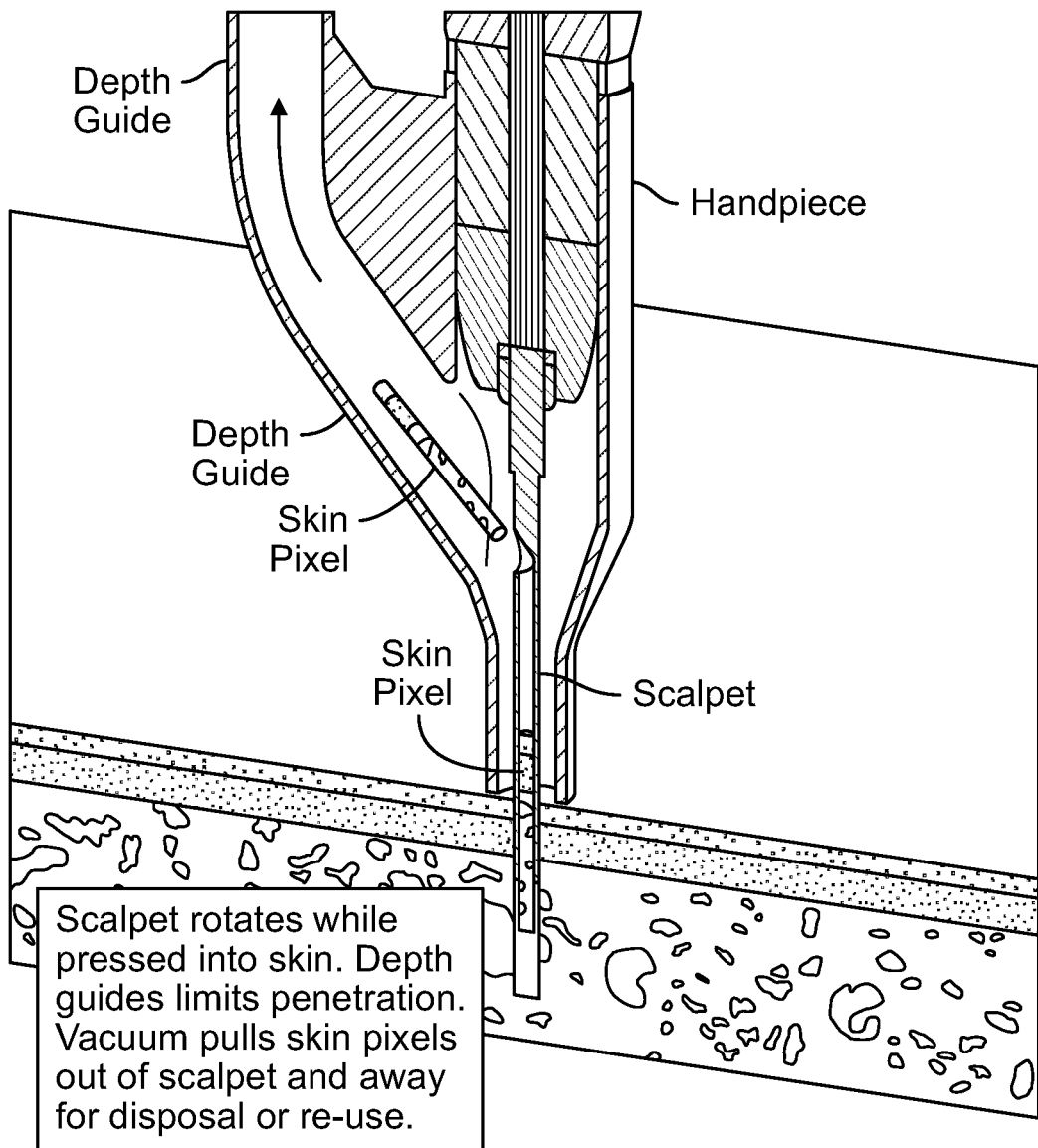

FIG. 148 shows application of the single scalpet device to a target site during a fractional resection procedure, under an embodiment.

Figure 149:
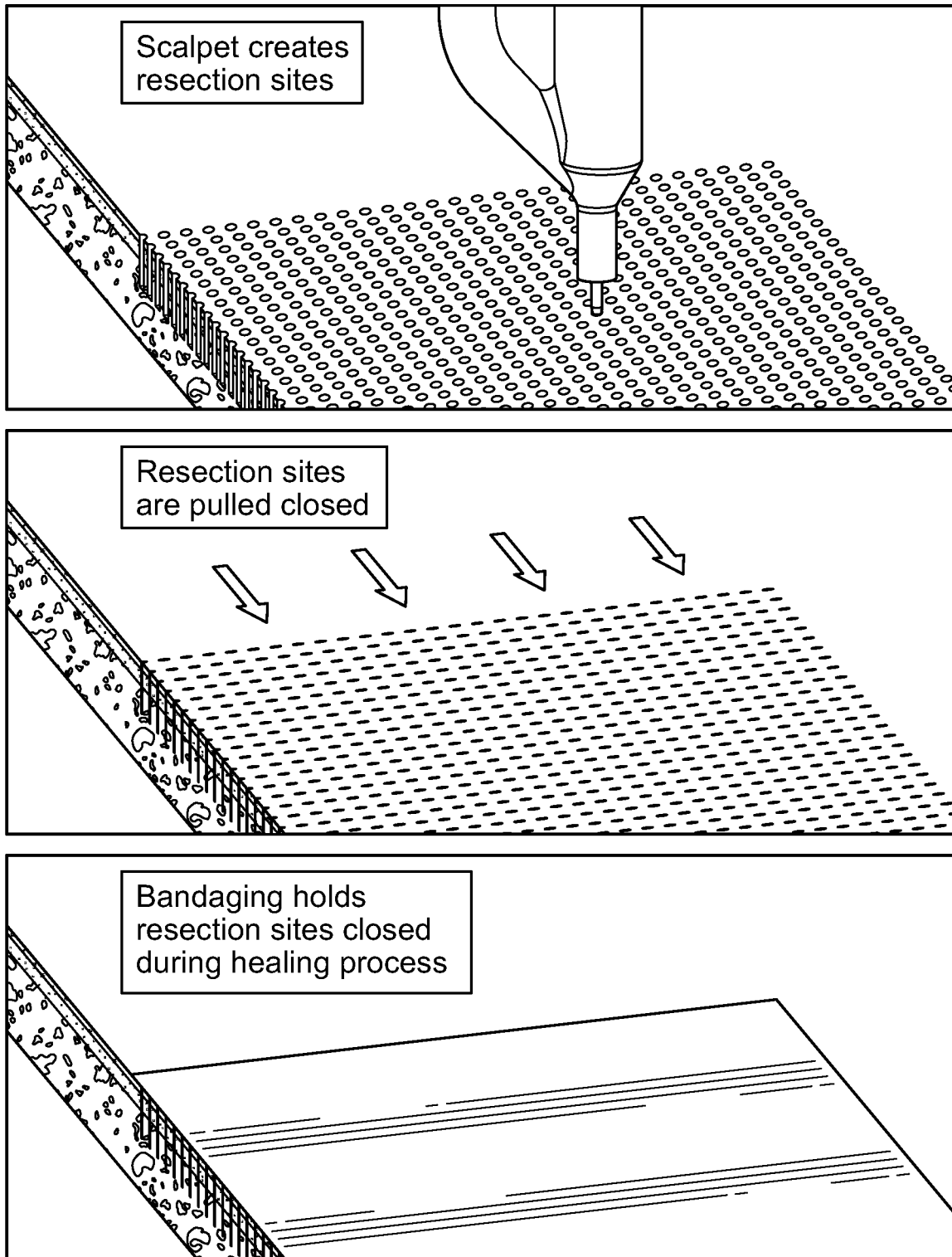

FIG. 149 shows a resection field generated through repeated application of the single scalpet device to a target site, and closure of the field, under an embodiment.

Figure 150:
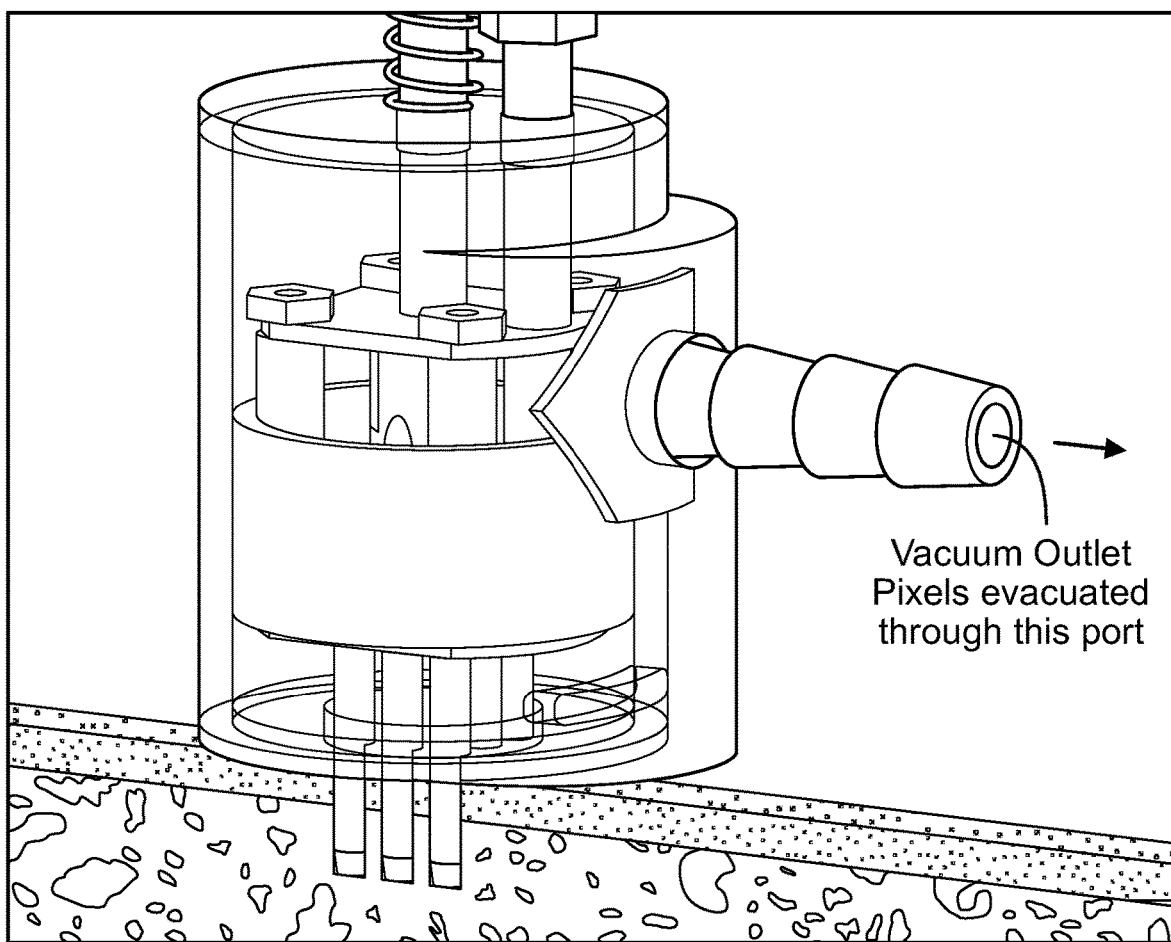

FIG. 150 shows a multi-scalpet array device with vacuum in an extended site as applied to a target site during a fractional resection procedure, under an embodiment.

Figure 151:
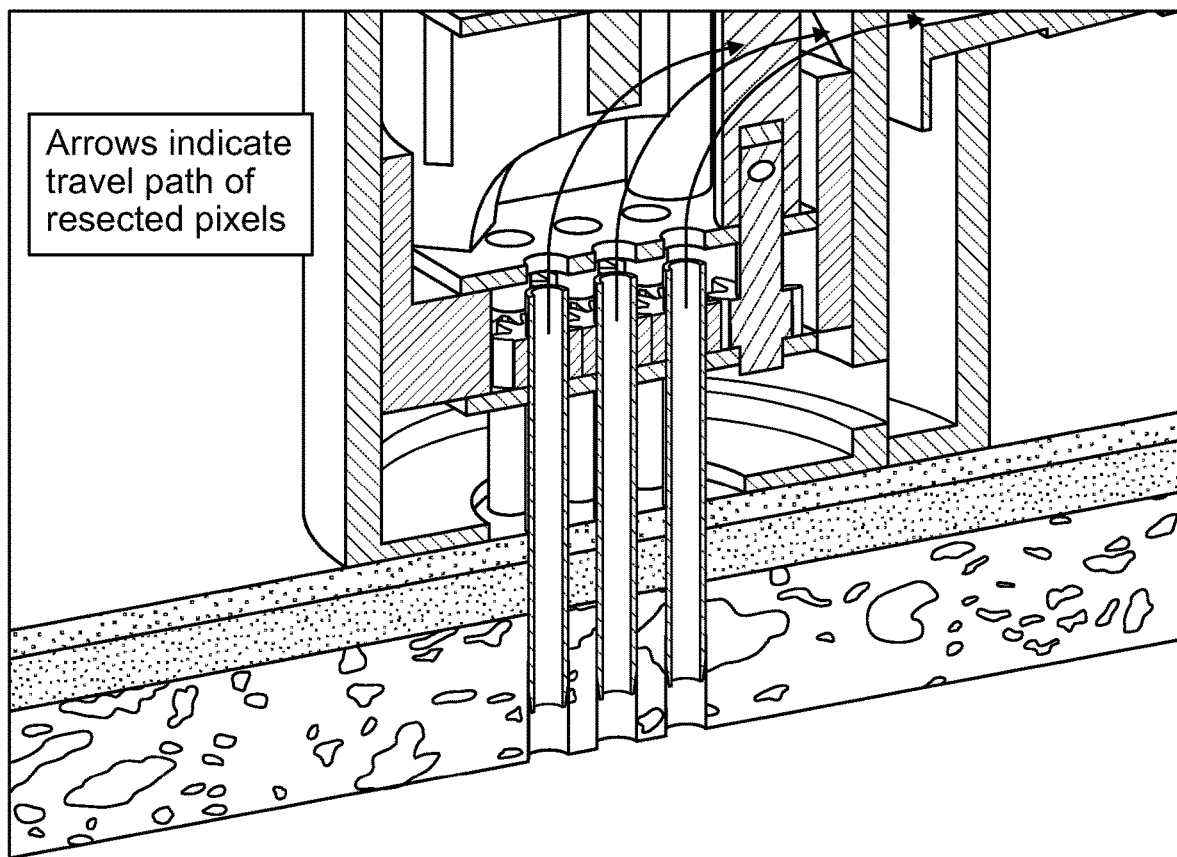

FIG. 151 shows a cross-section of the multi-scalpet array device in an extended site as applied to a target site during a fractional resection procedure, under an embodiment.

Figure 152:
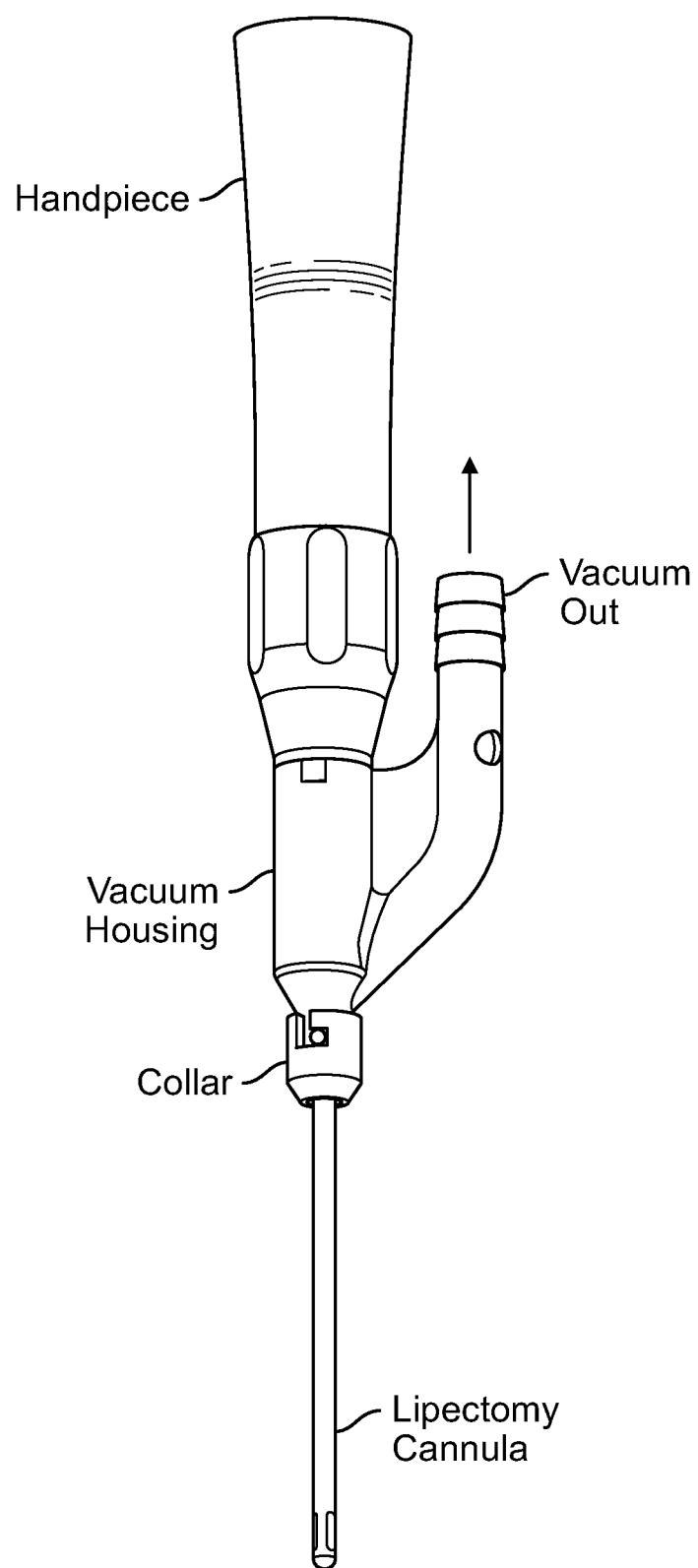

FIG. 152 shows a single scalpet device with vacuum configured for a fractional resection/lipectomy procedure, under an embodiment.

Figure 153:
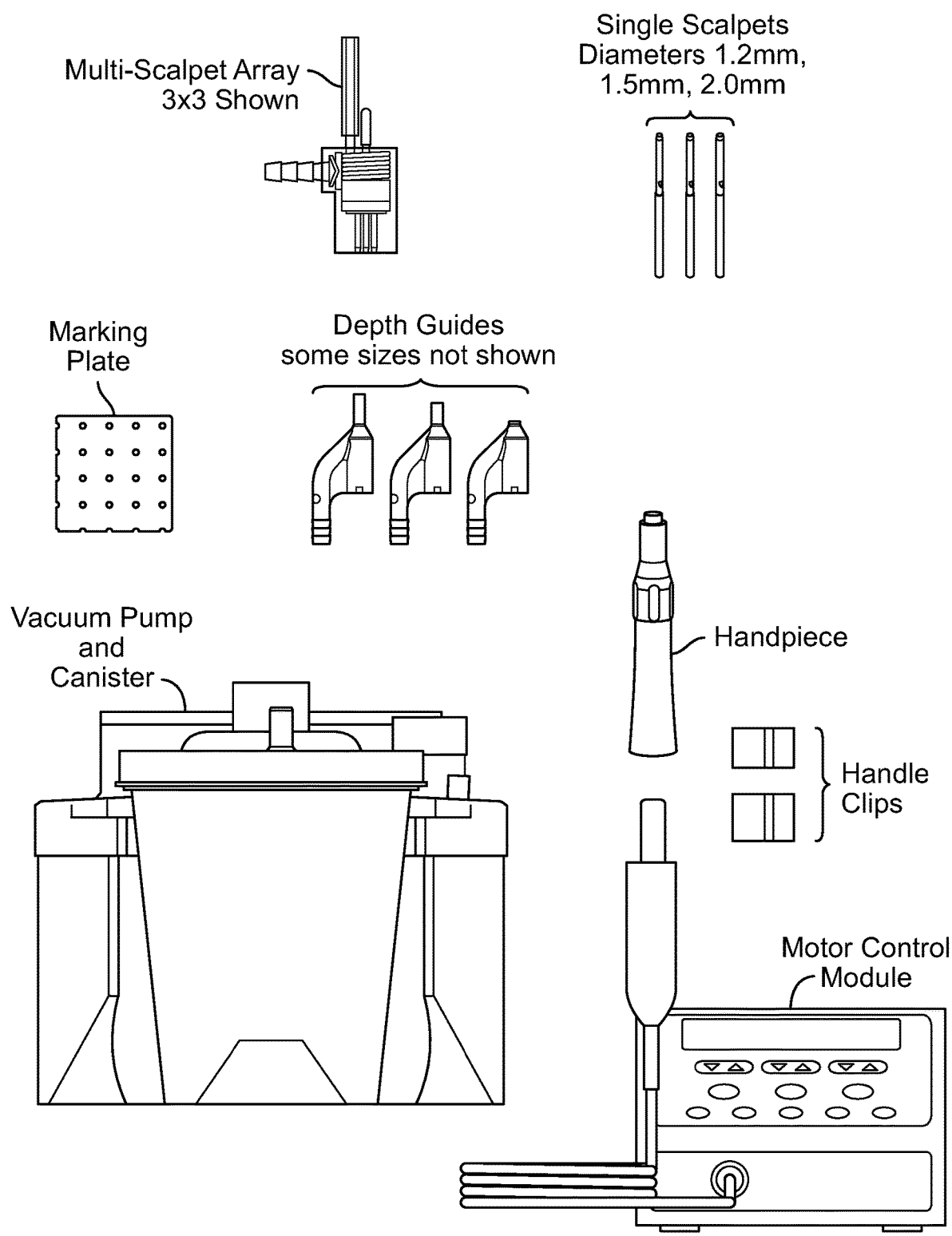

FIG. 153 shows the components of a fractional skin resection system, under an embodiment.

Figure 154:
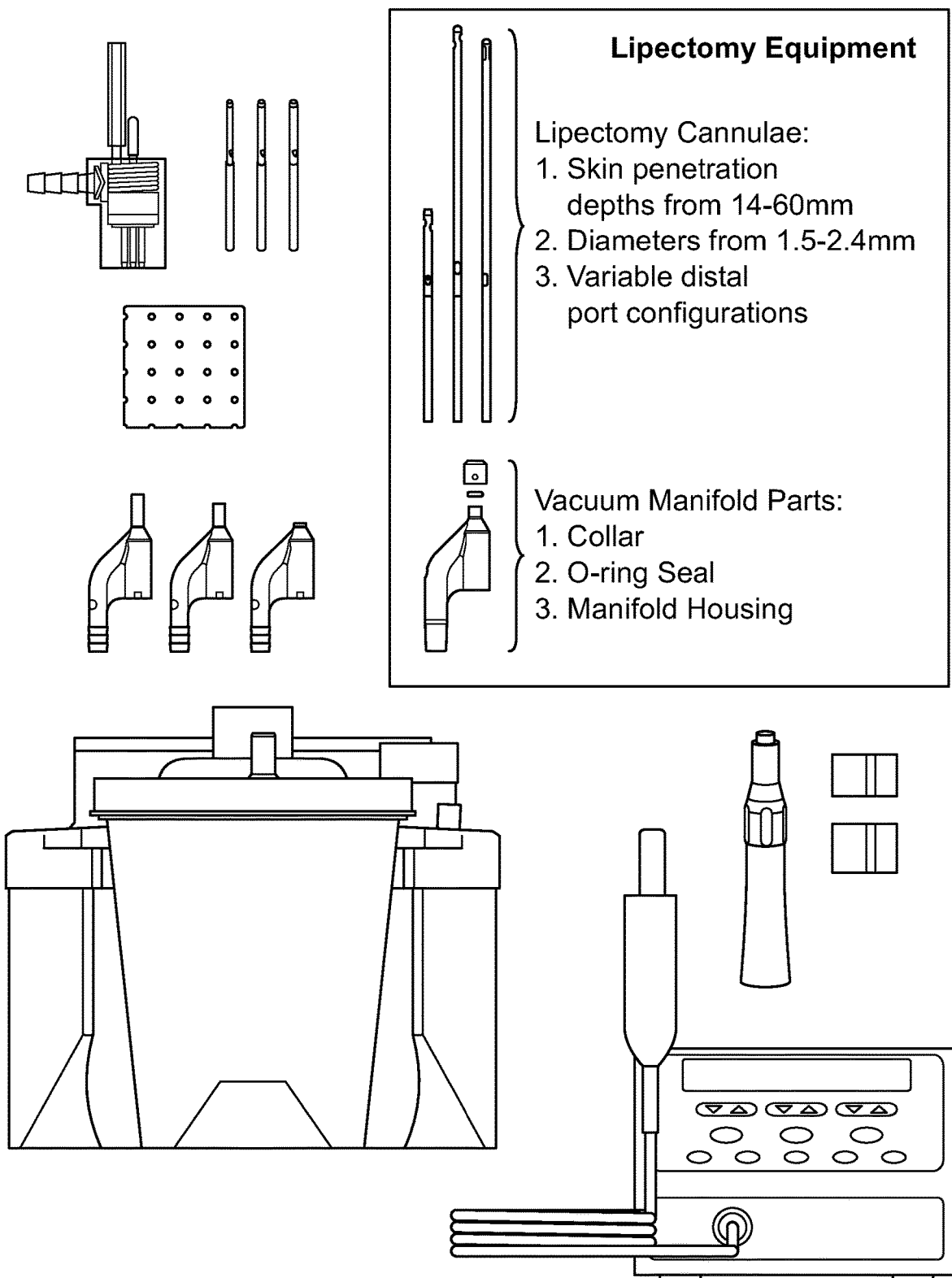

FIG. 154 shows the components of a fractional skin resection/lipectomy system, under an embodiment.

FIG. 155A is a table detailing procedural components of fractional skin grafting for skin defects including traumatic avulsive or full thickness abrasive loss, under an embodiment.

FIG. 155B is a table detailing procedural components of fractional skin grafting for skin defects including third degree burns, under an embodiment.

FIG. 155C is a table detailing procedural components of fractional skin grafting for lower extremity skin defects, under an embodiment.

FIG. 155D is a table detailing procedural components of fractional skin grafting for excisional skin defects, under an embodiment.

Figure 156A:
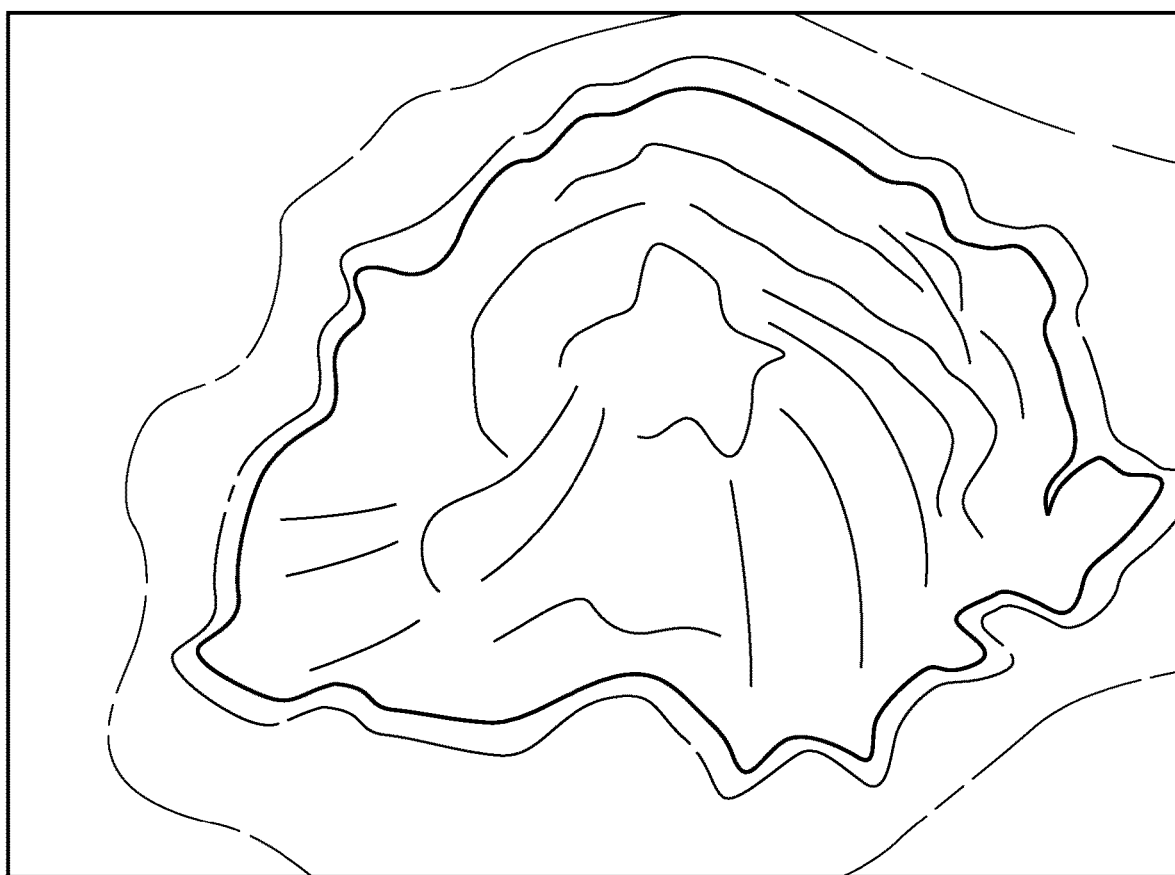
Figure 156B:
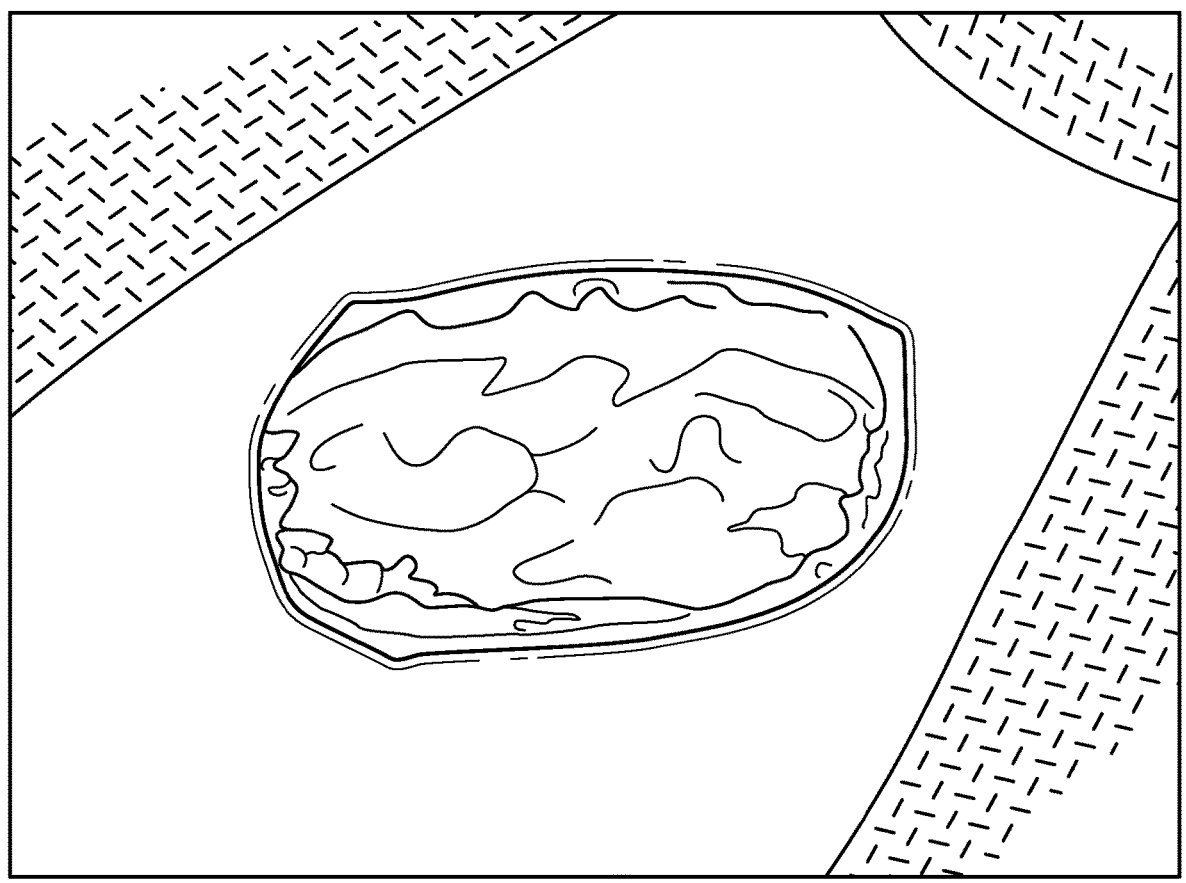

FIGS. 156A and 156B show cleaning and debridement of the wound, under an embodiment.

Figure 157:
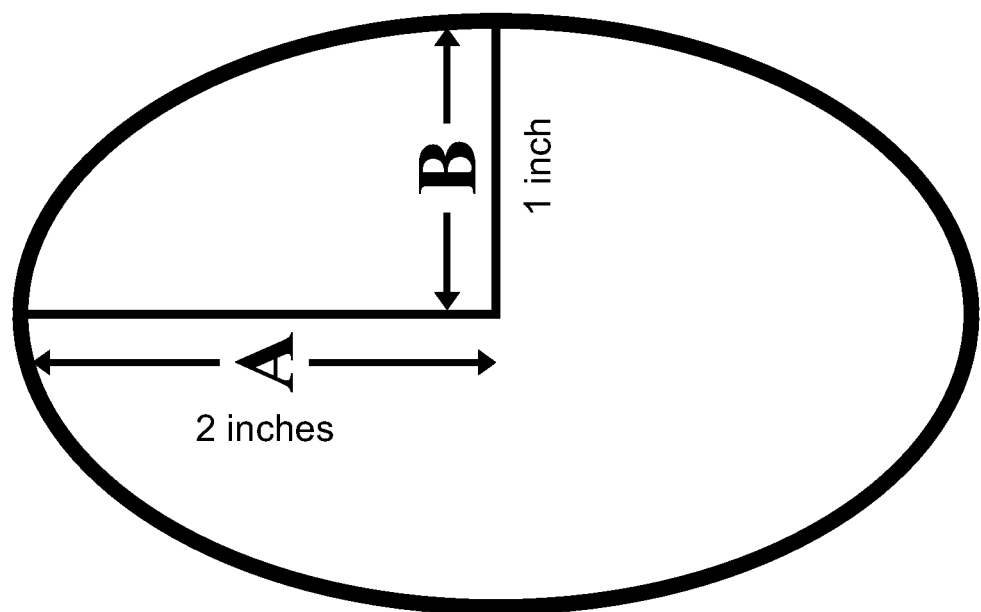

FIG. 157 is a geometrical representation of the four-to-one rule shown in a vertical fractional skin resection orientation, under an embodiment.

Figure 158A:
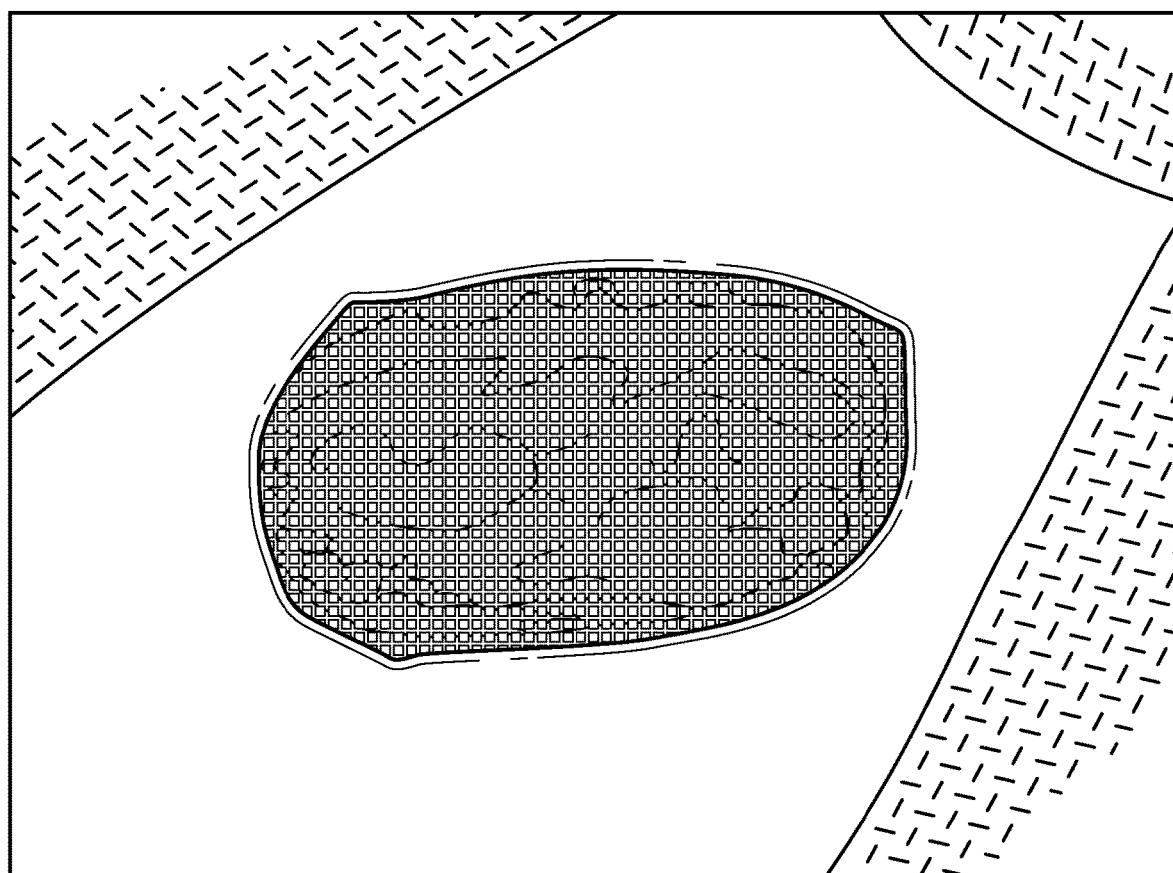

FIG. 158A shows orientation of skin plugs at the recipient site, under an embodiment.

Figure 158B:
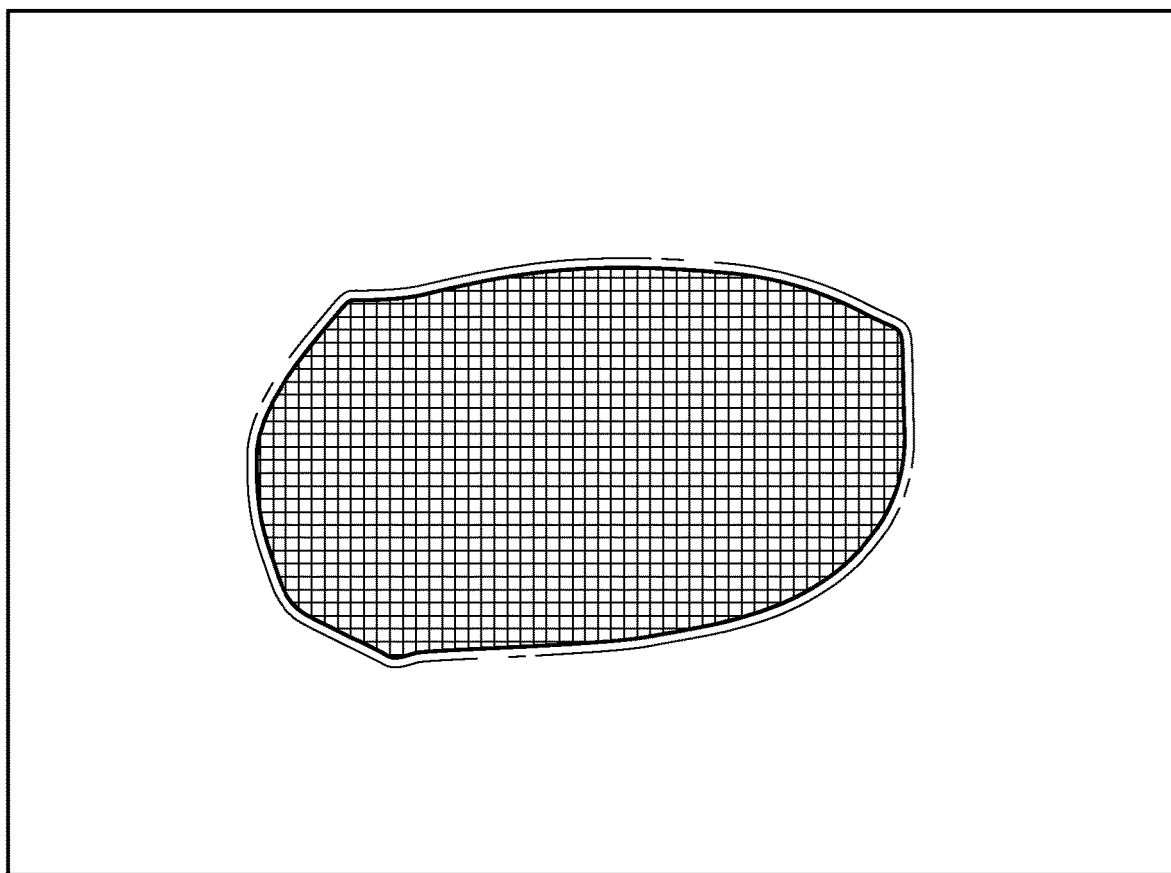

FIG. 158B shows the dressed recipient site, under an embodiment.

FIG. 159A is a table detailing procedural components of fractional skin resection of the anterior neck region and submentum neck region, under an embodiment.

FIG. 159B is a table detailing procedural components of fractional skin resection of the jowl region, under an embodiment.

Figure 160A:
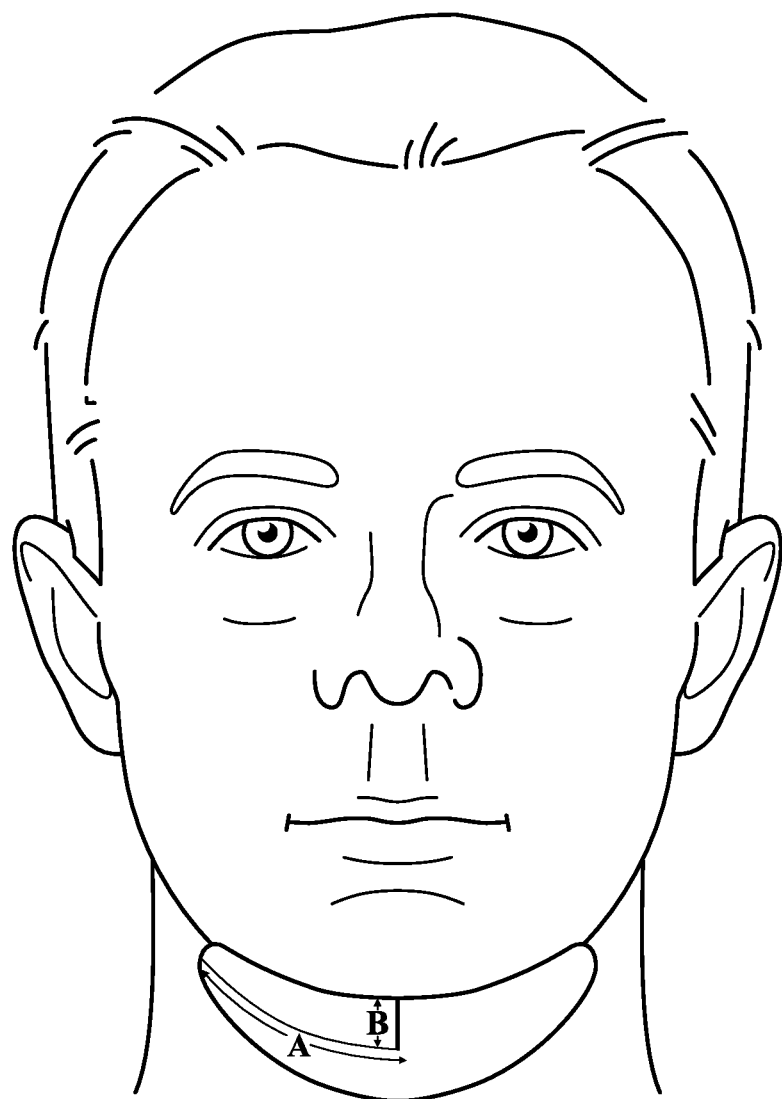

FIG. 160A is a front perspective view of a patient with a horizontal fractional resection skin resection area superimposed on a target area, under an embodiment.

Figure 160B:
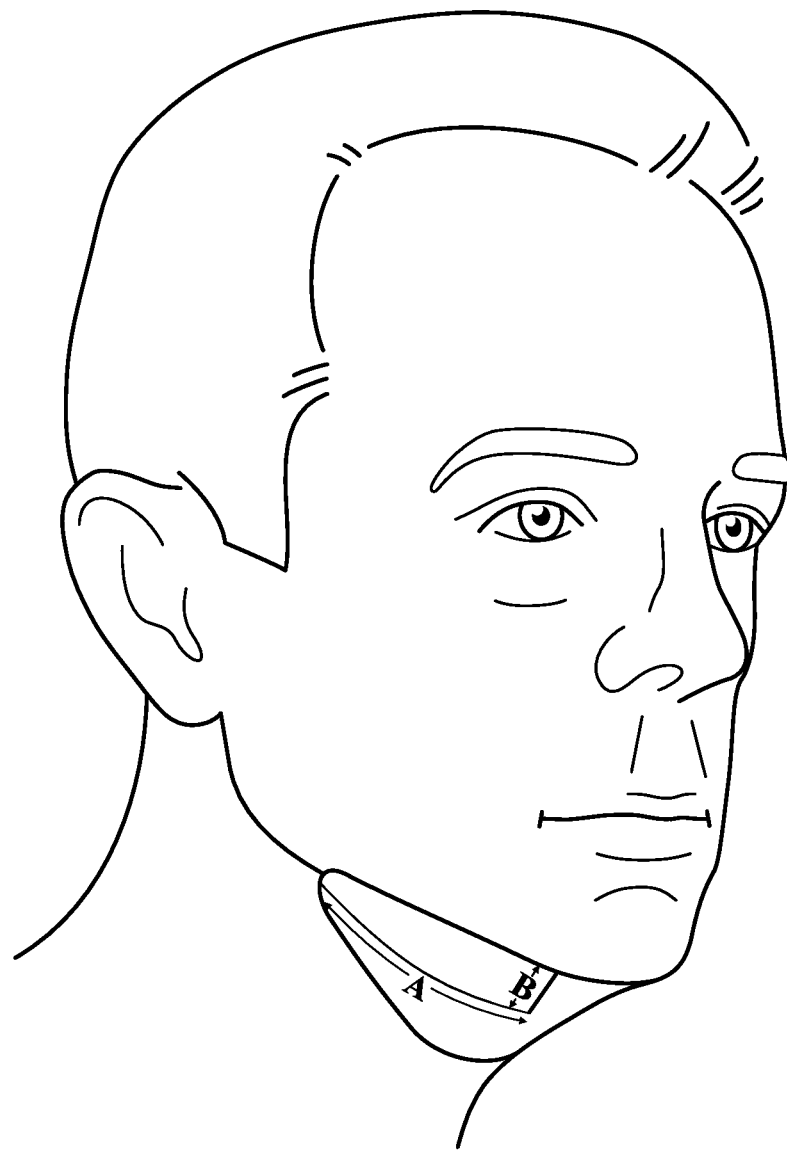

FIG. 160B is a right-front perspective view of a patient with a horizontal fractional resection skin resection area superimposed on a target area, under an embodiment.

Figure 160C:
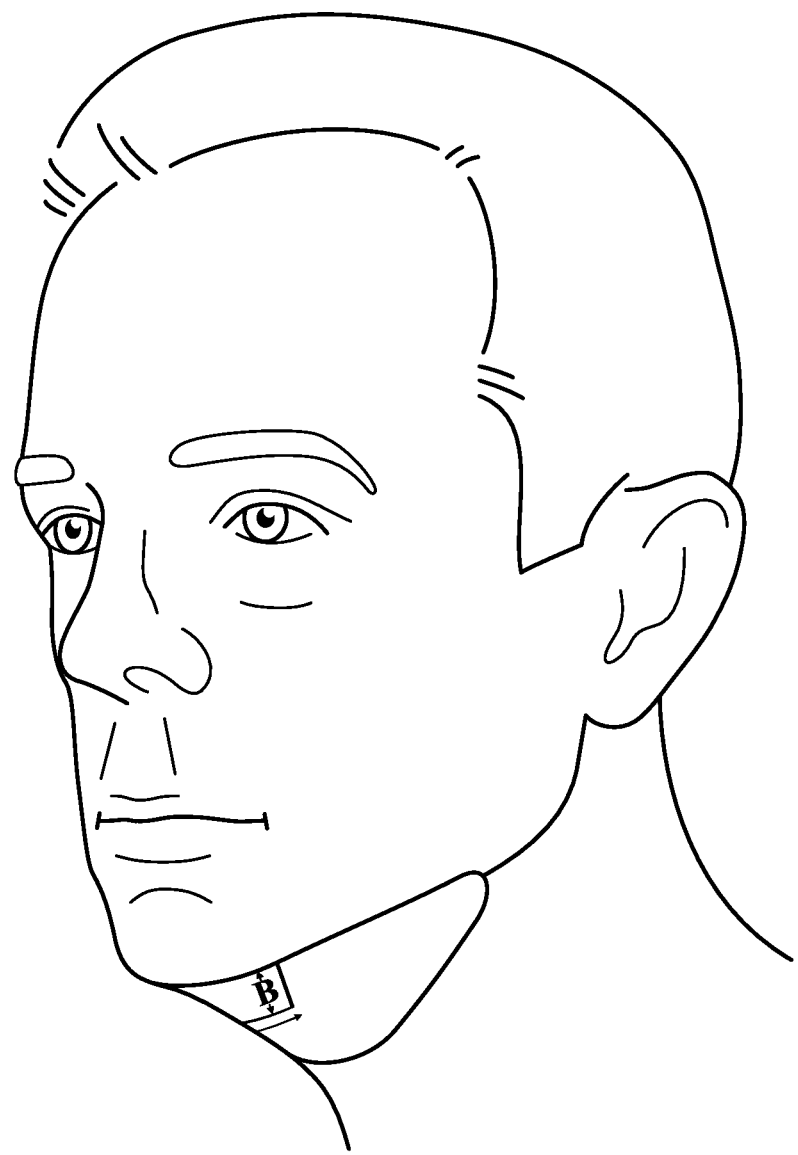

FIG. 160C is a left-front perspective view of a patient with a horizontal fractional resection skin resection area superimposed on a target area, under an embodiment.

Figure 161A:
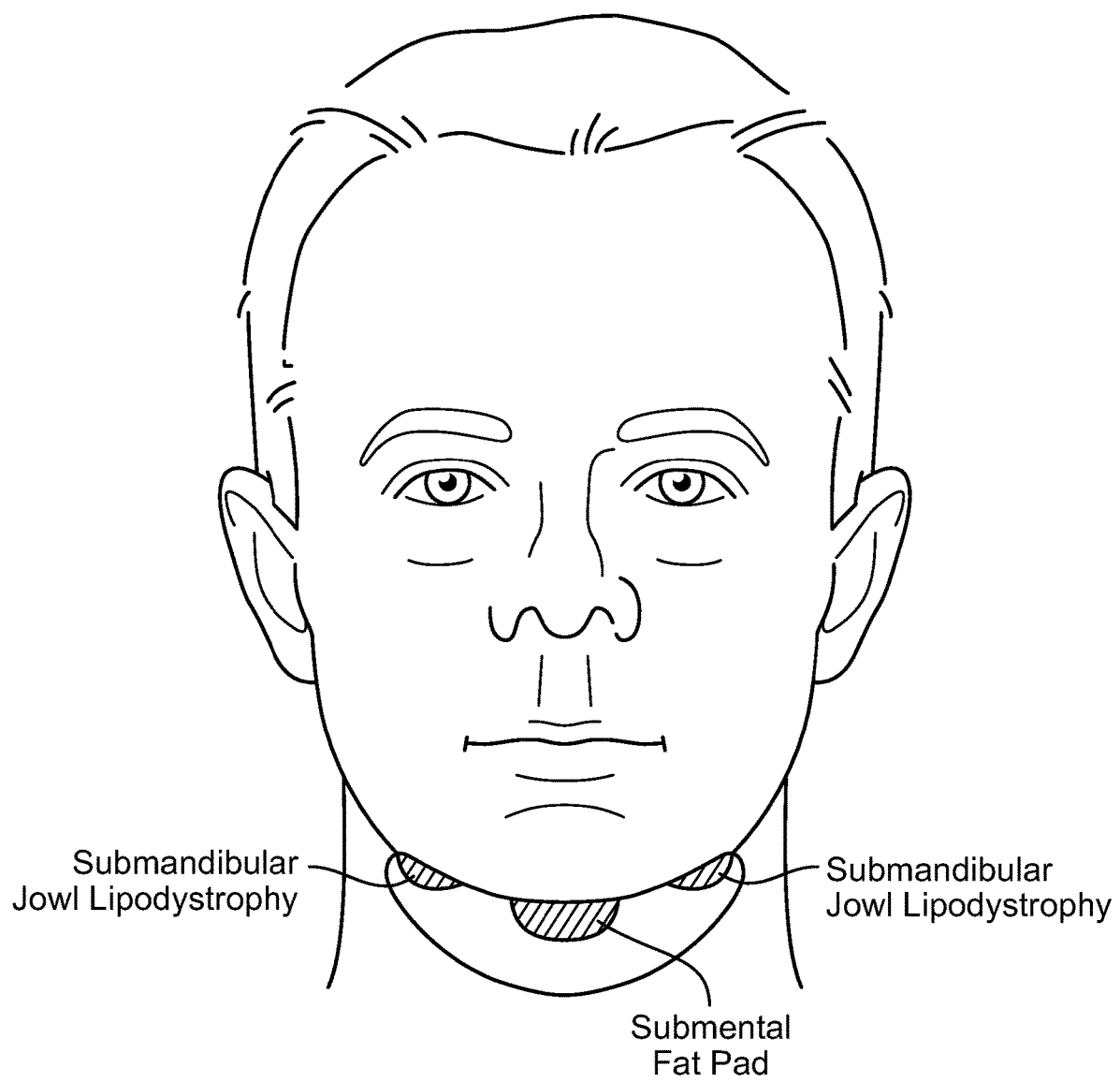

FIG. 161A is a front perspective view of topographical markings of a patient (labels added for clarity) for treatment of skin laxity of the neck and lipodystrophy of the submentum and jowls, under an embodiment.

Figure 161B:
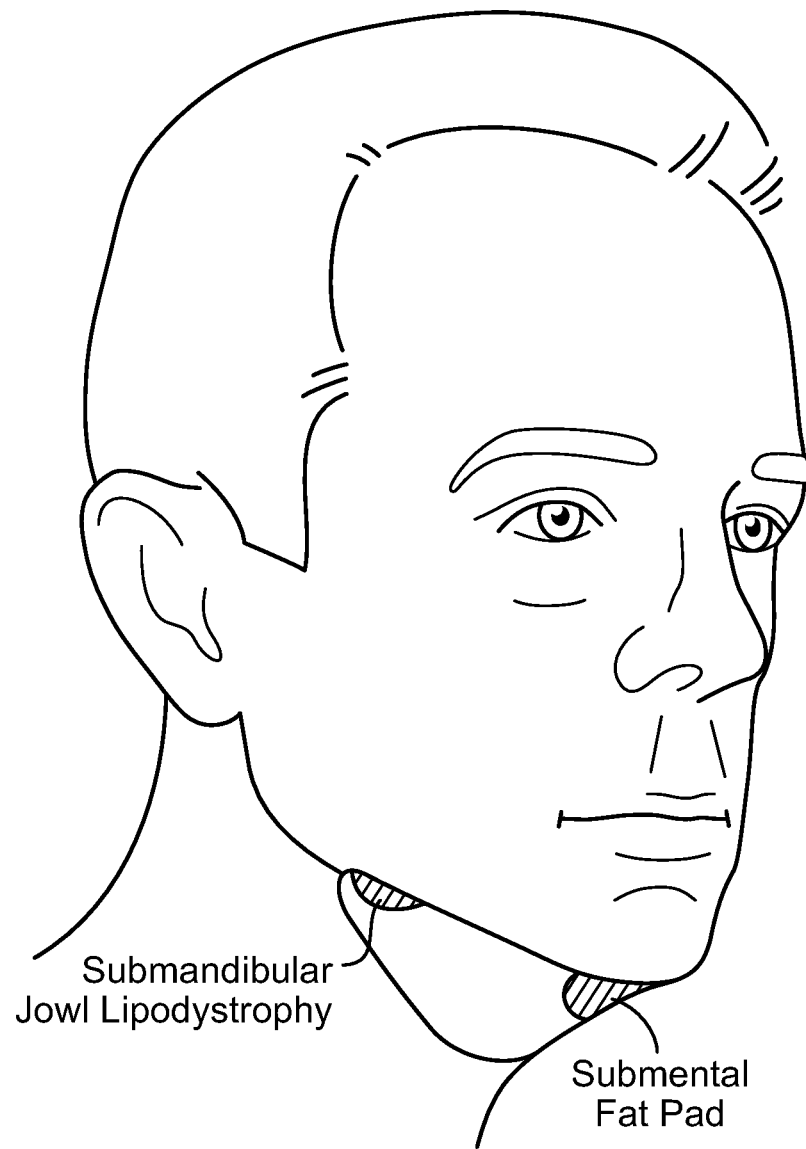

FIG. 161B is a right-front perspective view of topographical markings of a patient (labels added for clarity) for treatment of skin laxity of the neck and lipodystrophy of the submentum and jowls, under an embodiment.

Figure 161C:
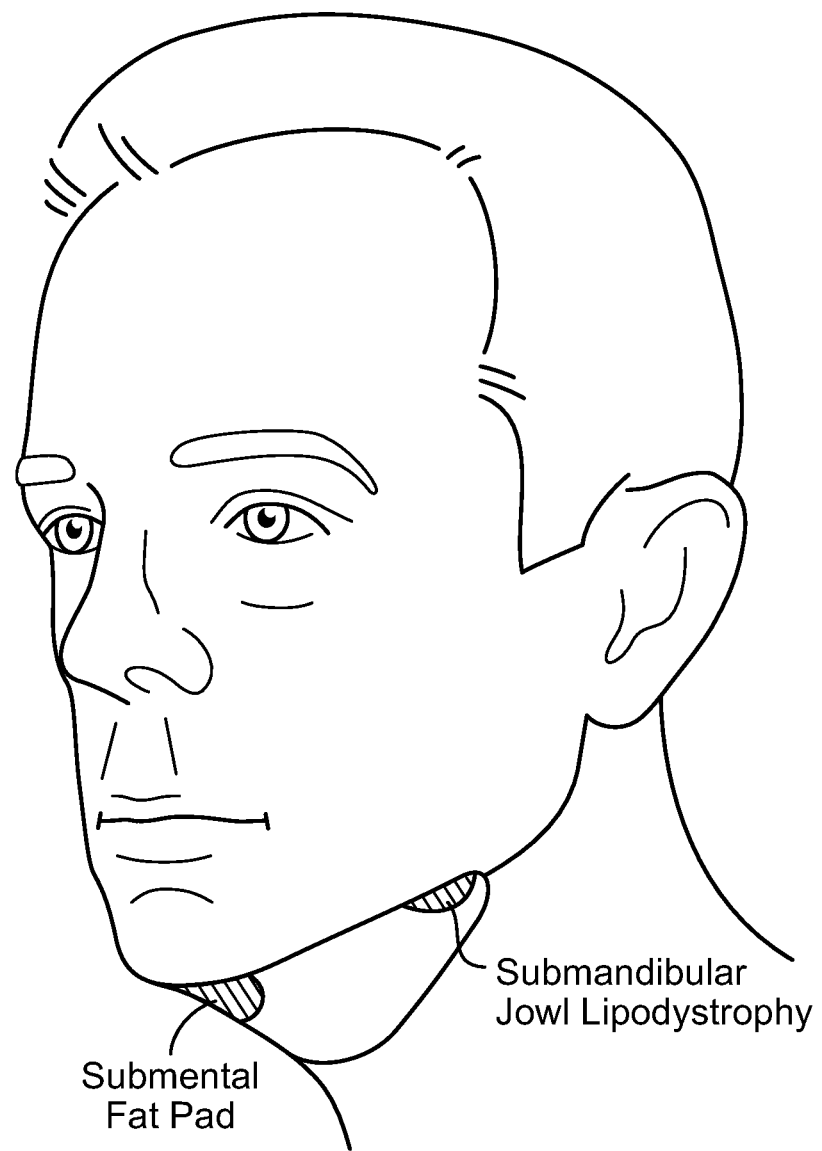

FIG. 161C is a left-front perspective view of topographical markings of a patient (labels added for clarity) for treatment of skin laxity of the neck and lipodystrophy of the submentum and jowls, under an embodiment.

Figure 162:
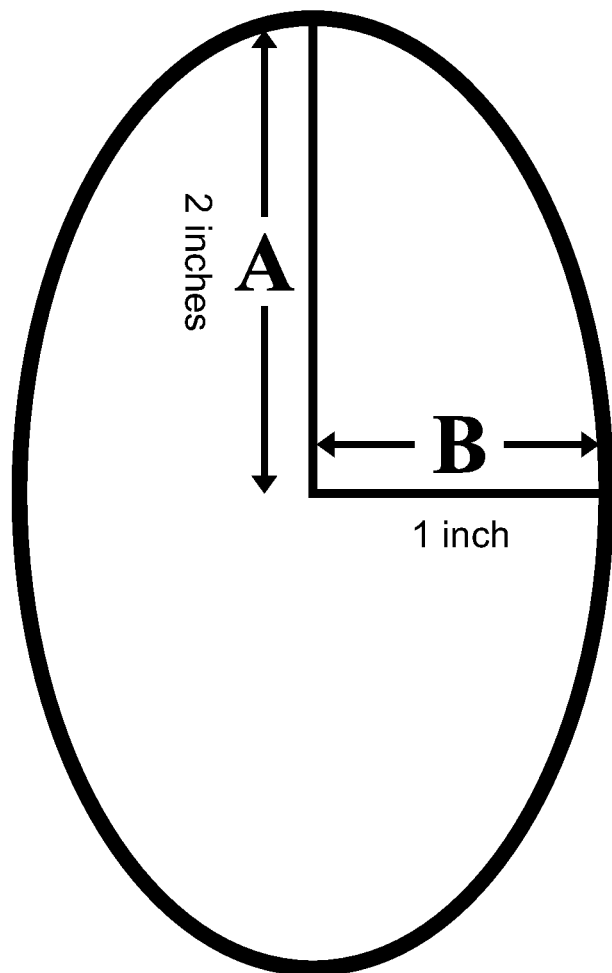

FIG. 162 shows a vertical fractional skin resection area (Technique 1), under an embodiment.

Figure 163:
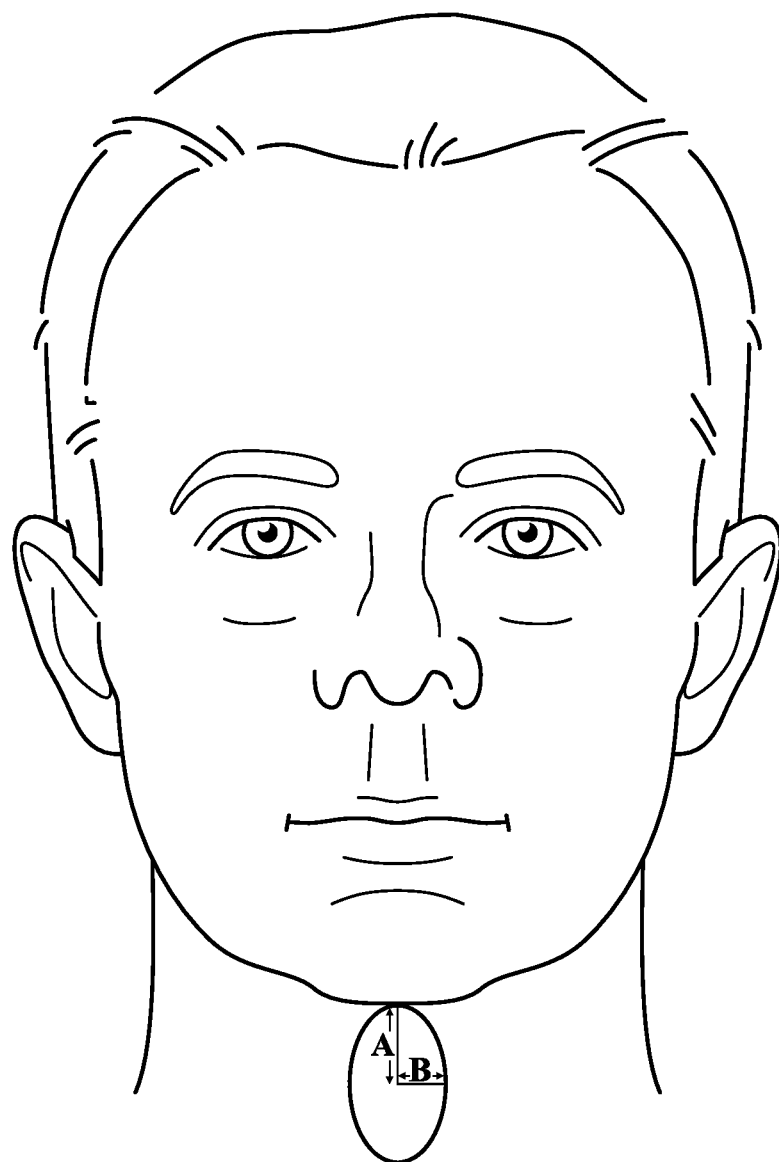

FIG. 163 shows a vertical fractional skin resection area (Technique 1) as applied to a target area of a patient, under an embodiment.

Figure 164:
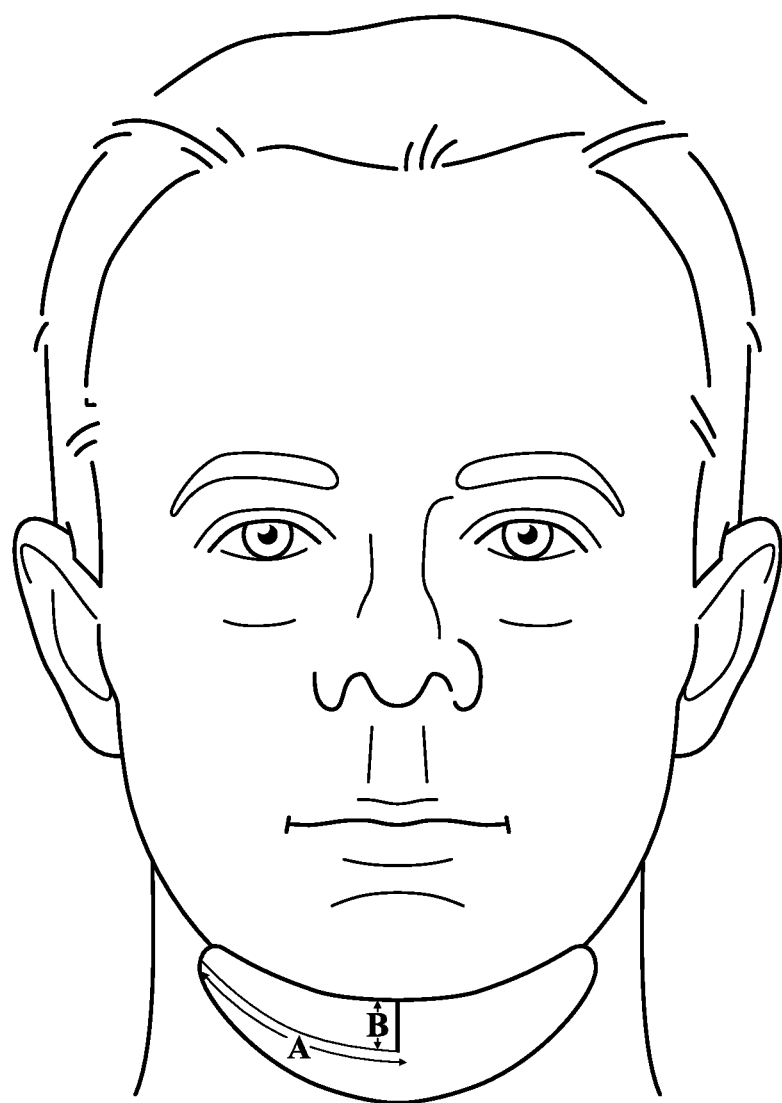

FIG. 164 shows a horizontal fractional skin resection area (Technique 2) as applied to a target area of a patient, under an embodiment.

FIG. 165A is a table detailing procedural components of fractional scar reduction of a linear scar, under an embodiment.

FIG. 165B is a table detailing procedural components of fractional scar reduction of a wide scar (hypotrophic, hypertrophic and scar contracture), under an embodiment.

FIG. 165C is a table detailing procedural components of fractional scar reduction of an acne scar, under an embodiment.

FIG. 165D is a table detailing procedural components of fractional scar reduction of an incisional scar from a primary excisional skin defect, under an embodiment.

Figure 166:
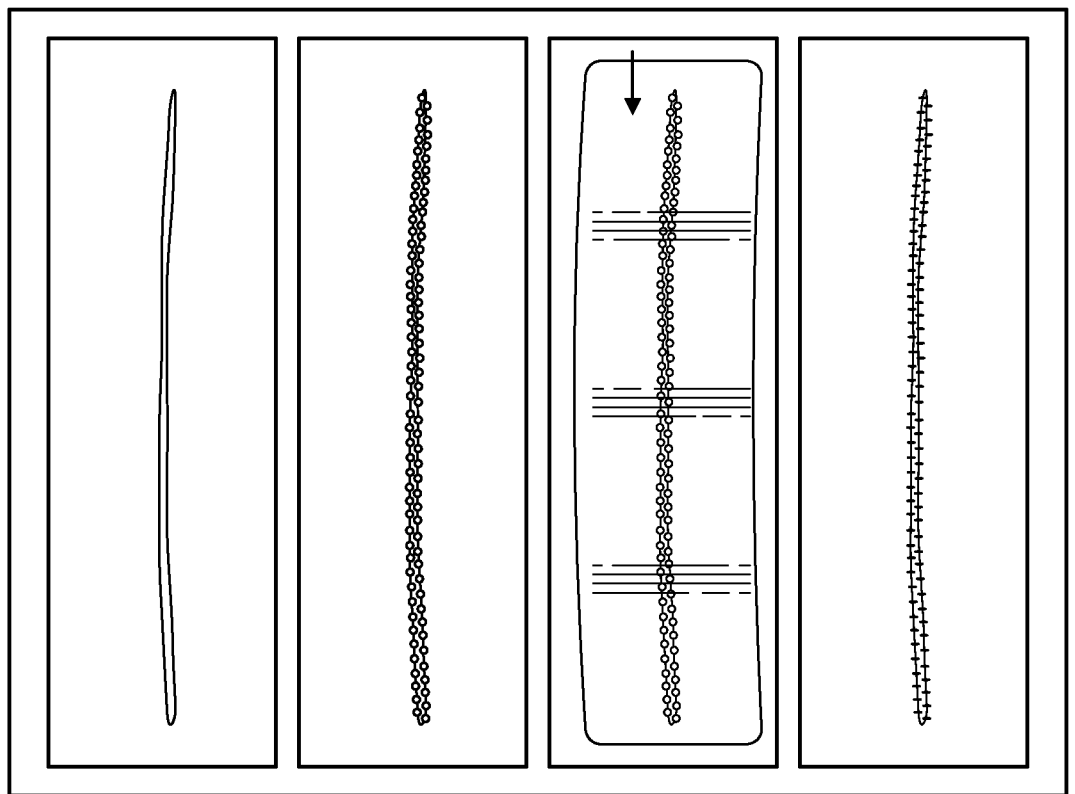

FIG. 166 shows a sequence of images (left-to-right) showing a scar, fractional resection of the scar, directed closure (direction of arrow) of the fractionally resected scar, and the scar post-procedure, under an embodiment.

Figure 167:
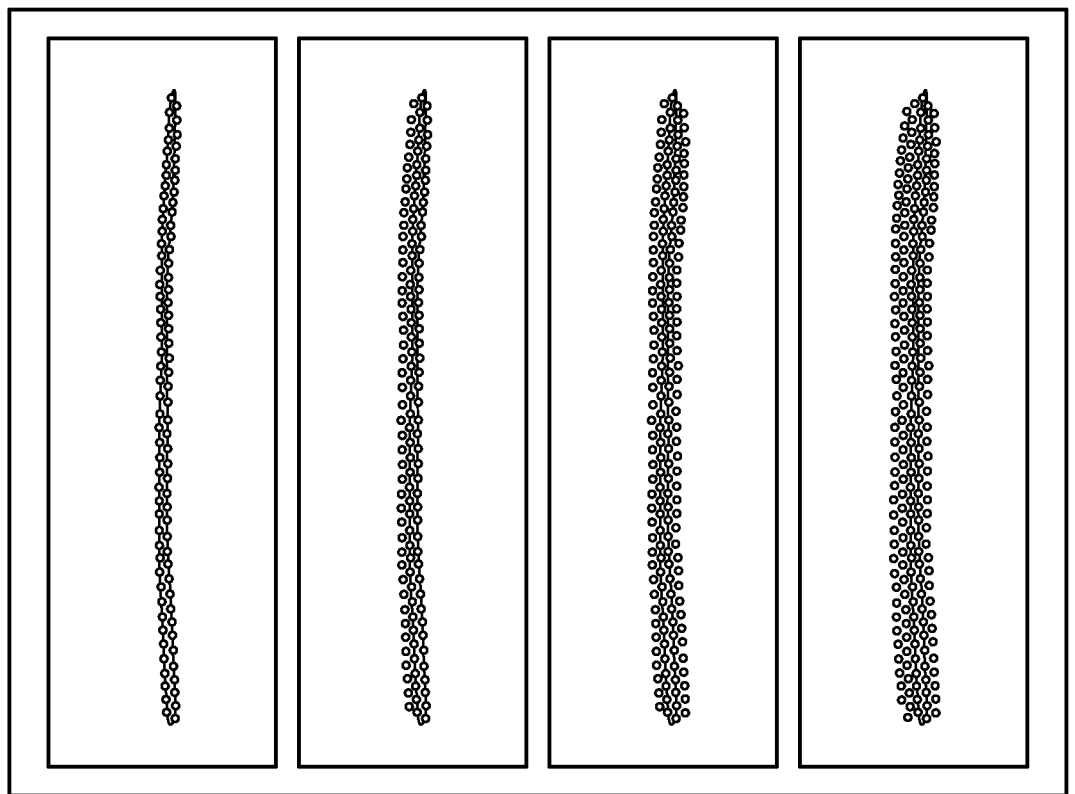

FIG. 167 shows a sequence of images (left-to-right) showing the addition of progressively more fractional resection areas for additional de-delineation of the scar, under an embodiment.

FIG. 168 shows a pre-op image (top left) and post-op image (top right) of a hypertrophic scar on the left hip, as well as an image (bottom) of the fractional scar revision procedure, under an embodiment.

Figure 169:
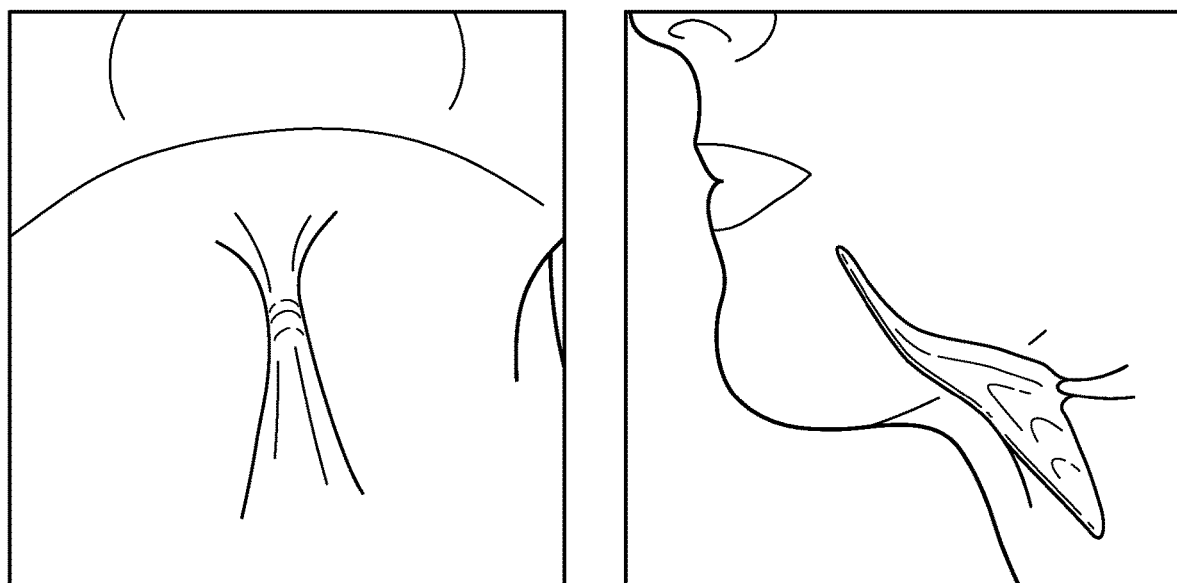

FIG. 169 shows front perspective (left) and front-left perspective (right) images of wider cervical scar contractures, under an embodiment.

Figure 170:
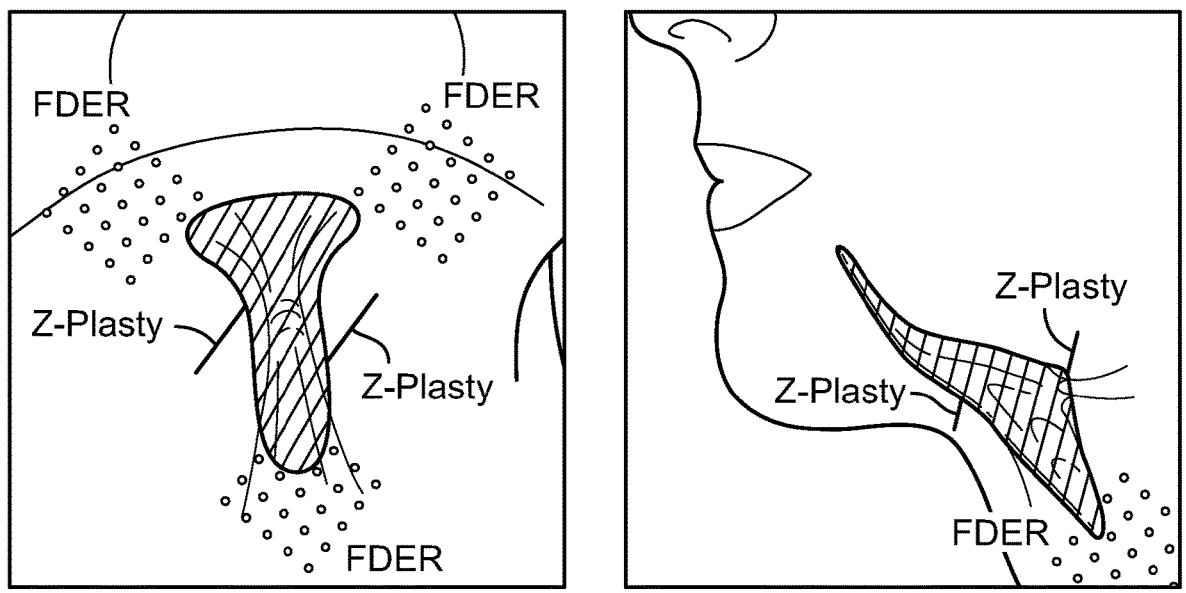

FIG. 170 shows front perspective (left) and front-left perspective (right) images of preoperative cervical scar contracture release, under an embodiment.

Figure 171:
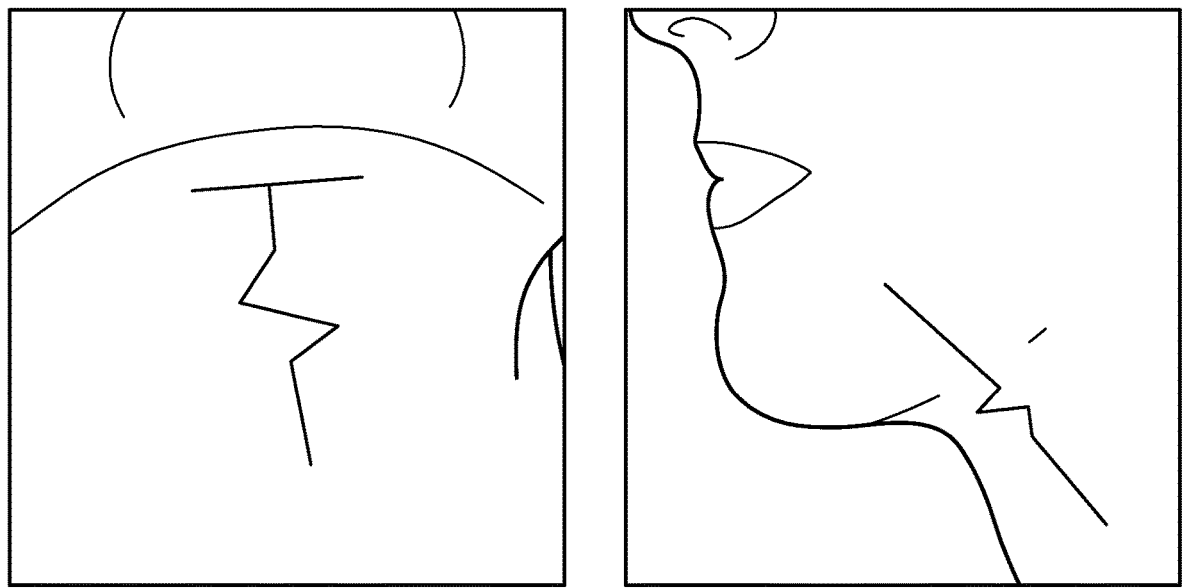

FIG. 171 shows front perspective (left) and front-left perspective (right) images of postoperative cervical scar contracture release, under an embodiment.

Figure 172:
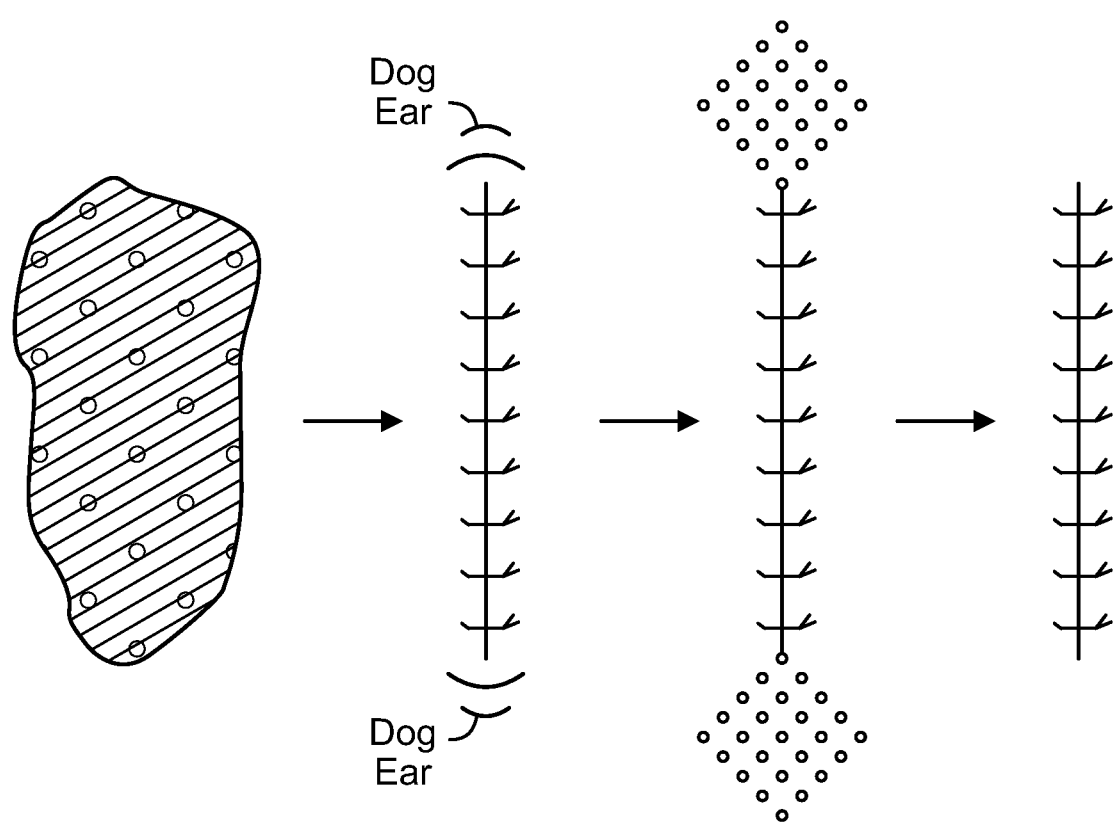

FIG. 172 is a sequence (left-to-right) showing a scar pre-op with the area to be resected indicated (diagonal markings), the resected scar closed with "dog-ears", fractional resection of "dog-ears", and post-op scar region, under an embodiment.

Figure 173:
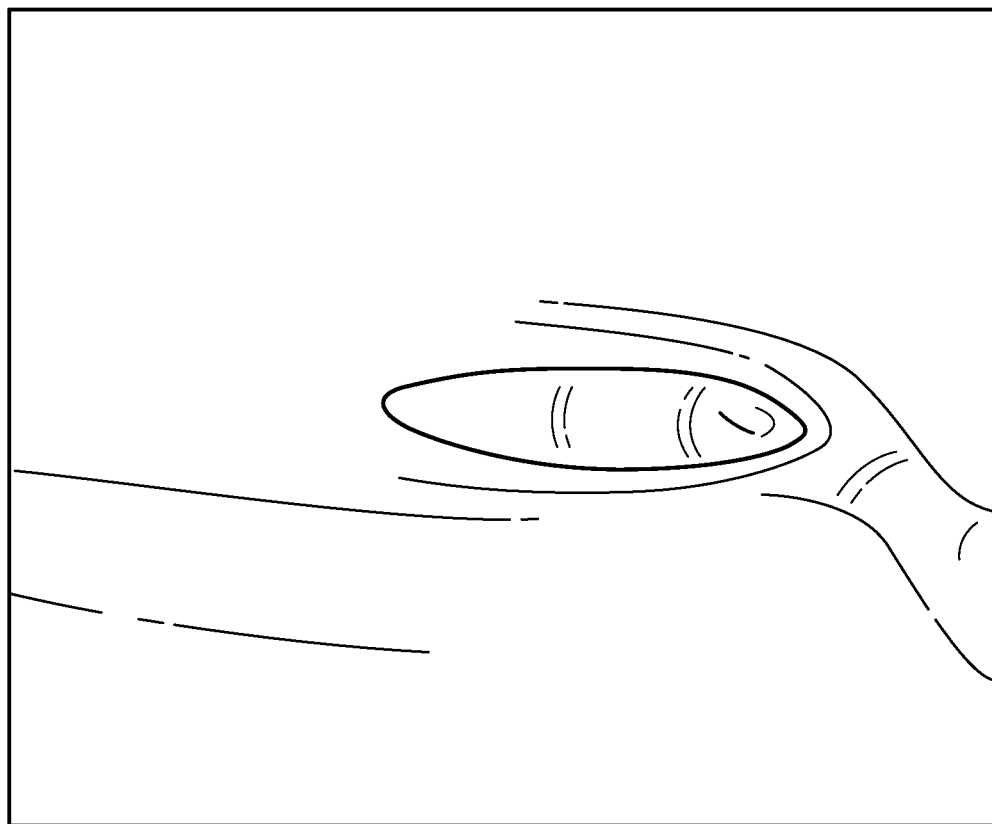
Figure 174:
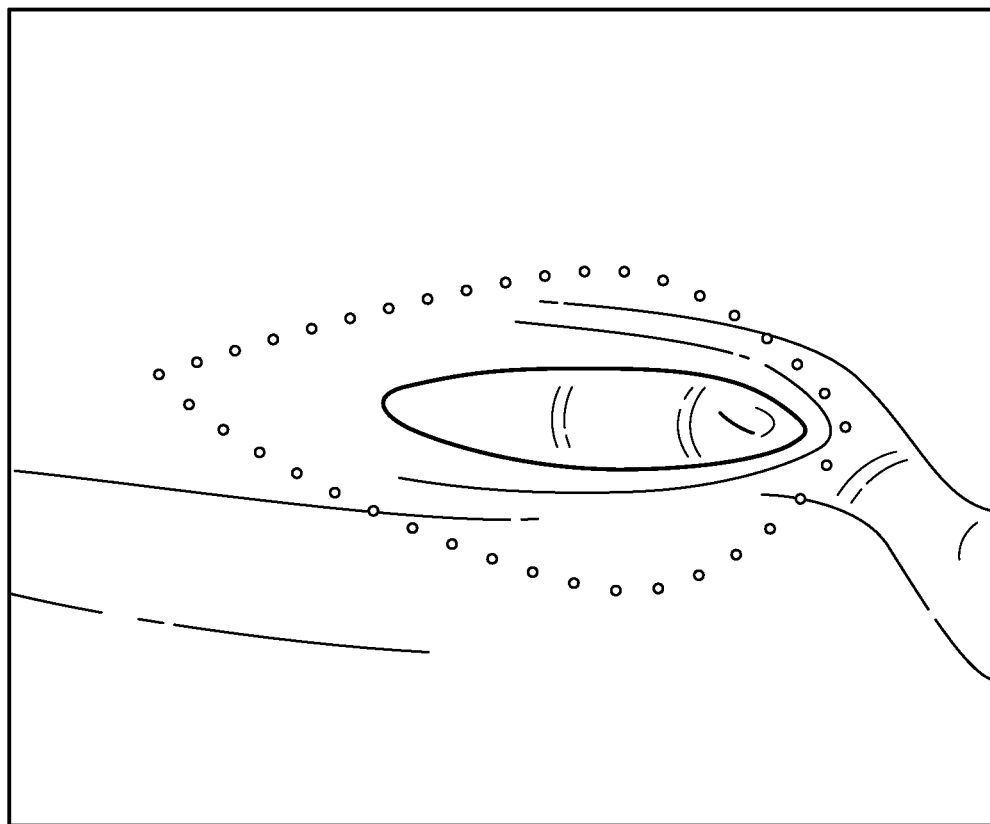

FIGS. 173 and 174 are images (pre-op) of a wide depressed scar showing the area involved in the resection (outlined), under an embodiment.

Figure 175:
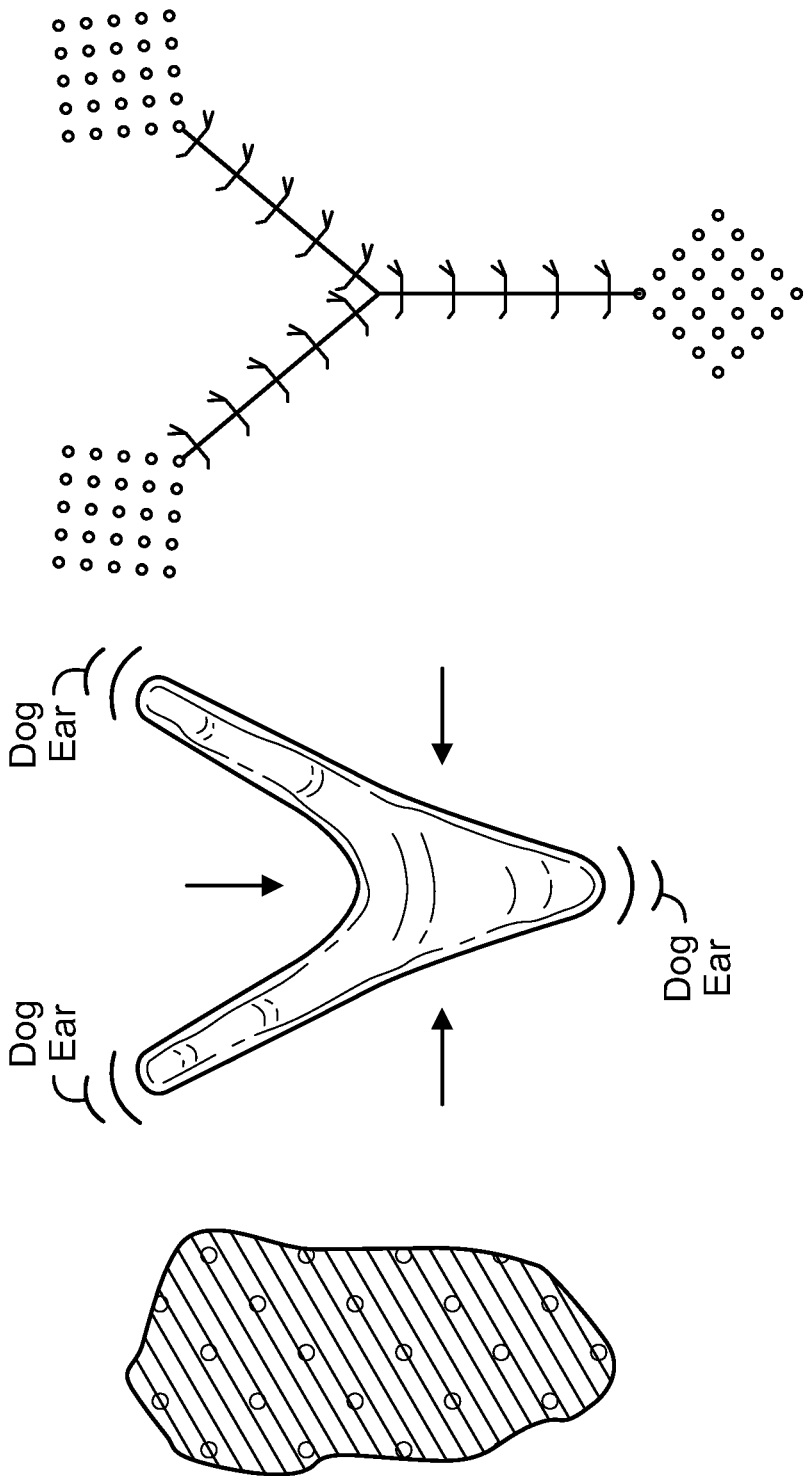

FIG. 175 is a sequence (left-to-right) showing a scar pre-op with the area to be resected indicated (diagonal markings), the V-Y advancement layered closure technique with "dog-ears", and fractional resection of "dog-ears", under an embodiment.

FIG. 176A is a table detailing procedural components of fractional tattoo removal of a solid tattoo, under an embodiment.

FIG. 176B is a table detailing procedural components of fractional tattoo removal of a cursive or non-solid tattoo, under an embodiment.

FIG. 176C is a table detailing procedural components of fractional tattoo removal of a large tattoo, under an embodiment.

Figure 177:
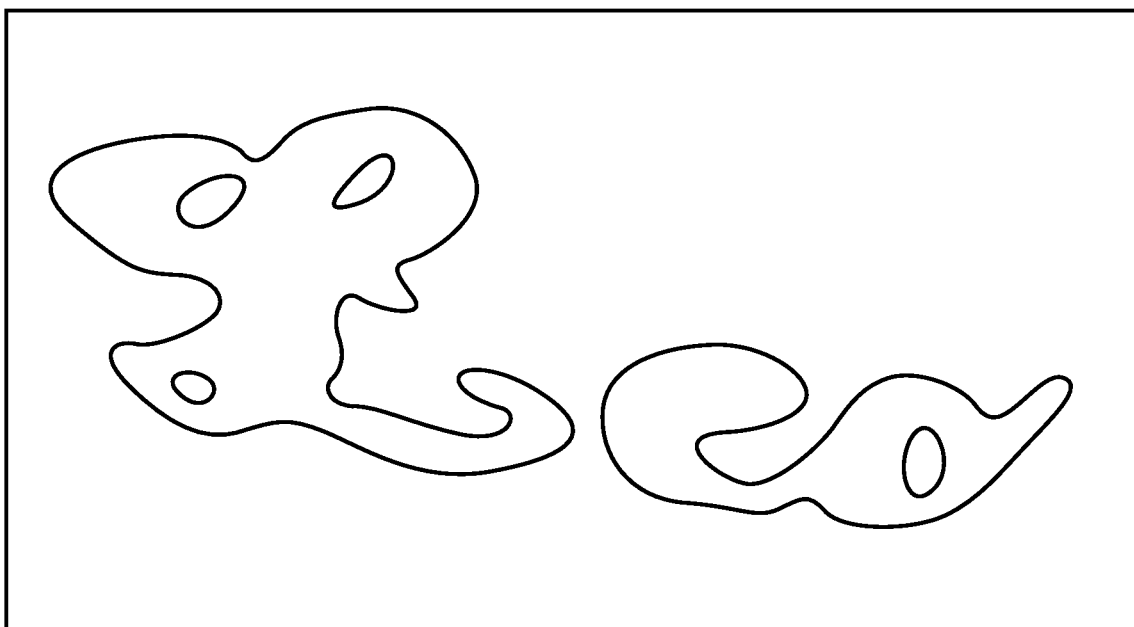

FIG. 177 is a pre-op image of a subject tattoo, under an embodiment.

Figure 178:
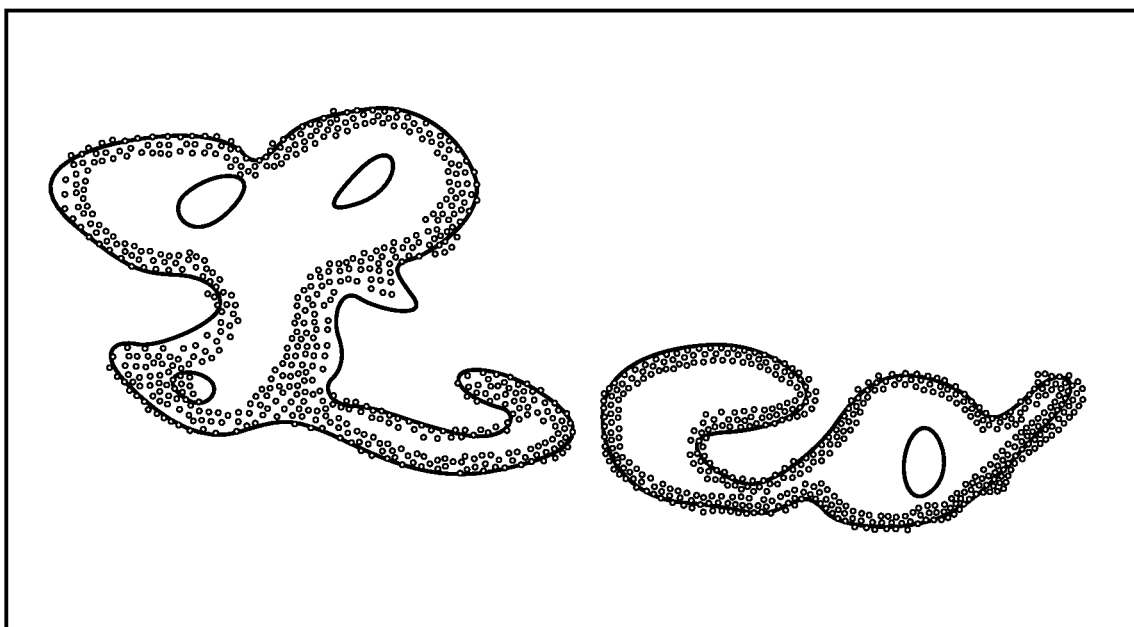

FIG. 178 is an image showing application of fractional resection to the tattoo, under an embodiment.

Figure 179:
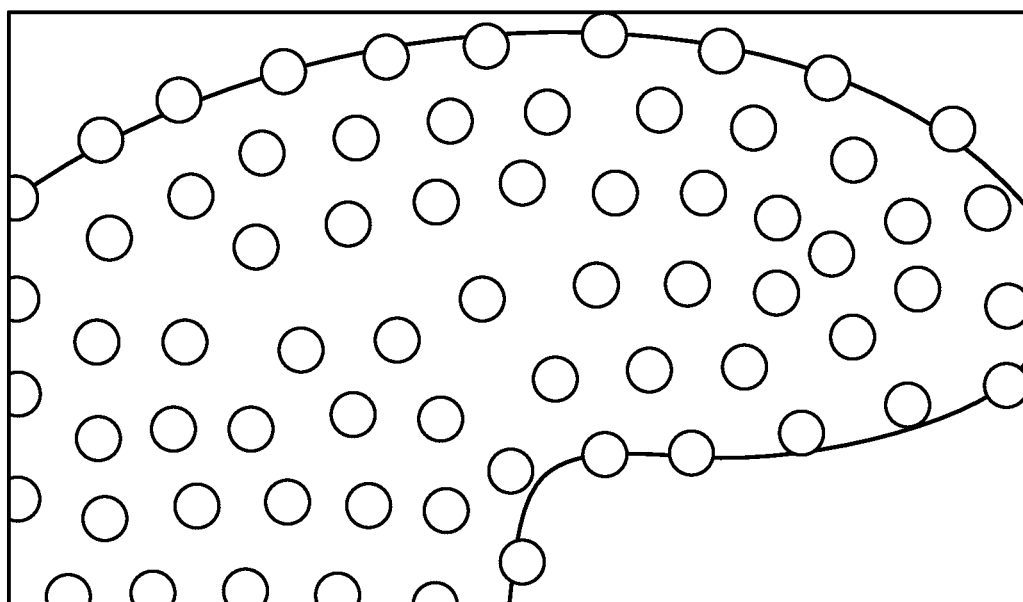

FIG. 179 is a close up image of the fractional field applied to the tattoo, under an embodiment.

Figure 180:
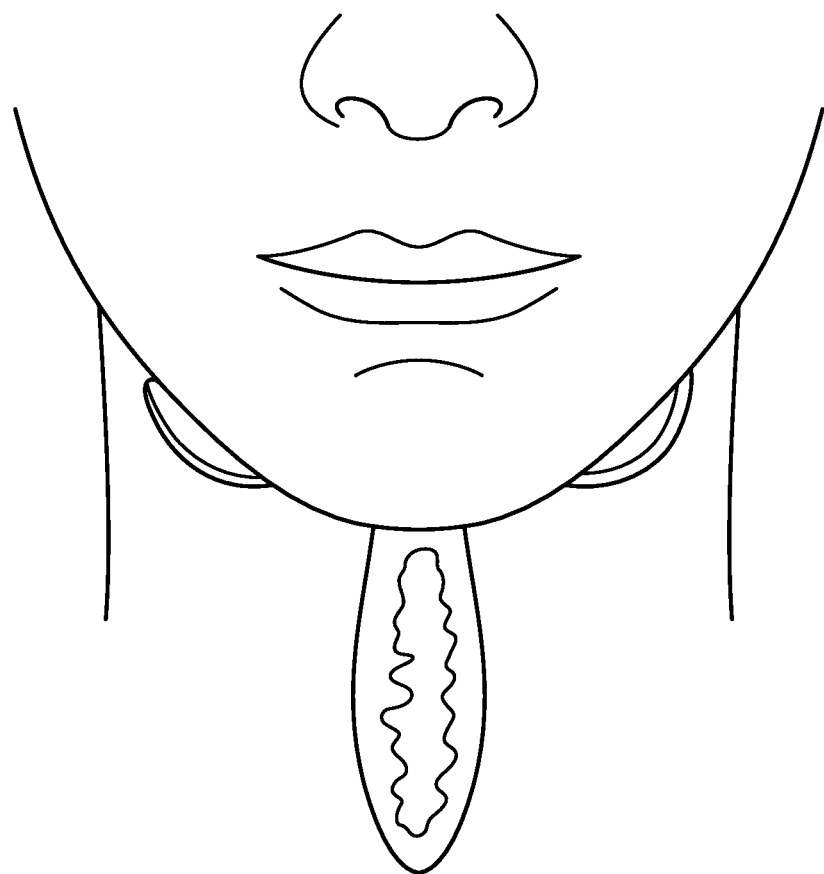

FIG. 180 shows vertically and horizontally aligned example fractional fields and corresponding vertical and horizontal deformities, under an embodiment.

Figure 181:
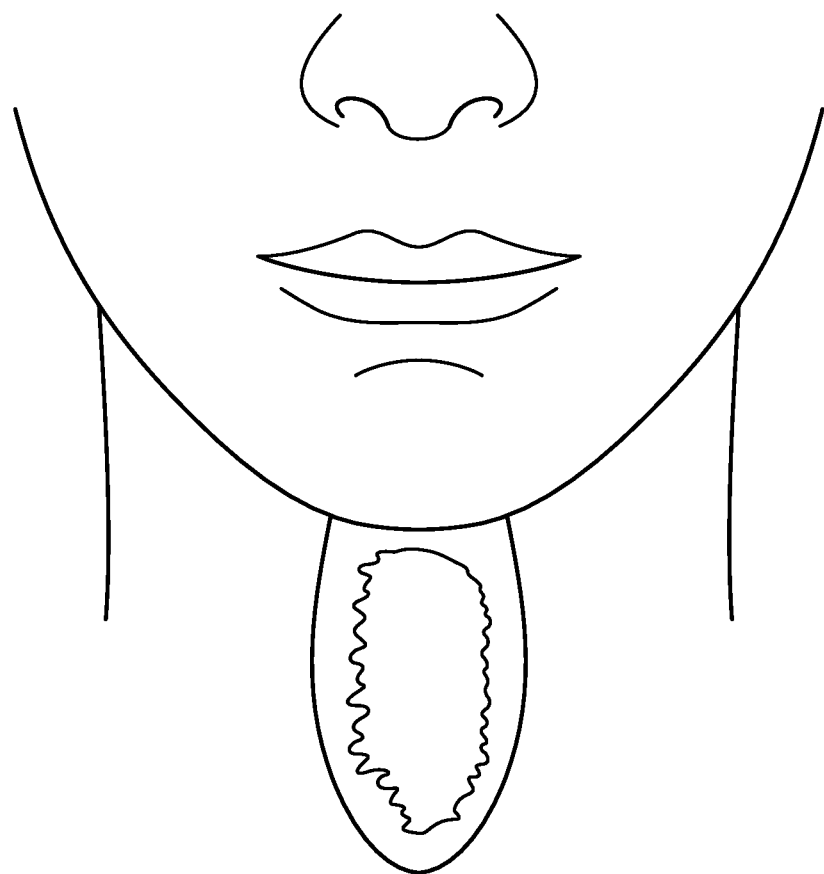

FIG. 181 shows a wider vertically aligned example fractional field with more severe skin laxity, under an embodiment.

Figure 182:
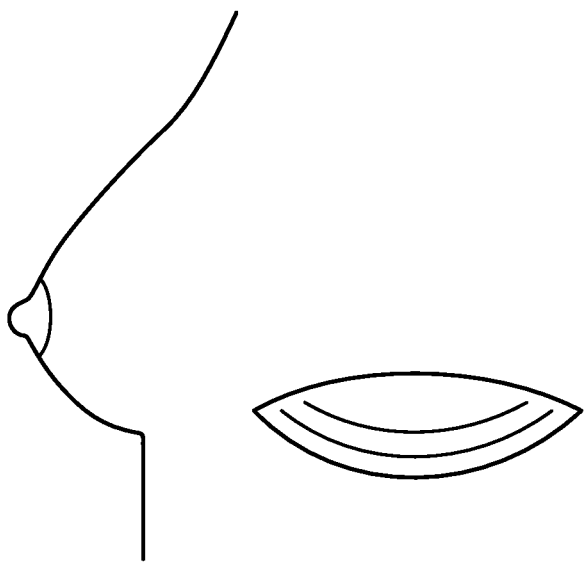

FIG. 182 shows a horizontal dependant curvilinear deformity with a horizontally aligned example fractional field, under an embodiment.

Figure 183:
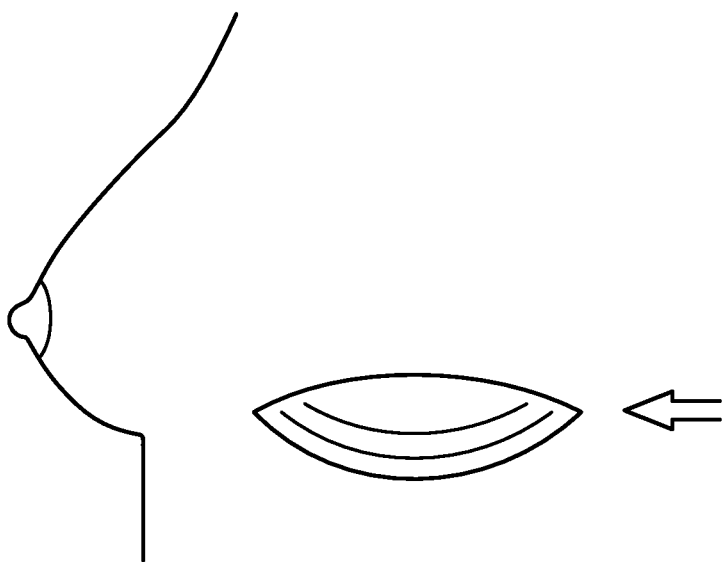

FIG. 183 shows a horizontal dependant curvilinear deformity with a horizontally aligned example vector of directed closure, under an embodiment.

Figure 184:
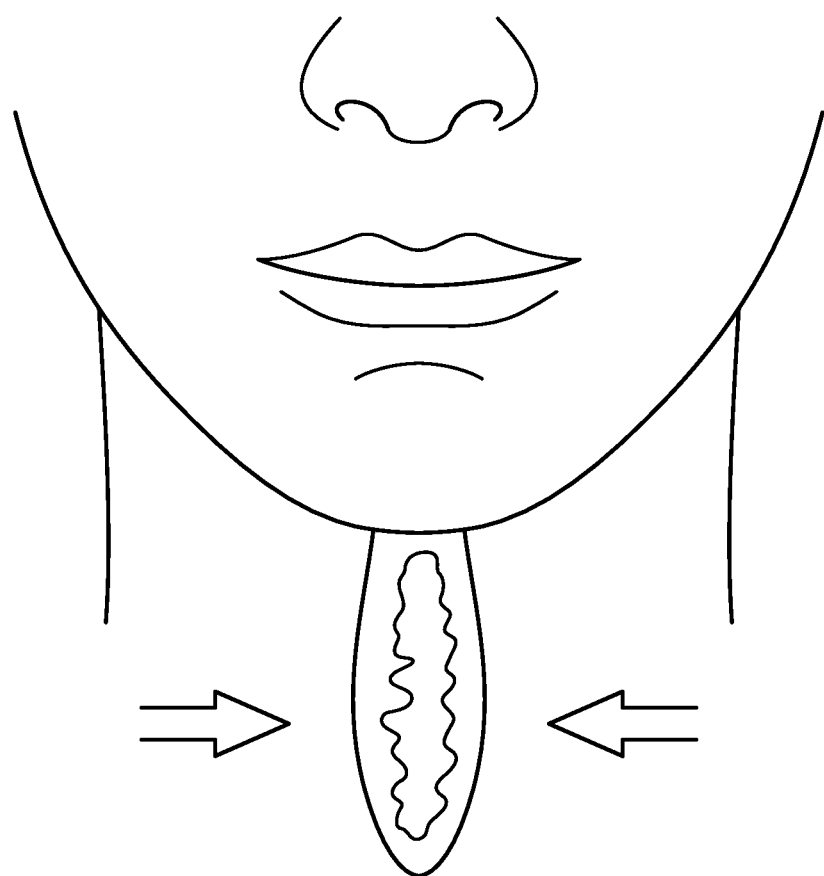

FIG. 184 shows an example fractional field vertically aligned with the vertical axis of the submental deformity, and having a horizontally aligned vector of directed closure at a right angle to the vertical axis of the fractional field, under an embodiment.

Figure 185:
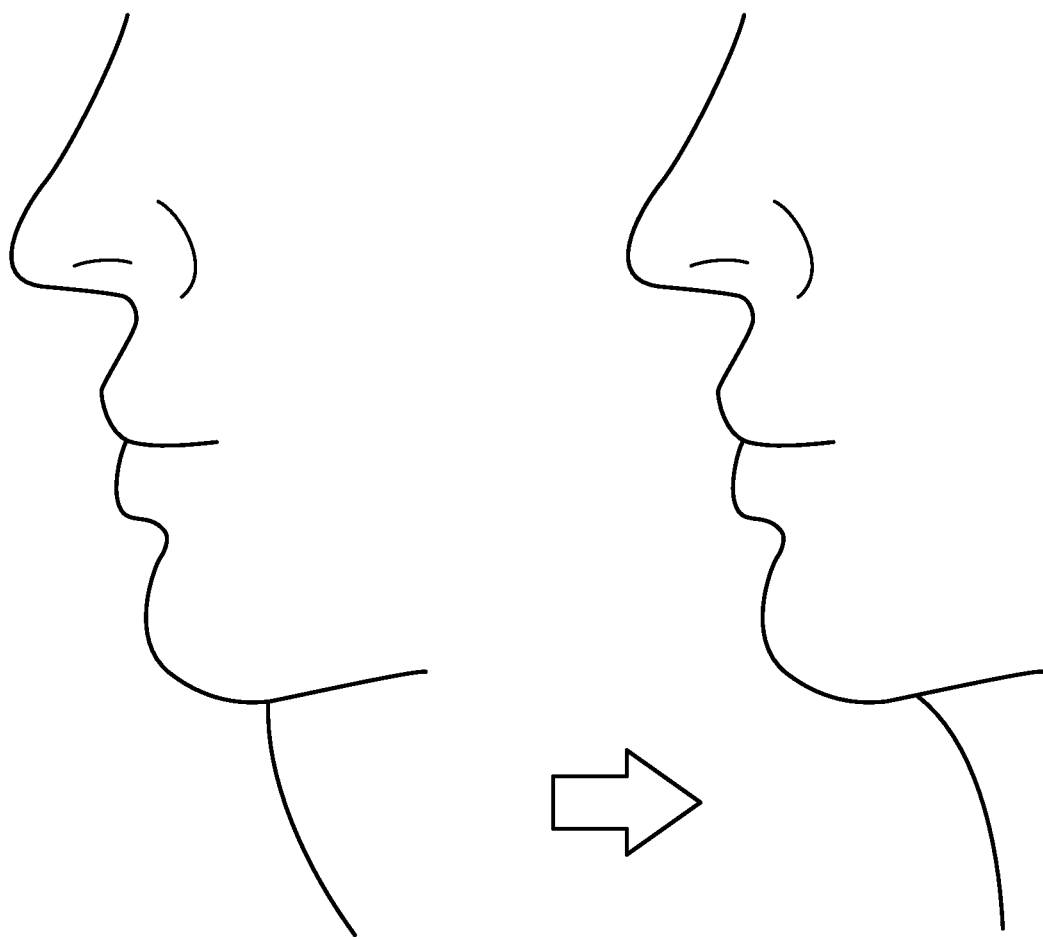

FIG. 185 shows a vertical deformity of the submentum requiring lengthening in the vertical axis and tightening in the horizontal axis (left), and the desired goal of the cervical mandibular angle having enhanced definition (right), under an embodiment.

Figure 186:
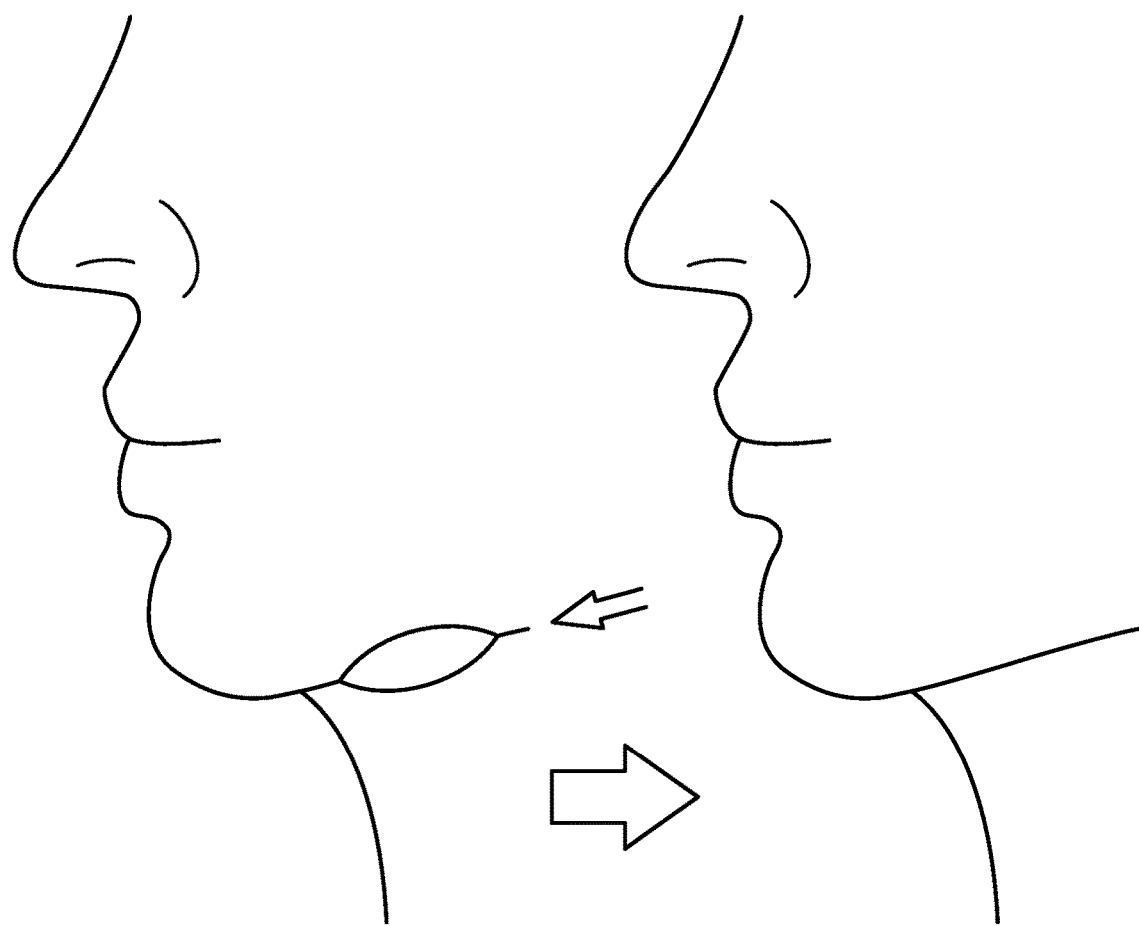

FIG. 186 shows a horizontal dependent curvilinear deformity with horizontally aligned fractional field and horizontal vector of directed closure (left), and the desired goal following raising and straightening of the curvilinear deformity in line with the jaw margin (right), under an embodiment.

Figure 187:
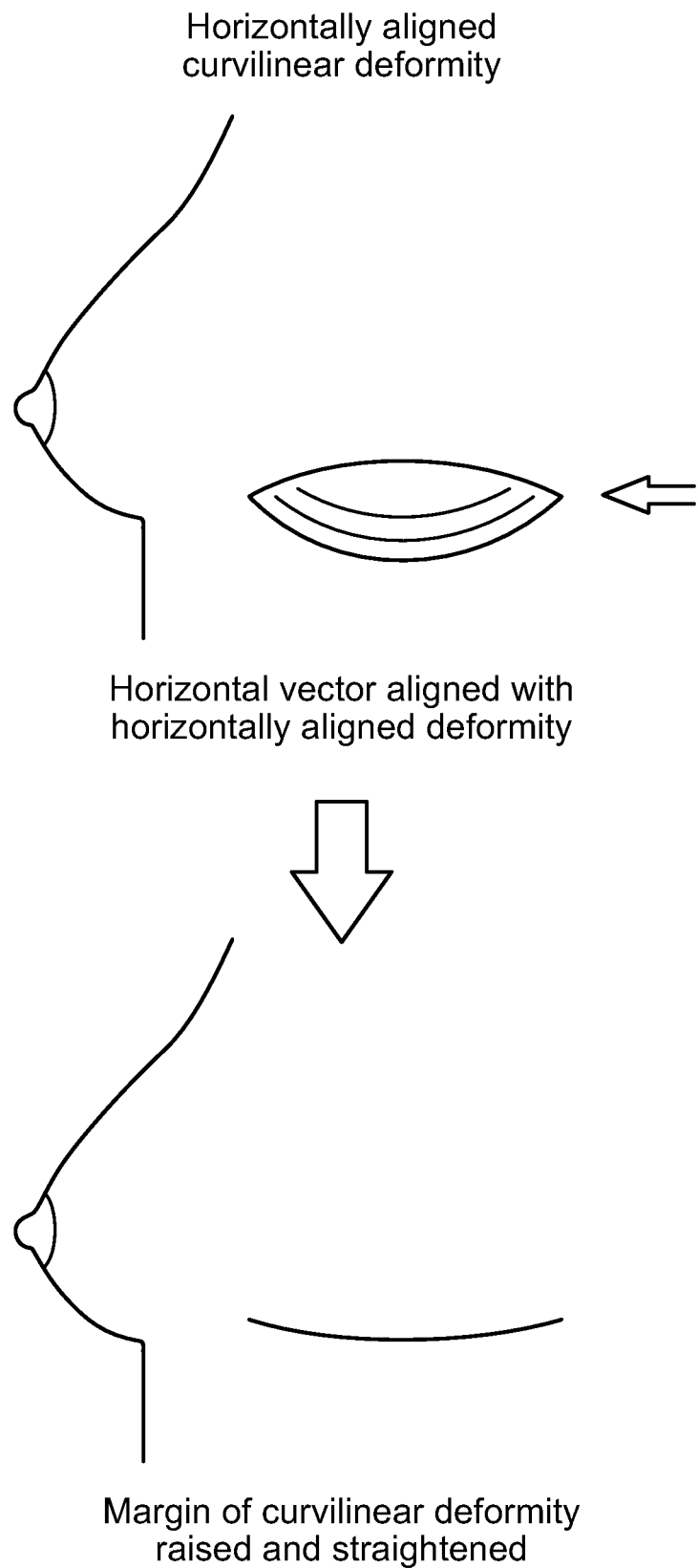

FIG. 187 shows the horizontally aligned fractional field (encompassing the horizontally aligned deformity) with a horizontal vector of directed closure (top), and the desired goal following raising and straightening of the margin of the curvilinear deformity (bottom), under an embodiment.

FIG. 188 shows an oblique fractional field (top), and the vector for directed closure is aligned obliquely (arrow) along the longitudinal axis of the field (bottom), under an embodiment.

FIG. 189 shows an elliptical horizontally aligned fractional field that extends from the axilla to the elbow with a vector of directed closure aligned at right angles (arrow) to the longitudinal axis of the fractional field (top), and the resulting upper arm with the raised inferior margin (bottom), under an embodiment.

FIG. 190 shows the dependent curvilinear deformity (top), the fractional field horizontally aligned to the curvilinear deformity (middle), and the vectored closure along the elongated horizontal axis of the fractional field with straightening of the margin (bottom), under an embodiment.

Figure 191:
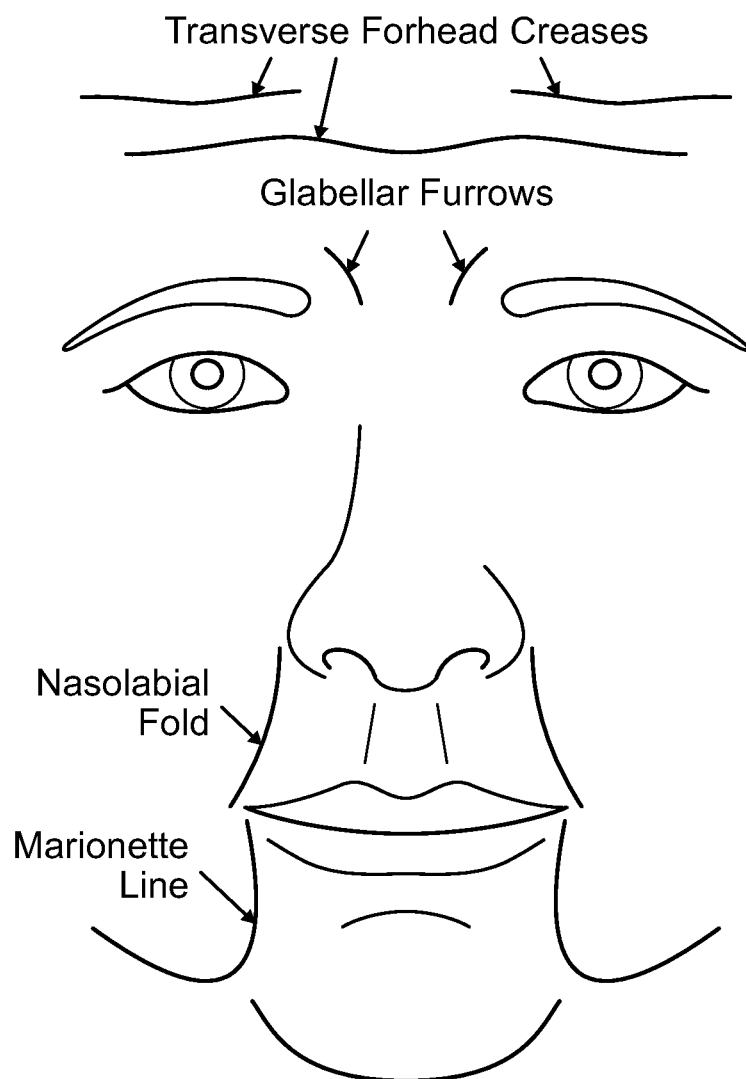

FIG. 191 shows a face having target tissue that includes, for example, furrows and folds.

Figure 192:
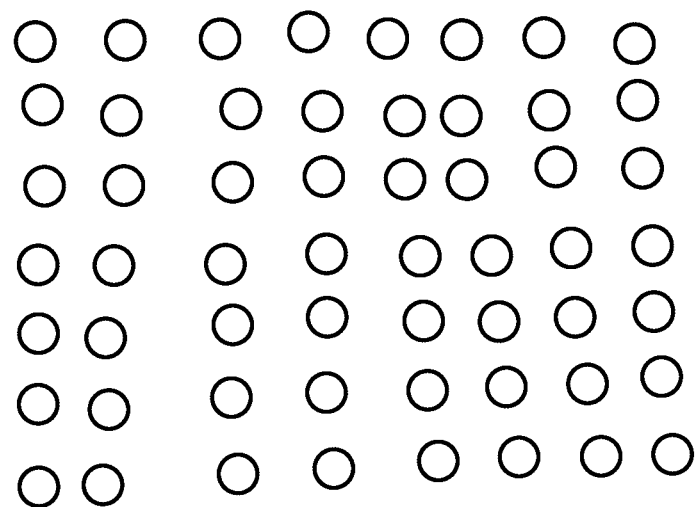

FIG. 192 shows a fractionally incised field (skin plugs insitu), under an embodiment.

Figure 193:
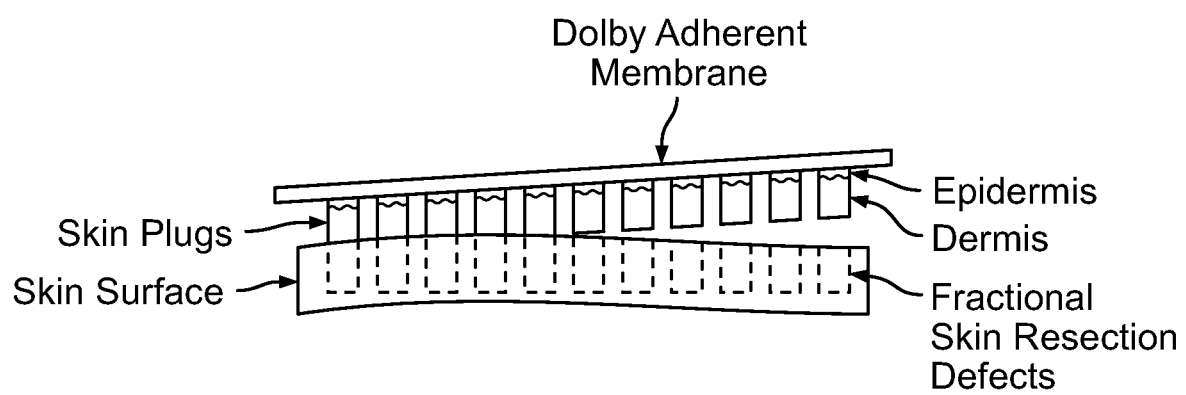

FIG. 193 is a detailed view of fractional skin resection defect harvesting, under an embodiment.

FIG. 194 shows an example with skin plugs harvested using a membrane applied directly to a drum dermatome, under an embodiment.

Figure 195:
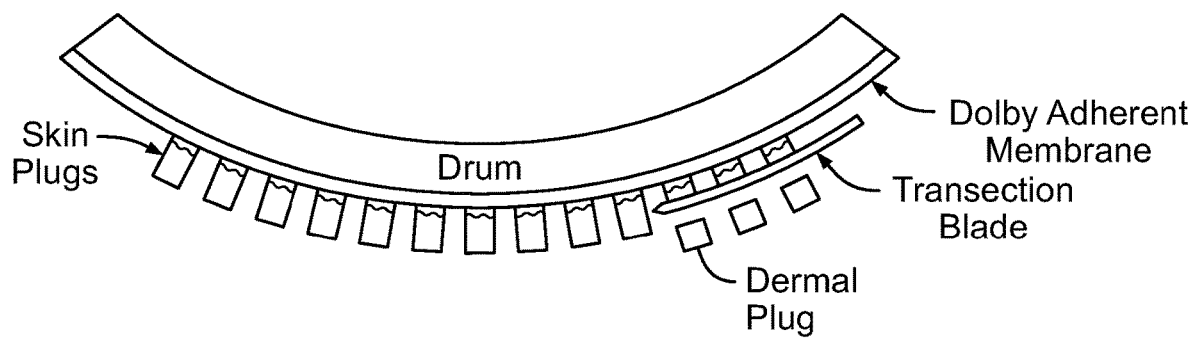

FIG. 195 shows removal of the epidermal component by transecting the skin plugs generated by the dermatome with an outrigger blade of the dermatome, under an embodiment.

Figure 196:
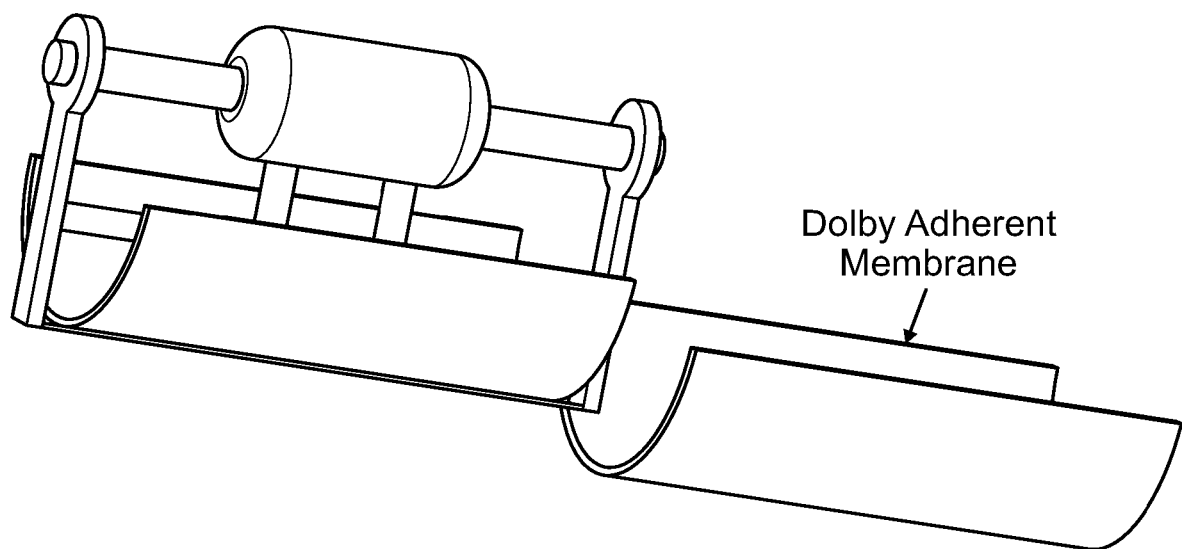

FIG. 196 shows skin plugs separately harvested onto a membrane, and the membrane is then applied to a dermatome (e.g., drum), under an embodiment.

Figure 197:
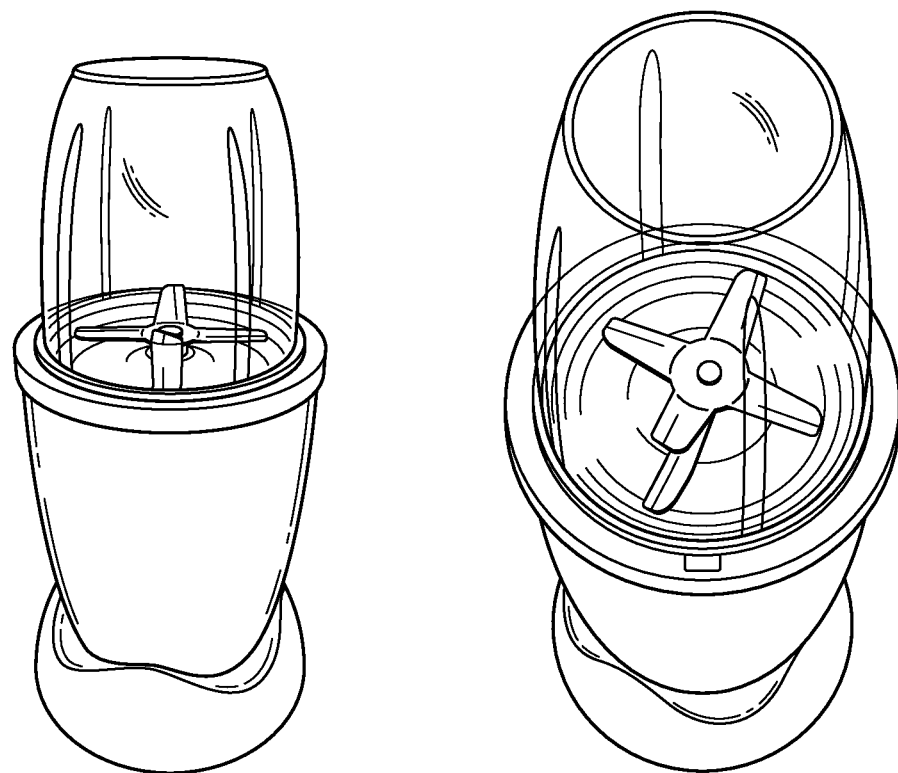

FIG. 197 shows a non-compressive moreselizer configured to mechanically mince the dermal plugs into a viscous liquid, under an embodiment.

Figure 198:
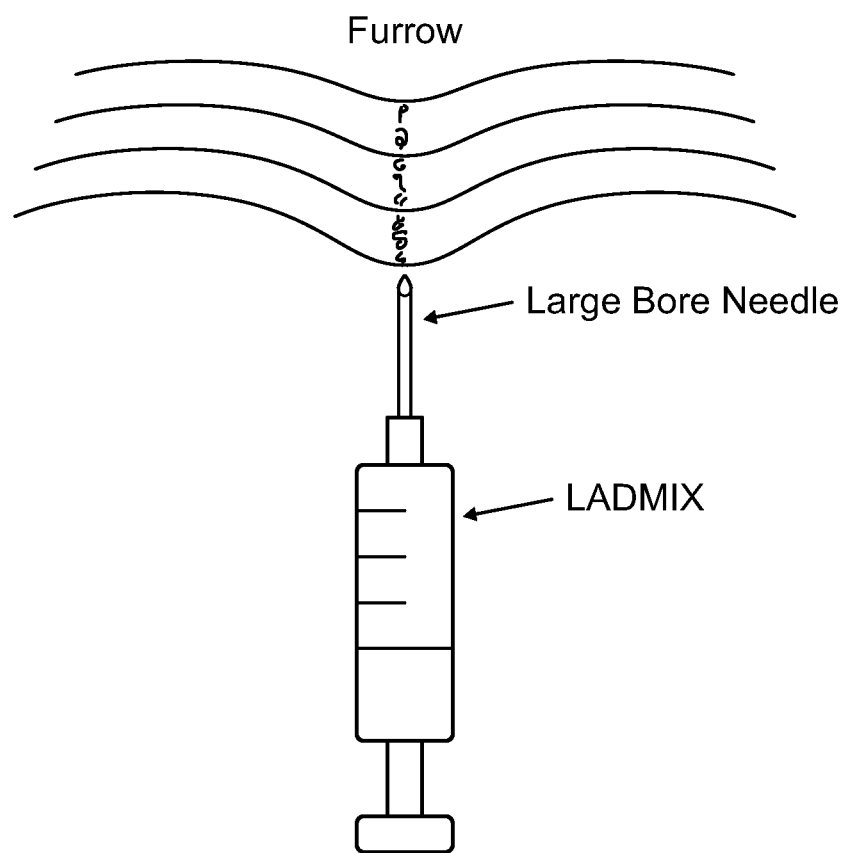

FIG. 198 shows injection of the LADMIX filler at a target tissue site, under an embodiment.

Figure 199:
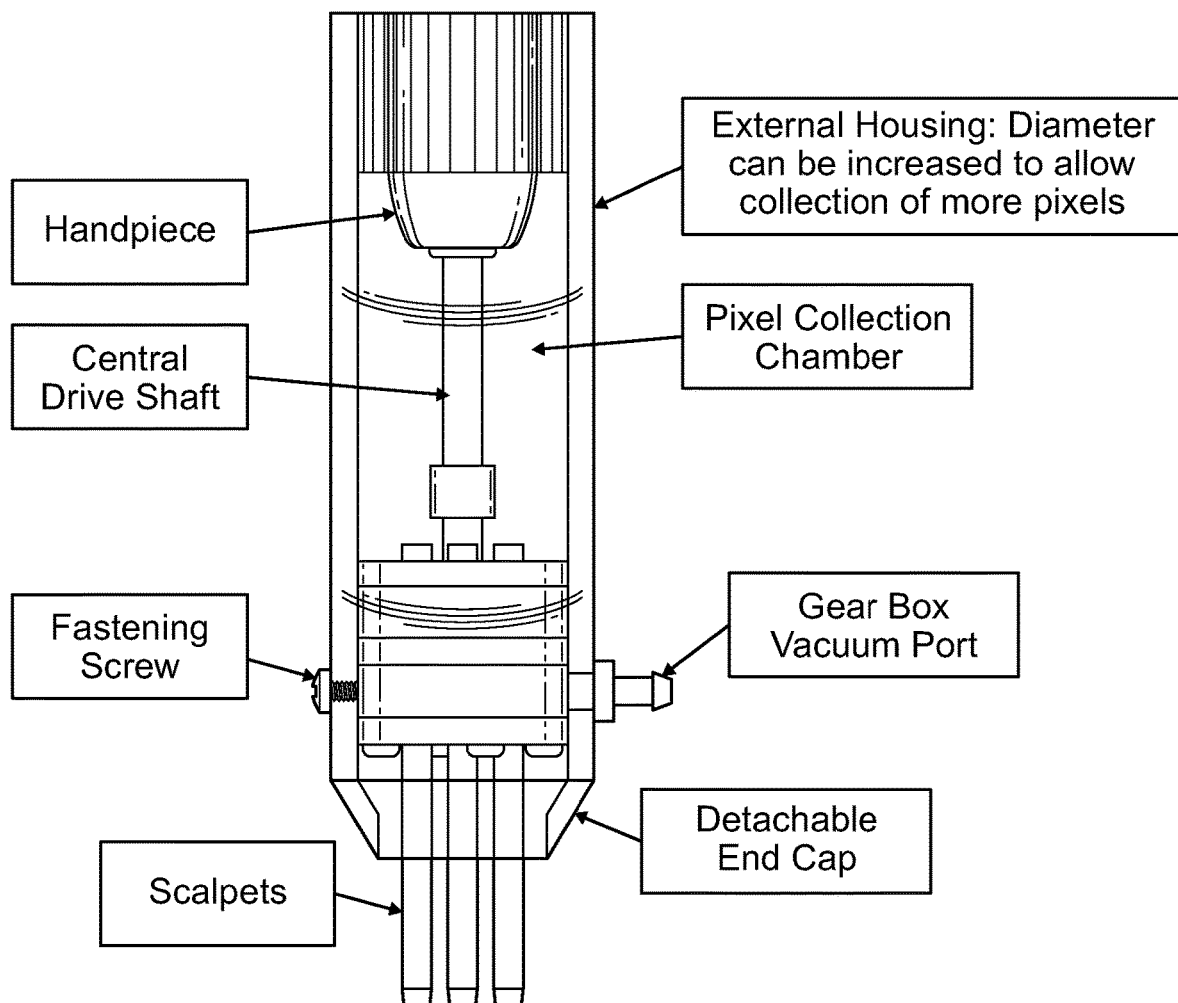

FIG. 199 shows an example of a scalpet device including a multi-functional chamber, under an embodiment.

Figure 200:
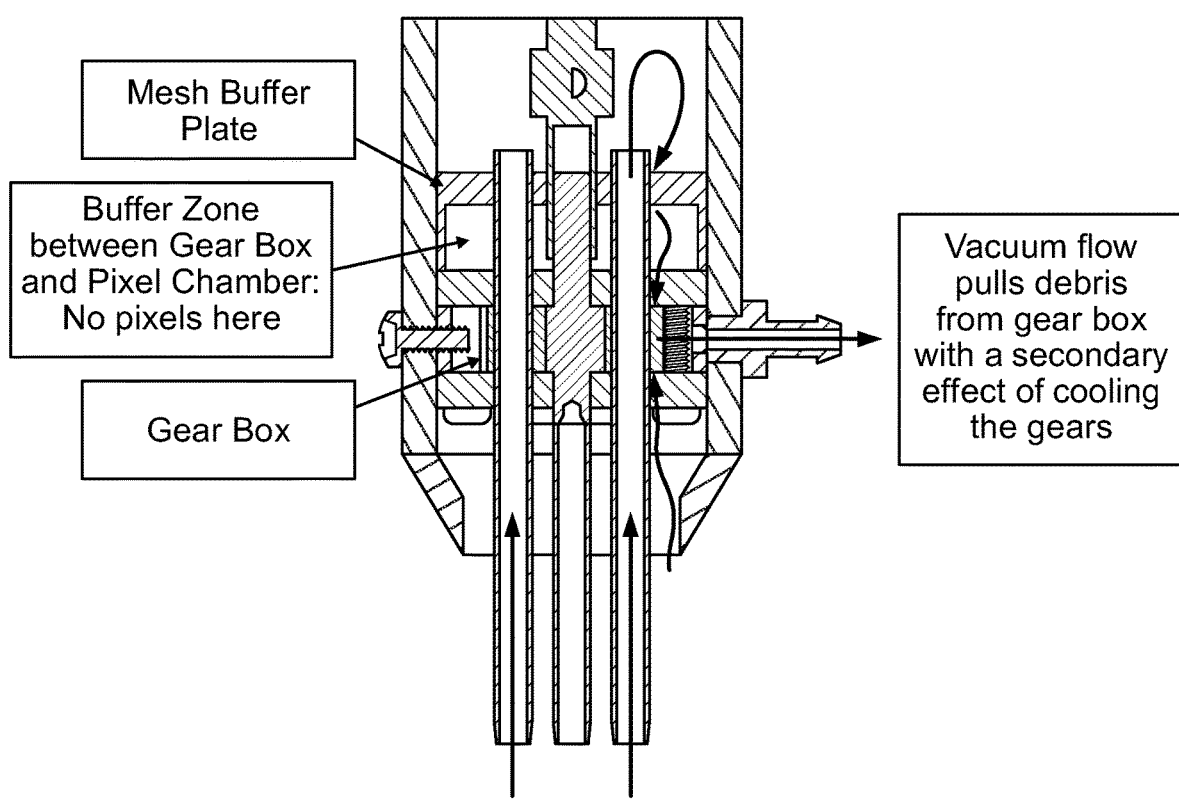

FIG. 200 shows an example vacuum flow path through the scalpet device, under an embodiment.

Figure 201:
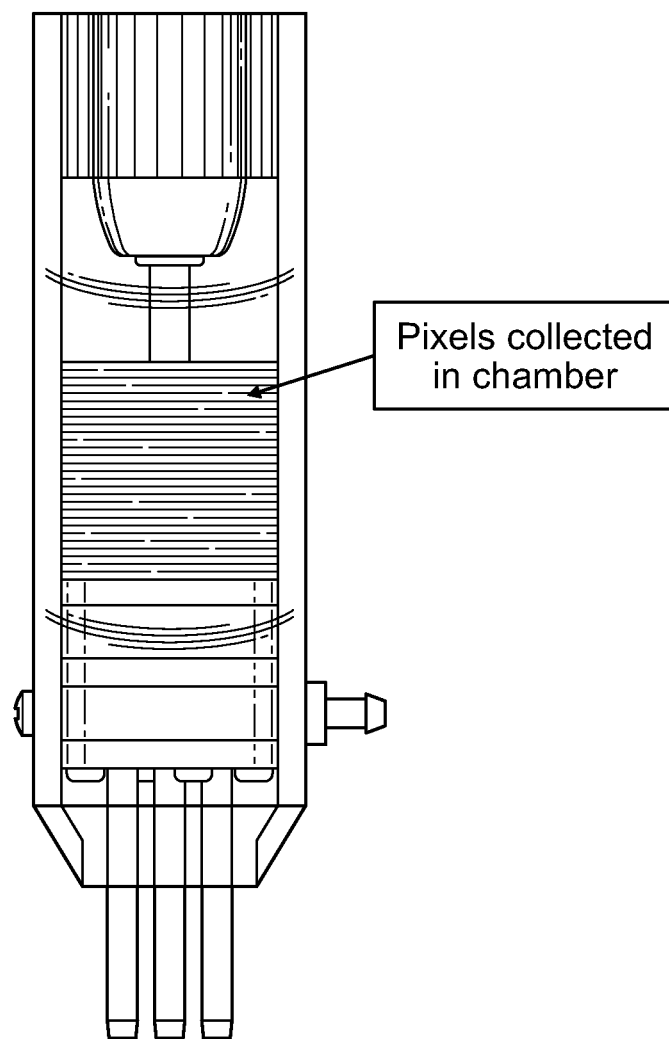

FIG. 201 shows an example scalpet device following collection of pixels in the collection chamber, under an embodiment.

Figure 202:
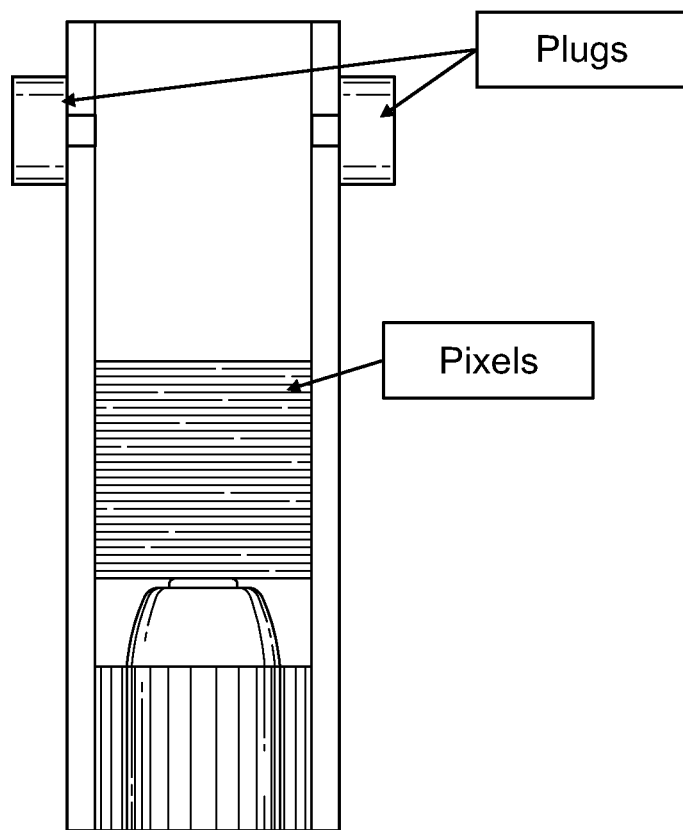

FIG. 202 shows an inverted handpiece with pixels in the collection chamber, under an embodiment.

Figure 203:
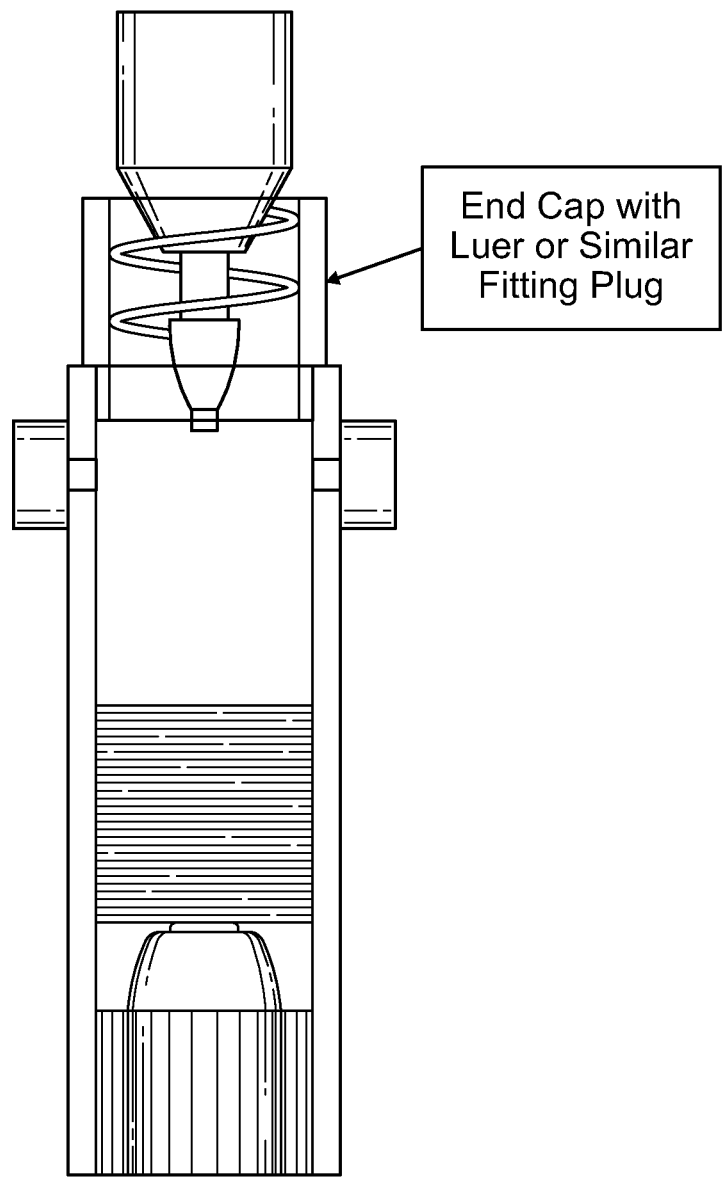

FIG. 203 shows the inverted handpiece with the alternative end cap and fitting plug installed, under an embodiment.

Figure 204:
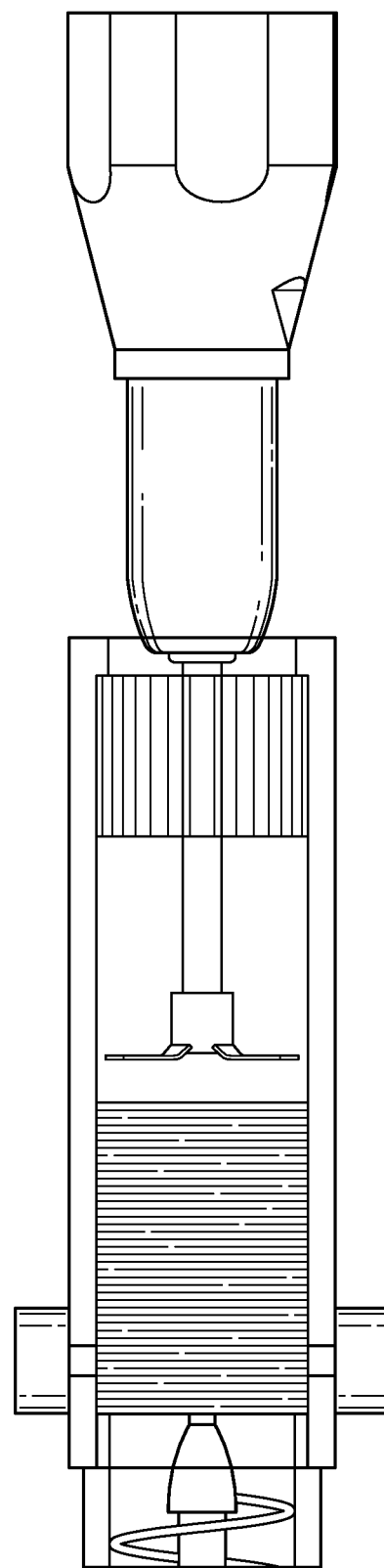

FIG. 204 shows the handpiece with mincing blade attached and positioned in the collection chamber with the pixel solution, under an embodiment.

Figure 205:
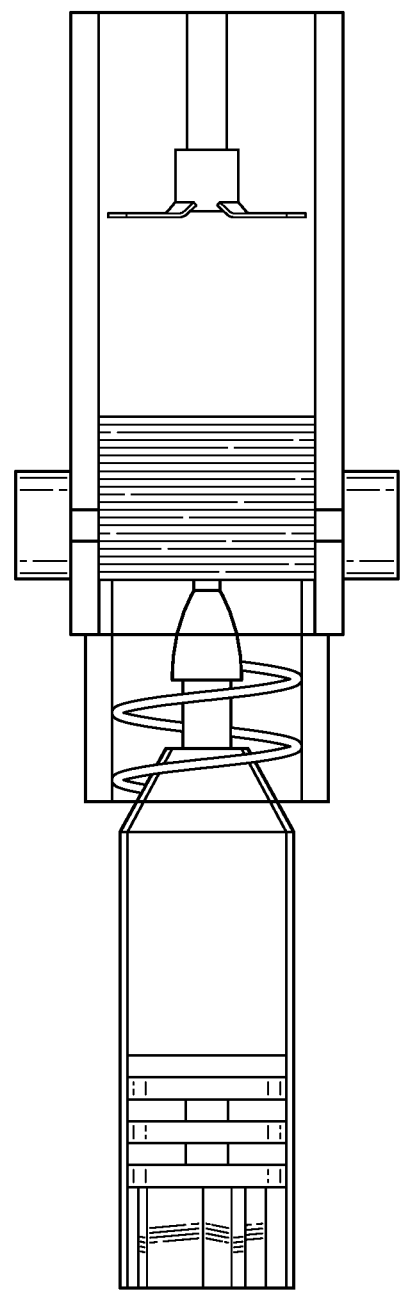

FIG. 205 shows the LADMIX filler drawn into the syringe, under an embodiment.

Figure 206:
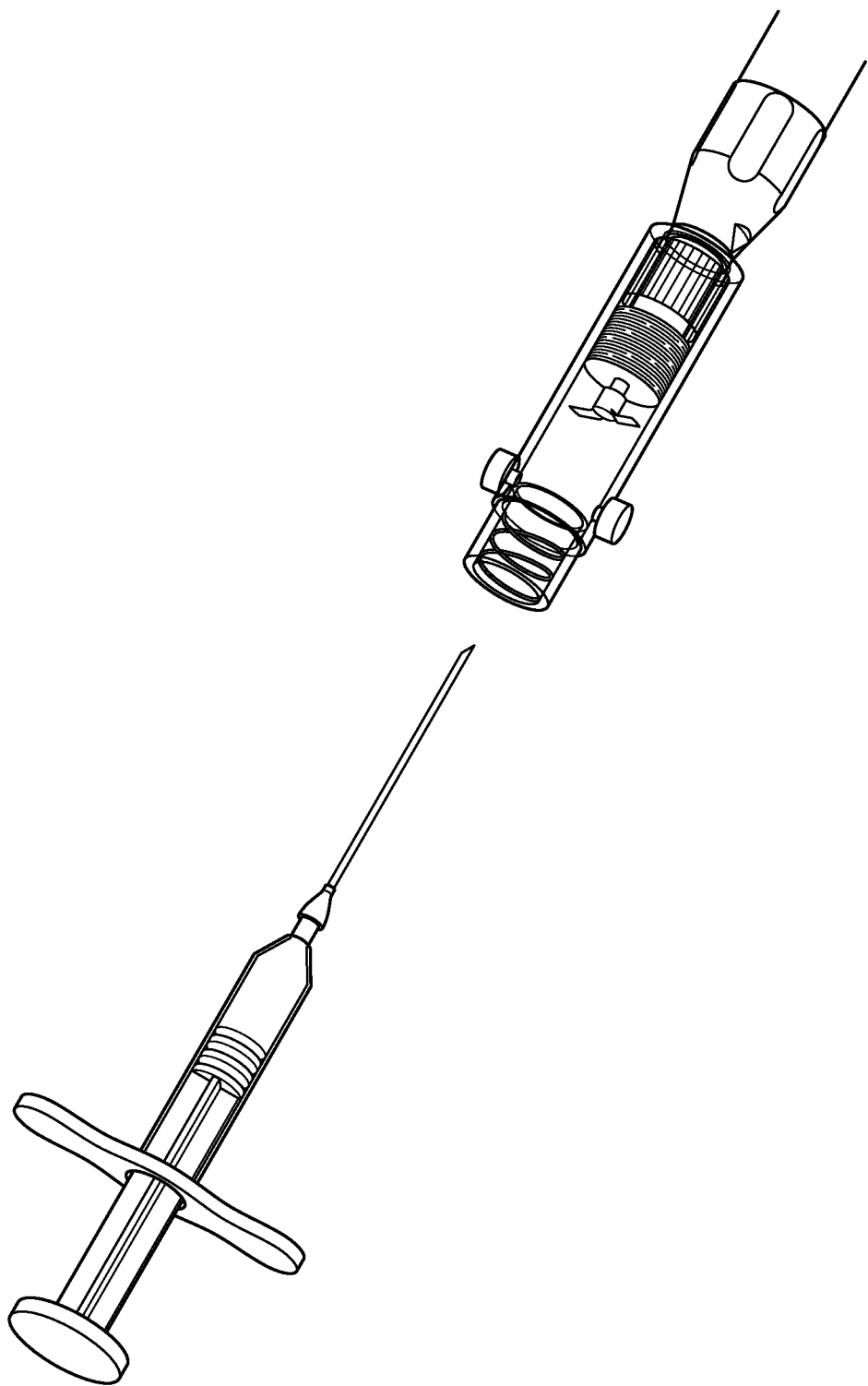

FIG. 206 shows the syringe and attached needle readied for injecting the LADMIX filler into the target tissue site, under an embodiment.

Figure 207:
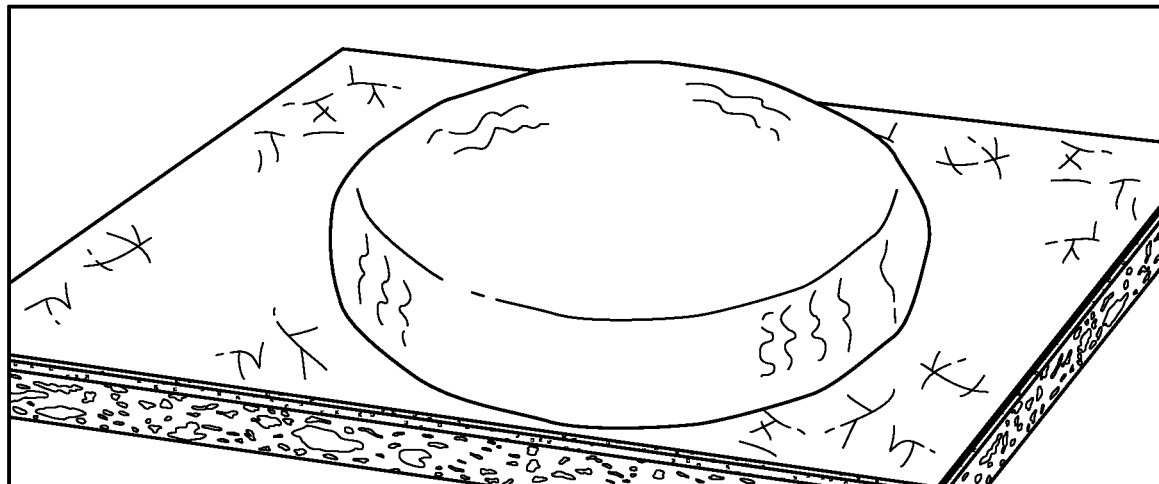

FIG. 207 shows a skin blister formed within an entire fractional field, under an embodiment.

Figure 208:
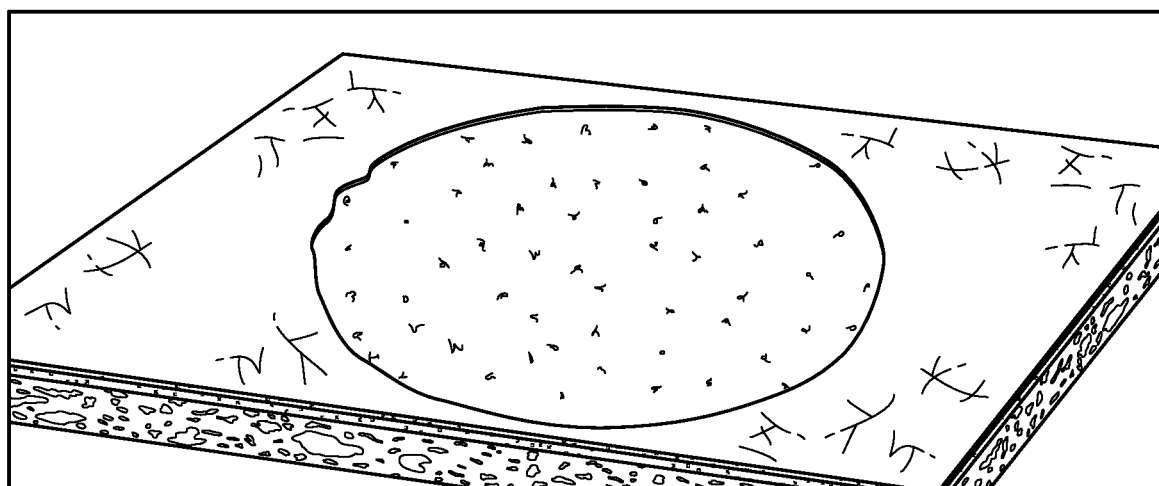

FIG. 208 shows the fractional field following removal of the blistered tissue overlying the entire fractional field, under an embodiment.

Figure 209:
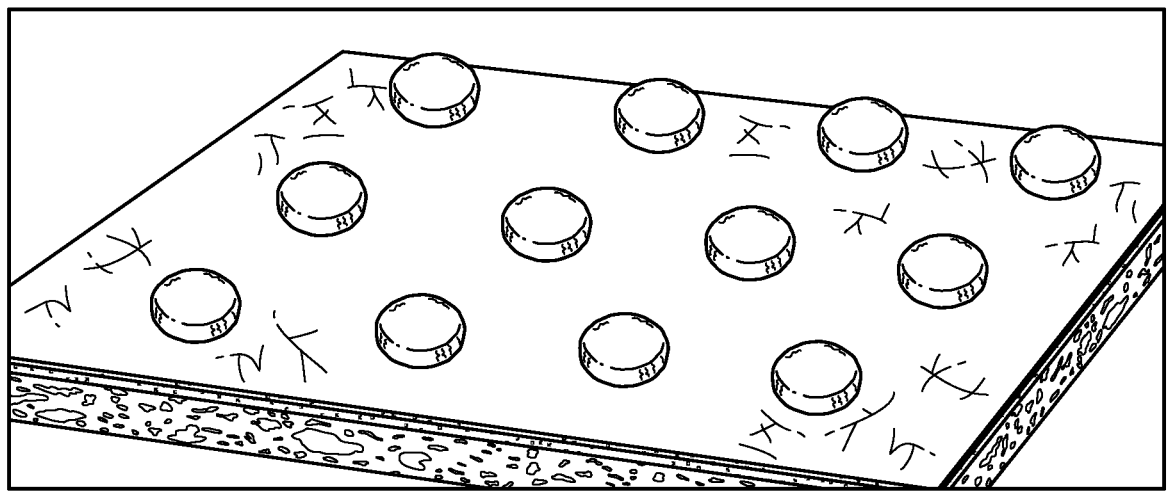

FIG. 209 shows formation of multiple skin blisters, under an embodiment.

Figure 210:
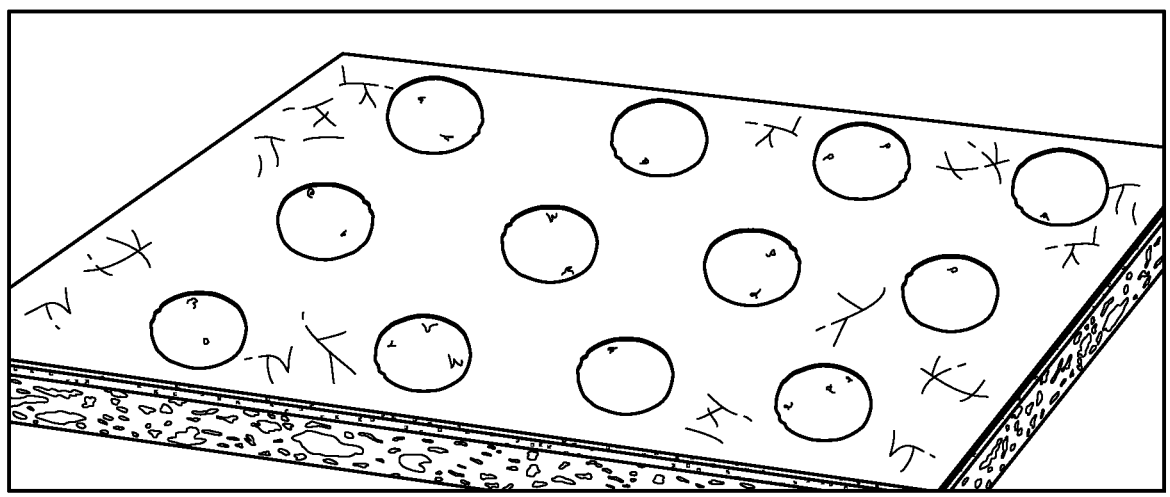

FIG. 210 shows multiple fractional fields following removal of the blistered tissue overlying the fractional fields, under an embodiment.

Figure 211:
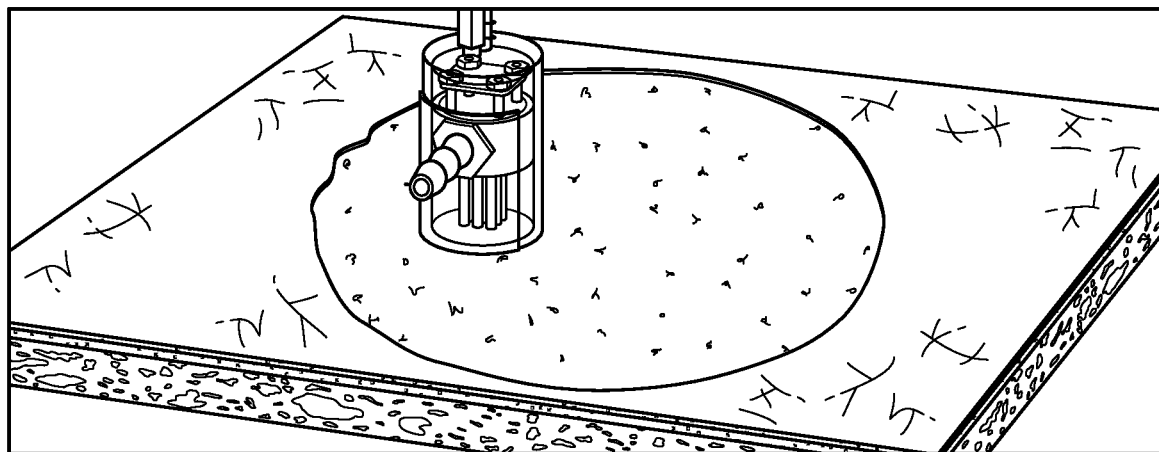

FIG. 211 shows harvesting of dermal plugs within a blistered region using a single scalpet system or a multiple scalpet array, under an embodiment.

Figure 212:
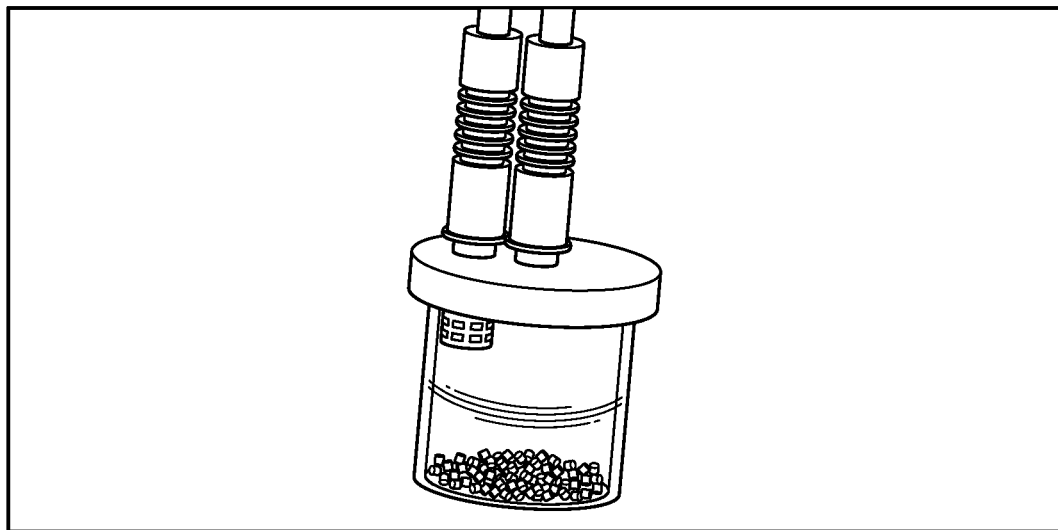

FIG. 212 shows a collection vessel or canister including harvested dermal plugs, under an embodiment.

Figure 213:
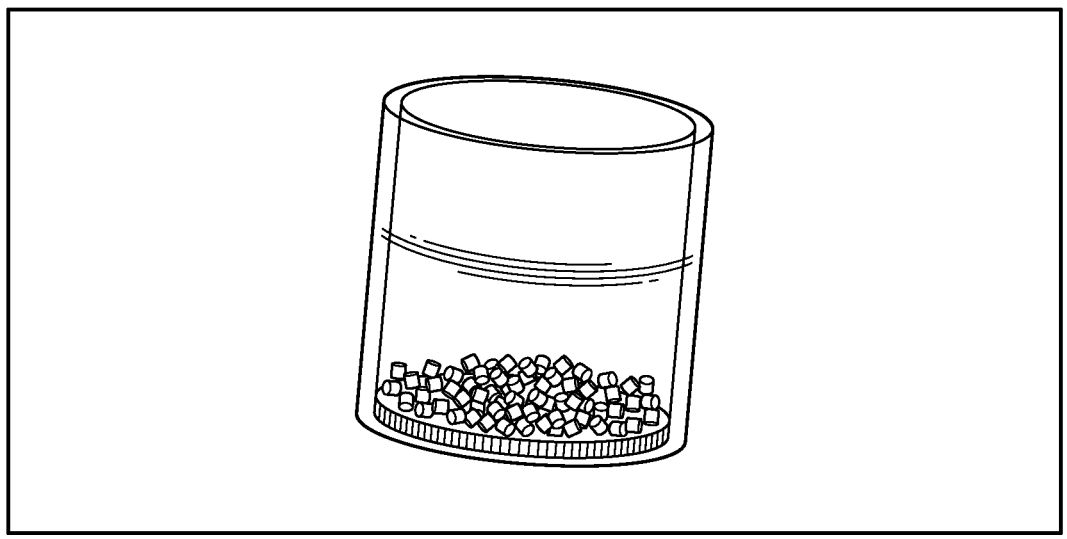

FIG. 213 shows a mincer container or canister including harvested dermal plugs, under an embodiment.

Figure 214:
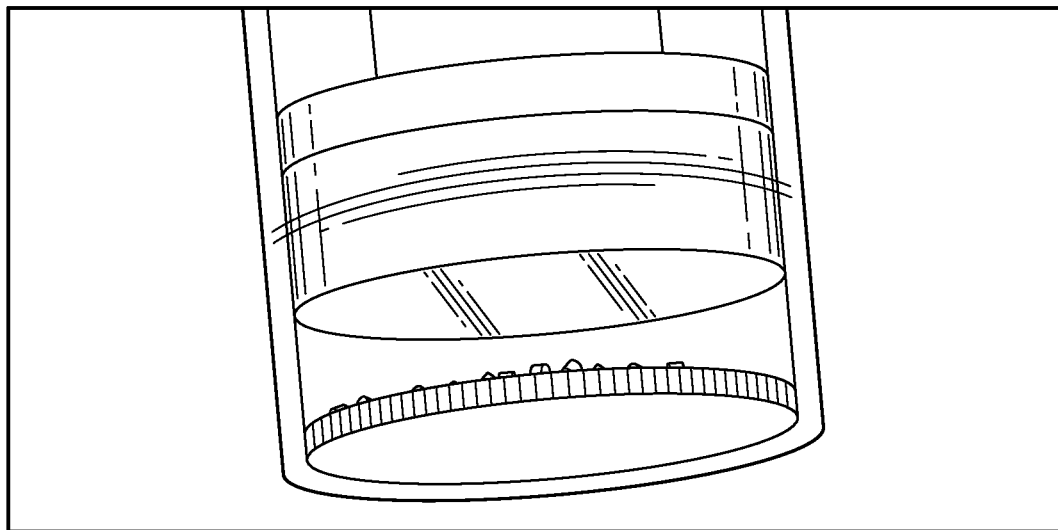

FIG. 214 shows a manual mincer including a blade device configured to be manipulated up/down and/or rotated, under an embodiment.

Figure 215:
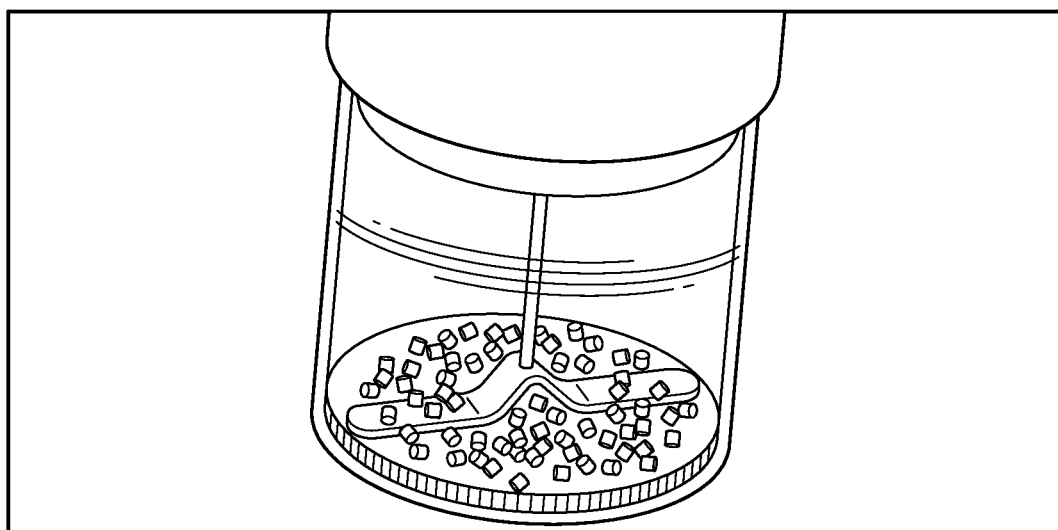

FIG. 215 shows an electric mincer including a blade or cutting device configured to be rotated under power, under an embodiment.

Figure 216:
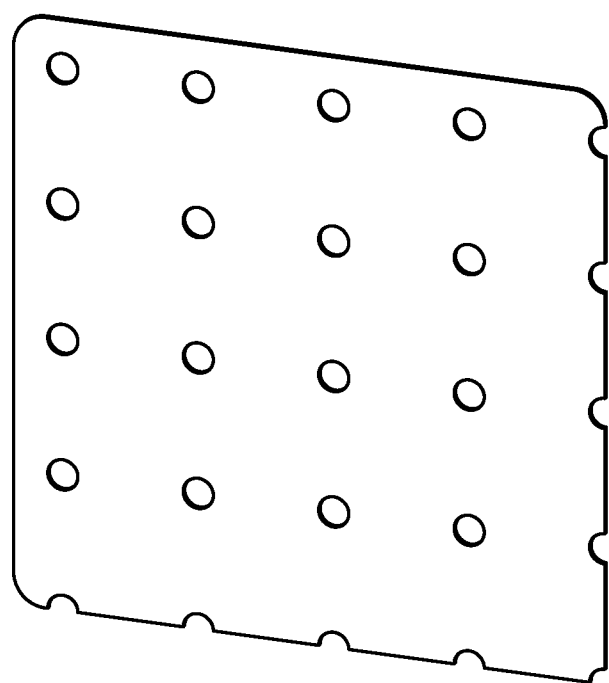

FIG. 216 is an example marking system template, under an embodiment.

Figure 217:
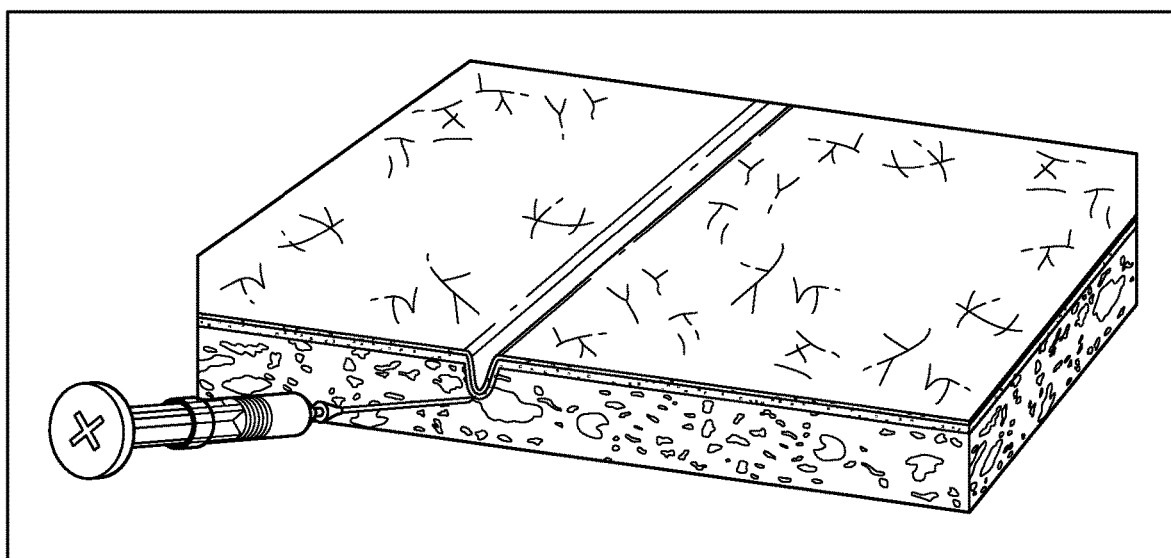

FIG. 217 shows creation of the recipient pocket for the injectable, under an embodiment.

Figure 218:
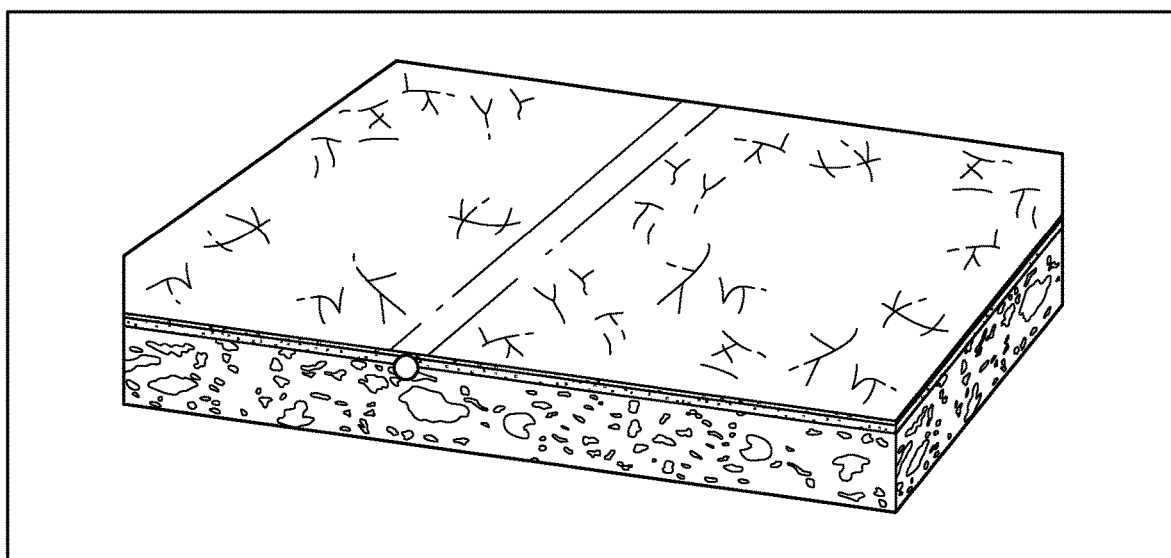

FIG. 218 the recipient pocket with the injected filler, under an embodiment.

Figure 219:
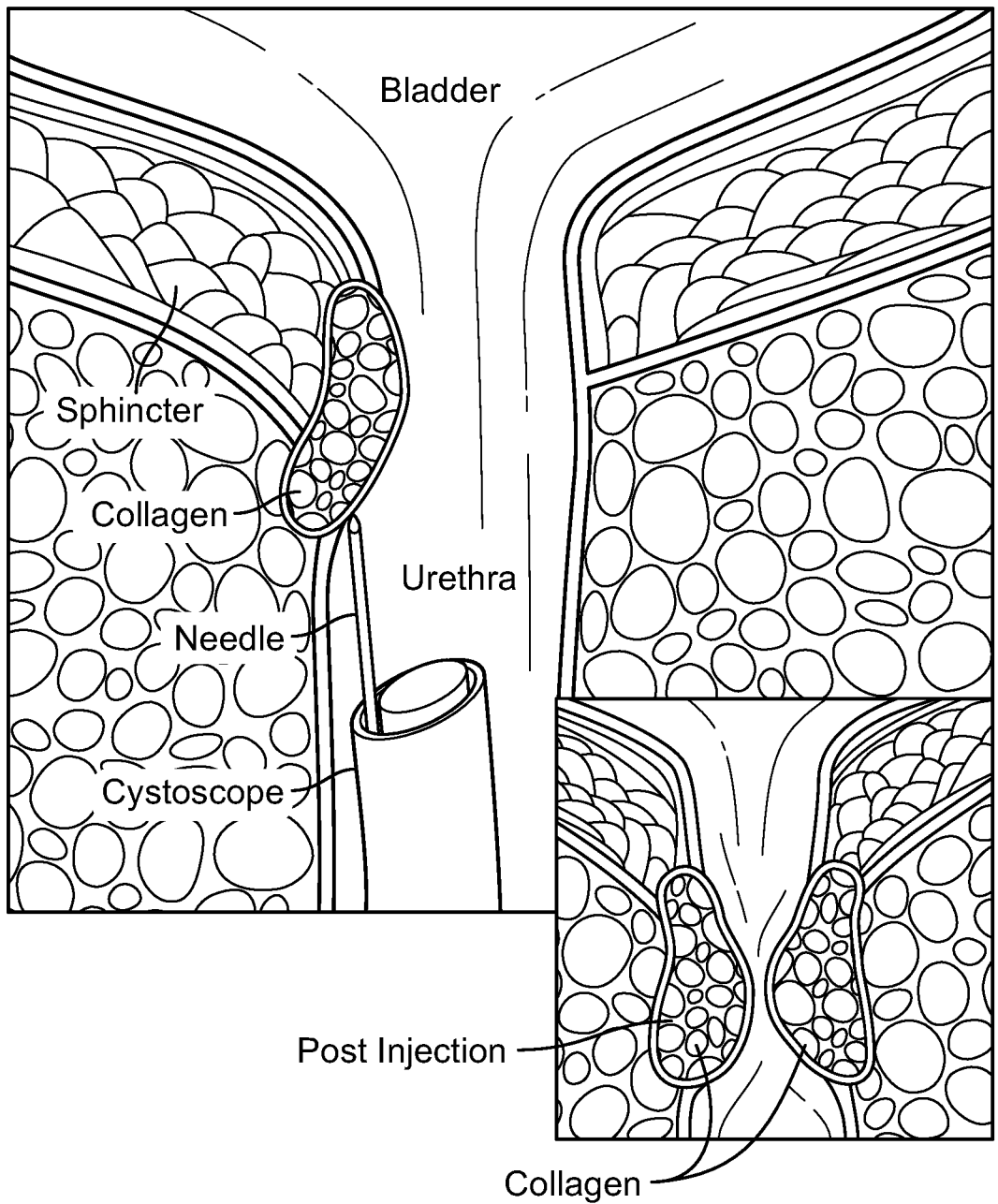

FIG. 219 shows treatment of female incontinence using injection of LADMIX, under an embodiment.

Figure 220A:
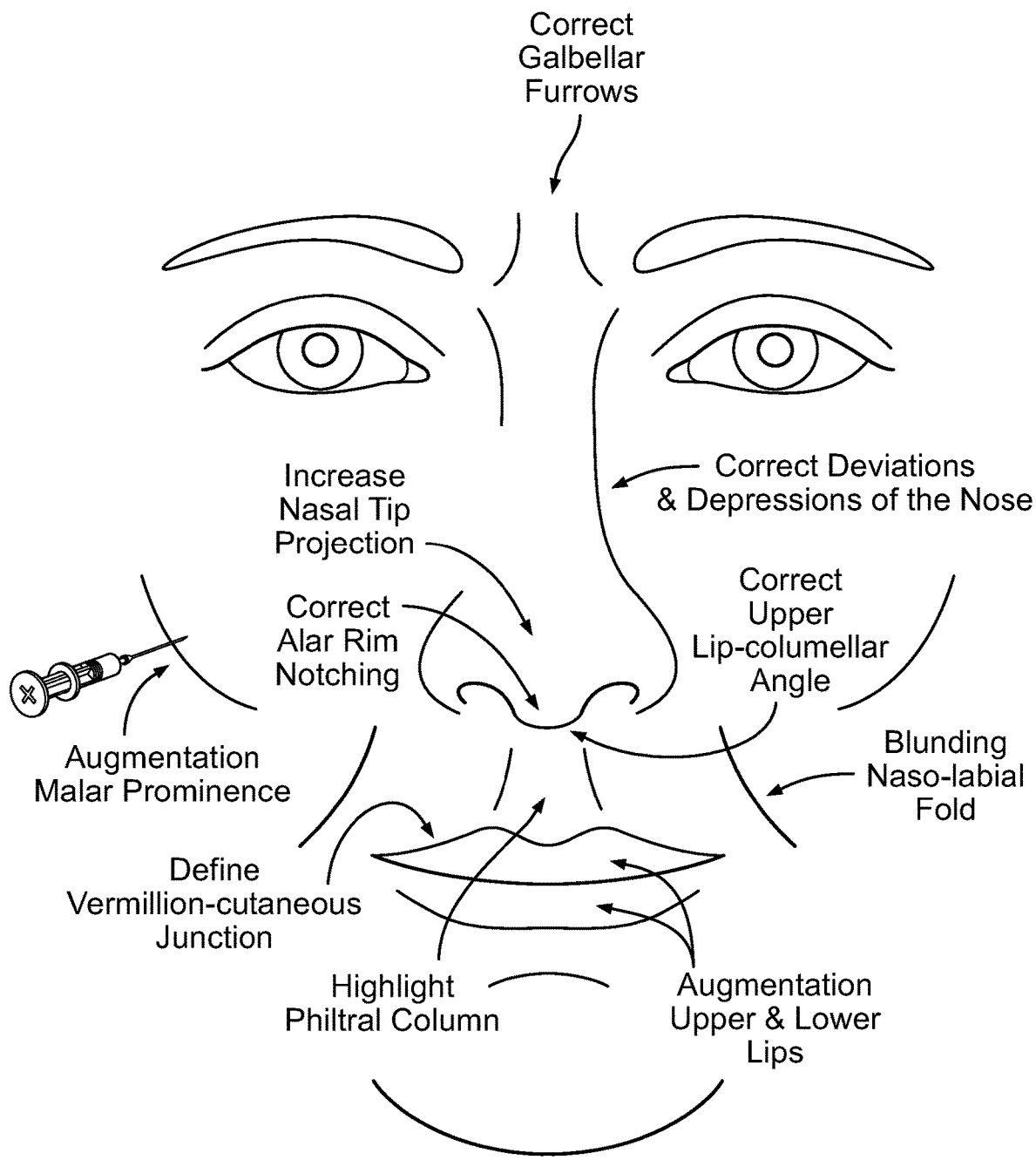

FIG. 220A shows an example malar prominence procedure, under an embodiment.

Figure 220B:
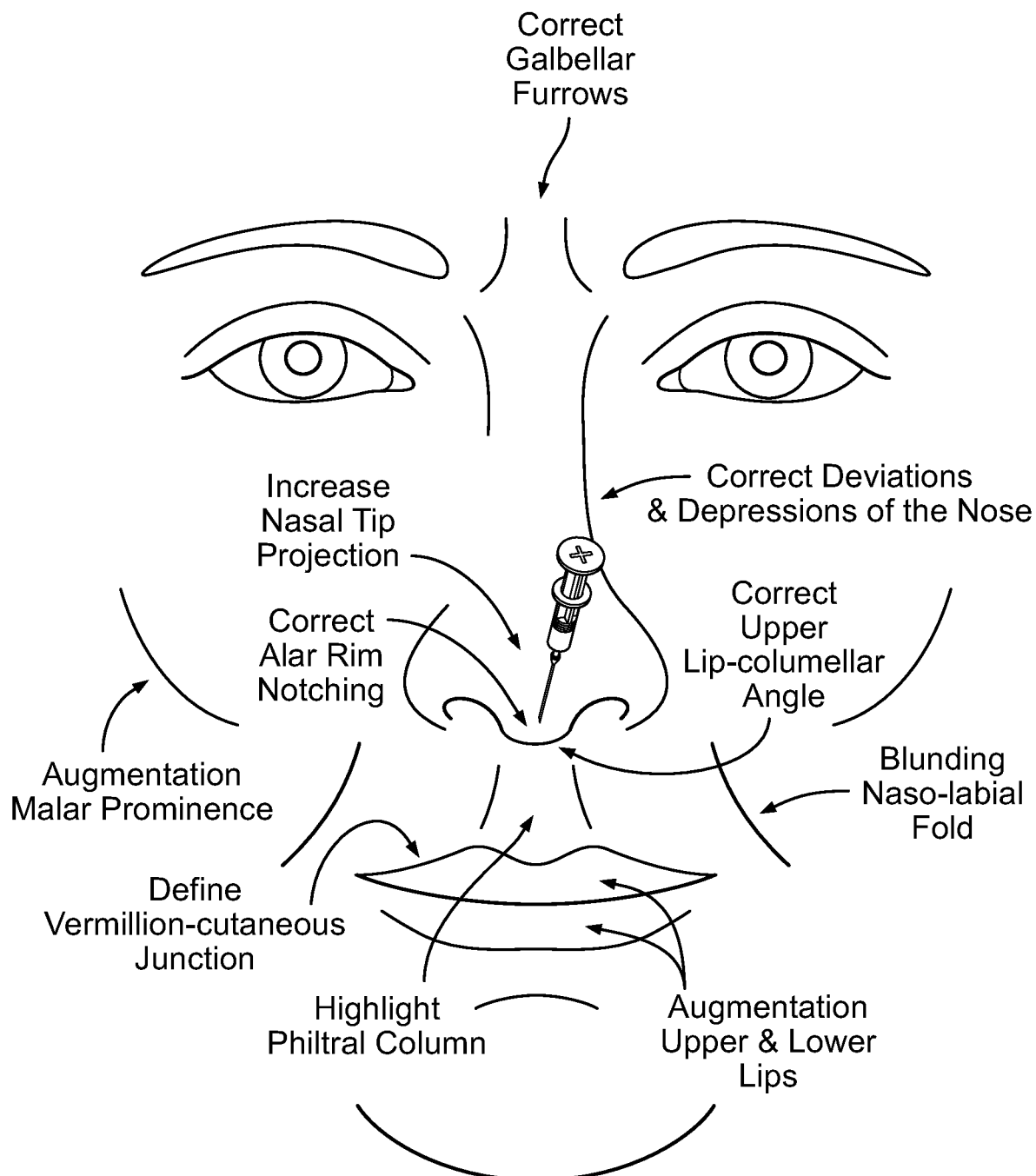

FIG. 220B shows an example procedure involving notching of the alar rim, under an embodiment.

Figure 220C:
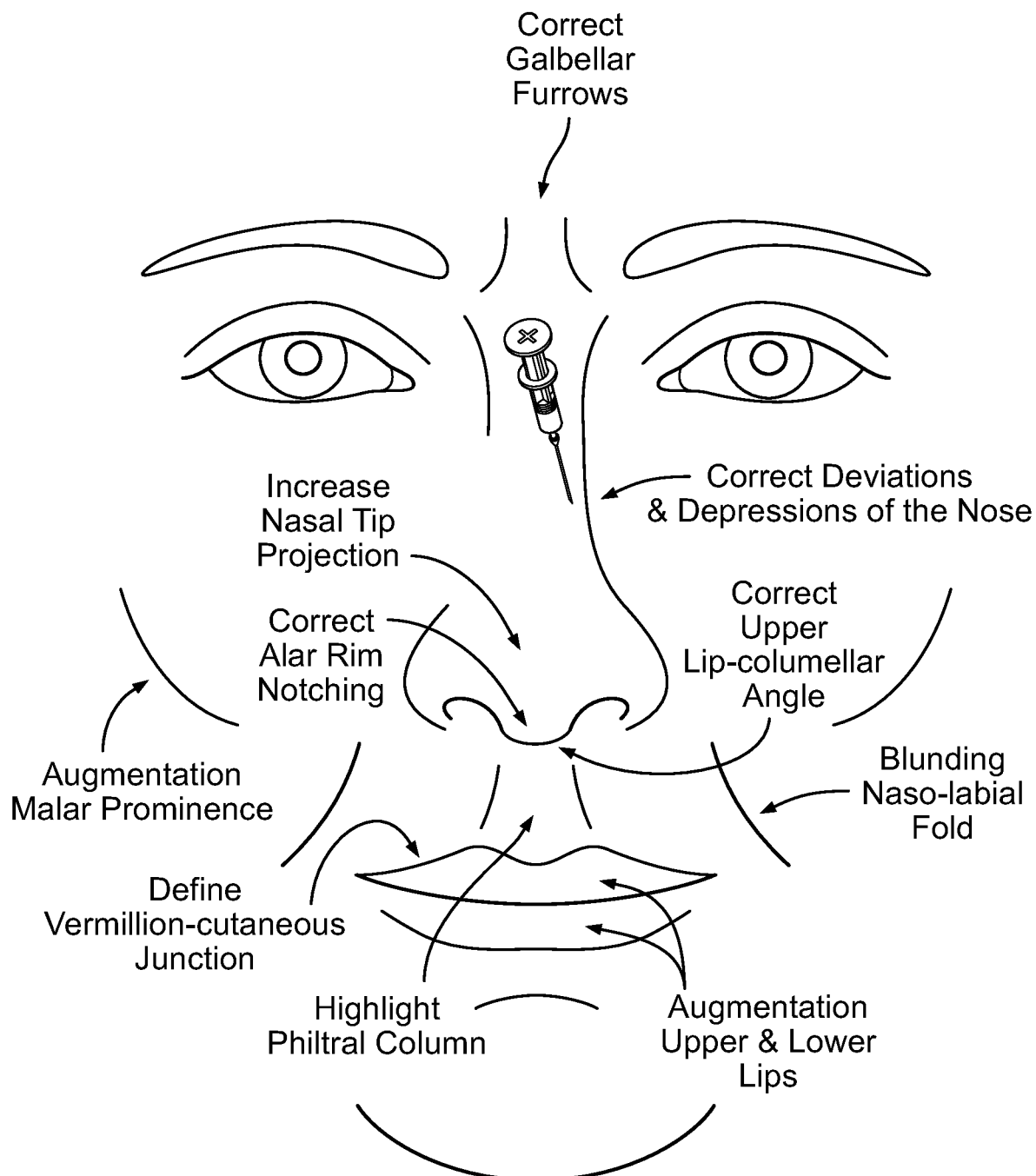

FIG. 220C shows an example procedure involving injecting of deviations and depressions of the nasal dorsum, under an embodiment.

Figure 220D:
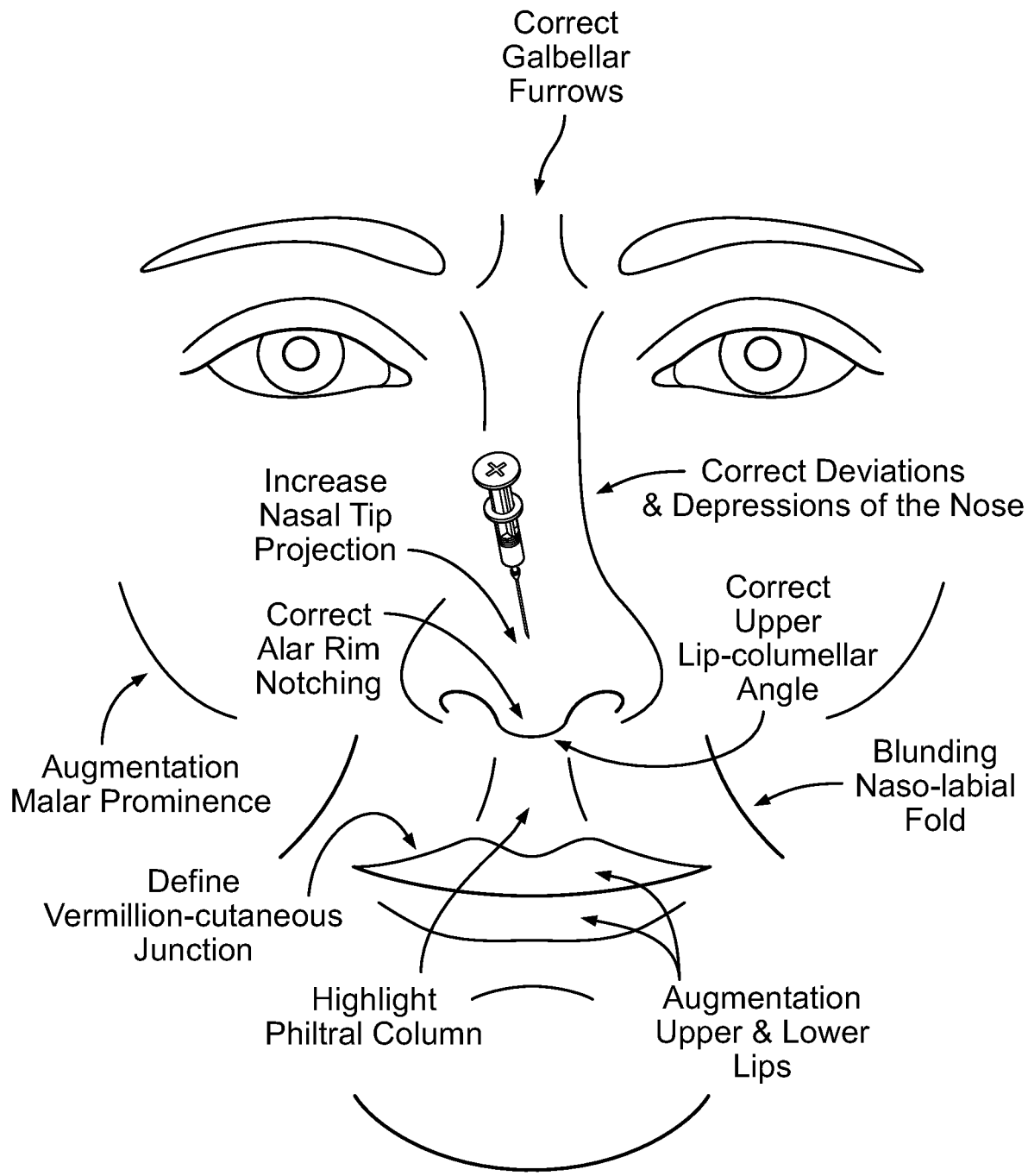

FIG. 220D shows an example procedure involving projection of the nasal tip, under an embodiment.

Figure 220E:
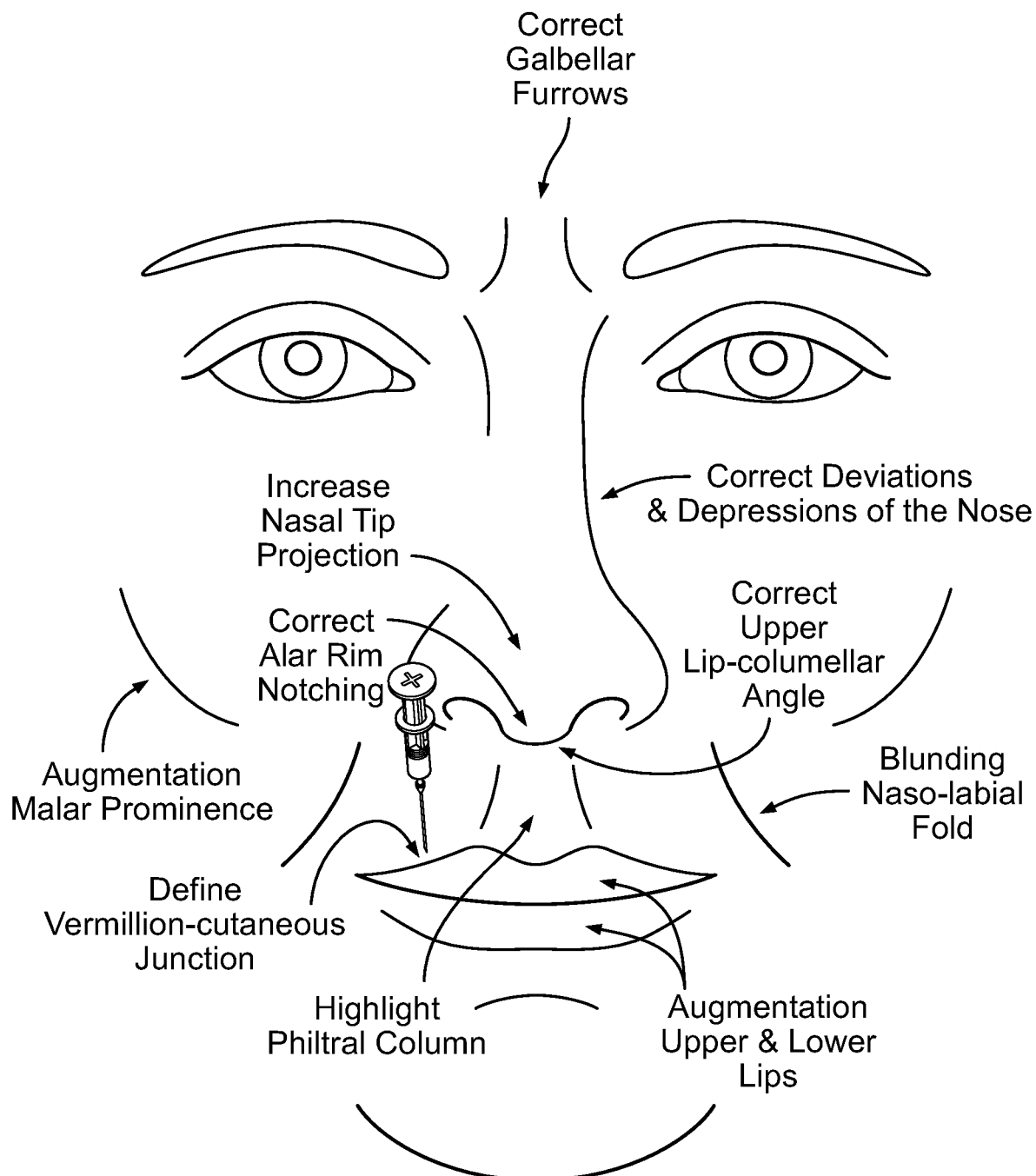

FIG. 220E shows an example procedure involving the vermillion cutaneous junction, under an embodiment.

Figure 220F:
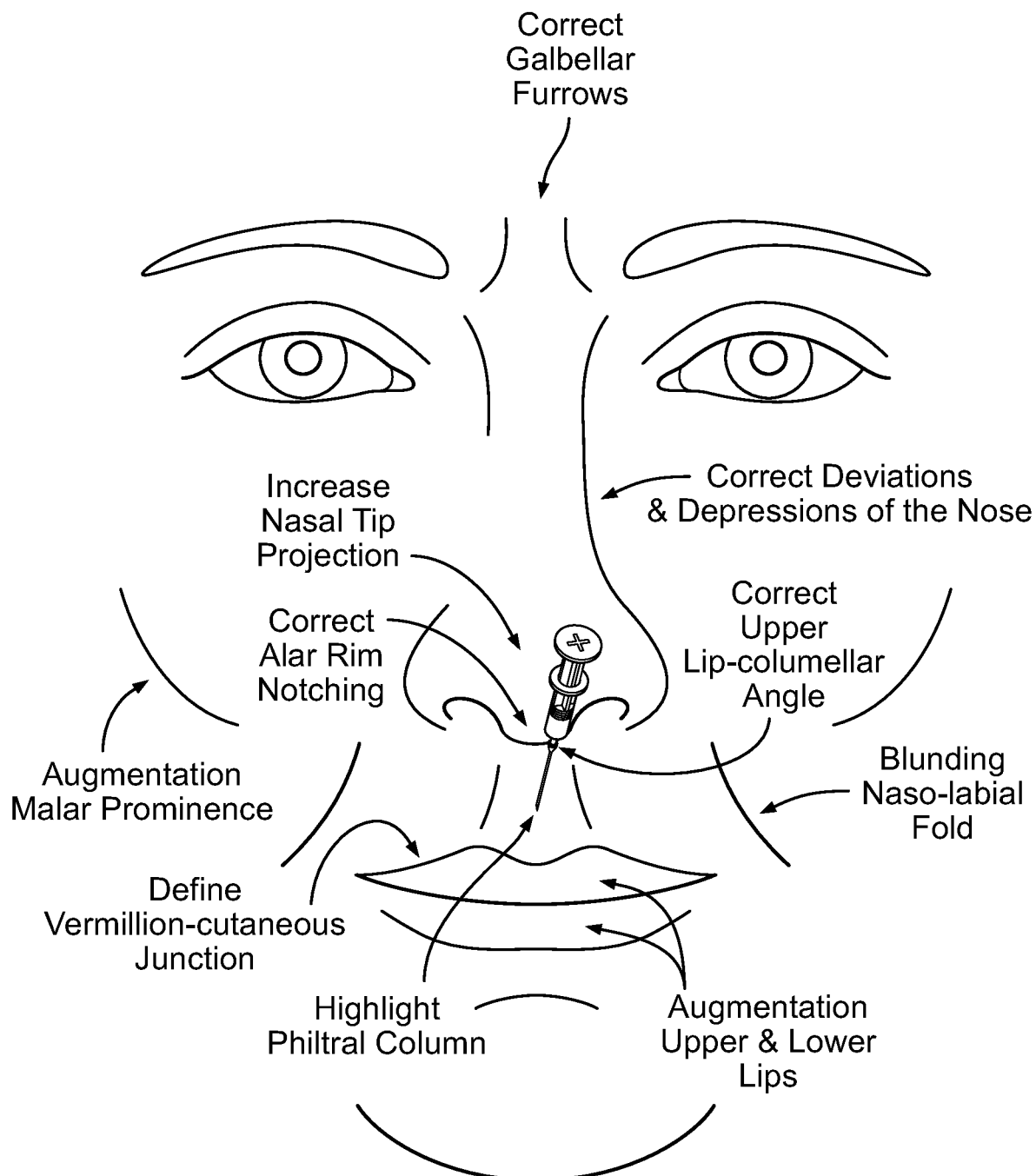

FIG. 220F shows an example procedure involving the philtral columns of the upper lip, under an embodiment.

Figure 220G:
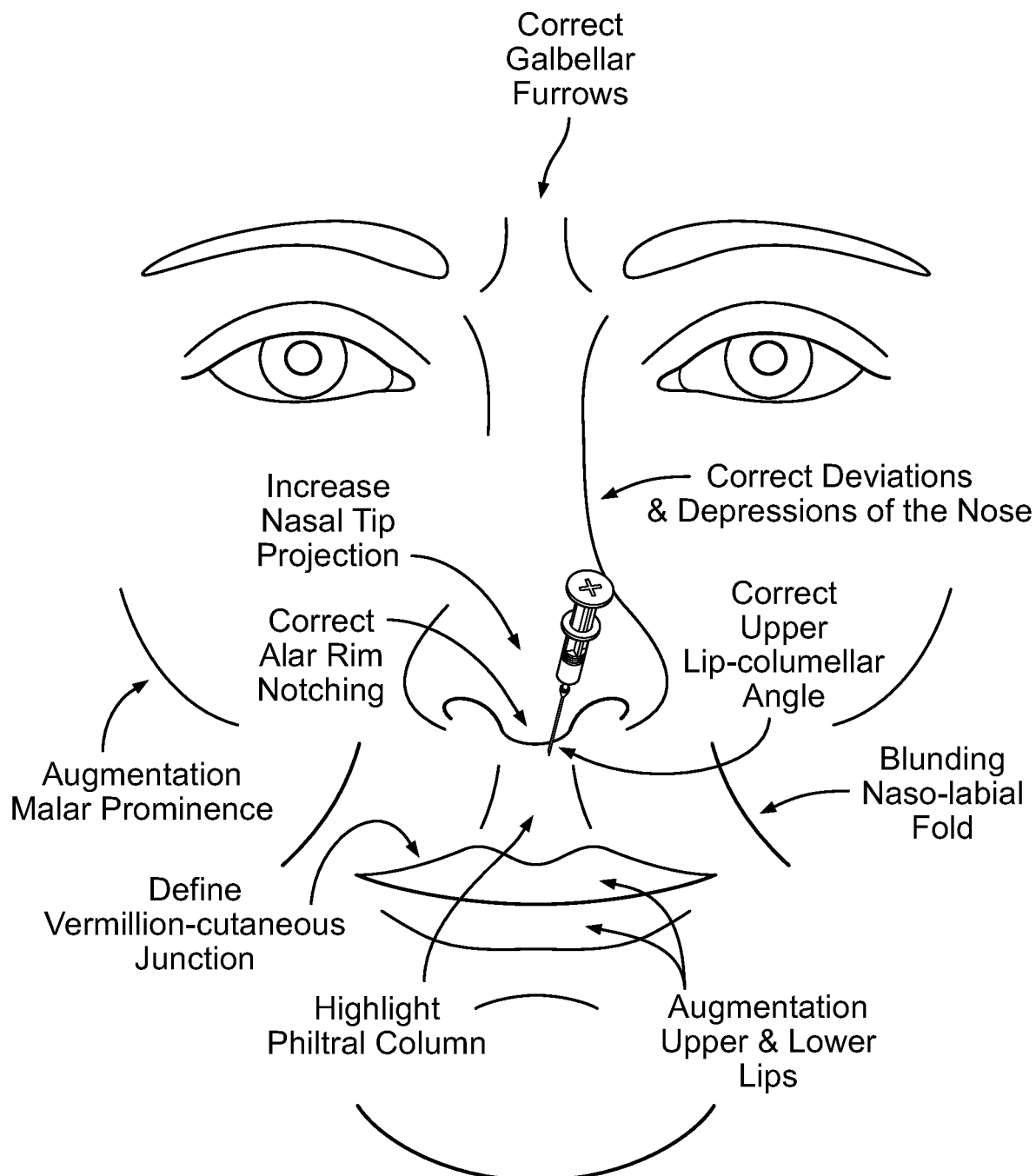

FIG. 220G shows an example procedure involving the upper lip/columellar angle, under an embodiment.

Figure 220H:
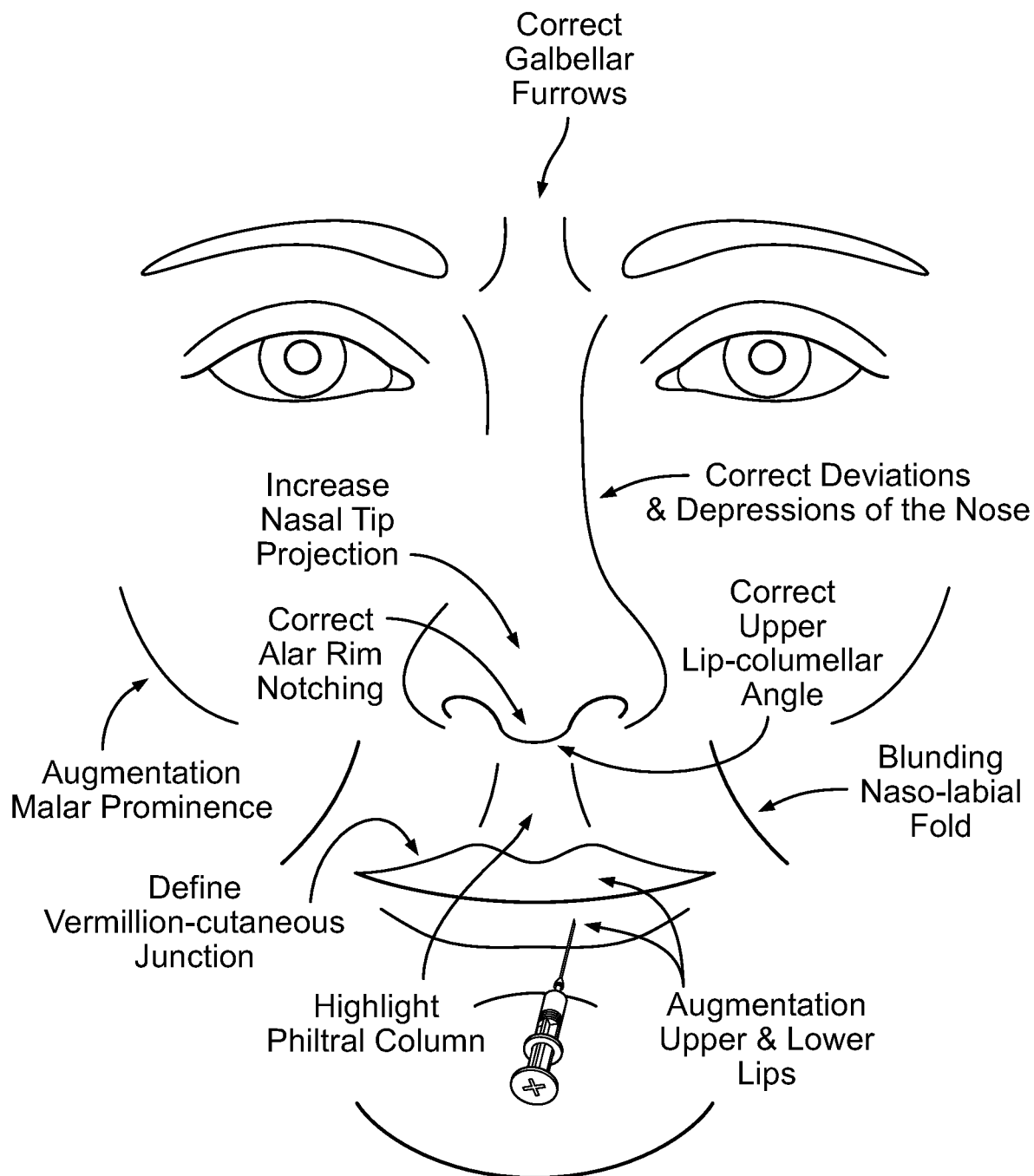

FIG. 220H shows an example procedure involving upper and lower lip augmentation, under an embodiment.

Figure 220I:
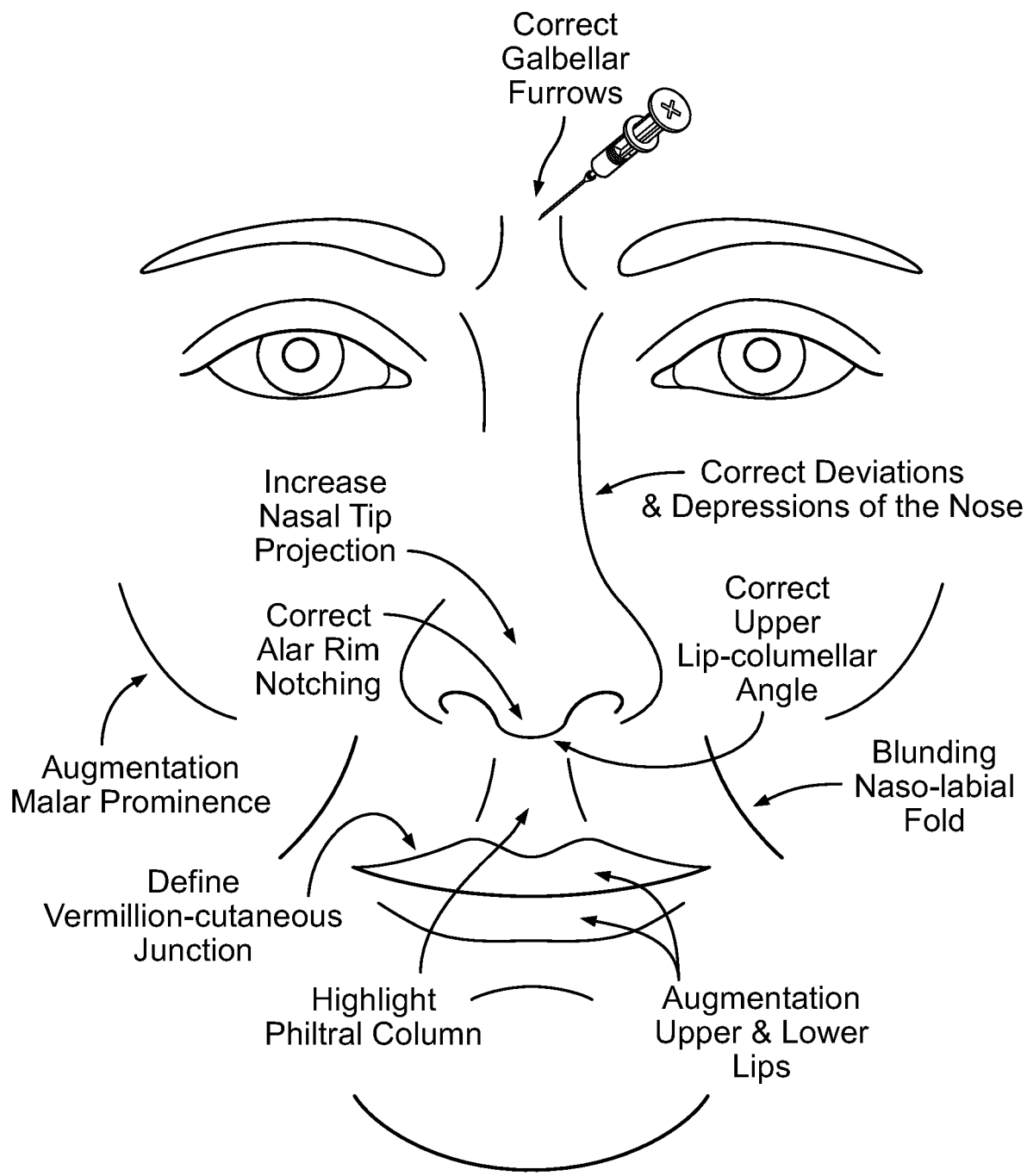

FIG. 220I shows an example procedure involving glabellar furrows, under an embodiment.

Figure 220J:
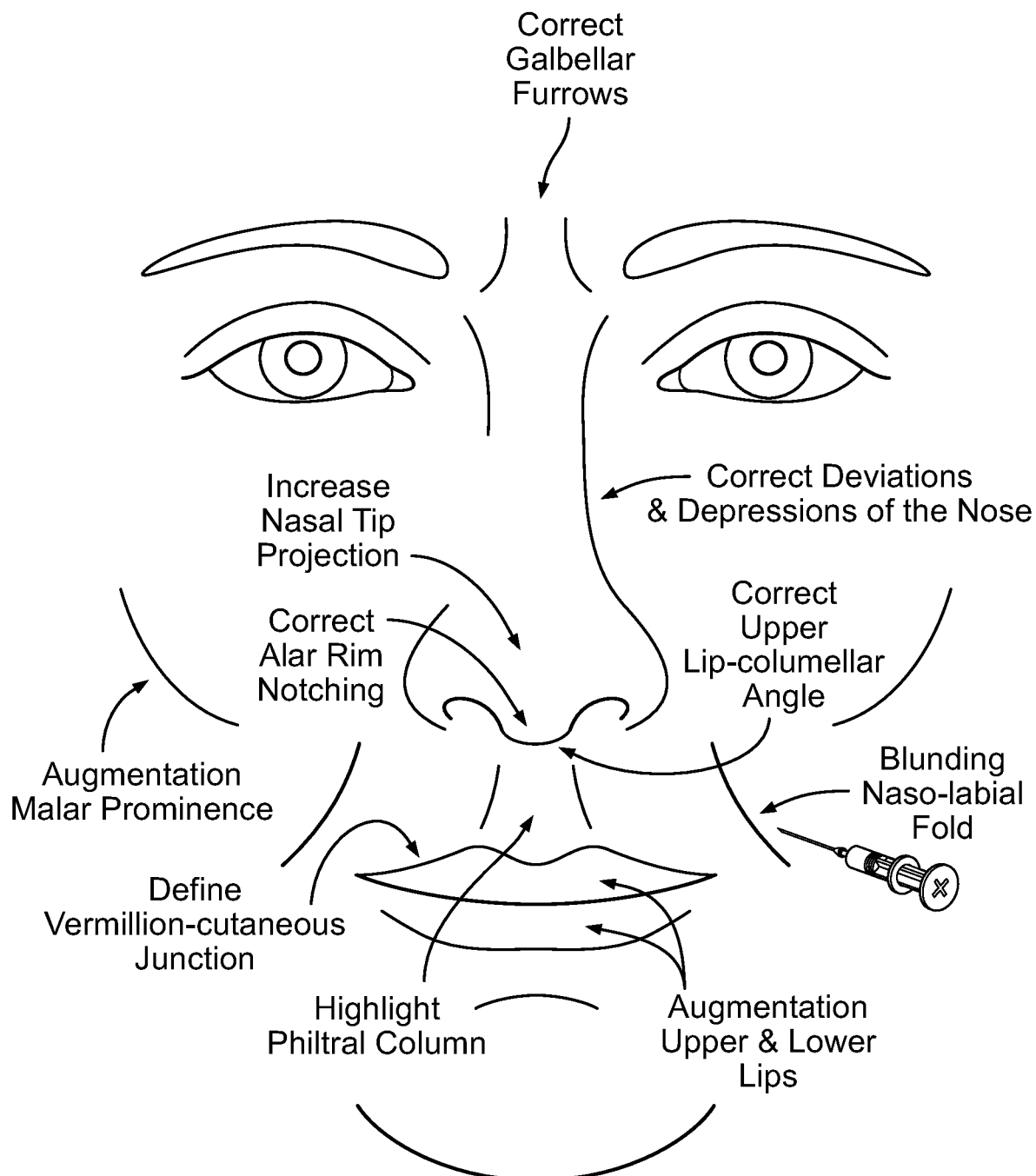

FIG. 220J shows an example procedure involving the nasolabial fold, under an embodiment.

Figure 220K:
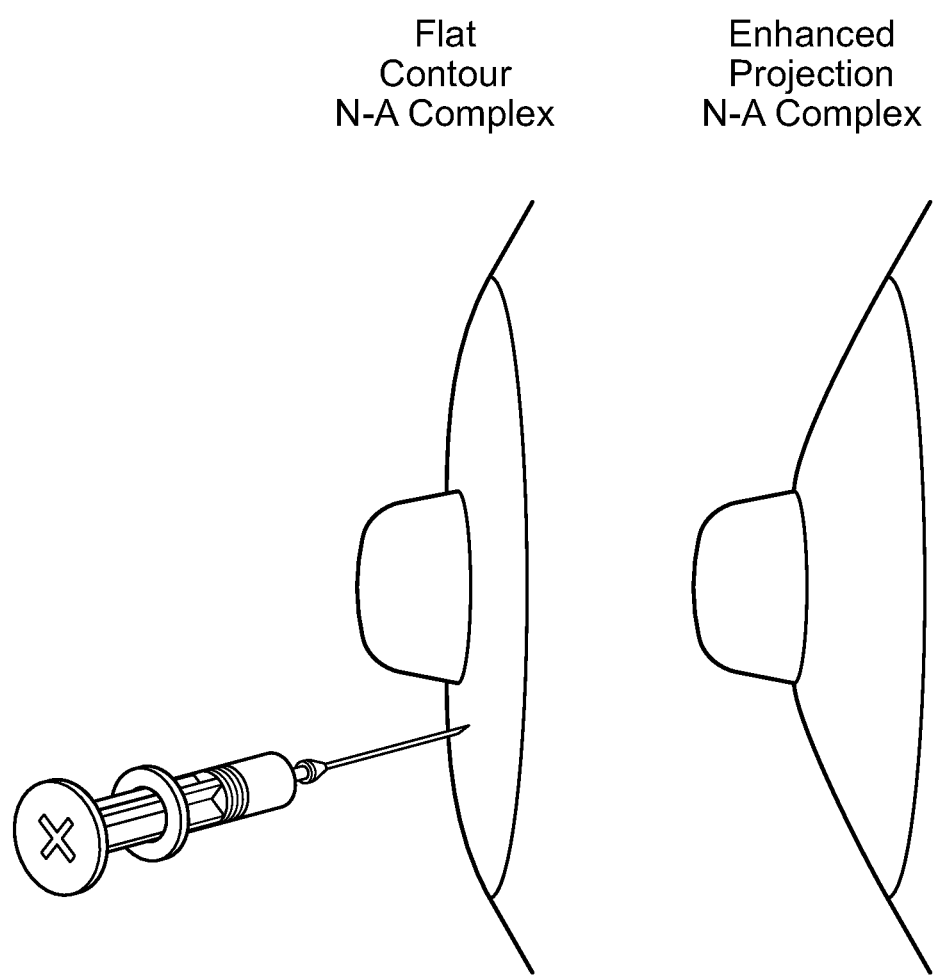

FIG. 220K shows an example procedure involving the nipple and nipple-areolar complex, under an embodiment.

Figure 220L:
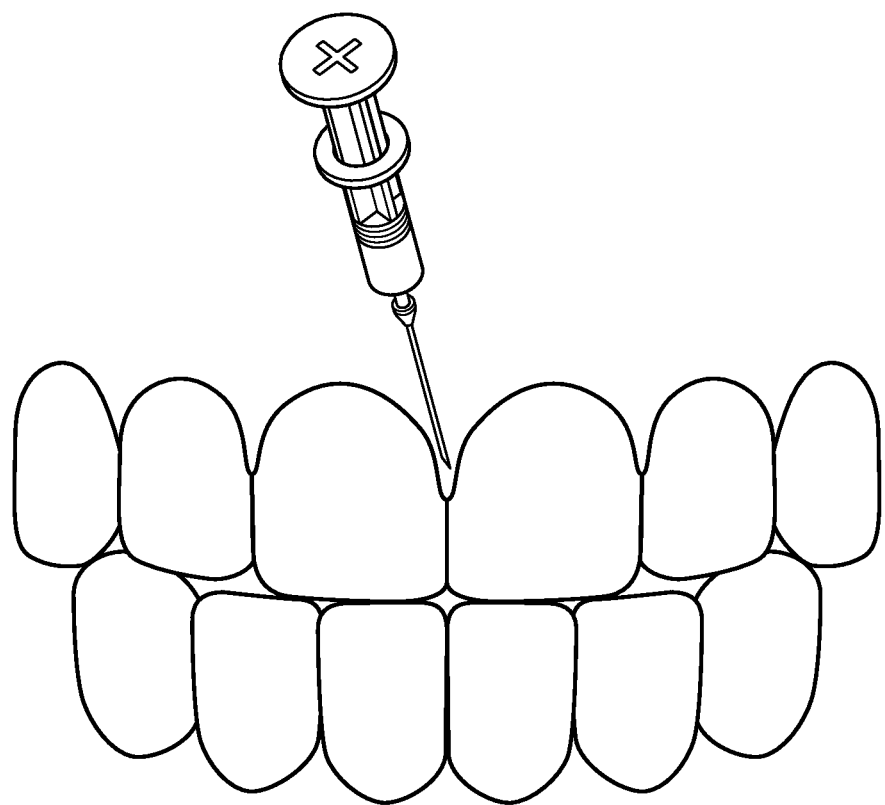

FIG. 220L shows an example procedure involving the treatment of receded gums, under an embodiment.

Figure 220M:
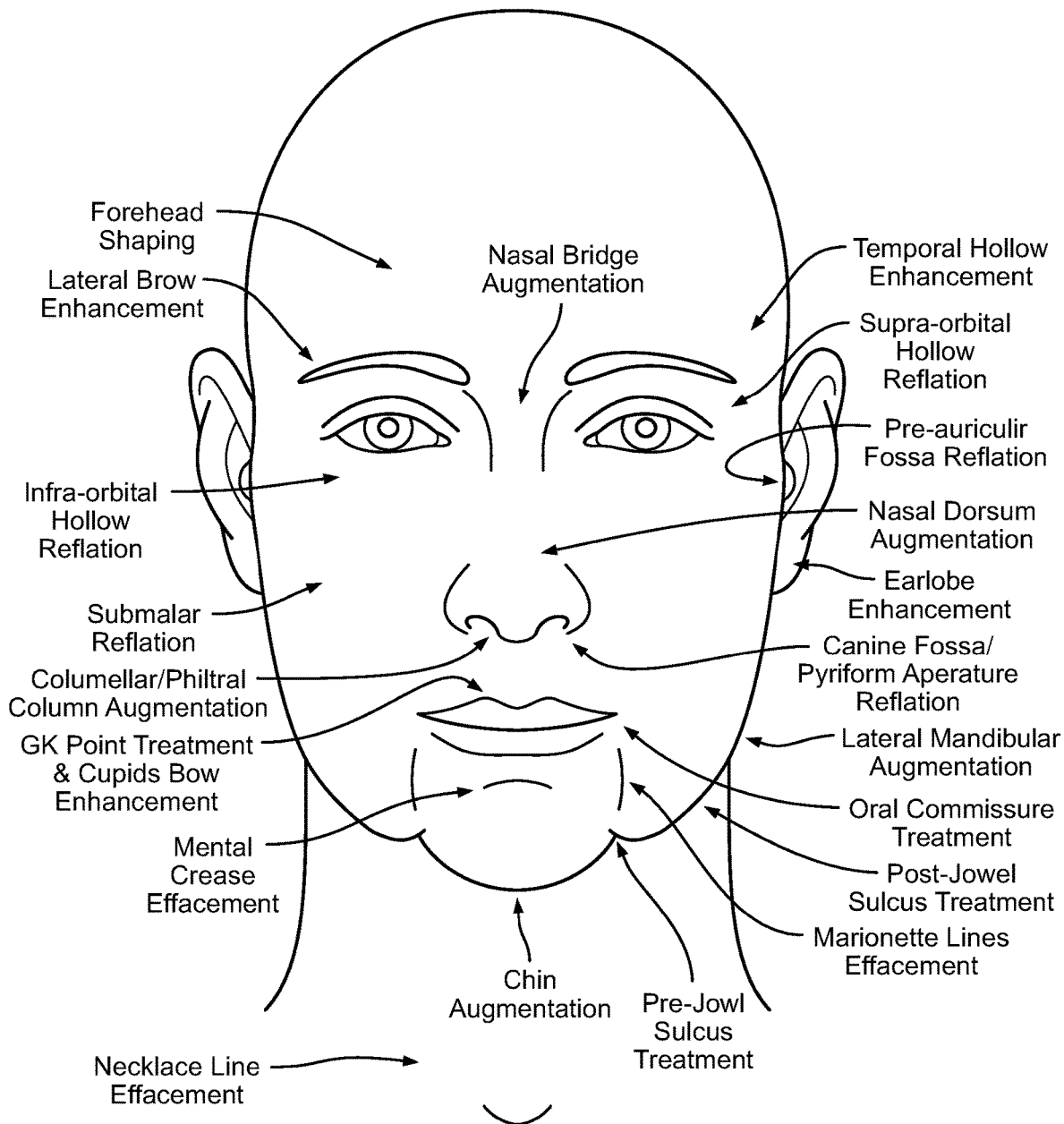

FIG. 220M shows an example procedure involving the additional examples of aesthetic bulk fill applications, under an embodiment.

Figure 221A:
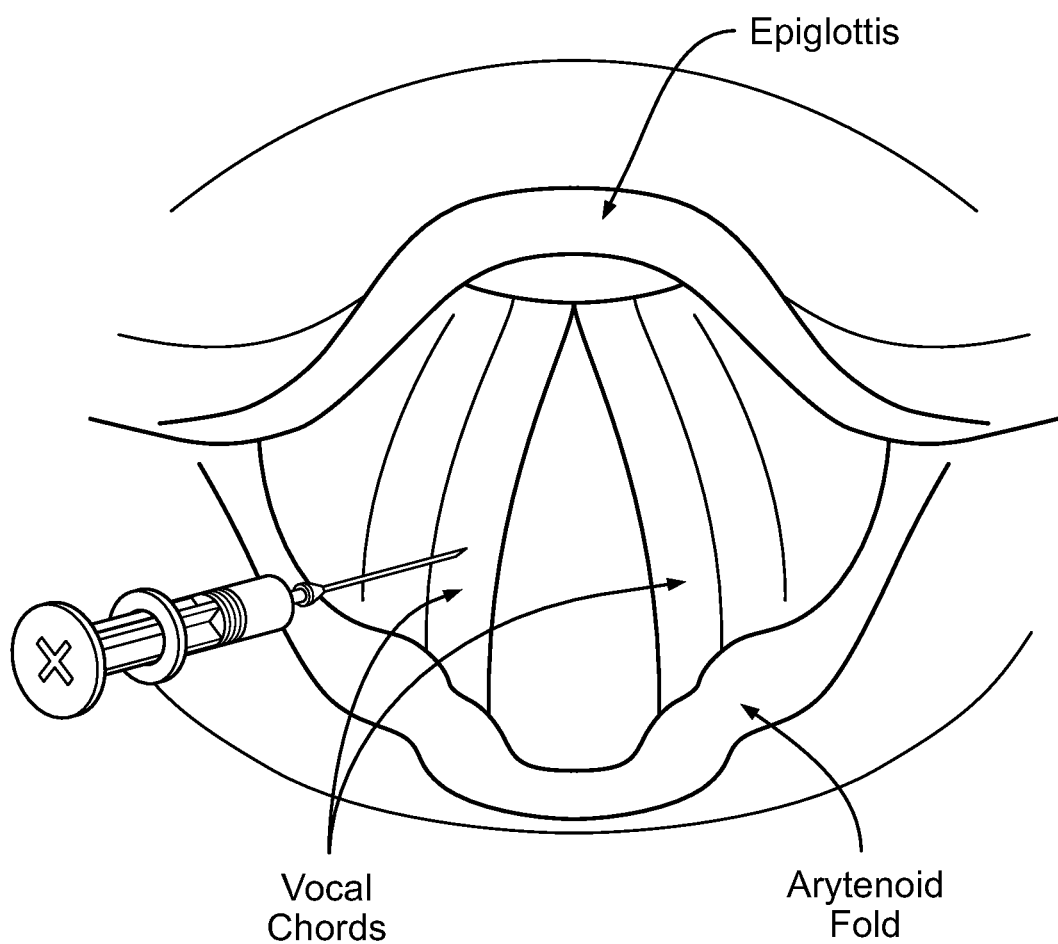

FIG. 221A shows an example procedure involving the treatment of vocal cords, under an embodiment.

Figure 221B:
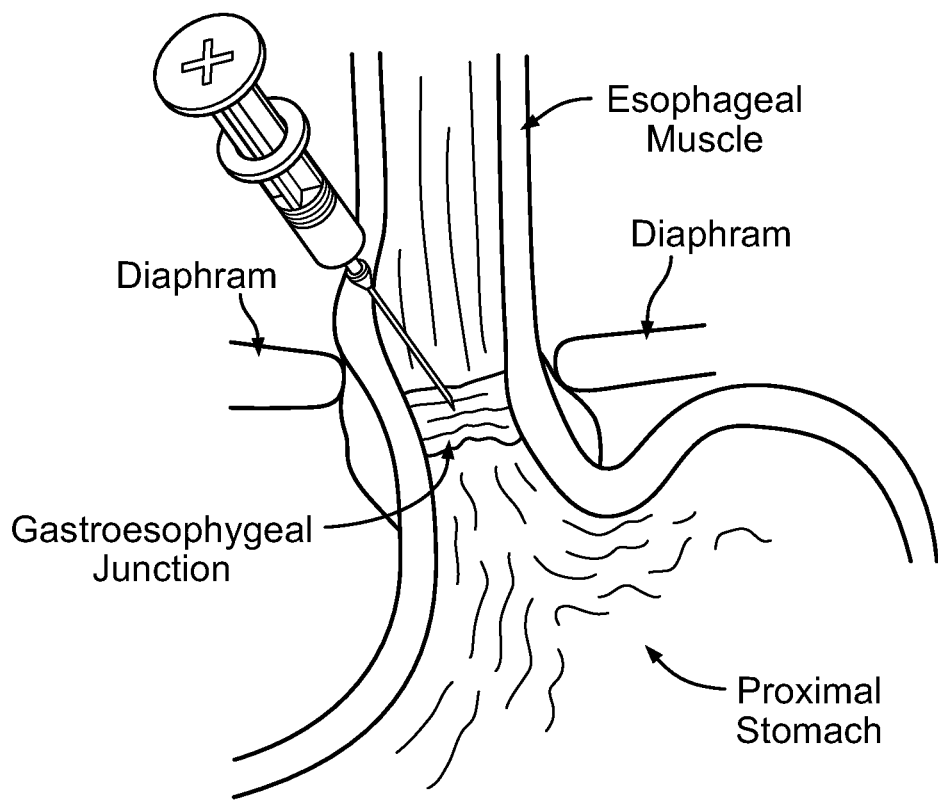

FIG. 221B shows an example procedure involving the treatment of gastro-esophageal reflux, under an embodiment.

Figure 221C:
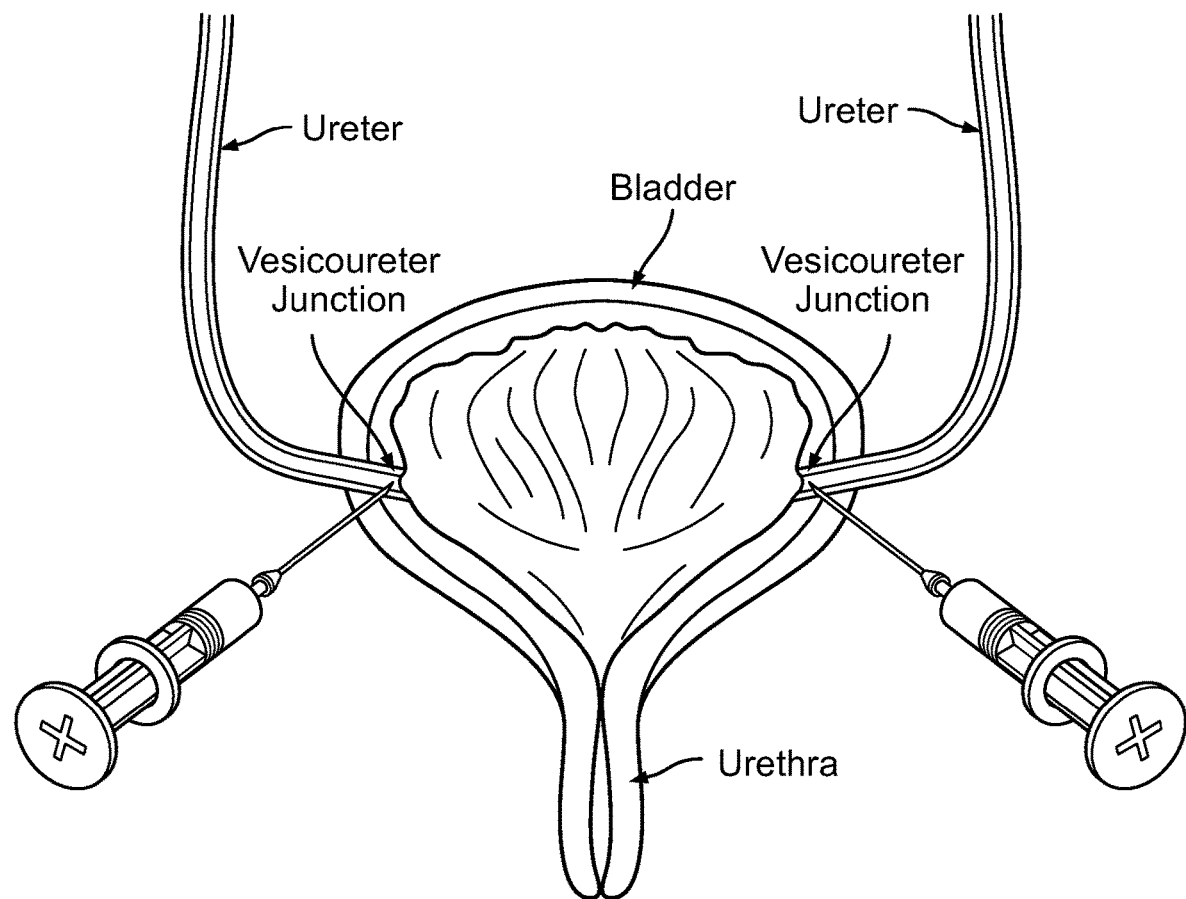

FIG. 221C shows an example procedure involving the treatment of vesicoureteral reflux, under an embodiment.

Figure 221D:
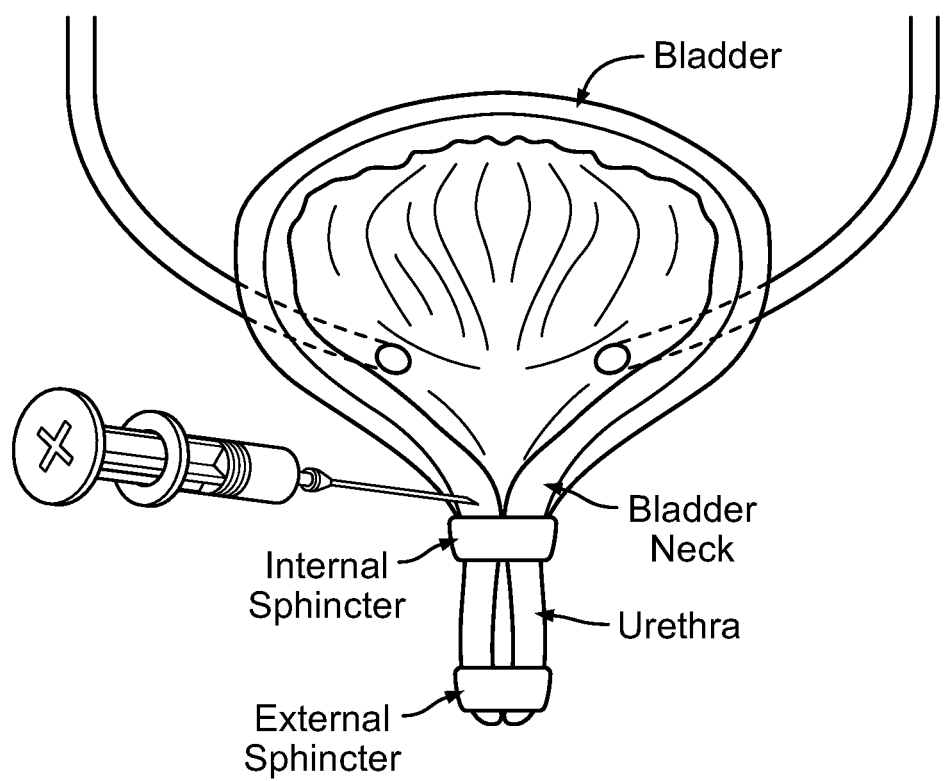

FIG. 221D shows an example procedure involving the treatment of urinary incontinence, under an embodiment.

Figure 221E:
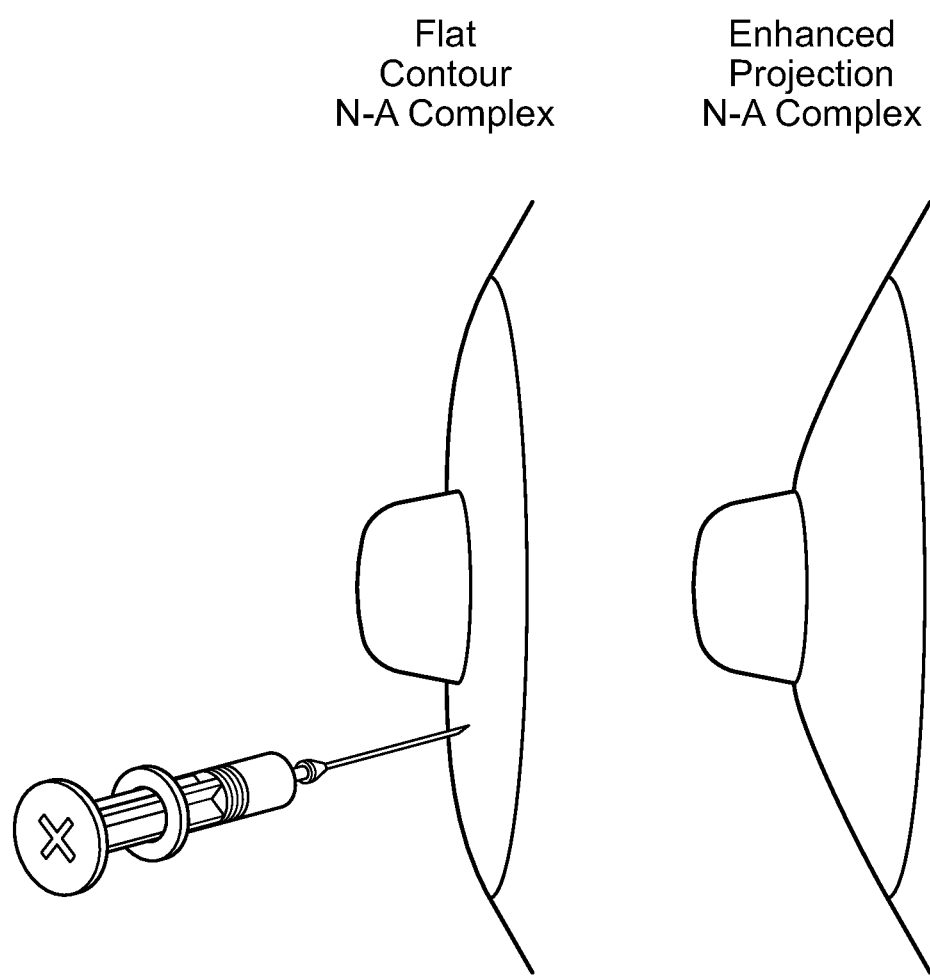

FIG. 221E shows an example procedure involving projection of the reconstructed nipple-areolar complex, under an embodiment.

Figure 221F:
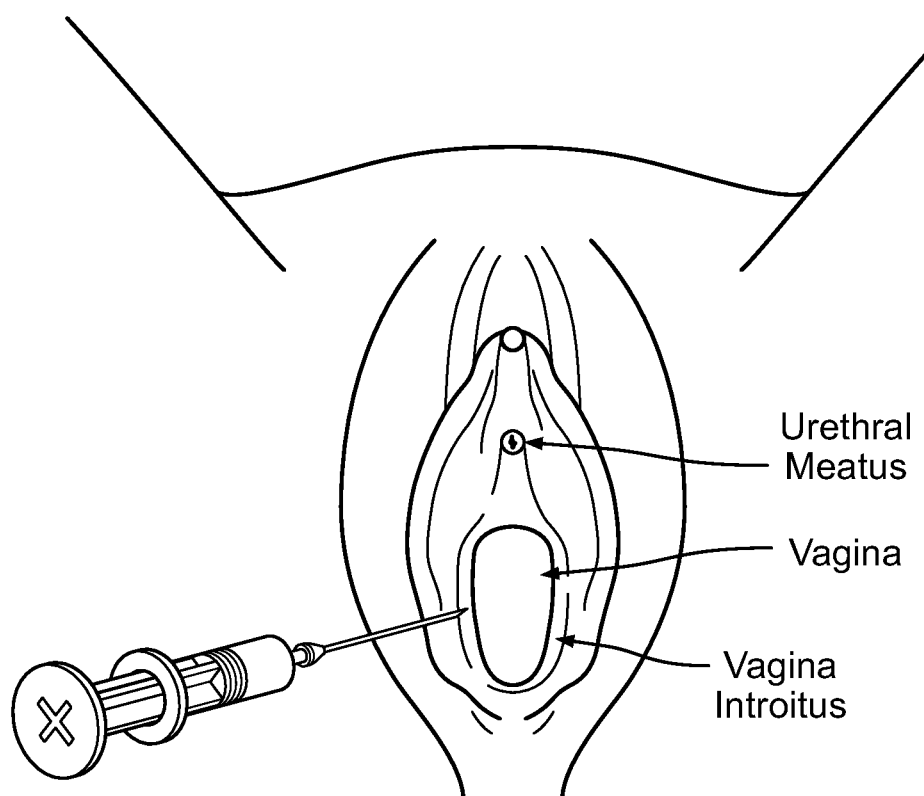

FIG. 221F shows an example procedure involving treatment of postpartum vaginal laxity, under an embodiment.

Figure 221G:
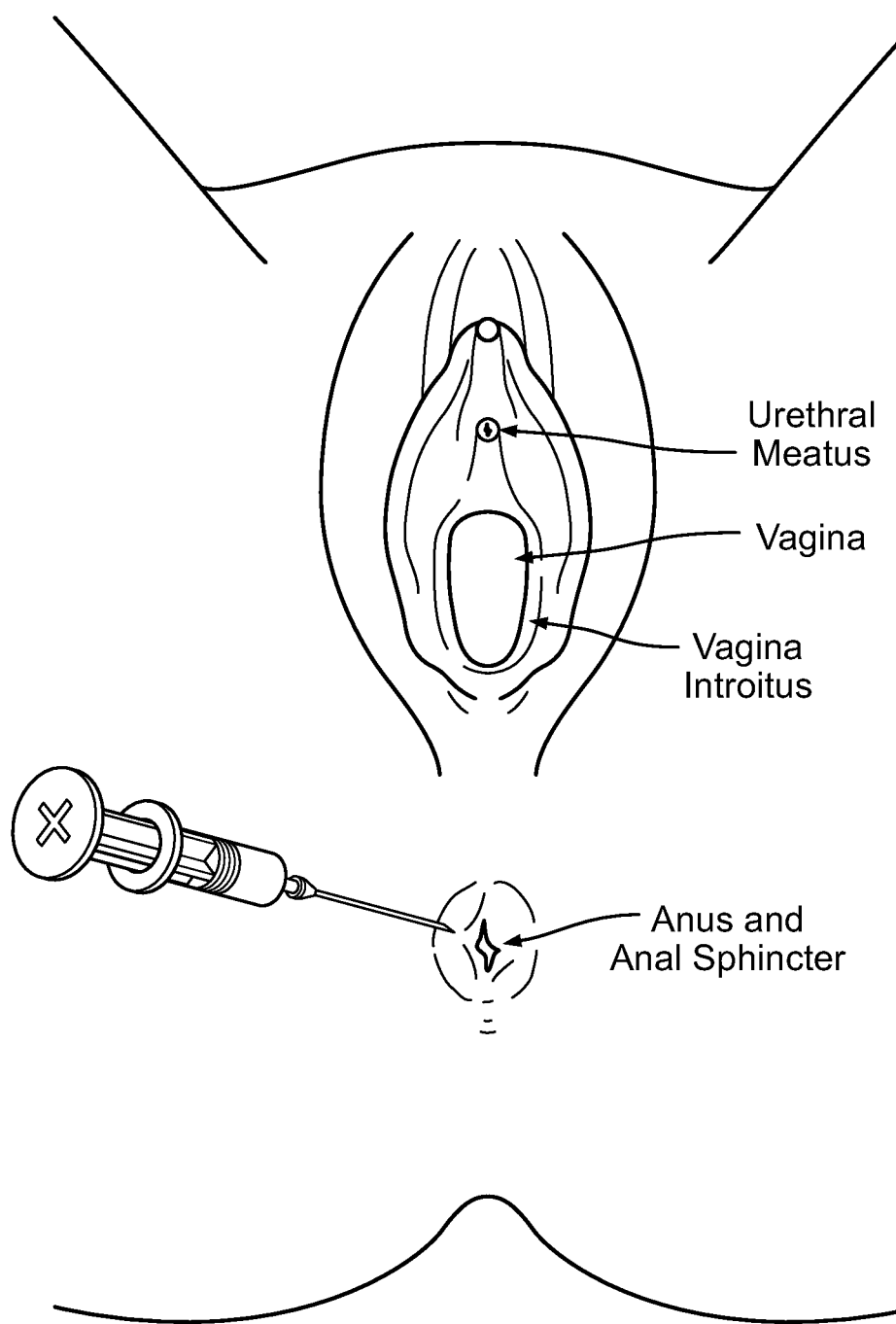

FIG. 221G shows an example procedure involving treatment of anal incontinence, under an embodiment.

Figure 221H:
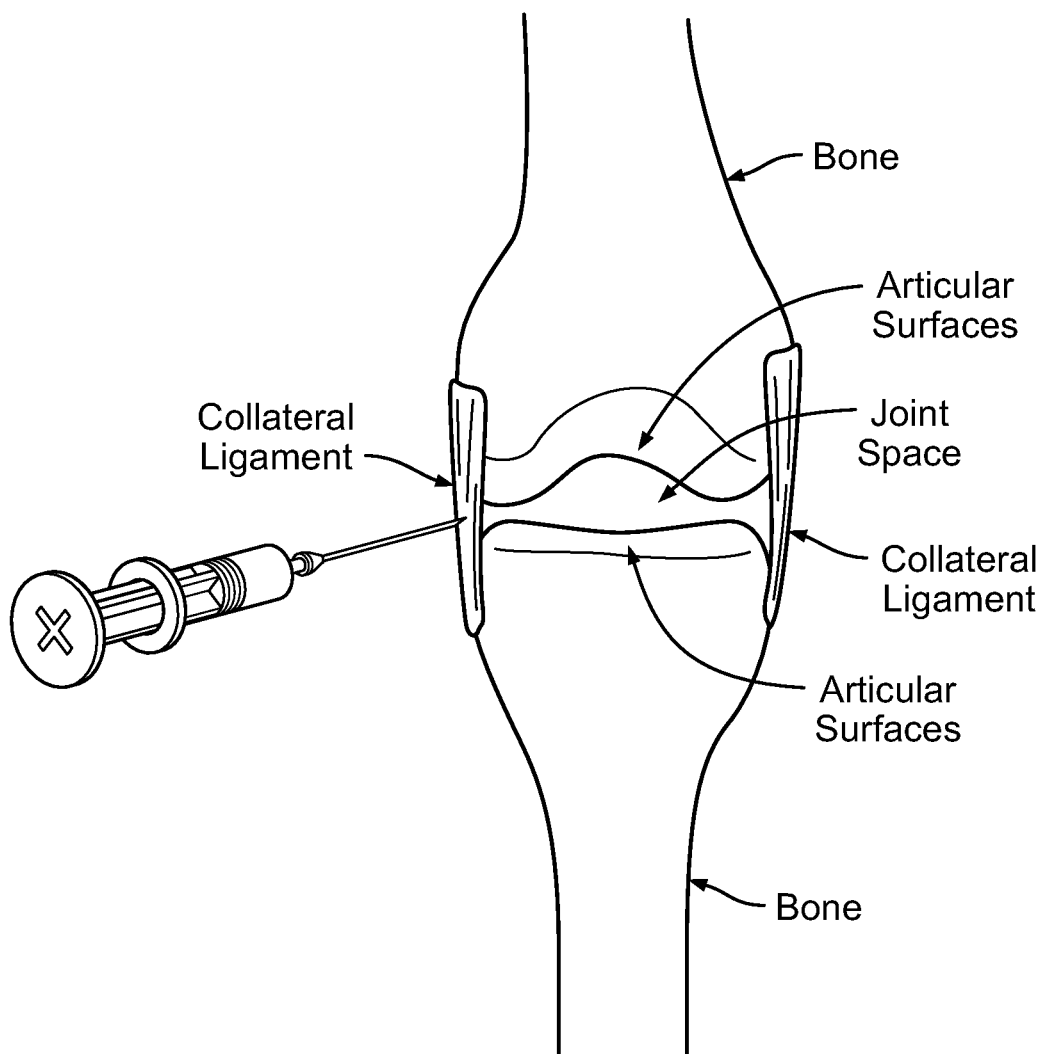

FIG. 221H shows an example procedure involving treatment of joint laxity and subluxation, under an embodiment.

Figure 221I:
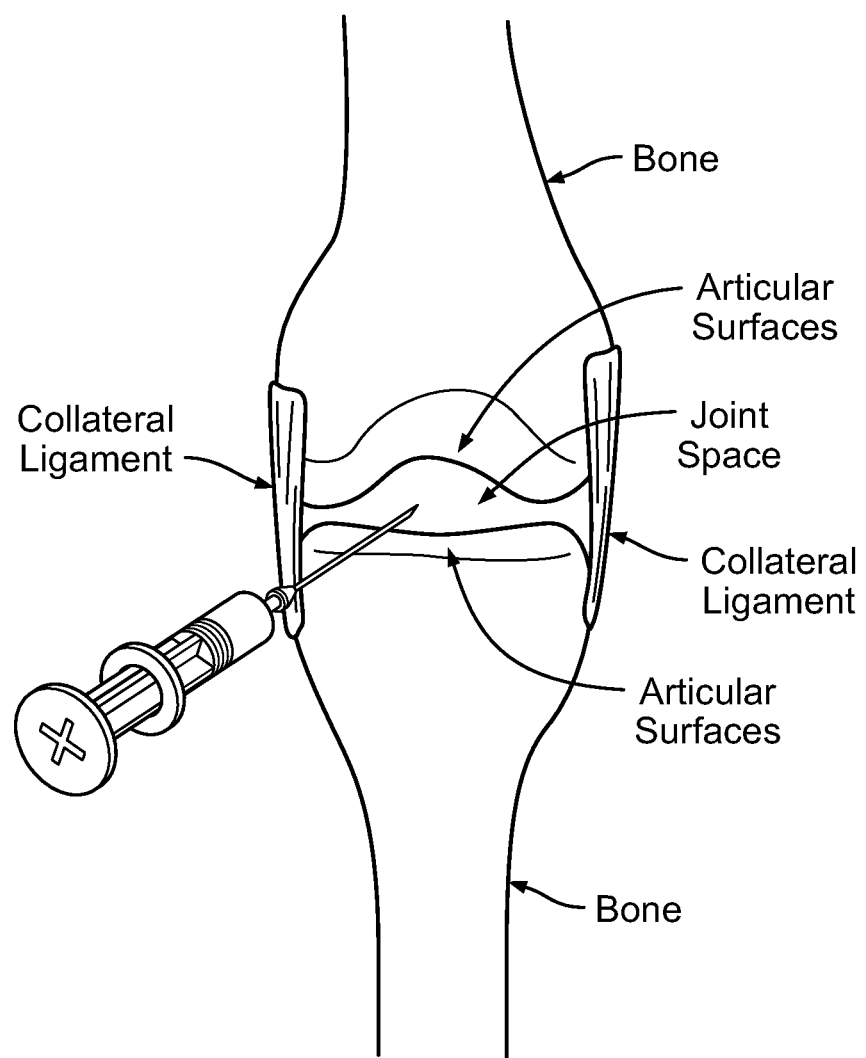

FIG. 221I shows an example procedure involving treatment of osteoarthritis, under an embodiment.

Figure 221J:
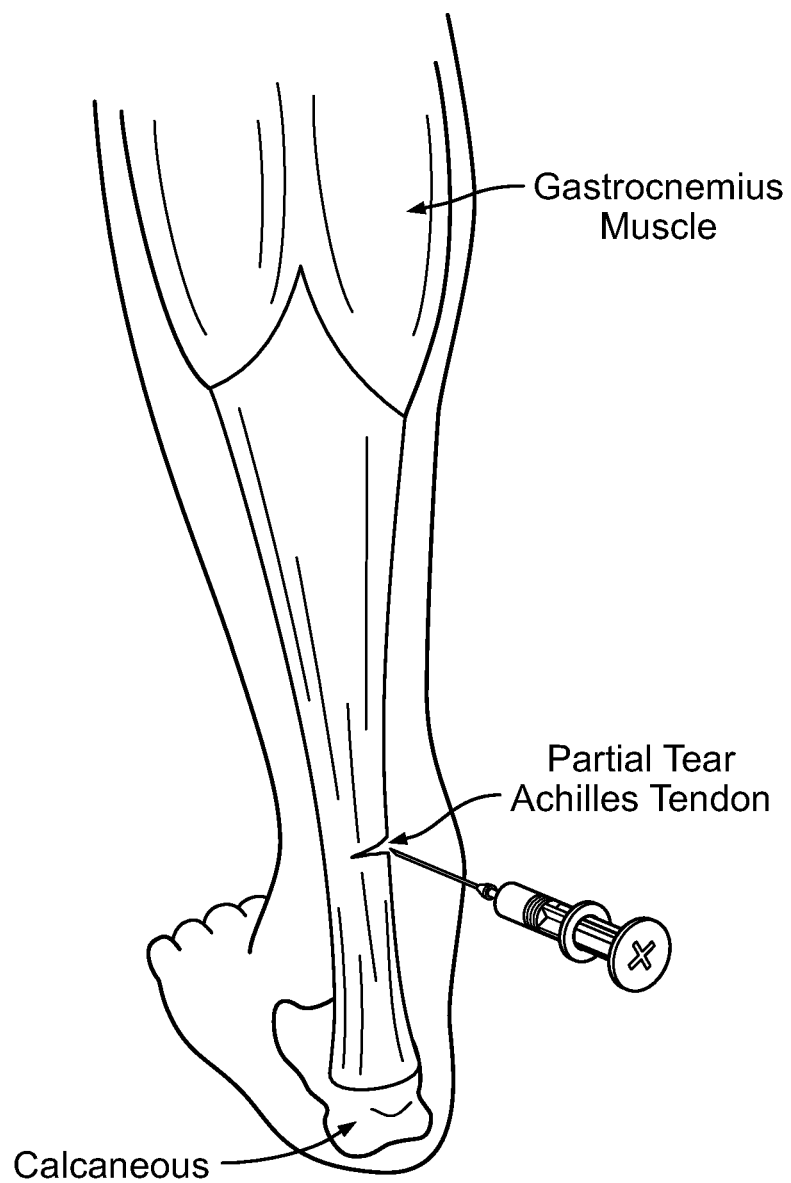

FIG. 221J shows an example procedure involving treatment of subtotal tendon tears, under an embodiment.

Figure 221K:
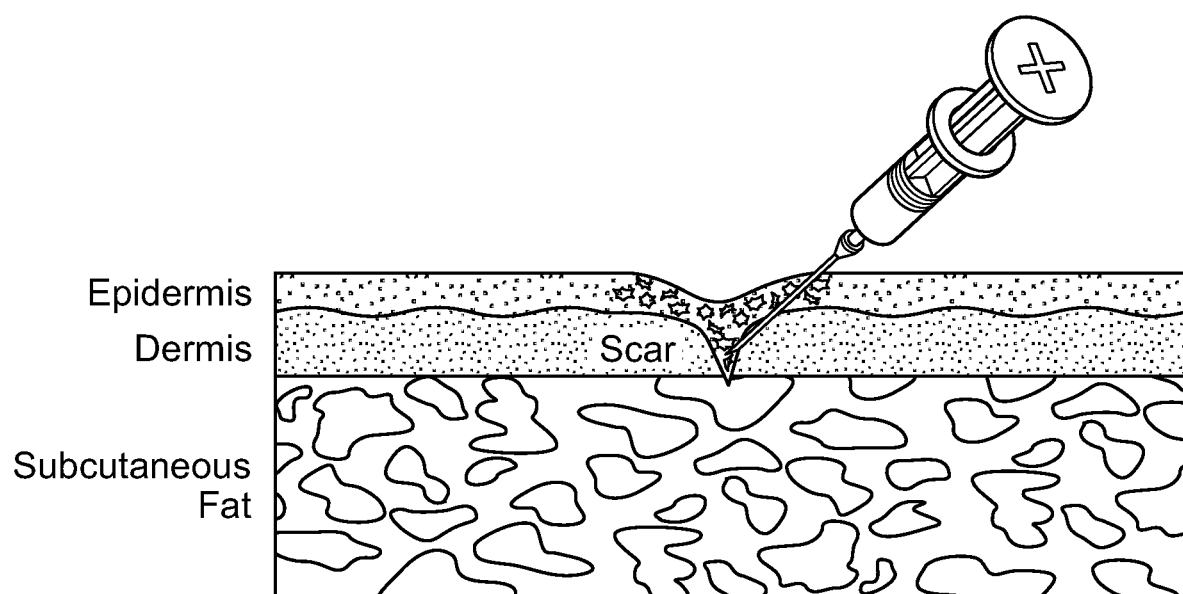

FIG. 221K shows an example procedure involving leveling of depressed traumatic scars, under an embodiment.

Figure 221L:
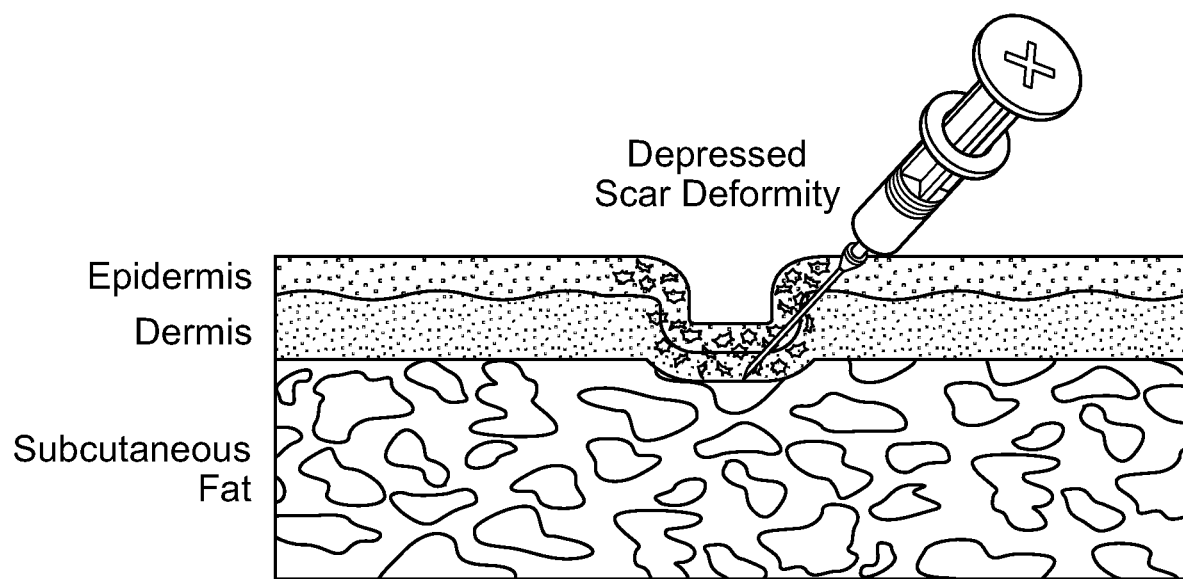

FIG. 221L shows an example procedure involving leveling of soft tissue contour deformities, including depressed skin graft deformities, under an embodiment.

Figure 221M:
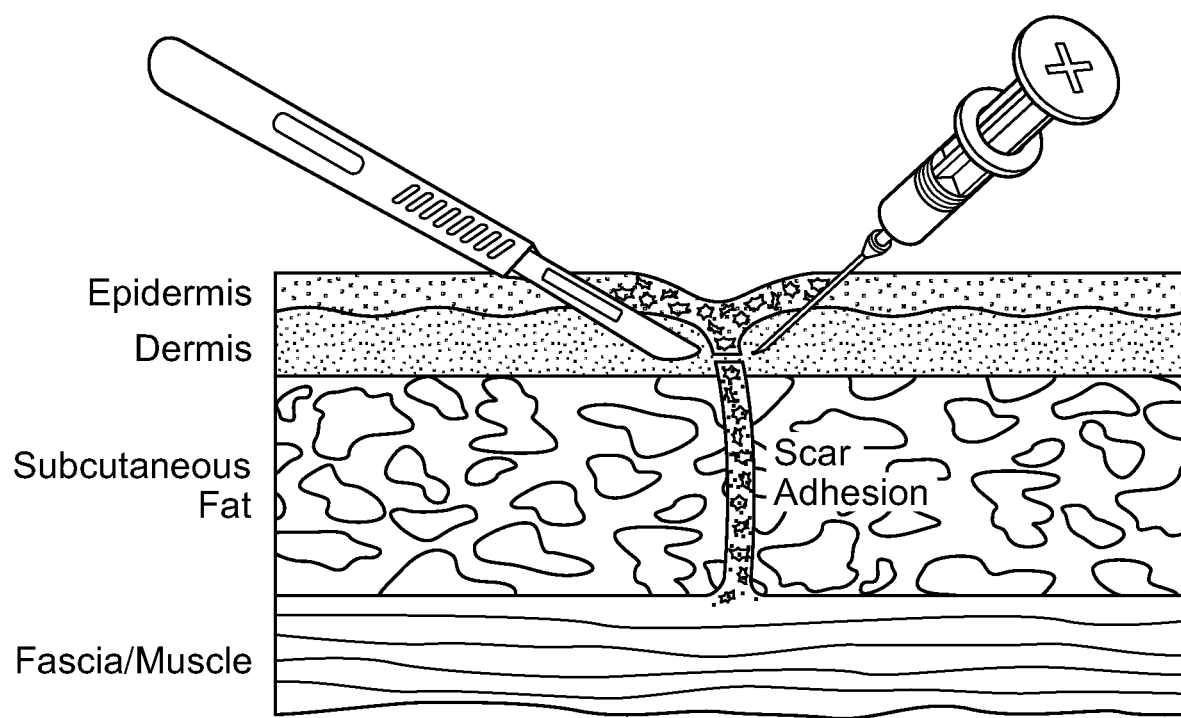

FIG. 221M shows an example procedure involving treatment of depressed scar adhesions, under an embodiment.

Figure 221N:
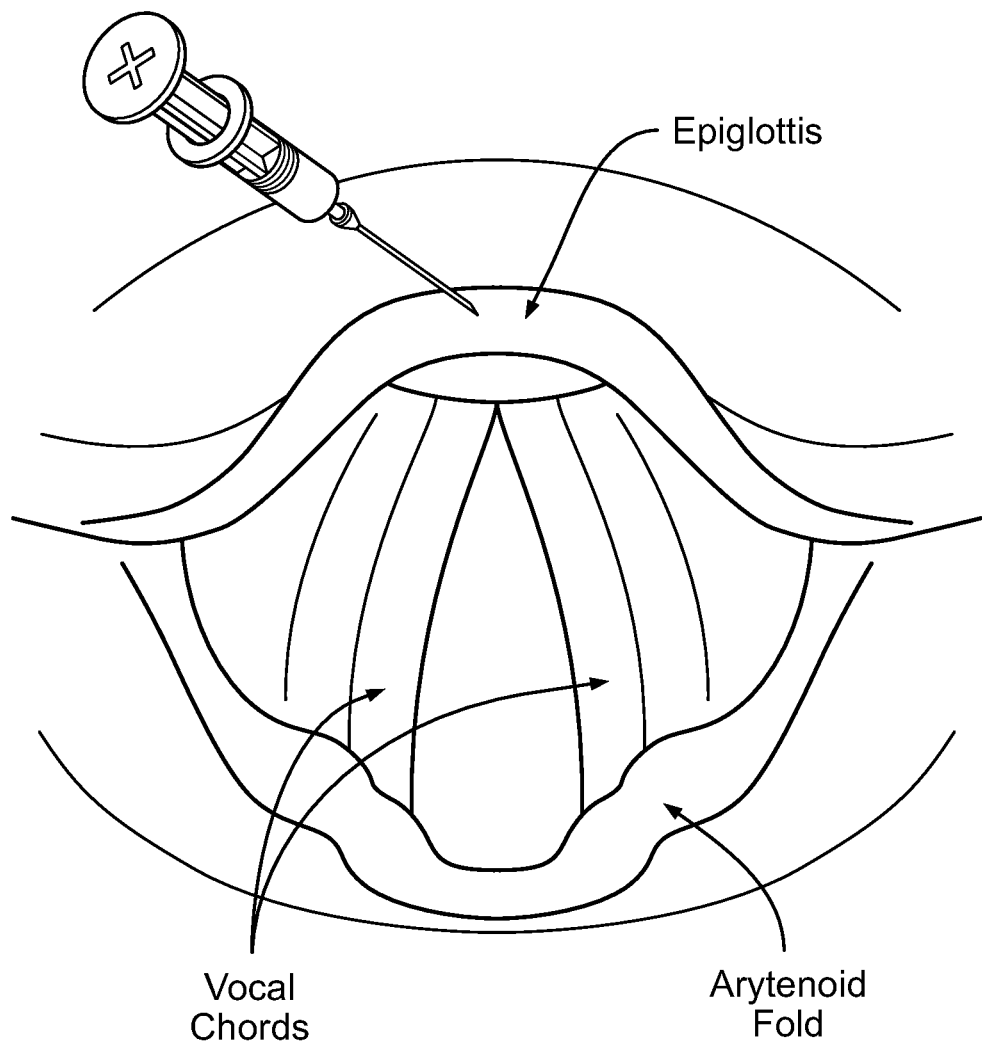

FIG. 221N shows an example procedure involving treatment of aspiration pneumonitis, under an embodiment.

Figure 221O:
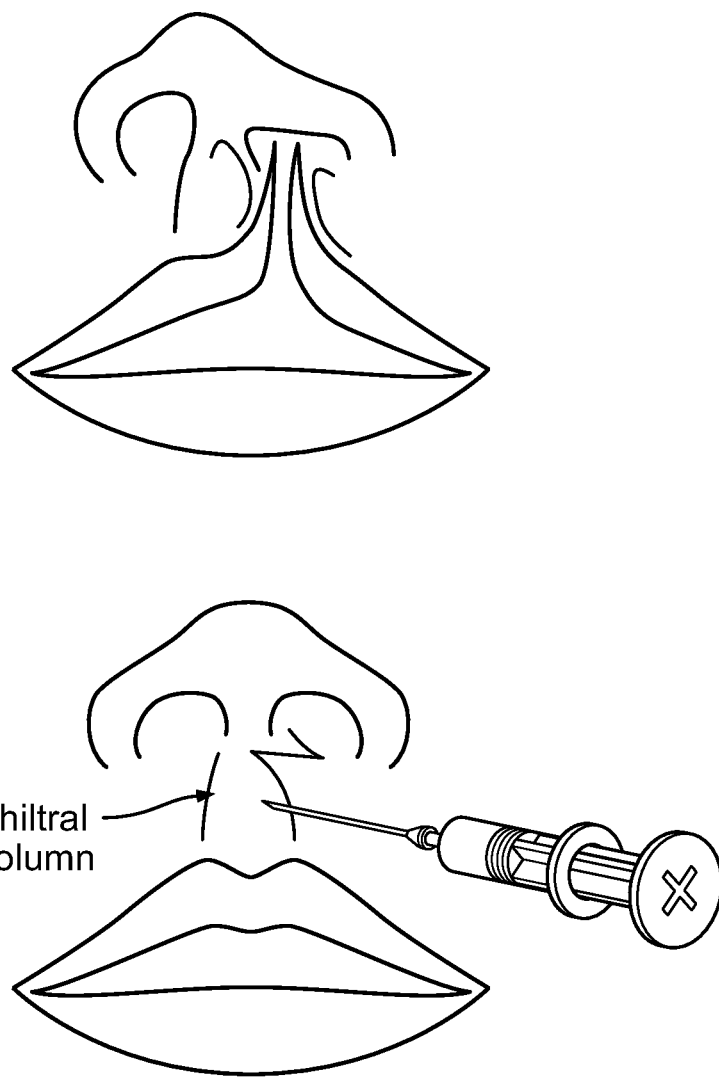

FIG. 221O shows an example procedure involving treatment of residual cleft lip deformity and residual cleft palate velopharyngeal incompetence, under an embodiment.

Figure 221P:
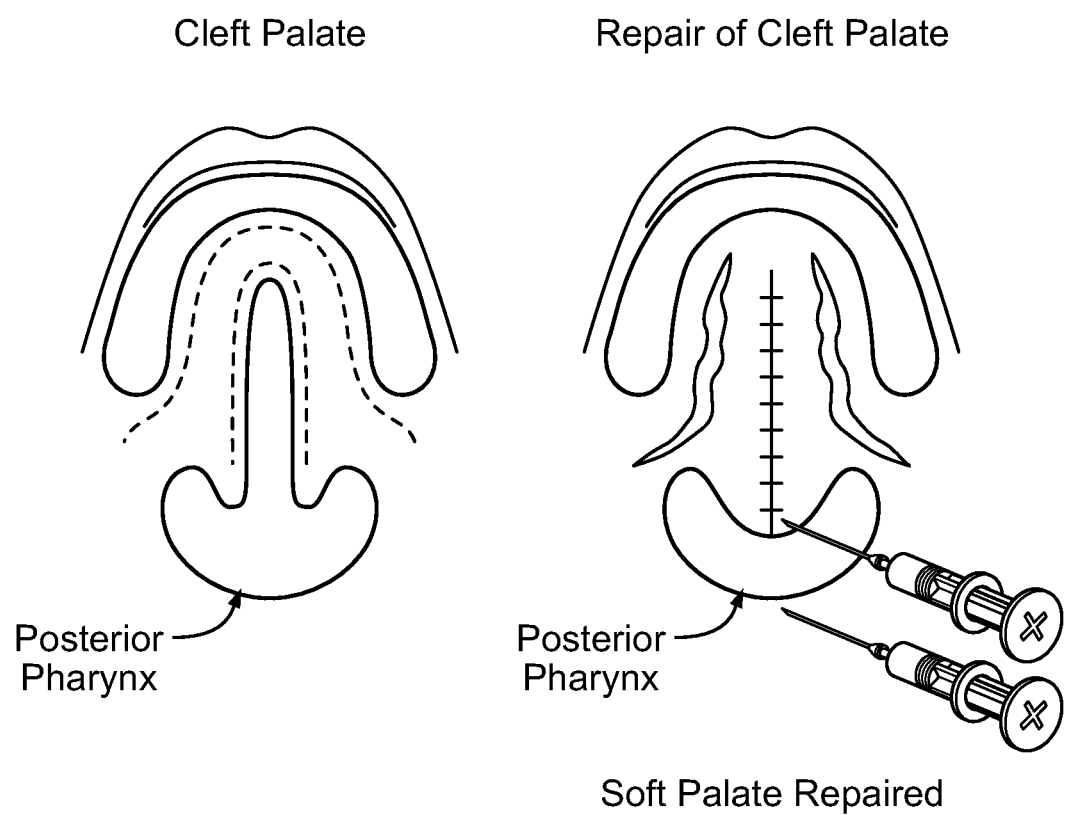

FIG. 221P shows an example procedure involving congenital cleft palate repairs, under an embodiment.

Figure 222:
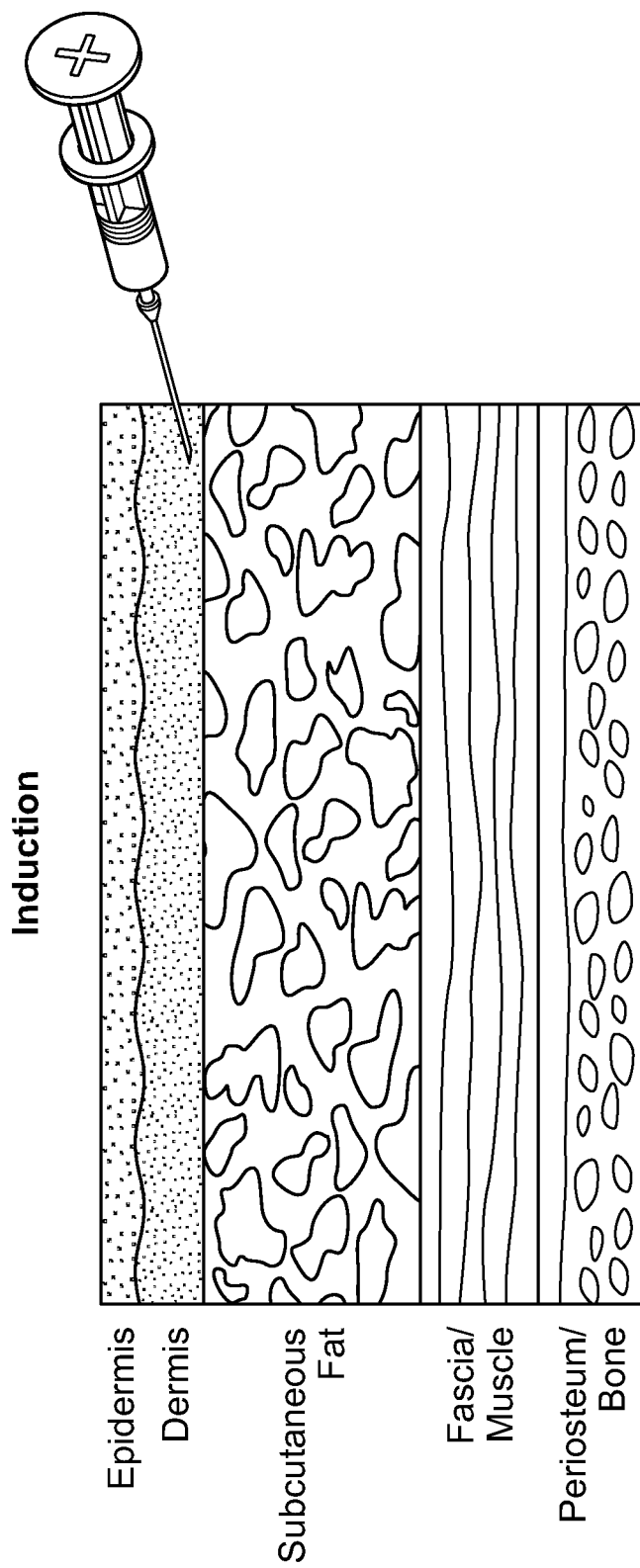

FIG. 222 shows an example aesthetic inductive application including skin rejuvenation, under an embodiment.

Figure 223:
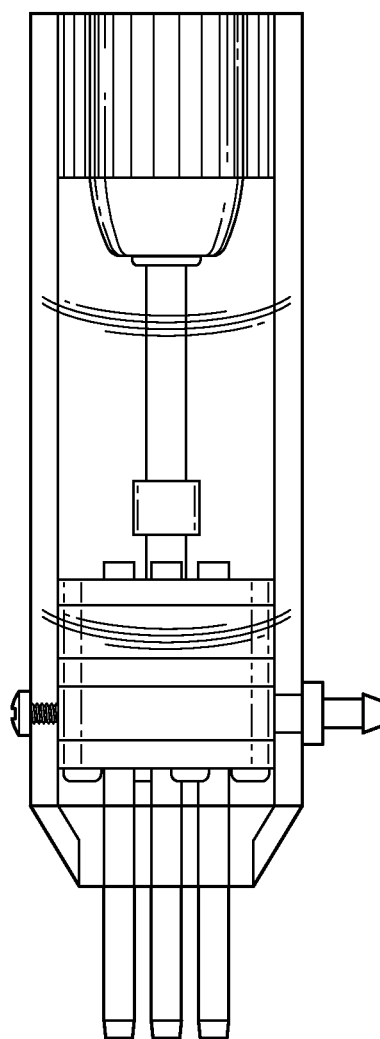

FIG. 223 is an example multifunctional canister, under an embodiment.

Figure 224:
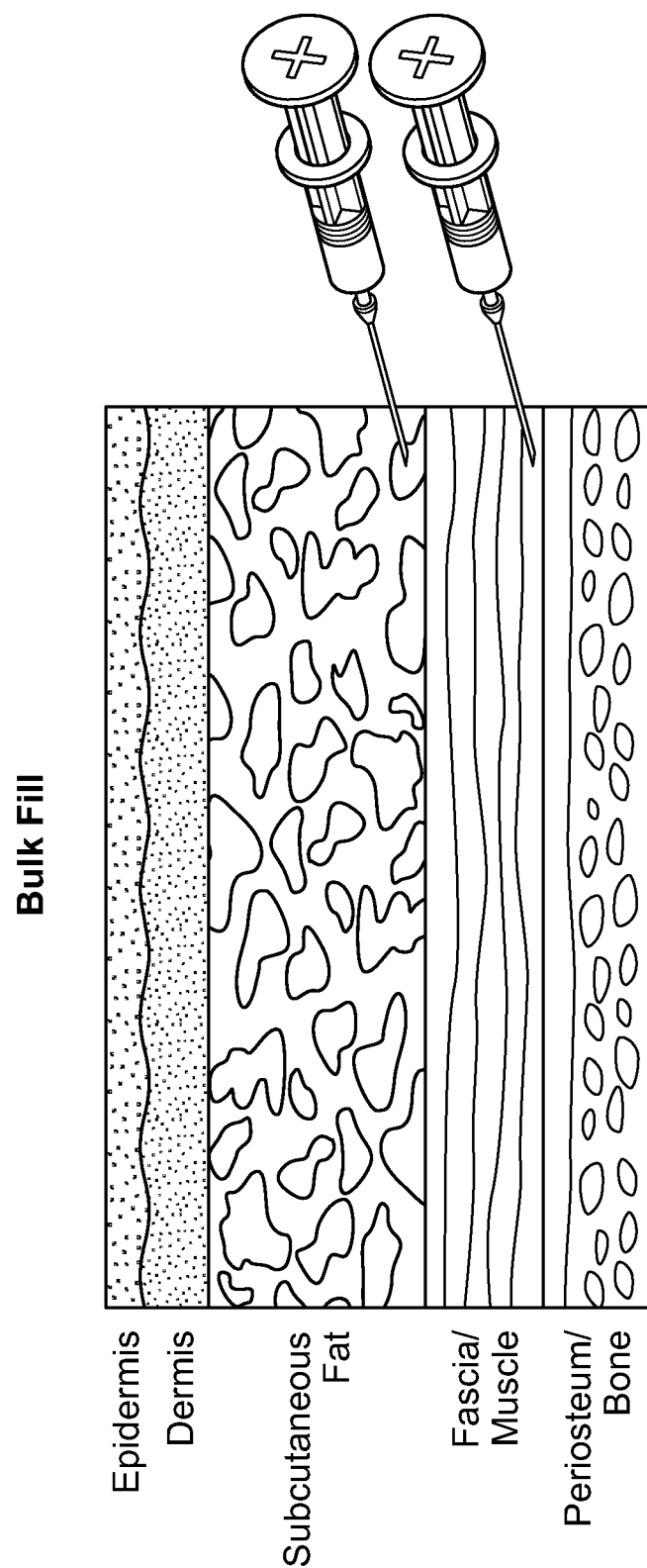

FIG. 224 shows an example intermediate depth aesthetic bulk fill injection, under an embodiment.

Figure 225A:
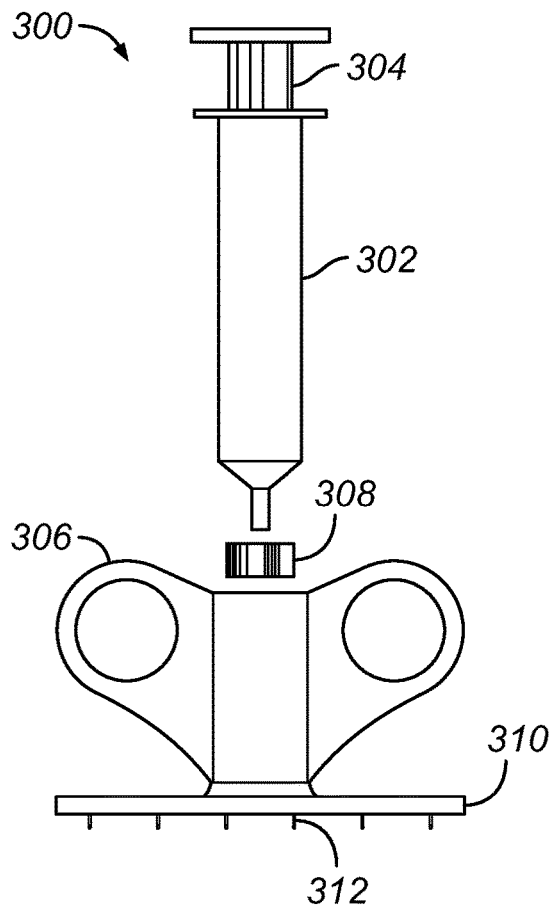
Figure 225B:
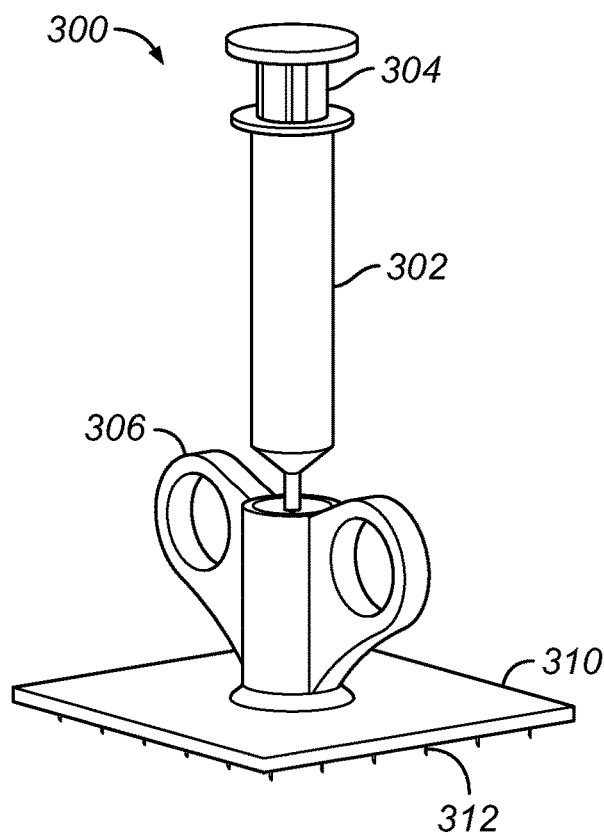
Figure 225C:
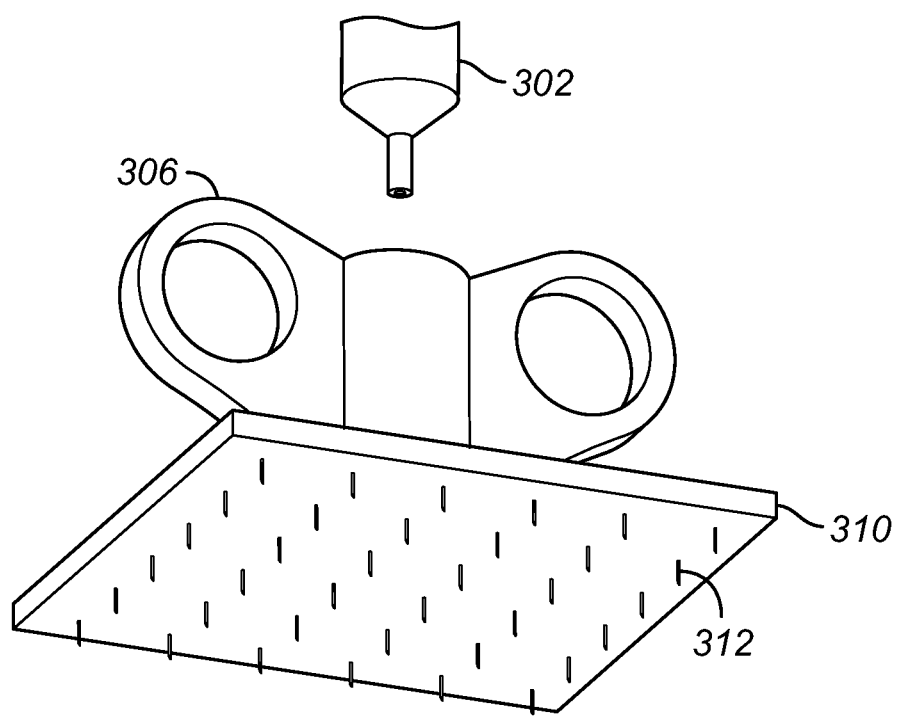

FIGS. 225A-225C show different views of a drug delivery device including a flat array of fine needles of differing lengths positioned on manifold, under an embodiment.

Figure 226:
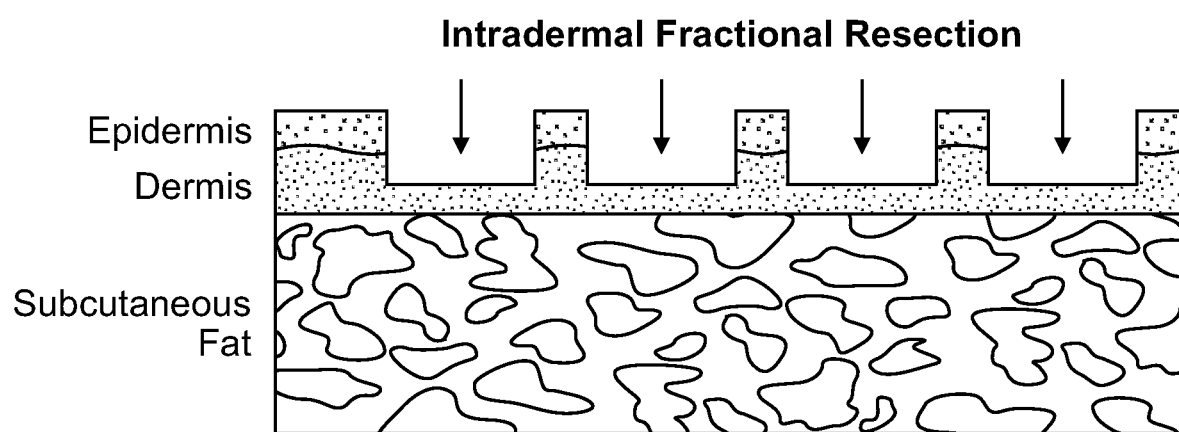

FIG. 226 depicts preservation of subdermal structures during intradermal fractional resection, under an embodiment.

Figure 227A:
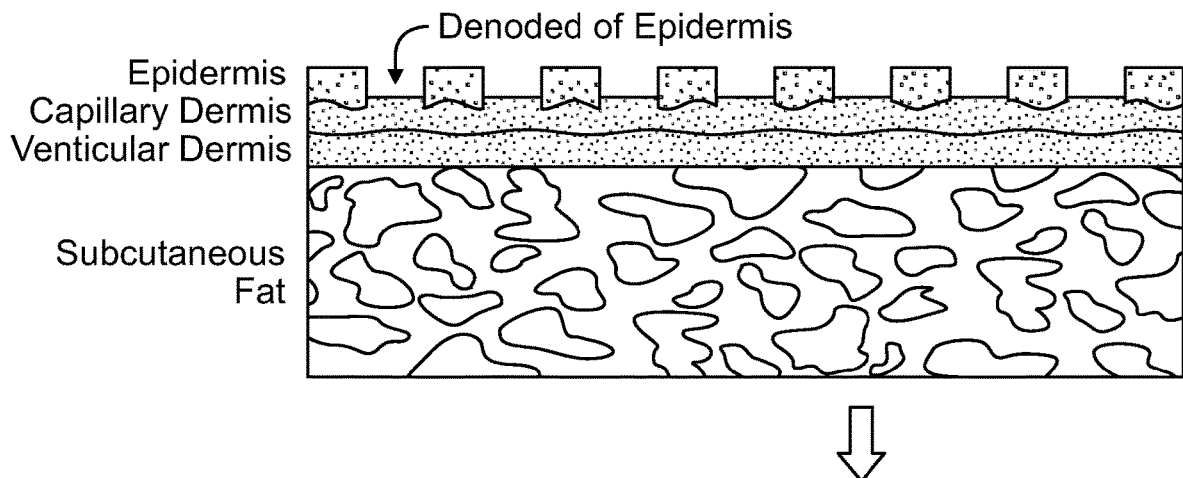

FIG. 227A shows harvesting of the epidermis at a donor site without removing the dermis, under an embodiment.

Figure 227B:
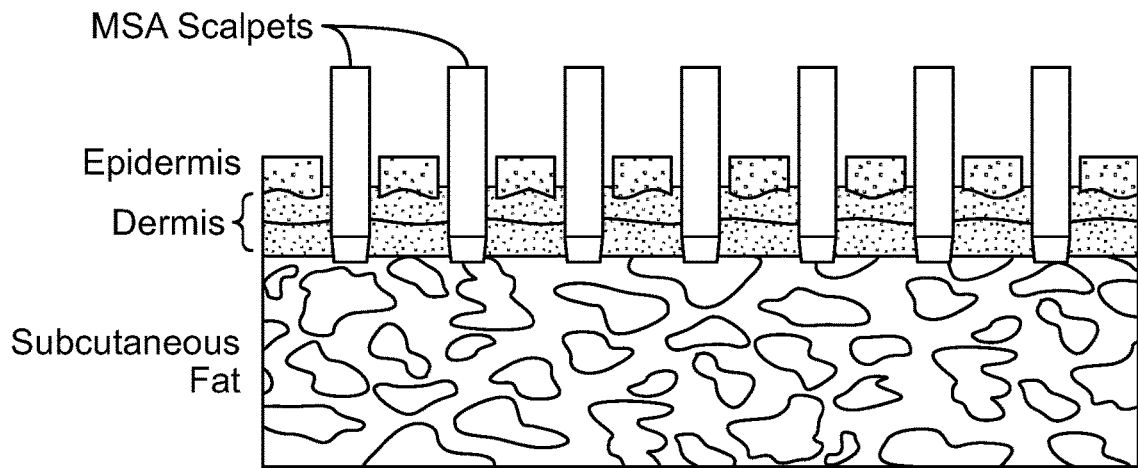

FIG. 227B shows fractional harvesting of the dermis at a donor site via the denuded regions of the epidermis, under an embodiment.

Figure 228A:
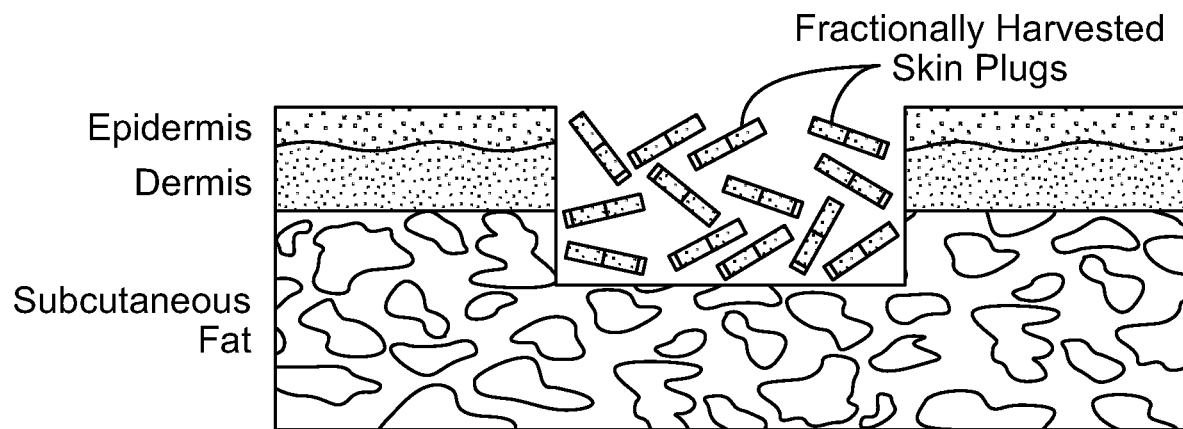

FIG. 228A shows dermal plugs applied directly to the recipient skin defect site, under an embodiment.

Figure 228B:
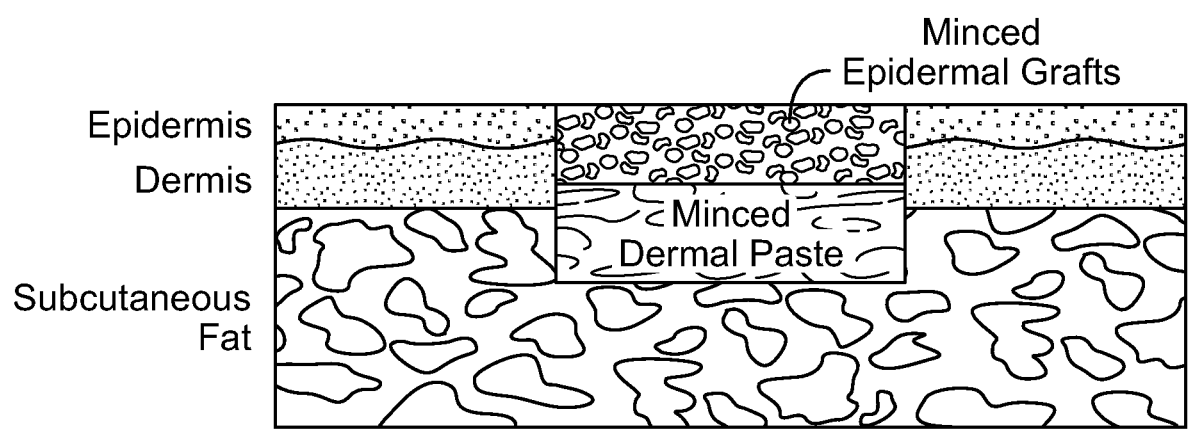

FIG. 228B shows the minced dermal paste applied directly to the recipient skin defect site, and the minced epidermal tissue or grafts applied to the subjacent dermal grafted layer, under an embodiment.

Figure 229:
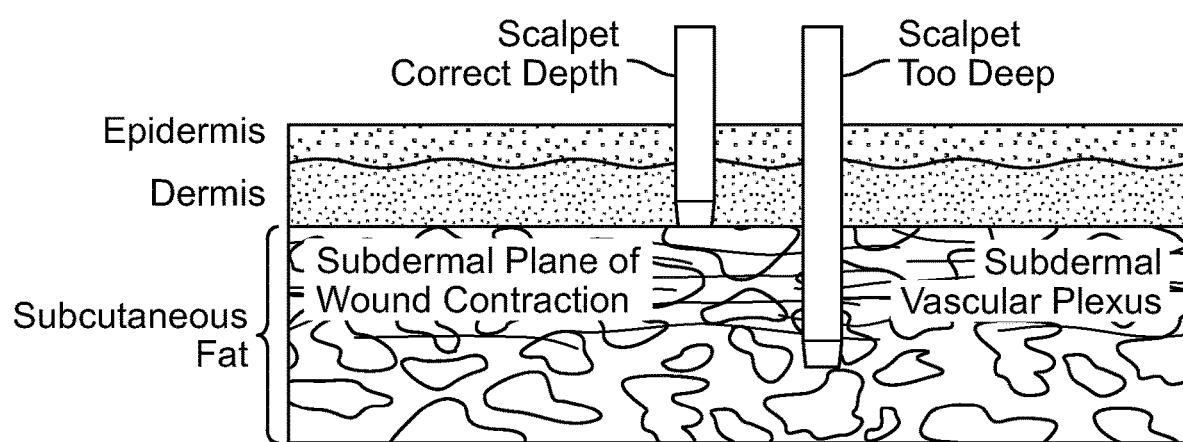

FIG. 229 shows a scalpet inserted to an appropriate depth in tissue (left), and a scalpet inserted to an excessive depth in tissue (right).

Figure 230:
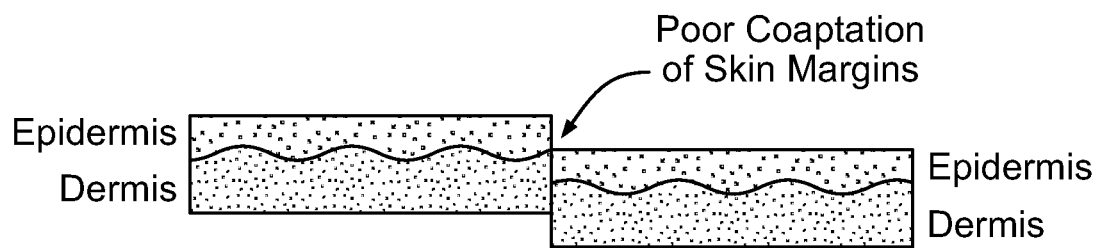

FIG. 230 shows poor coaptation and overlapping of fractional skin margins of the fractional field.

Figure 231:
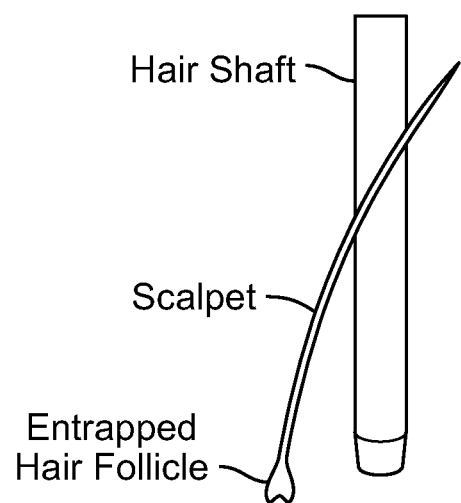

FIG. 231 shows a vertically applied scalpet transecting the hair shaft distal to an obliquely coursing hair follicle.

Figure 232:
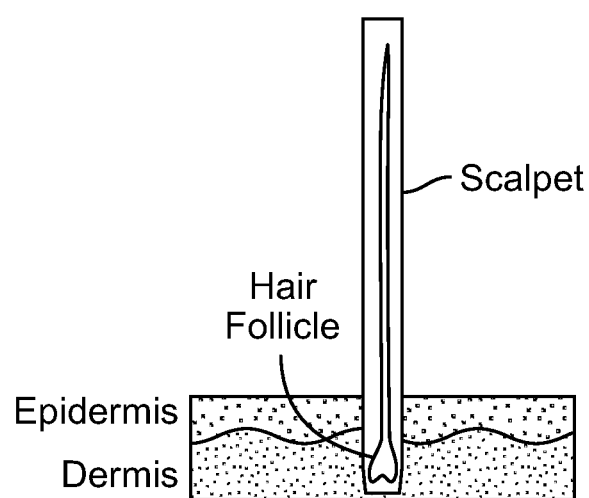

FIG. 232 shows tilting of the scalpet in line with an obliquely coursing hair shafts during fractional skin grafting, under an embodiment.

Figure 233:
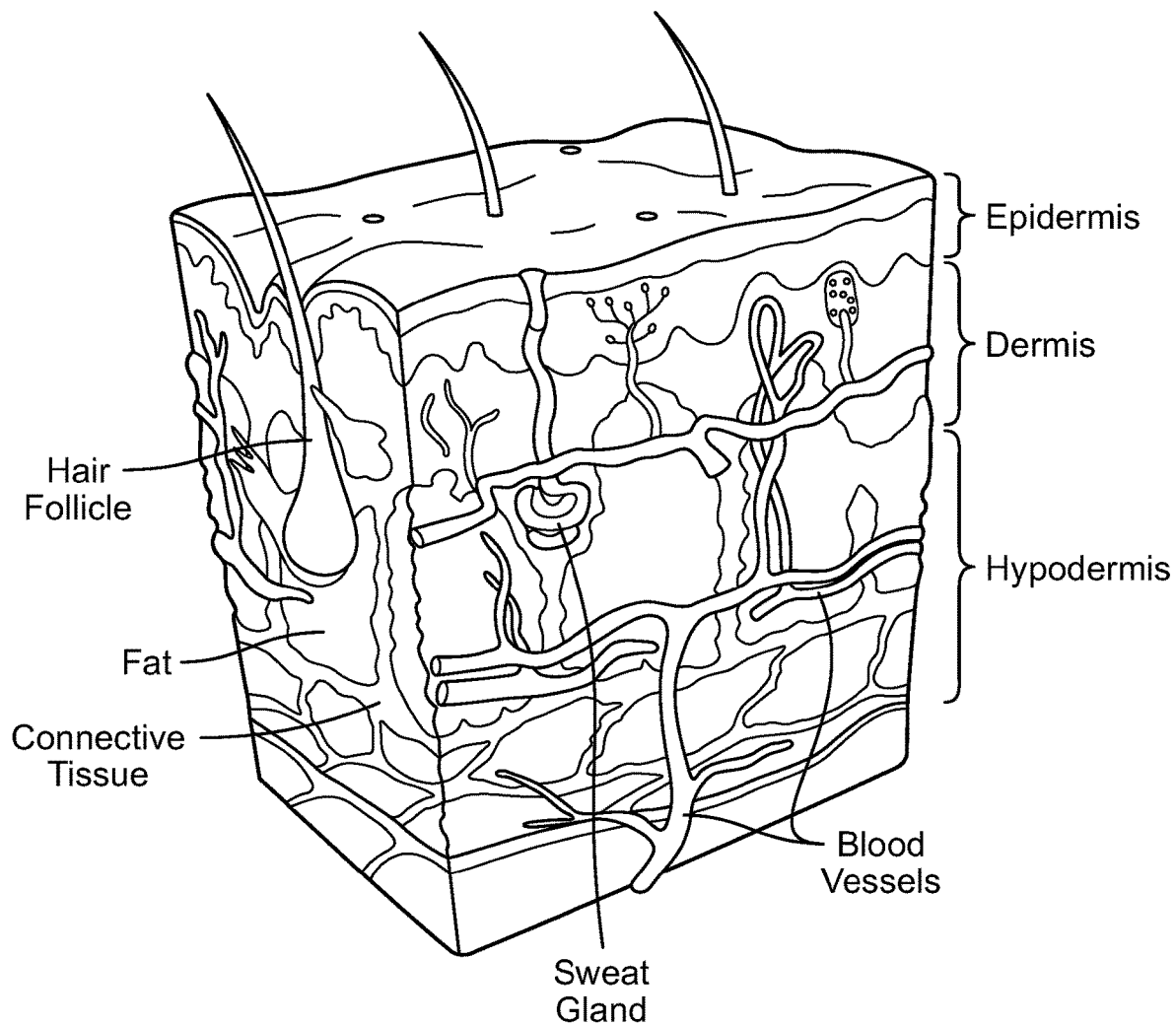

FIG. 233 shows the tissue layers forming human skin.

Figure 234:
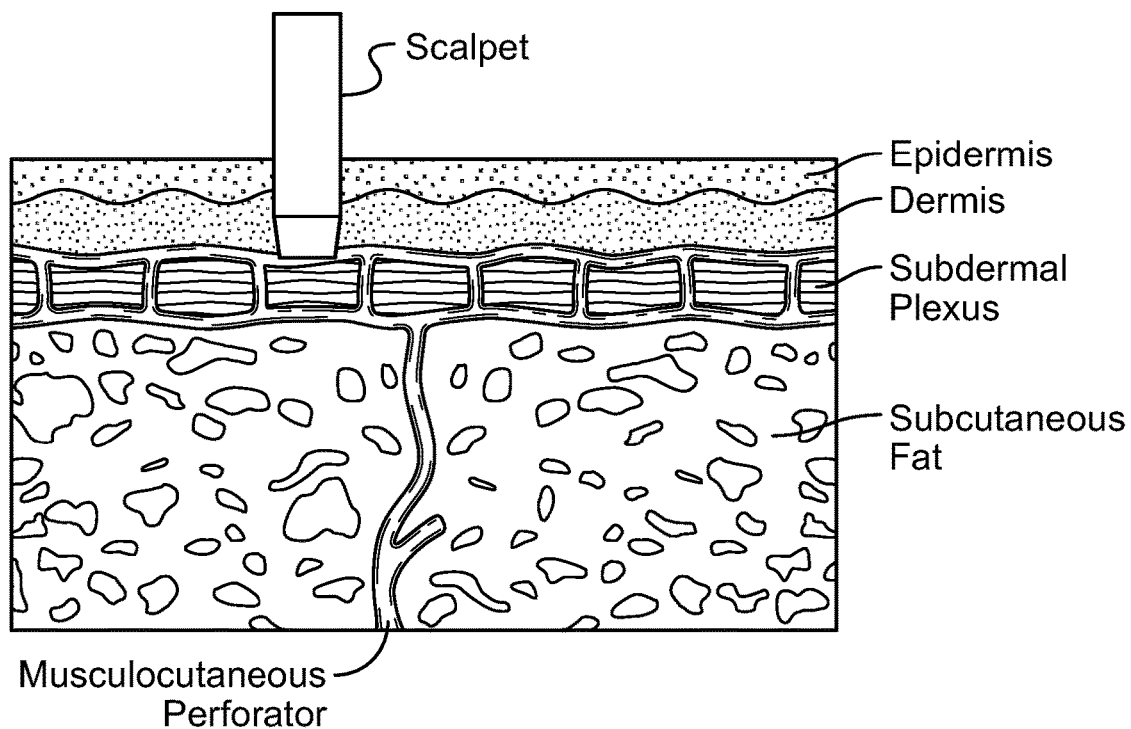

FIG. 234 shows a scalpet penetrating the epidermis and dermis of a subject during a fractional resection at an appropriate depth.

Figure 235:
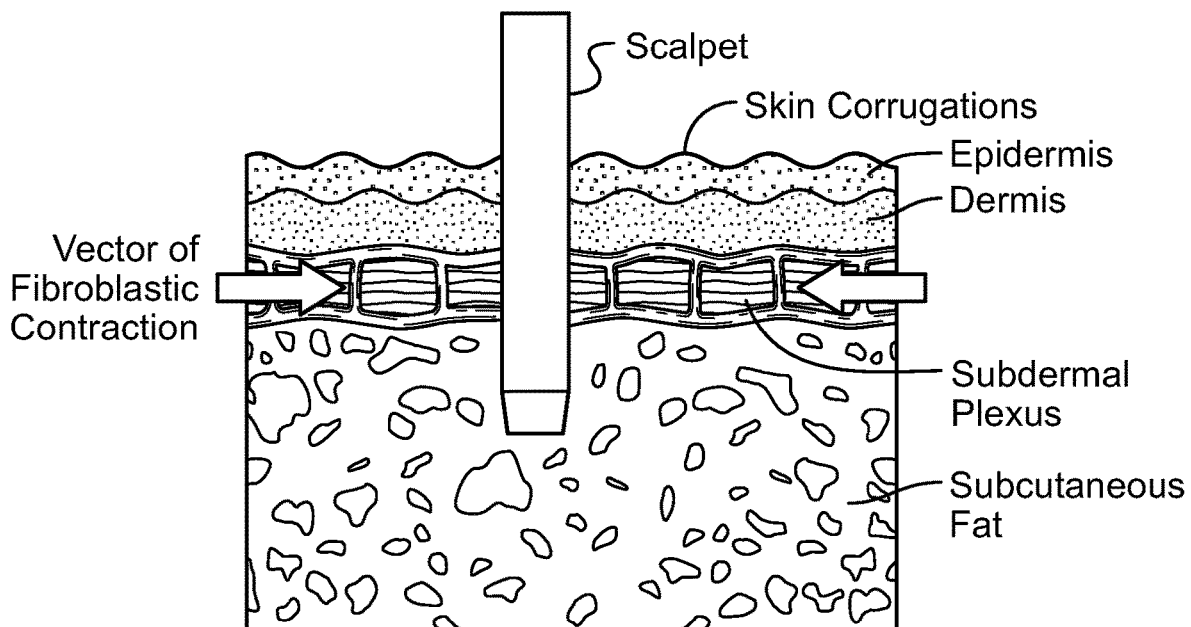

FIG. 235 shows a scalpet penetrating the subdermal plexus of a subject during a deeper fractional resection.

Figure 236:
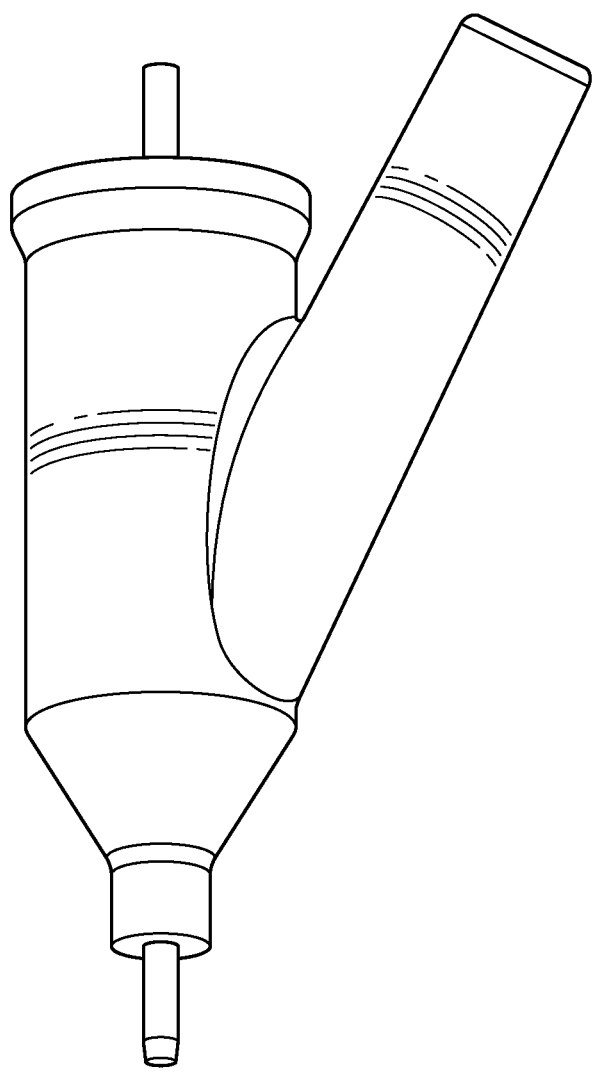

FIG. 236 is a perspective view of the single scalpet device in the depth guide, under an embodiment.

Figure 237:
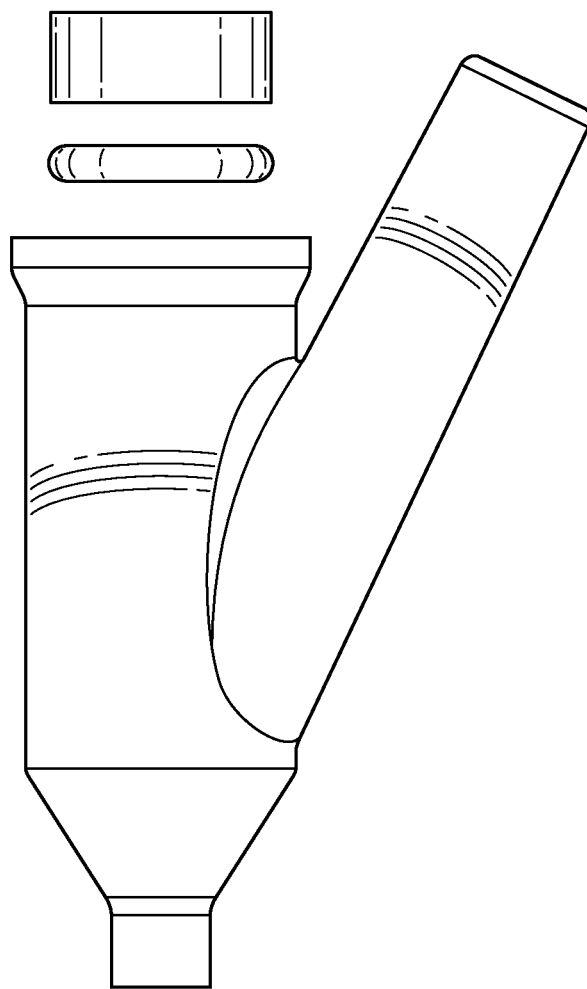

FIG. 237 is an exploded side view of the depth guide showing the O-ring distal between the depth guide and the distal end of the handpiece, under an embodiment.

Figure 238:
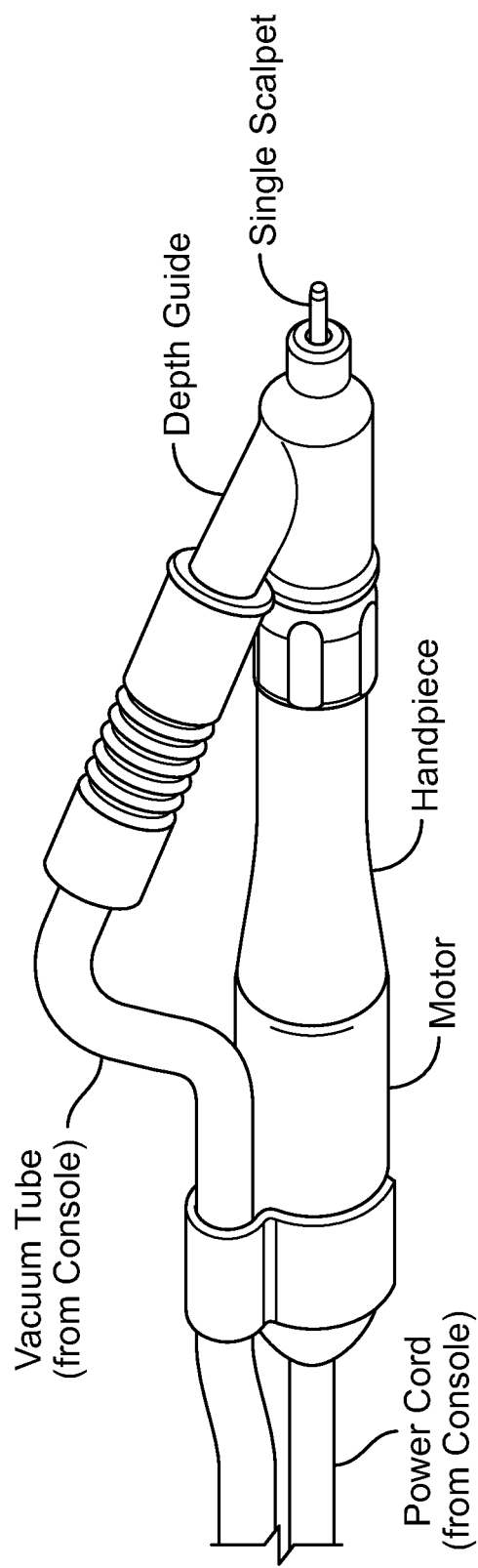

FIG. 238 is a perspective view of the RFR system including the single-scalpet device connected to the handpiece, under an embodiment.

Figure 239:
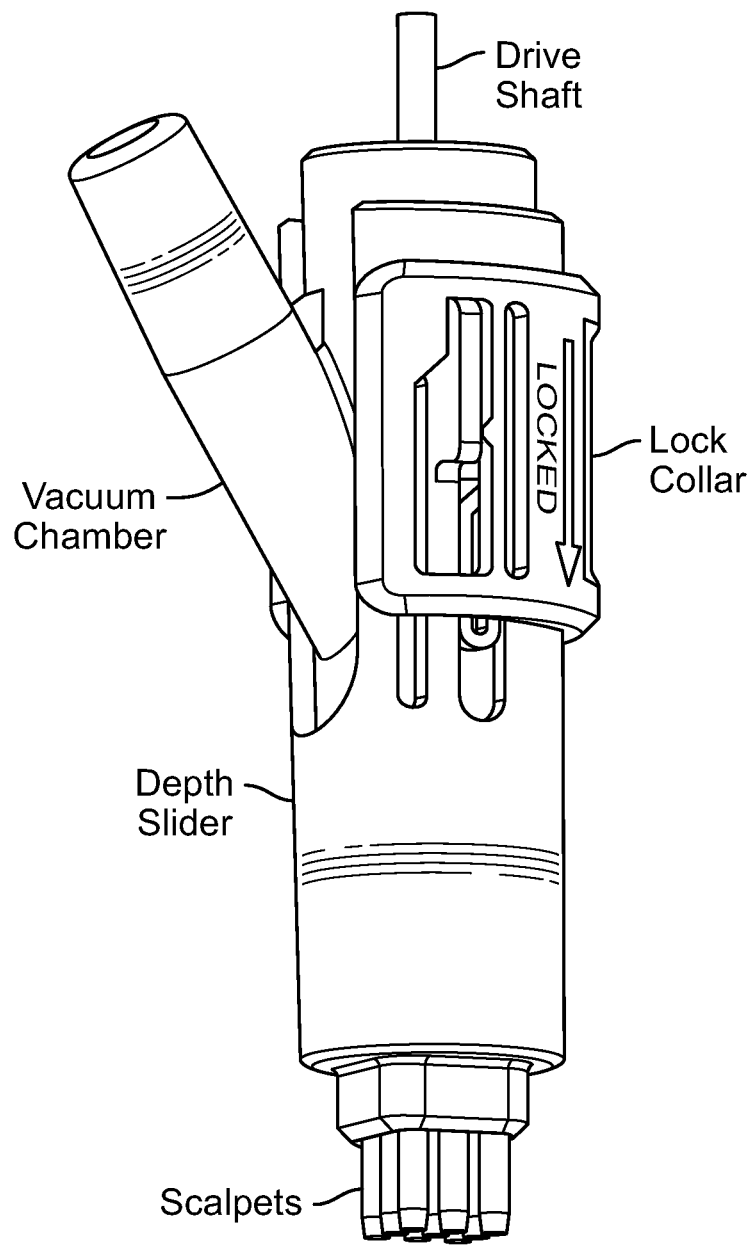

FIG. 239 is a perspective view of the Multi-Scalpet Array (MSA) device, under an embodiment.

Figure 240:
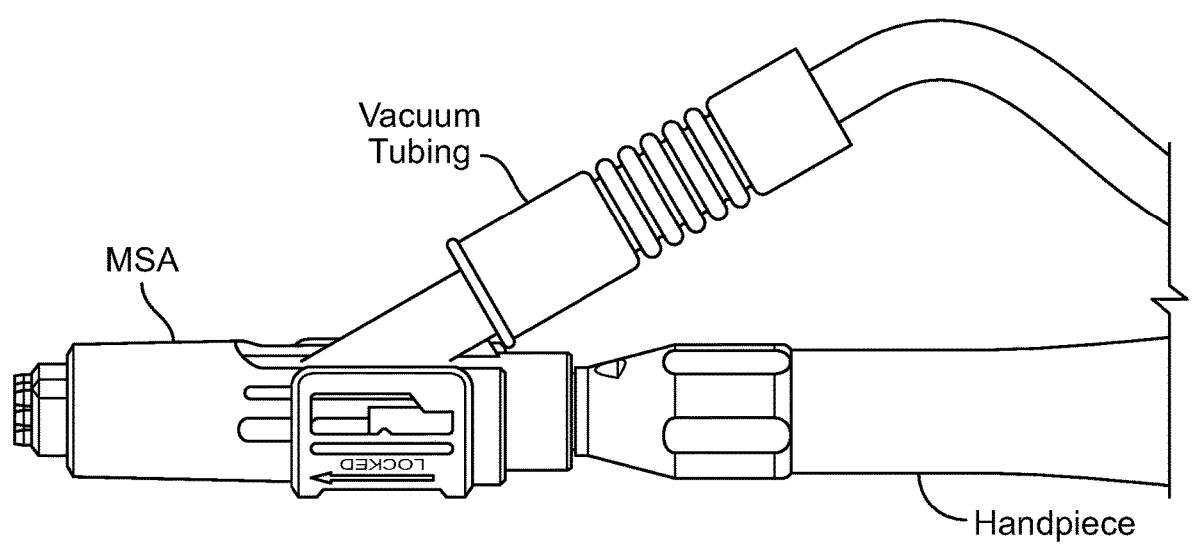

FIG. 240 is a perspective view of the RFR system including the MSA device connected to the handpiece, under an embodiment.

Figure 241:
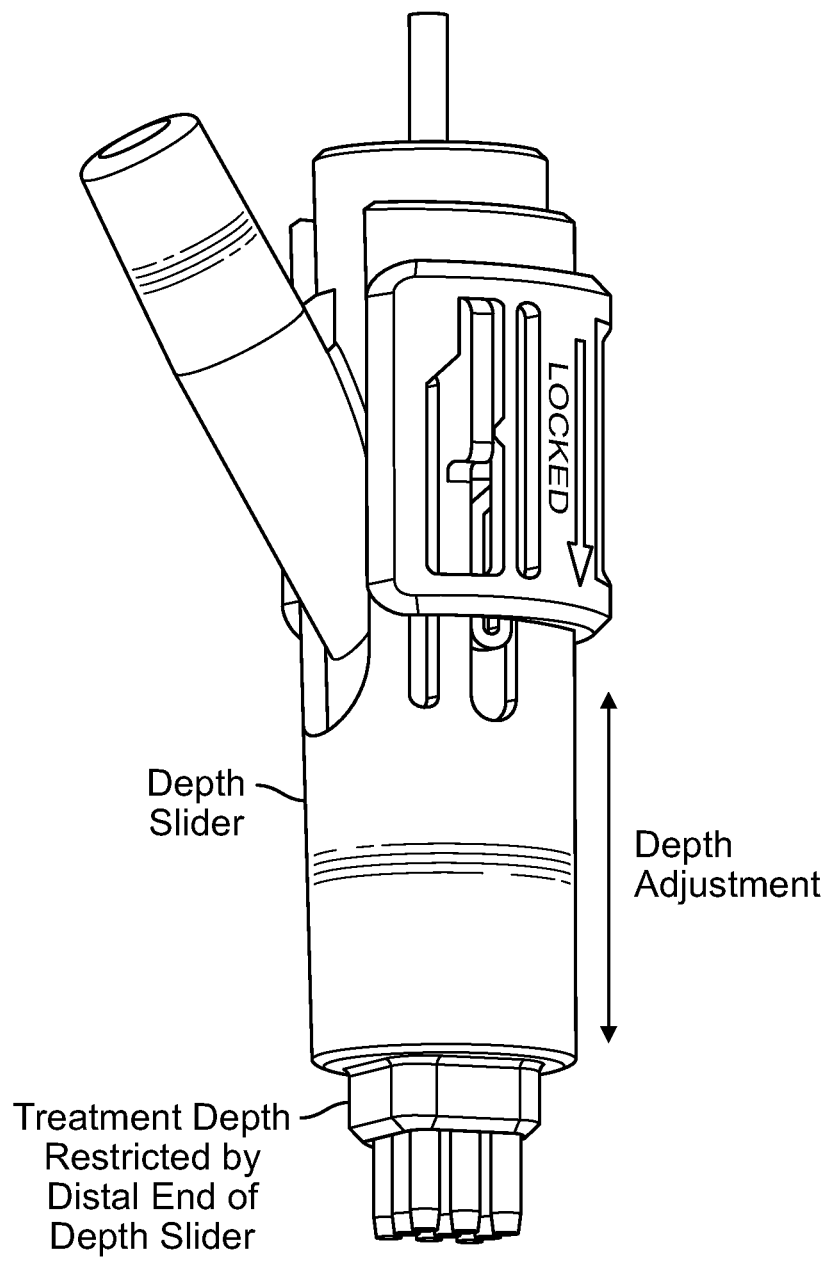

FIG. 241 is a perspective view of the MSA device showing operation of the depth slider, under an embodiment.

Figure 242:
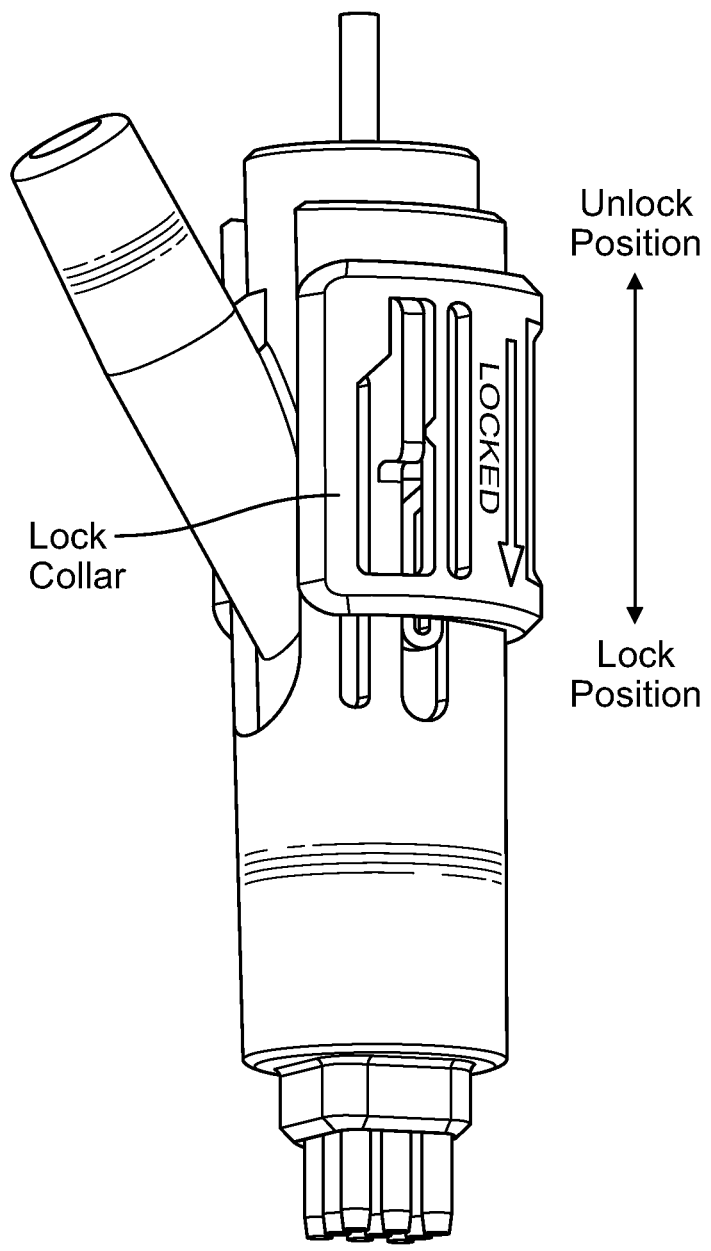

FIG. 242 is a perspective view of the MSA device showing operation of the lock collar, under an embodiment.

Figure 243:
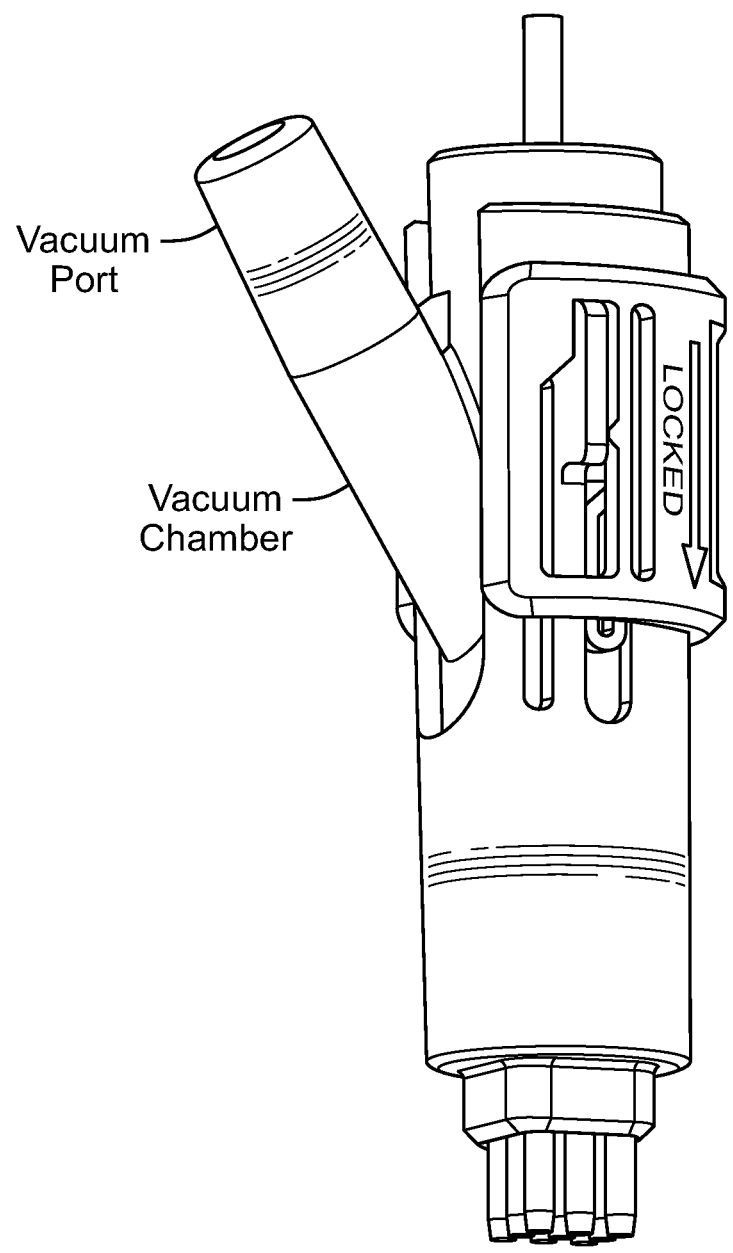

FIG. 243 is a perspective view of the MSA device showing the vacuum port and vacuum chamber, under an embodiment.

Figure 244:
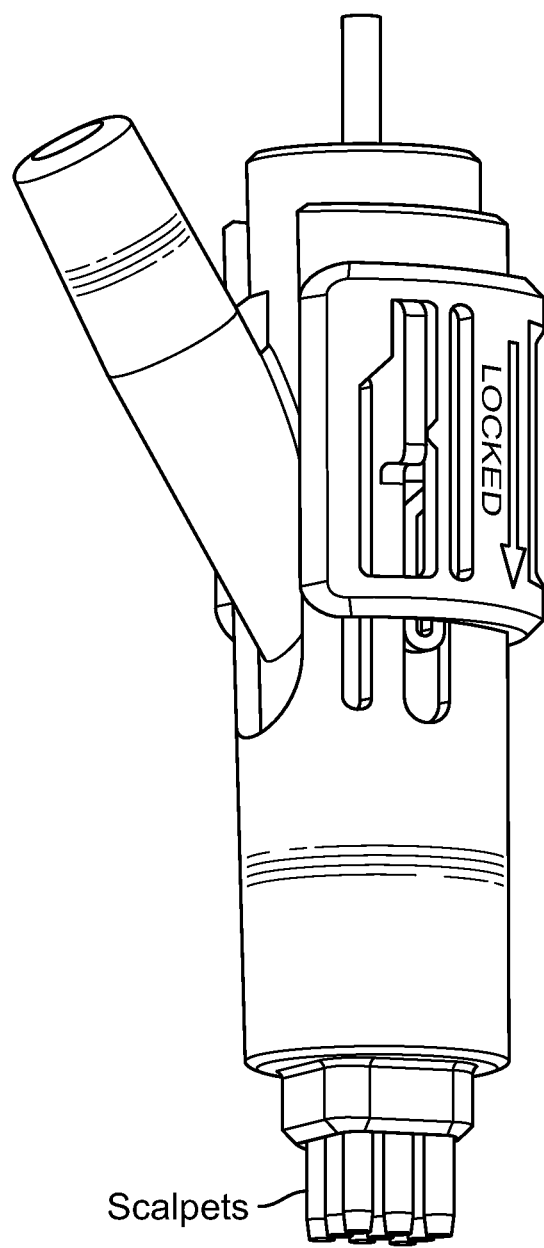

FIG. 244 is a perspective view of the MSA device showing the scalpets, under an embodiment.

Figure 245:
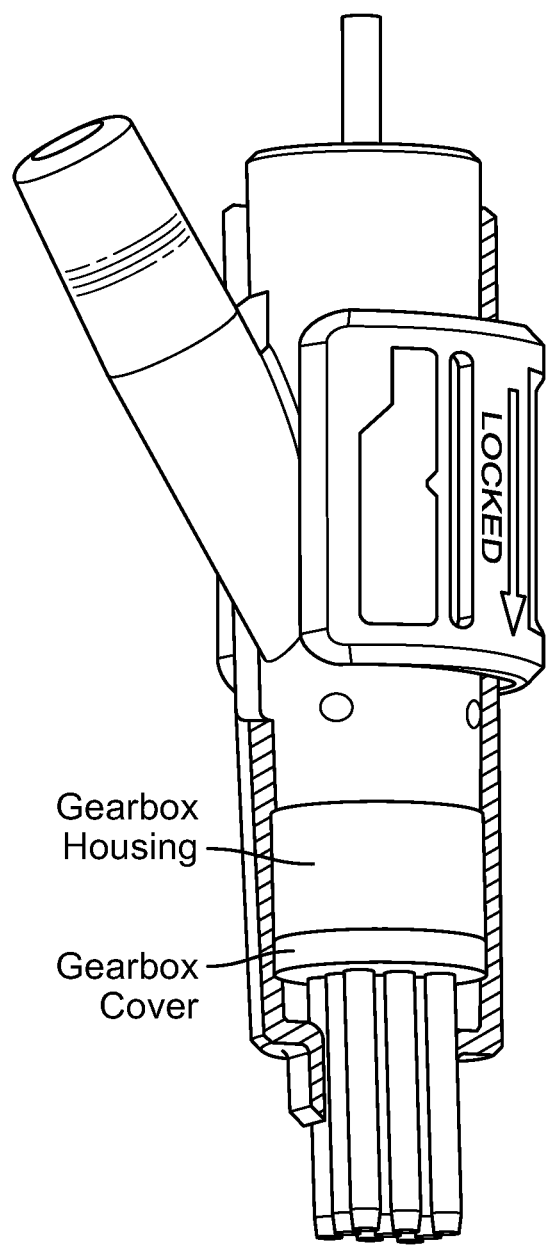

FIG. 245 is a perspective view of the MSA device showing the gearbox housing and gearbox cover, under an embodiment.

Figure 246:
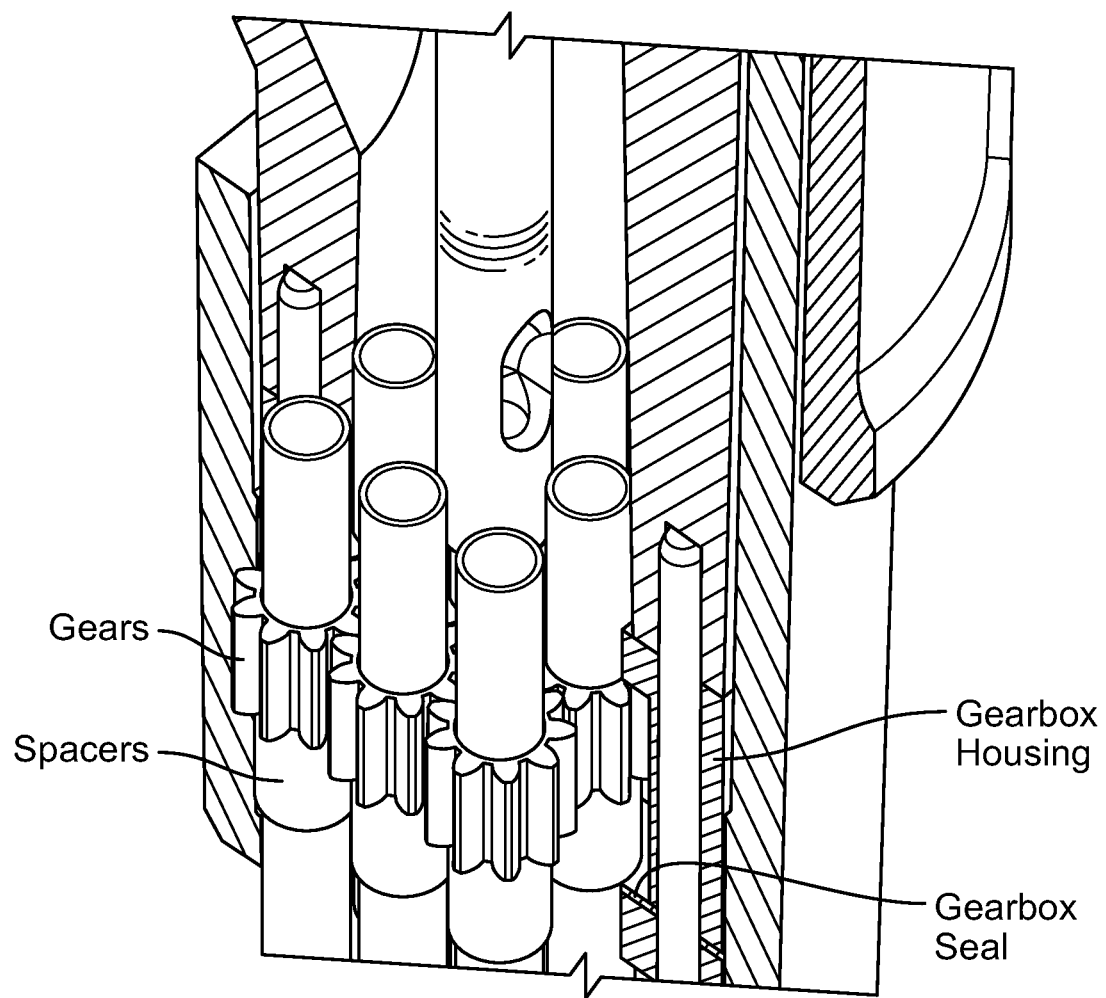

FIG. 246 is a perspective view of the MSA device showing the gear mechanism, under an embodiment.

Figure 247:
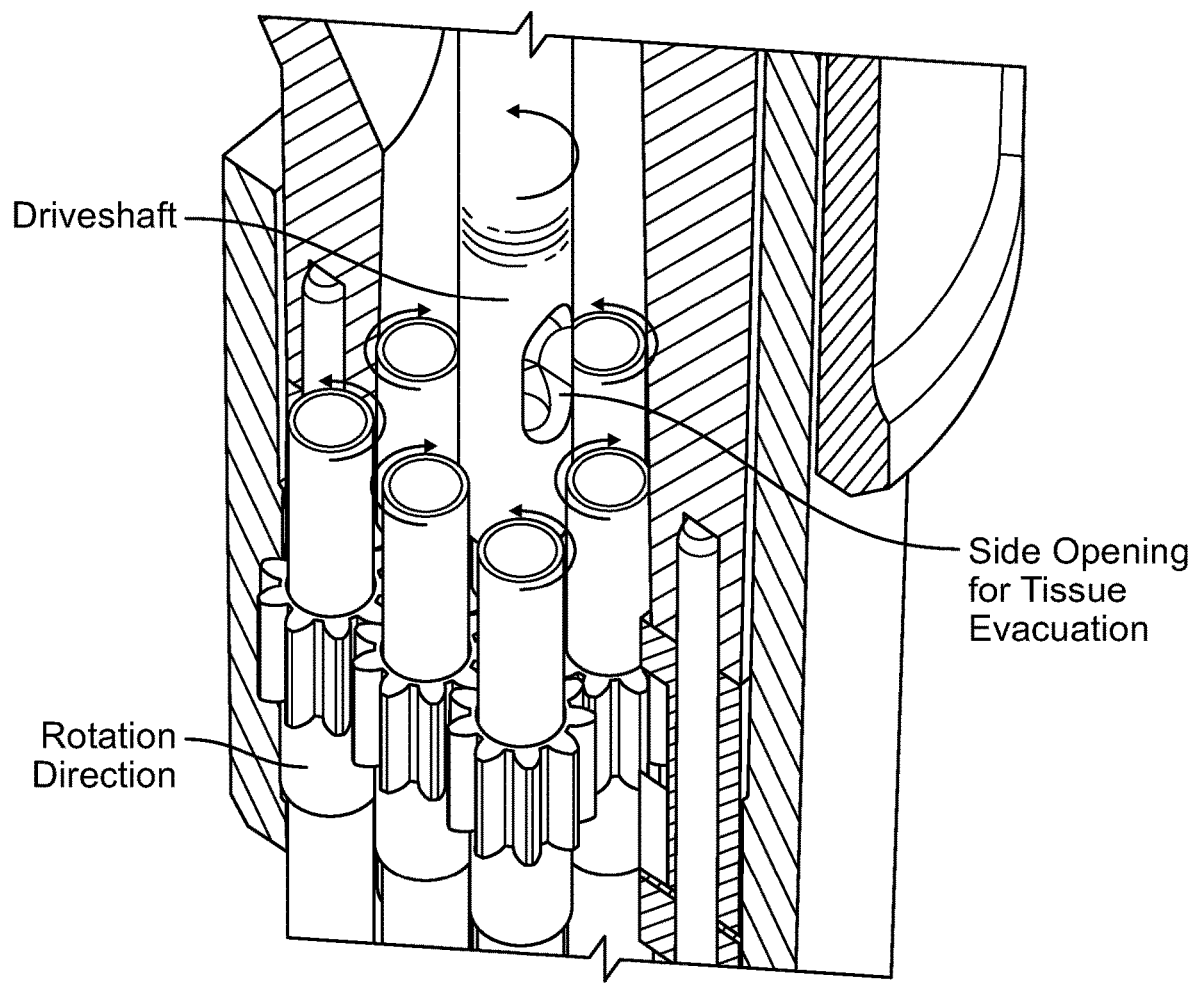

FIG. 247 is a perspective view of the gear mechanism of the MSA device showing the drive shaft and rotation directions of the scalpets, under an embodiment.

Figure 248:
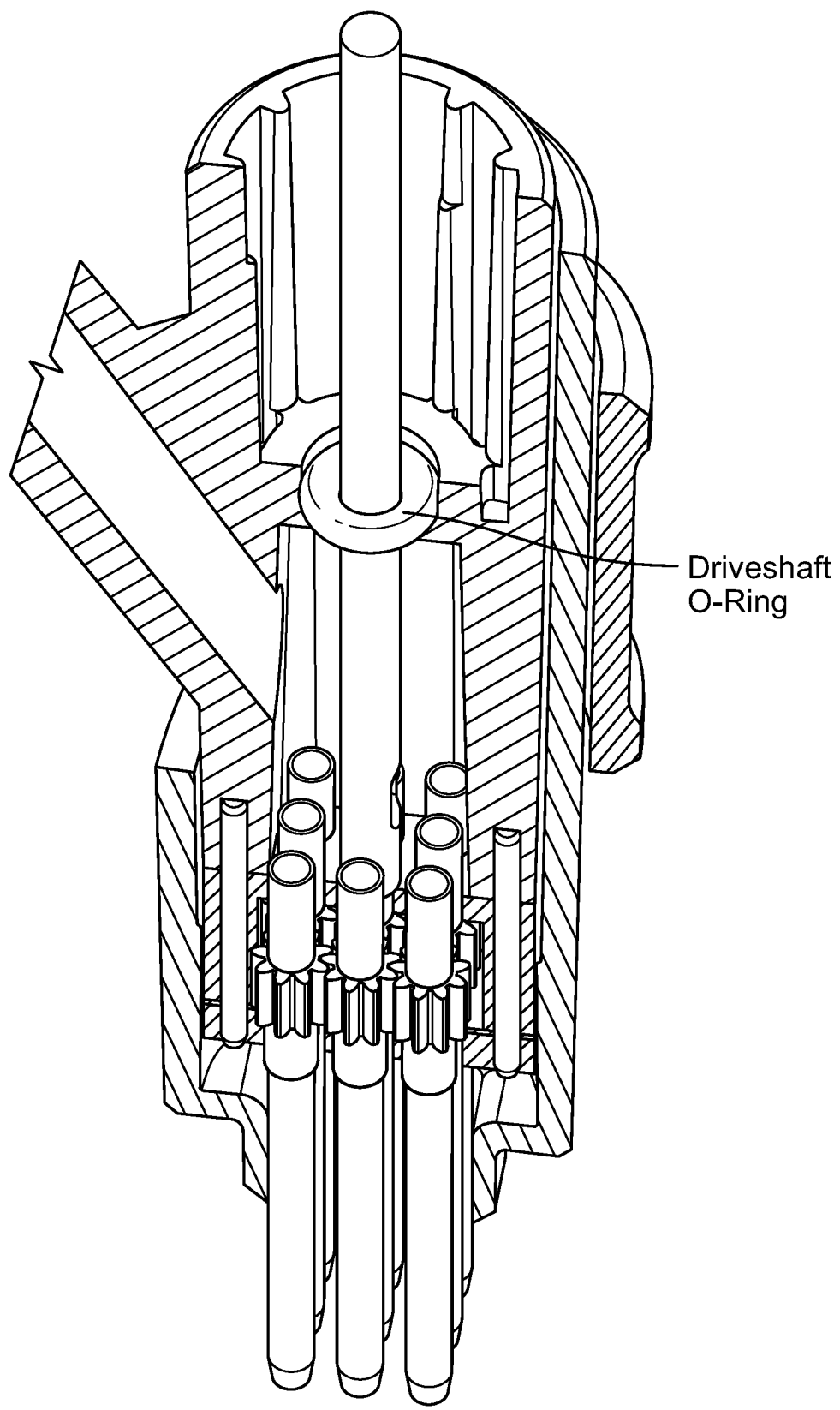

FIG. 248 is a perspective view of the gear mechanism of the MSA device showing the drive shaft and drive shaft O-ring, under an embodiment.

Figure 249:
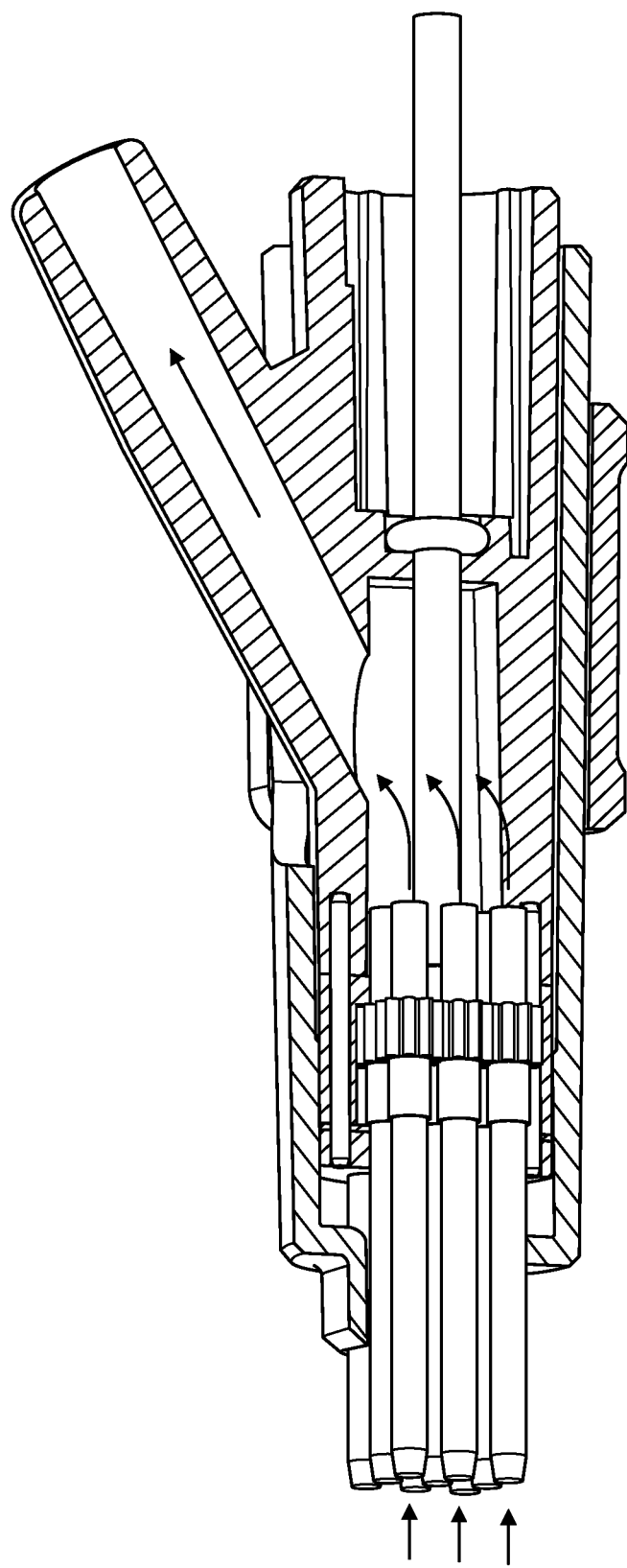

FIG. 249 is a cross-sectional view of the Multi-Scalpet Array (MSA) device showing the vacuum flow path (arrows) through the MSA, under an embodiment.

Figure 250:
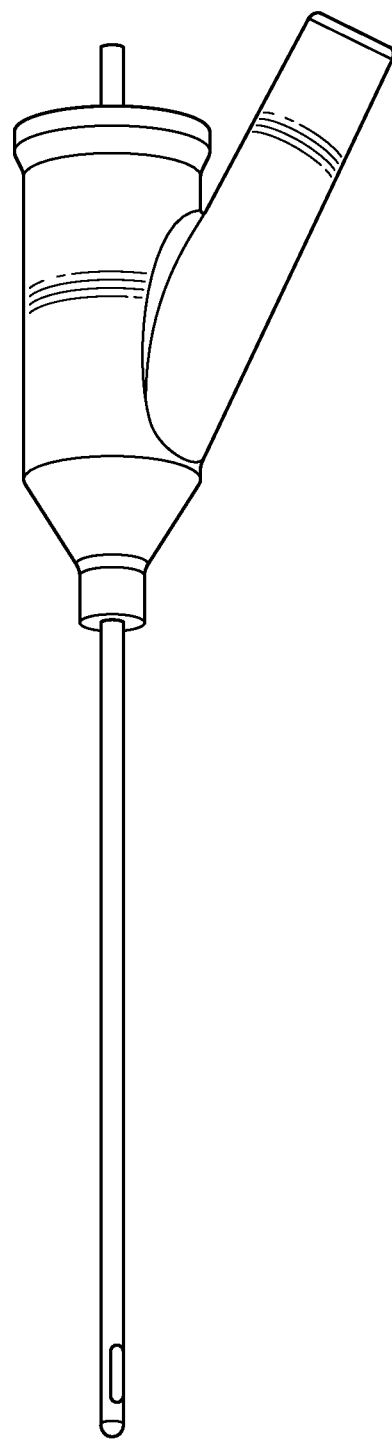

FIG. 250 is a perspective view of the fractional lipectomy cannula of the RFR system, under an embodiment.

Figure 251:
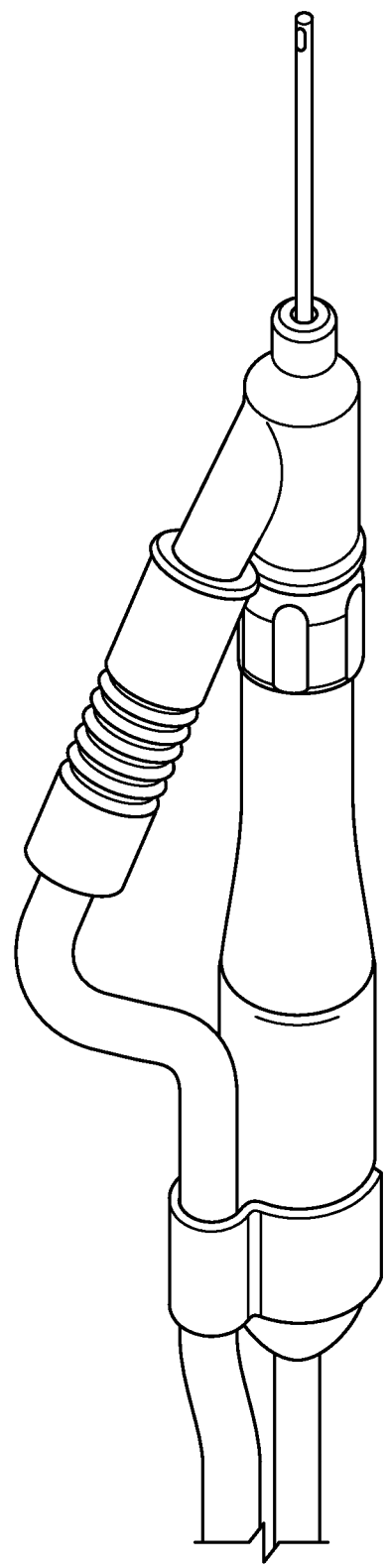

FIG. 251 is a perspective view of the RFR system including the fractional lipectomy cannula connected to the handpiece, under an embodiment.

Figure 252:
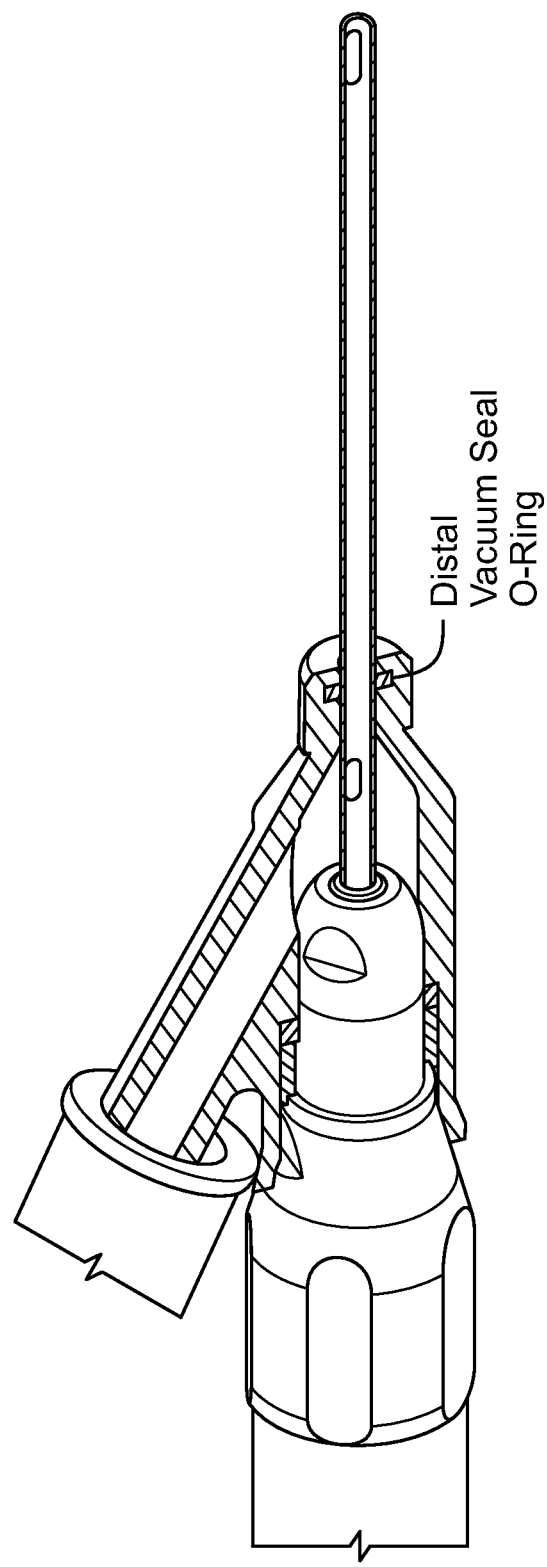

FIG. 252 is a perspective cross-sectional view of the fractional lipectomy cannula showing the vacuum flow path (arrows) through the device, under an embodiment.

Figure 253:
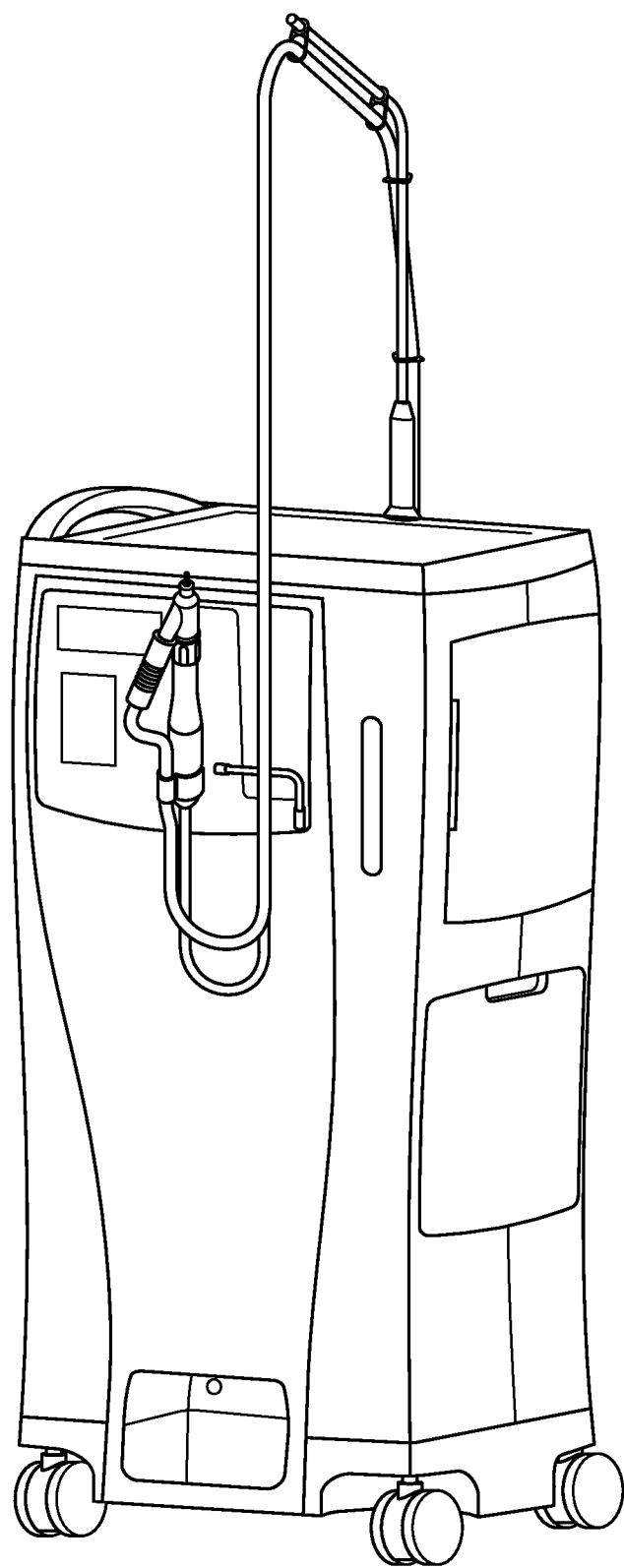

FIG. 253 shows the console, under an embodiment.

DETAILED DESCRIPTION

Systems, instruments, and methods for minimally invasive procedures including one or more of fractional resection, fractional lipectomy, fractional skin grafting, and/or fractional scar revision are described. Embodiments include instrumentation comprising a cannula assembly coupled to a carrier, and the cannula assembly includes a cannula array. The scalpet array includes one or more cannulas or scalpets configured for fractional resection, fractional lipectomy, fractional skin grafting, and/or fractional scar revision. The system includes a vacuum component coupled to the scalpet assembly and configured to evacuate tissue from a site. The carrier is configured to control application of a rotational force and/or a vacuum force to the scalpet assembly.

Embodiments include a method comprising determining histological factors at a target site of a subject, and determining parameters of a fractional resection based on the histological factors. The parameters include dimensionality of a fractional field, orientation of the fractional field, resection depth, and a vector of directed closure. The method includes configuring a cannula assembly for the fractional resection that includes a procedure to generate a fractional field at the target site by fractionally resecting tissue according to the parameters. The fractional resection includes applying a cannula array of the cannula assembly to the target site, and rotating at least one cannula of the cannula array to circumferentially incise and remove a plurality of skin plugs in the fractional field.

Embodiments include a system comprising a cannula assembly configured for rotational fractional resection (RFR). The cannula assembly includes at least one cannula configured for rotational operation and enclosed in a depth guide configured to control an insertion depth of the at least one cannula. The depth guide includes a vacuum chamber configured to maintain vacuum to evacuate resected tissue generated by the RFR.

Embodiments include a system comprising a carrier and a cannula assembly. The carrier includes a proximal end and a distal end, and the proximal end is configured to removeably couple to a remote console. The cannula assembly, which is configured to removeably couple to the distal end of the carrier, is configured for rotational fractional resection (RFR) and includes at least one cannula rotatably coupled to the carrier and enclosed in a depth guide configured to control an insertion depth of the at least one cannula. The depth guide includes a vacuum chamber configured to form vacuum to evacuate resected tissue generated by the RFR.

The scalpet device described herein satisfies the expanding aesthetic market for instrumentation and procedures for aesthetic surgical skin tightening. Additionally, the embodiments enable the repeated harvesting of skin grafts from the same donor site while eliminating donor site deformity. The embodiments described herein are configured to resect redundant lax skin without visible scarring so that all areas of redundant skin laxity can be resected by the pixel array dermatome and procedures may be performed in areas that were previously off limits due to the visibility of the surgical incision. The technical effects realized through the embodiments described herein include smooth, tightened skin without visible scarring or long scars along anatomical borders.

Embodiments described in detail herein, which include pixel skin grafting instrumentation and methods, are configured to provide the capability to repeatedly harvest split thickness skin grafts without visible scarring of the donor site. During the procedure, a Pixel Array Dermatome (PAD) is used to harvest the skin graft from the chosen donor site. During the harvesting procedure, a pixilated skin graft is deposited onto a flexible, semi-porous, adherent membrane. The harvested skin graft/membrane composite is then applied directly to the recipient skin defect site. The fractionally resected donor site is closed with the application of an adherent sheeting or bandage (e.g., Flexzan® sheeting, etc.) that functions for a period of time (e.g., one week, etc.) as a large butterfly bandage. The intradermal skin defects generated by the PAD are closed to promote a primary healing process in which the normal epidermal-dermal architecture is realigned in an anatomical fashion to minimize scarring. Also occurring postoperatively, the adherent membrane is desquamated (shed) with the stratum corneum of the graft; the membrane can then be removed without disruption of the graft from the recipient bed.

Numerous effects realized by the pixel skin grafting procedure deserve explanation. Because the skin graft is pixelated it provides interstices for drainage between skin plug components, which enhances the percentage of "takes," compared to sheet skin grafts. During the first post-operative week, the skin graft "takes" at the recipient site by a process of neovascularization in which new vessels from the recipient bed of the skin defect grow into the new skin graft. The semiporous membrane conducts the exudate into the dressing.

The flexible membrane is configured with an elastic recoil property that promotes apposition of component skin plugs within the graft/membrane composite; promoting primary adjacent healing of the skin graft plugs and converting the pixilated appearance of the skin graft into a more uniform sheet morphology. Furthermore, the membrane aligns the micro-architectural components skin plugs, so epidermis aligns with epidermis and dermis aligns with dermis, promoting a primary healing process that reduces scarring.

There are numerous major clinical applications for the dermatomes described in detail herein, including fractional skin resection for skin tightening, fractional hair grafting for alopecia, and fractional skin harvesting for skin grafting. Fractional skin resection of an embodiment comprises harvesting skin plugs using an adherent membrane, however the fractionally incised skin plugs can be evacuated without harvesting. The paradigm of incising, evacuating and closing is most descriptive of the clinical application of skin tightening. The embodiments described herein are configured to facilitate incising and evacuating and, in order to provide for a larger scalpet array with a greater number of scalpets, the embodiments include a novel means of incising the skin surface.

Pixel array medical systems, instruments or devices, and methods are described for skin grafting and skin resection procedures, and hair transplantation procedures. In the following description, numerous specific details are introduced to provide a thorough understanding of, and enabling description for, embodiments herein. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

The following terms are intended to have the following general meaning as they may be used herein. The terms are not however limited to the meanings stated herein as the meanings of any term can include other meanings as understood or applied by one skilled in the art.

"Abdominoplasty" as used herein includes a procedure that includes the transverse resection of skin from the pubic hairline extending out to the iliac crests. For many postpartum patients, the entire lower abdominal skin is resected to a level just above the umbilicus. The dissection is carried up to the costal margin and the entire flap is transposed downward to be closed with the supra-public incision line. The umbilicus, which was previously circumscribed, is then brought though a small incision at the same level in the midline. Additional flattening of the lower abdomen is produced by the plication of the anterior rectus sheath. A surgical adjunct of an abdominoplasty is Suction Assisted Lipectomy of the lateral thighs and iliac crests.

"Ablation" as used herein includes the removal of tissue by destruction of the tissue (e.g., thermal ablation of a skin lesion by a laser).

"Aesthetic Contouring" as used herein includes the three dimensional alteration of the human embodiment into a more youthful habitus. Different methods are used for aesthetic contouring, including two dimensional skin tightening and three dimensional lipectomy. In the face and neck, tightening of fascia (SMAS) and muscle (Platysma) are also employed. In the abdomen, plication of the anterior rectus fascia is used to flatten contour. The fractional procedures of an embodiment provide a novel capability for Aesthetic Contouring.

"Ancillary Fractional Device" as used herein includes medical devices used in concert with a primary medical device.

"Autograft" as used herein includes a graft taken from the same patient.

"Backed Adherent Membrane" as used herein includes the elastic adherent membrane that captures the transected skin plugs. The Backed Adherent Membrane of an embodiment is backed on the outer surface to retain alignment of the skin plugs during harvest. After harvesting of the skin plugs, the backing is removed from the adherent membrane with harvested skin plugs. The membrane of an embodiment is porous to allow for drainage when placed at the recipient site. The membrane of an embodiment also possesses an elastic recoil property, so that when the backing is removed, it brings the sides of the skin plugs closer to each other to promote healing at the recipient site as a sheet graft.

"Brachioplasty" as used herein includes an elliptical resection of excess skin along the medial aspect of the upper arm. The incision typically extends from the axilla to the elbow but "dog ear" skin redundancies are frequently present at both proximal and distal extents of the surgical resections. The "dog ear" skin redundancies may involve the entire elbow and the axillae leading down to the bra line and lateral inframmary folds.

"Burn Scar Contraction" as used herein includes the tightening of scar tissue that occurs during the wound healing process. This process is more likely to occur with an untreated third degree burn.

"Burn Scar Contracture" as used herein includes a band of scar tissue that either limits the range of motion of a joint or band of scar tissue that distorts the appearance of the patient i.e., a burn scar contracture of the face.

"Cellulite" as used herein includes the cobblestone contour deformity of the hips and thighs that is due to the prominence of fat loculations that are visible through the skin. Contributory conditions are skin laxity and the tethering by the fibrous septae between the fat loculations.

"Cervical Mandibular Angle" (CMA) as used herein includes the angle seen in profile that occurs from the juxtaposition of the submentum with the anterior neck at the level superior to the thyroid cartilage. The CMA is a key aesthetic anatomical feature that is restored during a Facial-Cervical Rhytidoplasty.

"De-delineation" as used herein includes a mechanism of action for Fractional Scar Revision. A slightly visible plexiform pattern of a healed fractional resection field encompassing a pre-existing scar is used to camouflage the visible linear impact of that scar.

"Dermatome" as used herein includes an instrument that "cuts skin" or harvests a sheet split thickness skin graft. Examples of drum dermatomes include the Padgett and Reese dermatomes. Electrically powered dermatomes are the Zimmer dermatome and one electric version of the Padgett dermatome.

"Dermis" as used herein includes the deep layer of skin that is the main structural support and primarily comprises non-cellular collagen fibers. Fibroblasts are cells in the dermis that produce the collagen protein fibers.

"Dimensionality of a fractional field" as used herein includes the overall length-width metric of a fractional field.

"Direct Fractional Skin Tightening" as used herein includes a corollary mechanism of action in which skin tightening and aesthetic contouring is achieved directly by fractionally resecting skin/fat in the area of the aesthetic deformity.

"Donor Site" as used herein includes the anatomical site from which a skin graft is harvested.

"Epidermis" as used herein includes the outer layer of skin comprising viable epidermal cells and nonviable stratum corneum that acts as a biological barrier.

"Excise" as used herein includes the surgical removal of tissue.

"Excisional Skin Defect" as used herein includes a partial thickness or, more typically, a full thickness defect that results from the surgical removal (excision/resection) of skin (lesion).

"Facial Cervical Rhytidoplasty" as used herein includes a procedure known as a facelift. However, a major part of this aesthetic surgical procedure involves the restoration of the cervical-mandibular angle in the neck. A facelift is performed through a curvilinear incision around the ear and extending into temporal/occipital scalp. Flap dissection (elevation) occurs over a significant portion of the face and neck. The vector for skin tightening in the neck is in a posterior-superior direction and the vector for skin tightening of the face is more vertical in a predominately superior-posterior direction. The excess skin is then resected along the existing curvilinear incision line. Additional tightening is also produced with a deeper fascial/muscle plane of dissection involving the SMAS and Platysma.

"First degree burn" as used herein includes a superficial thermal injury in which there is no disruption of the epidermis from the dermis. A first-degree burn is visualized as erythema (redness) of the skin.

"First Phase Wound Healing Response" as used herein includes the inflammatory phase where erythema is visibly apparent on the skin surface upon wounding.

"Flap elevation" as used herein includes the dissection of a surgically isolated segment of skin and soft tissue including its own blood supply. Numerous different flap types are included that each vary in their soft tissue components and the means of flap transfer. As an example, a random pattern flap includes skin and subcutaneous tissue with pedicle blood supply based on the subdermal plexus. A myocutaneous flap includes skin, subcutaneous tissue and muscle with a blood supply based on a named axial vascular pedicle that is attached to the deep surface of the muscle and courses parallel to the longitudinal axis of that muscle. Musculocutaneous perforators then course at right angles from the axial pedicle through muscle, investing fascia and subcutaneous tissue to perfuse the subdermal plexus of the skin.

"Follicular Unit Extraction" (FUE) as used herein includes the primary method used for hair transplantation. For alopecia, a single hair follicle is harvested from a donor site and is then grafted to a recipient site on the scalp.

"Fractional Encasement of a Pilo-sebaceous unit" as used herein includes, in a hirsute area such as the male beard, a vertical fractional resection of the hair shaft has the potential of forming an encasement of the Pilo-sebaceous unit upon healing. This complication is more probable if the hair follicle shaft runs obliquely with the skin surface. An encased Pilo-sebaceous is palpable as a dermal/subdermal mass that usually will be phagocytized over several months. Inadequate depth of resection along the hair shaft that does not resect that hair follicle is another potential means of encasement.

"Fractional Graft Harvest" as used herein includes the skin graft harvesting from a donor site using the devices and methods as described in detail herein.

"Fractional Lipectomy" as used herein includes a novel surgical technology using devices and methods described herein for fractional resection of lax skin involving direct removal of fat superficially. Methods of an embodiment include direct incontinutiy resection of fat with the fractionally resected skin plug, in which the scalpet is lengthened to fractionally resect fat sub-dermally. Methods of an embodiment also include transcutaneous vacuum-assisted lipectomy through the fractional skin defects, in which the fat is vacuum evacuated by placing the opening SAL tubing (or with a connected manifold cannula) over the fractionally resected skin defects. Methods of an embodiment further include intraluminal vacuum-assisted lipectomy, which comprises application of a vacuum to the interior of the scalpet(s) that is created with a housing surrounding a skived scalpet in series with a SAL aspirator. The principle clinical applications of fractional lipectomy that have been identified are aesthetic contouring and the treatment of cellulite, but are not so limited.

"Fractional Scar Revision" as used herein includes the reduction in the visual impact of a scar by fractional resection, and the primary mechanism of action includes the fractional de-delineation of the scar.

"Fractional Skin Resection" as used herein includes a novel surgical technology using devices and methods described herein for removal of lax skin.

"Fractional Scar Revision" as used herein includes the use of fractional skin/scar resection to de-delineate the visible impact of scaring.

"Fractional Surgical Adjunct" as used herein includes the complementary use of a medical device with an established surgical procedure. Fractional resection devices are used as described in detail herein to shorten incisions of standard plastic surgical procedures.

"Fractional Tattoo removal" as used herein includes the use of a fractional device as described herein to resect the ink of a tattoo without visible scarring. The primary effect is to fractionally remove enough ink to de-delineate the pattern of the tattoo.

"Full Thickness Skin Graft" (FTSG) as used herein includes procedures in which the entire thickness of the skin is harvested. With the exception of an instrument as described herein, the donor site is closed as a surgical incision. For this reason, FTSG is limited in the surface area that can be harvested.

"Granulation Tissue" as used herein includes highly vascularized tissue that grows in response to the absence of skin in a full-thickness skin defect, and is the base for a skin graft recipient site.

"Healing by primary intention" as used herein includes the wound healing process in which normal anatomical structures are realigned with a minimum of scar tissue formation. Morphologically the scar is less likely to be visible.

"Healing by secondary intention" as used herein includes a less organized wound healing process in which healing occurs with less alignment of normal anatomical structures and with an increased deposition of scar collagen. Morphologically, the scar is more likely to be visible.

"Homograft" as used herein includes a graft taken from a different human and applied as a temporary biological dressing to a recipient site on a patient. Homografts are typically harvested as cadaver skin. A temporary "take" of a homograft can be partially achieved with immunosuppression but homografts are eventually replaced by autografts if the patient survives.

"Horizontal axis" as used herein includes the width metric of the fractional field.

"Incise" as used herein includes the making of a surgical incision without removal of tissue.

"Indirect Fractional Skin Tightening" as used herein includes a corollary mechanism of action in which skin tightening and aesthetic contouring is achieved by the fractional resection of skin in an area distant but in continuity with the identified aesthetic deformity. This corollary MOA involves outlined treatment areas that incorporate both the direct and indirect effects of fractional tightening of skin/fat. The dimensions of the treatment area create the primary skin tightening MOA that results in the three dimensional aesthetic contouring of the clinical endpoint.

"Langer's Lines" as used herein includes the direction of elongation of skin perforations in a cadaver. These lines are indicative of a direction of incisional wound healing that will minimize scaring upon closure. For a fractionally resected field, the direction of closure is at right angles to Langer's lines.

"Live Autologous Dermal Graft Injectable" (LAD-MIX™) as used herein includes a novel composition generated by fractionally harvesting skin plugs from a donor site with an adherent dermatome tape. The epidermis of the skin plugs is then removed by placing the skin plug membrane preparation on a drum dermatome where the outrigger transection blade is placed on a deep setting to remove the subcutaneous fat of the skin plugs. The outrigger blade is then placed into a superficial setting to remove the epidermis. The prepared dermal plugs are then collected and moreselized into small fragments that are suspended into a carrier fluid with either hyaluronic acid and/or hydrogel. The dermal graft composition is then loaded into a syringe for injection as a living autologous collagen filler. The LAD-MIX™ dermal graft injectable is configured for use to treat folds, furrows, wrinkles and other contour depressions, and potentially to treat functional impairments such as female incontinence for example.

"Local anesthetic field block" as used herein includes the instillation of Xylocaine (or longer acting Marcaine) as an amide agent, which involves infusing the block via syringe/needle into the subdermal tissues over a wide surface area. The local anesthetic agent can be combined with an alpha-adrenergic vasoconstrictive agent such as epinephrine in concentrations of 1/100,000 or 2/100,000 parts constituent. The LD50 of 500 mg/70 Kg patient weight is a limit that constrains the overall surface area of the field block.

"Longitudinal axis" as used herein includes the length metric of the fractional field.

"Margin elevation" as used herein includes the fractional correction of a dependent curvilinear aesthetic deformity. The dependent inferior margin of the deformity is raised and straightened through the "Hammock Effect," and the curvilinear margin is shortened by the vectored closure along the elongated horizontal axis of the fractional field. FIG. 190 shows the dependent curvilinear deformity (top), the fractional field horizontally aligned to the curvilinear deformity (middle), and the vectored closure along the elongated horizontal axis of the fractional field with straightening of the margin (bottom), under an embodiment.

"Mechanism of Action" (MOA) as used herein includes the underlying physical processes of an effect that leads to a clinical endpoint.

"Membrane application" as used herein includes the drawing across of an elastic adhesive membrane that provides directed closure of the skin defects within a fractional field.

"Mesh Split Thickness Skin Graft" as used herein includes a split thickness skin graft that is expanded in its surface area by repetitiously incising the harvested skin graft with an instrument called a "mesher". A meshed split thickness skin graft has a higher percentage of "take" than a sheet graft because it allows drainage through the graft and conforms better to the contour irregularities of the recipient site.

"Neovascularization" as used herein includes the growth of new vessels into skin and soft tissue. A "take" of a skin graft depends fundamentally on a process in which the neovascular growth of new vessels occurs from the granulation base of the skin defect into the dermis of the skin graft. Skin grafts onto poorly perfused skin defects are much less likely to be neovascularized and will be "lost". Motion or shearing between the skin graft and the granulation base is another common cause of graft failure. More recently, the neovascularization of a healed mastectomy site has been described and employed as a key mechanism of action for a novel method of breast reconstruction).

"Oblique axis" as used herein includes an axis that having an oblique relationship to the longitudinal and horizontal axes.

"Orientation of a fractional field" as used herein includes the topographical relationship that the fractional field has with the aesthetic deformity.

"PAD" as used herein includes a Pixel Array Dermatome, the class of instruments configured for fractional skin resection.

"PAD Kit" as used herein includes the disposable single-use procedure kit or an embodiment comprising but not limited to the perforated guide plate, scalpet stamper, the guide plate frame, the backed adherent membrane and the transection blade.

"Perforated Guide Plate" as used herein includes a perforated plate of embodiments, comprising holes configured for alignment with the scalpets of the handled stamper or the Slip-on PAD. The plate is also configured as a guard to prevent inadvertent laceration of the adjacent skin. The perforations of the guide plate can be different geometries such as, but not limited to, round, oval, square. rectangular, and/or triangular.

"Pilo-Sebaceous unit" as used herein includes a skin appendage that includes a hair follicle and a sebaceous unit. Hair grows in different cycles such as anagen, which is the active growth cycle of hair, and telogen, which is the resting phase of hair growth in which hair falls out until the cycle repeats itself. The Dermal Papilla of the hair follicle is immediately subdermal.

"Pixelated Full Thickness Skin Graft" as used herein includes a Full Thickness Skin Graft that has been harvested with an instrument of embodiments described herein. The graft possess an enhanced appearance at the recipient site similar to a sheet FTSG but better conforms to the recipient site and has a higher percentage of 'take' due to drainage interstices between skin plugs. The pixelated FTSG also provides the ability to graft larger surface areas that would otherwise require a STSG, and this is due to the capability to harvest from multiple donor sites with reduced visible scarring.

"Pixelated Graft Harvest" as used herein includes the skin graft harvesting from a donor site by an instrument as described in detail herein.

"Pixelated Skin Resection" as used herein is synonymous with fractional skin resection.

"Pixelated Spilt Thickness Skin Graft" as used herein includes a partial thickness skin graft that has been harvested using devices and methods described in detail herein. The skin graft shares the advantages of a meshed skin graft without unsightly donor and recipient sites.

"Recipient Site" as used herein includes the skin defect site where a skin graft is applied.

"Resect" as used herein includes excising.

"Resting Skin Tension Lines" (RSTL) as used herein are indicative of the direction of dependent laxity of skin, and may correspond to Langer's lines. Aesthetic skin resections to correct dependent skin laxity are configured at right angles to the resting skin tension lines.

"Scalpel" as used herein includes the single-edged knife that incises skin and soft tissue.

"Scalpet" as used herein includes a small geometrically-shaped (e.g., circle, ellipse, rectangle, square, etc.) scalpel as described herein, configured to incise a plug of skin.

"Scalpet Array" as used herein includes an arrangement or array of multiple scalpets secured to a substrate (e.g., a base plate, stamper, handled stamper, tip, disposable tip, etc.) or other device component.

"Scalpet Stamper" as used herein includes a handled scalpet array instrument component of the PAD Kit that incises skin plugs through the perforated guide plate.

"Scar" as used herein includes the histological deposition of disorganized collagen following wounding, or the morphological deformity that is visually apparent from the histological deposition of disorganized collagen following wounding.

"Scar Revision" as used herein includes the surgical excision of a scar associated with a technique of wound closure that reduces the visual impact of the scar.

"Second degree burn" as used herein includes a relatively deeper burn in which there is disruption of the epidermis from the dermis and where a variable thickness of the dermis is also denatured. Most second-degree burns are associated with blister formation. Deep second-degree burns may convert to full thickness third degree burns, usually by oxidation or infection.

"Second Phase Wound Healing Response" as used herein includes the fibroblastic phase where neocollagen is produced by fibroblasts within the wound. This phase includes the physical contraction due to the presence of smooth muscle contractile proteins in the fibroblasts (myofibroblasts) and the collagen matrix of the extracellular fluid (ECF).

"Sheet Full Thickness Skin Graft" as used herein includes application of the FTSG at the recipient site as continuous sheet. The appearance of an FTSG is superior to the appearance of a STSG, and for this reason is primarily used for skin grafting in visually apparent areas such as the face.

"Sheet Split Thickness Skin Graft" as used herein includes a partial thickness skin graft that is a continuous sheet and is associated with the typical donor site deformity.

"Skin Defect" as used herein includes the absence of the full thickness of skin that may also include the subcutaneous fat layer and deeper structures such as muscle. Skin defects can occur from a variety of causes i.e., burns, trauma, surgical excision of malignancies and the correction of congenital deformities.

"Skin Pixel" as used herein includes a piece of skin comprising epidermis and a partial or full thickness of the dermis that is generated by the scalpet. The skin pixel may include skin adnexa such as a hair follicle with or without a cuff of subcutaneous fat.

"Skin Plug" as used herein includes a circular (or other geometric shaped) piece of skin comprising epidermis and a partial or full thickness of the dermis that is incised by the scalpet and captured as described in detail herein.

"Split Thickness Skin Graft" (STSG) as used herein includes a procedure in which only a portion of the dermis is harvested with the graft (e.g., partial thickness skin graft in which the epidermis and a portion of the dermis is harvested with the graft).

"Subcutaneous Fat Layer" as used herein includes the layer that is immediately below the skin and is principally comprised of fat cells referred to as lipocytes. This layer functions as the principle insulation from the environment.

"Suction Assisted Lipectomy" (SAL) as used herein includes use of a vacuum aspirator attached to a rigid tubing, and an apertured cannula that is inserted through a small skin incision into the subcutaneous fat layer. Vacuum suctioning of fat occurs due to the enhanced capability of surgical aspirators and the inherent tensile fragility of lipocytes. Typically, the patient is marked preoperatively in a standing position topographically. Although the patient is placed into a supine position, the standing topographical marking of the patient allows the procedure to be performed accurately in a supine position. The most frequently liposuctioned areas are the lateral thighs, Iliac crests and medial thighs. A compression garment is applied postoperatively for guided inward contouring.

"Sweat Gland" as used herein includes a separate skin appendage that produces sweat. Eccrine sweat glands produce a more aqueous non-odoriferous sweat that is used for thermoregulation. Apocrine sweat glands present in the axilla and inguinal regions produce body odor.

"Third degree burn" as used herein includes a burn associated with the full thickness thermal destruction of the skin including the epidermis and the dermis. A third degree burn may also be associated with thermal destruction of deeper, underlying tissues (subcutaneous and muscle layers).

"Third Phase Wound Healing Response" as used herein includes the scar maturation phase because the amount of collagen in the wound is reduced but the tensile strength of the scar increases due to the increased cross linkage between collagen fibers.

"Transection Blade" as used herein includes a horizontally-aligned single-edged blade that can be either slotted to the frame of the perforated plate or attached to the outrigger arm of the drum dermatome as described in detail herein. The transection blade transects the base of the incised skin plugs.

"Tumescent Anesthetic" combines the advantages of hydrostatic pressure with a dilute solution of a local anesthetic to provide several advantages over routinely administered field blocks that were inadequate for the resecting large volumes of subcutaneous tissue. A principle clinical application is Suction Assisted Lipectomy where large vacuum assisted segments of the subcutaneous tissue can be safely and uniformly resected with minimal blood loss, thereby transforming this surgical discipline into a standard of aesthetic contouring. More recently, the use of tumescent anesthesia has been applied in conjunction with the fractional skin resection where large surface areas of the skin laxity are tightened.

"Vector of directed closure" as used herein includes the direction that a fractional field is closed that corresponds to the direction that the adhesive membrane is drawn across the fractional field.

"Vectored tightening of skin" as used herein includes the pulling and closure of a surgical skin resection in a direction that creates enhanced aesthetic contouring.

"Vector of Skin Tightening" as used herein includes the direction in which skin is resected to create aesthetic contouring of an anatomical area. The vector of skin tightening may or may not correspond to either Langer's or resting skin tension lines. When there is conformity between Langer's lines and the vector of skin tightening, aesthetic contouring occurs with minimal scaring in a fractional field. An example is the skin tightening that occurs with a fractional resection of the lower abdomen. In contrast, the vector of aesthetic skin tightening in the neck for a Facial Cervical Rhytidoplasty ("Facelift") does not follow Langer's lines but is directed at right angles to the cervical mandibular angle. For fractional resections of the neck therefore, the most effective vector of aesthetic skin tightening will likely correspond to a direction that is at right angles to the closure indicated by Langer's lines.

"W plasty scar revision" and "Z plasty scar revision" as used herein include surgical techniques used to improve the functional impairment caused by a scar contracture across a joint. The lengthening of the scar by a "W" and "Z" plasty occurs when the flaps of the "W" are interposed or the flaps of the "Z" are transposed. An ancillary benefit of these procedures is the de-delineation of the linear scar into ascending and descending limbs of the scar revision. Although the scar is now longer post revision, the visual impact is reduced by de-delineation.

"Wound Healing" as used herein includes the obligate biological process that occurs from any type of wounding, whether it be one or more of thermal, kinetic and surgical wounding.

"Xenograft" as used herein includes a graft taken from a different species and applied as a temporary biological dressing to a recipient site on a patient.

Multiple embodiments of pixel array medical systems, instruments or devices, and methods for use are described in detail herein. The systems, instruments or devices, and methods described herein comprise minimally invasive surgical approaches for skin grafting and for skin resection that tightens lax skin without visible scarring via a device used in various surgical procedures such as plastic surgery procedures, and additionally for hair transplantation. In some embodiments, the device is a single use disposable instrument. The embodiments herein circumvent surgically related scarring and the clinical variability of electromagnetic heating of the skin and perform small multiple pixilated resections of skin as a minimally invasive alternative to large plastic surgical resections of skin. The embodiments herein can also be employed in hair transplantation, and in areas of the body that may be off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site.

For many patients who have age related skin laxity (for non-limiting examples, neck and face, arms, axillas, thighs, knees, buttocks, abdomen, bra line, ptosis of the breast, etc.), the minimally invasive pixel array medical devices and methods herein perform pixilated transection/resection of excess skin, replacing plastic surgery with its incumbent scarring. Generally, the procedures described herein are performed in an office setting under a local anesthetic with minimal perioperative discomfort, but are not so limited. In comparison to a prolonged healing phase from plastic surgery, only a short recovery period is required, preferably applying a dressing and a support garment worn over the treatment area for a pre-specified period of time (e.g., 5 days, 7 days, etc.).

There will be minimal or no pain associated with the procedure.

The relatively small (e.g., in a range of approximately 0.5 mm to 4.0 mm) skin defects generated by the instrumentation described herein are closed with the application of an adherent Flexan® sheet. Functioning as a large butterfly bandage, the Flexan® sheet can be pulled in a direction ("vector") that maximizes the aesthetic contouring of the treatment area. A compressive elastic garment is applied over the dressing to further assist aesthetic contouring. After completion of the initial healing phase, the multiplicity of small linear scars within the treatment area will have reduced visibility in comparison to larger plastic surgical incisions on the same area. Additional skin tightening is likely to occur over several months due to the delayed wound healing response. Other potential applications of the embodiments described herein include hair transplantation as well as the treatment of Alopecia, Snoring/Sleep apnea, Orthopedics/Physiatry, Vaginal Tightening, Female Urinary incontinence, and tightening of gastrointestinal sphincters.

Significant burns are classified by the total body surface burned and by the depth of thermal destruction, and the methods used to manage these burns depend largely on the classification. First-degree and second-degree burns are usually managed in a non-surgical fashion with the application of topical creams and burn dressings. Deeper third-degree burns involve the full thickness thermal destruction of the skin, creating a full thickness skin defect. The surgical management of this serious injury usually involves the debridement of the burn eschar and the application of split thickness grafts.

A full thickness skin defect, most frequently created from burning, trauma, or the resection of a skin malignancy, can be closed with either skin flap transfers or skin grafts using conventional commercial instrumentation. Both surgical approaches require harvesting from a donor site. The use of a skin flap is further limited by the need of to include a pedicle blood supply and in most cases by the need to directly close the donor site.

The split thickness skin graft procedure, due to immunological constraints, requires the harvesting of autologous skin grafts from the same patient. Typically, the donor site on the burn patient is chosen in a non-burned area and a partial thickness sheet of skin is harvested from that area. Incumbent upon this procedure is the creation of a partial thickness skin defect at the donor site. This donor site defect itself is similar to a deep second-degree burn. Healing by re-epithelialization of this site is often painful and may be prolonged for several days. In addition, a visible donor site deformity is typically created that is permanently thinner and more de-pigmented than the surrounding skin. For patients who have burns over a significant surface area, the extensive harvesting of skin grafts may also be limited by the availability of non-burned areas.

Both conventional surgical approaches to close skin defects (flap transfer and skin grafting) are not only associated with significant scarring of the skin defect recipient site but also with the donor site from which the graft is harvested. In contrast to the conventional procedures, embodiments described herein comprise Pixel Skin Grafting Procedures, also referred to as a pixel array procedures, that eliminate this donor site deformity and provide a method to re-harvest skin grafts from any pre-existing donor site including either sheet or pixelated donor sites. This ability to re-harvest skin grafts from pre-existing donor sites will reduce the surface area requirement for donor site skin and provide additional skin grafting capability in severely burned patients who have limited surface area of unburned donor skin.

The Pixel Skin Grafting Procedure of an embodiment is used as a full thickness skin graft. Many clinical applications such as facial skin grafting, hand surgery, and the repair of congenital deformities are best performed with full thickness skin grafts. The texture, pigmentation and overall morphology of a full thickness skin graft more closely resembles the skin adjacent to a defect than a split thickness skin graft. For this reason, full thickness skin grafting in visibly apparent areas is superior in appearance than split thickness skin grafts. The main drawback to full thickness skin grafts under conventional procedures is the extensive linear scarring created from the surgical closure of the full thickness donor site defect; this scarring limits the size and utility of full thickness skin grafting.

In comparison, the full thickness skin grafting of the Pixel Skin Grafting Procedure described herein is less limited by size and utility as the linear donor site scar is eliminated. Thus, many skin defects routinely covered with split thickness skin grafts will instead be treated using pixelated full thickness skin grafts.

The Pixel Skin Grafting Procedure provides the capability to harvest split thickness and full thickness skin grafts with minimal visible scarring of the donor site. During the procedure, a Pixel Array Dermatome (PAD) device is used to harvest the skin graft from a chosen donor site. During the harvesting procedure, the pixilated skin graft is deposited onto an adherent membrane. The adherent membrane of an embodiment includes a flexible, semi-porous, adherent membrane, but the embodiment is not so limited. The harvested skin graft/membrane composite is then applied directly to the recipient skin defect site. The fractionally resected donor site is closed with the application of an adherent Flexan® sheeting that functions for one week as a large butterfly bandage. The relatively small (e.g., 1.5 mm) intradermal circular skin defects are closed to promote a primary healing process in which the normal epidermal-dermal architecture is realigned in an anatomical fashion to minimize scarring. Also occurring approximately one week postoperatively, the adherent membrane is desquamated (shed) with the stratum corneum of the graft; the membrane can then be removed without disruption of the graft from the recipient bed. Thus, healing of the donor site occurs rapidly with minimal discomfort and scarring.

Because the skin graft at the recipient defect site using the Pixel Skin Grafting Procedure is pixelated it provides interstices for drainage between skin pixel components, which enhances the percentage of "takes," compared to sheet skin grafts. During the first post-operative week (approximate), the skin graft will "take" at the recipient site by a process of neovascularization in which new vessels from the recipient bed of the skin defect grow into the new skin graft. The semi-porous membrane will conduct the transudate (fluid) into the dressing. Furthermore, the flexible membrane is designed with an elastic recoil property that promotes apposition of component skin pixels within the graft/membrane composite and promotes primary adjacent healing of the skin graft pixels, converting the pixilated appearance of the skin graft to a uniform sheet morphology. Additionally, the membrane aligns the micro-architectural component skin pixels, so epidermis aligns with epidermis and dermis aligns with dermis, promoting a primary healing process that reduces scarring. Moreover, pixelated skin grafts more easily conform to an irregular recipient site.

Embodiments described herein also include a Pixel Skin Resection Procedure, also referred to herein as the Pixel Procedure. For many patients who have age related skin laxity (neck and face, arms, axillas, thighs, knees, buttocks, abdomen, bra line, ptosis of the breast, etc.), fractional resection of excess skin could replace a significant segment of plastic surgery with its incumbent scarring. Generally, the Pixel Procedure will be performed in an office setting under a local anesthetic. The post procedure recovery period includes wearing of a support garment over the treatment area for a pre-specified number (e.g., five, seven, etc.) of days (e.g., five days, seven days, etc.). Relatively little or no pain is anticipated to be associated with the procedure. The small (e.g., 1.5 mm) circular skin defects will be closed with the application of an adherent Flexan® sheet. Functioning as a large butterfly bandage, the Flexan® sheet is pulled in a direction ("vector") that maximizes the aesthetic contouring of the treatment area. A compressive elastic garment is then applied over the dressing to further assist aesthetic contouring. After completion of the initial healing phase, the multiplicity of small linear scars within the treatment area will not be visibly apparent. Furthermore, additional skin tightening will subsequently occur over several months due to the delayed wound healing response. Consequently, the Pixel Procedure is a minimally invasive alternative to the extensive scarring of Plastic Surgery.

Figure 1:
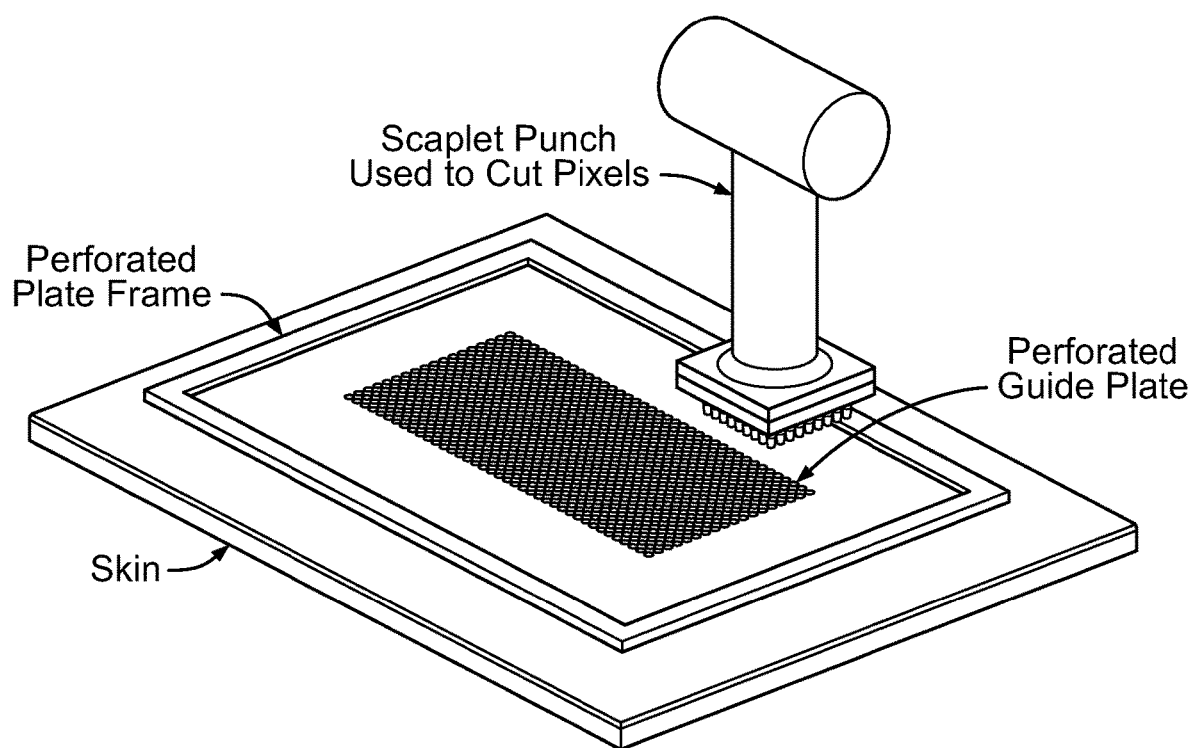
FIG. 1 shows the PAD Kit placed at a target site, under an embodiment.

The pixel array medical devices of an embodiment include a PAD Kit. FIG. 1 shows the PAD Kit placed at a target site, under an embodiment. The PAD Kit comprises a flat perforated guide plate (guide plate), a scalpet punch or device that includes a scalpet array (FIGS. 1-3), a backed adhesive membrane or adherent substrate (FIG. 4), and a skin pixel transection blade (FIG. 5), but is not so limited. The scalpet punch of an embodiment is a handheld device but is not so limited. The guide plate is optional in an alternative embodiment, as described in detail herein.

Figure 2:
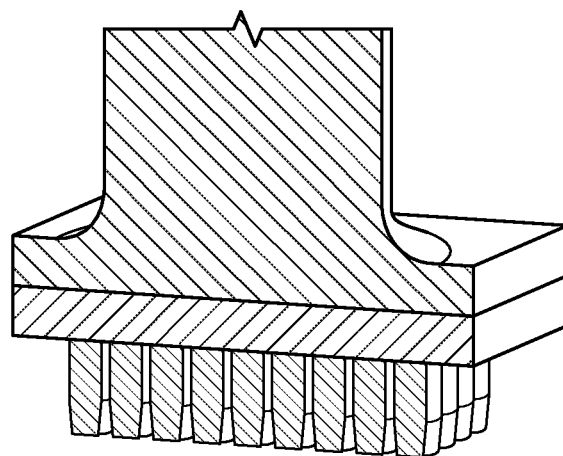
FIG. 2 is a cross-section of a scalpet punch or device including a scalpet array, under an embodiment.
Figure 3:
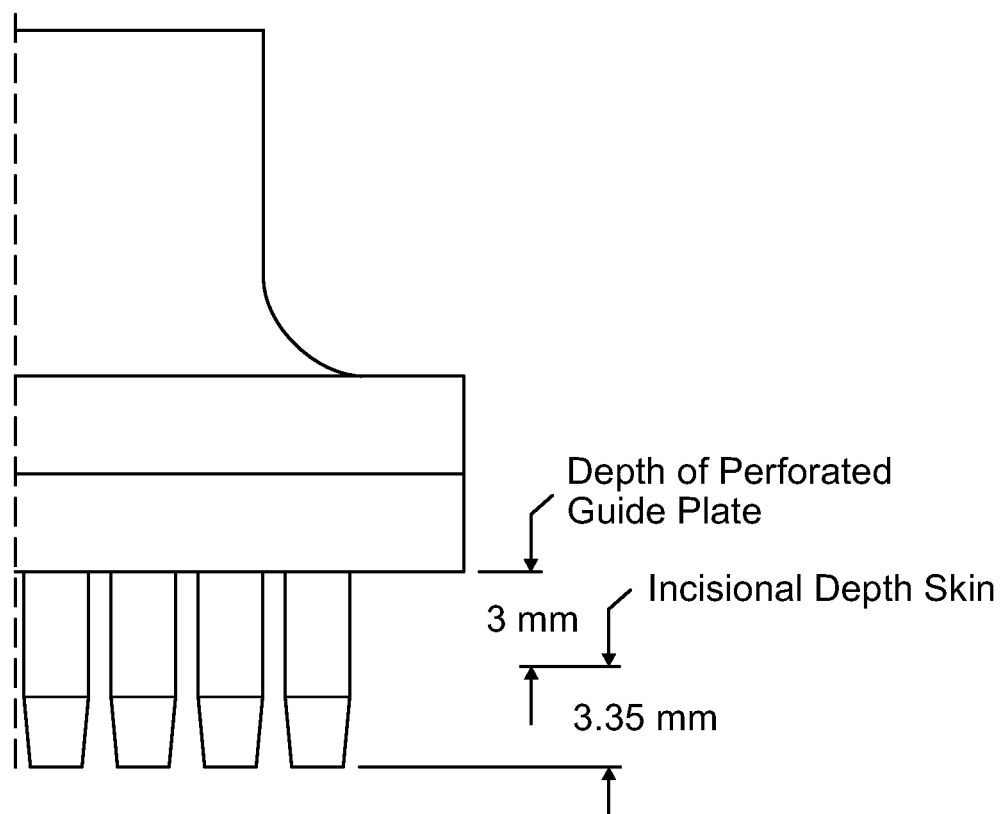
FIG. 3 is a partial cross-section of a scalpet punch or device including a scalpet array, under an embodiment.

FIG. 2 is a cross-section of a PAD Kit scalpet punch including a scalpet array, under an embodiment. The scalpet array includes one or more scalpets. FIG. 3 is a partial cross-section of a PAD Kit scalpet punch including a scalpet array, under an embodiment. The partial cross-section shows the total length of the scalpets of the scalpet array is determined by the thickness of the perforated guide plate and the incisional depth into the skin, but the embodiment is not so limited.

Figure 4:
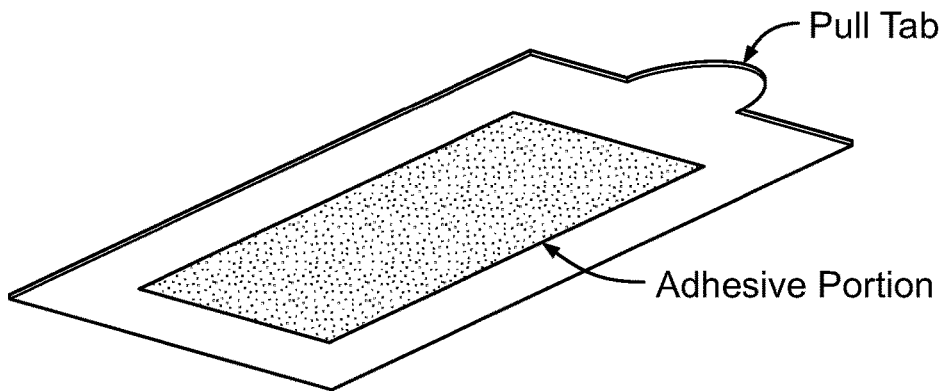
FIG. 4 shows the adhesive membrane with backing (adherent substrate) included in a PAD Kit, under an embodiment.

FIG. 4 shows the adhesive membrane with backing (adherent substrate) included in a PAD Kit, under an embodiment. The undersurface of the adhesive membrane is applied to the incised skin at the target site.

Figure 5:
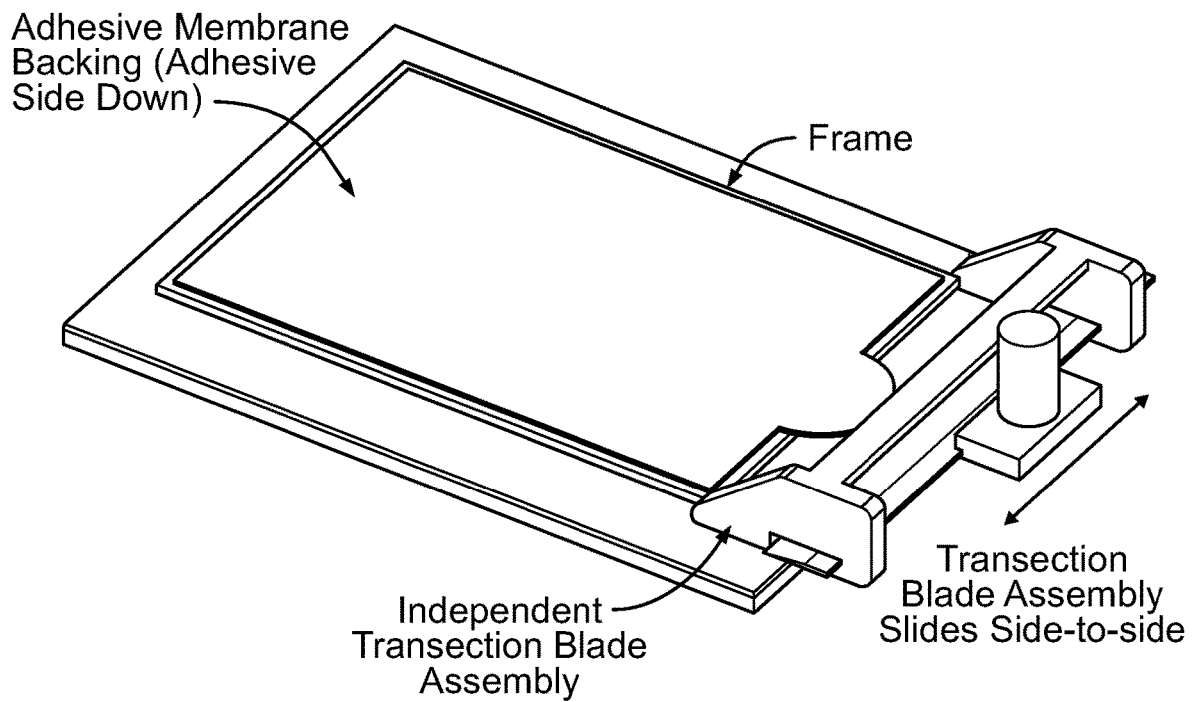
FIG. 5 shows the adhesive membrane (adherent substrate) when used with the PAD Kit frame and blade assembly, under an embodiment.

FIG. 5 shows the adhesive membrane (adherent substrate) when used with the PAD Kit frame and blade assembly, under an embodiment. The top surface of the adhesive membrane is oriented with the adhesive side down inside the frame and then pressed over the perforated plate to capture the extruded skin pixels, also referred to herein as plugs or skin plugs.

With reference to FIG. 1, the perforated guide plate is applied to the skin resection/donor site during a procedure using the PAD Kit. The scalpet punch is applied through at least a set of perforations of the perforated guide plate to incise the skin pixels. The scalpet punch is applied numerous times to a number of sets of perforations when the scalpet array of the punch includes fewer scalpets then the total number of perforations of the guide plate. Following one or more serial applications with the scalpet punch, the incised skin pixels or plugs are captured onto the adherent substrate. The adherent substrate is then applied in a manner so the adhesive captures the extruded skin pixels or plugs. As an example, the top surface of the adherent substrate of an embodiment is oriented with the adhesive side down inside the frame (when the frame is used) and then pressed over the perforated plate to capture the extruded skin pixels or plugs. As the membrane is pulled up, the captured skin pixels are transected at their base by the transection blade.

Figure 6:
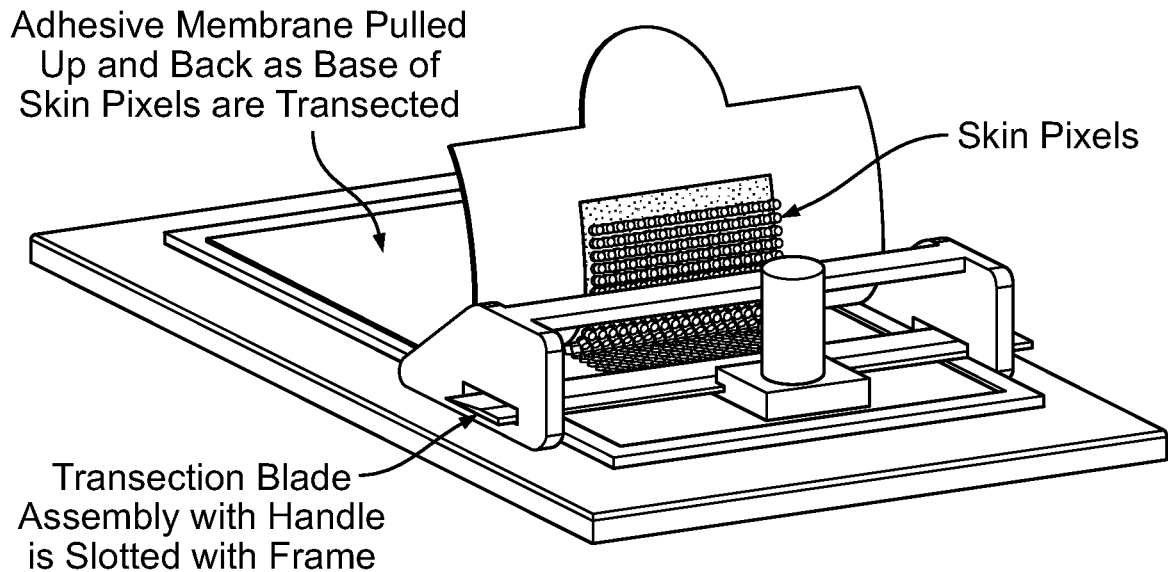
FIG. 6 shows the removal of skin pixels, under an embodiment.
Figure 7:
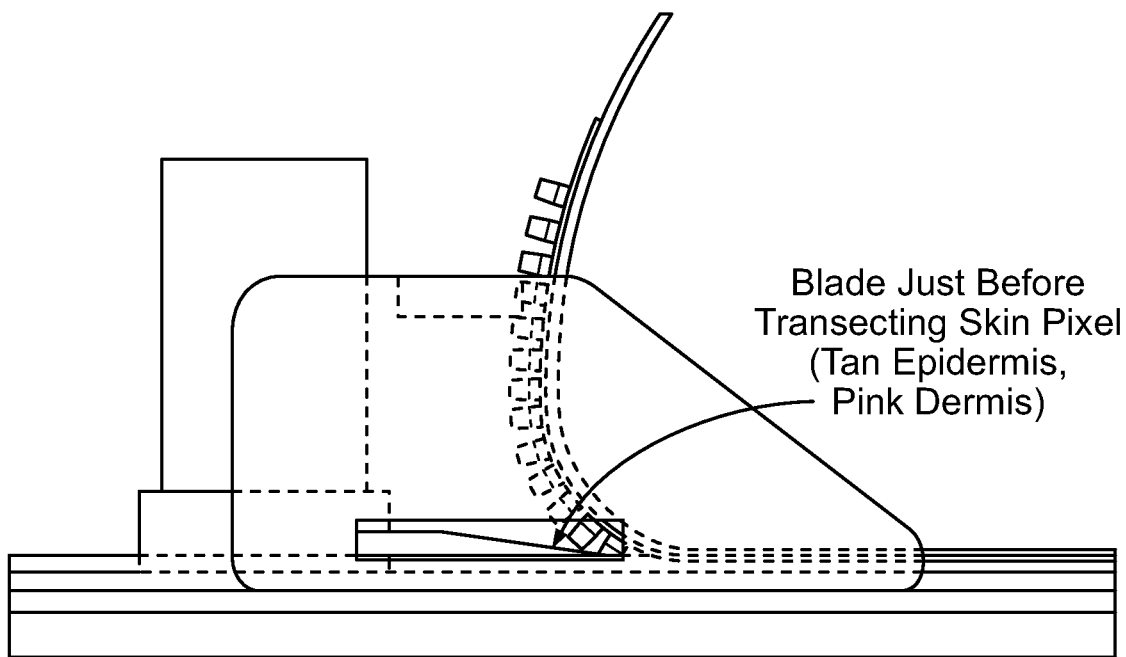
FIG. 7 is a side view of blade transection and removal of incised skin pixels with the PAD Kit, under an embodiment.
Figure 8:
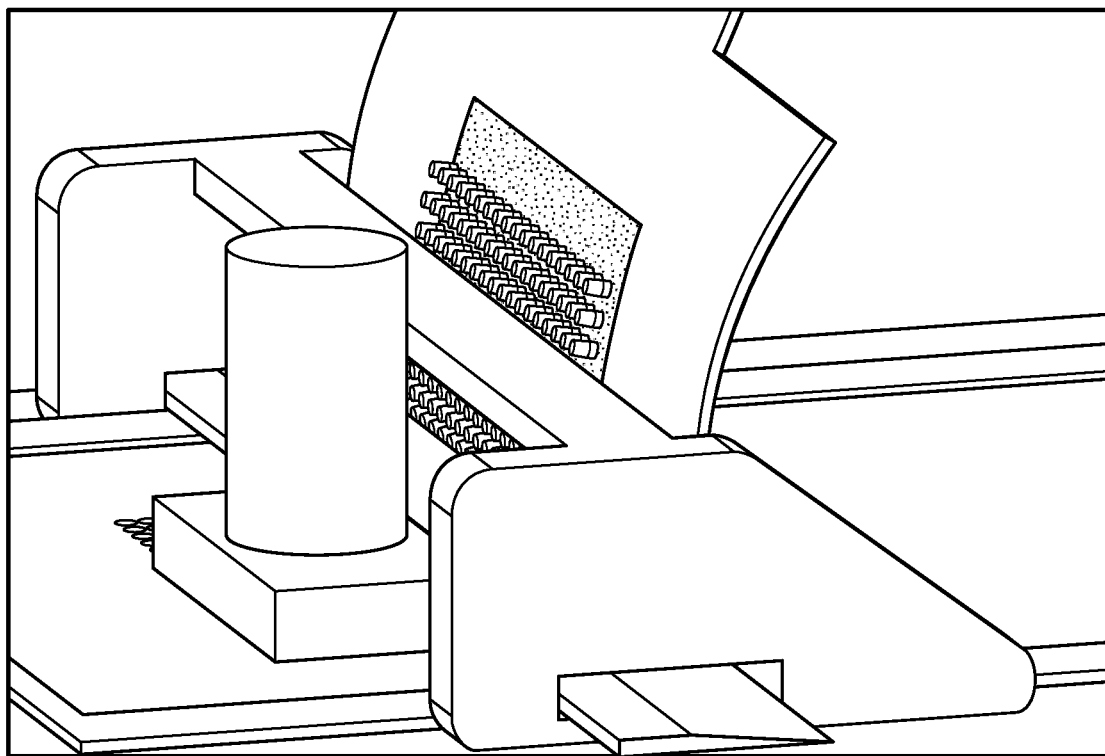
FIG. 8 is an isometric view of blade/pixel interaction during a procedure using the PAD Kit, under an embodiment.
Figure 9:
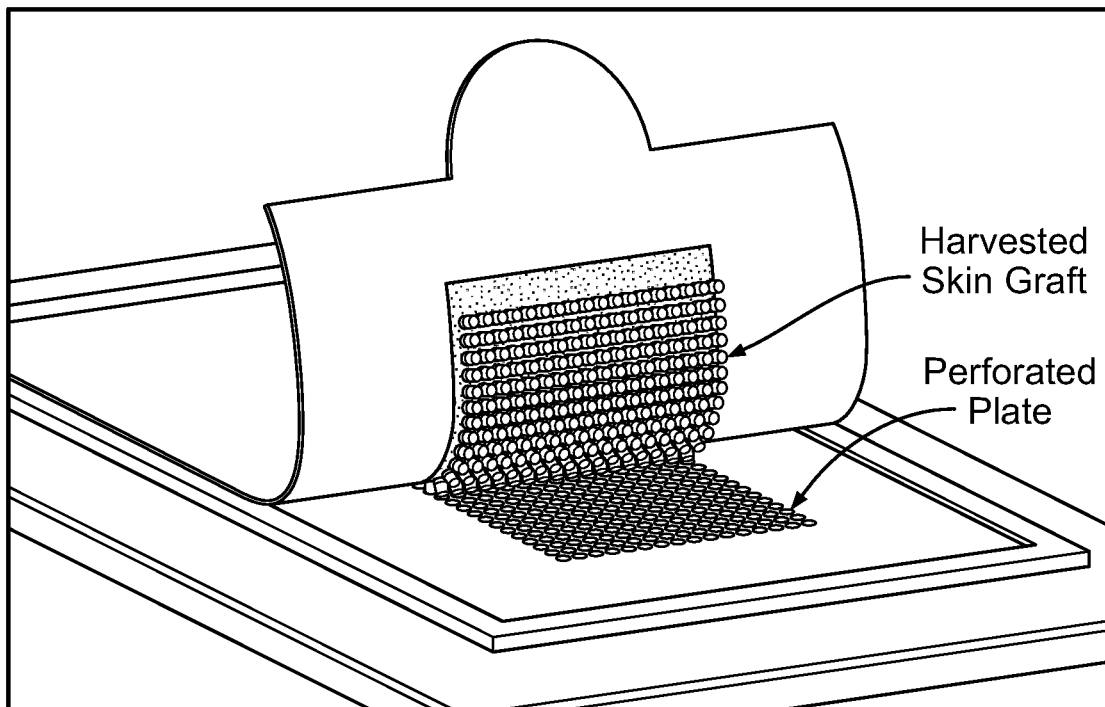
FIG. 9 is another view during a procedure using the PAD Kit (blade removed for clarity) showing both harvested skin pixels or plugs transected and captured and non-transected skin pixels or plugs prior to transection, under an embodiment.

FIG. 6 shows the removal of skin pixels, under an embodiment. The adherent substrate is pulled up and back (away) from the target site, and this act lifts or pulls the incised skin pixels or plugs. As the adherent substrate is being pulled up, the transection blade is used to transect the bases of the incised skin pixels. FIG. 7 is a side view of blade transection and removal of incised skin pixels with the PAD Kit, under an embodiment. Pixel harvesting is completed with the transection of the base of the skin pixels or plugs. FIG. 8 is an isometric view of blade/pixel interaction during a procedure using the PAD Kit, under an embodiment. FIG. 9 is another view during a procedure using the PAD Kit (blade removed for clarity) showing both harvested skin pixels or plugs transected and captured and non-transected skin pixels or plugs prior to transection, under an embodiment. At the donor site, the pixelated skin resection sites are closed with the application of Flexan® sheeting.

The guide plate and scalpet device are also used to generate skin defects at the recipient site. The skin defects are configured to receive the skin pixels harvested or captured at the donor site. The guide plate used at the recipient site can be the same guide plate used at the donor site, or can be different with a different pattern or configuration of perforations.

The skin pixels or plugs deposited onto the adherent substrate during the transection can next be transferred to the skin defect site (recipient site) where they are applied as a pixelated skin graft at a recipient skin defect site. The adherent substrate has an elastic recoil property that enables closer alignment of the skin pixels or plugs within the skin graft. The incised skin pixels can be applied from the adherent substrate directly to the skin defects at the recipient site. Application of the incised skin pixels at the recipient site includes aligning the incised skin pixels with the skin defects, and inserting the incised skin pixels into corresponding skin defects at the recipient site.

Figure 10A:
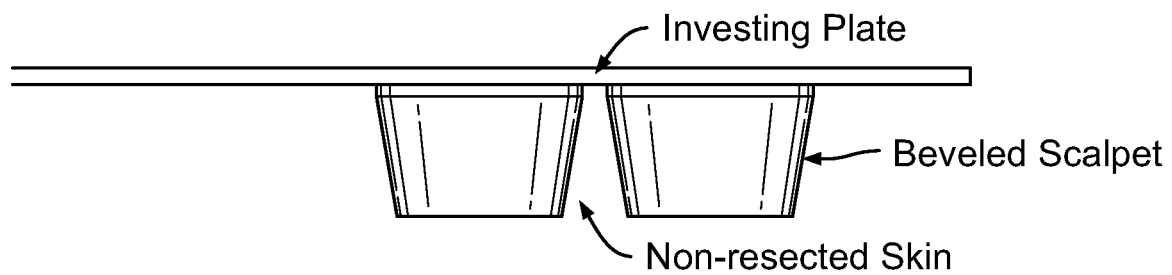
FIG. 10A is a side view of a portion of the pixel array showing scalpets secured onto an investing plate, under an embodiment.
Figure 10B:
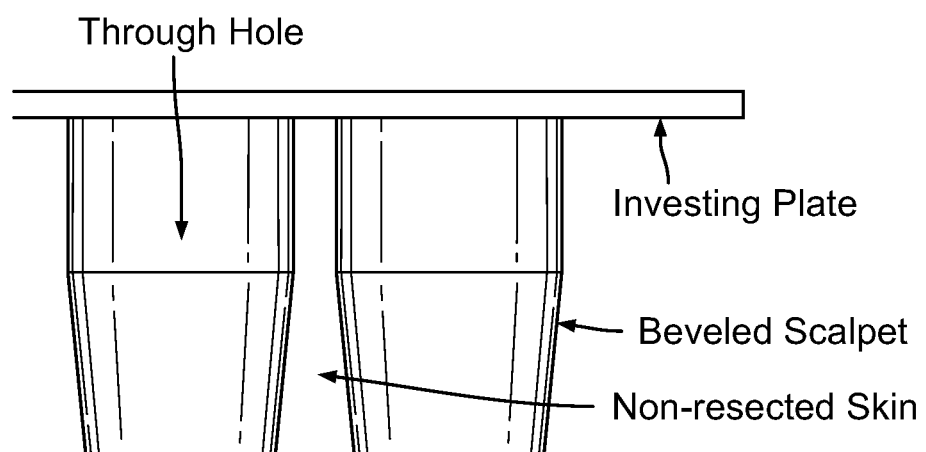
FIG. 10B is a side view of a portion of the pixel array showing scalpets secured onto an investing plate, under an alternative embodiment.
Figure 10C:
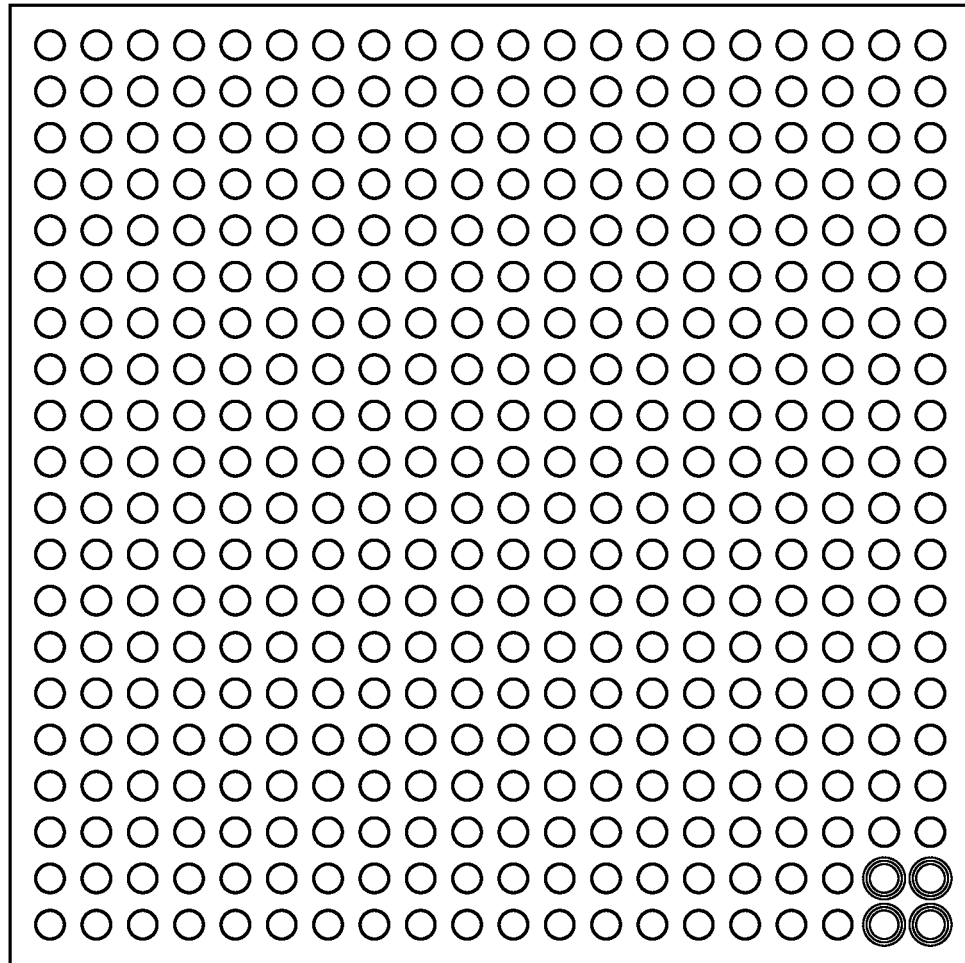
FIG. 10C is a top view of the scalpet plate, under an embodiment.
Figure 10D:
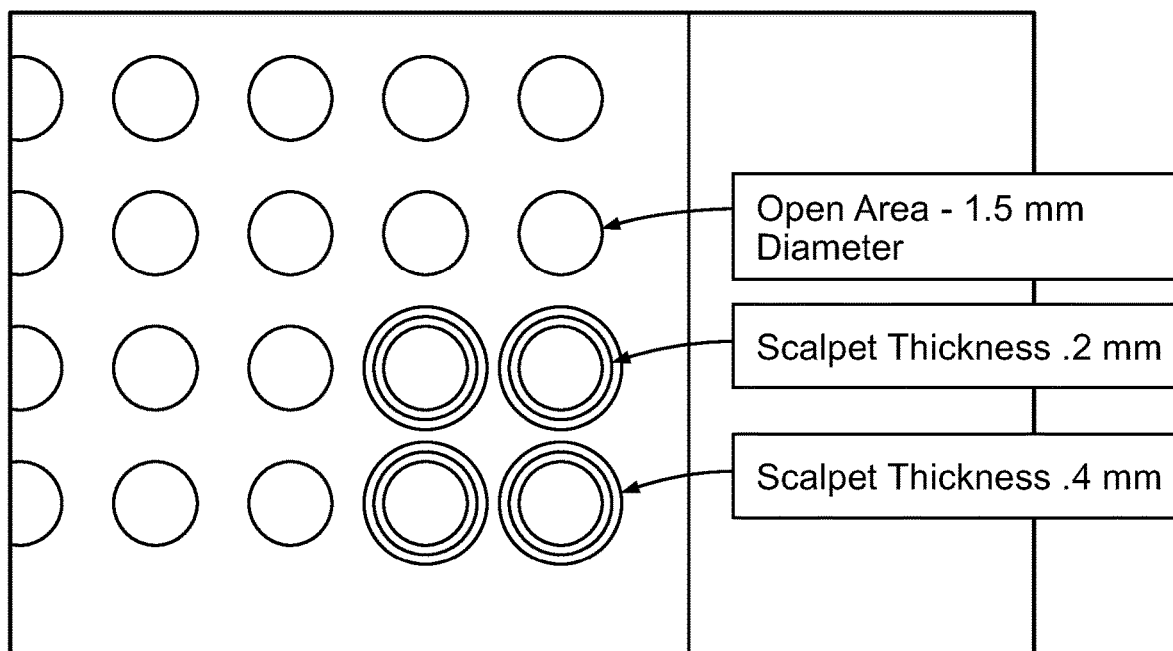
FIG. 10D is a close view of a portion of the scalpet plate, under an embodiment.

The pixel array medical devices of an embodiment include a Pixel Array Dermatome (PAD). The PAD comprises a flat array of relatively small circular scalpets that are secured onto a substrate (e.g., investing plate), and the scalpets in combination with the substrate are referred to herein as a scalpet array, pixel array, or scalpet plate. FIG. 10A is a side view of a portion of the pixel array showing scalpets secured onto an investing plate, under an embodiment. FIG. 10B is a side view of a portion of the pixel array showing scalpets secured onto an investing plate, under an alternative embodiment. FIG. 10C is a top view of the scalpet plate, under an embodiment. FIG. 10D is a close view of a portion of the scalpet plate, under an embodiment. The scalpet plate is applied directly to the skin surface. One or more scalpets of the scalpet array include one or more of a pointed surface, a needle, and a needle including multiple points.

Embodiments of the pixel array medical devices and methods include use of a harvest pattern instead of the guide plate. The harvest pattern comprises indicators or markers on a skin surface on at least one of the donor site and the recipient site, but is not so limited. The markers include any compound that may be applied directly to the skin to mark an area of the skin. The harvest pattern is positioned at a donor site, and the scalpet array of the device is aligned with or according to the harvest pattern at the donor site. The skin pixels are incised at the donor site with the scalpet array as described herein. The recipient site is prepared by positioning the harvest pattern at the recipient site. The harvest pattern used at the recipient site can be the same harvest pattern used at the donor site, or can be different with a different pattern or configuration of markers. The skin defects are generated, and the incised skin pixels are applied at the recipient site as described herein. Alternatively, the guide plate of an embodiment is used in applying the harvest pattern, but the embodiment is not so limited.

To leverage established surgical instrumentation, the array of an embodiment is used in conjunction with or as a modification to a drum dermatome, for example a Padget dermatome or a Reese dermatome, but is not so limited. The Padget drum dermatome referenced herein was originally developed by Dr. Earl Padget in the 1930s, and continues to be widely utilized for skin grafting by plastic surgeons throughout the world. The Reese modification of the Padget dermatome was subsequently developed to better calibrate the thickness of the harvested skin graft. The drum dermatome of an embodiment is a single use (per procedure) disposable, but is not so limited.

Figure 11A:
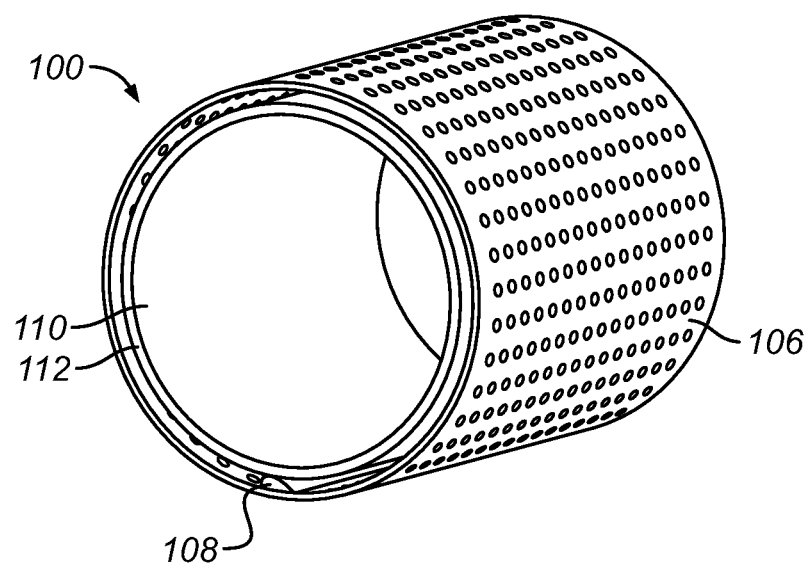
FIG. 11A shows an example of rolling pixel drum, under an embodiment.
Figure 11B:
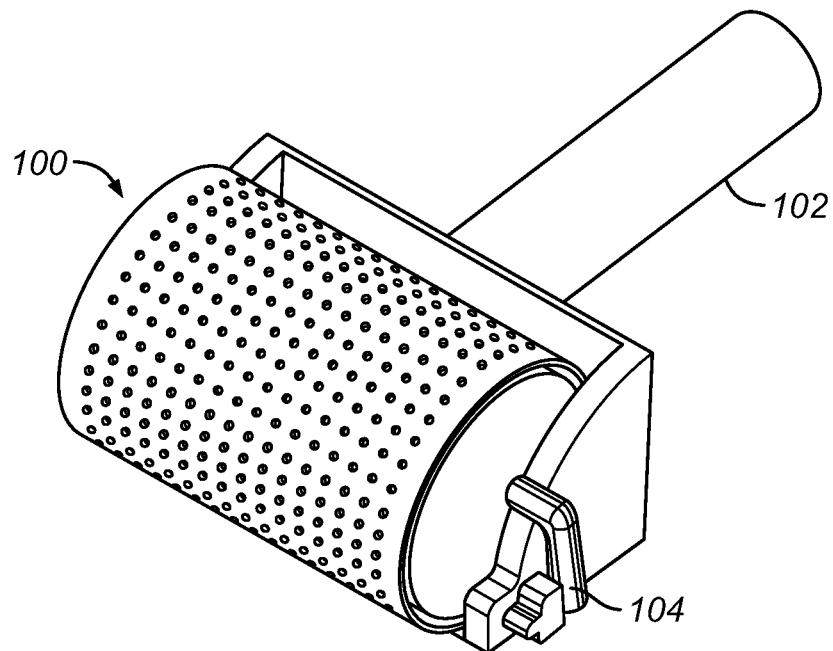
FIG. 11B shows an example of a rolling pixel drum assembled on a handle, under an embodiment.
Figure 11C:
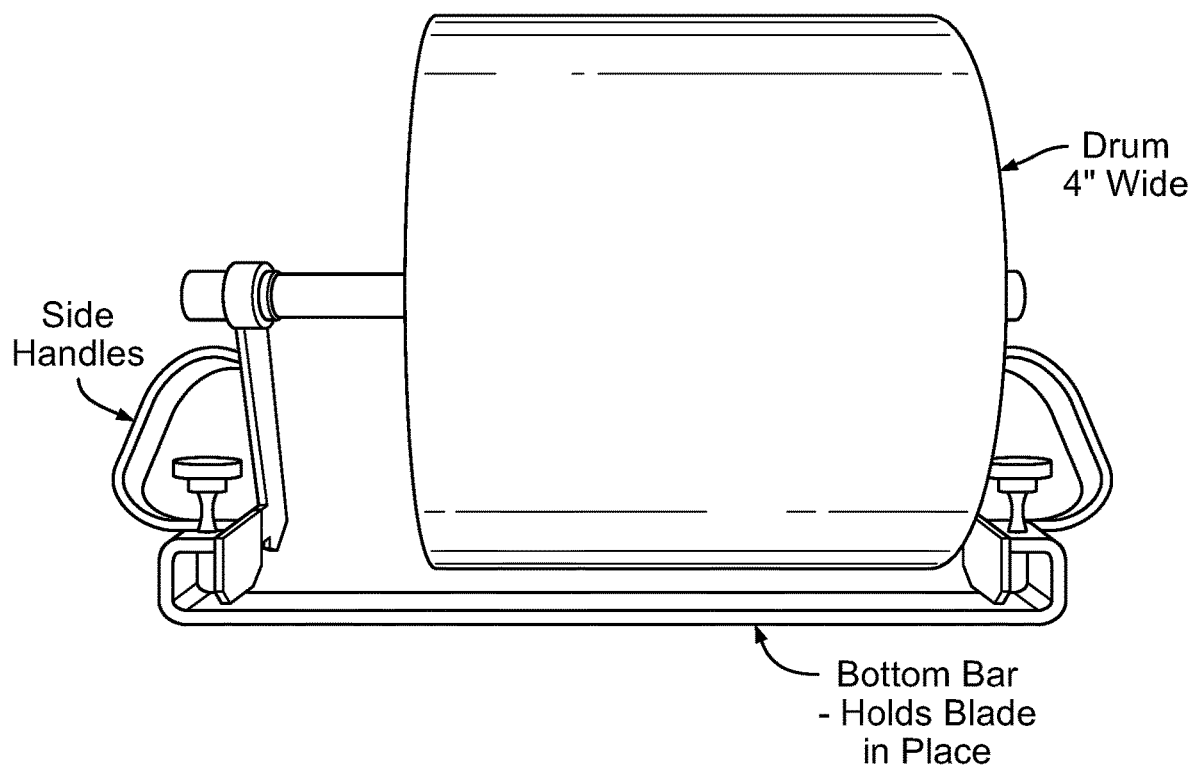
FIG. 11C depicts a drum dermatome for use with the scalpet plate, under an embodiment.

Generally, FIG. 11A shows an example of a rolling pixel drum 100, under an embodiment. FIG. 11B shows an example of a rolling pixel drum 100 assembled on a handle, under an embodiment. More specifically, FIG. 11C depicts a drum dermatome for use with the scalpet plate, under an embodiment.

Generally, as with all pixel devices described herein, the geometry of the pixel drum 100 can be a variety of shapes without limitation e.g., circular, semicircular, elliptical, square, flat, or rectangular. In some embodiments, the pixel drum 100 is supported by an axle/handle assembly 102 and rotated around a drum rotational component 104 powered by, e.g., an electric motor. In some embodiments, the pixel drum 100 can be placed on stand (not shown) when not in use, wherein the stand can also function as a battery recharger for the powered rotational component of the drum or the powered component of the syringe plunger. In some embodiments, a vacuum (not shown) can be applied to the skin surface of the pixel drum 100 and outriggers (not shown) can be deployed for tracking and stability of the pixel drum 100.

In some embodiments, the pixel drum 100 incorporates an array of scalpets 106 on the surface of the drum 100 to create small multiple (e.g., 0.5-1.5 mm) circular incisions referred to herein as skin plugs. In some embodiments, the border geometry of the scalpets can be designed to reduce pin cushioning ("trap door") while creating the skin plugs. The perimeter of each skin plug can also be lengthened by the scalpets to, for a non-limiting example, a, semicircular, elliptical, or square-shaped skin plug instead of a circular-shaped skin plug. In some embodiments, the length of the scalpets 106 may vary depending upon the thickness of the skin area selected by the surgeon for skin grafting purposes, i.e., partial thickness or full thickness.

When the drum 100 is applied to a skin surface, a blade 108 placed internal of the drum 100 transects the base of each skin plug created by the array of scalpets, wherein the internal blade 108 is connected to the central drum axle/handle assembly 102 and/or connected to outriggers attached to the central axle assembly 102. In some alternative embodiments, the internal blade 108 is not connected to the drum axle assembly 102 where the base of the incisions of skin is transected. In some embodiments, the internal blade 108 of the pixel drum 100 may oscillate either manually or be powered by an electric motor. Depending upon the density of the circular scalpets on the drum, a variable percentage of skin (e.g., 20%, 30%, 40%, etc.) can be transected within an area of excessive skin laxity.

In some embodiments, an added pixel drum harvester 112 is placed inside the drum 100 to perform a skin grafting operation by harvesting and aligning the transected/pixilated skin incisions/plugs (pixel graft) from tissue of a pixel donor onto an adherent membrane 110 lined in the interior of the pixel drum 100. A narrow space is created between the array of scalpets 106 and the adherent membrane 110 for the internal blade 108.

In an embodiment, the blade 108 is placed external to the drum 100 and the scalpet array 106 where the base of the incised circular skin plugs is transected. In another embodiment, the external blade 108 is connected to the drum axle assembly 102 when the base of the incisions of skin is transected. In an alternative embodiment, the external blade 108 is not connected to the drum axle assembly 102 when the base of the incisions of skin is transected. The adherent membrane 110 that extracts and aligns the transected skin segments is subsequently placed over a skin defect site of a patient. The blade 108 (either internal or external) can be a fenestrated layer of blade aligned to the scalpet array 106, but is not so limited.

The conformable adherent membrane 110 of an embodiment can be semi-porous to allow for drainage at a recipient skin defect when the membrane with the aligned transected skin segments is extracted from the drum and applied as a skin graft. The adherent semi-porous drum membrane 110 can also have an elastic recoil property to bring the transected/pixilated skin plugs together for grafting onto the skin defect site of the recipient, i.e., the margins of each skin plug can be brought closer together as a more uniform sheet after the adherent membrane with pixilated grafts extracted from the drum 100. Alternatively, the adherent semi-porous drum membrane 110 can be expandable to cover a large surface area of the skin defect site of the recipient. In some embodiments, a sheet of adhesive backer 111 can be applied between the adherent membrane 110 and the drum harvester 112. The drum array of scalpets 106, blade 108, and adherent membrane 110 can be assembled together as a sleeve onto a preexisting drum 100, as described in detail herein.

The internal drum harvester 112 of the pixel drum 110 of an embodiment is disposable and replaceable. Limit and/or control the use of the disposable components can be accomplished by means that includes but is not limited to electronic, EPROM, mechanical, durability. The electronic and/or mechanical records and/or limits of number of drum rotations for the disposable drum as well as the time of use for the disposable drum can be recorded, controlled and/or limited either electronically or mechanically.

During the harvesting portion of the procedure with a drum dermatome, the PAD scalpet array is applied directly to the skin surface. To circumferentially incise the skin pixels, the drum dermatome is positioned over the scalpet array to apply a load onto the subjacent skin surface. With a continuing load, the incised skin pixels are extruded through the holes of the scalpet array and captured onto an adherent membrane on the drum dermatome. The cutting outrigger blade of the dermatome (positioned over the scalpet array) transects the base of extruded skin pixels. The membrane and the pixelated skin composite are then removed from the dermatome drum, to be directly applied to the recipient skin defect as a skin graft.

Figure 12A:
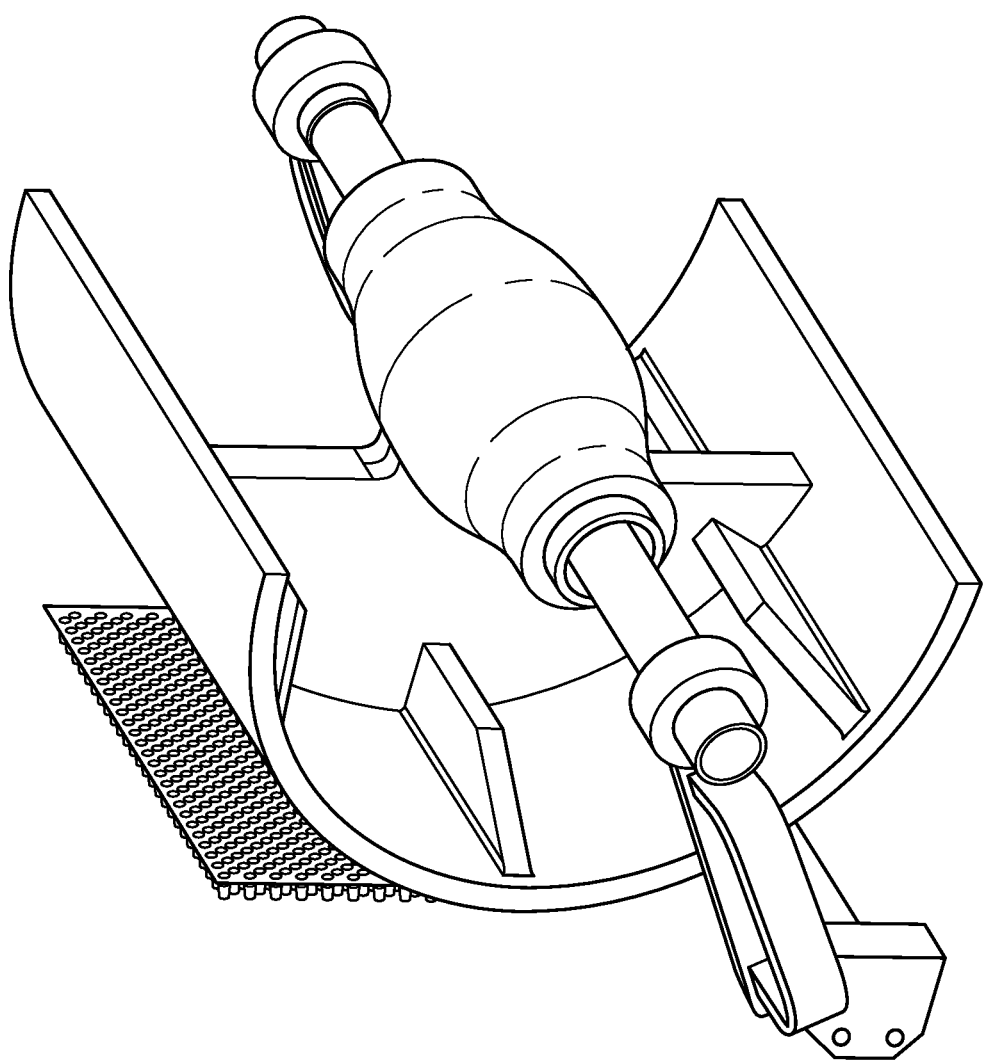
FIG. 12A shows the drum dermatome positioned over the scalpet plate, under an embodiment.
Figure 12B:
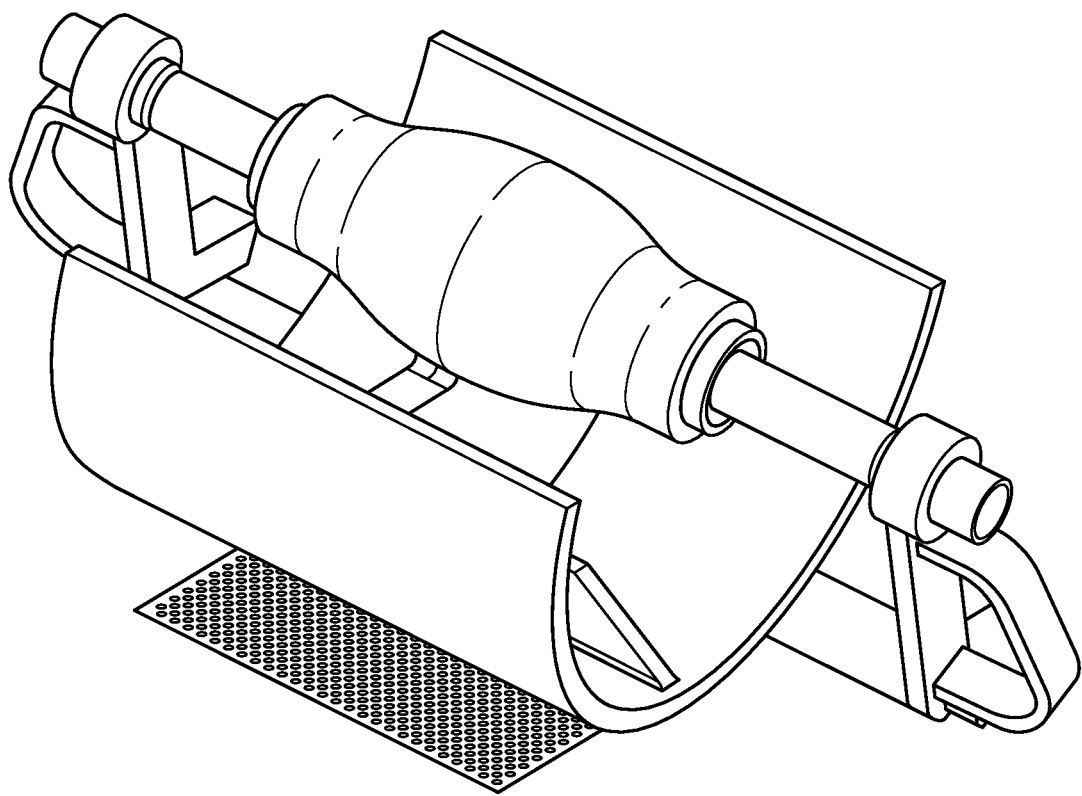
FIG. 12B is an alternative view of the drum dermatome positioned over the scalpet plate, under an embodiment.

With reference to FIG. 11C, an embodiment includes a drum dermatome for use with the scalpet plate, as described herein. More particularly, FIG. 12A shows the drum dermatome positioned over the scalpet plate, under an embodiment. FIG. 12B is an alternative view of the drum dermatome positioned over the scalpet plate, under an embodiment. The cutting outrigger blade of the drum dermatome is positioned on top of the scalpet array where the extruded skin plugs will be transected at their base.

Figure 13A:
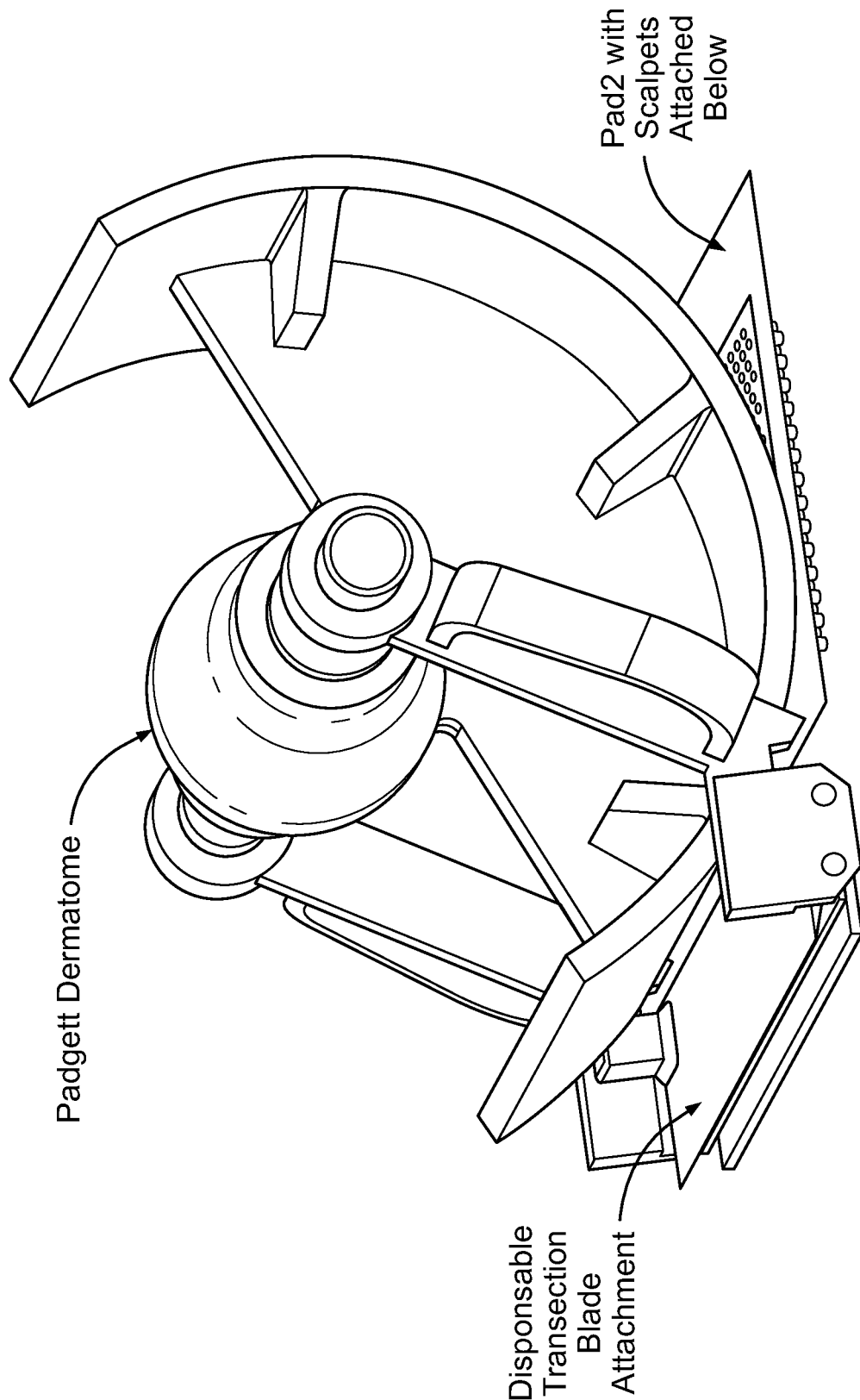
FIG. 13A is an isometric view of application of the drum dermatome (e.g., Padgett dermatome) over the scalpet plate, where the adhesive membrane is applied to the drum of the dermatome before rolling it over the investing plate, under an embodiment.
Figure 13B:
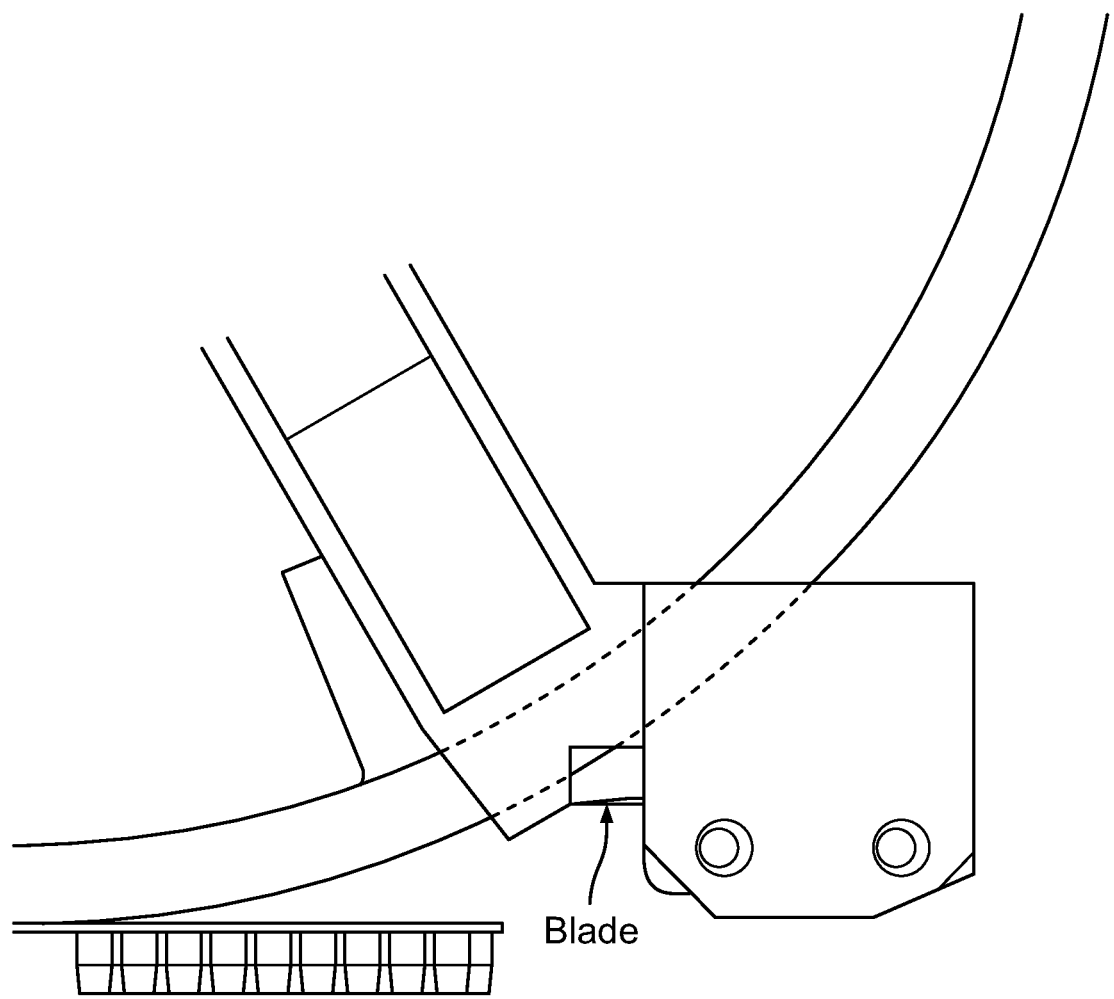
FIG. 13B is a side view of a portion of the drum dermatome showing a blade position relative to the scalpet plate, under an embodiment.
Figure 13C:
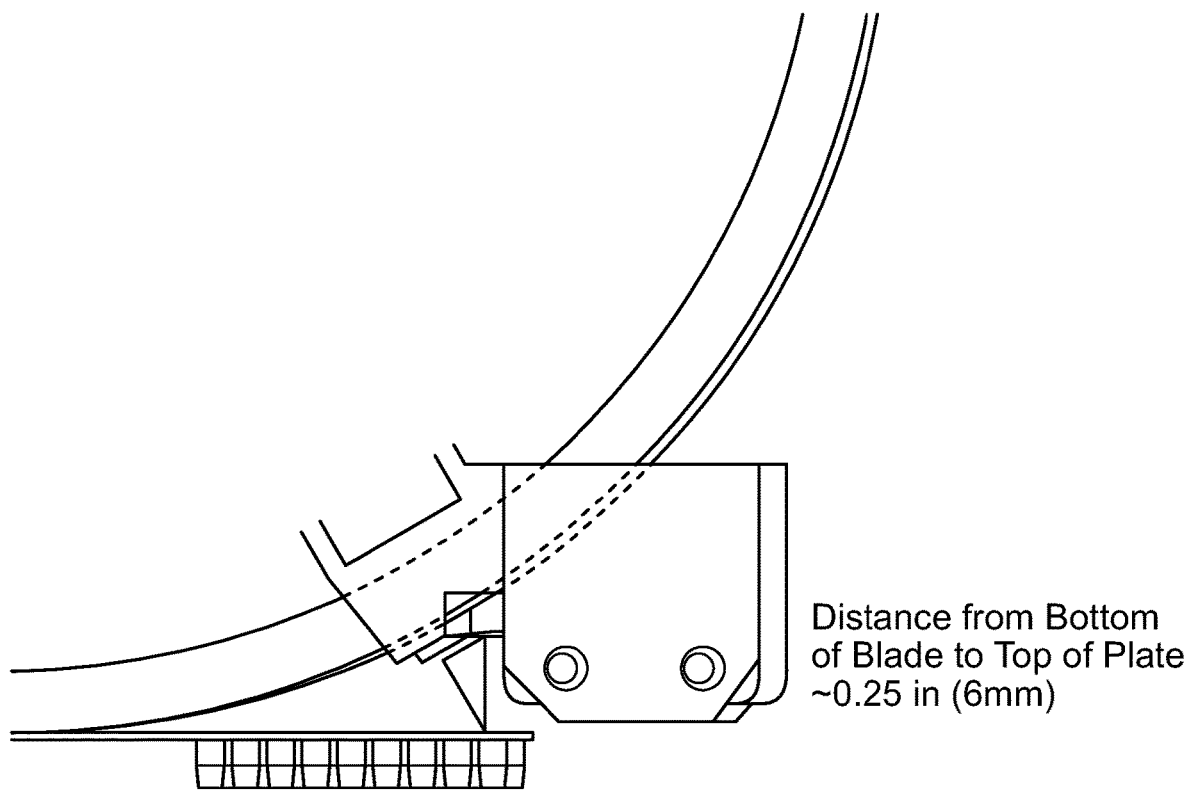
FIG. 13C is a side view of the portion of the drum dermatome showing a different blade position relative to the scalpet plate, under an embodiment.
Figure 13D:
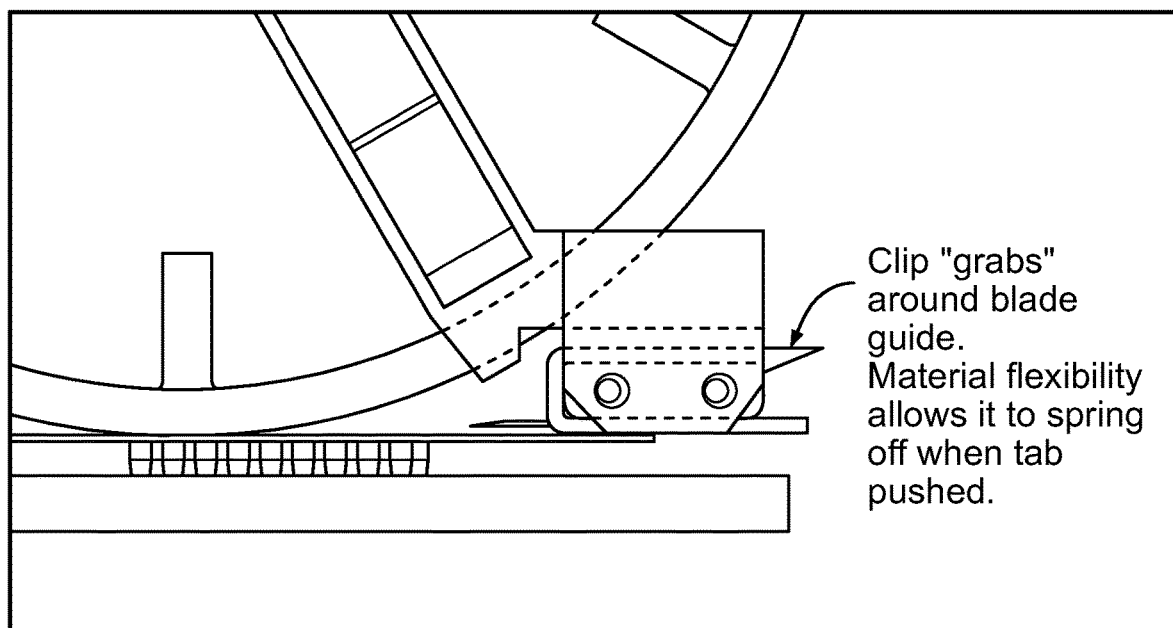
FIG. 13D is a side view of the drum dermatome with another blade position relative to the scalpet plate, under an embodiment.
Figure 13E:
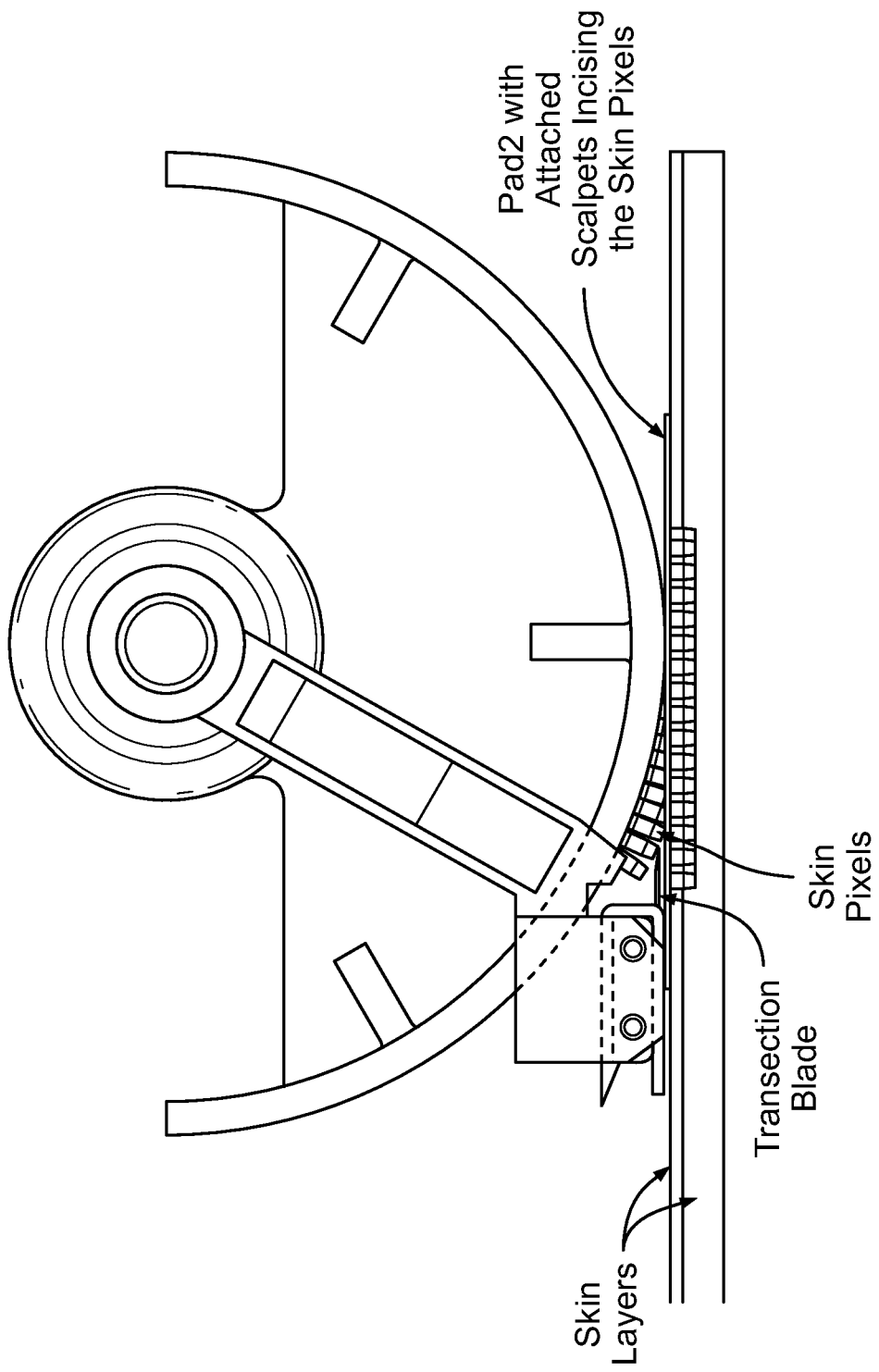
FIG. 13E is a side view of the drum dermatome with the transection blade clip showing transection of skin pixels by the blade clip, under an embodiment.
Figure 13F:
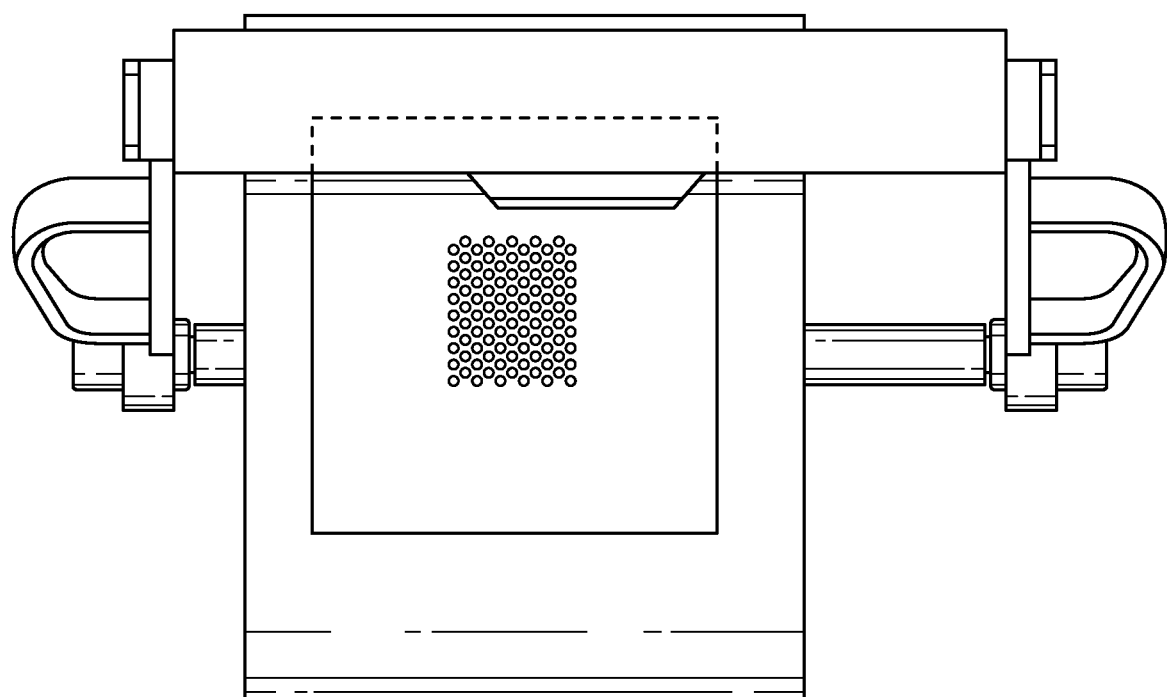
FIG. 13F is a bottom view of the drum dermatome along with the scalpet plate, under an embodiment.
Figure 13G:
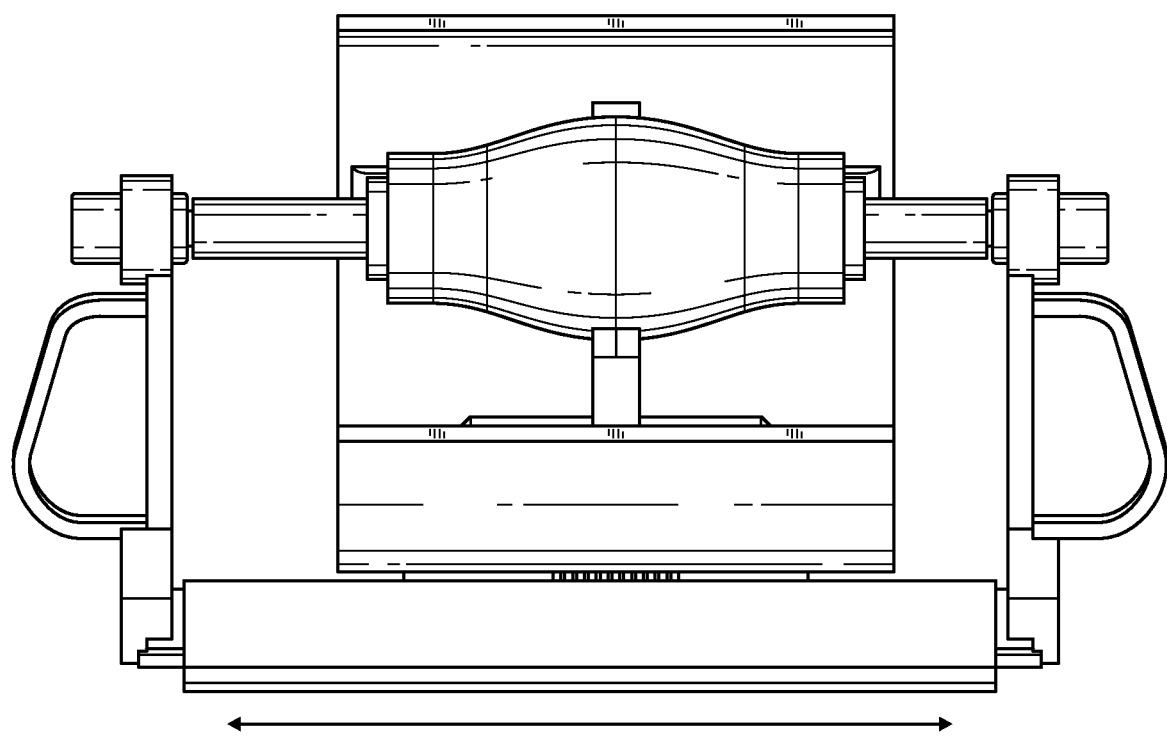
FIG. 13G is a front view of the drum dermatome along with the scalpet plate, under an embodiment.
Figure 13H:
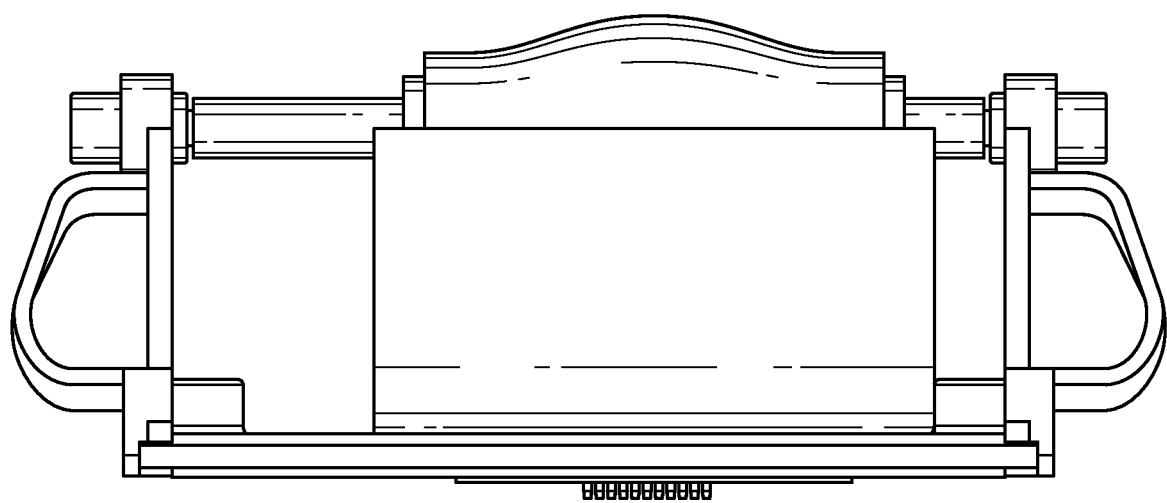

FIG. 13A is an isometric view of application of the drum dermatome (e.g., Padgett dermatome) over the scalpet plate, where the adhesive membrane is applied to the drum of the dermatome before rolling it over the investing plate, under an embodiment. FIG. 13B is a side view of a portion of the drum dermatome showing a blade position relative to the scalpet plate, under an embodiment. FIG. 13C is a side view of the portion of the drum dermatome showing a different blade position relative to the scalpet plate, under an embodiment. FIG. 13D is a side view of the drum dermatome with another blade position relative to the scalpet plate, under an embodiment. FIG. 13E is a side view of the drum dermatome with the transection blade clip showing transection of skin pixels by the blade clip, under an embodiment. FIG. 13F is a bottom view of the drum dermatome along with the scalpet plate, under an embodiment. FIG. 13G is a front view of the drum dermatome along with the scalpet plate, under an embodiment. FIG. 1311 is a back view of the drum dermatome along with the scalpet plate, under an embodiment.

Depending upon the clinical application, the disposable adherent membrane of the drum dermatome can be used to deposit/dispose of resected lax skin or harvest/align a pixilated skin graft.

Figure 14A:
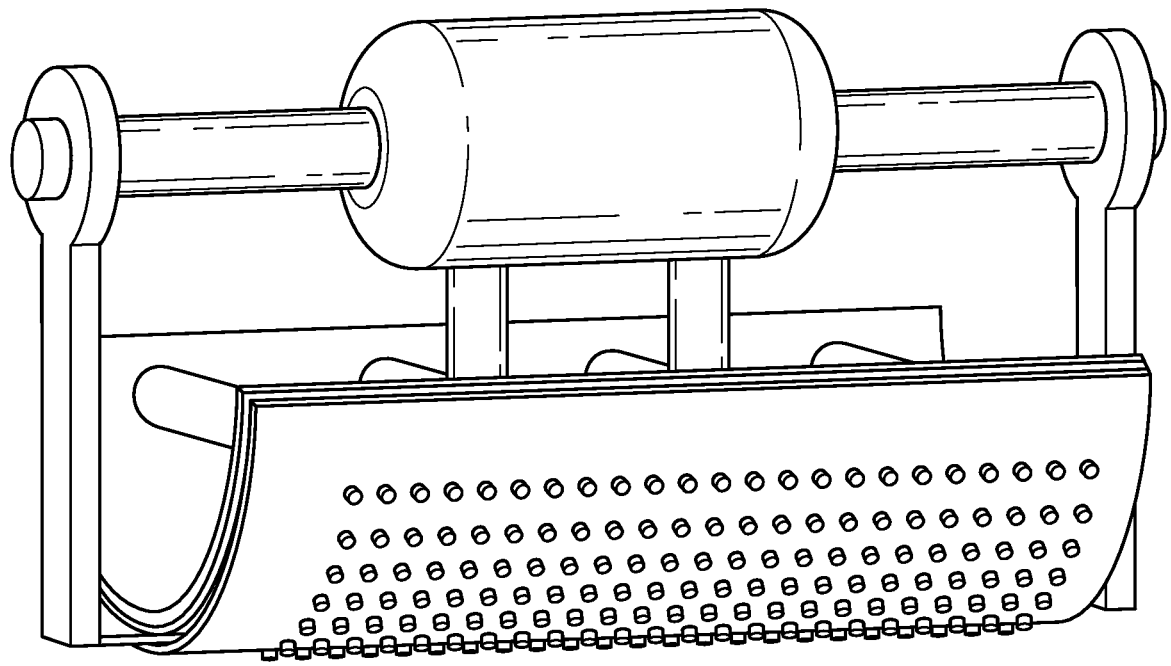
FIG. 14A shows an assembled view of the dermatome with the Pixel Onlay Sleeve (POS), under an embodiment.
Figure 14B:
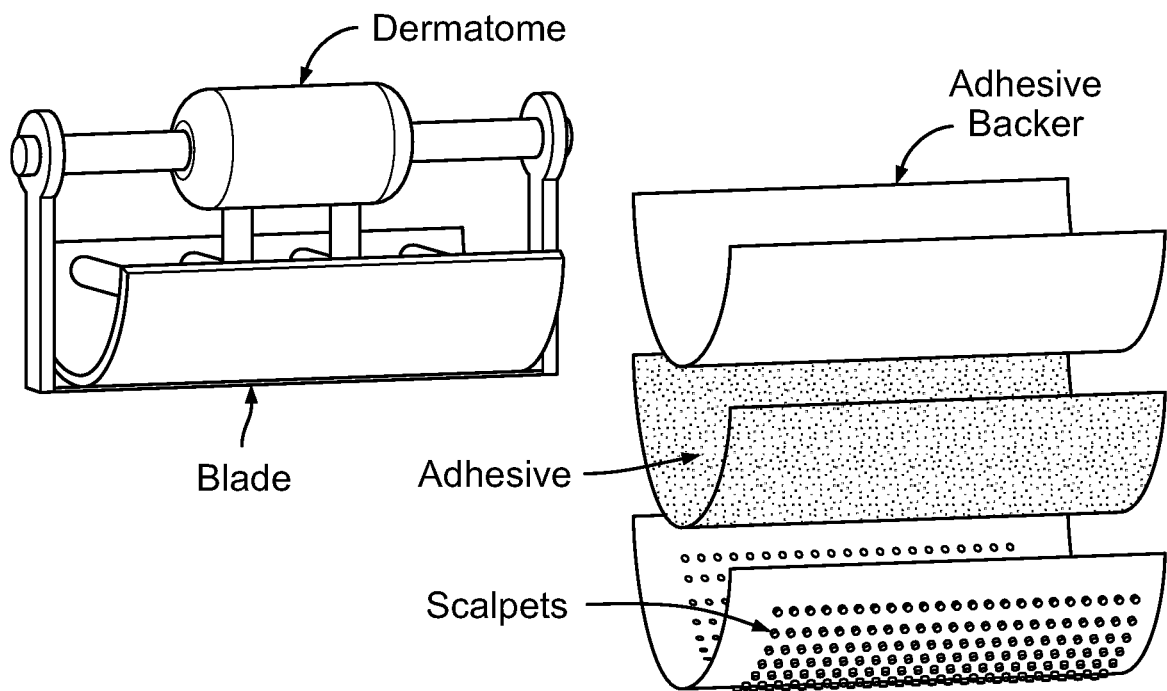
FIG. 14B is an exploded view of the dermatome with the Pixel Onlay Sleeve (POS), under an embodiment.
Figure 14C:
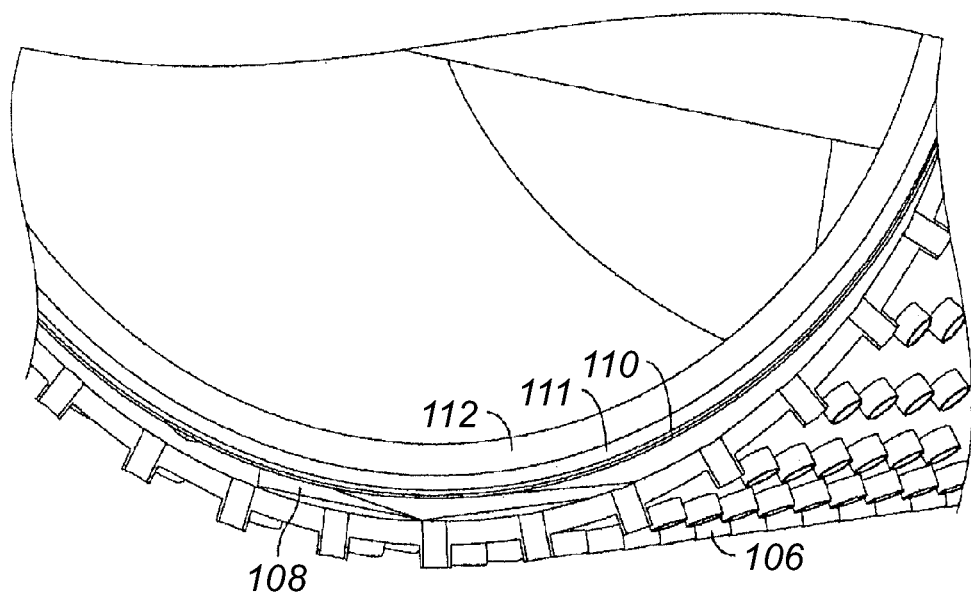
FIG. 14C shows a portion of the dermatome with the Pixel Onlay Sleeve (POS), under an embodiment.

Embodiments described herein also include a Pixel Onlay Sleeve (POS) for use with the dermatomes, for example the Padget dermatomes and Reese dermatomes. FIG. 14A shows an assembled view of the dermatome with the Pixel Onlay Sleeve (POS), under an embodiment. The POS comprises the dermatome and blade incorporated with an adhesive backer, adhesive, and a scalpet array. The adhesive backer, adhesive, and scalpet array are integral to the device, but are not so limited. FIG. 14B is an exploded view of the dermatome with the Pixel Onlay Sleeve (POS), under an embodiment. FIG. 14C shows a portion of the dermatome with the Pixel Onlay Sleeve (POS), under an embodiment.

The POS, also referred to herein as the "sleeve," provides a disposable drum dermatome onlay for the fractional resection of redundant lax skin and the fractional skin grafting of skin defects. The onlay sleeve is used in conjunction with either the Padget and Reese dermatomes as a single use disposable component. The POS of an embodiment is a three-sided slip-on disposable sleeve that slips onto a drum dermatome. The device comprises an adherent membrane and a scalpet drum array with an internal transection blade. The transection blade of an embodiment includes a single-sided cutting surface that sweeps across the internal surface of the scalpet drum array.

In an alternative blade embodiment, a fenestrated cutting layer covers the internal surface of the scalpet array. Each fenestration with its cutting surface is aligned with each individual scalpet. Instead of sweeping motion to transect the base of the skin plugs, the fenestrated cutting layer oscillates over the scalpet drum array. A narrow space between the adherent membrane and the scalpet array is created for excursion of the blade. For multiple harvesting during a skin grafting procedure, an insertion slot for additional adherent membranes is provided. The protective layer over the adherent membrane is pealed away insitu with an elongated extraction tab that is pulled from an extraction slot on the opposite side of the sleeve assembly. As with other pixel device embodiments, the adherent membrane is semi-porous for drainage at the recipient skin defect site. To morph the pixilated skin graft into a more continuous sheet, the membrane may also have an elastic recoil property to provide closer alignment of the skin plugs within the skin graft.

Figure 15A:
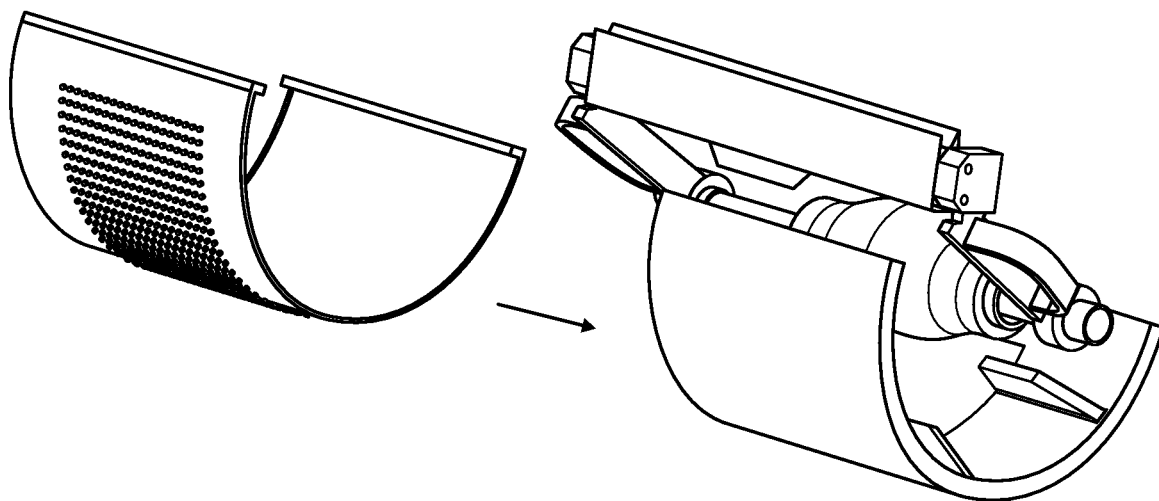
FIG. 15A shows the Slip-On PAD being slid onto a Padgett Drum Dermatome, under an embodiment.
Figure 15B:
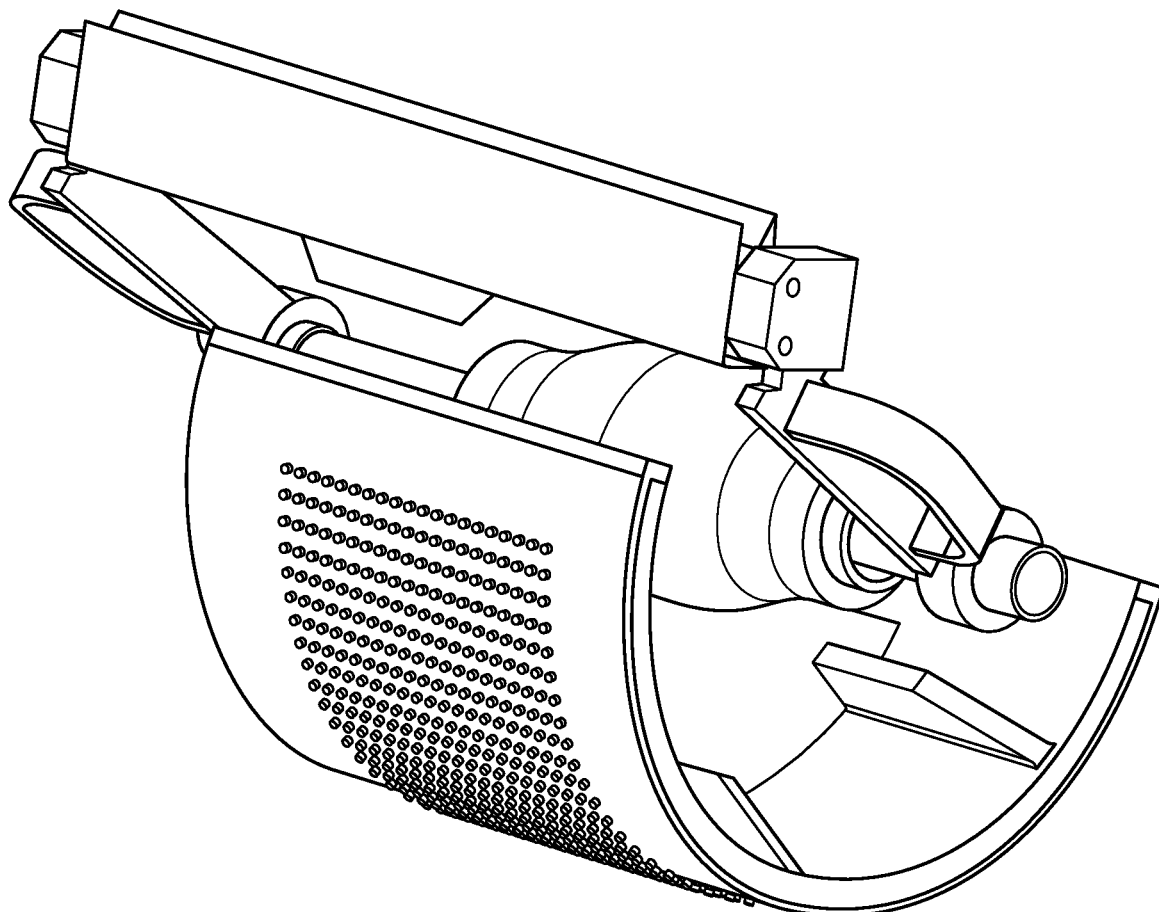
FIG. 15B shows an assembled view of the Slip-On PAD installed over the Padgett Drum Dermatome, under an embodiment.

Embodiments described herein include a Slip-On PAD that is configured as a single-use disposable device with either the Padgett or Reese dermatomes. FIG. 15A shows the Slip-On PAD being slid onto a Padgett Drum Dermatome, under an embodiment. FIG. 15B shows an assembled view of the Slip-On PAD installed over the Padgett Drum Dermatome, under an embodiment.

Figure 16A:
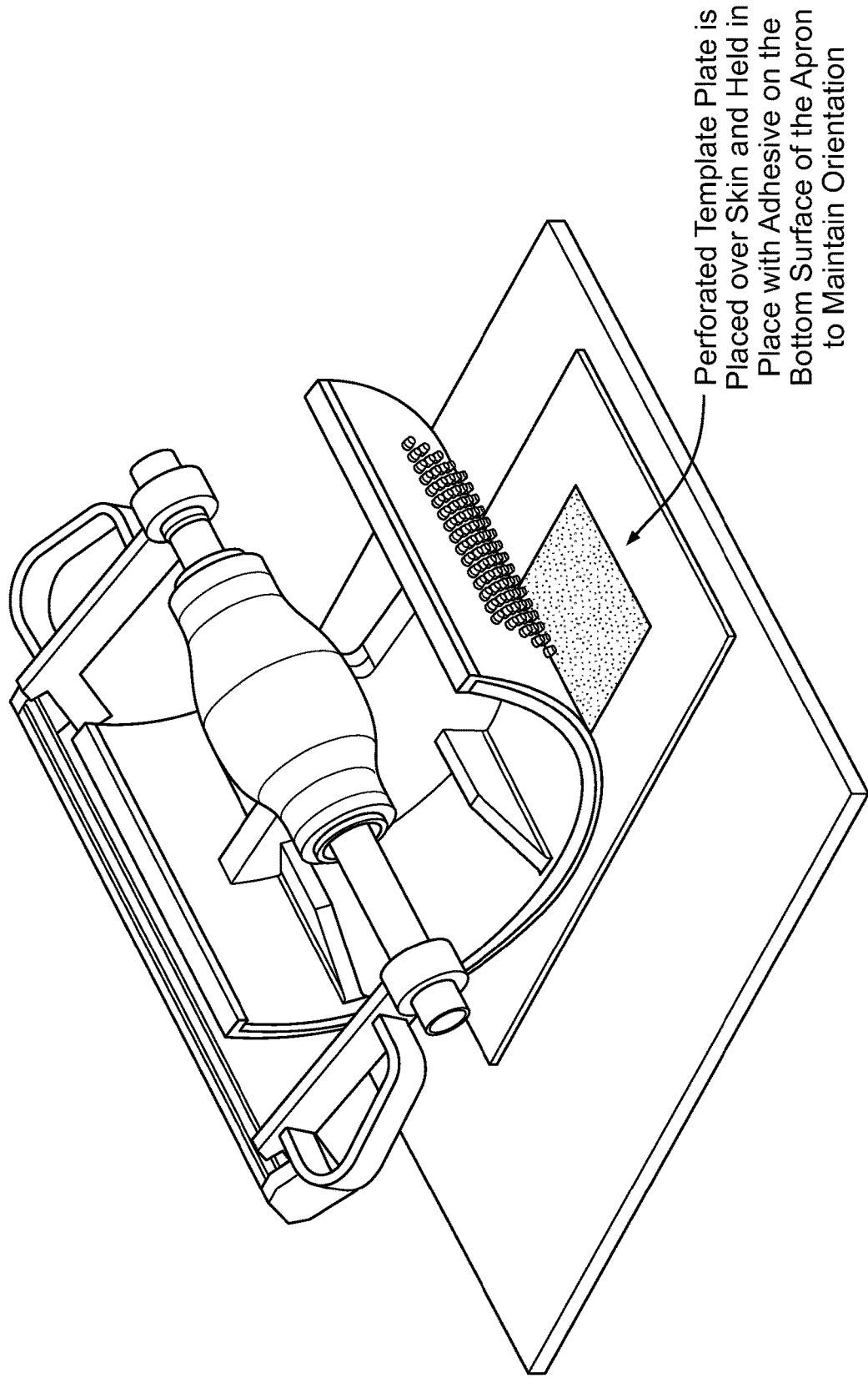
FIG. 16A shows the Slip-On PAD installed over a Padgett Drum Dermatome and used with a perforated template or guide plate, under an embodiment.

The Slip-on PAD of an embodiment is used (optionally) in combination with a perforated guide plate. FIG. 16A shows the Slip-On PAD installed over a Padgett Drum Dermatome and used with a perforated template or guide plate, under an embodiment. The perforated guide plate is placed over the target skin site and held in place with adhesive on the bottom surface of the apron to maintain orientation. The Padgett Dermatome with Slip-On PAD is rolled over the perforated guide plate on the skin.

Figure 16B:
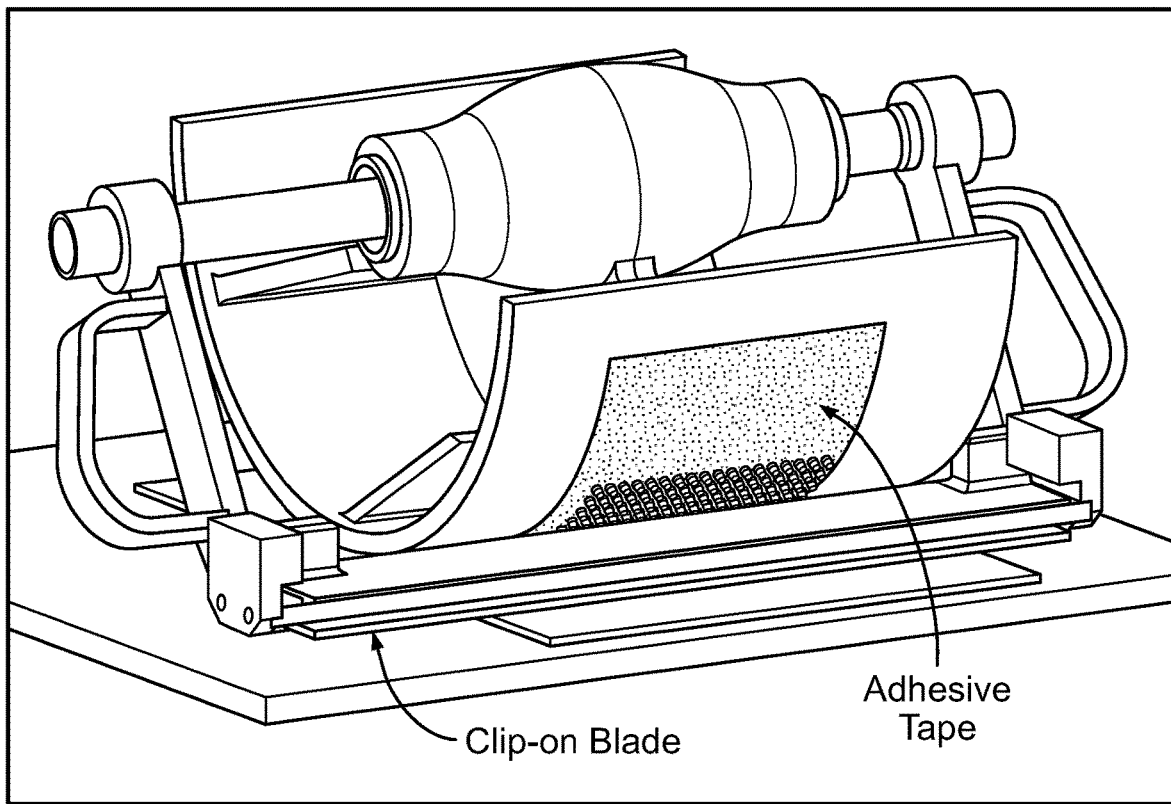
FIG. 16B shows skin pixel harvesting with a Padgett Drum Dermatome and installed Slip-On PAD, under an embodiment.

FIG. 16B shows skin pixel harvesting with a Padgett Drum Dermatome and installed Slip-On PAD, under an embodiment. For skin pixel harvesting, the Slip-On PAD is removed, adhesive tape is applied over the drum of the Padgett dermatome, and the clip-on blade is installed on the outrigger arm of the dermatome, which then is used to transect the base of the skin pixels. The Slip-on PAD of an embodiment is also used (optionally) with standard surgical instrumentation such as a ribbon retractor to protect the adjacent skin of the donor site.

Embodiments of the pixel instruments described herein include a Pixel Drum Dermatome (PD2) that is a single use disposable instrument or device. The PD2 comprises a cylinder or rolling/rotating drum coupled to a handle, and the cylinder includes a Scalpet Drum Array. An internal blade is interlocked to the drum axle/handle assembly and/or interlocked to outriggers attached to the central axle. As with the PAD and the POS described herein, small multiple pixilated resections of skin are performed directly in the region of skin laxity, thereby enhancing skin tightening with minimal visible scarring.

Figure 17A:
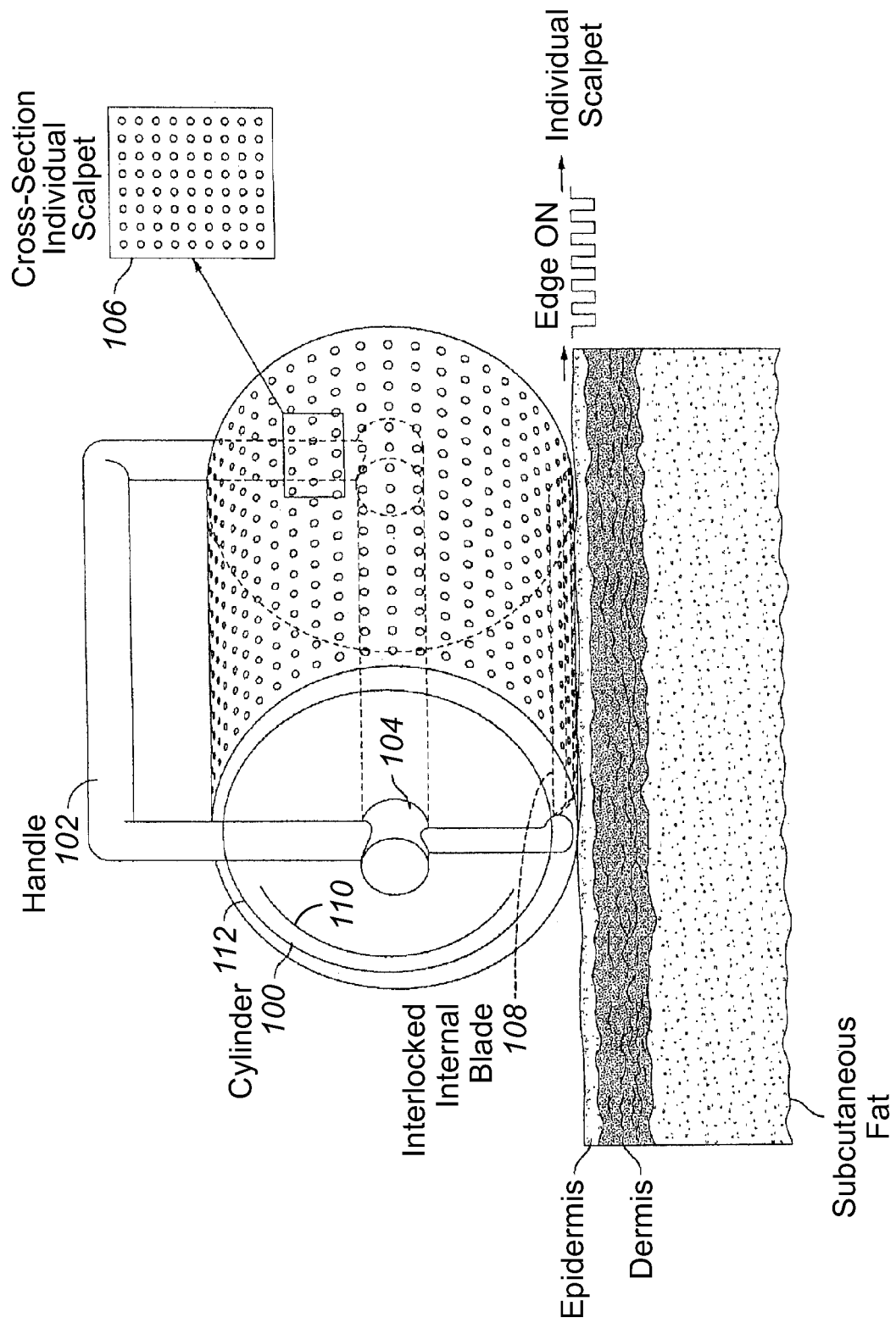
FIG. 17A shows an example of a Pixel Drum Dermatome being applied to a target site of the skin surface, under an embodiment.
Figure 17B:
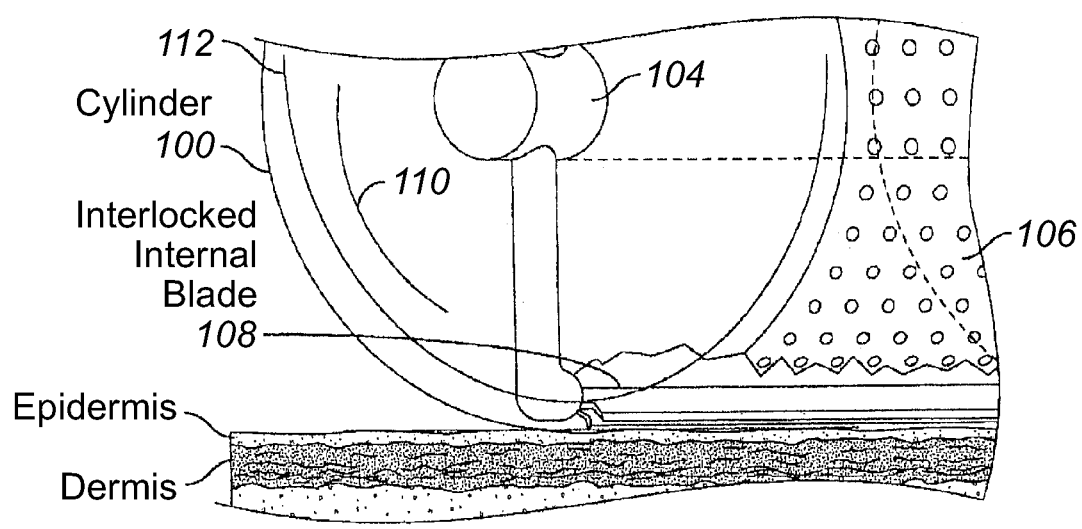
FIG. 17B shows an alternative view of a portion of the Pixel Drum Dermatome being applied to a target site of the skin surface, under an embodiment.

FIG. 17A shows an example of a Pixel Drum Dermatome being applied to a target site of the skin surface, under an embodiment. FIG. 17B shows an alternative view of a portion of the Pixel Drum Dermatome being applied to a target site of the skin surface, under an embodiment.

The PD2 device applies a full rolling/rotating drum to the skin surface where multiple small (e.g., 1.5 mm) circular incisions are created at the target site with a "Scalpet Drum Array". The base of each skin plug is then transected with an internal blade that is interlocked to the central drum axle/handle assembly and/or interlocked to outriggers attached to the central axle. Depending upon the density of the circular scalpets on the drum, a variable percentage of skin can be resected. The PD2 enables portions (e.g., 20%, 30%, 40%, etc.) of the skin's surface area to be resected without visible scarring in an area of excessive skin laxity, but the embodiment is not so limited.

Another alternative embodiment of the pixel instruments presented herein is the Pixel Drum Harvester (PDH). Similar to the Pixel Drum Dermatome, an added internal drum harvests and aligns the pixilated resections of skin onto an adherent membrane that is then placed over a recipient skin defect site of the patient. The conformable adherent membrane is semi-porous to allow for drainage at a recipient skin defect when the membrane with the aligned resected skin segments is extracted from the drum and applied as a skin graft. An elastic recoil property of the membrane allows closer approximation of the pixilated skin segments, partially converting the pixilated skin graft to a sheet graft at the recipient site.

The pixel array medical systems, instruments or devices, and methods described herein evoke or enable cellular and/or extracellular responses that are obligatory to the clinical outcomes achieved. For the pixel dermatomes, a physical reduction of the skin surface area occurs due to the pixilated resection of skin, i.e., creation of the skin plugs. In addition, a subsequent tightening of the skin results due to the delayed wound healing response. Each pixilated resection initiates an obligate wound healing sequence in multiple phases as described in detail herein.

The first phase of this sequence is the inflammatory phase in which degranulation of mast cells release histamine into the "wound". Histamine release may evoke dilatation of the capillary bed and increase vessel permeability into the extracellular space. This initial wound healing response occurs within the first day and will be evident as erythema on the skin's surface.

The second phase (of Fibroplasia) commences within three to four days of "wounding". During this phase, there is migration and mitotic multiplication of fibroblasts. Fibroplasia of the wound includes the deposition of neocollagen and the myofibroblastic contraction of the wound.

Histologically, the deposition of neocollagen can be identified microscopically as compaction and thickening of the dermis. Although this is a static process, the tensile strength of the wound significantly increases. The other feature of Fibroplasia is a dynamic physical process that results in a multi-dimensional contraction of the wound. This component feature of Fibroplasia is due to the active cellular contraction of myofibroblasts. Morphologically, myoblastic contraction of the wound will be visualized as a two dimensional tightening of the skin surface. Overall, the effect of Fibroplasia is dermal contraction along with the deposition of a static supporting scaffolding of neocollagen with a tightened framework. The clinical effect is seen as a delayed tightening of skin with smoothing of skin texture over several months. The clinical endpoint is generally a more youthful appearing skin envelope of the treatment area.

A third and final phase of the delayed wound healing response is maturation. During this phase there is a strengthening and remodeling of the treatment area due to an increased cross-linkage of the collagen fibril matrix (of the dermis). This final stage commences within six to twelve months after "wounding" and may extend for at least one to two years. Small pixilated resections of skin should preserve the normal dermal architecture during this delayed wound healing process without the creation of an evident scar that typically occurs with a larger surgical resection of skin. Lastly, there is a related stimulation and rejuvenation of the epidermis from the release of epidermal growth hormone. The delayed wound healing response can be evoked, with scar collagen deposition, within tissues (such as muscle or fat) with minimal pre-existing collagen matrix.

Other than tightening skin for aesthetic purposes, the pixel array medical systems, instruments or devices, and methods described herein may have additional medically related applications. In some embodiments, the pixel array devices can transect a variable portion of any soft tissue structure without resorting to a standard surgical resection. More specifically, the reduction of an actinic damaged area of skin via the pixel array devices should reduce the incidence of skin cancer. For the treatment of sleep apnea and snoring, a pixilated mucosal reduction (soft palate, base of the tongue and lateral pharyngeal walls) via the pixel array devices would reduce the significant morbidity associated with more standard surgical procedures. For birth injuries of the vaginal vault, pixilated skin and vaginal mucosal resection via the pixel array devices would reestablish normal pre-partum geometry and function without resorting to an A&P resection. Related female stress incontinence could also be corrected in a similar fashion.

The pixel array dermatome (PAD) of an embodiment, also referred to herein as a scalpet device assembly, includes a system or kit comprising a control device, also referred to as a punch impact hand-piece, and a scalpet device, also referred to as a tip device. The scalpet device, which is removeably coupled to the control device, includes an array of scalpets positioned within the scalpet device. The removeable scalpet device of an embodiment is disposable and consequently configured for use during a single procedure, but the embodiment is not so limited.

The PAD includes an apparatus comprising a housing configured to include a scalpet device. The scalpet device includes a substrate and a scalpet array, and the scalpet array includes a plurality of scalpets arranged in a configuration on the substrate. The substrate and the plurality of scalpets are configured to be deployed from the housing and retracted into the housing, and the plurality of scalpets is configured to generate a plurality of incised skin pixels at a target site when deployed. The proximal end of the control device is configured to be hand-held. The housing is configured to be removeably coupled to a receiver that is a component of a control device. The control device includes a proximal end that includes an actuator mechanism, and a distal end that includes the receiver. The control device is configured to be disposable, but alternatively the control device is configured to be at least one of cleaned, disinfected, and sterilized.

The scalpet array is configured to be deployed in response to activation of the actuator mechanism. The scalpet device of an embodiment is configured so the scalpet array is deployed from the scalpet device and retracted back into the scalpet device in response to activation of the actuator mechanism. The scalpet device of an alternative embodiment is configured so the scalpet array is deployed from the scalpet device in response to activation of the actuator mechanism, and retracted back into the scalpet device in response to release of the actuator mechanism.

Figure 18:
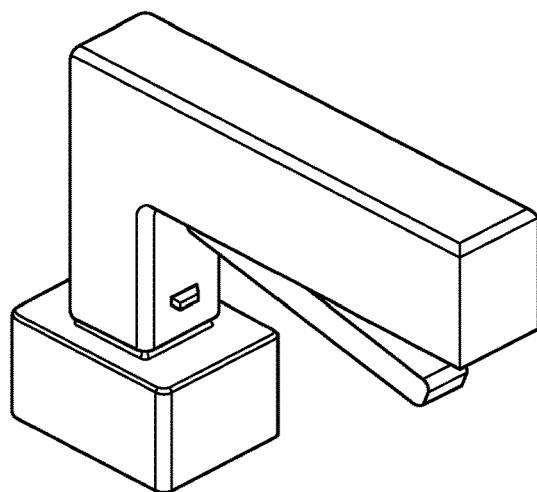
FIG. 18 shows a side perspective view of the PAD assembly, under an embodiment.

FIG. 18 shows a side perspective view of the PAD assembly, under an embodiment. The PAD assembly of this embodiment includes a control device configured to be hand-held, with an actuator or trigger and the scalpet device comprising the scalpet array. The control device is reusable, but alternative embodiments include a disposable control device. The scalpet array of an embodiment is configured to create or generate an array of incisions (e.g., 1.5 mm, 2 mm, 3 mm, etc.) as described in detail herein. The scalpet device of an embodiment includes a spring-loaded array of scalpets configured to incise the skin as described in detail herein, but the embodiments are not so limited.

Figure 19A:
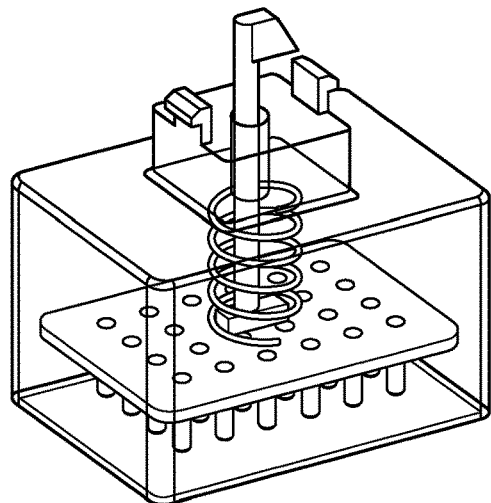
FIG. 19A shows a top perspective view of the scalpet device for use with the PAD assembly, under an embodiment.
Figure 19B:
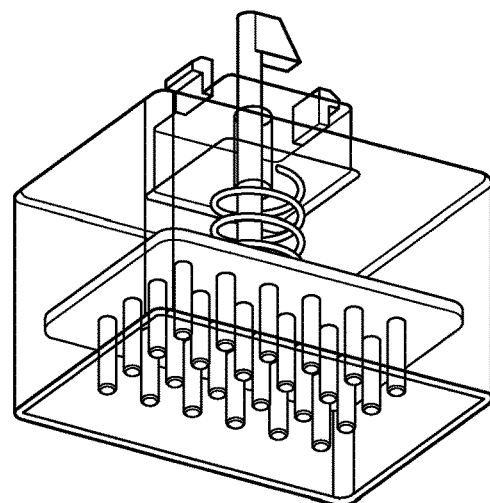
FIG. 19B shows a bottom perspective view of the scalpet device for use with the PAD assembly, under an embodiment.

FIG. 19A shows a top perspective view of the scalpet device for use with the PAD assembly, under an embodiment. FIG. 19B shows a bottom perspective view of the scalpet device for use with the PAD assembly, under an embodiment. The scalpet device comprises a housing configured to house a substrate that is coupled to or includes a plunger. The housing is configured so that a proximal end of the plunger protrudes through a top surface of the housing. The housing is configured to be removeably coupled to the control device, and a length of the plunger is configured to protrude a distance through the top surface to contact the control device and actuator when the scalpet device is coupled to the control device.

The substrate of the scalpet device is configured to retain numerous scalpets that form the scalpet array. The scalpet array comprises a pre-specified number of scalpets as appropriate to the procedure in which the scalpet device assembly is used. The scalpet device includes at least one spring mechanism configured to provide a downward, or impact or punching, force in response to activation of the scalpet array device, and this force assists generation of incisions (pixelated skin resection sites) by the scalpet array. Alternatively, the spring mechanism can be configured to provide an upward, or retracting, force to assist in retraction of the scalpet array.

One or more of the scalpet device and the control device of an embodiment includes an encryption system (e.g., EPROM, etc.). The encryption system is configured to prevent illicit use and pirating of the scalpet devices and/or control devices, but is not so limited.

During a procedure, the scalpet device assembly is applied one time to a target area or, alternative, applied serially within a designated target treatment area of skin laxity. The pixelated skin resection sites within the treatment area are then closed with the application of Flexan sheeting, as described in detail herein, and directed closure of these pixelated resections is performed in a direction that provides the greatest aesthetic correction of the treatment site.

Figure 20:
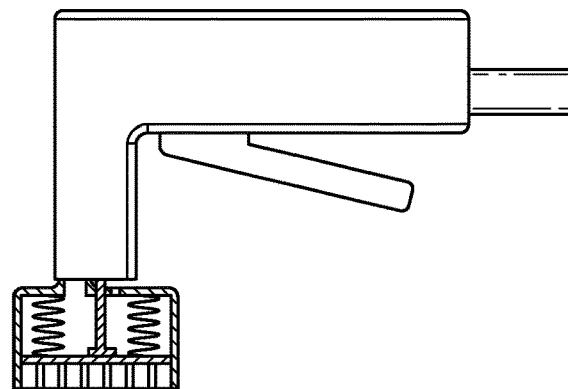
FIG. 20 shows a side view of the punch impact device including a vacuum component, under an embodiment.

The PAD device of an alternative embodiment includes a vacuum component or system for removing incised skin pixels. FIG. 20 shows a side view of the punch impact device including a vacuum component, under an embodiment. The PAD of this example includes a vacuum system or component within the control device to suction evacuate the incised skin pixels, but is not so limited. The vacuum component is removeably coupled to the PAD device, and its use is optional. The vacuum component is coupled to and configured to generate a low-pressure zone within or adjacent to one or more of the housing, the scalpet device, the scalpet array, and the control device. The low-pressure zone is configured to evacuate the incised skin pixels.

The PAD device of another alternative embodiment includes a radio frequency (RF) component or system for generating skin pixels. The RF component is coupled to and configured to provide or couple energy within or adjacent to one or more of the housing, the scalpet device, the scalpet array, and the control device. The RF component is removeably coupled to the PAD device, and its use is optional. The energy provided by the RF component includes one or more of thermal energy, vibrational energy, rotational energy, and acoustic energy, to name a few.

The PAD device of yet another alternative embodiment includes a vacuum component or system and an RF component or system. The PAD of this embodiment includes a vacuum system or component within the handpiece to suction evacuate the incised skin pixels. The vacuum component is removeably coupled to the PAD device, and its use is optional. The vacuum component is coupled to and configured to generate a low-pressure zone within or adjacent to one or more of the housing, the scalpet device, the scalpet array, and the control device. The low-pressure zone is configured to evacuate the incised skin pixels. Additionally, the PAD device includes an RF component coupled to and configured to provide or couple energy within or adjacent to one or more of the housing, the scalpet device, the scalpet array, and the control device. The RF component is removeably coupled to the PAD device, and its use is optional. The energy provided by the RF component includes one or more of thermal energy, vibrational energy, rotational energy, and acoustic energy, to name a few.

As one particular example, the PAD of an embodiment includes an electrosurgical generator configured to more effectively incise donor skin or skin plugs with minimal thermo-conductive damage to the adjacent skin. For this reason, the RF generator operates using relatively high power levels with relatively short duty cycles, for example. The RF generator is configured to supply one or more of a powered impactor component configured to provide additional compressive force for cutting, cycling impactors, vibratory impactors, and an ultrasonic transducer.

The PAD with RF of this example also includes a vacuum component, as described herein. The vacuum component of this embodiment is configured to apply a vacuum that pulls the skin up towards the scalpets (e.g., into the lumen of the scalpets, etc.) to stabilize and promote the RF mediated incision of the skin within the fractional resection field, but is not so limited. One or more of the RF generator and the vacuum appliance is coupled to be under the control of a processor running a software application. Additionally, the PAD of this embodiment can be used with the guide plate as described in detail herein, but is not so limited.

In addition to fractional incision at a donor site, fractional skin grafting includes the harvesting and deposition of skin plugs (e.g., onto an adherent membrane, etc.) for transfer to a recipient site. As with fractional skin resection, the use of a duty-driven RF cutting edge on an array of scalpets facilitates incising donor skin plugs. The base of the incised scalpets is then transected and harvested as described in detail herein.

The timing of the vacuum assisted component is processor controlled to provide a prescribed sequence with the RF duty cycle. With software control, different variations are possible to provide the optimal sequence of combined RF cutting with vacuum assistance. Without limitation, these include an initial period of vacuum prior to the RF duty cycle. Subsequent to the RF duty cycle, a period during the sequence of an embodiment includes suction evacuation of the incised skin plugs.

Other potential control sequences of the PAD include without limitation simultaneous duty cycles of RF and vacuum assistance. Alternatively, a control sequence of an embodiment includes pulsing or cycling of the RF duty cycle within the sequence and/or with variations of RF power or the use of generators at different RF frequencies.

Another alternative control sequence includes a designated RF cycle occurring at the depth of the fractional incision. A lower power longer duration RF duty cycle with insulated shaft with an insulated shaft an active cutting tip could generate a thermal-conductive lesion in the deep dermal/subcutaneous tissue interface. The deep thermal lesion would evoke a delayed wound healing sequence that would secondarily tighten the skin without burning of the skin surface.

With software control, different variations are possible to provide the optimal sequence of combined RF cutting and powered mechanical cutting with vacuum assistance. Examples include but are not limited to combinations of powered mechanical cutting with vacuum assistance, RF cutting with powered mechanical cutting and vacuum assistance, RF cutting with vacuum assistance, and RF cutting with vacuum assistance. Examples of combined software controlled duty cycles include but are not limited to precutting vacuum skin stabilization period, RF cutting duty cycle with vacuum skin stabilization period, RF cutting duty cycle with vacuum skin stabilization and powered mechanical cutting period, powered mechanical cutting with vacuum skin stabilization period, post cutting RF duty cycle for thermal conductive heating of the deeper dermal and/or subdermal tissue layer to evoke a wound healing response for skin tightening, and a post cutting vacuum evacuation period for skin tightening.

Figure 21A:
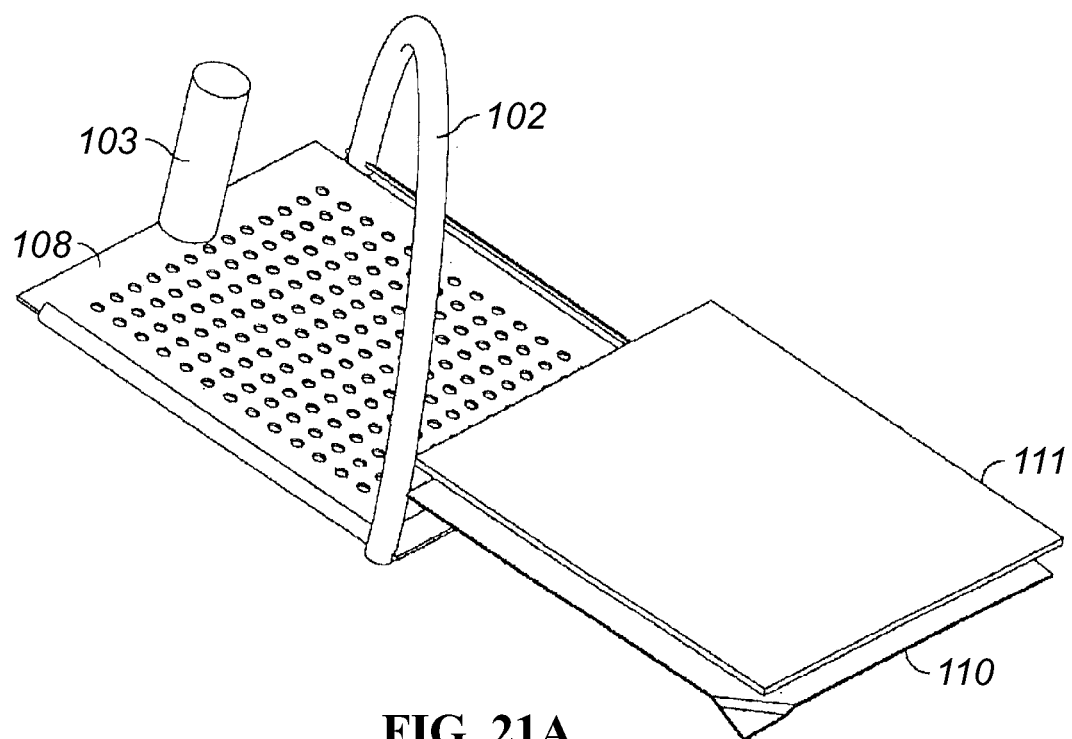
FIG. 21A shows a top view of an oscillating flat scalpet array and blade device, under an embodiment.
Figure 21B:
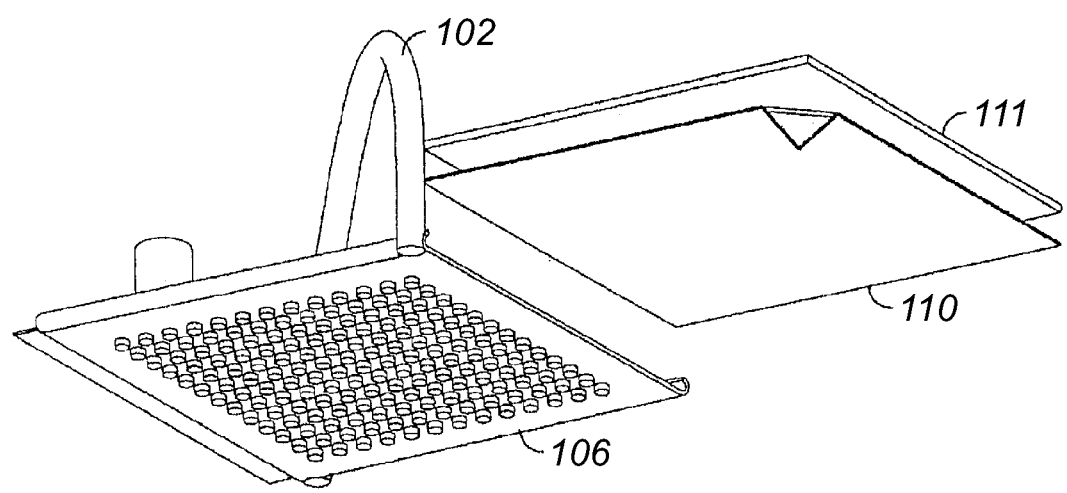
FIG. 21B shows a bottom view of an oscillating flat scalpet array and blade device, under an embodiment.
Figure 21C:
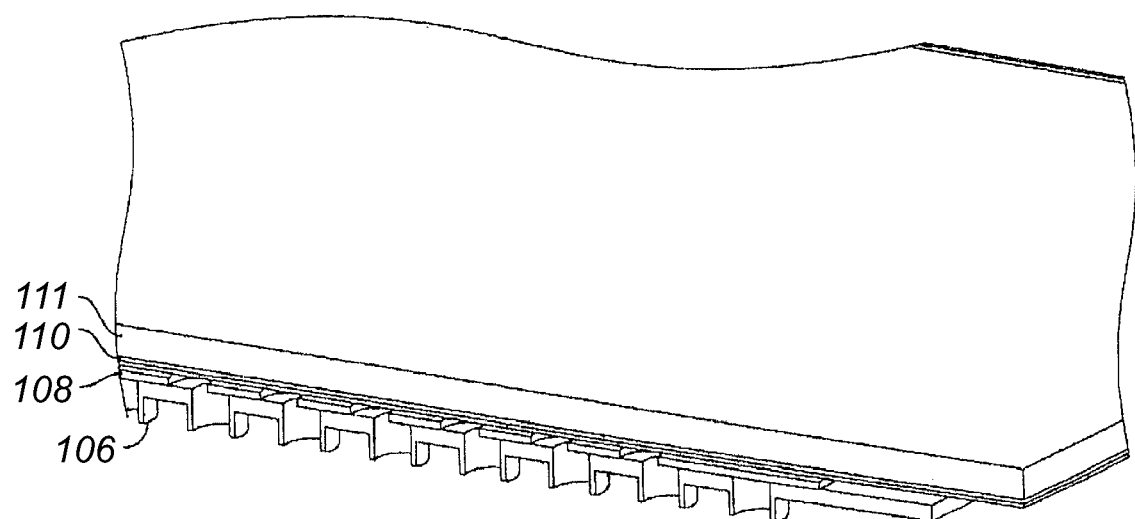
FIG. 21C is a close-up view of the flat array when the array of scalpets, blades, adherent membrane and the adhesive backer are assembled together, under an embodiment.
Figure 21D:
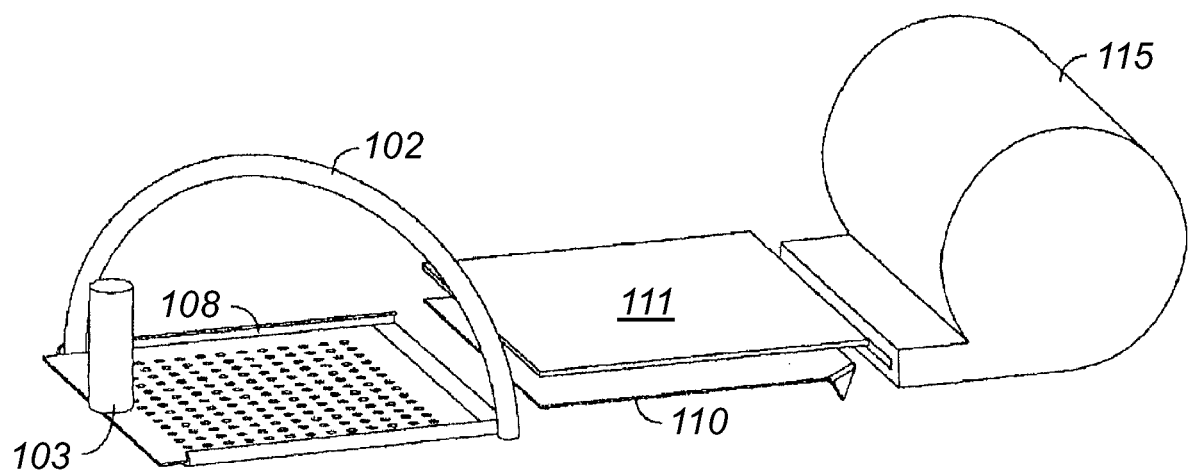
FIG. 21D is a close-up view of the flat array of scalpets with a feeder component, under an embodiment.

Another embodiment of pixel array medical devices described herein includes a device comprising an oscillating flat array of scalpets and blade either powered electrically or deployed manually (unpowered) and used for skin tightening as an alternative to the drum/cylinder described herein. FIG. 21A shows a top view of an oscillating flat scalpet array and blade device, under an embodiment. FIG. 21B shows a bottom view of an oscillating flat scalpet array and blade device, under an embodiment. Blade 108 can be a fenestrated layer of blade aligned to the scalpet array 106. The instrument handle 102 is separated from the blade handle 103 and the adherent membrane 110 can be peeled away from the adhesive backer 111. FIG. 21C is a close-up view of the flat array when the array of scalpets 106, blades 108, adherent membrane 110 and the adhesive backer 111 are assembled together, under an embodiment. As assembled, the flat array of scalpets can be metered to provide a uniform harvest or a uniform resection. In some embodiments, the flat array of scalpets may further include a feeder component 115 for the adherent harvesting membrane 110 and adhesive backer 111. FIG. 21D is a close-up view of the flat array of scalpets with a feeder component 115, under an embodiment.

Figure 22:
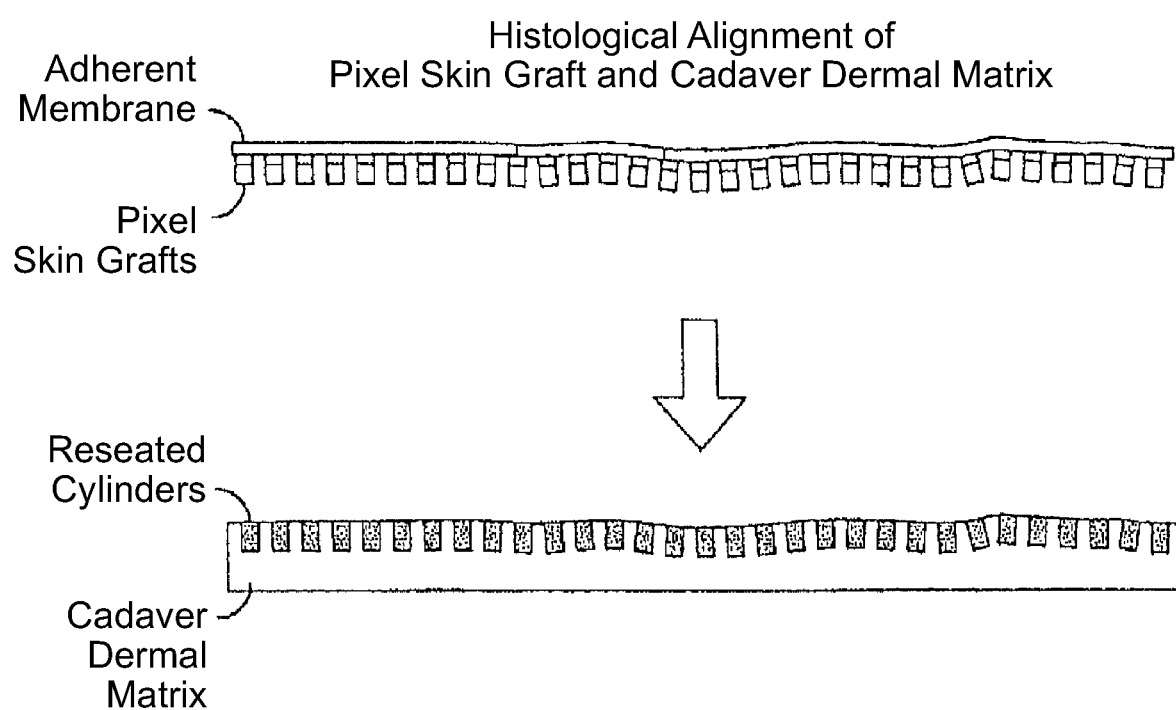
FIG. 22 shows a cadaver dermal matrix cylindrically transected similar in size to the harvested skin pixel grafts, under an embodiment.

In another skin grafting embodiment, the pixel graft is placed onto an irradiated cadaver dermal matrix (not shown). When cultured onto the dermal matrix, a graft of full thickness skin is created for the patient that is immunologically identical to the pixel donor. In embodiments, the cadaver dermal matrix can also be cylindrical transected similar in size to the harvested skin pixel grafts to provide histological alignment of the pixilated graft into the cadaver dermal framework. FIG. 22 shows a cadaver dermal matrix cylindrically transected similar in size to the harvested skin pixel grafts, under an embodiment. In some embodiments, the percentage of harvest of the donor site can be determined in part by the induction of a normal dermal histology at the skin defect site of the recipient, i.e., a normal (smoother) surface topology of the skin graft is facilitated. With either the adherent membrane or the dermal matrix embodiment, the pixel drum harvester includes the ability to harvest a large surface area for grafting with visible scarring of the patient's donor site significantly reduced or eliminated.

In addition to the pixel array medical devices described herein, embodiments include drug delivery devices. For the most part, the parenteral delivery of drugs is still accomplished from an injection with a syringe and needle. To circumvent the negative features of the needle and syringe system, the topical absorption of medication transcutaneously through an occlusive patch was developed. However, both of these drug delivery systems have significant drawbacks. The human aversion to a needle injection has not abated during the nearly two centuries of its use. The variable systemic absorption of either a subcutaneous or intramuscular drug injection reduces drug efficacy and may increase the incidence of adverse patient responses. Depending upon the lipid or aqueous carrier fluid of the drug, the topically applied occlusive patch is plagued with variable absorption across an epidermal barrier. For patients who require local anesthesia over a large surface area of skin, neither the syringe/needle injections nor topical anesthetics are ideal. The syringe/needle "field" injections are often painful and may instill excessive amounts of the local anesthetic that may cause systemic toxicity. Topical anesthetics rarely provide the level of anesthesia required for skin related procedures.

Figure 23:
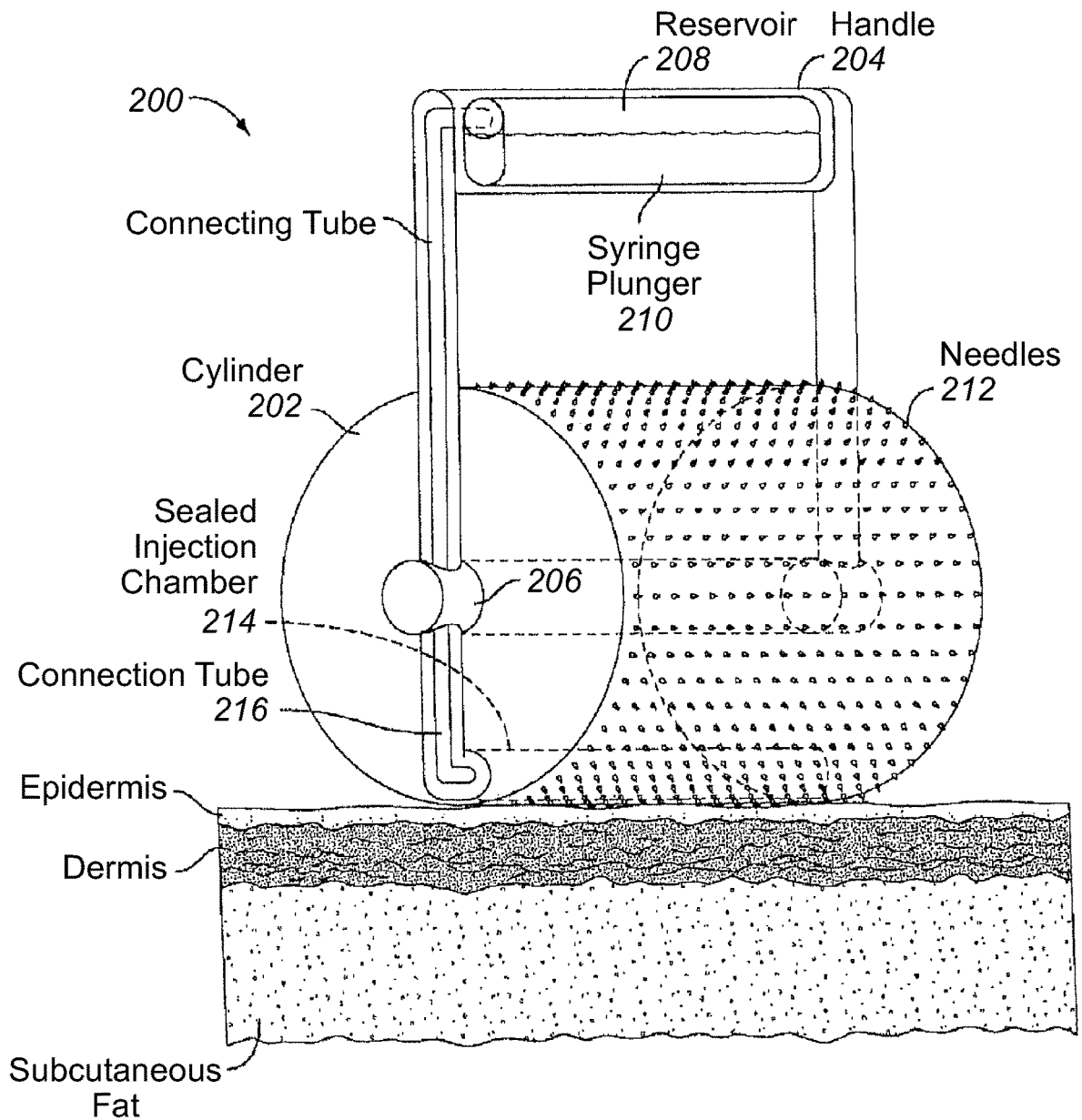
FIG. 23 is a drum array drug delivery device, under an embodiment.

FIG. 23 is a drum array drug delivery device 200, under an embodiment. The drug delivery device 200 successfully addresses the limitations and drawbacks of other drug delivery systems. The device comprises a drum/cylinder 202 supported by an axle/handle assembly 204 and rotated around a drum rotation component 206. The handle assembly 204 of an embodiment further includes a reservoir 208 of drugs to be delivered and a syringe plunger 210. The surface of the drum 202 is covered by an array of needles 212 of uniform length, which provide a uniform intradermal (or subdermal) injection depth with a more controlled volume of the drug injected into the skin of the patient. During operation, the syringe plunger 210 pushes the drug out of the reservoir 208 to be injected into a sealed injection chamber 214 inside the drum 202 via connecting tube 216. The drug is eventually delivered into the patient's skin at a uniform depth when the array of needles 212 is pushed into a patient's skin until the surface of the drum 202 hits the skin. Non-anesthetized skip area is avoided and a more uniform pattern of cutaneous anesthesia is created. The rolling drum application of the drug delivery device 200 also instills the local anesthetic faster with less discomfort to the patient.

Figure 24A:
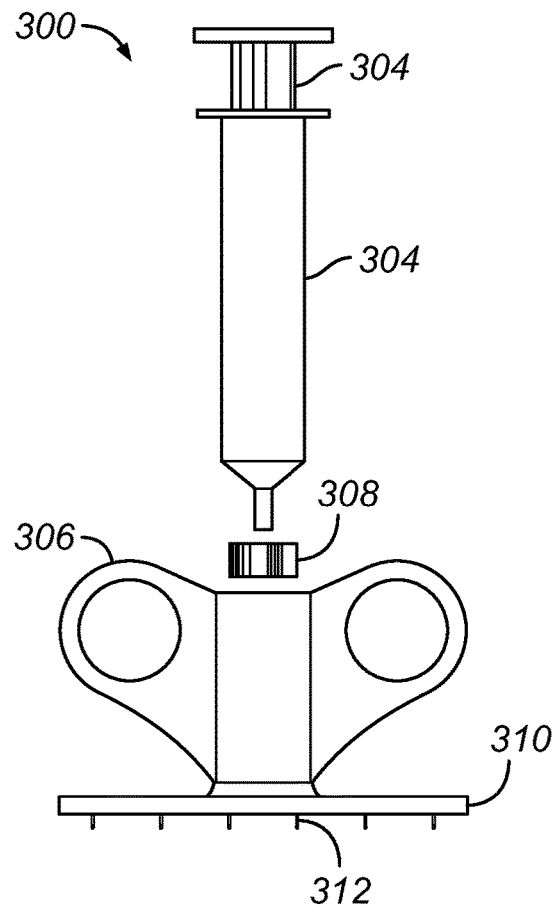
FIG. 24A is a side view of a needle array drug delivery device, under an embodiment.
Figure 24B:
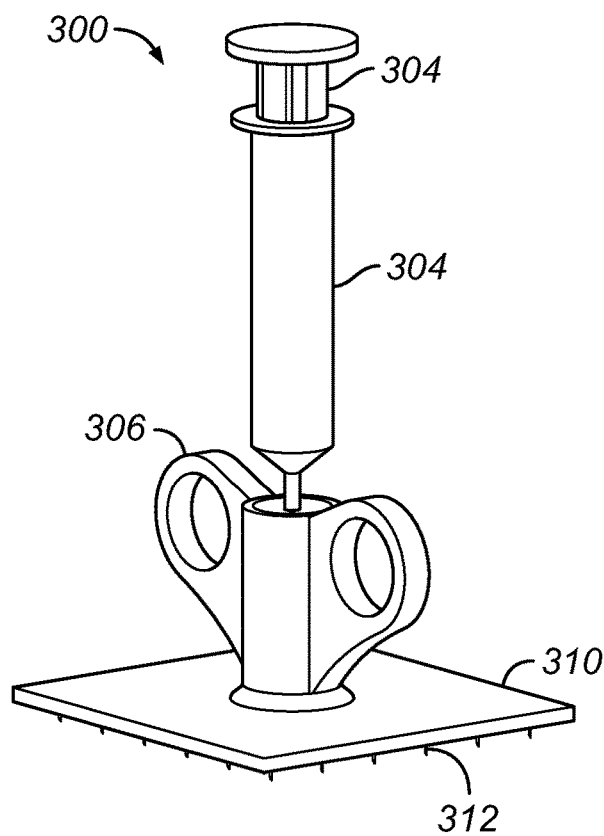
FIG. 24B is an upper isometric view of a needle array drug delivery device, under an embodiment.
Figure 24C:
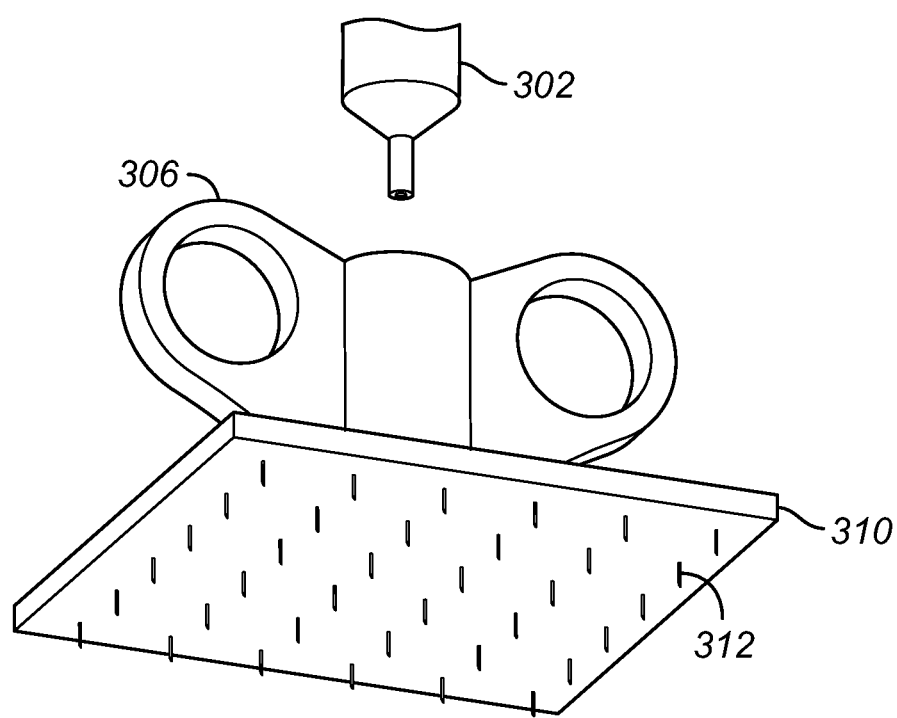
FIG. 24C is a lower isometric view of a needle array drug delivery device, under an embodiment.

FIG. 24A is a side view of a needle array drug delivery device 300, under an embodiment. FIG. 24B is an upper isometric view of a needle array drug delivery device 300, under an embodiment. FIG. 24C is a lower isometric view of a needle array drug delivery device 300, under an embodiment. The drug delivery device 300 comprises a flat array of fine needles 312 of uniform length positioned on manifold 310 can be utilized for drug delivery. In this example embodiment, syringe 302 in which drug for injection is contained can be plugged into a disposable adaptor 306 with handles, and a seal 308 can be utilized to ensure that the syringe 302 and the disposable adaptor 306 are securely coupled to each other. When the syringe plunger 304 is pushed, drug contained in syringe 302 is delivered from syringe 302 into the disposable adaptor 306. The drug is further delivered into the patient's skin through the flat array of fine needles 312 at a uniform depth when the array of needles 312 is pushed into a patient's skin until manifold 310 hits the skin.

The use of the drug delivery device 200 may have as many clinical applications as the number of pharmacological agents that require transcutaneous injection or absorption. For non-limiting examples, a few of the potential applications are the injection of local anesthetics, the injection of neuromodulators such as Botulinum toxin (Botox), the injection of insulin and the injection of replacement estrogens and corticosteroids.

In some embodiments, the syringe plunger 210 of the drug delivery device 200 can be powered by, for a non-limiting example, an electric motor. In some embodiments, a fluid pump (not shown) attached to an IV bag and tubing can be connected to the injection chamber 214 and/or the reservoir 208 for continuous injection. In some embodiments, the volume of the syringe plunger 210 in the drug delivery device 200 is calibrated and programmable.

Another application of pixel skin graft harvesting with the PAD (Pixel Array Dermatome) device as described in detail herein is Alopecia. Alopecia is a common aesthetic malady, and it occurs most frequently in the middle-aged male population, but is also observed in the aging baby boomer female population. The most common form of alopecia is Male Pattern Baldness (MPB) that occurs in the frontal-parietal region of the scalp. Male pattern baldness is a sex-linked trait that is transferred by the X chromosome from the mother to male offspring. For men, only one gene is needed to express this phenotype. As the gene is recessive, female pattern baldness requires the transfer of both X linked genes from both mother and father. Phenotypic penetrance can vary from patient to patient and is most frequently expressed in the age of onset and the amount of frontal/partial/occipital alopecia. The patient variability in the phenotypic expression of MPB is due to the variable genotypic translation of this sex-linked trait. Based upon the genotypic occurrence of MPB, the need for hair transplantation is vast. Other non-genetic related etiologies are seen in a more limited segment of the population. These non-genetic etiologies include trauma, fungal infections, lupus erythematosus, radiation and chemotherapy.

A large variety of treatment options have been proposed to the public. These include FDA approved topical medications such as Minoxidil and Finasteride which have had limited success as these agents require the conversion of dormant hair follicles into an anagen growth phase. Other remedies include hairpieces and hair weaving. The standard of practice remains surgical hair transplantation, which involves the transfer of hair plugs, strips and flaps from the hair-bearing scalp into the non hair-bearing scalp. For the most part, conventional hair transplantation involves the transfer of multiple single hair micrographs from the hair-bearing scalp to the non hair-bearing scalp of the same patient. Alternately, the donor plugs are initially harvested as hair strips and then secondarily sectioned into micrographs for transfer to the recipient scalp. Regardless, this multi-staged procedure is both tedious and expensive, involving several hours of surgery for the average patient.

The conventional hair transplantation market has been encumbered by lengthy hair grafting procedures that are performed in several stages. A typical hair grafting procedure involves the transfer of hair plugs from a donor site in the occipital scalp to a recipient site in the balding frontal-parietal scalp. For most procedures, each hair plug is transferred individually to the recipient scalp. Several hundred plugs may be transplanted during a procedure that may require several hours to perform. Post procedure "take" or viability of the transplanted hair plugs is variable due to factors that limit neovascularization at the recipient site. Bleeding and mechanical disruption due to motion are key factors that reduce neovascularization and "take" of hair grafts. Embodiments described herein include surgical instrumentation configured to transfer several hair grafts at once that are secured and aligned en masse at a recipient site on the scalp. The procedures described herein using the PAD of an embodiment reduce the tedium and time required with conventional instrumentation.

Figure 25:
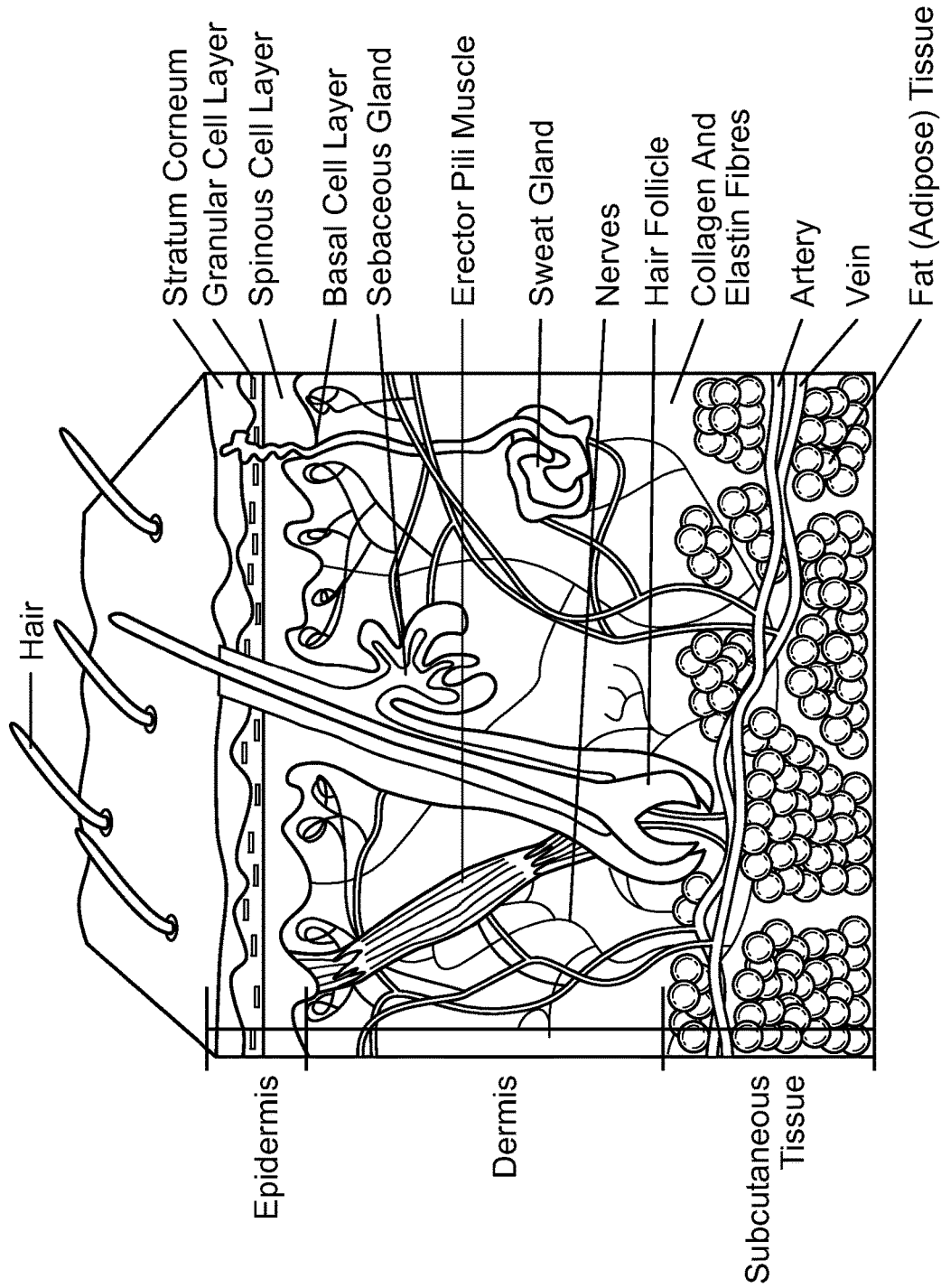
FIG. 25 shows the composition of human skin.

FIG. 25 shows the composition of human skin. Skin comprises two horizontally stratified layers, referred to as the epidermis and the dermis, acting as a biological barrier to the external environment. The epidermis is the enveloping layer and comprises a viable layer of epidermal cells that migrate upward and "mature" into a nonviable layer called the stratum corneum. The stratum corneum is a lipid-keratin composite that serves as a primary biological barrier, and this layer is continually shed and reconstituted in a process called desquamation. The dermis is the subjacent layer that is the main structural support of the skin, and is predominately extracellular and is comprised of collagen fibers.

In addition to the horizontally stratified epidermis and dermis, the skin includes vertically-aligned elements or cellular appendages including the pilosebaceous units, comprising the hair folical and sebacious gland. Pilosebaceous units each include a sebaceous oil gland and a hair follicle. The sebaceous gland is the most superficial and discharges sebum (oil) into the shaft of the hair follicle. The base of the hair follicle is called the bulb and the base of the bulb has a deep generative component called the dermal papilla. The hair follicles are typically aligned at an oblique angle to the skin surface. Hair follicles in a given region of the scalp are aligned parallel to each other. Although pilosebaceous units are common throughout the entire integument, the density and activity of these units within a region of the scalp is a key determinate as to the overall appearance of hair.

In additional to pilosebaceous units, sweat glands also course vertically through the skin. They provide a water-based transudate that assists in thermoregulation. Apocrine sweat glands in the axilla and groin express a more pungent sweat that is responsible for body odor. For the rest of the body, eccrine sweat glands excrete a less pungent sweat for thermoregulation.

Figure 26:
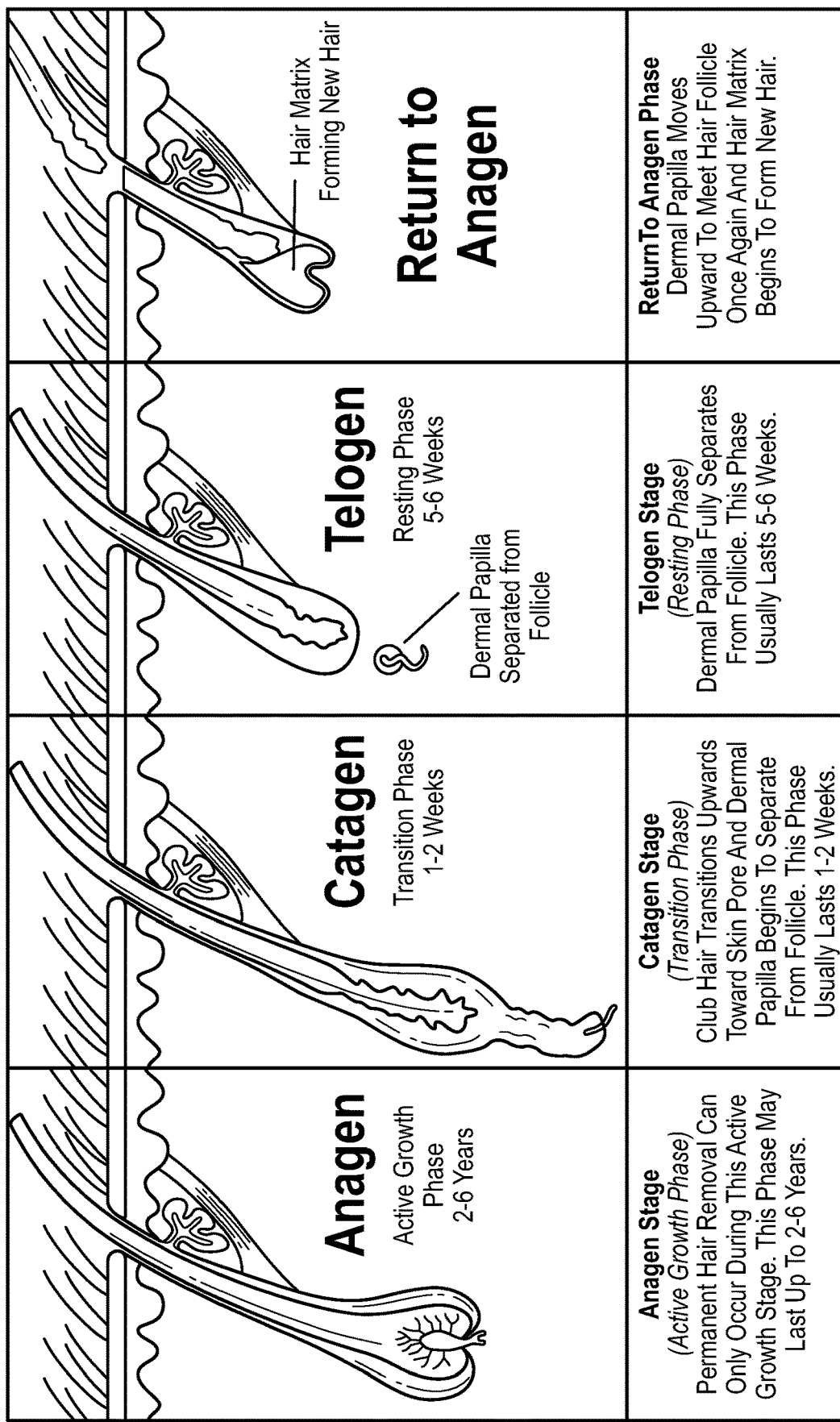
FIG. 26 shows the physiological cycles of hair growth.

Hair follicles proceed through different physiological cycles of hair growth. FIG. 26 shows the physiological cycles of hair growth. The presence of testosterone in a genetically-prone man will produce alopecia to a variable degree in the frontal-parietal scalp. Essentially, the follicle becomes dormant by entering the telogen phase without return to the anagen phase. Male Pattern Baldness occurs when the hair fails to return from the telogen phase to the anagen phase.

The PAD of an embodiment is configured for en-masse harvesting of hair-bearing plugs with en-masse transplantation of hair bearing plugs into non hair-bearing scalp, which truncates conventional surgical procedures of hair transplantation. Generally, the devices, systems and/or methods of an embodiment are used to harvest and align a large multiplicity of small hair bearing plugs in a single surgical step or process, and the same instrumentation is used to prepare the recipient site by performing a multiple pixelated resection of non hair-bearing scalp. The multiple hair-plug graft is transferred and transplanted en-masse to the prepared recipient site. Consequently, through use of an abbreviated procedure, hundreds of hair bearing plugs can be transferred from a donor site to a recipient site. Hair transplantation using the embodiments described herein therefore provides a solution that is a single surgical procedure having ease, simplicity and significant time reduction over the tedious and multiple staged conventional process.

Hair transplantation using the pixel dermatome of an embodiment facilitates improvements in the conventional standard follicular unit extraction (FUT) hair transplant approach. Generally, under the procedure of an embodiment hair follicles to be harvested are taken from the Occipital scalp of the donor. In so doing, the donor site hair is partially shaved, and the perforated plate of an embodiment is located on the scalp and oriented to provide a maximum harvest. FIG. 27 shows harvesting of donor follicles, under an embodiment. The scalpets in the scalpet array are configured to penetrate down to the subcutaneous fat later to capture the hair follicle. Once the hair plugs are incised, they are harvested onto an adhesive membrane by transecting the base of the hair plug with the transection blade, as described in detail herein. Original alignment of the hair plugs with respect to each other at the donor site is maintained by applying the adherent membrane before transecting the base. The aligned matrix of hair plugs on the adherent membrane will then be grafted en masse to a recipient site on the frontal-parietal scalp of the recipient.

FIG. 28 shows preparation of the recipient site, under an embodiment. The recipient site is prepared by resection of non-hair bearing skin plugs in a topographically identical pattern as the harvested occipital scalp donor site. The recipient site is prepared for the mass transplant of the hair plugs using the same instrumentation that was used at the donor site under an embodiment and, in so doing, scalp defects are created at the recipient site. The scalp defects created at the recipient site have the same geometry as the harvested plugs on the adherent membrane.

Figure 29:
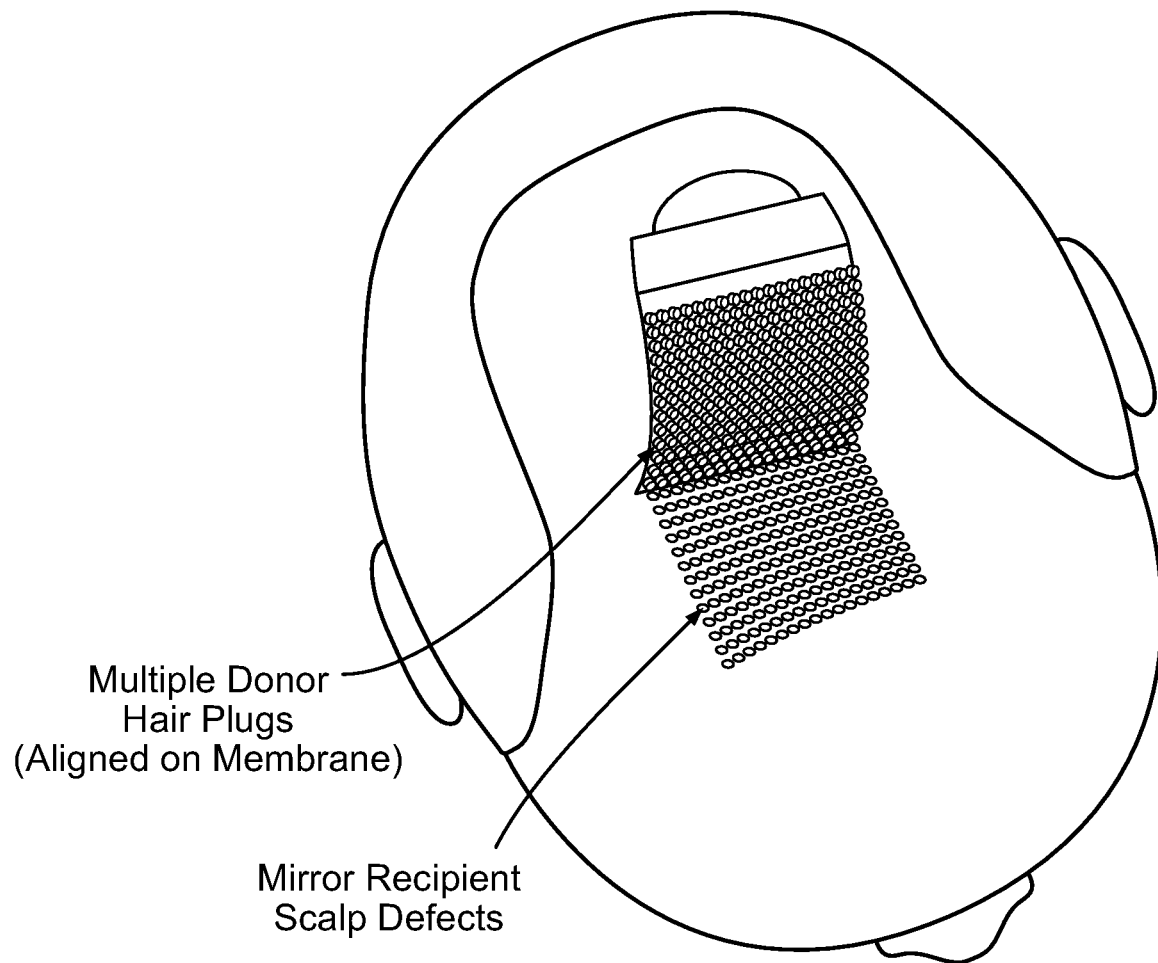
FIG. 29 shows placement of the harvested hair plugs at the recipient site, under an embodiment.

The adherent membrane laden with the harvested hair plugs is applied over the same pattern of scalp defects at the recipient site. Row-by-row, each hair-bearing plug is inserted into its mirror image recipient defect. FIG. 29 shows placement of the harvested hair plugs at the recipient site, under an embodiment. Plug-to-plug alignment is maintained, so the hair that grows from the transplanted hair plugs lays as naturally as it did at the donor site. More uniform alignment between the native scalp and the transplanted hair will also occur.

Figure 30:
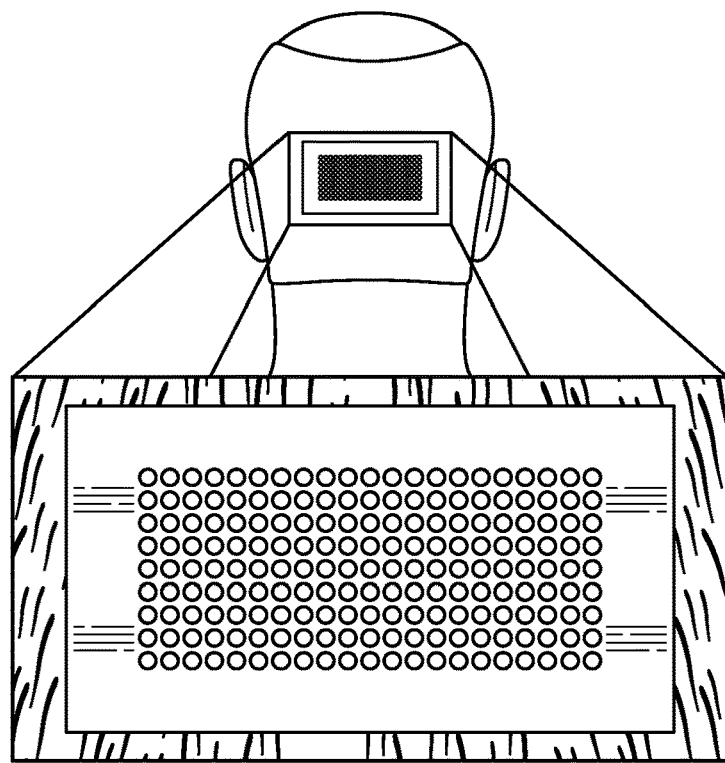
FIG. 30 shows placement of the perforated plate on the occipital scalp donor site, under an embodiment.

More particularly, the donor site hair is partially shaved to prepare for location or placement of the perforated plate on the scalp. The perforated plate is positioned on the occipital scalp donor site to provide a maximum harvest. FIG. 30 shows placement of the perforated plate on the occipital scalp donor site, under an embodiment. Mass harvesting of hair plugs is achieved using the spring-loaded pixilation device comprising the impact punch hand-piece with a scalpet disposable tip. An embodiment is configured for harvesting of individual hair plugs using off-the-shelf FUE extraction devices or biopsy punches; the holes in the perforated plates supplied are sized to accommodate off-the-shelf technology.

Figure 31:
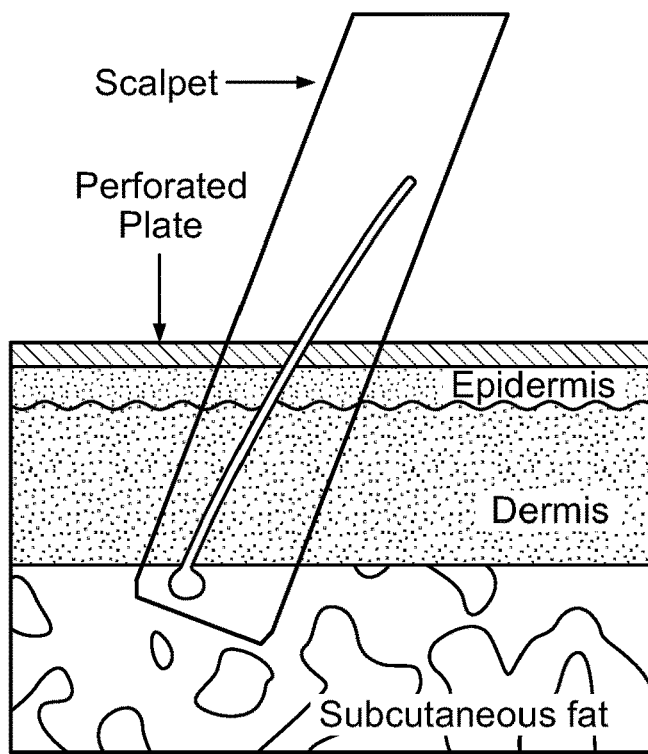
FIG. 31 shows scalpet penetration depth through skin when the scalpet is configured to penetrate to the subcutaneous fat layer to capture the hair follicle, under an embodiment.
Figure 32:
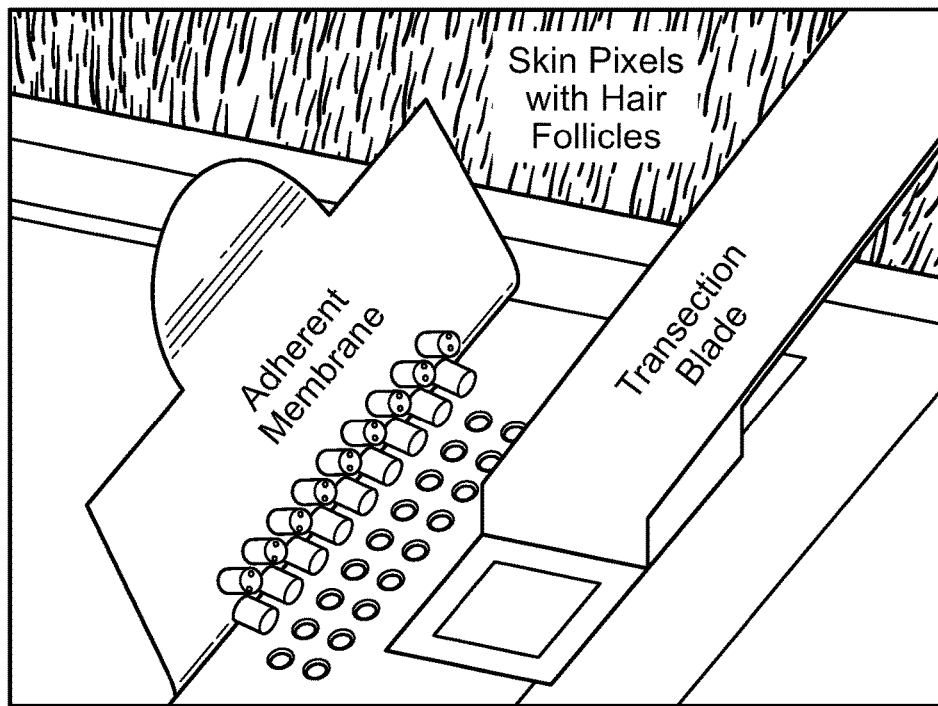
FIG. 32 shows hair plug harvesting using the perforated plate at the occipital donor site, under an embodiment.

The scalpets comprising the scalpet array disposable tip are configured to penetrate down to the subcutaneous fat later to capture the hair follicle. FIG. 31 shows scalpet penetration depth through skin when the scalpet is configured to penetrate to the subcutaneous fat layer to capture the hair follicle, under an embodiment. Once the hair plugs are incised, they are harvested onto an adhesive membrane by transecting the base of the hair plug with the transection blade, but are not so limited. FIG. 32 shows hair plug harvesting using the perforated plate at the occipital donor site, under an embodiment. The original alignment of the hair plugs with respect to each other is maintained by applying an adherent membrane of an embodiment. The adherent membrane is applied before transecting the base of the resected pixels, the embodiments are not so limited. The aligned matrix of hair plugs on the adherent membrane is subsequently grafted en masse to a recipient site on the frontal-parietal scalp.

Figure 33:
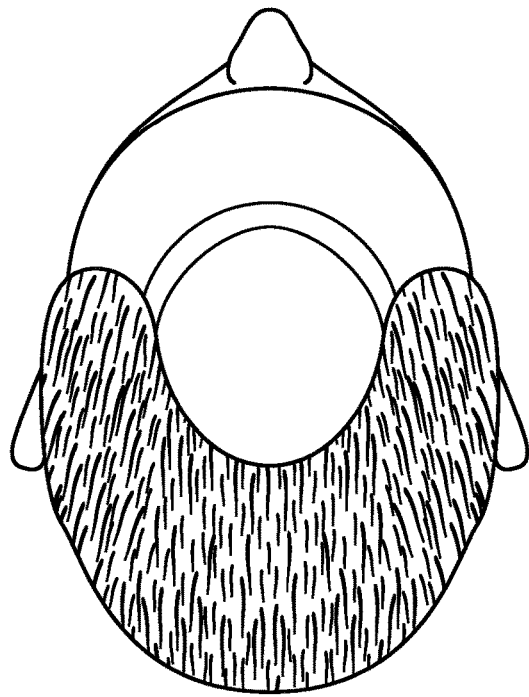
FIG. 33 shows creation of the visible hairline, under an embodiment.

Additional single hair plugs may be harvested through the perforated plate, to be used to create the visible hairline, for example. FIG. 33 shows creation of the visible hairline, under an embodiment. The visible hairline is determined and developed with a manual FUT technique. The visible hairline and the mass transplant of the vertex may be performed concurrently or as separate stages. If the visible hairline and mass transplant are performed concurrently, the recipient site is developed starting with the visible hairline.

Figure 34:
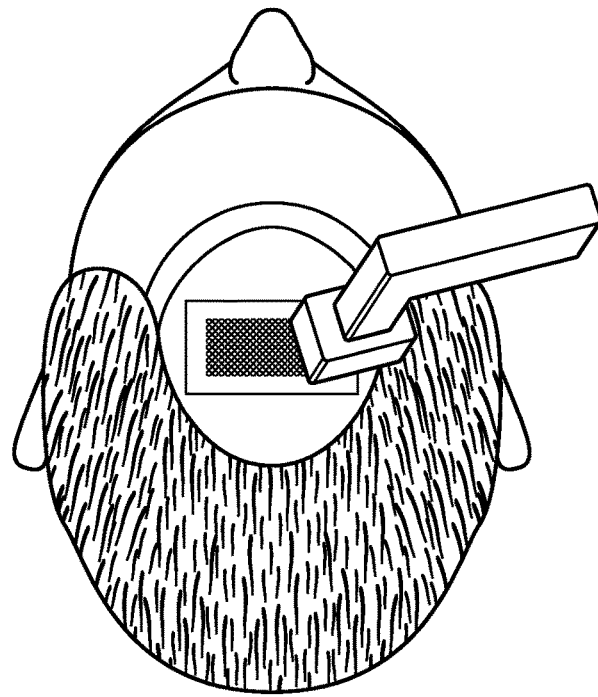
FIG. 34 shows preparation of the donor site using the patterned perforated plate and spring-loaded pixilation device to create identical skin defects at the recipient site, under an embodiment.

Transplantation of harvested hair plugs comprises preparing the recipient site is prepared by resecting non-hair bearing skin plugs in a topographically identical pattern as the pattern of the harvested occipital scalp donor site. FIG. 34 shows preparation of the donor site using the patterned perforated plate and spring-loaded pixilation device to create identical skin defects at the recipient site, under an embodiment. The recipient site of an embodiment is prepared for the mass transplant of the hair plugs using the same perforated plate and spring-loaded pixilation device that was used at the donor site. Scalp defects are created at the recipient site. These scalp defects have the same geometry as the harvested plugs on the adherent membrane.

Figure 35:
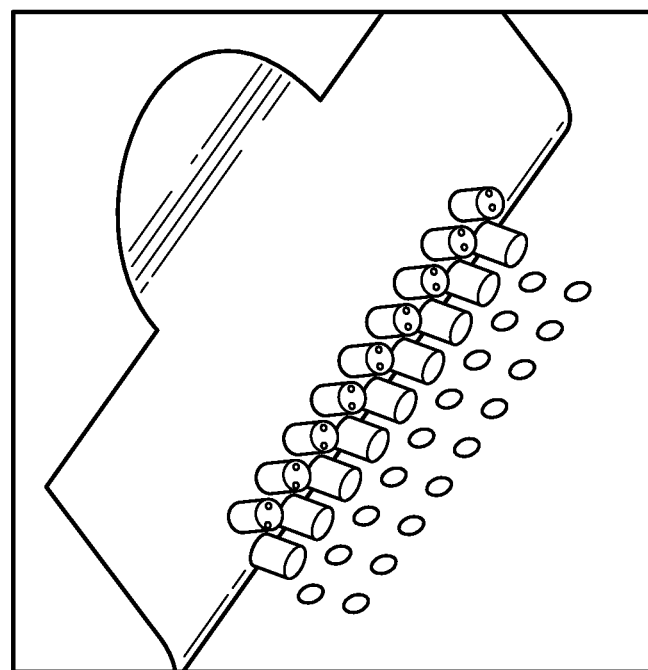
FIG. 35 shows transplantation of harvested plugs by inserting harvested plugs into a corresponding skin defect created at the recipient site, under an embodiment.

The adherent membrane carrying the harvested hair plugs is applied over the same pattern of scalp defects at recipient site. Row-by-row each follicle-bearing or hair-bearing skin plug is inserted into its mirror image recipient defect. FIG. 35 shows transplantation of harvested plugs by inserting harvested plugs into a corresponding skin defect created at the recipient site, under an embodiment. Plug-to-plug alignment is maintained, so the hair that grows from the transplanted hair plugs lays as naturally as it did at the donor site. More uniform alignment between the native scalp and the transplanted hair will also occur.

Figure 36:
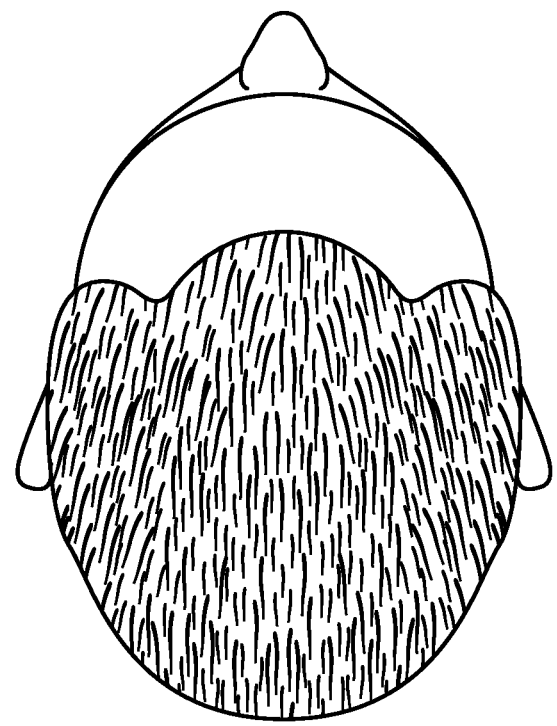
FIG. 36 shows a clinical end point using the pixel dermatome instrumentation and procedure, under an embodiment.

Clinical endpoints vary from patient to patient, but it is predicted that a higher percentage of hair plugs will "take" as a result of improved neovascularization. FIG. 36 shows a clinical end point using the pixel dermatome instrumentation and procedure, under an embodiment. The combination of better "takes", shorter procedure times, and a more natural-looking result, enable the pixel dermatome instrumentation and procedure of an embodiment to overcome the deficiencies in conventional hair transplant approaches.

Embodiments of pixelated skin grafting for skin defects and pixelated skin resection for skin laxity are described in detail herein. These embodiments remove a field of skin pixels in an area of lax skin where skin tightening is desired. The skin defects created by this procedure (e.g., in a range of approximately 1.5-3 mm-diameter) are small enough to heal per primam without visible scarring; the wound closure of the multiple skin defects is performed directionally to produce a desired contouring effect. Live animal testing of the pixel resection procedure has produced excellent results.

The pixel procedure of an embodiment is performed in an office setting under a local anesthetic but is not so limited. The surgeon uses the instrumentation of an embodiment to rapidly resect an array of skin pixels (e.g., circular, elliptical, square, etc.). Relatively little pain is associated with the procedure. The intradermal skin defects generated during the procedure are closed with the application of an adherent Flexan (3M) sheet, but embodiments are not so limited. Functioning as a large butterfly bandage, the Flexan sheet is pulled in a direction that maximizes the aesthetic contouring of the treatment area. A compressive elastic garment is then applied over the dressing to assist aesthetic contouring.

During recovery, the patient wears a support garment over the treatment area for a period of time (e.g., 5 days, etc.). After initial healing, the multiplicity of small linear scars within the treatment area is not visibly apparent. Additional skin tightening will occur subsequently over several months from the delayed wound healing response. Consequently, the pixel procedure is a minimally invasive alternative for skin tightening in areas where the extensive scarring of traditional aesthetic plastic surgery is to be avoided.

The pixel procedure evokes cellular and extracellular responses that are obligatory to the clinical outcomes achieved. A physical reduction of the skin surface area occurs due to the fractional resection of skin, which physically removes a portion of skin directly in the area of laxity. In addition, a subsequent tightening of the skin is realized from the delayed wound healing response. Each pixilated resection initiates an obligate wound healing sequence. The healing response effected in an embodiment comprises three phases, as previously described in detail herein.

The first phase of this sequence is the inflammatory phase in which degranulation of mast cells releases histamine into the "wound". Histamine release evokes dilatation of the capillary bed and increases vessel permeability into the extracellular space. This initial wound healing response occurs within the first day and will be evident as erythema on the skin's surface.

Within days of "wounding", the second phase of healing, fibroplasia, commences. During fibroplasia, there is migration and mitotic multiplication of fibroblasts. Fibroplasia has two key features: the deposition of neocollagen and the myofibroblastic contraction of the wound. Histologically, the deposition of neocollagen is identified microscopically as compaction and thickening of the dermis. Although this is a static process, the tensile strength of the skin significantly increases. Myofibroblastic contraction is a dynamic physical process that results in two-dimensional tightening of the skin surface. This process is due to the active cellular contraction of myofibroblasts and the deposition of contractile proteins within the extracellular matrix. Overall, the effect of fibroplasia will be dermal contraction and the deposition of a static supporting scaffolding of neocollagen with a tightened framework. The clinical effect is realized as a delayed tightening of skin with smoothing of skin texture over some number of months. The clinical endpoint is a more youthful appearing skin envelope of the treatment area.

A third and final phase of the delayed wound healing response is maturation. During maturation, there is a strengthening and remodeling of the treatment area due to increased cross-linkage of the collagen fibril matrix (of the dermis). This final stage commences within 6 to 12 months after "wounding" and may extend for at least 1-2 years. Small pixilated resections of skin should preserve the normal dermal architecture during maturation, but without the creation of a visually evident scar that typically occurs with a larger surgical resection of skin. Lastly, there is a related stimulation and rejuvenation of the epidermis from the release of epidermal growth hormone.

Figure 38:
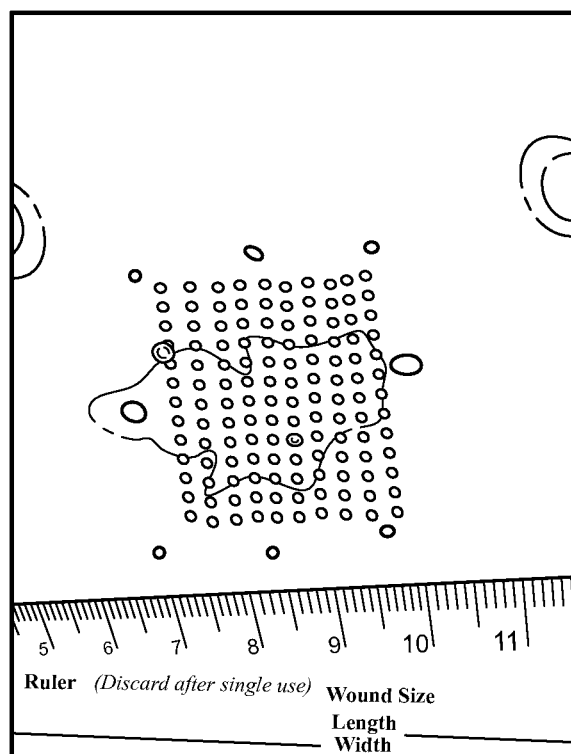
FIG. 38 is an image of the post-operative skin resection field, under an embodiment.
Figure 37:
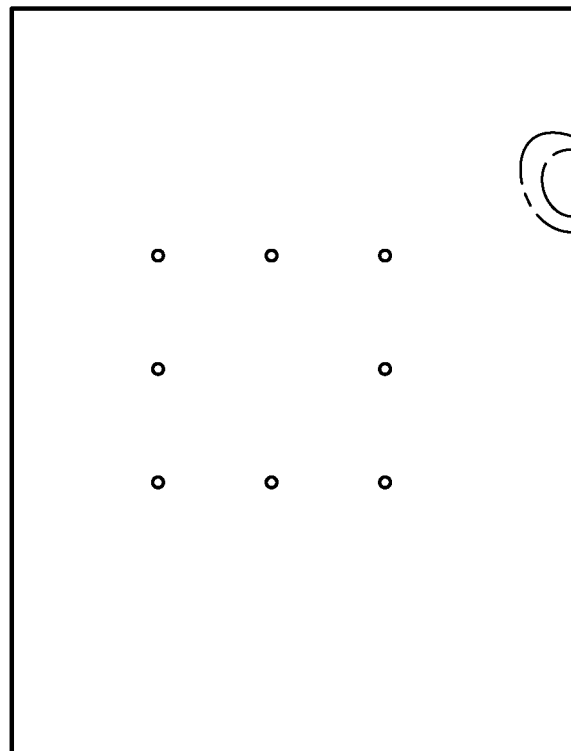
FIG. 37 is an image of the skin tattooed at the corners and midpoints of the area to be resected, under an embodiment.

FIGS. 37-42 show images resulting from a pixel procedure conducted on a live animal, under an embodiment. Embodiments described herein were used in this proof-of-concept study in an animal model that verified the pixel procedure produces aesthetic skin tightening without visible scarring. The study used a live porcine model, anesthetized for the procedure. FIG. 37 is an image of the skin tattooed at the corners and midpoints of the area to be resected, under an embodiment. The field margins of resection were demarcated with a tattoo for post-operative assessment, but embodiments are not so limited. The procedure was performed using a perforated plate (e.g., 10×10 pixel array) to designate the area for fractional resection. The fractional resection was performed using biopsy punches (e.g., 1.5 mm diameter). FIG. 38 is an image of the post-operative skin resection field, under an embodiment. Following the pixel resection, the pixelated resection defects were closed (horizontally) with Flexan membrane.

Figure 40:
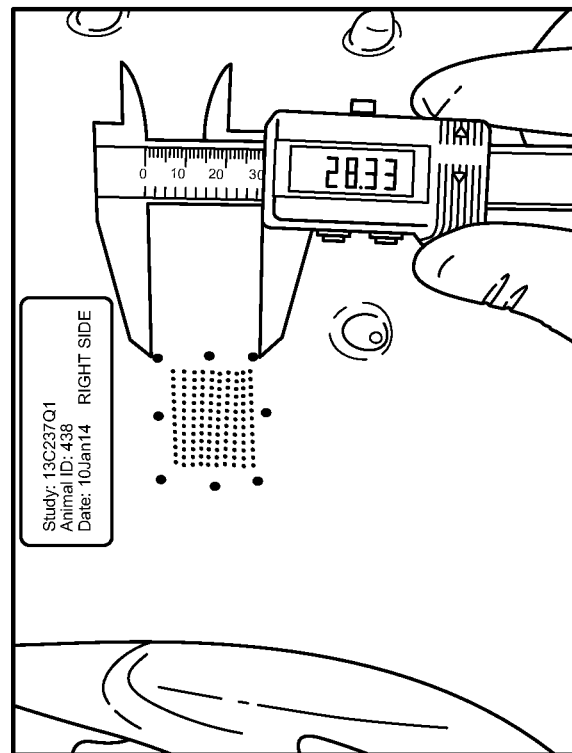
FIG. 40 is an image at 29 days following the procedure showing resections healed per primam and maturation of the resection field continuing per primam, with measured margins, under an embodiment.
Figure 39:
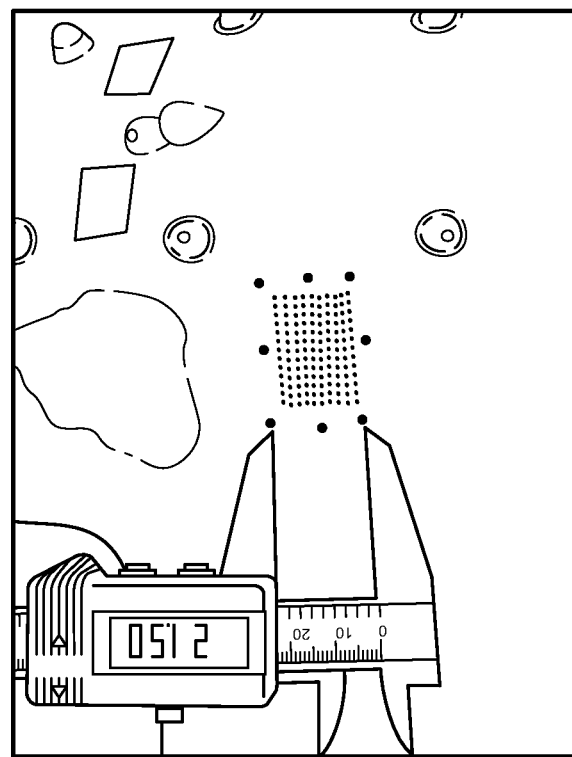
FIG. 39 is an image at 11 days following the procedure showing resections healed per primam, with measured margins, under an embodiment.
Figure 42:
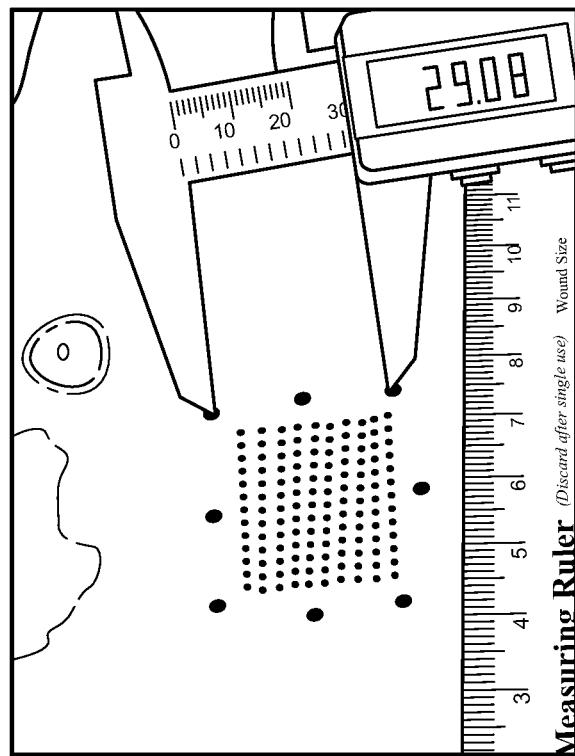
FIG. 42 is an image at 90 days post-operative showing resections healed per primam and maturation of the resection field continuing per primam, with measured lateral dimensions, under an embodiment.
Figure 41:
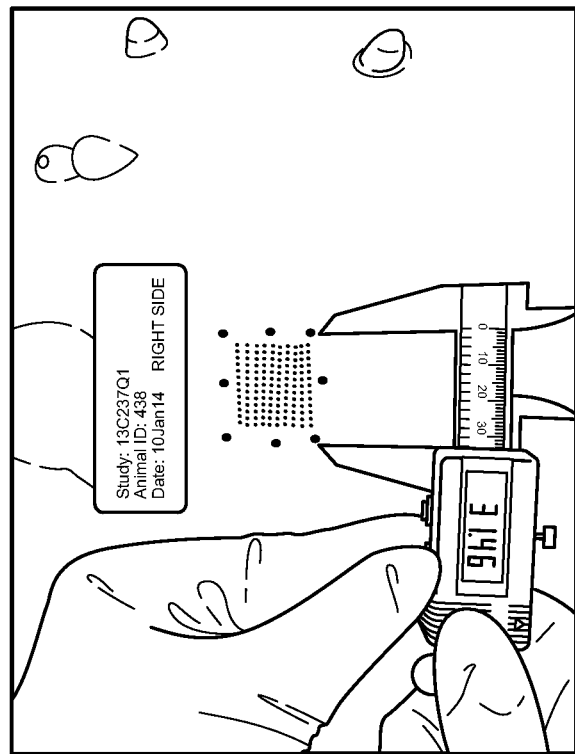
FIG. 41 is an image at 29 days following the procedure showing resections healed per primam and maturation of the resection field continuing per primam, with measured lateral dimensions, under an embodiment.

Eleven days following the procedure, all resections had healed per primam in the area designated by the tattoo, and photographic and dimensional measurements were made. FIG. 39 is an image at 11 days following the procedure showing resections healed per primam, with measured margins, under an embodiment. Photographic and dimensional measurements were subsequently made 29 days following the procedure. FIG. 40 is an image at 29 days following the procedure showing resections healed per primam and maturation of the resection field continuing per primam, with measured margins, under an embodiment. FIG. 41 is an image at 29 days following the procedure showing resections healed per primam and maturation of the resection field continuing per primam, with measured lateral dimensions, under an embodiment. Photographic and dimensional measurements were repeated 90 days post-operative, and the test area skin was completely smooth to touch. FIG. 42 is an image at 90 days post-operative showing resections healed per primam and maturation of the resection field continuing per primam, with measured lateral dimensions, under an embodiment.

Fractional resection as described herein is performed intradermally or through the entire thickness of the dermis. The ability to incise skin with a scalpet (e.g., round, square, elliptical, etc.) is enhanced with the addition of additional force(s). The additional force includes force applied to the scalpet or scalpet array, for example, where the force comprises one or more of rotational force, kinetic impact force, and vibrational force, all of which are described in detail herein for skin fractional resection.

The scalpet device of an embodiment generally includes a scalpet assembly and a housing. The scalpet assembly includes a scalpet array, which comprises a number of scalpets, and force or drive components. The scalpet assembly includes one or more alignment plates configured to retain and position the scalpets precisely according to the configuration of the scalpet array, and to transmit force (e.g., z-axis) from the operator to the subject tissue targeted for resection. The scalpet assembly includes spacers configured to retain alignment plates at a fixed distance apart and coaxial with the scalpet array, but is not so limited.

A shell is configured to retain the spacers and the alignment plates, and includes attachment point(s) for the housing and drive shaft. The alignment plates and/or the spacers are attached or connected (e.g., snapped, welded (e.g., ultrasonic, laser, etc.), heat-staked, etc.) into position in the shell, thereby providing a rigid assembly and discourages tampering or re-purposing of the scalpet array. Additionally, the shell protects the drive mechanism or gearing and scalpets from contamination during use and allows lubrication (if required) to be applied to the gearing to reduce the torque requirement and increase the life of the gears.

As an example of the application of force using the embodiments herein, the ability to incise skin with a circular scalpet is enhanced with the addition of a rotational torque. The downward axial force used to incise the skin is significantly reduced when applied in combination with a rotational force. This enhanced capability is similar to a surgeon incising skin with a standard scalpel where the surgeon uses a combination of movement across the skin (kinetic energy) with the simultaneous application of compression (axial force) to more effectively cut the skin surface.

For piercing the skin, the amount of surface compression required is significantly reduced if a vertical kinetic force is employed simultaneously. For example, a dart throwing technique for injections has previously been used by healthcare providers for piercing skin. An "impactor" action imparted on skin by a circular scalpet of an embodiment enhances this modality's cutting capability by simultaneously employing axial compressive and axial kinetic forces. The axial compressive force used to incise the skin surface is significantly reduced if applied in combination with kinetic force.

Conventional biopsy punches are intended for a single use application in the removal of tissue, which is generally achieved by pushing the punch directly into the tissue along its central axis. Similarly, the fractional resection of an embodiment uses scalpets comprising a circular configuration. While the scalpets of an embodiment can be used in a stand-alone configuration, alternative embodiments include scalpet arrays in which scalpets are bundled together in arrays of various sizes configured to remove sections of skin, but are not so limited. The force used to pierce the skin using the fractional resection scalpet is a function of the number of scalpets in the array, so that as the array size increases the force used to pierce the skin increases.

Figure 43:
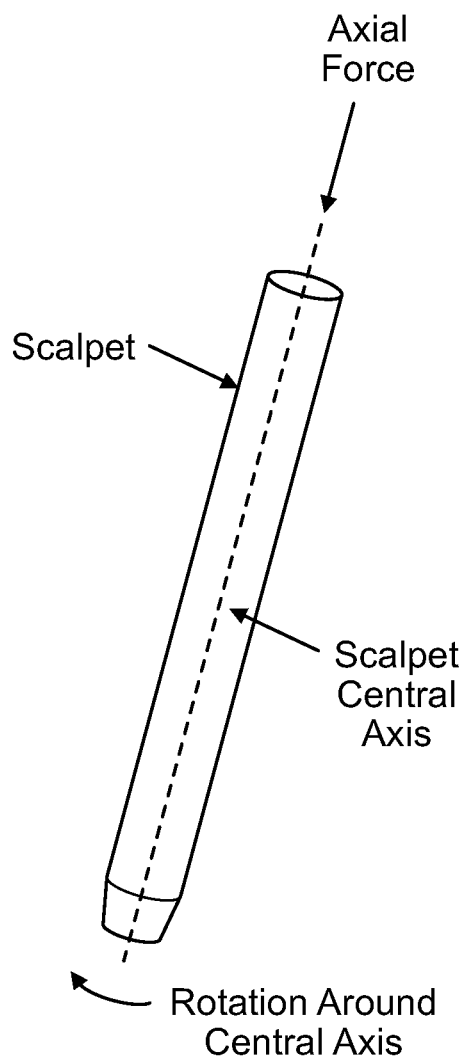
FIG. 43 is a scalpet showing the applied rotational and/or impact forces, under an embodiment.

The ability to incise skin with a circular scalpet is significantly enhanced with a reduction in the force needed to pierce the skin introduced through the addition of a rotational motion around its central axis and/or an impact force along its central axis. FIG. 43 is a scalpet showing the applied rotational and/or impact forces, under an embodiment. This enhanced rotational configuration has an affect similar to a surgeon incising skin with a standard scalpel where the surgeon uses a combination of movement across the skin (kinetic energy) with the simultaneous application of compression (axial force) to more effectively cut the skin surface. The impact force is similar to the use of a staple gun or by quickly moving a hypodermic needle prior to impacting the skin.

A consideration in the configuration of the scalpet rotation is the amount of torque used to drive multiple scalpets at a preferred speed, because the physical size and power of the system used to drive the scalpet array increases as the required torque increases. To reduce the incisional force required in a scalpet array, rows or columns or segments of the array may be individually driven or sequentially driven during an array application. Approaches for rotating the scalpets include but are not limited to geared, helical, slotted, inner helical, pin driven, and frictional (elastomeric).

The scalpet array configured for fractional resection using combined rotation and axial incision uses one or more device configurations for rotation. For example, the scalpet array of the device is configured to rotate using one or more of geared, external helical, inner helical, slotted, and pin drive rotating or oscillating mechanisms, but is not so limited. Each of the rotation mechanisms used in various embodiments is described in detail herein.

Figure 44:
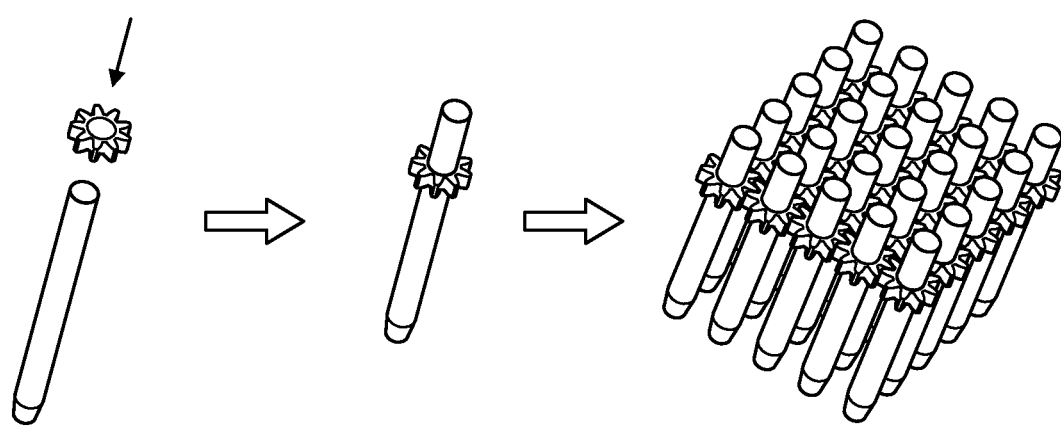
FIG. 44 shows a geared scalpet and an array including geared scalpets, under an embodiment.
Figure 45:
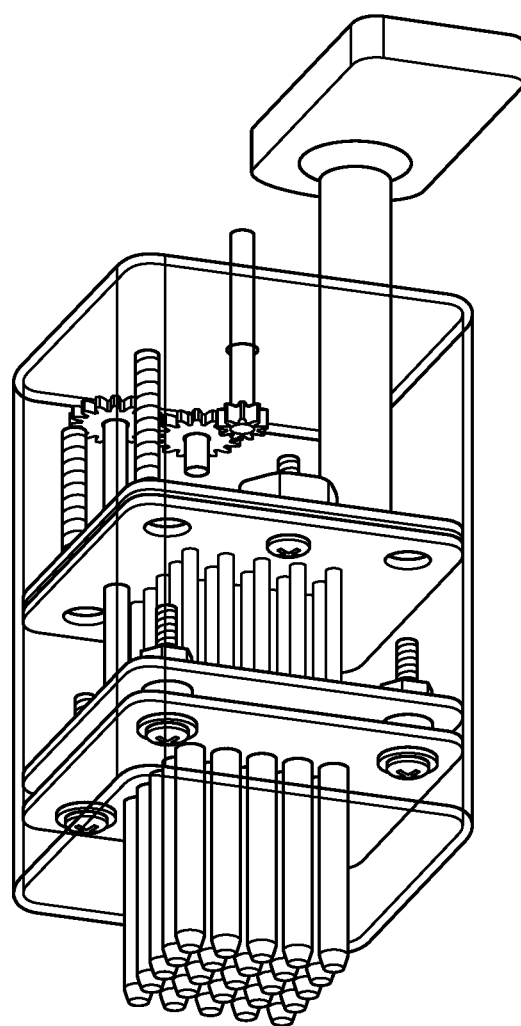
FIG. 45 is a bottom perspective view of a resection device including the scalpet assembly with geared scalpet array, under an embodiment.
Figure 46:
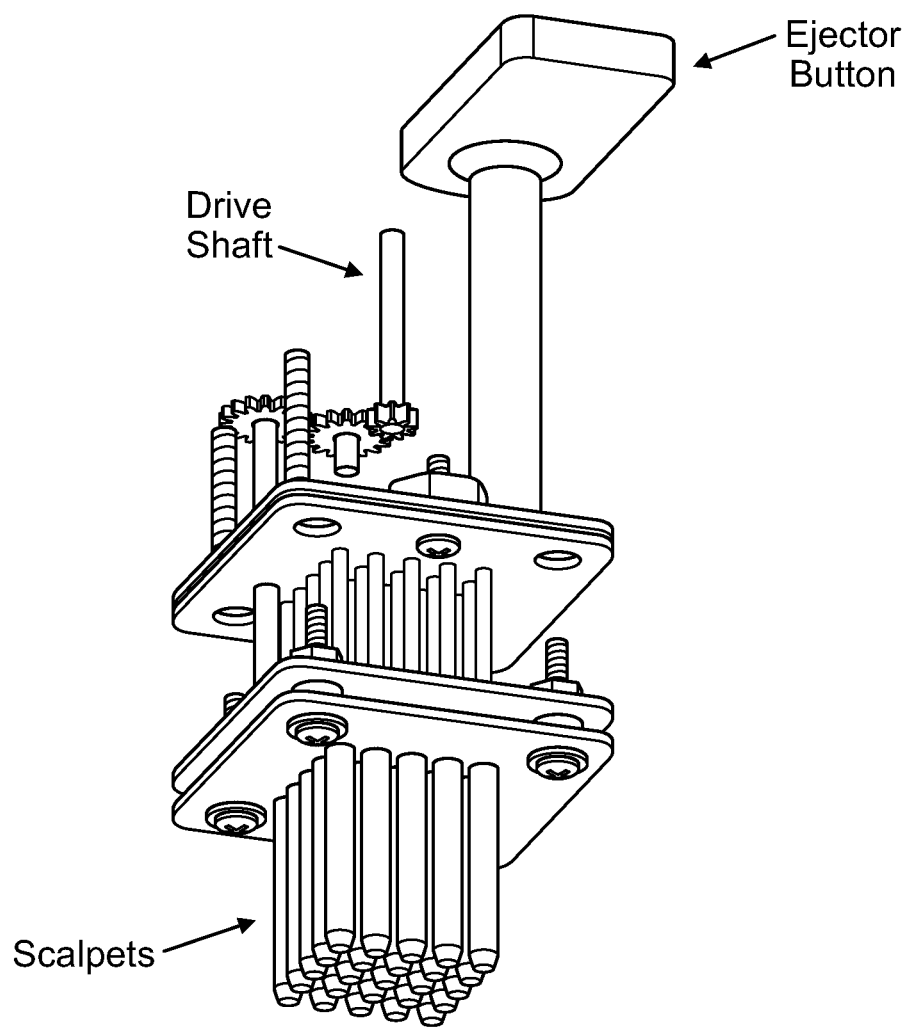
FIG. 46 is a bottom perspective view of the scalpet assembly with geared scalpet array (housing not shown), under an embodiment.
Figure 47:
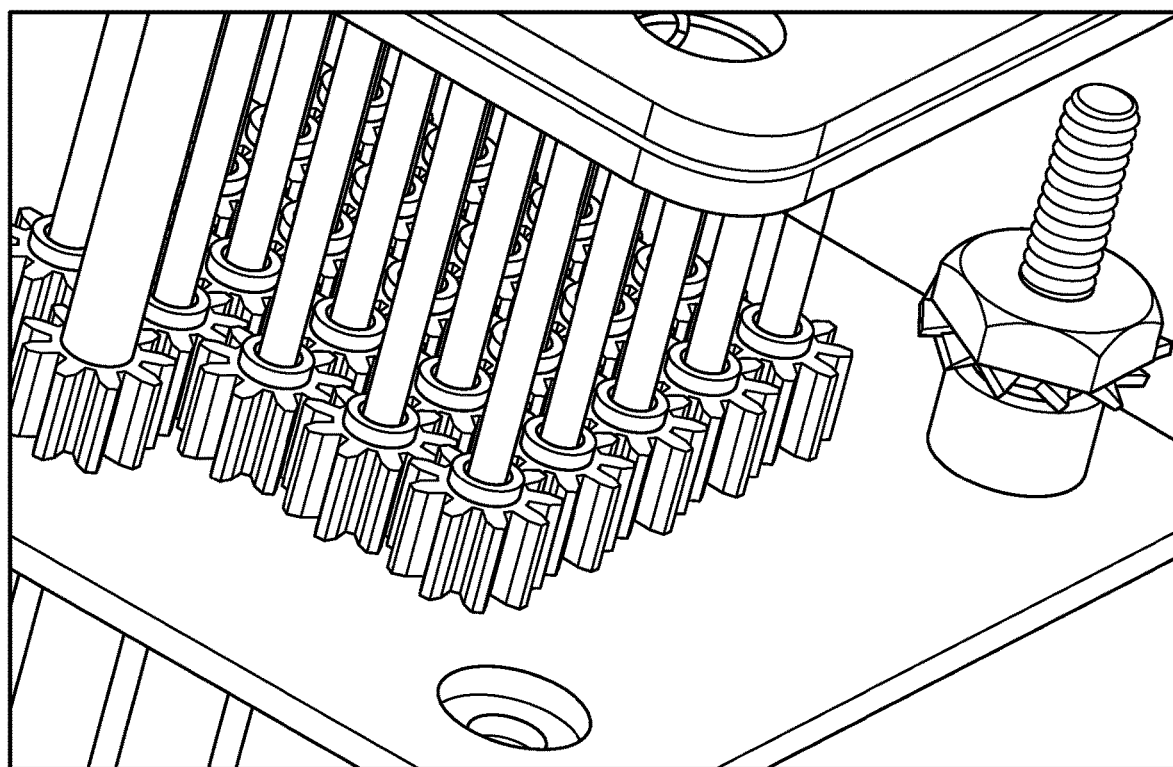
FIG. 47 is a detailed view of the geared scalpet array, under an embodiment.

FIG. 44 shows a geared scalpet and an array including geared scalpets, under an embodiment. FIG. 45 is a bottom perspective view of a resection device including the scalpet assembly with geared scalpet array, under an embodiment. The device comprises a housing (depicted as transparent for clarity of details) configured to include the geared scalpet array for the application of rotational torque for scalpet rotation. FIG. 46 is a bottom perspective view of the scalpet assembly with geared scalpet array (housing not shown), under an embodiment. FIG. 47 is a detailed view of the geared scalpet array, under an embodiment.

The geared scalpet array includes a number of scalpets as appropriate to a resection procedure in which the array is used, and a gear is coupled or connected to each scalpet. For example, the gear is fitted over or around a scalpet, but the embodiment is not so limited. The geared scalpets are configured as a unit or array so that each scalpet rotates in unison with adjacent scalpets. For example, once fit, the geared scalpets are installed together in alignment plates so that each scalpet engages and rotates in unison with its adjacent four scalpets and is thereby retained in precise alignment. The geared scalpet array is driven by at least one rotating external shaft carrying a gear at the distal end, but is not so limited. The rotational shaft(s) is configured to provide or transmit the axial force, which compresses the scalpets of the array into the skin during incision. Alternatively, axial force may be applied to the plates retaining the scalpets.

Figure 48:
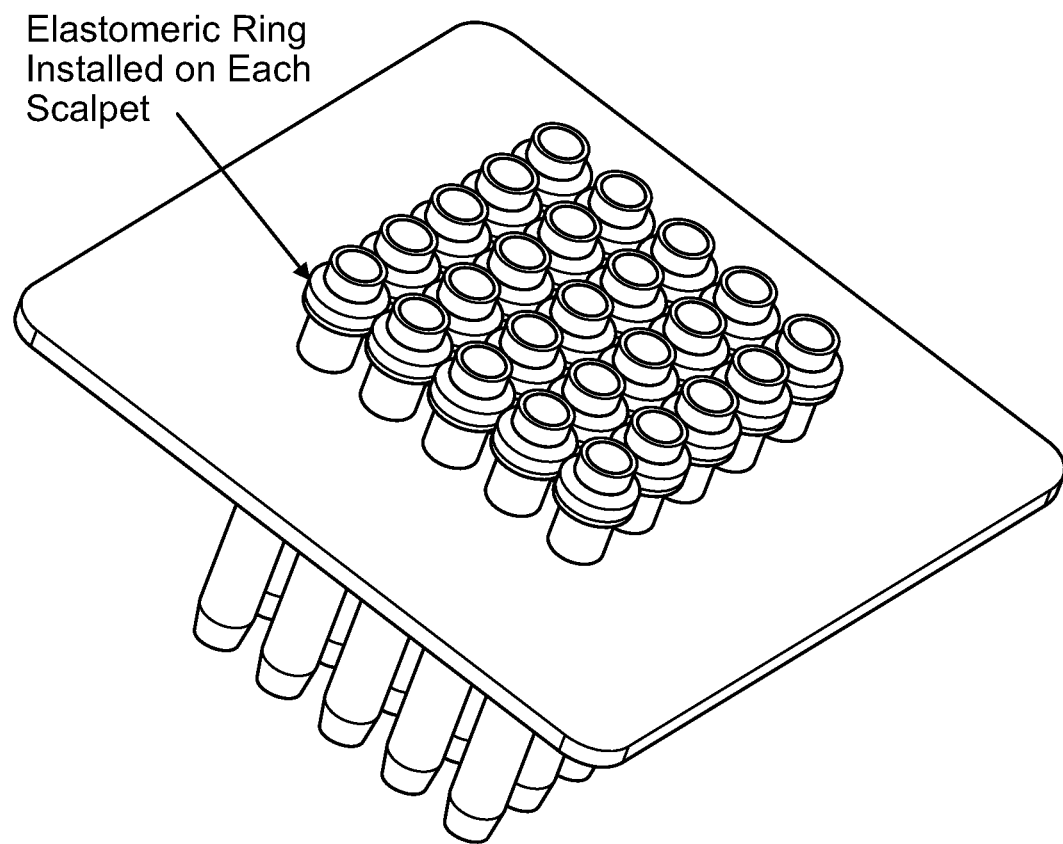
FIG. 48 shows an array including scalpets in a frictional drive configuration, under an embodiment.

In an alternative embodiment, a frictional drive is used to drive or rotate the scalpets of the arrays. FIG. 48 shows an array including scalpets in a frictional drive configuration, under an embodiment. The frictional drive configuration includes an elastomeric ring around each scalpet, similar to gear placement in the geared embodiment, and frictional forces between the rings of adjacent scalpets in compression results in rotation of the scalpets similar to the geared array.

Figure 49:
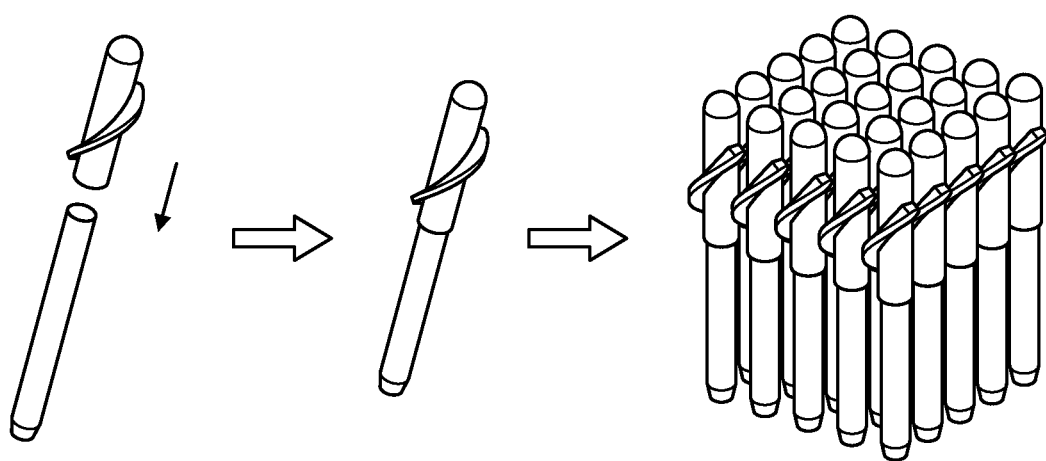
FIG. 49 shows a helical scalpet (external) and an array including helical scalpets (external), under an embodiment.
Figure 50:
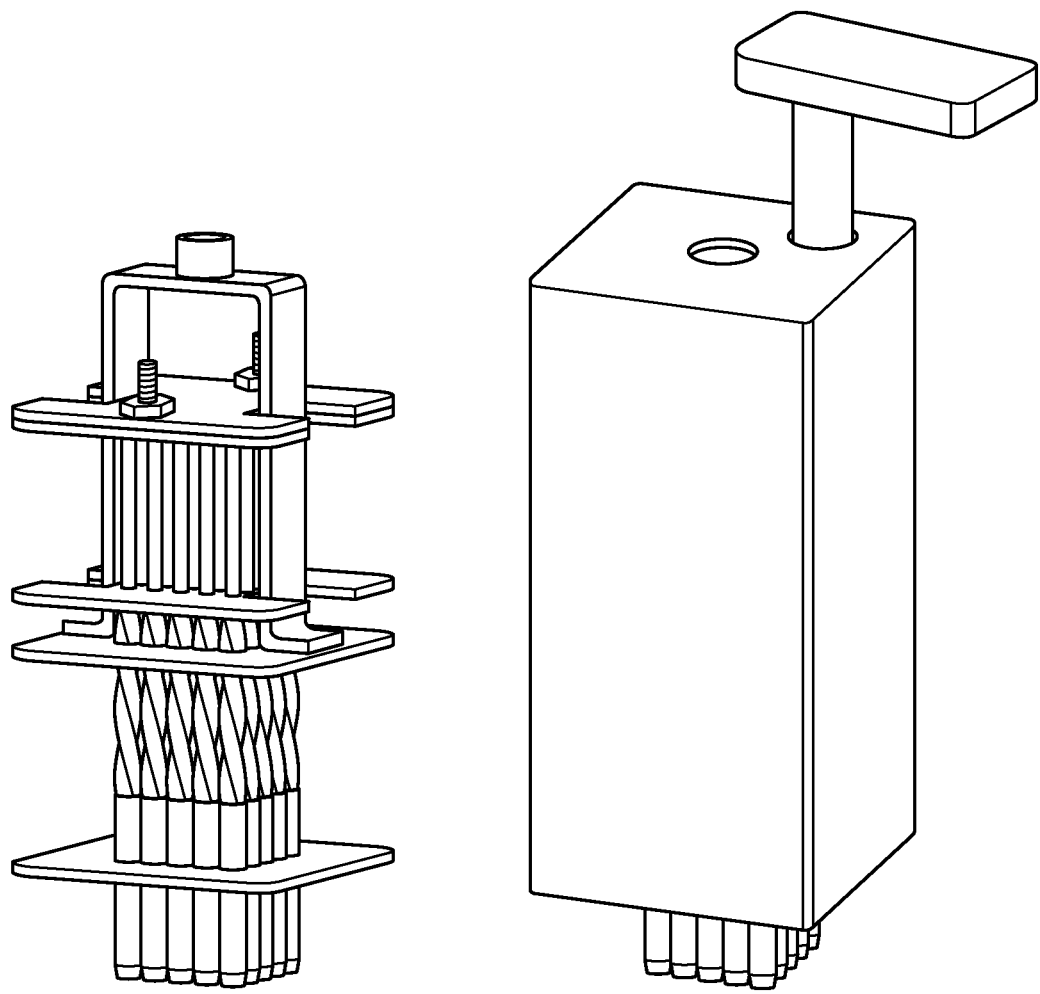
FIG. 50 shows side perspective views of a scalpet assembly including a helical scalpet array (left), and the resection device including the scalpet assembly with helical scalpet array (right) (housing shown), under an embodiment.
Figure 51:
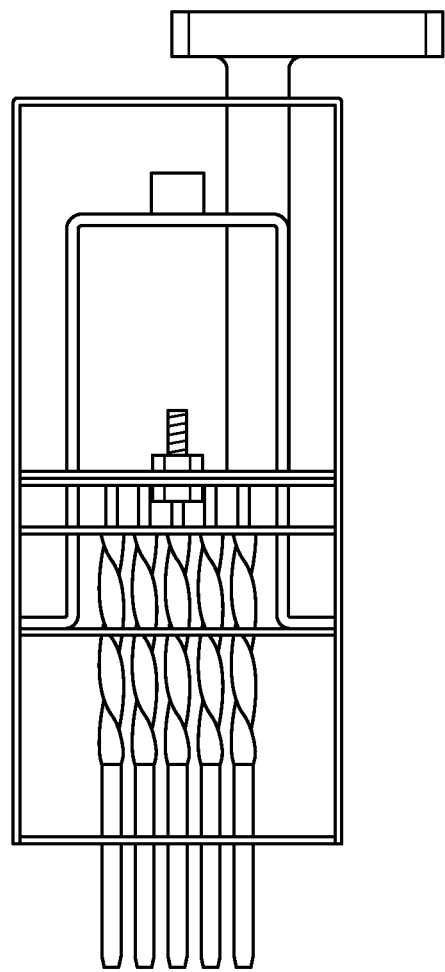
FIG. 51 is a side view of a resection device including the scalpet assembly with helical scalpet array assembly (housing depicted as transparent for clarity of details), under an embodiment.
Figure 52:
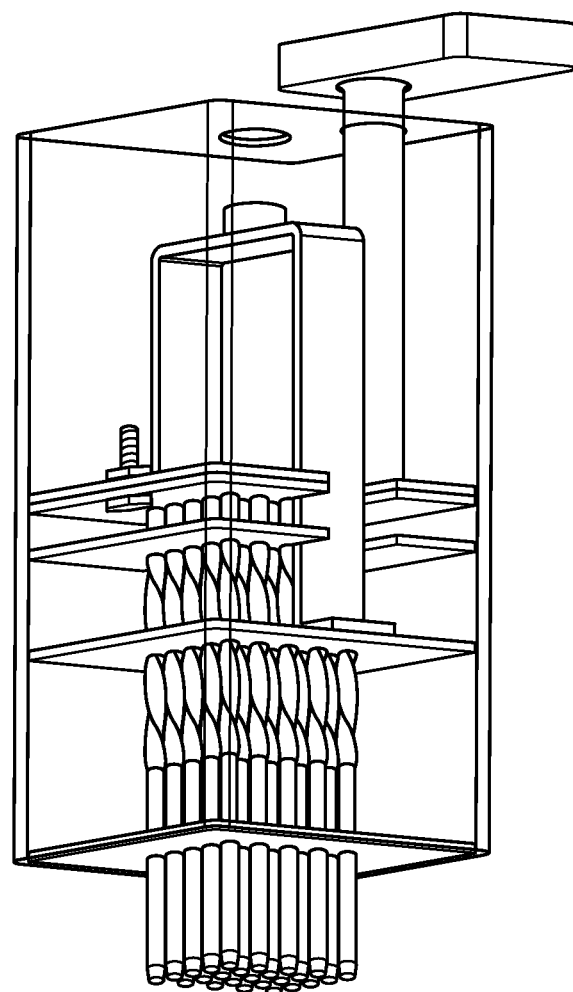
FIG. 52 is a bottom perspective view of a resection device including the scalpet assembly with helical scalpet array assembly (housing depicted as transparent for clarity of details), under an embodiment.
Figure 53:
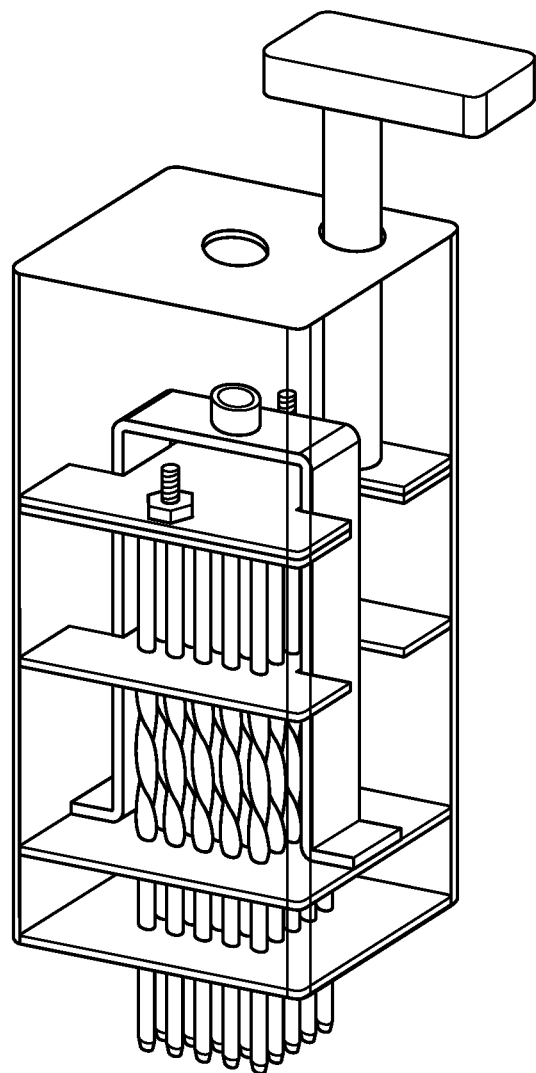
FIG. 53 is a top perspective view of a resection device including the scalpet assembly with helical scalpet array assembly (housing depicted as transparent for clarity of details), under an embodiment.

The resection devices comprise helical scalpet arrays, including but not limited to external and internal helical scalpet arrays. FIG. 49 shows a helical scalpet (external) and an array including helical scalpets (external), under an embodiment. FIG. 50 shows side perspective views of a scalpet assembly including a helical scalpet array (left), and the resection device including the scalpet assembly with helical scalpet array (right) (housing shown), under an embodiment. FIG. 51 is a side view of a resection device including the scalpet assembly with helical scalpet array assembly (housing depicted as transparent for clarity of details), under an embodiment. FIG. 52 is a bottom perspective view of a resection device including the scalpet assembly with helical scalpet array assembly (housing depicted as transparent for clarity of details), under an embodiment. FIG. 53 is a top perspective view of a resection device including the scalpet assembly with helical scalpet array assembly (housing depicted as transparent for clarity of details), under an embodiment.

The helical scalpet configuration comprises a sleeve configured to fit over an end region of the scalpet, and an external region of the sleeve includes one or more helical threads. Once each scalpet is fitted with a sleeve, the sleeved scalpets are configured as a unit or array so that each scalpet rotates in unison with the adjacent scalpets. Alternatively, the helical thread is formed on or as a component of each scalpet.

Figure 54:
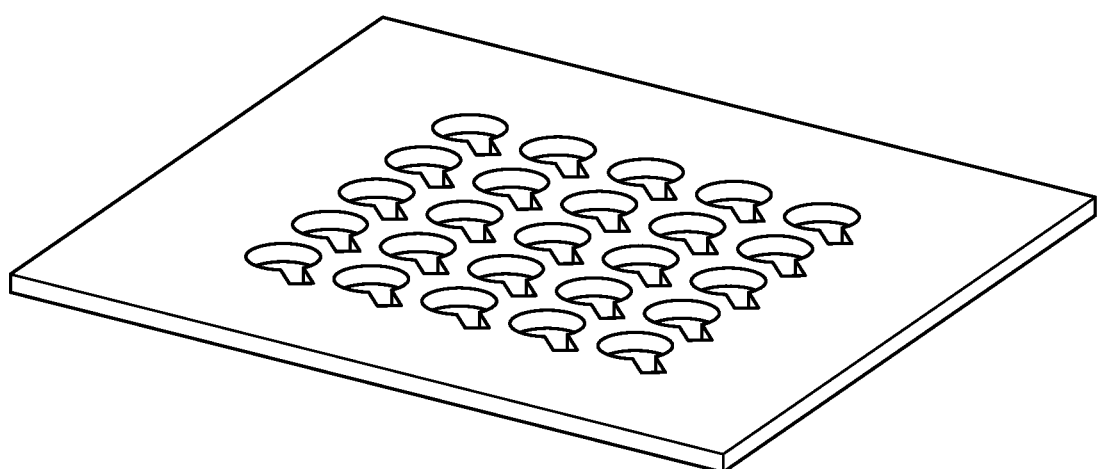
FIG. 54 is a push plate of the helical scalpet array, under an embodiment.

The helical scalpet array is configured to be driven by a push plate that oscillates up and down along a region of the central axis of the scalpet array. FIG. 54 is a push plate of the helical scalpet array, under an embodiment. The push plate includes a number of alignment holes corresponding to a number of scalpets in the array. Each alignment hole includes a notch configured to mate with the helical (external) thread on the scalpet sleeve. When the push plate is driven it causes rotation of each scalpet in the array. FIG. 55 shows the helical scalpet array with the push plate, under an embodiment.

Figure 56:
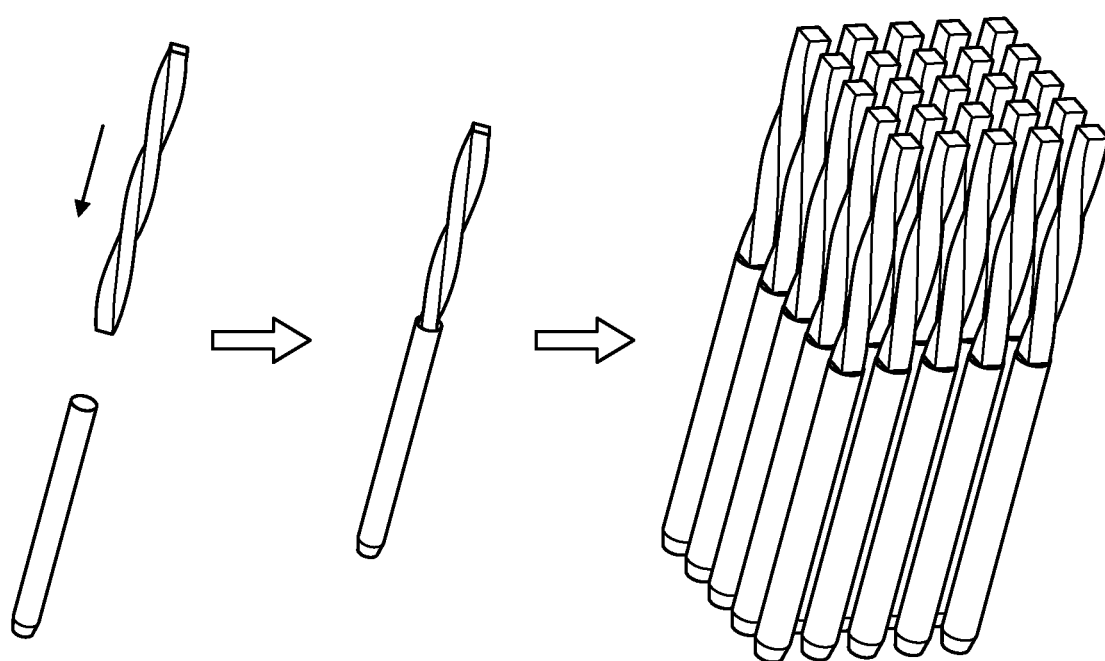
FIG. 56 shows an inner helical scalpet and an array including inner helical scalpets, under an embodiment.

The resection devices further comprise internal helical scalpet arrays. The device comprises a housing configured to include the helical scalpet array assembly for the application of rotational torque for scalpet rotation. FIG. 56 shows an inner helical scalpet and an array including inner helical scalpets, under an embodiment. The inner helical scalpet includes a twisted square rod (e.g., solid, hollow, etc.) or insert that is fitted into an open end of the scalpet. Alternatively, the scalpet is configured to include a helical region. The twisted insert is held in place by bonding (e.g., crimping, bonding, brazing, welding, gluing, etc.) a portion of the scalpet around the insert. Alternative, the insert is held in place with an adhesive bond. Inner helical scalpets are then configured as a unit or array so that each scalpet is configured to rotate in unison with the adjacent scalpets. The helical scalpet array is configured to be driven by a drive plate that moves or oscillates up and down along the helical region of each scalpet of the scalpet array. The drive plate includes a number of square alignment holes corresponding to a number of scalpets in the array. When the drive plate is driven up and down it causes rotation of each scalpet in the array. FIG. 57 shows the helical scalpet array with the drive plate, under an embodiment.

Figure 58:
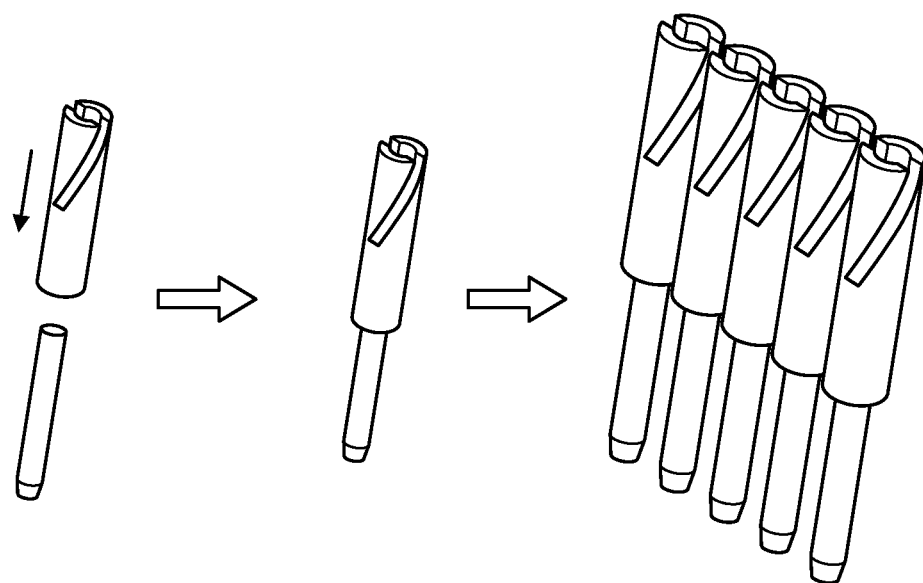
FIG. 58 shows a slotted scalpet and an array including slotted scalpets, under an embodiment.
Figure 59:
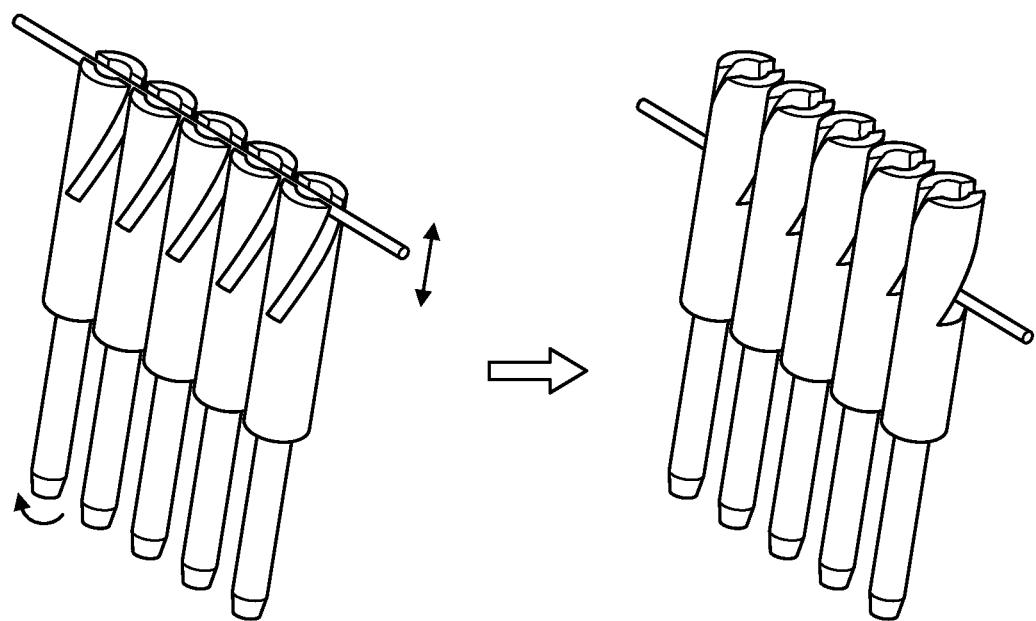
FIG. 59 shows a portion of a slotted scalpet array (e.g., four (4) scalpets) with the drive rod, under an embodiment.
Figure 60:
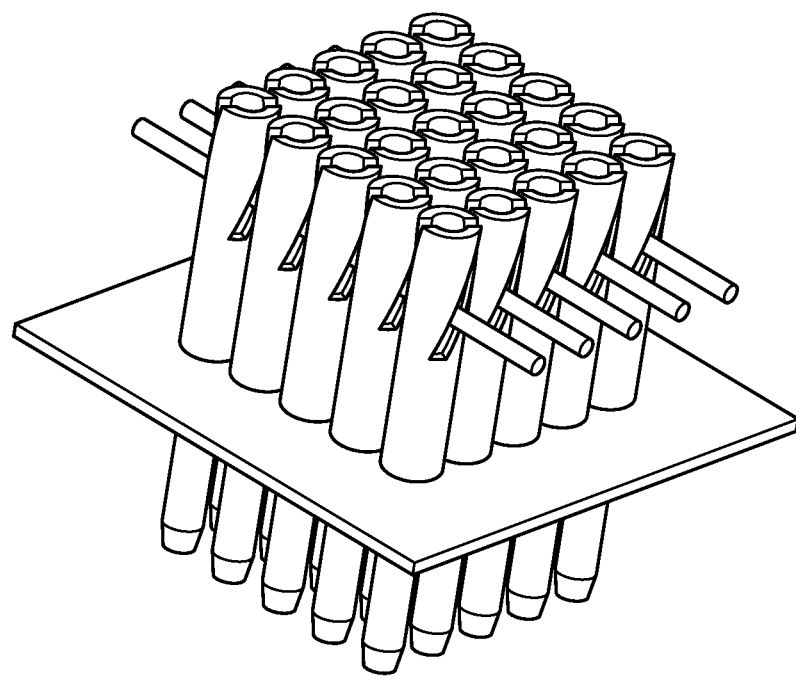
FIG. 60 shows an example slotted scalpet array (e.g., 25 scalpets) with the drive rod, under an embodiment.

FIG. 58 shows a slotted scalpet and an array including slotted scalpets, under an embodiment. The slotted scalpet configuration comprises a sleeve configured to fit over an end region of the scalpet, and the sleeve includes one or more spiral slots. Alternatively, each scalpet includes the spiral slot(s) without use of the sleeve. The sleeved scalpets are configured as a unit or array so that the top region of the slots of each scalpet are aligned adjacent one another. An external drive rod is aligned and fitted horizontally along the top of the slots. When the drive rod is driven downward, the result is a rotation of the scalpet array. FIG. 59 shows a portion of a slotted scalpet array (e.g., four (4) scalpets) with the drive rod, under an embodiment. FIG. 60 shows an example slotted scalpet array (e.g., 25 scalpets) with the drive rod, under an embodiment.

Figure 61:
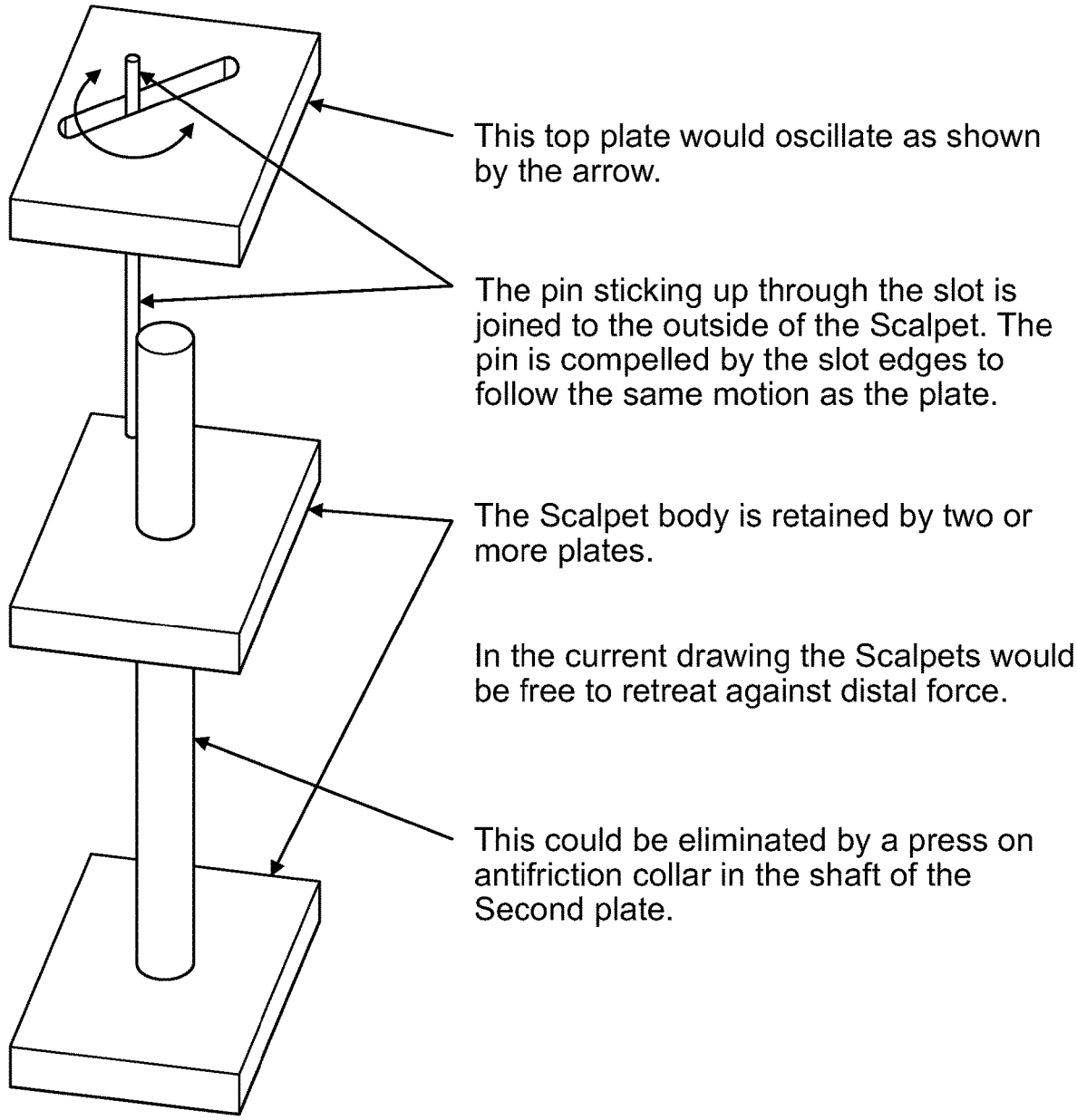
FIG. 61 shows an oscillating pin drive assembly with a scalpet, under an embodiment.

FIG. 61 shows an oscillating pin drive assembly with a scalpet, under an embodiment. The assembly includes a lower plate and a middle plate coupled or connected to the scalpet(s) and configured to retain the scalpet(s). A top plate, or drive plate, is positioned in an area above the scalpet and the middle plate, and includes a drive slot or slot. A pin is coupled or connected to a top portion of the scalpet, and a top region of the pin extends beyond a top of the scalpet. The slot is configured to receive and loosely retain the pin. The slot is positioned relative to the pin such that rotation or oscillation of the top plate causes the scalpet to rotate or oscillate via tracking of the pin in the slot.

One or more components of the scalpet device include an adjustment configured to control the amount (e.g., depth) of scalpet exposure during deployment of the scalpet array at the target site. For example, the adjustment of an embodiment is configured to collectively control a length of deployment of the scalpets of a scalpet array. The adjustment of an alternative embodiment is configured to collectively control a length of deployment of a portion or set of scalpets of a scalpet array. In another example embodiment, the adjustment is configured to separately control a length of deployment of each individual scalpet of a set of scalpets or scalpet array. The scalpet depth control includes numerous mechanisms configured for adjustable control of scalpet depth.

The depth control of an embodiment includes an adjustable collar or sleeve on each scalpet. The collar, which is configured for movement (e.g., slideable, etc.) along a length of the scalpet, is configured to prevent penetration of the scalpet into target tissue beyond a depth controlled by a position of the collar. The position of the collar is adjusted by a user of the scalpet device prior to use in a procedure, where the adjustment includes one or more of a manual adjustment, automatic adjustment, electronic adjustment, pneumatic adjustment, and adjustment under software control, for example.

The depth control of an alternative embodiment includes an adjustable plate configured for movement along a length of scalpets of the scalpet array. The plate is configured to prevent penetration of the scalpets of the scalpet array into target tissue beyond a depth controlled by a position of the plate. In this manner, the scalpet array is deployed into the target tissue to a depth equivalent to a length of the scalpets protruding beyond the plate. The position of the plate is adjusted by a user of the scalpet device prior to use in a procedure, where the adjustment includes one or more of a manual adjustment, automatic adjustment, electronic adjustment, pneumatic adjustment, and adjustment under software control, for example.

Figure 62:
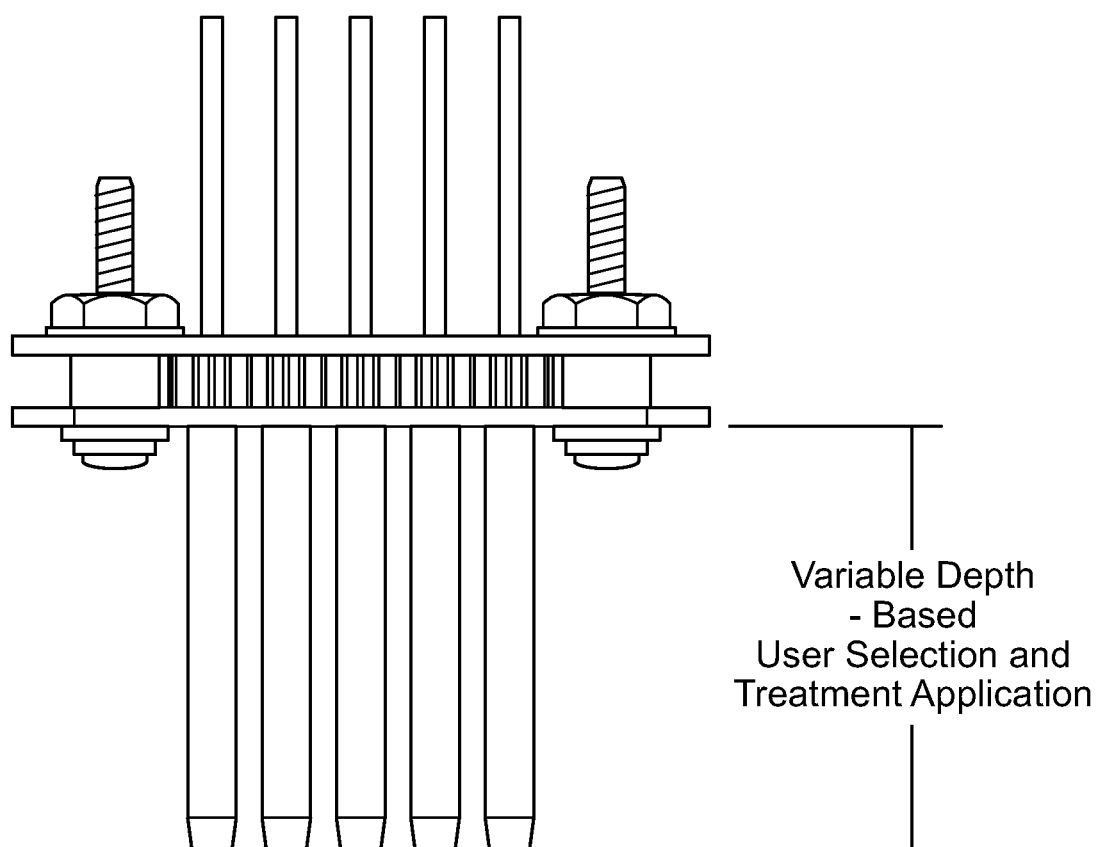
FIG. 62 shows variable scalpet exposure control with the scalpet guide plates, under an embodiment.

As an example of depth control adjustment using a plate, the variable length scalpet exposure is controlled through adjustments of the scalpet guide plates of the scalpet assembly, but is not so limited. FIG. 62 shows variable scalpet exposure control with the scalpet guide plates, under an embodiment. Alternative embodiments control scalpet exposure from within the scalpet array handpiece, and/or under one or more of software, hardware, and mechanical control.

Figure 63:
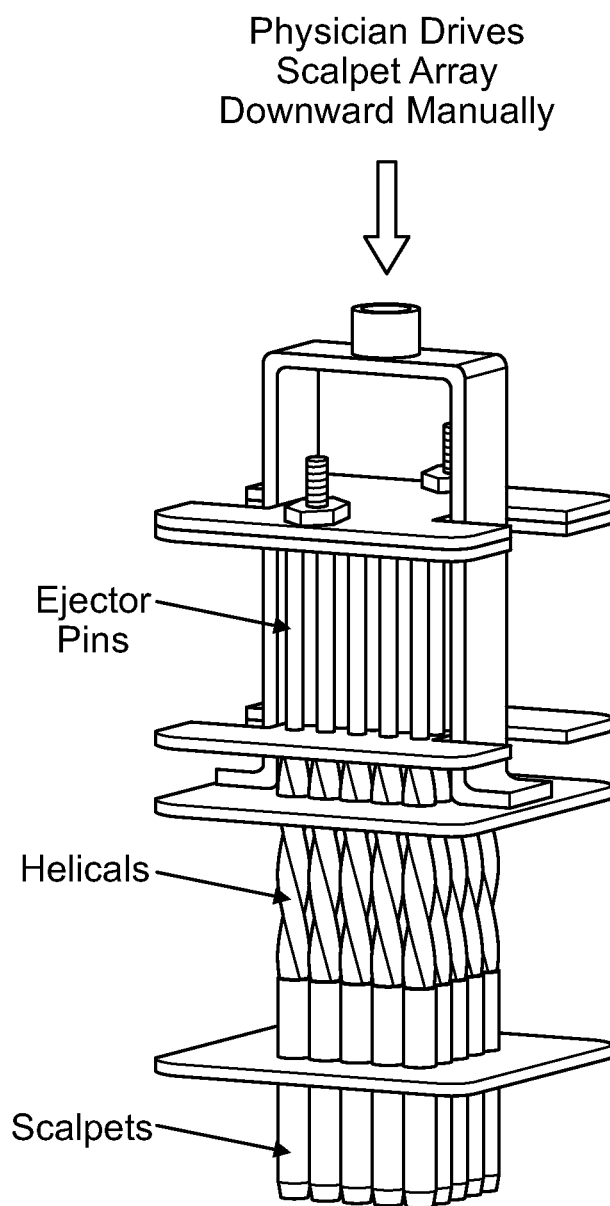
FIG. 63 shows a scalpet assembly including a scalpet array (e.g., helical) configured to be manually driven by an operator, under an embodiment.

Embodiments include a mechanical scalpet array in which axial force and rotational force are applied manually by the compressive force from the device operator. FIG. 63 shows a scalpet assembly including a scalpet array (e.g., helical) configured to be manually driven by an operator, under an embodiment.

Embodiments include and/or are coupled or connected to a source of rotation configured to provide optimal rotation (e.g., RPM) and rotational torque to incise skin in combination with axial force. Optimal rotation of the scalpets is configured according to the best balance between rotational velocity and increased cutting efficiency versus increased frictional losses. Optimal rotation for each scalpet array configuration is based on one or more of array size (number of scalpets), scalpet cutting surface geometry, material selection of scalpets and alignment plates, gear materials and the use of lubrication, and mechanical properties of the skin, to name a few.

Figure 64:
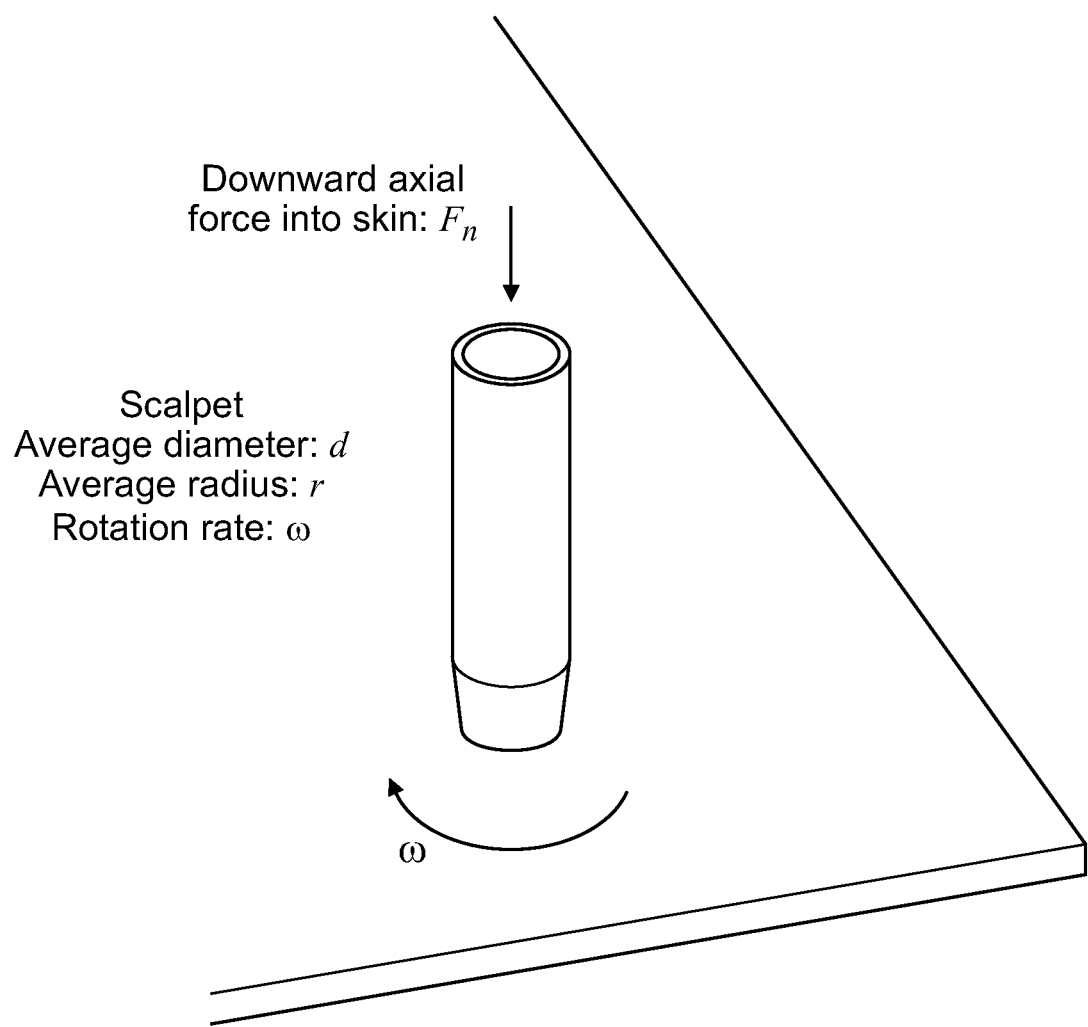
FIG. 64 shows forces exerted on a scalpet via application to the ski.

Regarding forces to be considered in configuration of the scalpets and scalpet arrays described herein, FIG. 64 shows forces exerted on a scalpet via application to the skin. The parameters considered in determining applicable forces under an embodiment include the following:

Average Scalpet Radius: r
Scalpet Rotation Rate: $\omega$
Scalpet Axial Force: $F_n$ (scalpet applied normal to skin)
Skin Friction Coefficient: $\mu$
Friction Force: $F_f$
Scalpet Torque: $\tau$
Motor Power: $P_{hp}$.

Upon initial application, the torque used to rotate the scalpet is a function of the axial force (applied normally to the surface of the skin) and the coefficient of friction between the scalpet and the skin. This friction force initially acts on the cutting surface of the scalpet. At initial application of scalpet to skin:

$$F_f = \mu \cdot F_n$$

$$\tau = F_f \cdot r$$

$$P_{hp} = \tau \cdot \omega / 63025$$

The initial force for the scalpet to penetrate the skin, is a function of the scalpet sharpness, the axial force, the tensile strength of the skin, the coefficient of friction between the skin and the scalpet. Following penetration of the scalpet into the skin, the friction force increases as there are additional friction forces acting on the side walls of the scalpet.

Figure 65:
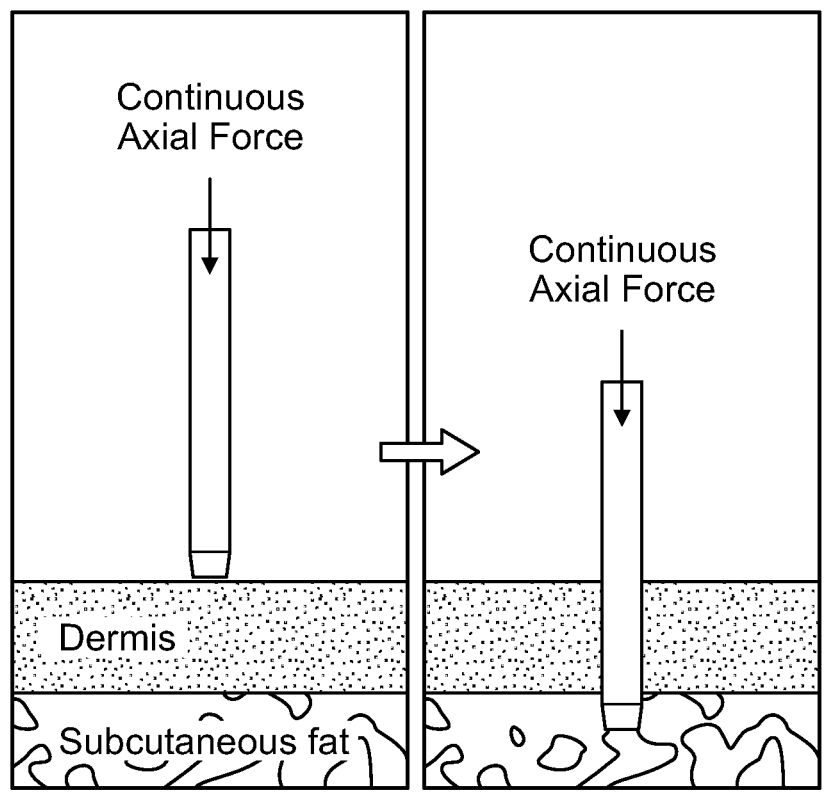
FIG. 65 depicts steady axial force compression using a scalpet, under an embodiment.

Resection devices of embodiments include kinetic impaction incision devices and methods for non-rotational piercing of the skin. Approaches for direct compression of the scalpet into the skin include, but are not limited to, axial force compression, single axial force compression plus kinetic impact force, and moving of the scalpet at a high velocity to impact and pierce the skin. FIG. 65 depicts steady axial force compression using a scalpet, under an embodiment. Steady axial force compression places the scalpet in direct contact with the skin. Once in place, a continuous and steady axial force is applied to the scalpet until it pierces the skin and proceeds through the dermis to the subcutaneous fat layer.

Figure 66:
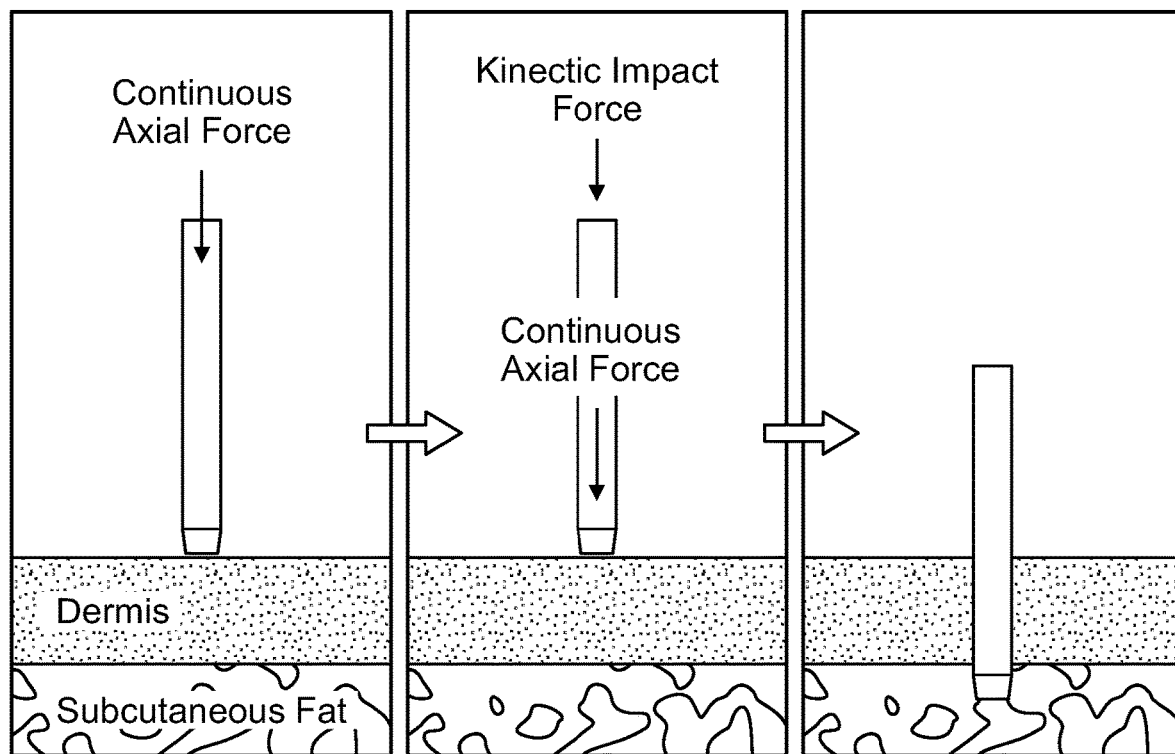
FIG. 66 depicts steady single axial force compression plus kinetic impact force using a scalpet, under an embodiment.

FIG. 66 depicts steady single axial force compression plus kinetic impact force using a scalpet, under an embodiment. Steady single axial force compression plus kinetic impact force places the scalpet in direct contact with the skin. An axial force is applied to maintain contact. The distal end of the scalpet is then struck by another object, imparting additional kinetic energy along the central axis. These forces cause the scalpet to pierce the skin and proceed through the dermis to the subcutaneous fat layer.

Figure 67:
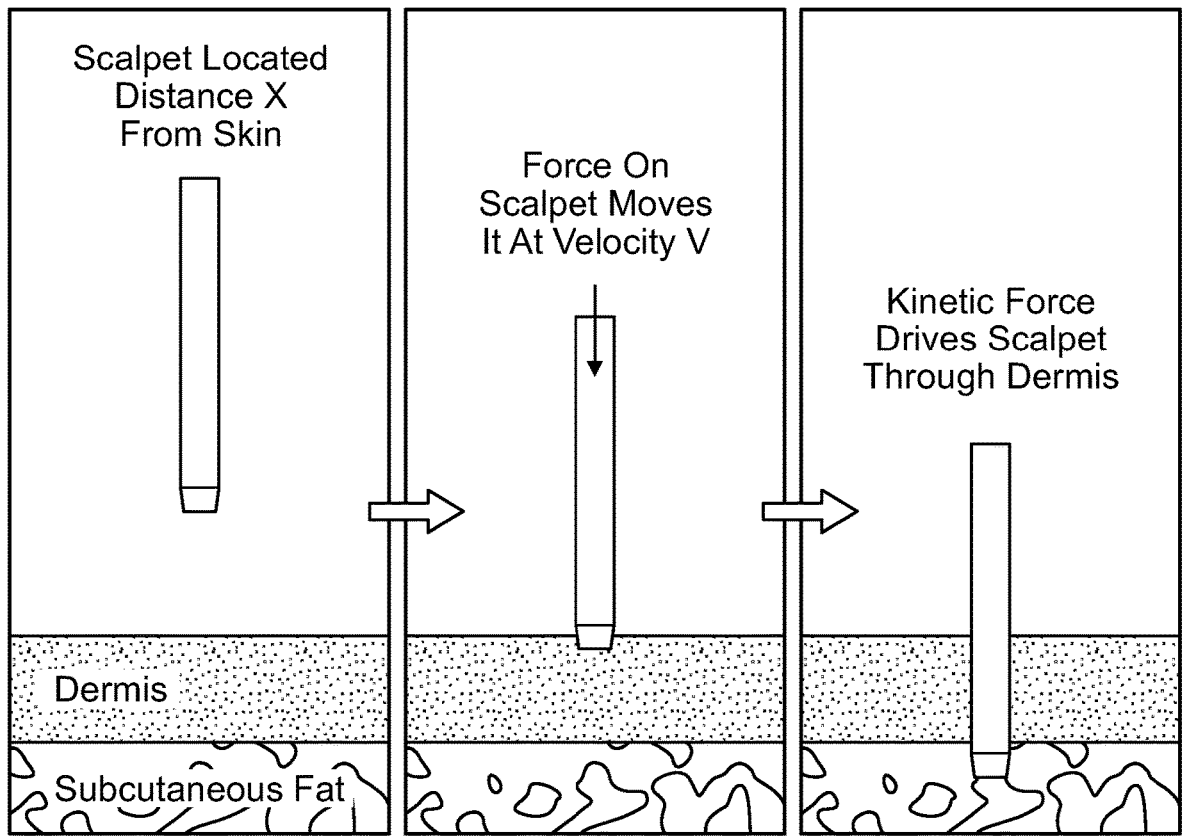
FIG. 67 depicts moving of the scalpet at a velocity to impact and pierce the skin, under an embodiment.

FIG. 67 depicts moving of the scalpet at a velocity to impact and pierce the skin, under an embodiment. The scalpet is positioned a short distance away from a target area of the skin. A kinetic force is applied to the scalpet to achieve a desired velocity for piercing the skin. The kinetic force causes the scalpet to pierce the skin and proceed through the dermis to the subcutaneous fat layer.

Figure 68:
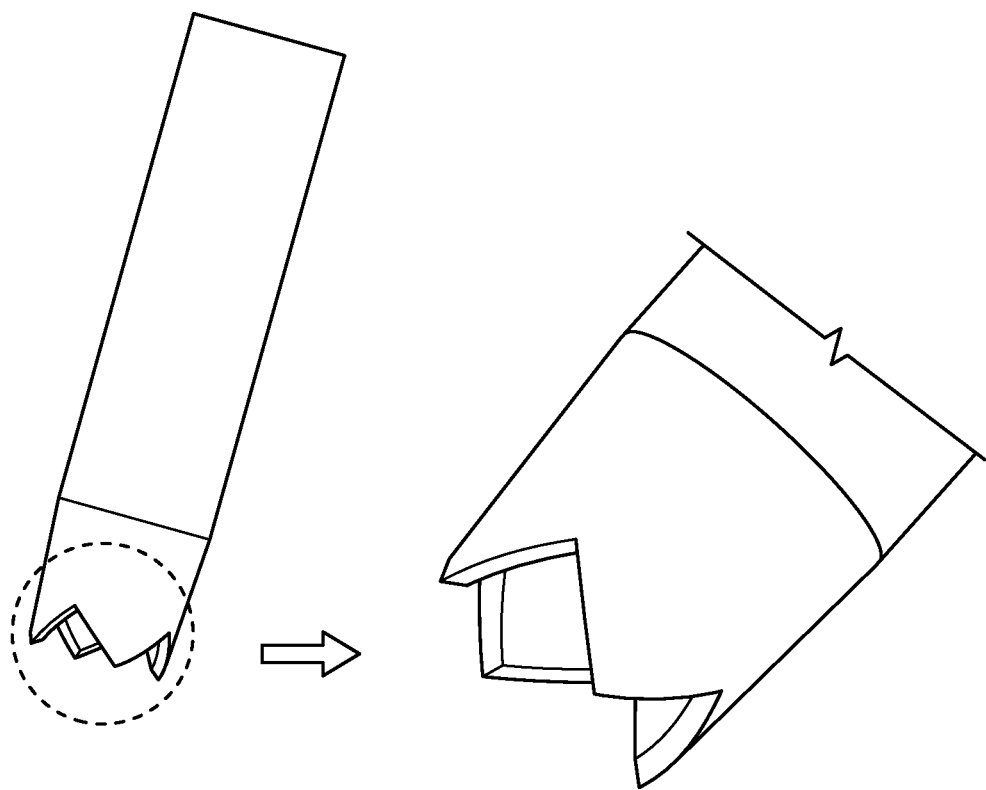
FIG. 68 depicts a multi-needle tip, under an embodiment.

Scalpets of an embodiment include numerous cutting surface or blade geometries as appropriate to an incision method of a procedure involving the scalpet. The scalpet blade geometries include, for example, straight edge (e.g., cylindrical), beveled, multiple-needle tip (e.g., sawtooth, etc.), and sinusoidal, but are not so limited. As but one example, FIG. 68 depicts a multi-needle tip, under an embodiment.

Figure 69:
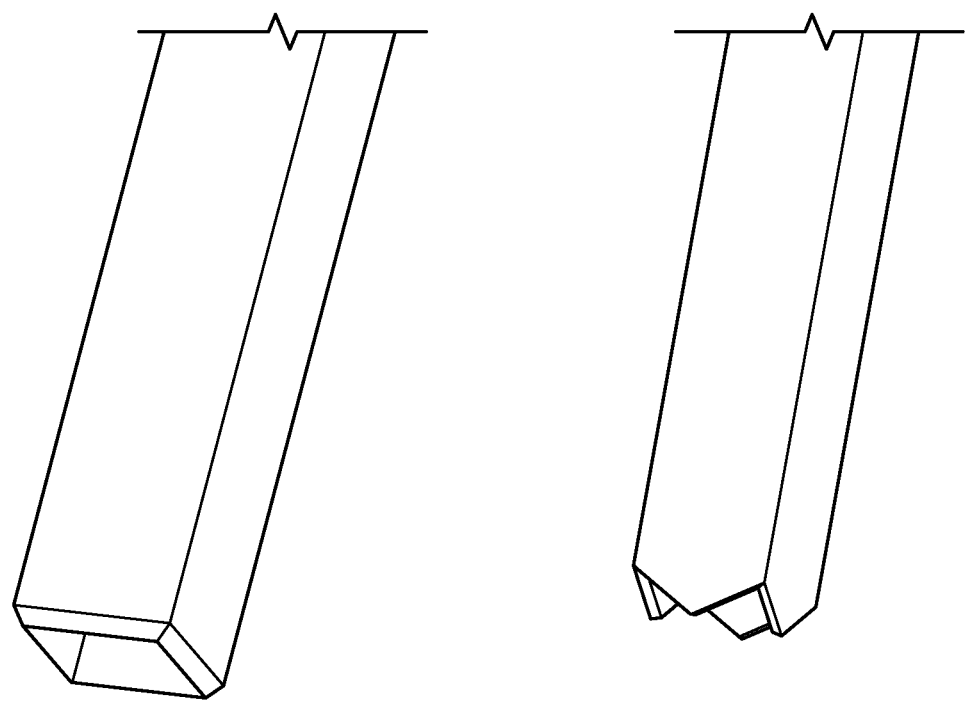
FIG. 69 shows a square scalpet without teeth (left), and a square scalpet with multiple teeth (right), under an embodiment.

The scalpets include one or more types of square scalpets, for example. The square scalpets include but are not limited to, square scalpets without multiple sharpened points, and square scalpets with multiple sharpened points or teeth. FIG. 69 shows a square scalpet without teeth (left), and a square scalpet with multiple teeth (right), under an embodiment.

The fractional resection devices of an embodiment involve the use of a square scalpet assembled onto a scalpet array that has multiple sharpened points to facilitate skin incising through direct non-rotational kinetic impacting. The square geometry of the harvested skin plug provides side-to-side and point-to-point approximation of the assembled skin plugs onto the adherent membrane. Closer approximation of the skin plugs provides a more uniform appearance of the skin graft at the recipient site. In addition, each harvested component skin plug will have additional surface area (e.g., 20-25%).

Figure 70:
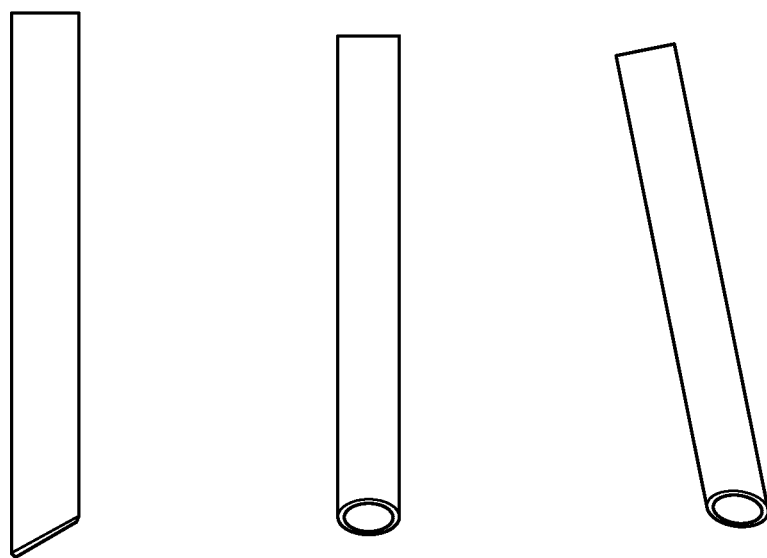
FIG. 70 shows multiple side, front (or back), and side perspective views of a round scalpet with an oblique tip, under an embodiment.
Figure 71:
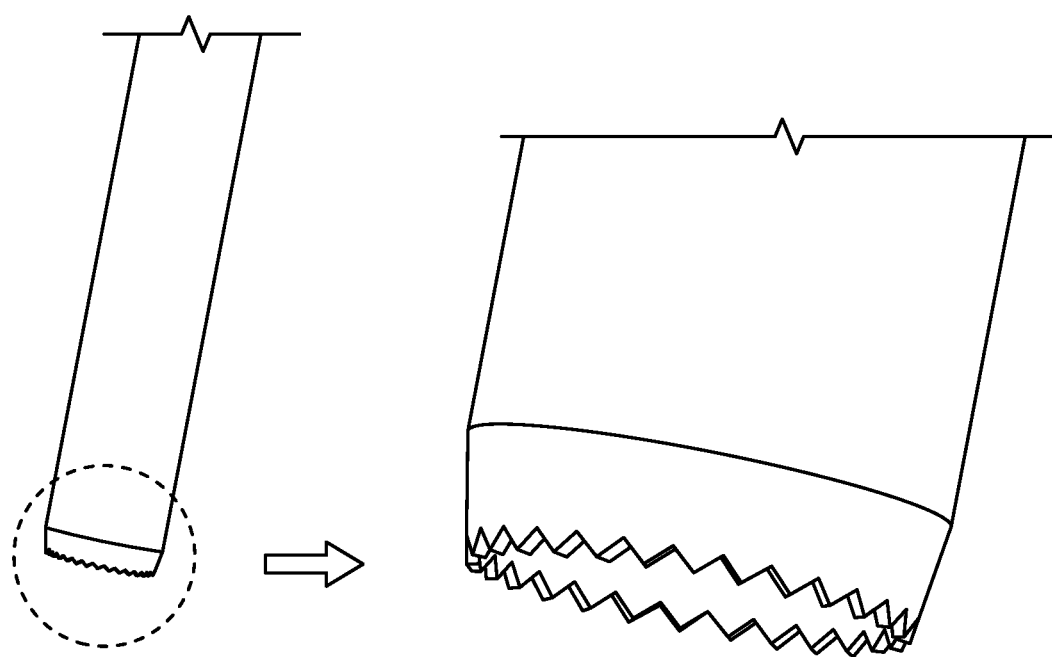
FIG. 71 shows a round scalpet with a serrated edge, under an embodiment.

Further, the scalpets include one or more types of elliptical or round scalpets. The round scalpets include but are not limited to, round scalpets with oblique tips, round scalpets without multiple sharpened points or teeth, and round scalpets with multiple sharpened points or teeth. FIG. 70 shows multiple side, front (or back), and side perspective views of a round scalpet with an oblique tip, under an embodiment. FIG. 71 shows a round scalpet with a serrated edge, under an embodiment.

Figure 72:
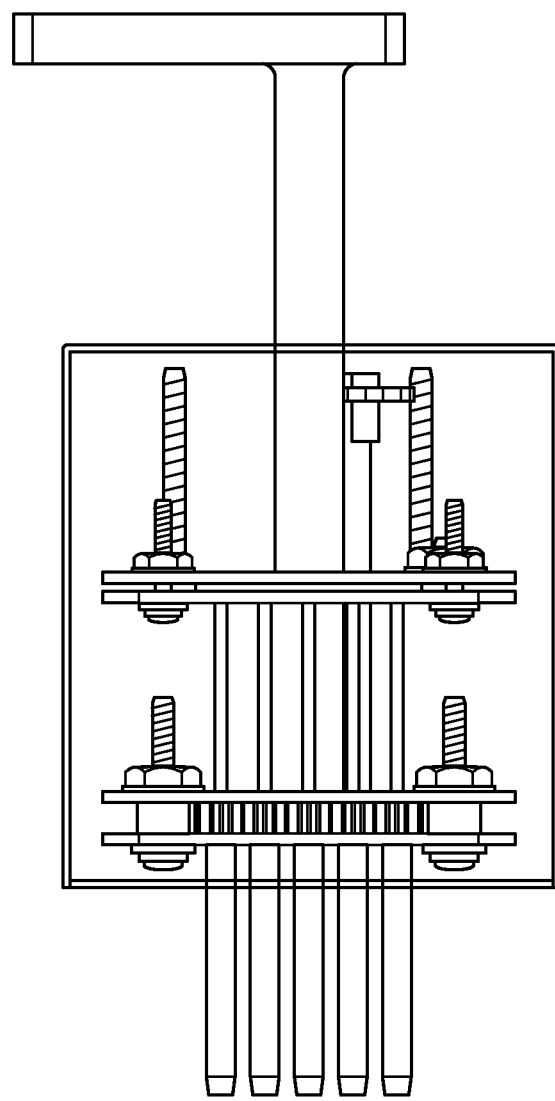
FIG. 72 shows a side view of the resection device including the scalpet assembly with scalpet array and extrusion pins (housing depicted as transparent for clarity of details), under an embodiment.
Figure 73:
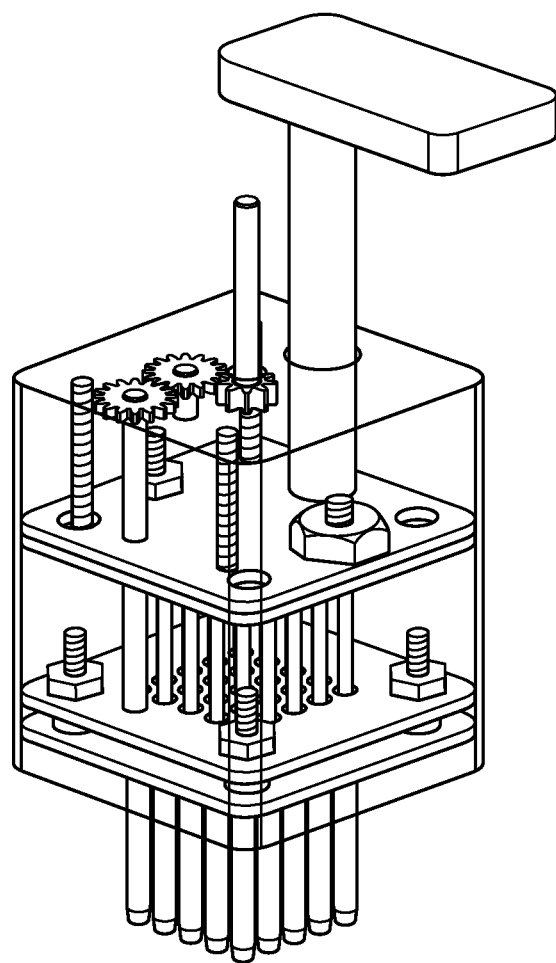
FIG. 73 shows a top perspective cutaway view of the resection device including the scalpet assembly with scalpet array and extrusion pins (housing depicted as transparent for clarity of details), under an embodiment.
Figure 74:
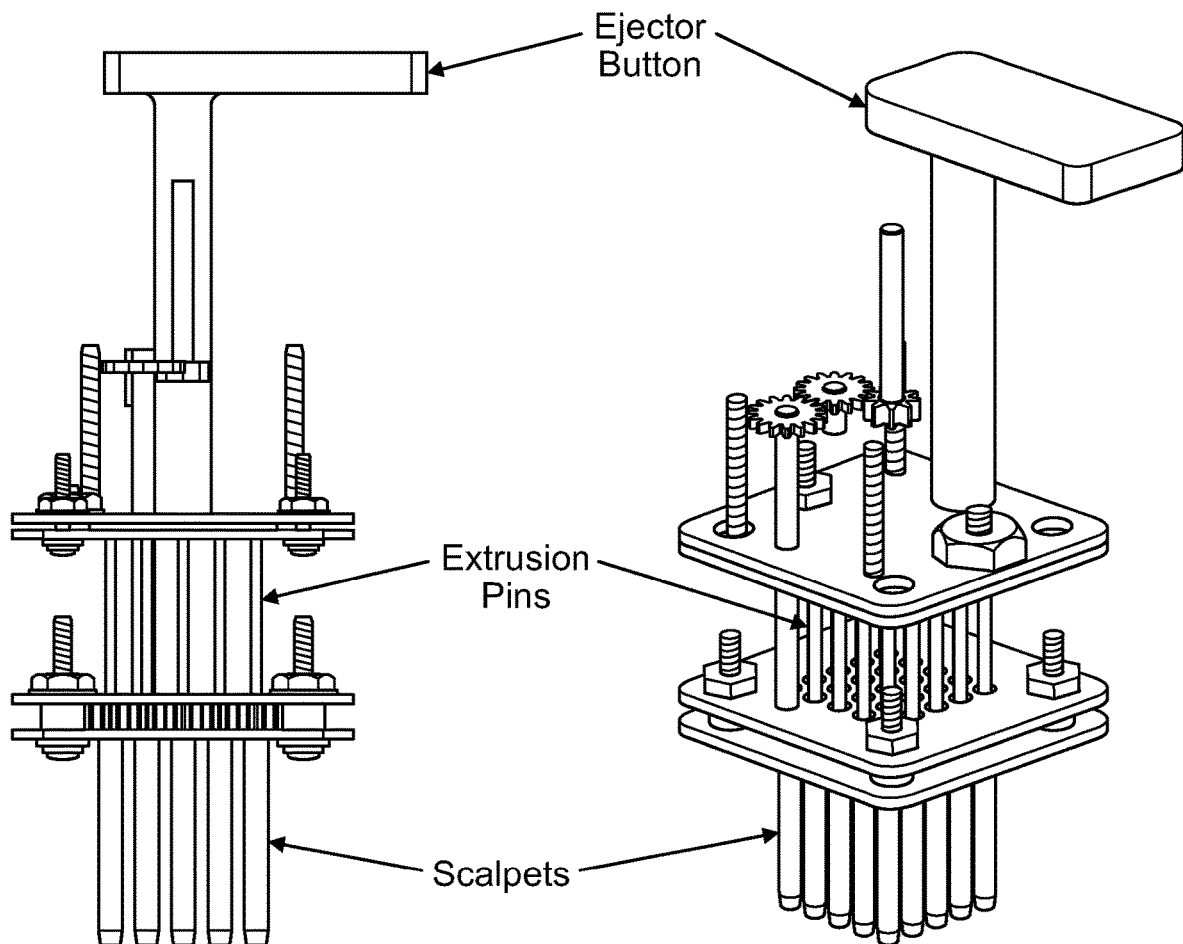
FIG. 74 shows side and top perspective views of the scalpet assembly including the scalpet array and extrusion pins, under an embodiment.

The resection device of an embodiment is configured to include extrusion pins corresponding to the scalpets. FIG. 72 shows a side view of the resection device including the scalpet assembly with scalpet array and extrusion pins (housing depicted as transparent for clarity of details), under an embodiment. FIG. 73 shows a top perspective cutaway view of the resection device including the scalpet assembly with scalpet array and extrusion pins (housing depicted as transparent for clarity of details), under an embodiment. FIG. 74 shows side and top perspective views of the scalpet assembly including the scalpet array and extrusion pins, under an embodiment.

The extrusion pins of an embodiment are configured to clear retained skin plugs, for example. The extrusion pins of an alternative embodiment are configured to inject into fractional defects at the recipient site. The extrusion pins of another alternative embodiment are configured to inject skin plugs into pixel canisters of a docking station for fractional skin grafting.

Figure 75:
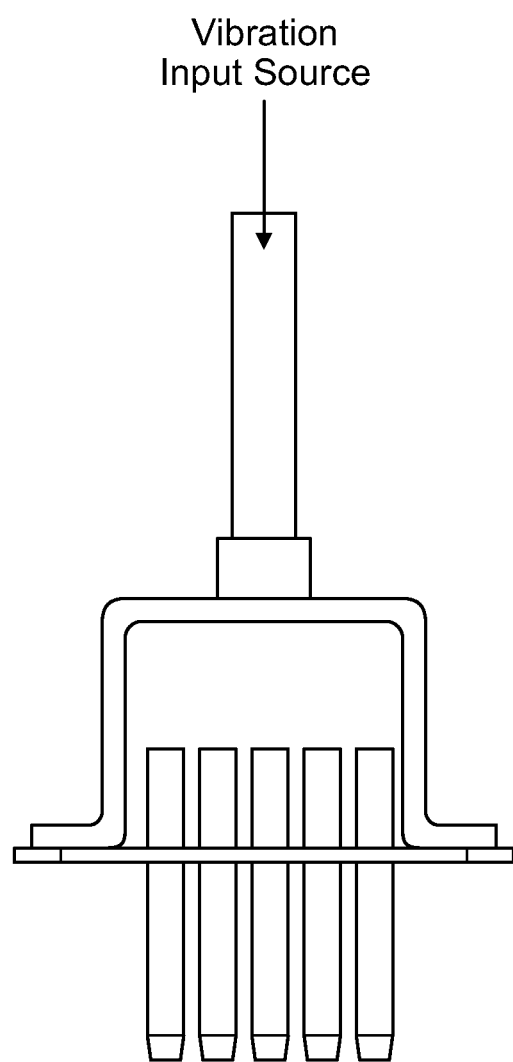
FIG. 75 is a side view of a resection device including the scalpet assembly with scalpet array assembly coupled to a vibration source, under an embodiment.

Embodiments herein include the use of a vibration component or system to facilitate skin incising with rotation torque/axial force and to use vibration to facilitate skin incising with direct impaction without rotation. FIG. 75 is a side view of a resection device including the scalpet assembly with scalpet array assembly coupled to a vibration source, under an embodiment.

Figure 76:
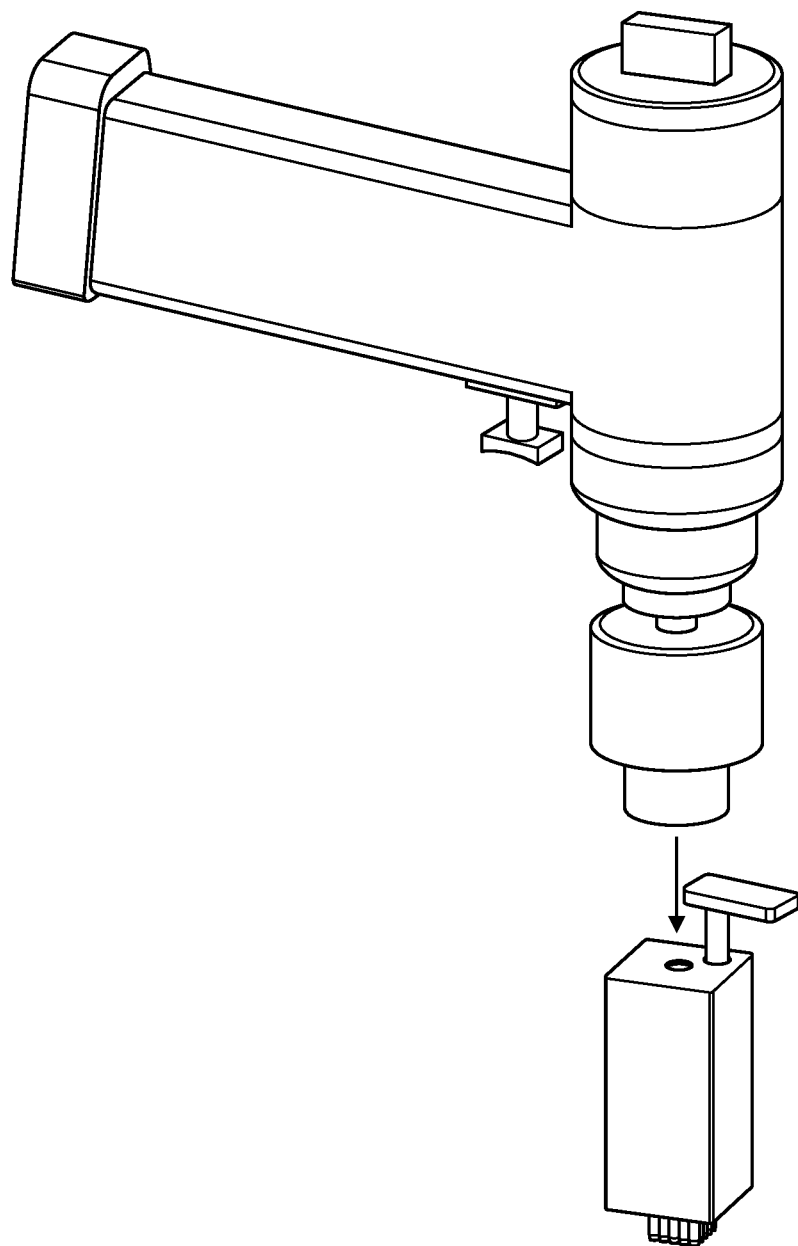
FIG. 76 shows a scalpet array driven by an electromechanical source or scalpet array generator, under an embodiment.

Embodiments herein include an electro-mechanical scalpet array generator. FIG. 76 shows a scalpet array driven by an electromechanical source or scalpet array generator, under an embodiment. The function of the generator is powered but is not electronically controlled, but embodiments are not so limited. The platform of an embodiment includes control software.

Embodiments include and/or are coupled or connected to a supplementary energy or force configured to reduce the axial force used to incise skin (or another tissue surface such as mucosa) by a scalpet in a scalpet array. Supplemental energies and forces include one or more of rotational torque, rotational kinetic energy of rotation (RPM), vibration, ultrasound, and electromagnetic energy (e.g., RF, etc.), but are not so limited.

Embodiments herein include a scalpet array generator comprising and/or coupled to an electromagnetic radiation source. The electromagnetic radiation source includes, for example, one or more of a Radio Frequency (RF) source, a laser source, and an ultrasound source. The electromagnetic radiation is provided to assist cutting with the scalpets.

Embodiments include a scalpet mechanism configured as a "sewing machine" scalpet or scalpet array in which the scalpets are repeatedly retracted and deployed under one or more of manual, electromechanical, and electronic control. This embodiment includes a moving scalpet or scalpet array to resect a site row-by-row. The resection can, for example take the form of a stamping approach where the scalpet or scalpet array moves, or the array could be rolled over the surface to be treated and the scalpet array resection at given distances traveled to achieve the desired resection density.

The fractional resection devices described herein are configured for fractional resection and grafting in which the harvesting of fractionally incised skin plugs is performed with a vacuum that deposits the plugs within the lumen of each scalpet shaft. The skin plugs are then inserted into a separate docking station described herein by a proximal pin array that extrudes the skin plug from within the shaft of the scalpet.

Figure 77:
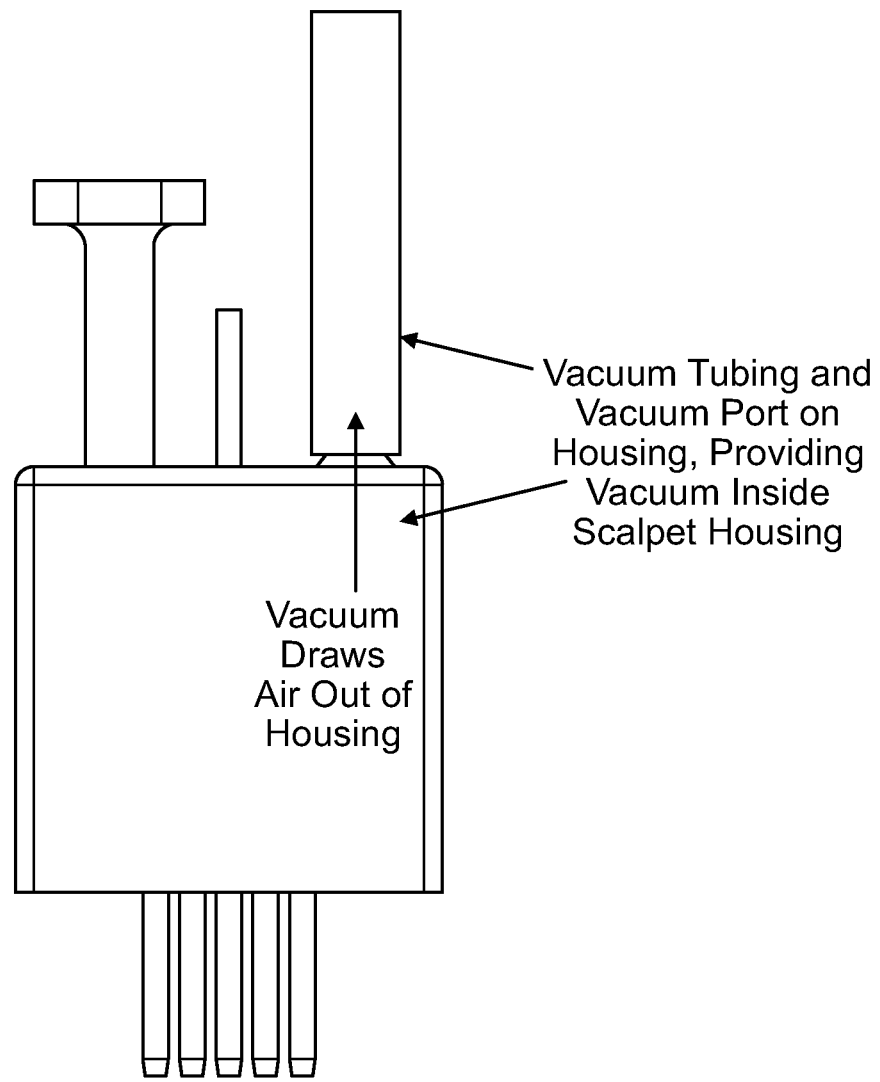
FIG. 77 is a diagram of the resection device including a vacuum system, under an embodiment.

FIG. 77 is a diagram of the resection device including a vacuum system, under an embodiment. The vacuum system comprises vacuum tubing and a vacuum port on/in the device housing, configured to generate a vacuum within the housing by drawing air out of the housing. The vacuum of an embodiment is configured to provide vacuum stenting/fixturing of the skin for scalpet incising, thereby providing improved depth control and cutting efficiency.

Figure 78:
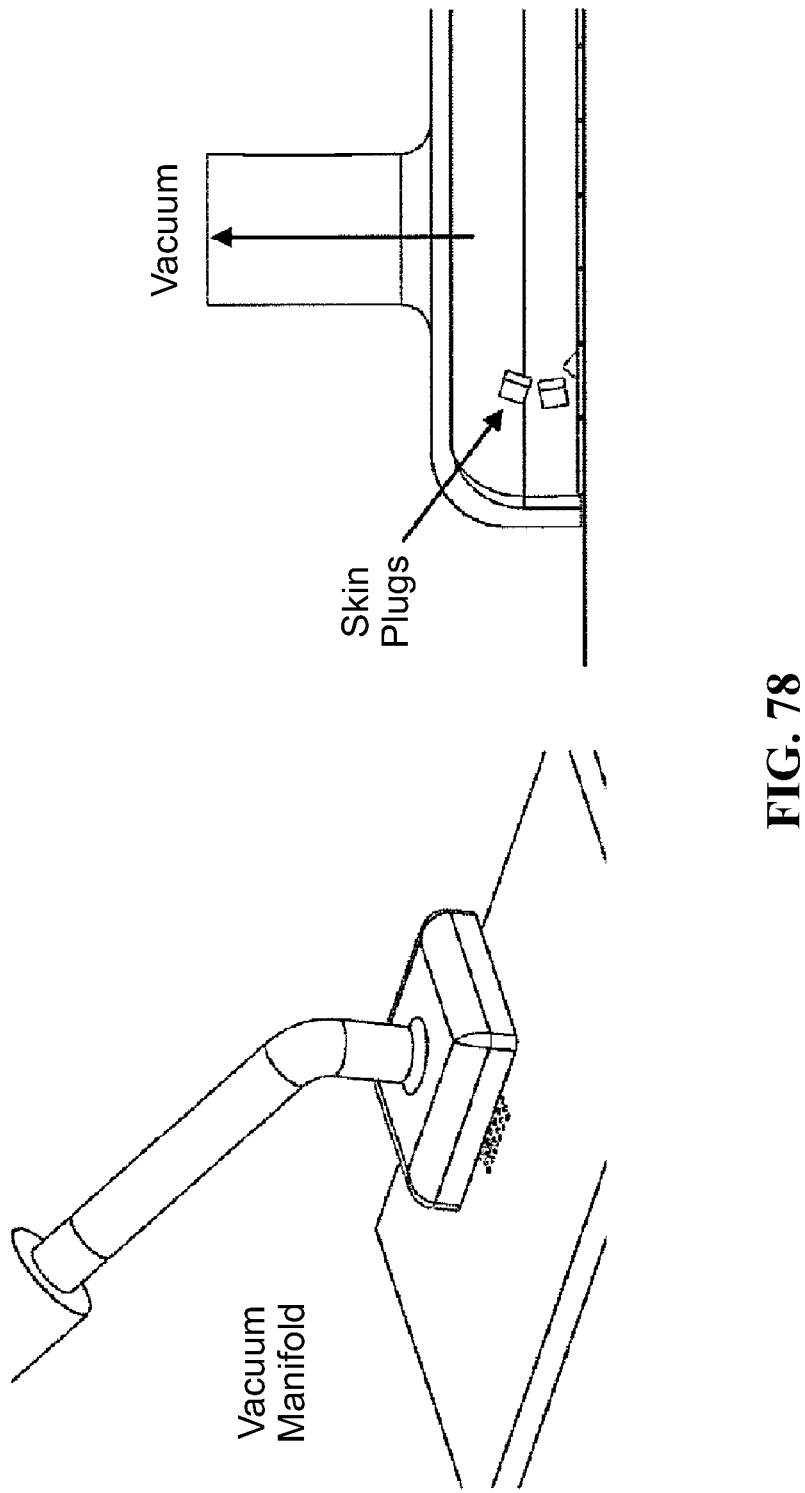
FIG. 78 shows a vacuum manifold applied to a target skin surface to evacuate/harvest excised skin/hair plugs, under an embodiment.
Figure 79:
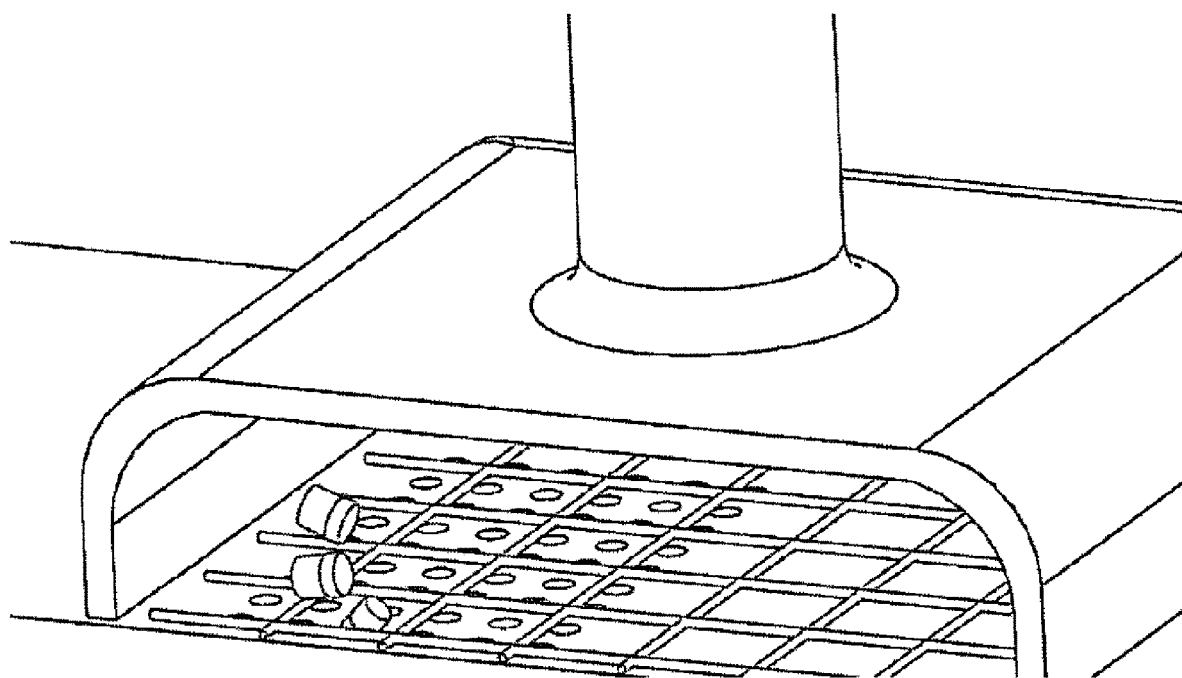
FIG. 79 shows a vacuum manifold with an integrated wire mesh applied to a target skin surface to evacuate/harvest excised skin/hair plugs, under an embodiment.

The vacuum of an alternative embodiment is configured for vacuum evacuation or harvesting of skin plugs and/or hair plugs through one or more of a scalpet lumen and an array manifold housing. FIG. 78 shows a vacuum manifold applied to a target skin surface to evacuate/harvest excised skin/hair plugs, under an embodiment. The vacuum manifold, which is configured for direct application onto a skin surface, is coupled or connected to a vacuum source. FIG. 79 shows a vacuum manifold with an integrated wire mesh applied to a target skin surface to evacuate/harvest excised skin/hair plugs, under an embodiment.

Figure 80:
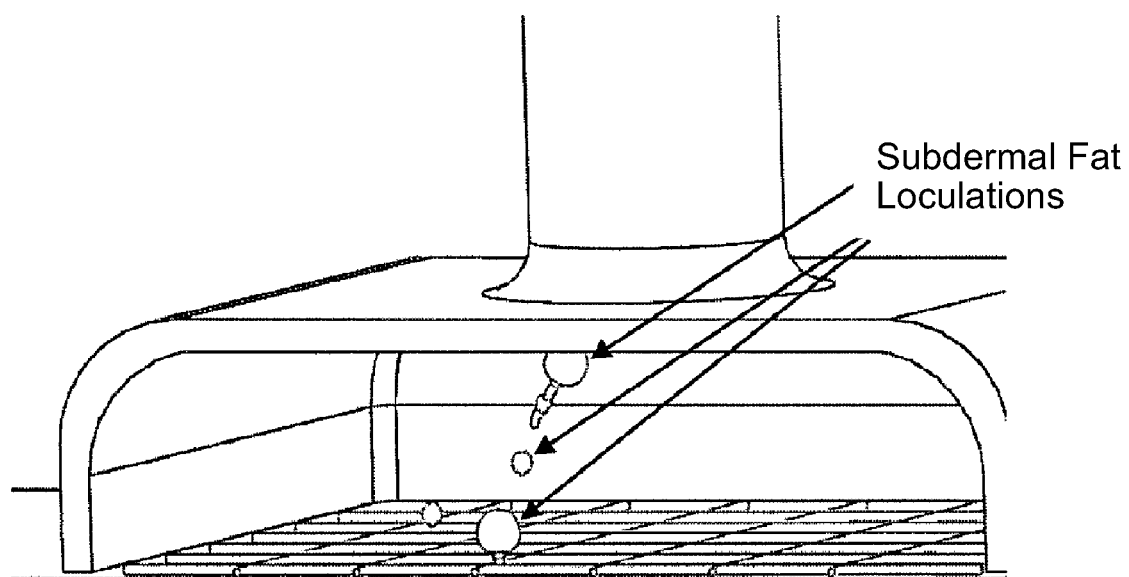
FIG. 80 shows a vacuum manifold with an integrated wire mesh configured to vacuum subdermal fat, under an embodiment.

Additionally, an external vacuum manifold is used with a suction-assisted lipectomy machine to percutaneously evacuate superficial sub-dermal fat through fractionally resection skin defects in a fractionally created field for the treatment of cellulite. FIG. 80 shows a vacuum manifold with an integrated wire mesh configured to vacuum subdermal fat, under an embodiment.

The external vacuum manifold can also be configured to include and be deployed with an incorporated docking station (described herein) to harvest skin plugs for grafting. The docking station can be one or more of static, expandable, and/or collapsible.

The fractional resection devices described herein comprise a separate docking station configured as a platform to assemble the fractionally harvested skin plugs into a more uniform sheet of skin for skin grafting. The docking station includes a perforated grid matrix comprising the same pattern and density of perforations as the scalpets on the scalpet array. A holding canister positioned subjacent to each perforation is configured to retain and maintain alignment of the harvested skin plug. In an embodiment, the epidermal surface is upward at the level of the perforation. In an alternative embodiment, the docking station is partially collapsible to bring docked skin plugs into closer approximation prior to capture onto an adherent membrane. The captured fractional skin graft on the adherent membrane is then defatted with either an incorporated or non-incorporated transection blade. In another alternative embodiment, the adherent membrane itself has an elastic recoil property that brings or positions the captured skin plugs into closed alignment. Regardless of embodiment, the contracted fractional skin graft/adherent membrane composite is then directly applied to the recipient site defect.

Figure 81:
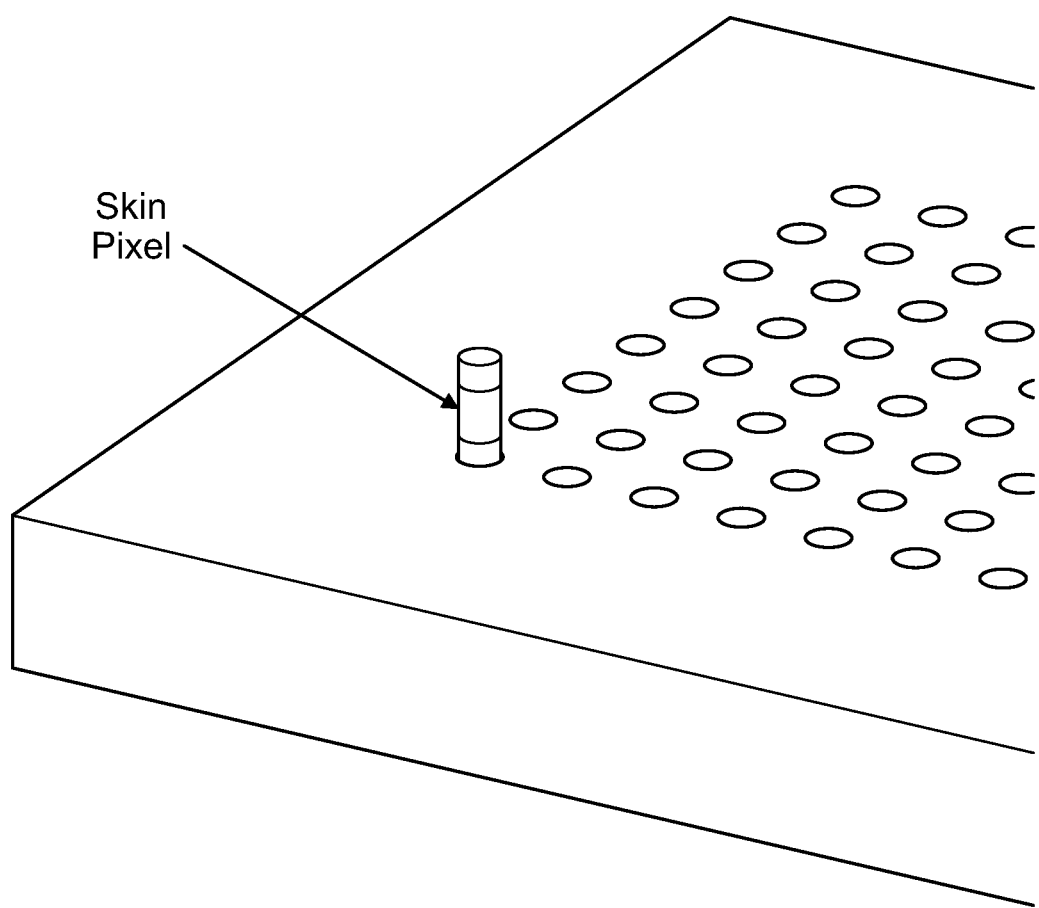
FIG. 81 depicts a collapsible docking station and an inserted skin pixel, under an embodiment. The docking station is formed from elastomeric material but is not so limited.
Figure 82:
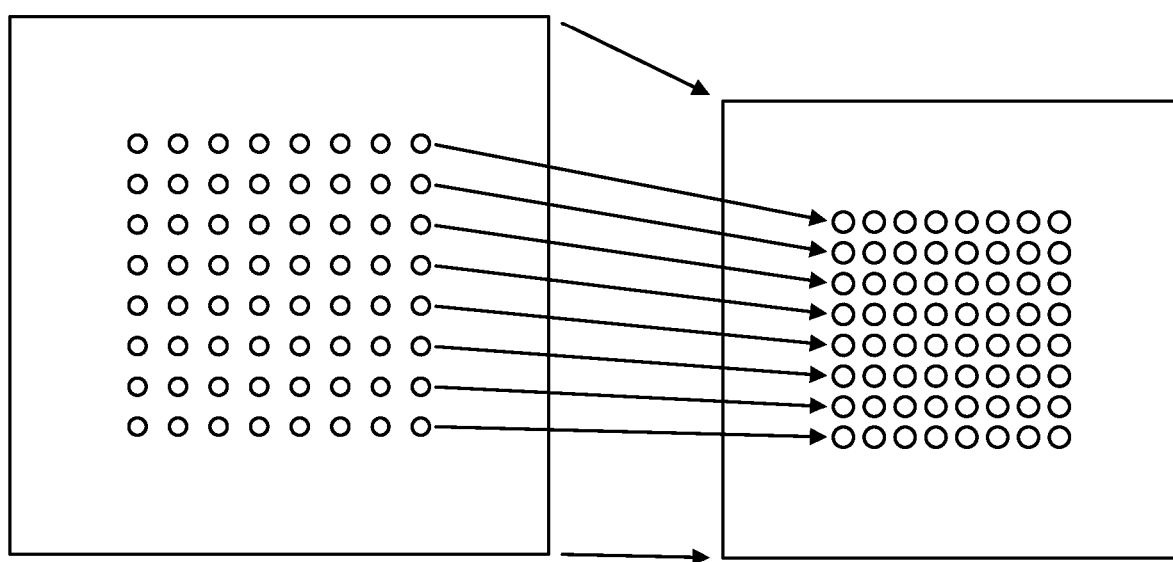
FIG. 82 is a top view of a docking station (e.g., elastomeric) in stretched (left) and un-stretched (right) configuration, under an embodiment, under an embodiment.

Embodiments include a collapsible docking station or tray configured to accept and maintain orientation of harvested skin and/or hair plugs once they have been removed or ejected from the scalpets via the extrusion pins. FIG. 81 depicts a collapsible docking station and an inserted skin pixel, under an embodiment. The docking station is formed from elastomeric material but is not so limited. The docking station is configured for stretching from a first shape to a second shape that aligns the pixel receptacles with the scalpet array on the handpiece. FIG. 82 is a top view of a docking station (e.g., elastomeric) in stretched (left) and un-stretched (right) configuration, under an embodiment, under an embodiment.

The pixels are ejected from the scalpet array into the docking station until it is full, and the docking station is then relaxed to its pre-stretched shape, which has the effect of bringing the pixels in closer proximity to each other. A flexible semi-permeable membrane with adhesive on one side is then stretched and placed over the docking station (adhesive side down). Once the pixels are adhered to the membrane, it is lifted away from the docking station. The membrane then returns to its normal un-stretched state, which also has the effect of pulling the pixels closer to each other. The membrane is then placed over the recipient defect.

Resection devices described herein include delivery of therapeutic agents through resectioned defects generated with the resection devices described herein. As such, the resection sites are configured for use as topically applied infusion sites for delivery or application of therapeutic agents for the reduction of fat cells (lipolysis) during or after a resectioning procedure.

Embodiments herein are configured for hair transplantation that includes vacuum harvesting of hair plugs into the scalpet at the donor site, and direct mass injection (without a separate collection reservoir) of harvested hair plugs into the fractionally resected defects of the recipient site. Under this embodiment, the donor scalpet array deployed at the occipital scalp comprises scalpets having a relatively larger diameter than the constituent scalpets of the scalpet array deployed to generate defects at the recipient site. Following harvesting of hair plugs at the donor site, the defects generated at the recipient site are plugged using the harvested hair plugs transferred in the scalpet array.

Due to the elastic retraction of the incised dermis, the elastically retracted diameter of the hair plug harvested at the occipital scalp will be similar to the elastically retracted diameter of the fractionally resected defect of the recipient site at the frontal-parietal-occipital scalp. In an embodiment, hair plugs harvested within the donor scalpet array are extruded directly with proximal pins in the lumen of the scalpet into a same pattern of fractionally defects created by the recipient site scalpet array. The scalpets (containing the donor hair plugs) of the scalpet array deployed at the donor site are aligned (e.g., visually) with the same pattern of fractionally resected field of defects at the recipient scalp site. Upon alignment, a proximal pin within the shaft of each scalpet is advanced down the shaft of the scalpet to extrude the hair plug into the fractionally resected defect of the recipient site, thereby effecting a simultaneous transplantation of multiple hair plugs to the recipient site. This mass transplantation of hair plugs into a fractionally resected recipient site (e.g., of a balding scalp) is more likely to maintain the hair shaft alignment with other mass transplanted hair plugs of that recipient scalp site. Directed closure of the donor site field is performed in the most clinically effective vector, but is not so limited.

The fractional resection devices described herein are configured for tattoo removal. Many patients later in life desire removal of pigmented tattoos for a variety of reasons. Generally, removal of a tattoo involves the removal of the impregnated pigment within the dermis. Conventional tattoo removal approaches have been described from thermal ablation of the pigment to direct surgical excision. Thermal ablation by lasers frequently results in depigmentation or area surface scarring. Surgical excision of a tattoo requires the requisite linear scarring of a surgical procedure. For many patients, the tradeoff between tattoo removal and the sequela of the procedure can be marginal.

The use of fractional resection to remove a tattoo allows for fractional removal of a significant proportion of the dermal pigment with minimal visible scarring. The fractional resection extends beyond the border of the tattoo to blend the resection into the non-resected and non-tattooed skin. Most apparently, de-delineation of the pattern of the tattoo will occur even if all residual pigment is not or cannot be removed. In an embodiment, initial fractional resections are performed with a scalpel array, and any subsequent fractional resections are performed by singular scalpel resections for residual dermal pigment. As with other applications described herein, directed closure is performed in the most clinically effective vector.

The fractional resection devices described herein are configured for treatment of cellulite. This aesthetic deformity has resisted effective treatment for several decades as the pathologic mechanism of action is multifactorial. Cellulite is a combination of age or weight loss skin laxity with growth and accentuation of the superficial fat loculations. The unsightly cobblestone appearance of the skin is commonly seen in the buttocks and lateral thighs. Effective treatment should address each contributing factor of the deformity.

The fractional resection devices described herein are configured for fractional resection of the skin in order to tighten the affected skin and to simultaneously reduce the prominent fat loculations that are contributing to the cobblestone surface morphology. Through the same fractionally resected defects created for skin tightening, topically applied vacuum is used to suction the superficial fat loculations percutaneously. In an embodiment, a clear manifold suction cannula is applied directly to the fractionally resected skin surface. The appropriate vacuum pressure used with the suction-assisted lipectomy (SAL) unit is determined by visually gauging that the appropriate amount of sub-dermal fat being suction resected. The appropriate time period of manifold application is also a monitored factor in the procedure. When combined with fractional skin tightening, only a relatively small amount of fat is suction resected to produce a smoother surface morphology. As with other applications described herein, the fractionally resected field will be closed with directed closure.

The fractional resection devices described herein are configured for revision of abdominal striae and scarring. Visually apparent scarring is a deformity that requires clear delineation of the scar from the adjacent normal skin. Delineation of the scar is produced by changes in texture, in pigment and in contour. To make a scar less visibly apparent, these three components of scarring must be addressed for a scar revision to significantly reduce the visual impact. Severe scars called contractures across a joint may also limit the range of motion. For the most part, scar revisions are performed surgically where the scar is elliptically excised and carefully closed by careful coaptation of excised margins of the non-scarred skin. However, any surgical revision reintroduces and replaces the pre-existing scar with an incumbent surgical scar that may be also be delineated or only partially de-delineated by a Z or W plasty.

Scarring is bifurcated diagnostically into hypertrophic and hypotrophic types. The hypertrophic scar typically has a raised contour, irregular texture and is more deeply pigmented. In contrast, the hypotrophic scar has a depressed contour below the level of the adjacent normal unscarred skin. In addition, the color is paler (depigmented) and the texture is smoother than the normal adjacent skin. Histologically, hypertrophic scars posses an abundance of disorganized dermal scar collagen with hyperactive melanocytes. Hypotrophic scars have a paucity of dermal collagen with little or no melanocytic activity.

The fractional resection devices described herein are configured for fractional scar revision of a scar that does not reintroduce additional surgical scarring but instead significantly de-delineates the visual impact of the deformity. Instead of a linear surgically induced scar, the fractional resection of the scar results in a net reduction of the pigmentary, textural and contour components. A fractional revision is performed along the linear dimension of the scar and also extends beyond the boundary of the scar into the normal skin. The fractional revision of a scar involves the direct fractional excision of scar tissue with micro-interlacing of the normal non-scarred skin with the residual scar. Essentially, a micro W-plasty is performed along the entire extent of the scar. As with other applications, the fractionally resected field is closed with directed closure. An example of the use of fractional revision includes revising a hypotrophic post-partum abdominal stria. The micro-interlacing of the depressed scar epithelium and dermis of the stria with the adjacent normal skin significantly reduces the depressed, linear and hypo-pigmented appearance of this deformity.

The fractional resection devices described herein are configured for vaginal repair for postpartum laxity and prolapse. The vaginal delivery of a full term fetus involves in part the massive stretching of the vaginal introitus and vaginal canal. During delivery, elongation of the longitudinal aspect of the vaginal canal occurs along with cross-sectional dilatation of the labia, vaginal introitus and vaginal vault. For many patients, the birth trauma results in a permanent stretching of the vaginal canal along the longitudinal and cross-sectional aspects. Vaginal repair for prolapse is typically performed as an anterior-posterior resection of vaginal mucosa with insertion of prosthetic mesh. For patients with severe prolapse, this procedure is required as addition support of the anterior and posterior vaginal wall is needed. However, many patients with post-partum vaginal laxity may be candidates for a less invasive procedure.

The fractional resection devices described herein are configured for fractional resection of the vaginal mucosa circumferentially to narrow the dilated vaginal canal at the labia and the introitus. The pattern for fractional resection can also be performed in a longitudinal dimension when the vaginal canal is elongated. Directed closure of the fractional field can be assisted with a vacuum tampon that will act as stent to shaped the fractionally resected vaginal canal into a pre-partum configuration.

The fractional resection devices described herein are configured for treatment of snoring and sleep apnea. There are few health implications of snoring but the disruptive auditory effect upon the relationship of sleeping partners can be severe. For the most part, snoring is due to the dysphonic vibration of intraoral and pharyngeal soft tissue structures within the oral, pharyngeal and nasal cavities during inspiration and expiration. More specifically, the vibration of the soft palate, nasal turbinates, lateral pharyngeal walls and base of the tongue are the key anatomic structures causing snoring. Many surgical procedures and medical devices have had limited success in ameliorating the condition. Surgical reductions of the soft palate are frequently complicated with a prolonged and painful recovery due to bacterial contamination of the incision site.

The fractional resection devices described herein are configured for fractional resection of the oropharyngeal mucosa in order to reduce the age related mucosal redundancy (and laxity) of intraoral and pharyngeal soft tissue structures and not be complicated with prolonged bacterial contamination of the fractional resection sites. The reduction in size and laxity of these structures reduces vibration caused by the passage of air. A perforated (to spray a topical local anesthetic onto the fractional resection field) intraoral dental retainer (that is secured to the teeth and wraps around the posterior aspect of the soft palate) is used to provide directed closure in the anterior-posterior dimension of the soft palate. A more severe condition called sleep apnea does have serious health implications due to the hypoxia caused by upper airway obstruction during sleep. Although CPAP has become a standard for the treatment of sleep apnea, selective fractional resection of the base of the tongue and the lateral pharyngeal walls can significantly reduce sleep related upper airway obstruction.

The fractional resection devices described herein are configured for fractional skin culturing/expansion, also referred to herein as "Culturespansion". The ability to grow skin organotypically would be a major accomplishment for patients with large skin defects such as burns and trauma and major congenital skin malformations such port wine stains and large 'bathing trunk' nevi. Conventional capability is limited to providing prolonged viability of harvested skin, although some reports have indicated that wound healing has occurred with organotypic skin cultured specimens. It has been reported that enhanced cultured outcomes will occur with better substrates, cultured media and more effective filtration of metabolic byproducts. The use of gene expression proteinomics for growth hormone and wound healing stimulation is also promising. To date however, there is no report that skin has been grown organotypically.

The fractional harvesting of autologous donor skin for skin grafting under an embodiment provides an opportunity in the organotypic culture of skin that did not previously exist. The deposition of a fractionally harvested skin graft onto a collapsible docking station, as provided by the embodiments described herein, enables skin plugs to be brought into contact apposition with each other. The induction of a primary wound healing process can convert a fractional skin graft into a solid sheet by known or soon to be developed organotypic culture methodology. Further, the use of mechanical skin expansion can also greatly increase the surface area of the organotypically preserved/grown skin. Invitro substrate device iterations include without limitation, an expandable docking station comprising fractionally harvested skin plugs and a separate substrate (e.g., curved, flat, etc.) expander that is controllable to provide a gradual and continual expansion of the full thickness organotypically cultured skin. Additionally, the use of organotypic skin expansion may provide a continual and synergistic wound-healing stimulus for organotypic growth. A gradual and continual expansion is less likely to delaminate (the basement membrane) the epidermis from the dermis. Additionally, organotypic skin expansion helps avoid the surgical risk and pain associated in-vivo skin expansion.

The fractional resection devices described herein enable methods for the organotypic expansion of skin. The methods comprise an autologous fractional harvest of skin from a donor site of a patient. The use of a square scalpel array, for example, provides upon transfer side-to-side and tip-to-tip coaptation of fractionally harvested skin plugs. The method comprises transfer of the fractional skin plugs to a collapsible docking station that maintains orientation and provides apposition of skin plugs. The docked skin plugs are captured onto a porous adherent membrane that maintains orientation and apposition. The semi-elastic recoil property of the adherent membrane provides additional contact and apposition of skin plugs. The method includes transfer of the adherent membrane/fractional graft composite to a culture bay comprising a substrate and a culture media that retains viability and promotes organotypic wound healing and growth. Following healing of skin plug margins, the entire substrate is placed into a culture bath that has a mechanical expander substrate. Organotypic expansion is then initiated in a gradual and continuous fashion. The expanded full thickness skin is then autologously grafted to the patient's recipient site defect.

Organotypic skin expansion can be performed on non-fractional skin grafts or more generally, on any other tissue structure as organotypic expansion. The use of mechanical stimulation to evoke a wound healing response for organotypic culture can also be an effective adjunct.

The embodiments described herein are used with and/or as components of one or more of the devices and methods described in detail herein and in the Related Applications incorporated herein by reference. Additionally, the embodiments described herein can be used in devices and methods relating to fractional resection of skin and fat.

Embodiments include a novel minimally invasive surgical discipline with far-reaching advantages to conventional plastic surgery procedures. Fractional resection of skin is applied as new stand-alone procedures in anatomical areas that are off limits to conventional plastic surgery due to the poor tradeoff between the visibility of the incisional scar and amount of enhancement obtained. Fractional resection of skin is also applied as an adjunct to established plastic surgery procedures such as liposuction, and is employed to significantly reduce the length of incisions required for a particular application. The shortening of incisions has application in both the aesthetic and reconstructive realms of plastic surgery. Without limitation, both the procedural and apparatus development of fractional resection are described in detail herein.

Figure 83:
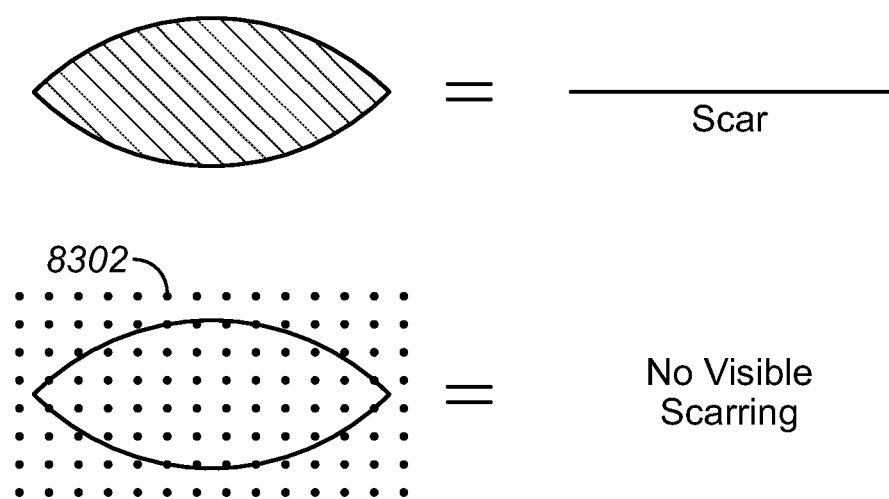
FIG. 83 depicts removal of lax excess skin without apparent scarring, under an embodiment.
Figure 84:
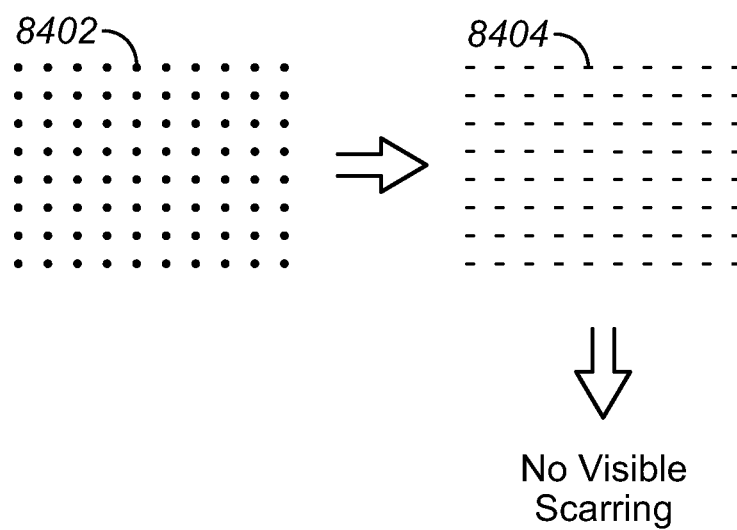
FIG. 84 depicts tightening of skin without apparent scarring, under an embodiment.
Figure 85:
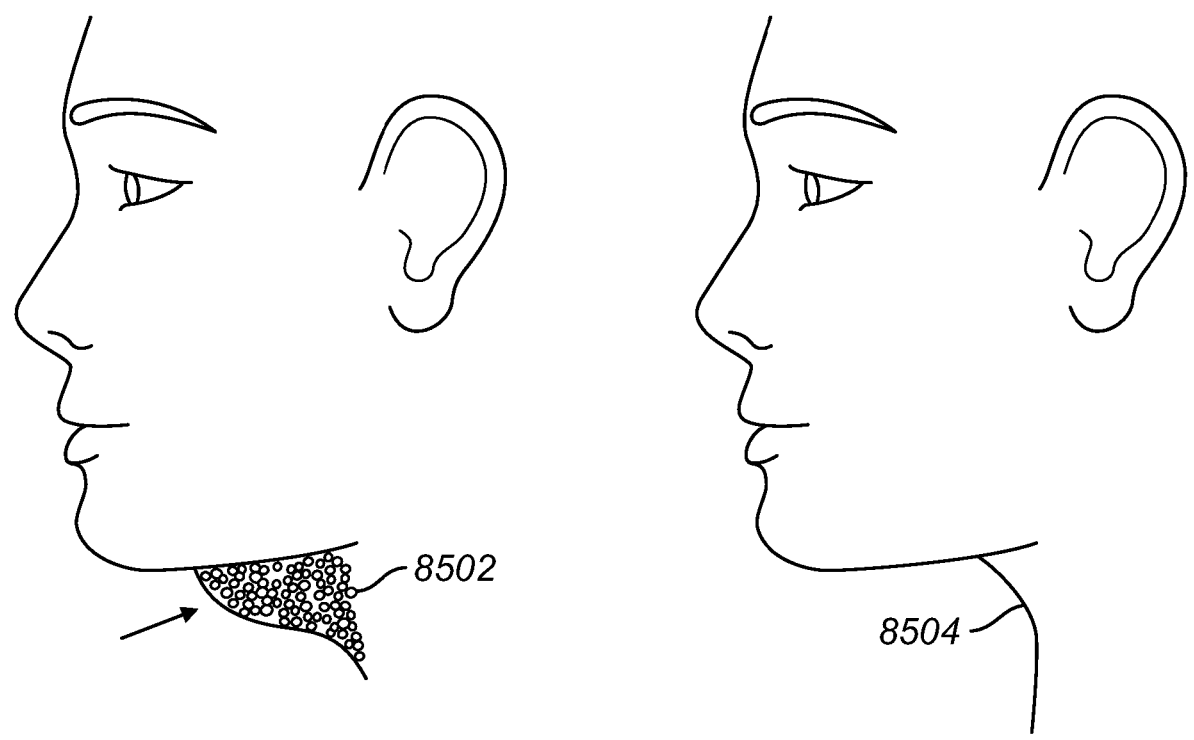
FIG. 85 depicts three-dimensional contouring of the skin envelop, under an embodiment.

Embodiments described herein are configured to remove multiple small sections of skin without scarring in lieu of the conventional linear resections of skin. The removal of multiple small sections of skin includes removal of lax excess skin without apparent scarring. As an example, FIG. 83 depicts removal of lax excess skin without apparent scarring, under an embodiment. The removal of multiple small sections of skin also includes tightening of skin without apparent scaring, for example, FIG. 84 depicts tightening of skin without apparent scaring, under an embodiment. The removal of multiple small sections of skin further includes fractional skin tightening in which the clinical endpoint results in three-dimensional contouring of the skin envelop. FIG. 85 depicts three-dimensional contouring of the skin envelop, under an embodiment.

The clinical effectiveness of any surgical manipulation requires a through understanding of the underlying processes that lead reliably to a clinical endpoint. For fractional skin tightening and contouring, a number of mechanisms of action are described herein. The principle mechanism of action identified is the conversion of two-dimensional fractional skin tightening into three-dimensional aesthetic contouring (e.g., see FIG. 3). Contributory to that principle clinical endpoint are secondary mechanisms of action that serve in concert with each other. The contributory mechanisms of action are described herein according to their capability to achieve the clinical endpoint, but are not so limited.

Figure 86:
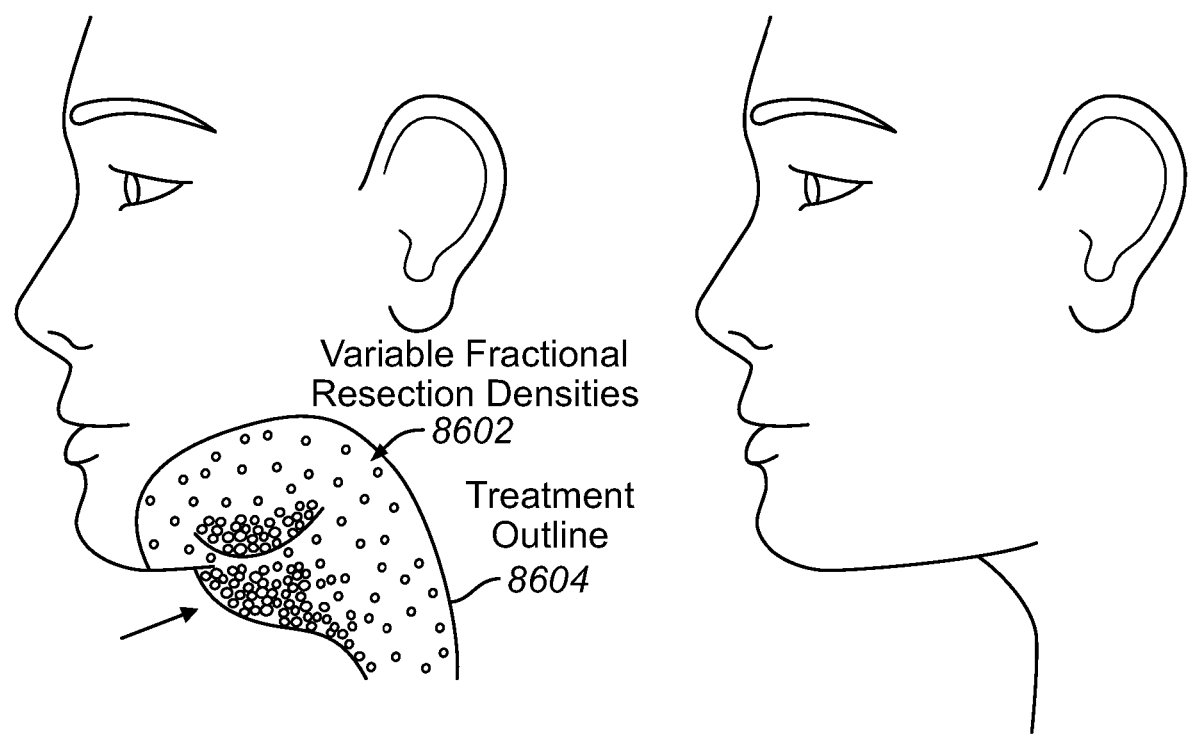
FIG. 86 depicts variable fractional resection densities in a treatment area, under an embodiment.

The density of fractional resection within an outlined fractional field is a primary determinate of two-dimensional skin tightening contributing to three-dimensional contouring. Generally, the density is the percentage of fractionally resected skin within the fractional field but is not so limited. FIG. 86 depicts variable fractional resection densities in a treatment area, under an embodiment. The density of fractional resection ("fractional density") can be varied to provide more selected skin tightening and contouring while providing smoother transitions into non-fractionally resected areas. Therefore, for example, transitions into non-fractionally resected areas include a reduction in the fractional density but are not so limited.

Figure 87:
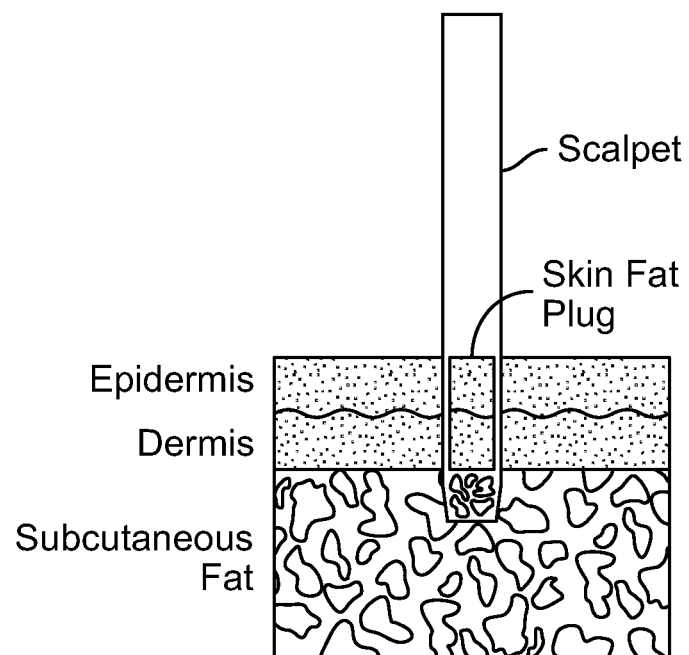
FIG. 87 depicts fractional resection of fat, under an embodiment.

Another mechanism of action associated with fractional skin resection is the fractional resection of fat. FIG. 87 depicts fractional resection of fat, under an embodiment. Immediately subjacent to the skin are the sub-dermal and subcutaneous fat layers where a variable amount of fat (based on depth and/or amount) can be fractionally resected in anatomical continuity with the resected skin plug. A variable amount of fat fractionally resected, and hence an amount of skin tightening and contouring, is controlled in an embodiment by controlling one or more of a depth of the resection at the target site and an amount of fat resected. Thus, the density of fractional resection ("fractional density") can be varied by controlling one or more of fractional density, resection depth, and amount of fact resected in order to provide more selected skin tightening and contouring while providing smoother transitions into non-fractionally resected areas. Therefore, for example, transitions into non-fractionally resected areas include a reduction in a combination of fractional density, resection depth, and amount of fact resected, but are not so limited.

Figure 88:
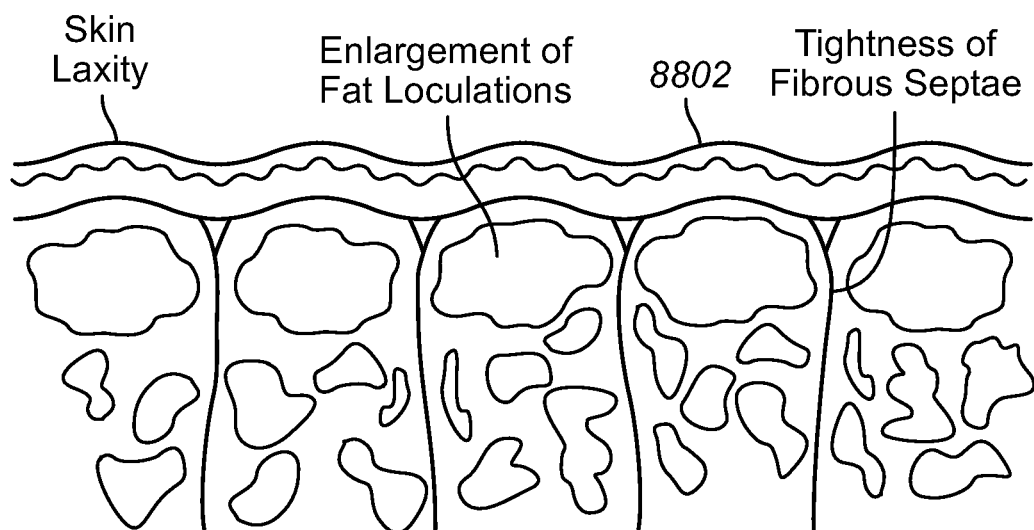
FIG. 88 depicts cobblestoning of the skin surface.

An additional modality for fractional fat resection is the percutaneous vacuum resection (PVR) of fat directly through the skin fractional defects. Numerous clinical applications of fractional fat resection are anticipated in the embodiments herein. The most significant aesthetic application of fractional fat resection is the reduction of cellulite. The combined in-continuity application of fractional skin and fat resection directly addresses the underlying pathology of this aesthetic deformity. The skin laxity and prominent loculations of fat producing visible surface cobblestoning of skin morphology are each resolved in concert with the application of this minimally invasive resection capability. FIG. 88 depicts cobblestoning of the skin surface.

Figure 89:
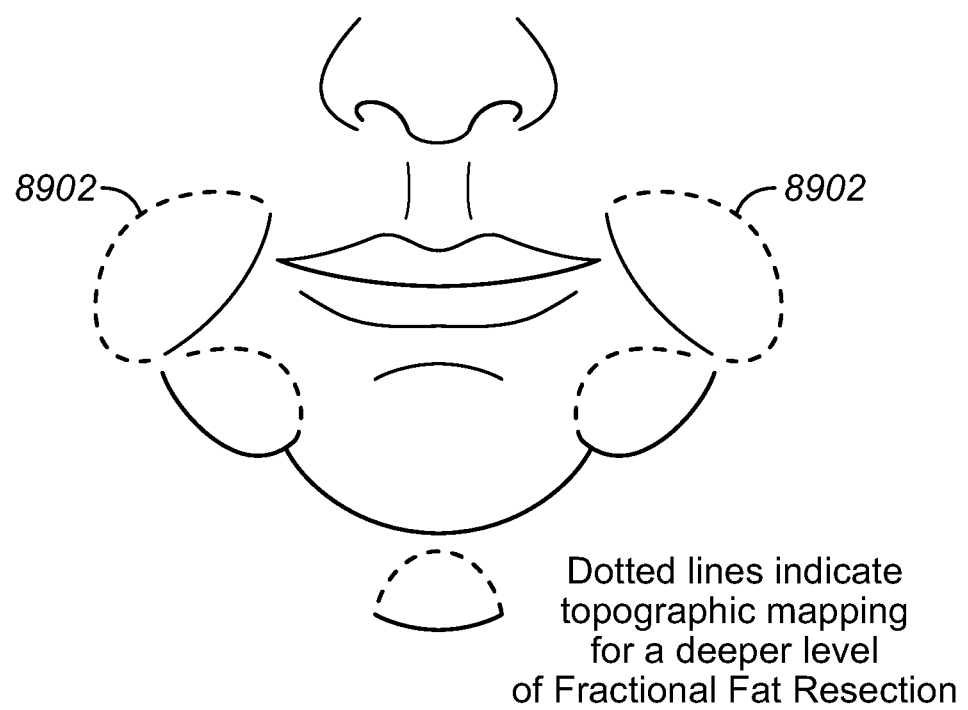
FIG. 89 depicts topographic mapping for a deeper level of fractional fat resection, under an embodiment.

Furthermore, another general application includes the ability to alter three-dimensional contour abnormalities with a combined in-continuity approach of fractional skin tightening and inward contouring from fractional fat resection. The pre-operative topographical contour mapping of the fractional field assists in providing a more predictable clinical outcome. Essentially, a topographical mapping of two-dimensional fractional skin resection is combined with a variable marking for fat resection. FIG. 89 depicts topographic mapping for a deeper level of fractional fat resection, under an embodiment. Mapping also includes the feathering or transition zones into non-resected areas where the fractional density is reduced. Depending upon the pre-operative topographical marking of the patient, a variable amount of fat is fractionally resected in continuity with fractional skin resection.

Areas to be corrected comprising convex contours undergo deeper fractional fat resections. Concave (or depressed) areas to be corrected are corrected using fractional skin resection. The net result within the mapped fractional field is overall smoothing of three-dimensional contours with two-dimensional tightening of the skin.

The use of combined fractional resection is most apparent with the reduction in the length required for conventional plastic surgery incisions and with the elimination of iatrogenic incisional skin redundancies ("Dog Ears"). Standard resection of skin lesions does not require the additional scarring of elliptical incisions but is significantly reduced in the linear dimension required for closure of an excised lesion (see FIG. 94).

Figure 90:
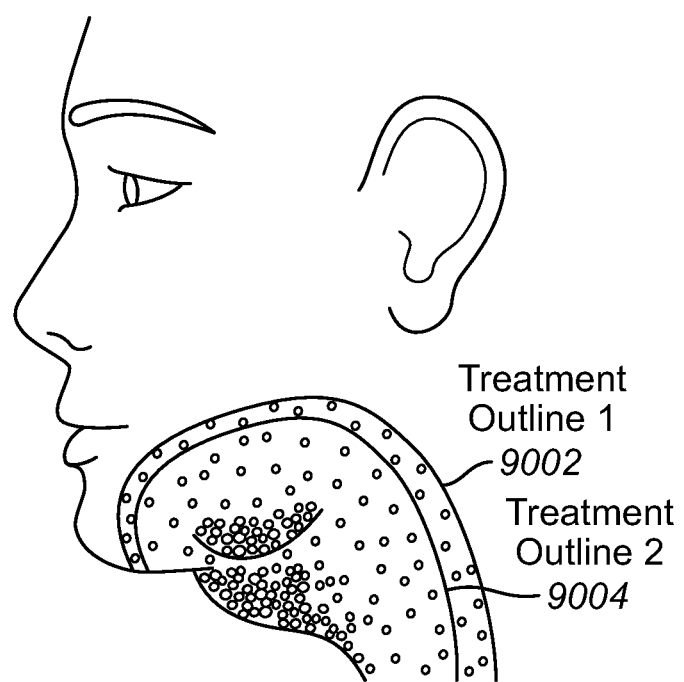
FIG. 90 depicts multiple treatment outlines, under an embodiment.

An additional mechanism of action associated with fractional skin resection is the size of the overall outlined pattern of the fractional resection field. The overall amount of fractionally resected skin also depends on the size of the fractionally resected field. The larger the field, the more skin tightening occurs with a specified density of fractional resection. FIG. 90 depicts multiple treatment outlines, under an embodiment.

Figure 91:
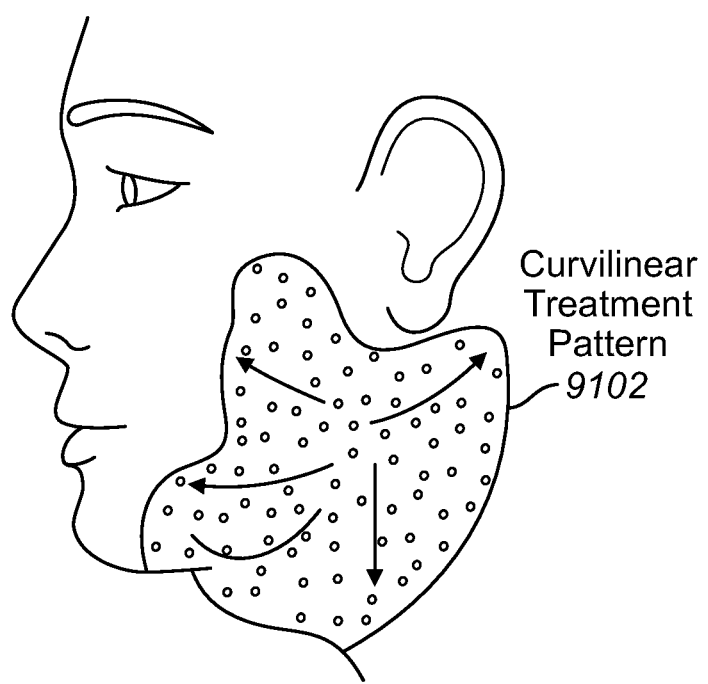
FIG. 91 depicts a curvilinear treatment pattern, under an embodiment.
Figure 92:
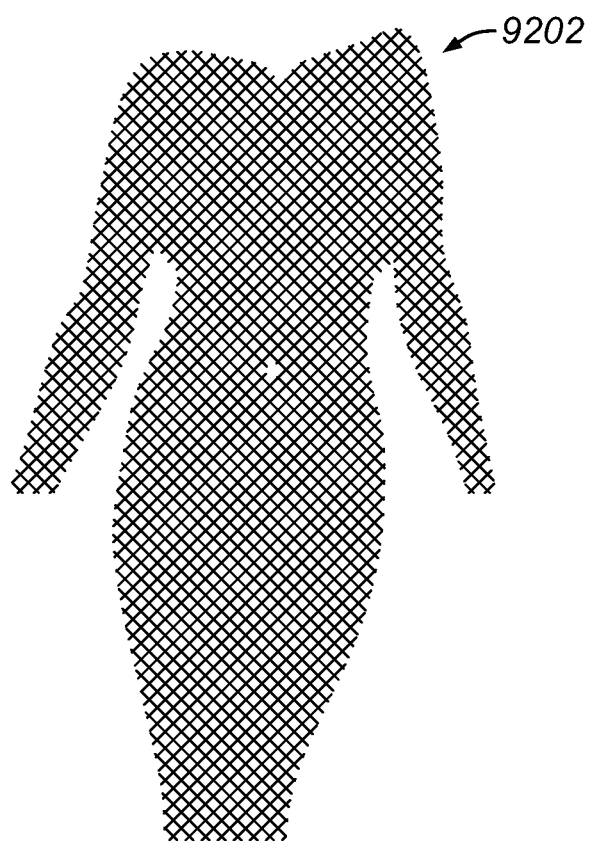
FIG. 92 depicts a digital image of a patient with rendered digital wire mesh program, under an embodiment.

The mechanism of action of a patterned outline includes the selective curvilinear patterning of each particular anatomical area for each particular patient. A topographical analysis with a digitally captured image of the patient involving a rendered (and re-rendered to an enhanced contour) digital wire mesh program assists in formatting the size and curvilinear outline for a selected anatomical region and patient. The pattern of standard aesthetic plastic surgery excisions for a particular anatomic region also assists in the formatting of the fractional resection pattern. FIG. 91 depicts a curvilinear treatment pattern, under an embodiment. FIG. 92 depicts a digital image of a patient with rendered digital wire mesh program, under an embodiment.

Embodiments comprise directed closure to close a multiplicity of incisional defects (without suturing) within a fractional field while providing significant advantages for aesthetic contouring. Directed closure provides the ability to close the fractional field in the most effective vector for three-dimensional aesthetic contouring. An example of directed closure involves the use of Langer's lines where the vector of directed closure is indicated according to the deformation of the fractionally resected defects. In this case, the vector of closure is performed at right angles to the longitudinal deformation of the defects. Closure as indicated by Langer's lines promotes primary healing of the fractionally resected field by decreasing the tension of the closure.

Another example involves the use of directed closure in the submentum where two vectors are used to provide aesthetic contouring by accentuating the cervical mandibular and cervical mental angles. The vectors used for closure are obliquely horizontal along the inferior portion of the field and obliquely vertical along the superior portion of the field that is immediately inferior to the chin.

Directed closure includes numerous techniques involving an elastic membrane (e.g., Flexzan), but is not so limited. Embodiments include a single mooring technique to close the fractional defects by first mooring the adherent Flexzan sheet adjacent to the fractional field and then pulling the membrane in the direction of the optimal vector for either aesthetic contour or for closure with reduced tension (as indicated by Langer's lines). The material is then adhered on the other opposing side of the fractional field. Alternatively, a double mooring technique is used when two separated sheets of Flexzan are each moored on opposite sides of the field and then pulled and adhered together in the center of the fractional field.

Directed closure of a fractionally resected field of an embodiment provides the capability of selectively tightening skin to achieve enhanced aesthetic contouring. For most applications, the closure occurs at right angles to Langer's lines but may also be done at a different direction that achieves maximal aesthetic contour such as closures that are based on resting skin tension lines. FIG. 93 depicts directed closure of a fractionally resected field, under an embodiment. The directed closure may also follow known vectors of closure used in conventional plastic surgery procedures (e.g., facelift for the facial/submental component of the facelift is upwards (corresponding to a horizontal directed closure of a fractional field) and the neck component below the cervical mandibular angle is more obliquely posterior (corresponding to a more vertical directed closure of the fractional field)). Multiple vectors of directed closure may also be used in more complicated topographical regions such as the face and neck.

Figure 94:
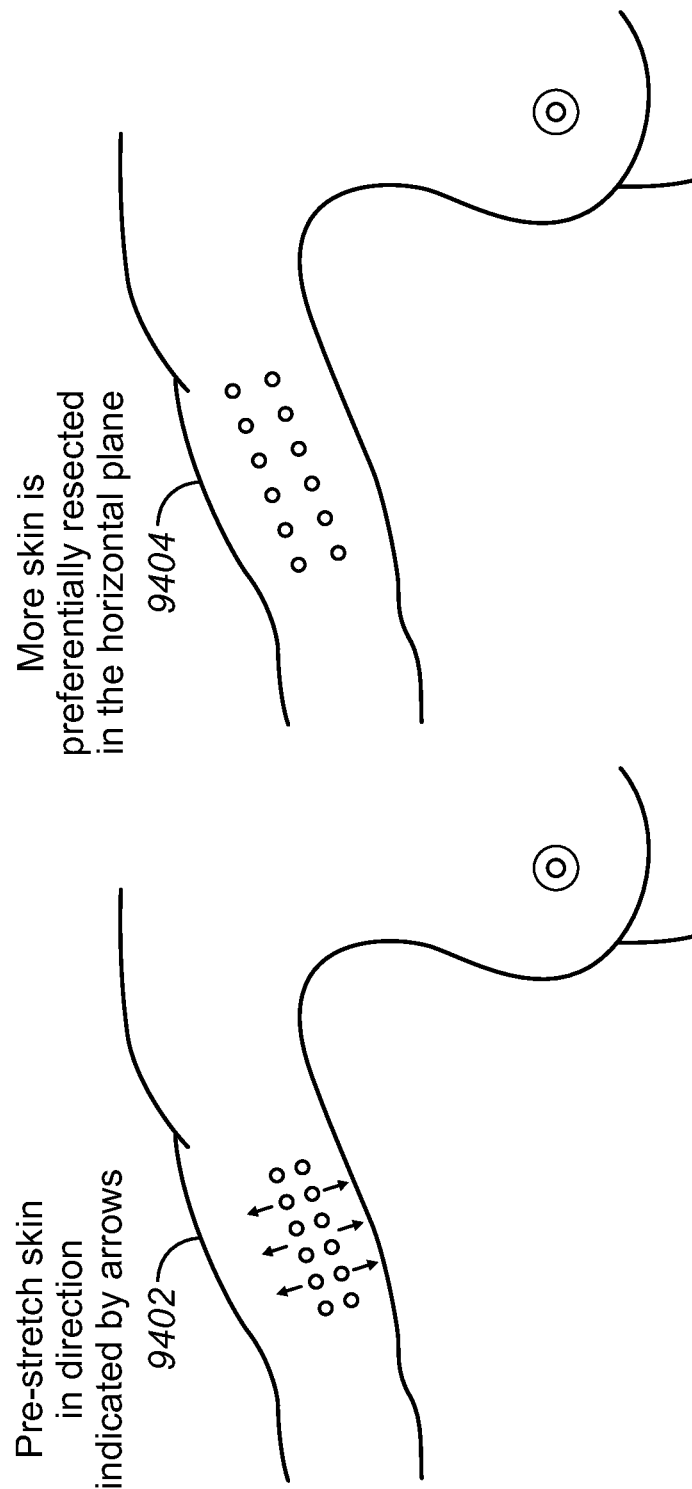
FIG. 94 depicts directed fractional resection of skin, under an embodiment.

Embodiments include directed fractional resection of skin, which enhances the effectiveness of the procedure. This process is performed by pre-stretching the skin at right angles to the preferred direction of maximal skin resection. FIG. 94 depicts directed fractional resection of skin, under an embodiment.

Embodiments include aesthetic contouring resulting from the mechanical pull (or vector) created from an adjacent fractional field adjacent to the targeted contour. This effect for a fractional field is based on plastic surgical procedures that are directed a distance from the targeted contour. Further, variable topographical transitioning of resection densities within the field and along the pattern outline are realized, which provide selective contouring and smoother transitioning into non-resected areas. Additionally, variable topographical transitioning of scalpel size resections within a patterned outline (and with different scalpel sizes within an array) provides selective two-dimensional skin tightening and three-dimensional contouring.

Embodiments described herein evoke a selective wound healing sequence with promotion of primary healing during the immediate post-operative period and delayed secondary contraction of skin during the collagen proliferative phase. Promotion of accurate coaptation of the skin margins is inherent to the multiple (fractional) resections of small segments of skin i.e., skin margins are more closely aligned prior to closure than larger linear resections of skin that are common with standard plastic surgery incisions. Subsequent evoking of wound contraction is also inherent to a fractionally resected field where elongation of the pattern of fractional resection provides a directed wound healing response along the longitudinal dimension of the fractionally resected pattern.

Clinical methods of fractional skin resection involve methods of directional closure. Depending upon the anatomical area, the directed closure of excisional skin defects within a fractional resection field is achieved by following Langer's lines, the resting skin lines, and/or in a direction that achieves the maximal of aesthetic contouring. The direction in which closure is most easily achieved can also be used as a guide for the most effective vector of directed closure. For many applications, the use of Langer's lines is used as a guide to provide maximal aesthetic tightening. Following the original work of Dr. Langer, the fractionally resected defects will elongate in the direction of a Langer line. The directed closure is performed at right angles to Langer's lines in an anatomical region where the skin margins of each fractional resection defect are in closest approximation.

In continuity fractional procedures that are deployed adjacent or in continuity with plastic surgery incisions, the most significant capability provided by the embodiments herein includes the ability to shorten incisions. The need for elliptical excisions of skin tumors is reduced in both the application of this technique and in the length of the incision. Thus, the need to excise the lateral extension of a tumor resection is obviated by the fractional resection at that same lateral aspect. FIG. 95 depicts shortening of incisions through continuity fractional procedures, under an embodiment.

Figure 96:
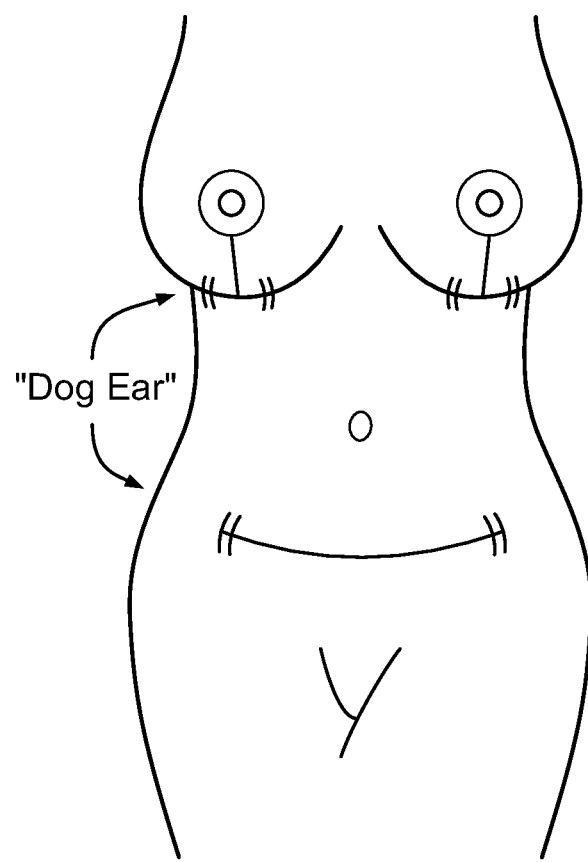

As the fractional field under an embodiment heals without visible scarring, the net result is significant reduction in the length of the excisional scar. Another application within this category is the shortening of conventional plastic surgery incisions used for breast reduction, Mastopexy and abdominoplasty. The lateral extent of these incisions can be shortened without the creation of "dog ear" skin redundancies that would otherwise occur with the same length incision. FIG. 96 is an example depiction of "dog ear" skin redundancies in breast reduction and abdominoplasty. For example, extensions of the incision beyond the lateral inframmary fold for breast reduction or beyond the Iliac crest for abdominoplasty would no longer be required. Fractional revisions of post-operative "dog ear" skin redundancies could also be performed without extension of the existing incision.

Embodiments include combined procedures that provide aesthetic enhancement at both the fractional resection harvest site and a recipient site. The most apparent application of this method is the use of fractional harvesting of the cervical beard for hair transplantation in the frontal and parietal scalp. A dual benefit is created by the procedure in which aesthetic contouring is created along the anterior neck and with restoration of the hair bearing scalp.

Embodiments include separate fractional procedures in anatomical areas that are not currently addressed by plastic surgery due to the poor tradeoff between the visibility of the surgical incision and the amount of aesthetic enhancement. Several examples exist in this category such as the suprapatellar knee, the upper arm, the elbow, bra skin redundancy of the back, and the medial and lateral thighs and the infragluteal folds.

Embodiments include adjunct fractional procedures that are deployed with conventional plastic surgery incisions in a non-contiguous fashion. This category includes suction-assisted lipectomy in which subcutaneous fat is removed by suction in areas of lipodystrophy such as the lateral hips and thighs. However, many patients have pre-existing skin laxity that is aggravated by suction lipectomy. The tightening of the skin envelope over these areas by fractional resection has several benefits to these patients. Many patients with skin laxity and lipodystrophy become candidates for liposuction who otherwise not qualify for the procedure. For patients without preexisting skin laxity but with more significant lipodystrophy, a larger contour reduction can be performed without iatrogenic skin laxity. The procedure can be deployed as a single combined procedure for smaller fractional resections or as a staged procedure.

Directed closure of the fractional field is performed without suturing and is achieved with the application of an adhesive stent membrane as described in detail herein. The fractional field is closed with an adhesive membrane using a number of methods. An example method includes anchoring the membrane outside the perimeter of the fractional field. Tension is then applied to the opposite end of the adhesive membrane. The body of the adhesive membrane is then applied to the fractional field row by row to the remaining skin within the field. The direction of application follows the selected vector of directed closure. This direction of application at times is at right angles to Langer's lines but is not so limited, and any direction of application can be chosen that provides maximal aesthetic contouring.

Another method includes use of the elastic property of the adherent stent dressing to selectively close a fractional field. With this method, the ends of the elastic stent dressing are stretched or preloaded, and the stent dressing is then applied to the fractional field. Upon release of the ends of the membrane, the elastic recoil of the stent dressing closes the fractional defects in a direction that is at right angles to the elastic recoil.

Embodiments described in detail herein include a skin Pixel Array Dermatome, also referred to herein as a "sPAD". The sPAD is a ganged multiple-scalpet array comprising a multiplicity of individual circular scalpels. The circular configuration enables rotational torque to be applied to the skin to facilitate incising. A coupling or linkage of the scalpets to an electromechanical power source is provided by series of gears between each scalpet and a drive shaft, as described herein. In addition, a vacuum is created within a housing and configured for stenting stabilization during incising. The same vacuum capability can also be applied as a pneumatic assist to apply additional axial (Z-axis) force during the incising duty cycle. Another vacuum application is the evacuation of incised skin plugs in the fractional field.

Figure 97:
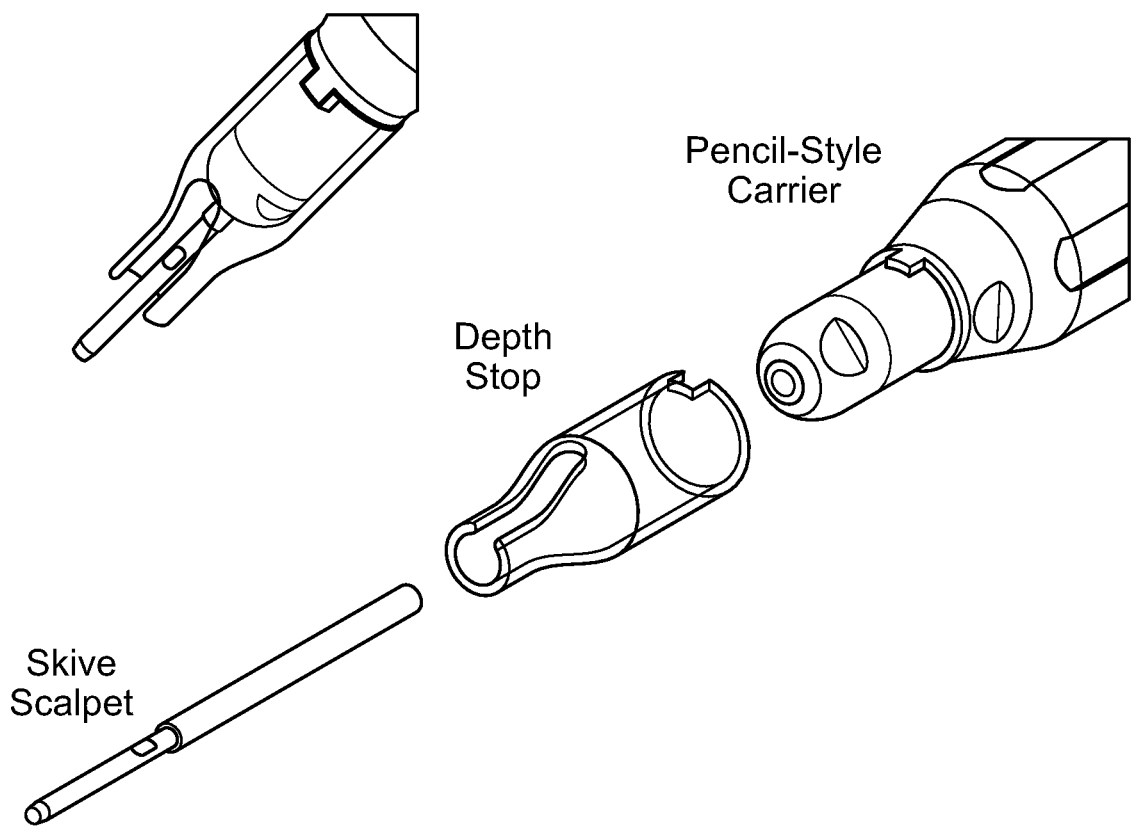
Figure 98:
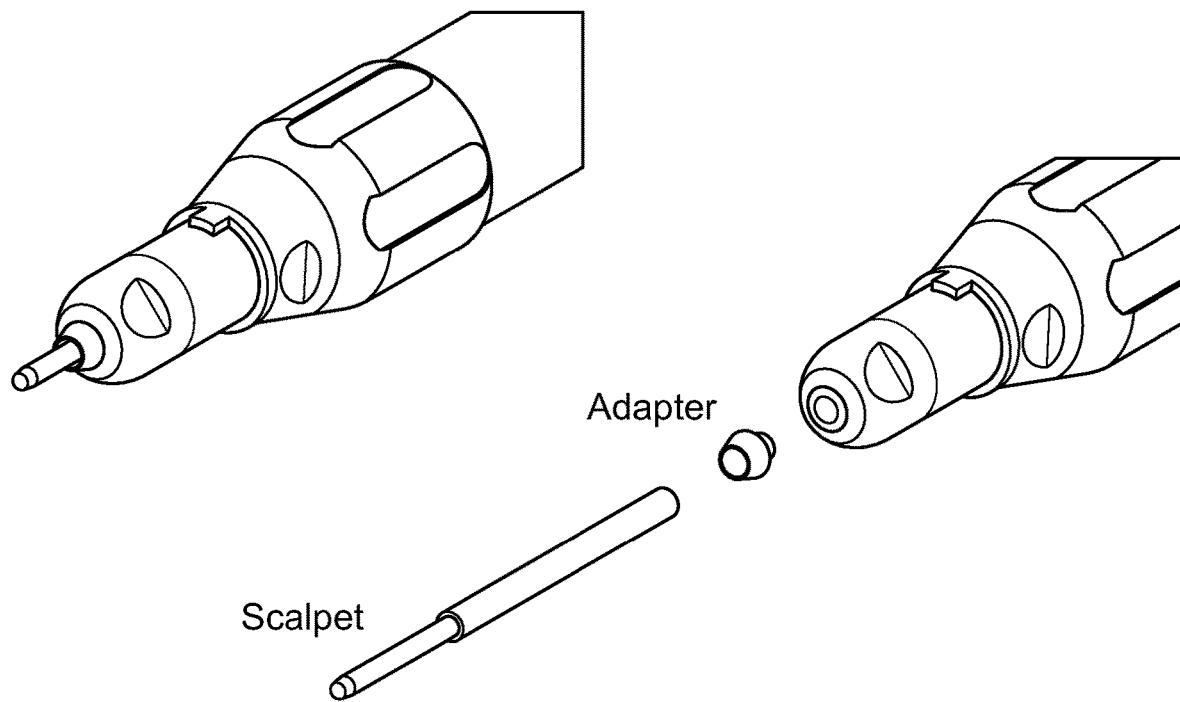
Figure 99:
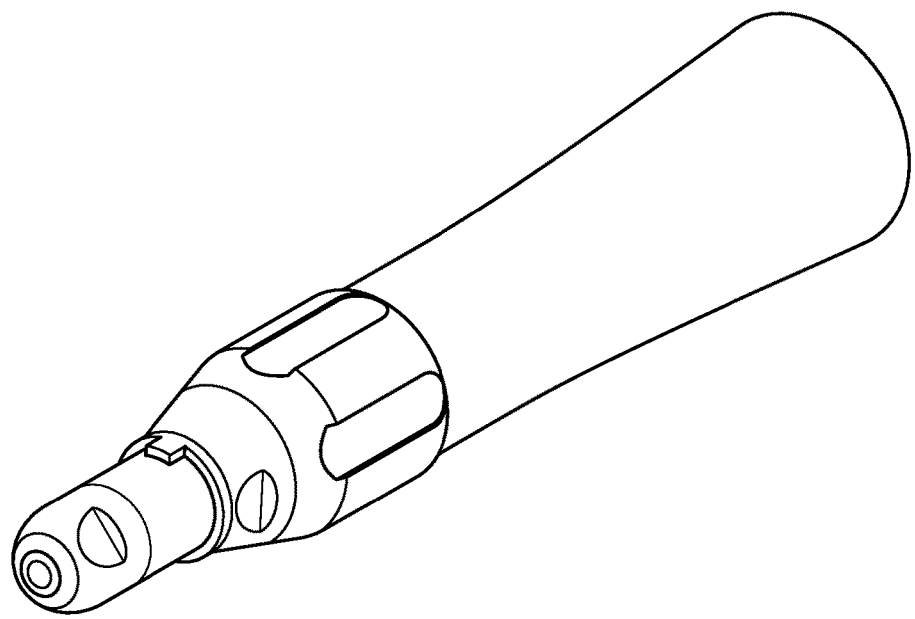
Figure 100:
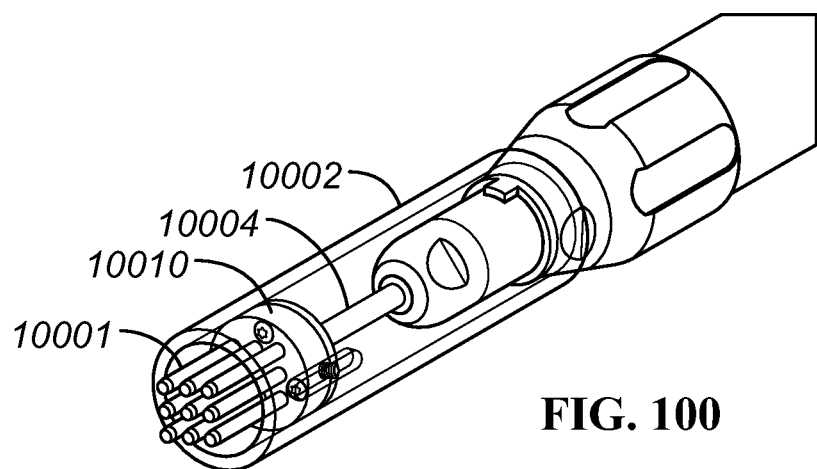

The sPAD includes numerous configurations as described in detail herein. FIG. 97 is a sPAD including a skived single scalpet with depth control, under an embodiment. FIG. 98 is a sPAD including a standard single scalpet, under an embodiment. FIG. 99 is a sPAD including a pencil-style gear reducing handpiece, under an embodiment. FIG. 100 is a sPAD including a 3×3 centerless array, under an embodiment.

Figure 101:
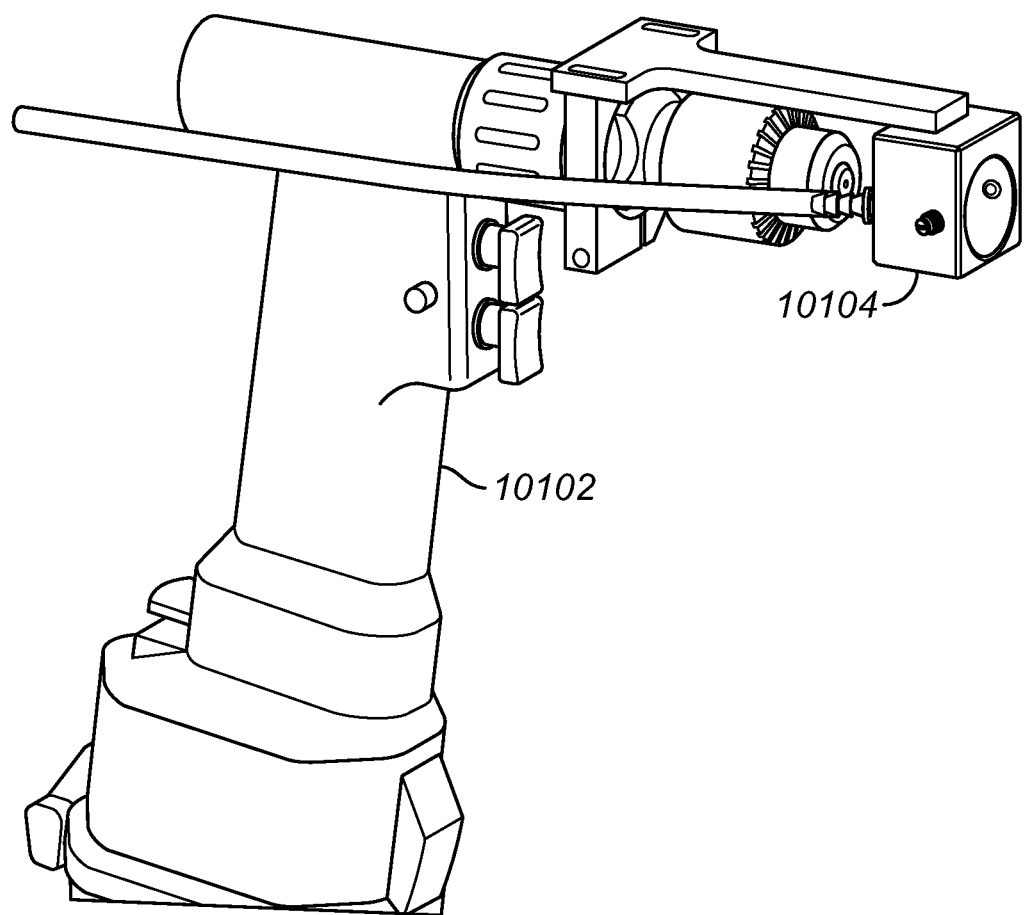
Figure 102:
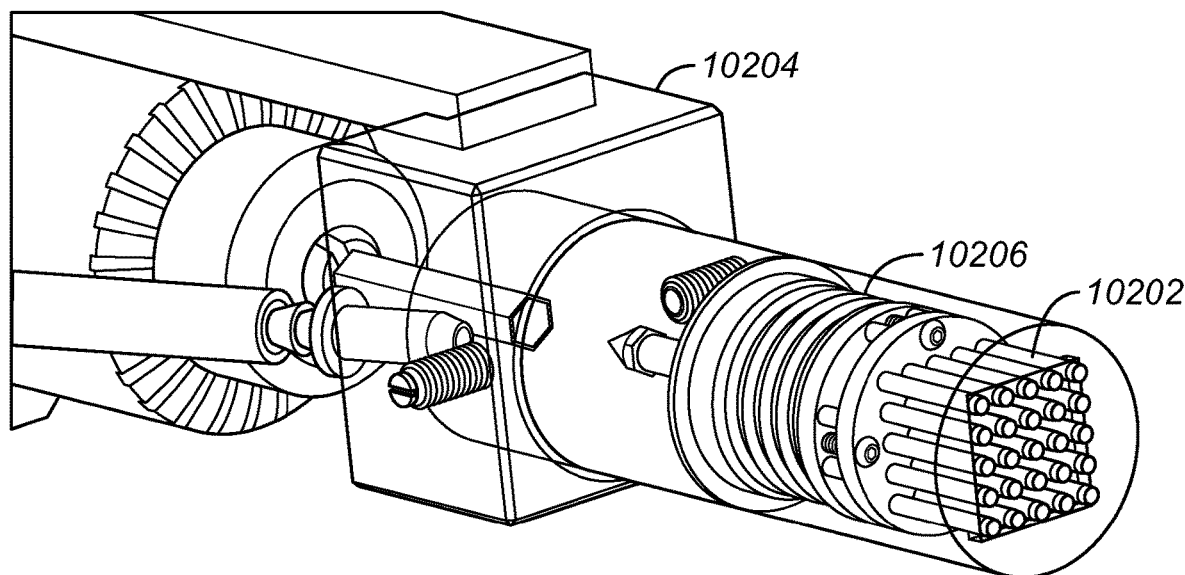

An instrument comprising a surgical drill is provided for use with the sPAD. FIG. 101 is a sPAD including a cordless surgical drill for large arrays, under an embodiment. FIG. 102 is a sPAD comprising a drill mounted 5×5 centerless array, under an embodiment.

Figure 103:
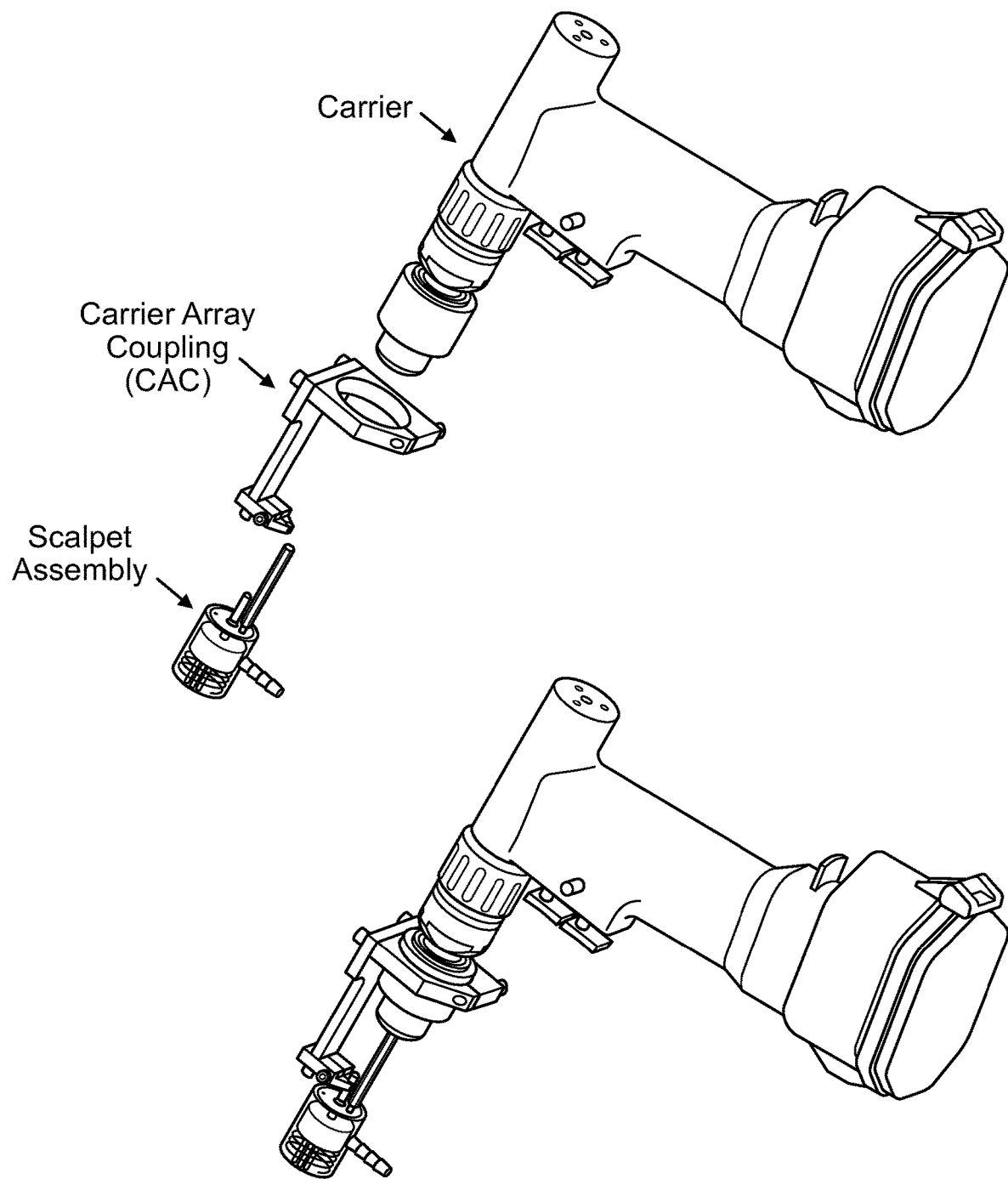
Figure 104:
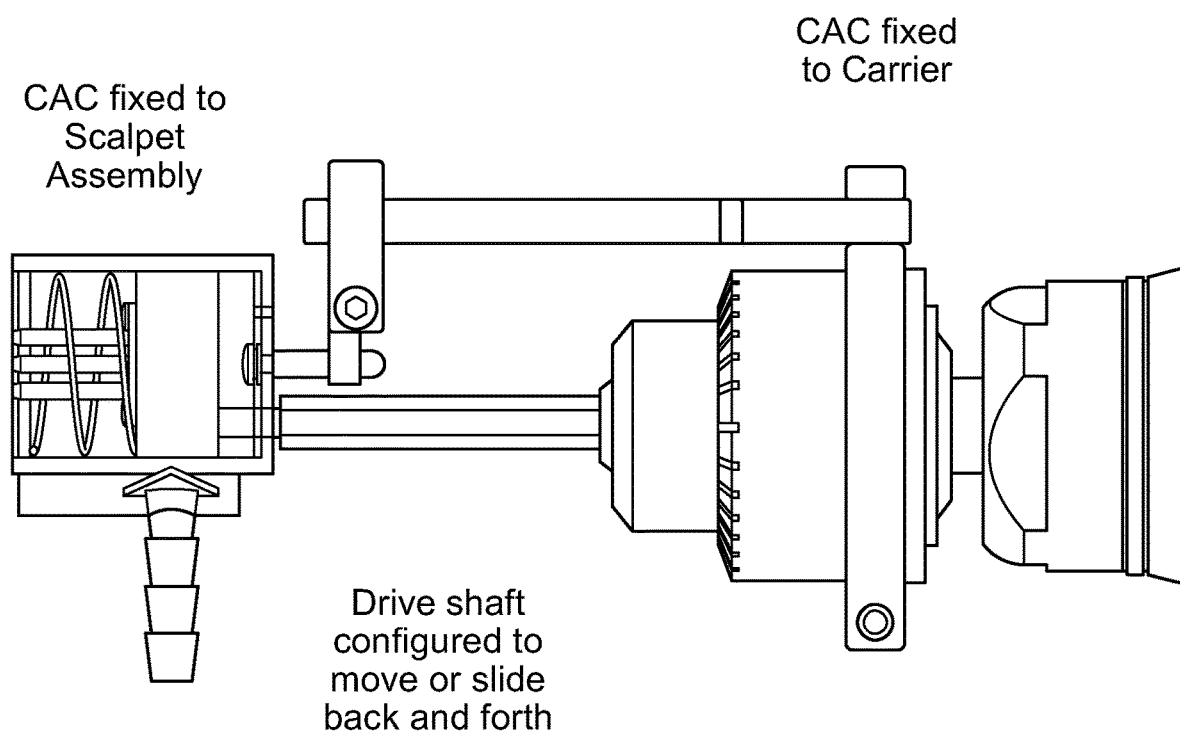

Embodiments include a Vacuum Assisted Pneumatic Resection (VAPR) Array sPAD, also referred to herein as a "VAPR sPAD". FIG. 103 is a sPAD including a vacuum assisted pneumatic resection sPAD, under an embodiment. The VAPR sPAD uses vacuum pressure configured to drive the scalpets from the sPAD into the treatment site. The VAPR sPAD is coupled or connected to a drill via a Drill Array Coupling (DAC). FIG. 104 is a VAPR sPAD coupled to a drill via a DAC, under an embodiment. The DAC fixes the housing of the VAPR sPAD to the drill, while the hexagonal tubing allows the VAPR sPAD drive shaft to slide up and down during the treatment. An externally supplied vacuum (not shown) is coupled or connected to the VAPR sPAD via the vacuum port.

Figure 105:
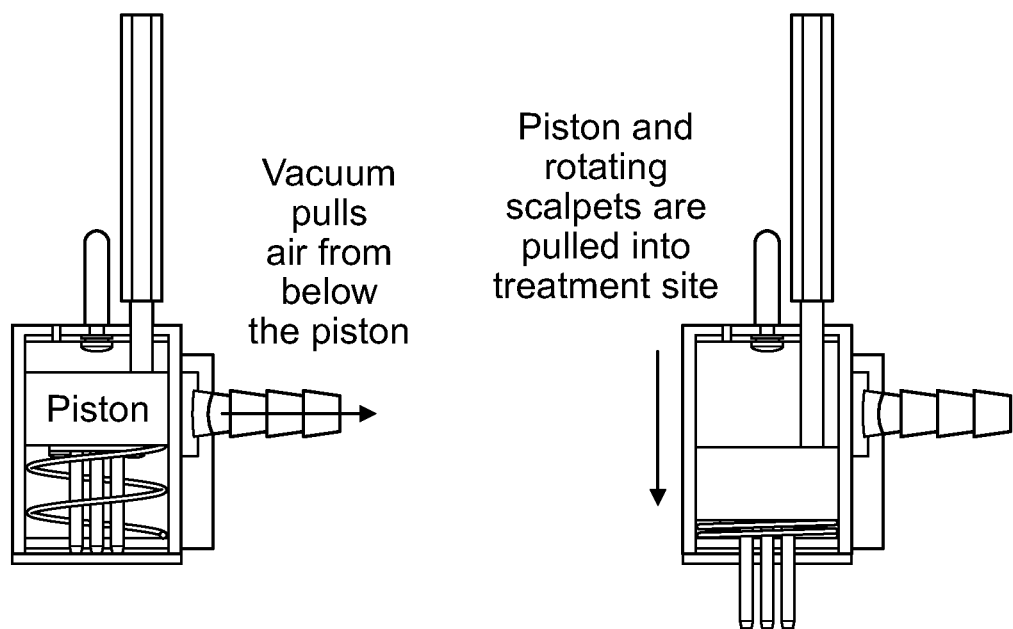

FIG. 105 depicts the VAPR sPAD in a ready state (left), and an extended treatment state (right), under an embodiment. With the vacuum and drill operating, a single treatment cycle comprises placing the VAPR sPAD against the treatment site, creating a seal between the housing and the treatment site. Once this seal is established, the vacuum pulls the piston with the rotating gears into the treatment site. After the desired depth of cutting has been achieved the SPAD is pulled away from the treatment site. This breaks the seal, and the spring inside the sPAD forces it back into its ready state. The cycle can now be repeated at a new treatment site.

Figure 106:
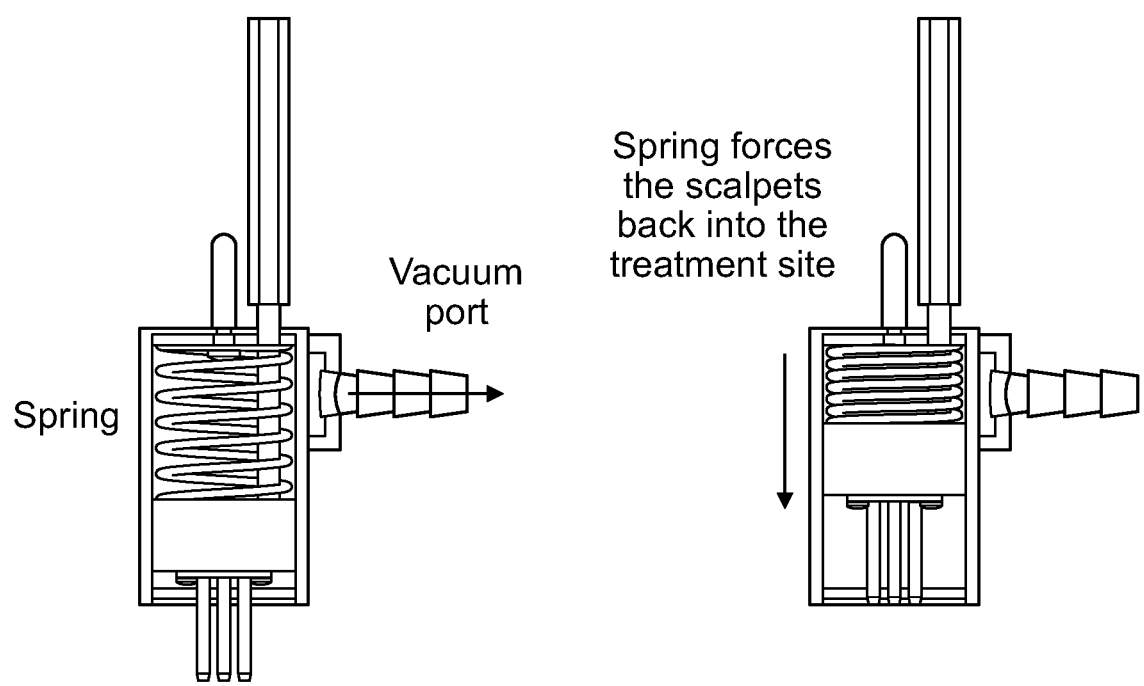

Embodiments include a Spring Assisted Vacuum Resection (SAVR) sPAD, which operates in a similar manner to the VAPR sPAD. FIG. 106 depicts the SAVR sPAD in a ready state (left), and a retracted state (right), under an embodiment. The SAVR sPAD is coupled or connected to the drill via the DAC. The vacuum port is attached to a separate vacuum supply. The drive shaft slides back and forth within the tube attached to the drill.

In the SAVR sPAD, the spring and vacuum locations have generally been reversed from the VAPR sPAD. The spring and vacuum port are both located on the proximal side of the piston but are not so limited. The vacuum assists in drawing the skin pixels out through the scalpets and hence away from the treatment site. The spring provides the axial force for the rotating scalpets to drive into the treatment site and resect the skin. The scalpets are extended outside the housing in array ready state.

The treatment cycle starts with the placement of the scalpets over the desired treatment location. The vacuum is turned on and the drill is applied downward, forcing the piston and scalpets back up into the housing (retracted state). The drill is turned, causing the scalpets to rotate. The spring force coupled with the scalpet rotation results in the resection. The vacuum draws the pixels generated by the resection up into and subsequently out of the housing. Once the desired cutting depth has been achieved, the SAVR sPAD is lifted off the treatment site and the cycle can be repeated.

Embodiments are described herein comprising instrumentation and procedures for aesthetic surgical skin tightening including, but not limited to, instruments or devices, and procedures that enable the repeated harvesting of skin grafts from the same donor site while eliminating donor site deformity. Embodiments herein include devices configured for fractional resection and corresponding methods or procedures, including single-scalpet and multi-scalpet array (MSA) platforms using a vacuum manifold. Additional disclosure of corresponding devices configured for fractional resection and corresponding methods or procedures is found in the Related Applications, each of which is herein incorporated by reference in its entirety. Regarding the use of vacuum in a fractionally resected field, the vacuum manifold is configured to apply vacuum intraluminally within the scalpet (or within a multi-scalpet array). Alternatively, the vacuum manifold is configured to apply vacuum extraluminally as either a component of the scalpet assembly or as a separate manifold device that is directly applied to the skin of the fractional field.

Applications of the vacuum capacity of the scalpet assembly include the suction evacuation of fractionally incised skin plugs (e.g., FIGS. 108, 112, and 113). Furthermore, applications of the vacuum capacity of the scalpet assembly include the vacuum stabilization of the skin surface during fractional resection (e.g., FIGS. 109 and 114). Additional applications of the vacuum capacity of the scalpet assembly include fractional vacuum-assisted lipectomy of the subcutaneous and subdermal fat layer (e.g., FIG. 114).

FIG. 107A is a cross-sectional side view of a carrier 1071 including a vacuum manifold 1072, under an embodiment. FIG. 107B is an isometric cross-sectional side view of the carrier 1071 including the vacuum manifold 1072, under an embodiment. FIG. 107C is a side view of the carrier 1071 including the vacuum manifold 1072, under an embodiment. The vacuum manifold 1072 is configured to be coupled or attached to a distal region of the carrier 1071 and scalpet assembly/scalpet array 1073. The vacuum manifold 1072 of an embodiment comprises a "slip-on" or overlay encasement configured to be removeably coupled to the distal end of the carrier 1071. This embodiment includes a scalpet array 1073 with a single scalpet, but is not so limited.

The vacuum manifold 107-2 includes a vacuum port 1074 configured to couple to a vacuum source (not shown). The vacuum manifold 1072 of an embodiment also includes an aspirator (not shown) but is not so limited. The vacuum manifold 1072 is configured, for example, to couple to an aperture (e.g., distal, proximal, side, etc.) and/or lumen of the scalpet(s) 1073 to intraluminally direct vacuum force to the target site. Alternatively, the vacuum manifold 1072 is configured to direct the vacuum force to the target site extraluminally (not shown).

Vacuum delivery of the device of an embodiment is controlled by an aperture component configured for manipulation by a device operator. FIG. 108 is a solid side view of the carrier 107-1 with the vacuum manifold 1072 configured for manual control via an aperture 1075, under an embodiment. Alternatively, the vacuum component is controlled electronically. For example, the cycling on/off of the vacuum source is at least in part computer controlled (e.g., computer controlled duty cycle, etc.). The electronic controller can also be used to cycle a change in the rotary (RPM) component of the scalpet assembly. Scalpet length may also be one or more of manually and computer controlled.

The vacuum manifold 1072 of an embodiment is extended distally onto the scalpet to serve as a depth guide 1076, such that a distal end of the vacuum manifold 1072 is configured to control a depth of penetration of the scalpet array 1073 into the tissue. Various depth guide-dependent vacuum manifolds address different clinical applications and variable dermal depths at different anatomical sites. In an embodiment, a plastic manifold is created as a single procedure disposable that has a separate vacuum port incorporated into the manifold, but embodiments are not so limited.

In an alternative embodiment, the vacuum capability is an "in-line" or "in-series" configuration of the carrier or handpiece through which the vacuum is applied internally and can extend down the length of the lumen and scalpet proximally or is diverted through a separate side aperture of the scalpet. FIG. 109A is an isometric view of a handpiece configured to include or incorporate vacuum, under an embodiment. FIG. 109B is an isometric cutaway view of the handpiece configured to include or incorporate vacuum, under an embodiment.

FIG. 110A is a cross-sectional side view of a vacuum manifold 1101 configured to be coupled or connected to an in-line vacuum component 1102, under an embodiment. FIG. 110B is an isometric cross-sectional view of a vacuum manifold configured to be coupled or attached to an in-line vacuum component, under an embodiment. FIG. 110C is a solid side view of a vacuum manifold configured to be coupled or attached to an in-line vacuum component, under an embodiment. This embodiment includes the vacuum manifold FIG. 111A is a cross-sectional side view of a scalpet array used with a vacuum aspirator, under an alternative embodiment. The device of this embodiment includes a scalpet assembly 1111 including a scalpet array 1112 with multiple scalpets, but is not so limited. FIG. 111B is an isometric cross-sectional view of a scalpet array used with a vacuum aspirator, under an embodiment. FIG. 111C is a side view of a scalpet array used with a vacuum aspirator, under an embodiment. The vacuum aspirator is coupled or connected to the scalpet assembly and is configured as one or more of a specifically adapted aspirator for fractional resection, and a device such as a conventional surgical aspirator or an aspirator used specifically for suction assisted lipectomy (SAL). In an embodiment, the intraluminal vacuum scalpet or scalpet array has a rotary component to enhance both a skin incisional and fat suction curettage capability, but is not so limited.

FIG. 112 is a cross-sectional side view of a single-scalpet device applied to a target tissue site, under an embodiment. This example operational embodiment shows tissue extracted with vacuum force from a fractional resection site via the lumen and side aperture of the scalpet. FIG. 113 is an isometric cross-sectional view of a single-scalpet device applied to a target tissue site, under an embodiment.

FIG. 114A is a cross-sectional side view of a multi-scalpet device applied to a target tissue site, under an embodiment. FIG. 114B is an isometric cross-sectional view of a multi-scalpet device applied to a target tissue site, under an embodiment. This example embodiment shows use of vacuum aspiration to remove fractionally resected tissue from the target site.

The scalpet devices of various embodiments include one or more scalpets. The scalpet types of an embodiment include one or more of a slotted scalpet and a slotted blunt micro-tip cannula. The scalpets or scalpet devices of an embodiment include one or more apertures or orifices positioned axially in the scalpet adjacent the scalpet interior lumen, but are not so limited. FIG. 115 is an example scalpet 1150 including apertures or slots 1151, under an embodiment. FIG. 116 is an example blunt micro-tip scalpet or cannula 1160 including apertures or slots 1161, under an embodiment.

The ability to fractionally suction subdermal/subcutaneous fat under embodiments herein has several applications depending upon the target anatomical region. These applications include without limitation, the flattening of a convex three-dimensional contour and the inward contouring of an anatomical region to restore an aesthetic feature such as the submentum and the cervical-mandibular angle, for example. For these applications, a side-slotted aperture scalpet and a blunt tip side-slotted aperture fractional cannula are described herein. The blunt tip cannula is configured for use in anatomical regions where key vascular or nerve structures are immediately subjacent to the fractional lipectomy field. Regardless of the type of scalpet/cannula, the combining of the rotary function of the system with a vacuum capability provides a means to more effectively suction curette the subdermal/subcutaneous fat layer.

Embodiments include, without limitation, fractional marking systems configured as guides to assure an adequate fractional resection density. The guides include, for example, a stencil and/or Adherent Semitransparent Perforated Plastic Membrane Guide (ASPPMP) configured for use as a guide for fractional resection. The stencil marking system includes a stencil (e.g., ink, etc.) comprising a grid pattern of either circles or dots that is temporarily applied preoperatively to a target site. The circles or dots include at least one of a positive and a negative stencil of the grid pattern, and the ink material is biocompatible and configured to not smear or degrade during prepping of the patient or during the conduct of the procedure. FIG. 117 is an example negative stencil marking system, under an embodiment. FIG. 118 is an example positive stencil marking system, under an embodiment.

The ASPPMP marking system includes an adherent semitransparent perforated plastic membrane. FIG. 119A shows a side view of the ASPPMP in use as a depth guide with the single-scalpet device, under an embodiment. FIG. 119B shows a top isometric view of the ASPPMP in use as a depth guide with the single-scalpet device, under an embodiment. The perforated plastic membrane is also configured to serve as a depth guide that assures that the prescribed depth of fractional resection is not exceeded.

The marking of an alternative embodiment comprises a plate that is notched and perforated at the corners of each grid, and adapted for the inside diameter of the scalpet. Staggering of the fractional resections also avoids row and column delineation of the fractional field. An alternative embodiment includes a semi-transparent, semi-flexible adherent plastic membrane that is perforated at the corner of the each grid. The membrane perforations are larger than the outside diameter of the scalpet in order to avoid shaving of the perforated margins.

Clinical applications of the single-scalpet and multi-scalpet array platform include aesthetic contouring, which is most effectively produced by a combination of skin tightening and inward contouring of an embodiment, but is not so limited. The ability to fractionally resect skin and fat during a procedure has produced a significant capability over previous electromagnetic devices and aesthetic plastic surgery procedures because the fractional resection includes the direct removal of skin (in an area of skin laxity) without visible scarring. The enhanced capability of an embodiment to fractionally resect skin is combined with fractional subdermal/subcutaneous lipectomy to restore more youthful aesthetic contours.

FIG. 120 shows fractional resection of skin and fractional subdermal/subcutaneous lipectomy, under an embodiment. An example of fractional resection of skin and fractional subdermal/subcutaneous lipectomy, without limitation, is the treatment of the submentum (under the chin). FIG. 121 shows a side view of the submentum as a target area for fractional resection of skin and fractional subdermal/subcutaneous lipectomy, under an embodiment. FIG. 122 shows an inferior view (looking upward) of the fractional resection field submentum as a target area for fractional resection of skin and fractional subdermal/subcutaneous lipectomy, under an embodiment. The presence of skin laxity and prominence of the submental fat pad are the main components of this aesthetic deformity. Each patient will have a variable amount of each soft tissue component requiring a selective correction tailored or configured for each particular patient. More specifically, the convex contour of the submentum is caused predominately by lipodystrophy of the submental fat pad and the loss of the cervical-mandibular angle is predominately due to skin laxity.

Patients typically present with a variable amount of submentum skin laxity and lipodystrophy, so embodiments use planning and marking of a patient for a specific procedure. The combined capability of the assembly of an embodiment correlates well with the need to modify the specific soft tissue components of the aesthetic deformity. For patients with more severe skin laxity, a larger horizontally aligned treatment area in the submentum and lateral neck is marked for fractional skin resection. FIG. 123 shows a horizontally aligned treatment area in the submentum and lateral neck for severe skin laxity, under an embodiment.

For patients will more severe lipodystrophy, a broader fractional lipectomy (through fractional resection skin defects) is marked within the treatment area. The depth of the fractional lipectomy may also be selectively altered to address the topographic features of this convex contour deformity. FIG. 124 shows broader fractional lipectomy in the submentum for severe lipodystrophy, under an embodiment.

Clinical applications of the single-scalpet and multi-scalpet array platform include directed closure specifications. To promote primary healing (healing per primum) that reduces scarring, an accurate closure of the incision is a key principle employed in plastic surgery procedures. However, the direction of the closure is also important for aesthetic contouring. The appropriate vector of skin tightening takes into account the anatomical structure to be aesthetically enhanced. For more complicated aesthetic contours such as the face and neck, multiple vectors of sign tightening are employed during a procedure.

FIG. 125 shows example face vector and neck vector directed closures, under an embodiment. In addition to the skin tightening vectors, various lines of closure also limit tension upon closure. Lines of closure include those described by Karl Langer, and FIG. 126 shows Langer's lines of closure. Closure of skin incisions as indicated by Langer's lines promotes primary healing because it reduces the tension of the closure. When there is conformity between the vector of skin tightening and Langer's lines, the resultant aesthetic contouring and primary healing will work in concert with each other to provide the optimal clinical outcome.

Embodiments herein include stepwise procedure algorithms configured to provide a more uniform reduction to practice that produces predictable clinical outcomes. Many of the procedural steps (and the sequences of steps) herein are unique developments for fractional resection procedures. Without limitation, a procedural algorithm is included for the fractional resection of the submentum.

According to the treatment procedures of an embodiment, initially, a patient is marked preoperatively in a sitting position. For patients with relatively more skin laxity, the area outlined for fractional resection is broader and extends onto the lateral neck. For patients with relatively little or no skin laxity, the outlined fractional resection area is limited to the area in which lipodystrophy of the submentum fat pad is producing a convex contour deformity. For patients with both skin laxity and lipodystrophy, both areas are individually outlined as components of a single combined treatment outline. FIG. 127 shows marked target areas for fractional resection of neck and submental lipectomy, under an embodiment.

To avoid a reduction in the fractional field density, a local anesthetic field block is administered to the demarcated area of the submentum/neck. A dot/circle stencil is then applied to assure adequacy of the fractional resectional density, as described in detail herein. FIG. 128 shows an example marking stencil, under an embodiment. These procedure steps can be reversed where stenciling is performed prior to injection of the local anesthetic. The distension of the stenciled skin can be compensated with a larger outlined treatment area. A fractional skin resection is then performed within the boundary of the entire demarcated treatment area.

Fractional lipectomy is limited to the topographically outlined area of lipodystrophy (e.g., FIG. 127) and is performed either during fractional skin resection or as a subsequent procedural step. Transitioning or freehand feathering beyond the demarcated outline is performed to de-delineate the boundary of the fractional resection. A directed closure of the fractional defects is performed with an absorbent adherent elastic bandage that is stretched (preloaded) in the preferred vector of closure/skin tightening.

The bandage (e.g., Flexzan, etc.) can be preloaded by first applying one end of the bandage at a lateral mooring point beyond the fractional field. Once secure, the load is then applied at the opposite end of the bandage. The load is maintained during application. An alternative loading technique is to first apply opposing loads at each lateral extend of the elastic bandage i.e., the bandage is first stretched along the longitudinal axis of the material prior to application. With the load being maintained, the elastic bandage is then fully applied to the fractional field. Release of the load results in an elastic recoil that closes the defects of the fractional field along the designated vector. In the submentum where skin laxity of the anterior neck is present, a bi-directional closure with two vectors is pursued, but embodiments are not so limited.

FIG. 129 shows example directed closure vectors of the submentum and anterior neck, under an embodiment. The vector for the anterior neck (below the submentum) is more transverse and is used to accentuate the cervical-mandibular angle. For the submentum, the vector of closure (as indicated by Langer's lines) is vertical. A sterile dressing is then applied to conclude the procedure. A compression garment is also applied to provide compression and vectored support during the post-operative phase.

Embodiments include fractional scar revision. The reduction of the visible impact of a pre-existing scar deformity has been a major focus of plastic surgery since the inception of this surgical specialty. Depending upon the type of scar deformity, different surgical techniques have been employed. A commonly employed technique is elliptical excision of the scar with a layered closure. Other techniques such as Z-plasty and W-plasty attempt to reduce the linearity of the scar. FIG. 130 depicts Z-plasty and W-plasty scar revision. However, these conventional techniques lengthen the scar deformity. Fractional scar revision is configured to reduce the visible impact of the scar without lengthening of the scar.

For linear scar deformities, embodiments include a fractional de-delineation technique in which an interdigitating fractional resection is performed along each margin of the scar. To maximize de-delineation, directed closure of the fractional field is performed at right angles to the linear scar. FIG. 131 shows an example of the fractional de-delineation technique of scar resection, under an embodiment.

Additional de-delineation is produced under an embodiment with freehand fractional resection beyond the margins of the scar. Embodiments include a fractional technique for broad hypotrophic scars that occur from shaved biopsy excisions of skin lesions. To reduce the width of the scar deformity, a fractional scar excision is performed within the margin of the scar. Directed closure is performed as described in detail herein. FIG. 132 shows an example of the fractional scar resection for broad hypotrophic scars, under an embodiment. Another alternative embodiment combines both fractional scar revision techniques where the combined revision is performed as a single procedure or as a planned sequence of procedures, but is not so limited.

Additional embodiments include application of fractional resection to shorten incisions required to excise lesions. This novel capability can also be applied to shorten longer plastic surgery incisions that are used to resect redundant skin. The elliptical extension of an incision (to avoid a "dog-ear" skin redundancy) is no longer required if the lateral aspect of each incision is fractionally resected using devices and methods described herein.

The fractional procedure can be performed concurrently or as a planned subsequent revision of the primary excisional procedure. Fractional resection of embodiments can also be used for pre-existing dog-ear redundancies post excision. An example is the shortening of the inframmary incision required for breast reduction and breast repositioning. FIG. 133 shows an example comprising shortening of the inframmary incision as applied to breast reduction and/or breast repositioning, under an embodiment. The incision becomes less visible as it no longer extends beyond the inframmary fold.

Embodiments described herein include fractional skin grafting. This includes the closure of full thickness skin defects, which has also been a primary focus of plastic surgeons. Large defects that cannot be closed by direct closure require a more complicated approach. The two conventional approaches developed by plastic surgery are flap closure and skin grafting. FIG. 134 shows an example flap closure. Local or distant flap closures require an intrinsic or pedicle blood supply that is harvested with the flap at the donor site. Flap closure of skin defects is also complicated by the formation of additional scarring at the donor site.

Skin grafting (either split thickness or full thickness) is the other approach used to close large full thickness skin defects. Using the skin grafting approach, skin graft donor sites are required and are associated with significant scarring and morbidity.

After the several decades in which these two plastic surgical approaches have been employed, a novel third approach is now described in the embodiments herein. Fractional skin grafting can avoid the side effects associated with sheet skin grafting because fractional skin grafting has the unique capability to avoid the donor site deformity associated with sheet skin grafting. Fractional skin grafting also provides the additional capability to harvest subsequent skin grafts from the same donor site. FIG. 135 shows an example comprising fractional skin graft harvesting to be applied to a donor site, under an embodiment.

Fractional skin grafting is especially important with patients having large surface area burns for which donor site availability is severely limited. This unique capability of serial harvest at the same donor site is also important in patients with skin defects of the lower extremity that are caused by reduced circulation. Patients such as these with venous stasis, ischemic and diabetic ulcers are especially at risk to sustain the loss of the extremity if skin coverage of the vascular compromised ulcer is not promptly obtained. Many of these patients must undergo a sequence of skin grafts before skin coverage is obtained. The morbidity associated with this prolonged skin grafting process involving multiple donor sites can be especially vexing in patients who also have other serious systemic conditions. With fractional skin grafting described herein, the absence of a single visible donor site deformity coupled with the capability of serial harvesting of skin grafts from the same donor site provides a uniquely capable treatment option for these patients. In comparison to split thickness skin graft donor sites, the directed closure of the fractional donor site provides more rapid healing that dramatically reduces donor site morbidity and scarring.

As the fractional skin graft of an embodiment is full thickness, the durability of the skin coverage is also enhanced over split thickness skin grafts. For wound healing in these compromised recipient sites, the application of the fractional skin graft can be performed without the forming of the fractional skin segments (pixels) onto a more uniform sheet. In this clinical setting, "side neovascularization" occurs between the individual fractional skin segments and the recipient bed. FIG. 136 shows an example comprising neovascularization of a fractional skin graft at a recipient site, under an embodiment. The recipient site functions as a biological docking station that organizes the fractional skin segments into a side orientation with the recipient bed.

For other non-compromised and more visible skin defects, embodiments include the option to first form the fractionally harvested skin segments into a more uniform graft at a mechanical docking station. FIG. 137 shows an example docking station comprising a docking tray and adjustable slides, under an embodiment. In this clinical setting, "bottom up neovascularization" occurs from the recipient bed into deep aspect of dermis (e.g., FIG. 136). With each clinical setting, a compressive stent dressing provides additional support and immobilization that promotes neovascularization or "take" of the skin graft.

Fractional skin resection is an intradermal fractional resection defined as the fractional removal of a partial thickness segment of skin involving the dermis, as described in detail herein. FIG. 138 shows the segment of skin removed in a fractional skin resection, under an embodiment. Fractional resection/evacuation/harvesting of an embodiment includes fractional skin resection for skin laxity, skin grafting, fractional lipectomy, and autologous filler. Technology differentiators found in the embodiments herein include the use of a device (array) with a single circular rotating scalpet, or multiple circular rotating scalpets, configured to fractionally incise skin instead of puncturing or stamping the skin as with conventional devices. The fractional resection is also assisted with vacuum generated through the lumen of the scalpet.

Generally, many of the differences between the embodiments herein and the conventional technology relate to the scientific or technical differences between the fractional resection and/or fractional harvesting of the embodiments herein, and puncturing or piercing with punches or needles. Conventional apparatus and methods involving puncturing or stamping with punches or needles, while using a simpler device, require a significantly larger z-axis force, resulting in more trauma to the skin edges and the resected segments of skin, and consequently more scarring. Additionally, size constraints are imparted on the resected segments as a result of the punch-type devices.

In contrast to the conventional punches or needles, fractional resection using rotational fractional incising with one or more circular scalpets involves a minimal use of force (z-axis) applied to the skin because of the rotating scalpets, and the force variances required for larger incisions are negligible. The skin edges of fractional defects resulting from harvest with circular scalpets therefore heal with less scarring, and the viability of the fractionally harvested skin segments is enhanced. The enhanced viability of the fractionally harvested segments of skin increases the viability of the fractional skin graft at the recipient site, thereby providing a greater percentage "take." Furthermore, the creation of circular fractional defects enables directed closure with a chosen (optimal) vector of skin tightening, thereby providing the most effective three-dimensional contouring of the anatomical region. Moreover, an optimal range exits in which the rotational resection devices of embodiments herein can fractionally incise/resect larger segments of skin due to the reduction in z-axis force, while the upper limit of the larger diameter of the fractional circular scalpets (e.g., approximately 3 mm) is limited by the creation of visible dog-ear redundancies.

Fractional skin resection reduces scarring in anatomical areas of thicker skin by limiting the resection depth to the papillary dermis and superficial reticular dermis. Therefore, intradermal fractional resection reduces the potential of scarring in areas such as the back and bra line, which may otherwise be more prone to scarring due the thickness of the dermis. Fractional skin resection also produces a smoother skin surface with a reduction of pitting, while preserving skin circulation as the subdermal plexus of vessels is not transected, and skin sensory innervation as the subdermal nerve plexus is not transected. Further, a reduction of bleeding is realized during fractional resection because the subdermal plexus is not transected. Fractional skin resection reduces hypertrophic scaring in ethnic groups more prone to scarring (FP scale 4-6), and decreases hyperpigmentation when combined with a hydroquinone derivative. Additionally, as described in detail herein, fractional skin resection is used in embodiments to remove tattoos where the impregnated ink is in the superficial dermis.

Many patients undergoing three-dimensional aesthetic contouring also require tightening of the skin envelope along with the reduction of the soft tissue filler of subcutaneous fat. Similarly, for patients having both skin laxity and lipodystrophy, the correction of a single component does not provide optimal aesthetic contouring and may even create an iatrogenic deformity. An example of this complication is where only fractional liposuction is used in a patient with pre-existing skin laxity. Many of these patients post-procedure suffer an increase in the skin laxity in the area that has been lipo-resected. Therefore, embodiments combine fractional lipectomy with fractional skin resection so that the fractional lipectomy is performed through a fractional resection field generated according to the fractional resection described herein.

When fractional skin resection is used as an adjunct with standard liposuction, the fractional skin tightening deployed with standard liposuction concurrently tightens any preexisting skin laxity and also counteracts any iatrogenic induced skin laxity from the liposuction. The vascular supply to the skin should not be impacted as the musculocutaneous perforators are not typically transected and the majority of the subdermal circulation remains intact. This is especially true if an intradermal fractional skin resection is performed that does not involve the transection of the subdermal plexus.

A fractional lipectomy apparatus of an embodiment includes a powered rotational suction-assisted lipectomy cannula, thereby providing a more efficient lipectomy capability for both standard and fractional lipectomy. Vacuum sealing of the rotating cannula with the manifold is achieved with "0" rings, but is not so limited. Due to the elastic recoil of the skin margins, a larger diameter fractional lipectomy cannula/scalpet can be inserted through a fractional skin defect that was previously created with a smaller diameter scalpet. This elastic recoil property of skin enables the surgeon to choose a variety of fractional lipectomy "portal(s)" within of a fractional field.

The fractional lipectomy apparatus includes rotational fractional cannulas having two configurations. A shorter rotational fractional cannula, which has a length of approximately 14 mm for example, is configured for use in smaller areas of lipodystrophy such the submentum, C-section scars, trapdoor scars and cellulite where a vertical/oblique technique of cannula application will be employed. Additionally, a longer rotational fractional cannula, which has a length approximately in a range of 30-60 mm for example, is configured for use in larger areas of lipodystrophy where a pronated tangential fanning technique of cannula application is used. Without limitation, these larger areas of lipodystrophy are the submentum, submandibular jowls, lower abdomen, and cellulite of the hip and lateral thigh.

The devices described herein include a device configured for fractional resection and fractional lipectomy. The components of the fractional resection/lipectomy device include but are not limited to a scalpet, a multi-scalpet array, a depth guide, a vacuum manifold, a lipectomy cannula, a handpiece, and a motor control module (MCM). Each of these is described in detail herein.

The scalpet is a small cylindrical device used to cut into the skin while rotating, creating a column of tissue material (pixel). The scalpets are operated at a rotational speed of approximately 1500 revolutions per minute (RPM), but are not so limited. The end of the scalpet that cuts into the skin is the distal end, and the non-cutting end is the proximal end. The scalpet comes in numerous configurations based on scalpet diameter, scalpet length, the inclusion of a skive, the inclusion of side ports at the distal end to help remove subdermal fat, and the inclusion an open distal proximal end. Scalpets can be used individually or, alternatively, in an array of multiple scalpets. When used individually (single scalpet operation where the user creates one pixel at a time), the scalpets include a shank at the proximal end that configures them for use with conventional handpieces. Scalpets used in an array do not have a shank, but generally have an open proximal end. The scalpets generally comprise stainless steel hypodermic tubing, but are not so limited.

FIGS. 139A-139C show different scalpet configurations, under an embodiment. The scalpet configurations include a variety of scalpets having different dimensions (e.g., length, diameter, etc.) and configurations, and with or without one or more of solid shanks, open shanks, skives, side distal ports, open proximal ends (sharpened), sharpened distal ends, and blunt distal ends. More particularly, the scalpet configurations, in addition to having differing lengths, include 1.5 mm and/or 2.0 mm skived scalpets, 1.5 mm and/or 2.0 mm skived distal port scalpets, and/or a 1.5 mm and/or 2.0 mm blunt scalpets. Generally, when considering scalpet configurations for the procedures described herein, submental skin resection involves use of a 1.5 mm skived scalpet and/or a 2.0 mm skived scalpet. Submental fractional lipectomy involves use of a 1.5 mm and/or 2.0 mm skived scalpet, 1.5 mm and/or 2.0 mm skived distal port scalpet, and/or a 1.5 mm/2.0 mm blunt scalpet. Scar revision involves use of a 1.5 mm skived scalpet and/or a 2.0 mm skived scalpet. Tattoo removal involves use of a 1.5 mm skived scalpet and/or a 2.0 mm skived scalpet. Abdominoplasty involves use of a 1.5 mm and/or 2.0 mm skived scalpet, and/or a 1.5 mm and/or 2.0 mm skived distal port scalpet. Brachioplasty involves use of a 1.5 mm skived scalpet and/or a 2.0 mm skived scalpet.

The single-scalpet system of an embodiment includes an adjustable depth guide that provides a more precise capability of fractional depth control without the need to change to a different static guide. While this capability is most applicable during the first and second pass of a fractional dermal plug harvest phase of the autologous injectable, it also provides the capability to accurately perform intradermal (and full thickness) fractional resections of skin in a variety of anatomical regions.

In additional to the scalpet(s), the device includes a depth guide configured to limit the depth the scalpet can penetrate into the skin. In the case of the single scalpet operation, the depth guide is configured to fit over the scalpet and attach to the handpiece. FIG. 140A shows a single scalpet depth guide configured for use without vacuum, under an embodiment. The depth guide includes a distal end, a proximal end, and a handpiece interface portion.

The depth guide of an alternative embodiment is configured to operate with a vacuum system to remove pixels from the scalpet. FIG. 140B shows a single scalpet depth guide configured for use with vacuum, under an embodiment. In addition to the distal end, proximal end, and handpiece interface portion, the depth guide also includes a vacuum tube interface configured to couple to a vacuum source, and a vacuum control port. The vacuum control port is configured to enable a user to control the flow of vacuum to the scalpet.

The lipectomy cannula includes a hollow cylindrical tube configured for rotational use with vacuum to remove fat. Embodiments include numerous lipectomy cannulas comprising cannulas of differing sizes (e.g., length, diameter). For example, FIG. 141A shows a lipectomy cannula having first dimensions, under an embodiment. FIG. 141B shows a lipectomy cannula having second dimensions, under an embodiment. Regardless of dimensions, each lipectomy cannula includes a proximal end and a distal end. The distal end of each cannula includes open side ports, and the proximal end includes a shank or similar feature configured for attachment to a handpiece. The handpiece is configured to control rotation of the cannula during operation, in contrast to conventional liposuction devices that do not rotate during operation. The handpiece is also configured to couple a vacuum source to the cannula, and the vacuum source is configured remove tissue including fat via the cannula from a target region of a subject. Each cannula also includes a skive feature configured to enable the movement of tissue including fat through the cannula.

Embodiments of the lipectomy cannula include a vacuum manifold configured to couple the cannula to a vacuum source for removal of tissue via the cannula. FIG. 142 shows a vacuum manifold, under an embodiment. The vacuum manifold includes a housing having a handpiece interface portion and a vacuum tube interface configured to couple to a vacuum source. The housing also includes a vacuum control port configured to enable a user to control the flow of vacuum to the cannula. A distal end of the housing includes a seal (e.g., O-ring seal) configured to seal around a distal region of the cannula to improve vacuum flow through the cannula. The distal end also includes a collar.

In addition to single-scalpet devices described herein, embodiments include a scalpet array comprising numerous scalpets in a housing. The multi-scalpet array is configured to rotate a number of scalpets simultaneously to remove skin tissue. Embodiments include numbers of scalpets ranging from four to 25, but are not so limited. The proximal end of each scalpet is open and configured to enable skin pixels to move through the scalpet via a pushing force generated by subsequently harvested pixels pushing and/or a vacuum pressure. Application of the scalpet array into the skin is controlled through use of a control spring and/or vacuum pressure. A collar at the distal end of the housing is configured to control the depth of penetration of the scalpets at the target site. FIG. 143 shows a multi-scalpet array (3×3 array) including a housing and a handpiece interface, under an embodiment.

FIG. 144 shows a multi-scalpet array (3×3 array) in a housing, under an alternative embodiment. The housing includes a control spring configured to control application of the array to the target site. The housing is coupled to a vacuum port, and a vacuum source coupled to the vacuum port provides the vacuum pressure for use in harvesting pixels and/or controlling application of the array to the target site. A drive shaft is coupled to the scalpets and configured to provide the driving force for rotation of the scalpets. The scalpet array includes a gear drive mechanism coupled to the drive shaft, but is not so limited.

The multiple-scalpet array includes an adjustable investing plate depth guide configured to enable fractional skin resection over larger anatomical areas where dermal depth has greater variances. The adjustable depth guide, also referred to herein as a depth control collar, is configured to provide the capability of full thickness and partial thickness dermal resections in a particular anatomical area. Intradermal partial thickness fractional skin resections reduce the potential for hypertrophic scarring, and also provide the capability of epidermal removal during a dermal plug harvest for the living autologous injectable. The adjustable plate also enhances intradermal harvest capability in areas of variable dermal thickness.

FIG. 145A shows a multi-scalpet array (3×3 array) in a retracted state, under an embodiment. FIG. 145B shows a multi-scalpet array (3×3 array) in an extended state, under an embodiment. The multi-scalpet array is in a housing, and the housing includes a depth control collar. The housing includes a control spring configured to control application of the array (extended state) to the target site. The housing is coupled to a vacuum port, and a vacuum source coupled to the vacuum port provides the vacuum pressure for use in harvesting pixels and/or controlling application of the array to the target site. A drive shaft is coupled to the scalpets and configured to provide the driving force for rotation of the scalpets. The scalpet array includes a gear drive mechanism coupled to the drive shaft, but is not so limited.

FIG. 146 shows a gear drive mechanism of the multi-scalpet array, under an embodiment. The gear drive mechanism includes a scalpet gear coupled to a proximal end of each scalpet, and a drive gear coupled to a distal end of a drive shaft. The gears include any type of gear (e.g., spur, helical, etc.). The scalpet gear of each scalpet is configured to mesh with the scalpet gear of the adjacent scalpets, and the drive gear is configured to mesh or interface with one or more scalpet gears. Therefore, rotation of the drive gear causes rotation of all scalpets as a result of the intermeshed gear configuration of the scalpet gears.

The fractional resection/lipectomy device includes a handpiece and an MCM as described herein. The handpiece, which includes custom and off-the-shelf handpieces, is configured for hand-held operation. The handpiece is configured as the interface between the motor and the scalpets, cannulas, depth guides, vacuum manifold, and multi-scalpet array. The MCM of an embodiment is a remote component coupled or connected to the handpiece. Alternatively, the MCM can be included as a component of the handpiece. Regardless of configuration, the MCM is configured as the user interface for motor speed control and on/off rotation for the scalpet.

FIGS. 147-149 shows a sequence of operations including use of a single scalpet with vacuum. More particularly, FIG. 147 shows a single scalpet device with vacuum configured for a fractional resection procedure, under an embodiment. The single scalpet device includes a scalpet coupled to a handpiece. Further, a depth guide including a vacuum system interface is coupled to the handpiece.

FIG. 148 shows application of the single scalpet device to a target site during a fractional resection procedure, under an embodiment. The scalpet rotates while being pressed into the skin at the target site, and the depth guide limits the depth of penetration. The vacuum force pulls excised skin pixels or plugs through the scalpet and into the vacuum port of the depth guide via a skive in the scalpet.

FIG. 149 shows a resection field generated through repeated application of the single scalpet device to a target site, and closure of the field, under an embodiment. The top panel shows generation of a resection field through repeated application of the scalpet device to the target site. The middle panel shows the resection sites being pulled closed via directed closure in a direction specified by the depicted arrows. The bottom panel shows the resection field following application of a bandage to hold the resection sites closed.

FIG. 150 shows a multi-scalpet array device with vacuum in an extended site as applied to a target site during a fractional resection procedure, under an embodiment. FIG. 151 shows a cross-section of the multi-scalpet array device in an extended site as applied to a target site during a fractional resection procedure, under an embodiment. As described in detail herein, the multi-scalpet array is in a housing, and the housing includes a depth control collar. The housing is coupled to a vacuum port, and a vacuum source coupled to the vacuum port provides the vacuum pressure for use in evacuating tissue from the target site. The depicted arrows indicate a travel path of excised skin pixels or plugs evacuated from the target site via the scalpet array and open distal ends of the scalpets and into the vacuum port.

FIG. 152 shows a single scalpet device with vacuum configured for a fractional resection/lipectomy procedure, under an embodiment. The single scalpet device includes a lipectomy cannula coupled to a handpiece. Further, a vacuum housing and collar is coupled to the handpiece, and the vacuum housing is configured to couple to a vacuum system.

FIG. 153 shows the components of a fractional skin resection system, under an embodiment. The system includes components for procedures involving single and multi-scalpet operations. For example, the system includes a single scalpet handpiece, handle clips, and a motor control module. The handpiece is configured for use with scalpets having numerous configurations, for example scalpets having a variety of diameters (e.g., 1.2 mm, 1.5 mm, 2.0 mm, etc.). Numerous different housings are included having depth guides of differing lengths. The system also includes a marking plate, and vacuum pump and canister as described in detail herein. For multi-scalpet procedures, the system includes a multi-scalpet array.

FIG. 154 shows the components of a fractional skin resection/lipectomy system, under an embodiment. The system includes components for fractional resection procedures involving single and multi-scalpet operations. For example, the system includes a single scalpet handpiece, handle clips, and a motor control module. The handpiece is configured for use with scalpets having numerous configurations, for example scalpets having a variety of diameters (e.g., 1.2 mm, 1.5 mm, 2.0 mm, etc.). Numerous different housings are included having depth guides of differing lengths. The system also includes a marking plate, and vacuum pump and canister as described in detail herein. For multi-scalpet procedures, the system includes a multi-scalpet array.

In addition to the components for fractional resection procedures, the system includes components for fractional lipectomy. The lipectomy components or equipment include a variety of lipectomy cannulas and vacuum manifold components. The lipectomy cannulas include cannulas configured for one or more of skin penetration depths in a range of approximately 14-60 mm, diameters in a range of approximately 1.5-2.4 mm, and variable distal port configurations. The lipectomy components also include a vacuum manifold housing configured for fractional lipectomy, and a corresponding collar and seal (e.g., O-ring) as described in detail herein.

Embodiments of the system described in detail herein include a console with a handpiece and scalpet devices configured to interact for rotational fractional skin resection, focal lipectomy, skin grafting, and tissue harvesting procedures for the autologous dermal injectable, as described in detail herein. The console comprises multiple components or systems such as rotation (powered), vacuum, and a multifunction canister configured for harvesting skin tissue and grafts and for composing an autologous dermal injectable.

The scalpet devices include a scalpet array comprising one or more scalpets, but are not so limited. The handpiece is configured as a linkage or intermediary between the powered console and the single/multiple scalpet array. In an embodiment, the scalpet device includes a single-scalpet system configured for use in smaller applications such as the malar pouches, jowls, and nasolabial folds to name a few.

The scalpet devices of alternative embodiments include multi-scalpet arrays configured to de-delineate the fractional field border and to fill in skip areas with field. The multi-scalpet arrays include numerous embodiments having differing numbers of scalpets and/or configurations of scalpets, but are not so limited. The multi-scalpet array is configured for use in larger surface area applications where it reduces the time and tedium of these procedures. These applications include the submentum, upper arm, bra line, suprapatellar knee, posterior elbow, and thighs to name a few. The multi-scalpet array is also configured to include self-marking capability in which each previous stamp of the array indicates the next adjacent stamp of the device.

The rotation component of the console is configured to cause rotation of scalpets of the scalpet devices with variable rotational speed configured to reduce the z-axis compression forces required for fractional skin resection and focal lipectomy using the single/multiple scalpet array. The rotating scalpet(s) of the scalpet devices also improves graft fibroblast viability for fractional harvesting and composition into an autologous injectable. Rotational fractional resection further enables use of larger diameter scalpets, which increases the percent fractional resection percentage when compared to a non-rotational stamping configuration.

The vacuum component of the console is configured as a source of vacuum force for one or more of stabilization of the skin surface, skin plug evacuation, focal lipectomy, fractional skin graft harvesting and dermal graft harvesting for composition of an autologous dermal injectable. In an embodiment, the vacuum component is coupled or connected to the handpiece, but is not so limited. In an alternative embodiment, the vacuum component is coupled or connected to the scalpet devices, but is not so limited. In at least one other alternative embodiment, the vacuum component is coupled or connected to the scalpet devices via the handpiece, but is not so limited.

The handpiece is also coupled or connected as the linkage between the scalpet array and the multifunction canister. The canister is configured as a reservoir for fractional skin graft harvesting and for the composition of dermal grafts into an autologous dermal injectable. The multiple functions of the canister include dermal graft harvesting, mincing, and mixing with a carrier fluid and as a port for syringe loading.

Example embodiments include a Rotational Fractional Resection (RFR) system configured to achieve focal aesthetic contouring by removing lax or loose skin and excess fat tissue. Skin is removed by the use of a rotating cannula including a scalpet, which is a hollow, sharpened tube configured to excise full thickness dermal resections as described herein. The RFR system includes two devices or assemblies comprising different versions of a scalpet for removing skin. These two devices, both of which comprise single-patient, single-use devices, include a single-scalpet device or tool, and a multi-scalpet array device comprising multiple scalpets, as described in detail herein. Embodiments also include a rotating lipectomy cannula configured to remove focal fat deposits. The Single-Scalpet, Multi-Scalpet Array (MSA), and focal lipectomy tools are configured to be coupled or connected to a handpiece, which is powered by a console coupled or connected to a motor. The console also includes a vacuum pump configured to provide suction for removal of both focal fat deposits and lax skin.

The Single-Scalpet and MSA include numerous operating parameters, and use similar cutting edge geometries on the scalpets. The parameters include but are not limited to the cutting edge diameter, scalpet rotation speed, resection or cutting depth, and operating vacuum pressure. Exemplary values of these parameters are described herein but the RFR system is not limited to these exemplary values. The scalpet cutting edge diameter is approximately 1.5 mm. The cutting rotation speed is approximately 1400 revolutions per minute (RPM), but the RFR system can operate in a range of speeds of approximately 75-2000 RPM. The cutting depth is in a range of approximately 2-8 mm (e.g., 2 mm increments). The operating vacuum pressure is approximately 25 inches mercury.

The single-scalpet device includes a single scalpet, which is a circular skin cutting tool configured to resect single plugs of skin as described herein. The single-scalpet device is also configured to create access ports to allow for entry of the lipectomy cannula described in detail herein. The scalpet has an inner diameter of approximately 1.5 mm, and comprises stainless steel (e.g., grade 304 stainless steel, etc.), but is not so limited. The scalpet is supplied sterile and is intended for a single use.

The single scalpet is enclosed and carried in a depth guide comprising a distal end configured to control a depth of resection by limiting a depth of penetration of the scalpet at the target site. FIG. 236 is a perspective view of the single scalpet device in the depth guide, under an embodiment. The depth guide comprises a biocompatible ABS polymer but is not so limited. The depth guide comprises different guides spanning a range of depths of approximately 2 mm to 8 mm. Selection of a resection depth as appropriate to a patient and/or a procedure therefore involves selecting the appropriate depth guide.

The depth guide is configured for the application of vacuum adjacent the target site to facilitate the skin resection and evacuate the resected tissue. As such, the depth guide includes a vacuum chamber or port, and the vacuum port is configured to couple or connect to a remote vacuum source (not shown).

The depth guide with the single scalpet is configured to couple or connect to a distal end of a handpiece. Embodiments include an O-ring configured to generate a seal in a region between a distal end of the handpiece and the portion of the depth guide that couples or connects to the handpiece. FIG. 237 is an exploded side view of the depth guide showing the O-ring distal between the depth guide and the distal end of the handpiece, under an embodiment. The O-ring comprises silicone rubber but is not so limited. The seal generated between the handpiece and the depth guide by the O-ring is configured to maintain a vacuum force at the target site.

FIG. 238 is a perspective view of the RFR system including the single-scalpet device connected to the handpiece, under an embodiment. The depth guide including the single scalpet is coupled or connected to the distal end of the handpiece. The handpiece is configured to be a handheld device. A motor is coupled or connected to the handpiece, and the motor is configured to provide rotational force to rotate the single scalpet. The motor of an embodiment includes an electric motor, and a power cord or other power transmission means is configured to provide electrical power to the motor from the console (not shown). A vacuum tube is coupled to the vacuum port of the depth guide and is configured to provide vacuum force at the single scalpet device from the console (not shown).

Rotation of the scalpet is configured for rapid excision of entry holes for the lipectomy cannula and to resect skin. Also, rotation of the lipectomy cannula is configured for separation of the subcutaneous fat prior to suction. The handpiece of the single scalpet device comprises a reusable handpiece configured for rotational speed control of the scalpet and lipectomy cannula. The handpiece is controlled by the motor on a console but is not so limited. The handpiece of an embodiment is an NSK handpiece but is not so limited.

The RFR system also includes an MSA device as described herein. FIG. 239 is a perspective view of the Multi-Scalpet Array (MSA) device, under an embodiment. The MSA device includes multiple scalpets configured for simultaneous removal of multiple tissue plugs. This example embodiment includes a 3×3 array of scalpets configured to simultaneously remove nine skin plugs, but the array of alternative embodiments can include any number of scalpets. Each scalpet has an inner diameter of approximately 1.5 mm, and comprises stainless steel (e.g., grade 304 stainless steel, etc.), but is not so limited.

The MSA device includes an integrated vacuum chamber/depth slider that is generally configured to include gear rotational operation, adjustable depth selection, and delivery of vacuum force to the target site during a procedure. The gear mechanism (not shown) is housed or contained within a gearbox (not shown). The depth guide includes a vacuum chamber or port configured for the application of vacuum adjacent the target site to facilitate the skin resection and evacuate the resected tissue. The vacuum port is configured, when coupled or connected to a vacuum source, to cause tissue to move proximally from the target site and through each scalpet, exiting the rear of the scalpet. In the case of the center scalpet, the scalpet includes an aperture or skive, and tissue exits through the skive and moves up through the vacuum tube. The MSA is supplied sterile and is for single use, but is not so limited.

FIG. 249 is a cross-sectional view of the Multi-Scalpet Array (MSA) device showing the vacuum flow path (arrows) through the MSA, under an embodiment. The vacuum assists in pulling the treatment site skin to the scalpets, and in drawing the pixels removed from the target site away from the MSA. The vacuum flow also helps assist with the removal of any particulates generated in the gearbox away from the treatment site.

The depth slider is configured to enable a user to select a depth of resection approximately in a range of 2 mm to 10 mm. The locking mechanism is then used to avoid an inadvertent nuisance change in depth. The housing/depth guide component is injection molded from a biocompatible plastic. The components of the MSA are described in detail herein.

The MSA attaches to the handpiece in a manner similar to that of the single scalpet, but is not so limited. FIG. 240 is a perspective view of the RFR system including the MSA device connected to the handpiece, under an embodiment. The MSA including the depth guide is coupled or connected to the distal end of the handpiece. The handpiece is configured as a handheld device. A motor (not shown) is coupled or connected to the handpiece, and the motor is configured to provide rotational force to rotate the scalpets of the scalpet array via a driveshaft. The motor of an embodiment includes an electric motor, and a power cord or other power transmission means (not shown) is configured to provide electrical power to the motor from the console (not shown). The handpiece of the single scalpet device comprises a reusable handpiece configured for rotational speed control of the scalpets of the scalpet array. The handpiece is controlled by the motor on a console but is not so limited. The MSA device includes a vacuum port, and a vacuum tube is coupled to the vacuum port of the depth guide and is configured to provide vacuum force at the single scalpet device from the console (not shown).

The MSA device includes a depth slider that is configured to control the cutting or resection depth of the scalpet array as described herein. FIG. 241 is a perspective view of the MSA device showing operation of the depth slider, under an embodiment. The depth slider is configured to change position by sliding along the MSA device longitudinal axis, thereby changing a position of a distal end of the depth guide relative to a distal end of the scalpets. An embodiment includes two tabs on the side of the depth slider that are configured to set the depth slider at a selected state. The selected state is selected from among a 2 mm, 4 mm, 6 mm, or 8 mm depth state, but is not so limited. The depth slider has a small tooth that couples with the vacuum chamber to secure it in place.

The lock collar provides a safety feature that assures the MSA device resects tissue at a uniform depth throughout the procedure by securing the depth slider in the selected or set position. FIG. 242 is a perspective view of the MSA device showing operation of the lock collar, under an embodiment. The lock collar is configured to slide proximally along the MSA longitudinal axis to unlock the depth slider so that it can be moved to a selected depth. The lock collar is also configured to slide distally along the longitudinal axis, and lock into place upon selection of the appropriate scalpet depth.

The MSA device includes a vacuum port and vacuum chamber. FIG. 243 is a perspective view of the MSA device showing the vacuum port and vacuum chamber, under an embodiment. The vacuum port is configured as the interface to couple or connect to a vacuum source (now shown). The vacuum force delivered through the vacuum chamber causes resected tissue to be drawn proximally from the target site and through each scalpet, exiting the rear of the scalpet and passing through the vacuum chamber. The vacuum chamber comprises multiple small ribs that enable it to connect to the handpiece. The vacuum chamber also includes teeth configured to interface with the depth slider to control scalpet depth.

The scalpets (e.g., nine scalpets) of the scalpet array extend beyond the distal end of the depth slider and are configured to resect the skin at the treatment site. FIG. 244 is a perspective view of the MSA device showing the scalpets, under an embodiment. The proximal end of each scalpet is open and configured to pass a vacuum force that draws resected pixels away from the target site as they are resected. The scalpets operate or rotate in unison, with each rotating in a direction opposite that of the adjacent scalpets. The scalpets, which comprise biocompatible stainless steel hypodermic needle tubing, each include drive gears pressed or otherwise coupled or connected to the proximal end of the scalpet. The scalpets are driven by the gears, which receive a rotational force via a motor and drive shaft (not shown).

The MSA device includes a gearbox configured to house the scalpet gears and drive mechanism. The gearbox comprises a gearbox housing and a gearbox cover. FIG. 245 is a perspective view of the MSA device showing the gearbox housing and gearbox cover, under an embodiment. The gearbox housing and cover are joined together using screws and dowels configured to hold and isolate the scalpet drive gears. The gearbox housing and cover are also configured as bearing plates for the rotating gears. Further, the housing is configured as an interface to the vacuum chamber. A thin silicone seal is located at the internal distal end of the gearbox to mitigate debris from leaving the gearbox, but is not so limited.

The scalpets each include drive gears coupled or connected to the proximal end of the scalpet, and the gears in conjunction with a drive shaft couple a rotational force to the scalpets. FIG. 246 is a perspective view of the MSA device showing the gear mechanism, under an embodiment. The gear mechanism includes the gears and the associated drive components. The scalpet array includes a central scalpet that is positioned at the center of the array and surrounded by the remaining peripheral scalpets of the array. The central scalpet is includes a central gear coupled or connected to the proximal end of the scalpet. Likewise, each peripheral scalphet includes a gear coupled or connected to the proximal end of the respective scalpet. The central gear couples or meshes with the gears of the peripheral scalpets. Further, spacers are fit over the scalpets adjacent to the gears in order to assure proper alignment and operation of the scalpets.

The gears of the MSA device comprise various materials coupled to the corresponding scalpets using numerous methods. In an embodiment, the gears comprise brass and are press fit on a proximal region of the scalpets. In an alternative embodiment, the gears comprise plastic and are directly molded onto a distal region of the scalpet. In yet another alternative embodiment, the gears comprise plastic and are affixed to the distal region of the scalpet via an adhesive material. Various additional alternative embodiments include alternative gear materials and fitting methods.

A driveshaft is coupled or connected to the central scalpet, and the drive shaft is configured to deliver a rotational force from a drive device (e.g., motor) to drive the central scalpet in a rotation direction. The driveshaft of an embodiment is laser-welded to the central scalpet, or alternatively coupled or connected to the central scalpet using mechanical component(s). Rotation of the central scalpet in turn causes the peripheral scalpets to rotate in a rotation direction because the gears of the peripheral scalpets are coupled to the central gear. FIG. 247 is a perspective view of the gear mechanism of the MSA device showing the drive shaft and rotation directions of the scalpets, under an embodiment.

The driveshaft includes a side port configured to enable the vacuum force to draw pixels through the central scalpet to the vacuum chamber. Further, an O-ring is located along the proximal region or end of the driveshaft, and the O-ring is configured to assist in maintaining greater vacuum forces or pressures for pixel removal and to minimize tissue debris from coming in to contact with the handpiece. FIG. 248 is a perspective view of the gear mechanism of the MSA device showing the drive shaft and drive shaft O-ring, under an embodiment.

FIG. 250 is a perspective view of the fractional lipectomy cannula of the RFR system, under an embodiment. FIG. 251 is a perspective view of the RFR system including the fractional lipectomy cannula connected to the handpiece, under an embodiment. The fractional lipectomy cannula is configured for the application of vacuum adjacent the target site to facilitate evacuation of tissue from a target site. The fractional lipectomy cannula includes a housing or manifold coupled to the cannula. The lipectomy housing or manifold includes an O-ring seal (not shown) at the distal end to facilitate high vacuum pressures while the cannula is rotating. The device includes a vacuum chamber or port, and the vacuum port is configured to couple or connect to a remote vacuum source (not shown). The cannula comprises stainless steel (e.g., grade 304 stainless steel, etc.), and the manifold comprises a biocompatible plastic polymer, but is not so limited. The scalpet is supplied sterile and is intended for a single use.

The handpiece is configured as a handheld device. A motor is coupled or connected to the handpiece, and the motor is configured to provide rotational force to rotate the fractional lipectomy cannula. The motor of an embodiment includes an electric motor, and a power cord or other power transmission means is configured to provide electrical power to the motor from the console (not shown). A vacuum tube is coupled to the vacuum port of the device and is configured to provide vacuum force at the single scalpet device from the console (not shown).

The focal lipectomy cannula is configured to remove focal fat deposits from a treatment area. The focal lipectomy cannula of an embodiment is approximately 4 cm in length, with an inner diameter of 2 mm, but is not so limited. The cannula includes a blunt distal end, one or more apertures through which fat tissue is aspirated, and an internal port configured to enable fat evacuation through the cannula. FIG. 252 is a perspective cross-sectional view of the fractional lipectomy cannula showing the vacuum flow path (arrows) through the device, under an embodiment. The vacuum assists in pulling the tissue removed from the target site away from the device.

The RFR system of an embodiment includes a console comprising an electro-mechanical device configured to provide services to the above components. FIG. 253 shows the console, under an embodiment. The console includes a motor that couples or connects to a handpiece to rotate the scalpet and the lipectomy cannula at controlled speeds. The console also provides a source of vacuum configured to be coupled or connected to the components, and the vacuum source is configured to provide force appropriate for removal of the aspirated fat and skin tissues.

FIGS. 155A-155D include tables detailing procedural components of fractional skin grafting, under an embodiment. More particularly, FIG. 155A is a table detailing procedural components of fractional skin grafting for skin defects including traumatic avulsive or full thickness abrasive loss, under an embodiment. The mechanism of action includes cleaning and debridement of the wound with partial closure and immediate fractional skin graft. FIGS. 156A and 156B show cleaning and debridement of the wound, under an embodiment. Delay in skin grafting to establish a granulation base may not be required due to the ability of the skin plugs to neovascularize within an uneven contour of the recipient site. Scalpet diameter and type comprises standard surgical instruments and 2.0 mm scalpet (skived and non-slotted) or scalpet array. The stop guide is 3-4 mm. Suction used includes a "wall suction" aspirator on lowest vacuum setting providing evacuation and canister harvest of the skin plugs. Fat resection is to be minimized. Directed closure technique and recipient site dressing includes Flexzan/Optifoam with single or double mooring technique at the donor site. The dressing at the recipient site includes Xeroform gauze (4×4s) and an ABD, and splint immobilization across a joint surface may be required. Vector of directed closure includes the donor site fractional field being closed according to the deformation of the fractional resection defects corresponding to Langer's lines.

Pre-op and intra-op considerations include generation of photo and video documentation perioperatively. Additionally, the four-to-one rule applies to the size of the donor fractional harvest field. FIG. 157 is a geometrical representation of the four-to-one rule shown in a vertical fractional skin resection orientation, under an embodiment. The geometric parameters of the four-to-one rule along with an example surface area calculation are as follows:

Surface Area of skin defect=$\pi \times A \times B$

Surface Area of the skin defect=$(3.14) A \times B$

Example: A=1 inch radius, B=2 inches radius

Surface Area of the skin defect=(3.14)1 inch×2 inches=6.2 sq inches

Application of this example to a resection using a 25% fractional resection density is as follows:

Surface Area Fractional Graft Harvest=$(3.14) A \times B$

4×6.2 square inches=24.8 square inches 24.8 square inches=(3.14)2 inches×4 inches B=2 inch radius, A=4 inch radius Therefore, for a 25% fractional resection density, the fractional harvest field should be 4× larger than the skin defect, so the treatment pattern radii A and B should therefore be approximately twice the size of the skin defect.

The canister of harvested full thickness skin plugs are directly applied and oriented at the recipient site. Orientation of the skin plugs includes either a vertical or side orientation as neovascularization and vertical top-down growth reorientation of the plugs will occur with either type of initial plug application i.e., the recipient site acts as its own biological docking station. FIG. 158A shows orientation of skin plugs at the recipient site, under an embodiment. FIG. 158B shows the dressed recipient site, under an embodiment. Post-op considerations include removal of the Flexzan dressing at the donor site approximately 7-10 days following application of the skin plugs. The recipient site dressing is changed at one week. Photo documentation is obtained of Flexzan removal. A vertical (FR) technique of skin plug harvest is used, and the amount of fat resection is minimized. Both vertical and side neovascularization occurs at the recipient site.

FIG. 155B is a table detailing procedural components of fractional skin grafting for skin defects including third degree burns, under an embodiment. The mechanism of action includes debridement of the burn eshcar (see FIGS. 156A and 156B), which may require multiple procedures. The delay required for granulation formation may be reduced with a fractional skin graft due to the ability of the skin plugs to neovascularize within an uneven contour of the recipient site. Scalpet diameter and type comprises standard surgical instruments and 2.0 mm scalpet (skived and non-slotted) or scalpet array. The stop guide is 3-4 mm. Suction used includes a "wall suction" aspirator on lowest vacuum setting providing evacuation and canister harvest of the skin plugs. Fat resection is to be minimized. Directed closure technique and recipient site dressing includes Flexzan/Optifoam with single or double mooring technique at the donor site. The dressing at the recipient site includes Xeroform gauze (4×4s) and an ABD, and splint immobilization across a joint surface may be required. Vector of directed closure includes the donor site fractional field being closed according to the deformation of the fractional resection defects corresponding to Langer's lines.

Pre-op and intra-op considerations include generation of photo and video documentation perioperatively. Additionally, the four-to-one rule applies to the size of the donor fractional harvest field. The canister of harvested full thickness skin plugs are directly applied and oriented at the recipient site. Orientation of the skin plugs (see FIG. 158A) includes either a vertical or side orientation as neovascularization and vertical top-down growth reorientation of the plugs will occur with either type of initial plug application i.e., the recipient site acts as its own biological docking station. Post-op considerations include removal of the Flexzan dressing at the donor site approximately 7-10 days following application of the skin plugs. The recipient site dressing is changed at one week. Photo documentation is obtained of Flexzan removal. A vertical (FR) technique of skin plug harvest is used, and the amount of fat resection is minimized. Both vertical and side neovascularization occurs at the recipient site.

FIG. 155C is a table detailing procedural components of fractional skin grafting for lower extremity skin defects, under an embodiment. The mechanism of action includes repeated debridement (see FIGS. 156A and 156B) of a vascular compromised recipient site, and may also require a vascular procedure to revascularize the lower extremity. The most common ulcers of the lower extremity are Venous stasis, ischemic and diabetic ulcers. The delay required for granulation base formation may be reduced with a fractional skin graft. Many of these patients require multiple skin grafts to achieve closure. The ability to serially harvest a skin graft from the same donor site will be a distinct advantage. Scalpet diameter and type comprises standard surgical instruments and 2.0 mm scalpet (skived and non-slotted) or scalpet array. The stop guide is 3-4 mm. Suction used includes a "wall suction" aspirator on lowest vacuum setting providing evacuation and canister harvest of the skin plugs. Fat resection is to be minimized. Directed closure technique and recipient site dressing includes Flexzan/Optifoam with single or double mooring technique at the donor site. The dressing at the recipient site includes Xeroform gauze (4×4s) and an ABD, and splint immobilization across a joint surface may be required. Vector of directed closure includes the donor site fractional field being closed according to the deformation of the fractional resection defects corresponding to Langer's lines.

Pre-op and intra-op considerations include generation of photo and video documentation perioperatively. Additionally, the four-to-one rule applies to the size of the donor fractional harvest field. The canister of harvested full thickness skin plugs are directly applied and oriented at the recipient site. Orientation of the skin plugs (see FIG. 158A) includes either a vertical or side orientation as neovascularization and vertical top-down growth reorientation of the plugs will occur with either type of initial plug application i.e., the recipient site acts as its own biological docking station. Post-op considerations include removal of the Flexzan dressing at the donor site approximately 7-10 days following application of the skin plugs. The recipient site dressing is changed at one week. Photo documentation is obtained of Flexzan removal. A vertical (FR) technique of skin plug harvest is used, and the amount of fat resection is minimized. Both vertical and side neovascularization occurs at the recipient site.

FIG. 155D is a table detailing procedural components of fractional skin grafting for excisional skin defects, under an embodiment. The mechanism of action includes skin defect creation (see FIG. 156B) from the lesion resection such as melanoma or large squamous cell carcinomas where skin grafting to close the defect is indicated. A factional full thickness skin graft will provide durable coverage in areas requiring such coverage. Scalpet diameter and type comprises standard surgical instruments and 2.0 mm scalpet (skived and non-slotted) or scalpet array. The stop guide is 3-4 mm. Suction used includes a "wall suction" aspirator on lowest vacuum setting providing evacuation and canister harvest of the skin plugs. Fat resection is to be minimized. Directed closure technique and recipient site dressing includes Flexzan/Optifoam with single or double mooring technique at the donor site. The dressing at the recipient site includes Xeroform gauze (4×4s) and an ABD, and splint immobilization across a joint surface may be required. Vector of directed closure includes the donor site fractional field being closed according to the deformation of the fractional resection defects corresponding to Langer's lines.

Pre-op and intra-op considerations include generation of photo and video documentation perioperatively. Additionally, the four-to-one rule applies to the size of the donor fractional harvest field. The canister of harvested full thickness skin plugs are directly applied and oriented at the recipient site. Orientation of the skin plugs (see FIG. 158A) includes either a vertical or side orientation as neovascularization and vertical top-down growth reorientation of the plugs will occur with either type of initial plug application i.e., the recipient site acts as its own biological docking station. Post-op considerations include removal of the Flexzan dressing at the donor site approximately 7-10 days following application of the skin plugs. The recipient site dressing is changed at one week. Photo documentation is obtained of Flexzan removal. A vertical (FR) technique of skin plug harvest is used, and the amount of fat resection is minimized. Both vertical and side neovascularization occurs at the recipient site.

FIGS. 159A-159B include tables detailing procedural components of fractional skin resection of submentum-neck regions, under an embodiment. More particularly, FIG. 159A is a table detailing procedural components of fractional skin resection of the anterior neck region and submentum neck region, under an embodiment. The fractional skin resection of the anterior neck region includes use of a vertical fractional resection technique with a minimal amount of tissue resection. A primary purpose includes a first pass comprising fractional skin resection of the entire demarcated treatment area. Scalpet diameter, length and type include a 1.5, skived, non-slotted. The stop depth is 4 mm. Suction is used and includes "wall suction" with the aspirator on lower vacuum setting for evacuation of the skin plugs only. The directed closure technique includes Flexzan/Optifoam with single or double mooring technique. The vector of directed closure is horizontal, at right angles to lines indicated by Langer. Fractional defects are closed vertically to accentuate the cervical-mandibular angle. Pre-op and intra-op considerations include generation of photo and video documentation perioperatively (treatment areas demarcated and stencil applied preoperatively). Post-op considerations include use of compression garment for approximately two weeks postoperatively, and photo documentation with use of ImageJ/NIH software for six months.

The fractional skin resection of the submentum region includes use of a vertical and horizontal tissue resection technique (techniques 1 and 2, respectively, as described herein). A primary purpose includes a second pass comprising fractional tissue resection in the topographically marked submentum area. Scalpet diameter, length and type include a 1.5/2.0, skived and slotted (sharp and/or blunt tip). The stop depth is 14 mm. Suction is used and includes vacuum-assisted tissue resection (with scalpet manifold and "wall suction" aspirator on higher setting). The directed closure technique includes Flexzan/Optifoam with a single mooring technique. The vector of directed closure is vertical as indicated by Langer's Lines. Fractional defects are closed horizontally to flatten contour of the submentum. Pre-op and intra-op considerations include generation of photo and video documentation perioperatively (treatment areas demarcated and stencil applied preoperatively). Post-op considerations include use of compression garment for approximately two weeks postoperatively, and photo documentation with use of ImageJ/NIH software for six months.

FIG. 159B is a table detailing procedural components of fractional skin resection of the jowl region, under an embodiment. The fractional skin resection of the jowl region includes use of a horizontal tissue resection technique (technique 2 as described herein). A primary purpose includes a second pass comprising fractional tissue resection in the topographically marked submentum area. Scalpet diameter, length and type include a 1.5/2.0, skived and slotted (sharp and/or blunt tip). The stop depth is 14 mm. Suction is used and includes vacuum-assisted tissue resection (with scalpet manifold and "wall suction" aspirator on higher setting). The directed closure technique includes Flexzan/Optifoam with a single mooring technique. The vector of directed closure is vertical as indicated by Langer's Lines. Fractional defects are closed horizontally to flatten contour of the jowl. Pre-op and intra-op considerations include generation of photo and video documentation perioperatively (treatment areas demarcated and stencil applied preoperatively). Post-op considerations include use of compression garment for approximately one week postoperatively, and photo documentation with use of ImageJ/NIH software for six months.

With reference to FIGS. 159A-159B including tables detailing procedural components of fractional skin resection of submentum-neck regions, an example perioperative sequence begins with intravenous (IV) administration of 1 gm of Ancef (assuming no known allergies to penicillin or cephalosporins). Sedative premedication is then provided as needed following a protocol to be established by the anesthesiologist i.e., 5-10 mg of diazepam (Valium) orally or by IV.

The perioperative sequence continues with outlining or marking of the treatment area in the submentum and neck regions while the patient is in preop holding and in a sitting position. The treatment area is topographically marked for areas of skin resection only, and in areas of the submentum and jowls that are to undergo fractional tissue resection. As an example of topographical marking of a patient, FIG. 160A is a front perspective view of a patient with a horizontal fractional resection skin resection area superimposed on a target area, under an embodiment. FIG. 160B is a right-front perspective view of a patient with a horizontal fractional resection skin resection area superimposed on a target area, under an embodiment. FIG. 160C is a left-front perspective view of a patient with a horizontal fractional resection skin resection area superimposed on a target area, under an embodiment. FIG. 161A is a front perspective view of topographical markings of a patient (labels added for clarity) for treatment of skin laxity of the neck and lipodystrophy of the submentum and jowls, under an embodiment. FIG. 161B is a right-front perspective view of topographical markings of a patient (labels added for clarity) for treatment of skin laxity of the neck and lipodystrophy of the submentum and jowls, under an embodiment. FIG. 161C is a left-front perspective view of topographical markings of a patient (labels added for clarity) for treatment of skin laxity of the neck and lipodystrophy of the submentum and jowls, under an embodiment.

With the patient placed into a supine position, the stencil is trimmed to the exact dimensions of the demarcated fractional resection area. The skin is first cleaned with isopropyl alcohol. The area is then slightly wetted dried 4×4 gauze dressing. The stencil is then applied (ink side down) for 15 seconds. If inadequate stenciling occurs, the stencil is then removed with isopropyl alcohol and the procedure is repeated. Frontal and oblique photos are taken (including scale and paper clip for image j analysis) with the patient in a supine and sitting position. The patient is then taken into the operating room where additional IV sedation is routinely provided by an attending physician.

A field block is then administered to the submentum and neck with a 0.5% Xylocaine with 1/200,000 parts epinephrine. Additional tumescent local anesthesia with 0.25% Xylocaine with 1/400,000 epinephrine is administered to the demarcated submentum and jowl areas that will undergo fractional tissue resection. To minimize distention of the neck treatment area, a reduced volume of the local anesthetic is injected (large volumes of local anesthetic will result in greater distension of the skin, which reduces the percent of fractional resection and inhibits directed closure). The face and neck are then prepped and draped in a sterile fashion.

For Fractional resection of the neck skin, the patient's neck is extended (directed resection) and a 1.5 mm or a 2.0 mm skived non-slotted scalpet with a vacuum manifold depth guide of 4 mm is used. For the submentum, the directed fractional resection of skin within the topographically demarcated area is performed with the neck in a slightly flexed position. It is expected that thorough vacuum evacuation of the skin plugs will occur during this initial pass (to avoid inadvertent suctioning of fat, the vacuum aspirator is set on a lowest setting that will evacuate the skin plugs, as the goal is to remove as little fat as possible during this initial pass). Feathering (free hand de-delineation) is performed beyond treatment outline with the exception of the mandibular jowl line in which a straight-line demarcation is preserved.

A second pass is performed in the demarcated areas of the submentum and jowls where a fractional tissue resection will be performed. The second pass is performed using Technique 1 followed by Technique 2. Technique 1 comprises, in the submentum, a 1.5 mm/2.0 mm skived blunt/sharp side slotted scalpet with a 10 mm depth guide vacuum manifold is inserted into the previously resected fractional defect of the demarcated submentum. Each fractional defect within the submentum may undergo a vertical fractional tissue resection as described. FIG. 162 shows a vertical fractional skin resection area (Technique 1), under an embodiment. FIG. 163 shows a vertical fractional skin resection area (Technique 1) as applied to a target area of a patient, under an embodiment.

To provide a more even surface contour, Technique 2 comprises a subsequent horizontal technique with the 1.5 mm/2.0 mm skived blunt/sharp side slotted scalpet with a 14 mm depth guide inserted in as many fractional defects as needed to achieve a uniform horizontally aligned contour. FIG. 157 shows a horizontal fractional skin resection area (Technique 2), under an embodiment. FIG. 164 shows a horizontal fractional skin resection area (Technique 2) as applied to a target area of a patient, under an embodiment. For insertion and extraction of the slotted fractional tissue scalpets, rotation and vacuum are discontinued.

For the demarcated jowl area of lipodystrophy, a vertical technique is not used. Instead, horizontal Technique 2 is used to perform a horizontally aligned fractional tissue resection with the 14 mm skived blunt tip side slotted scalpet.

A bi-directional directed closure of the anterior neck and submentum is used in embodiments. For the cervical skin inferior to the submentum and starting at a point above the cervical mandibular angle, the directed closure is performed horizontally, and the fractional defects are closed vertically. A single mooring technique is used. For the submentum, directed closure is performed vertically as indicated by Langer's lines. The mooring point is the superior margin of the Flexzan/Optifoam that was previously applied. If a reapplication of the Flexzan/Optifoam is required (due to a less optimal application), only new material is used for the reapplication i.e., the previous material is discarded. A dressing of 4×4s and one-half of an ABD are then applied followed by a (Marena group) cervical-facial compression garment.

FIGS. 165A-165D include tables detailing procedural components of fractional scar reduction, under an embodiment. More particularly, FIG. 165A is a table detailing procedural components of fractional scar reduction of a linear scar, under an embodiment. The fractional scar reduction of a linear scar includes use of a vertical fractional resection of skin and scar epithelium in which the amount of fat resection is minimized. The mechanism of action is the scar is less visibly apparent by fractional delineation of the scar/skin margins (see FIGS. 166-168). Scalpet diameter and type include a 1.5 and 2.0 mm skived, non-slotted scalpet (see FIGS. 139A-139C). The stop guide is configured for a depth approximately in a range of 3-4 mm. Suction is used and includes "wall suction" with the aspirator on lower vacuum setting for evacuation of the skin plugs only while minimizing fat resection. The directed closure technique includes Flexzan/Optifoam with single or double mooring technique. The vector of directed closure is parallel to the longitudinal axis of the scar. Fractional resection defects are closed horizontally at right angles to the linear scar (see FIG. 166). Pre-op and intra-op considerations include generation of photo and video documentation perioperatively. A freehand interdigitating pattern of fractional scar margin resection is used (see FIGS. 166-167). Post-op considerations include removal of the Flexzan dressing approximately 7-10 days following the procedure. Photo documentation is obtained of Flexzan removal.

FIG. 165B is a table detailing procedural components of fractional scar reduction of a wide scar (hypotrophic, hypertrophic and scar contracture), under an embodiment. Scar examples include post-tangential split dermal excision, cervical and axillary contractures. The fractional scar reduction of a wide scar includes use of a vertical fractional resection of skin for "dog-ear" resection, and layered linear wound closure, V-Y advancement and flap transfer techniques are standardized (see FIGS. 169-174). A mechanism of action includes direct surgical excision of scar with shortening of scar revision incision by fractional "dog-ear" resection (see FIGS. 169-174). Scalpet diameter and type includes a 1.5 mm (skived, non-slotted) scalpet and a 2.0 mm (skived, slotted) scalpet (see FIGS. 139A-139C). The stop guide is configured for a depth approximately in a range of 3-6 mm. Suction is used and includes "wall suction" with the aspirator on lower vacuum setting for evacuation of the skin plugs only while minimizing fat resection. The directed closure technique includes a Steristrip (e.g., 0.5 or 1 inch) with a single mooring technique. The vector of directed closure is at right angles to longitudinal axis of wound closure. The fractional resection defects are closed longitudinally with the long axis of the scar. Pre-op and intra-op considerations include generation of photo and video documentation perioperatively. Additionally, the four-to-one rule described herein applies to the size of the fractional resection field and the dimensions of an elliptical excision of the "dog-ear". Post-op considerations include removal and reapplication of the Steristrips approximately 7-10 days following the procedure. Photo documentation is obtained of Steristrip reapplication.

FIG. 165C is a table detailing procedural components of fractional scar reduction of an acne scar, under an embodiment. The fractional scar reduction of a wide scar includes use of a vertical fractional resection technique of skin and scar epithelium, in which the amount of fat resection is minimized in the acne pit. Fractional fat resection is used with fractional skin resection at the peak to flatten contour. A mechanism of action includes flattening of contour with a combined surgical (pit) scar resection and a fractional skin resection of the adjacent skin. Instruments used include standard plastic surgical instrumentation including a 3.0/4.0 punch biopsy, microtome scalpel, and 1.5/2.0 mm skived scalpel. The stop guide is configured for a depth approximately in a range of 2-4 mm. Suction is used and includes "wall suction" with the aspirator on lower vacuum setting for evacuation of the skin plugs. Fat resection is to be minimized at the scar pit and the pit scar epithelium is removed surgically. The directed closure technique includes Flexzan/Optifoam with single or double mooring technique. The vector of directed closure is as indicated by Langer's Lines. Pre-op and intra-op considerations include generation of photo and video documentation perioperatively. Topographical marking of the pits and peaks is performed preoperatively with patient in a sitting position. A microtome release of the base of the pit is performed following punch biopsy excision of the scar epithelium. Fat resection is not performed at the base of the acne pit. Closure of the resected pit defect is performed with a 6.0 nylon horizontal mattress suture. Post-op considerations include removal of the Flexzan/Optifoam dressing approximately 4-6 days following the procedure. Photo documentation is obtained of removal of the Flexzan/Optifoam dressing.

FIG. 165D is a table detailing procedural components of fractional scar reduction of an incisional scar from a primary excisional skin defect, under an embodiment. The fractional scar reduction of the incisional scar includes use of a vertical fractional resection of skin and fat for "dog-ear" resection, and layered wound closure and flap transfer techniques are standardized (see FIGS. 172 and 175). A mechanism of action includes reduction in length of incisional scarring due to fractional resection of "dog-ear" skin redundancies (see FIGS. 169-174). Instruments used include standard plastic surgical instrumentation including a 1.5/2.0 skived scalpel, and 2.0 skived and slotted scalpel (see FIGS. 139A-139C). The stop guide is configured for a depth approximately in a range of 4-6 mm. Suction is used and includes "wall suction" with the aspirator on a vacuum setting appropriate for evacuation of the skin and fat plugs. The directed closure technique includes a Steristrip (e.g., 0.5 or 1 inch) with a single mooring technique. The vector of directed closure is at right angles to longitudinal axis of wound closure. The fractional resection defects are closed longitudinally with the long axis of the scar. Pre-op and intra-op considerations include generation of photo and video documentation perioperatively. Either direct linear or V-Y advancement is used to close the excisional defects (see FIGS. 172 and 175) or V-Y advancement at the perimeter of the excisional defect to reduce the size of a local flap closure. Dog-ear redundancies of the V-Y closures are then fractionally resected (see FIG. 175) in accordance with the four-to-one rule described herein. Post-op considerations include removal and reapplication of the Steristrips approximately 7 days following the procedure. Photo documentation is obtained of Steristrip removal and/or reapplication.

With reference to FIGS. 165A-165D including tables detailing procedural components of fractional scar reduction, the visible impact of a linear scar is dependent upon the direction and anatomical location of the scar. Additional impact is the limitation in the range of motion if the linear scar courses across a joint. This functional impediment is called a scar contracture where severe disability can occur in the neck and axillary regions. Historically, linear scar revisions have employed surgical techniques that visibly de-delineate the scar and lengthen the scar for functional purposes. Many of these plastic surgical procedures employ "W" plasty (for de-delineation) and "Z" plasty (for lengthening) techniques. Fractional scar revision has the potential to digitally de-delineate the visible impact of a linear scar in a manner similar to a "W" plasty, but with a modicum of the incumbent procedural scarring.

Fractional de-delineation of a scar involves each margin of the scar being fractionally resected in a staggered inter-digitating fashion with the opposite scar margin. A vector of directed closure is achieved in a direction along the longitudinal dimension of the linear scar. The fractional procedure is performed "free hand" and additional columns (or rows) can be added for additional de-delineation. FIG. 166 shows a sequence of images (left-to-right) showing a scar, fractional resection of the scar, directed closure (direction of arrow) of the fractionally resected scar, and the scar post-procedure, under an embodiment. FIG. 167 shows a sequence of images (left-to-right) showing the addition of progressively more fractional resection areas for additional de-delineation of the scar, under an embodiment. For wider linear scars, a wider pattern is required with de-delineation of both the scar and the fractional field margins. For these wider linear scars, consideration should also be given to first perform a standard scar revision procedure.

Both the single scalpet and the ganged array will be employed for larger linear scars. FIG. 168 shows a pre-op image (top left) and post-op image (top right) of a hypertrophic scar on the left hip, as well as an image (bottom) of the fractional scar revision procedure, under an embodiment.

For a thin linear scar contracture, the fractional contracture release is similar in technique to linear fractional revision except the directed closure is performed at right angle to the longitudinal dimension of the scar. For a wider scar contracture, an initial surgical release with Z-plasty will be used; fractional reduction of any dog-ear redundancies is performed during this initial procedure. Many of these patients will also benefit from a second-stage fractional de-delineation. FIG. 169 shows front perspective (left) and front-left perspective (right) images of wider cervical scar contractures, under an embodiment. FIG. 170 shows front perspective (left) and front-left perspective (right) images of preoperative cervical scar contracture release, under an embodiment. FIG. 171 shows front perspective (left) and front-left perspective (right) images of postoperative cervical scar contracture release, under an embodiment.

Fractional scar revision of embodiments includes fractional revision of a wide depressed scar from post-tangential intradermal lesion excision. A standard dermatologic technique of excisional lesion biopsy is to shave the lesion tangentially through a variable intradermal plane. Although effective for most lesion resections, many of these procedures result in a wide depressed scar. For these scar deformities, a dual approach to the scar revision is described herein. The wide thin scar epithelium is first resected and closed in layers. With standard techniques, each lateral extent of the layered closure would previously require an additional elliptical excision to avoid a "dog-ear" skin redundancy. Instead of lengthening the closure with an elliptical excision, each lateral "dog-ear" skin redundancy is fractionally resected to reduce the overall length of the scar revision. FIG. 172 is a sequence (left-to-right) showing a scar pre-op with the area to be resected indicated (diagonal markings), the resected scar closed with "dog-ears", fractional resection of "dog-ears", and post-op scar region, under an embodiment. FIGS. 173 and 174 are images (pre-op) of a wide depressed scar showing the area involved in the resection (outlined), under an embodiment. For even wider depressed scars, a V-Y advancement layered closure technique is proposed with fractional resection of each "dog-ear" end of the "Y". FIG. 175 is a sequence (left-to-right) showing a scar pre-op with the area to be resected indicated (diagonal markings), the V-Y advancement layered closure technique with "dog-ears", and fractional resection of "dog-ears", under an embodiment.

With reference to FIG. 165C and the table detailing procedural components of fractional scar reduction of an acne scar, the topographical facial scar irregularities of acne scarring represents one of the most difficult and complex deformities. Deep scar pitting resulting from abscess destruction of the subdermal layer is tightly juxtaposed with normal skin morphology. To achieve a smoother appearance, the irregular cheek topography requires a combined approach of scar pit resection/release/closure with reduction of the "peak" of the adjacent normal skin. Resection of the acne pit is performed with either a 3 mm or 4 mm punch biopsy. The margins of the pit resection are then released with a microtome scalpel. Everted closure is achieved with a 6.0 nylon horizontal mattress suture. The height of the adjacent "peaks" of normal skin is then reduced with fractional resection of skin (and fat as indicated). Directed closure is achieved according to Langer's lines. The patient should also be placed on an anti-acne regiment for at least two weeks post-operatively.

With reference to FIG. 165D and the table detailing procedural components of fractional scar reduction of an incisional scar from a primary excisional skin defect, excisional skin defects are most commonly created from the resection of skin malignancies. Mohs chemosurgery is the most frequently employed modality for the resection of basal cell carcinomas. Following histological verification of the margins of resection, the wound is typically closed with either a direct layered elliptical closure or local flap transposition. With the development of fractional resection, elliptical resection will become less frequently employed as "dog-ear" redundancies can be removed without elliptical extension of the closure, as described in detail herein. For larger excisional defects, closure can be achieved with advancement techniques that would not otherwise be used due to the creation of significant "dog-ear" skin redundancies. The technique of V-Y advancement with fractional resection may reduce the size and need of larger transposition flap techniques.

FIGS. 176A-176C include tables detailing procedural components of fractional tattoo removal, under an embodiment. FIG. 177 is a pre-op image of a subject tattoo, under an embodiment. FIG. 178 is an image showing application of fractional resection to the tattoo, under an embodiment. FIG. 179 is a close up image of the fractional field applied to the tattoo, under an embodiment.

More particularly, FIG. 176A is a table detailing procedural components of fractional tattoo removal of a solid tattoo, under an embodiment. The amount of fat resection is minimized and de-delineation of the pattern of the tattoo may be required using the fractional resection of non-tattooed skin. A mechanism of action includes removing enough ink that the pattern or presence of the tattoo is no longer visibly apparent (see FIGS. 177-179). Instruments used include a 1.5 and 2.0 mm skived and non-slotted scalpet as described herein. The stop guide is configured for a depth approximately in a range of 2-4 mm. Suction is used and includes "wall suction" with the aspirator on a vacuum setting appropriate for evacuation of the skin plugs. The directed closure technique includes Flexzan/Optifoam with single or double mooring technique. The vector of directed closure is as indicated by Langer's Lines to reduce visible scarring, and the vector of closure is at right angles to the longitudinal deformation of the fractional skin defects.

Pre-op and intra-op considerations include generation of photo and video documentation perioperatively. A freehand resection of inked skin is employed where the margin of the tattoo includes non-tattooed skin. As most tattoos are created with impregnation of ink in the superficial dermis, an intradermal fractional resection will be performed (see FIGS. 178-179). Post-op considerations include removal of the Flexzan/Optifoam dressing approximately 7-10 days following the procedure. Photo documentation is obtained of removal of the Flexzan/Optifoam dressing.

FIG. 176B is a table detailing procedural components of fractional tattoo removal of a cursive or non-solid tattoo, under an embodiment. The amount of fat resection is minimized and de-delineation of the pattern of the tattoo may be required using the fractional resection of non-tattooed skin. A mechanism of action includes removing enough ink that the pattern or presence of the tattoo is no longer visibly apparent (see FIGS. 177-179). Instruments used include a 1.5 and 2.0 mm skived and non-slotted scalpet as described herein. The stop guide is configured for a depth approximately in a range of 2-4 mm. Suction is used and includes "wall suction" with the aspirator on a vacuum setting appropriate for evacuation of the skin plugs. The directed closure technique includes Flexzan/Optifoam with single or double mooring technique. The vector of directed closure is as indicated by Langer's Lines to reduce visible scarring, and the vector of closure is at right angles to the longitudinal deformation of the fractional skin defects.

Pre-op and intra-op considerations include generation of photo and video documentation perioperatively. A freehand resection of inked skin is employed where the margin of the tattoo includes non-tattooed skin. As most tattoos are created with impregnation of ink in the superficial dermis, an intradermal fractional resection will be performed (see FIGS. 178-179). Post-op considerations include removal of the Flexzan/Optifoam dressing approximately 7-10 days following the procedure. Photo documentation is obtained of removal of the Flexzan/Optifoam dressing.

FIG. 176C is a table detailing procedural components of fractional tattoo removal of a large tattoo, under an embodiment. The amount of fat resection is minimized and de-delineation of the pattern of the tattoo may be required using the fractional resection of non-tattooed skin. A mechanism of action includes removing enough ink that the pattern or presence of the tattoo is no longer visibly apparent (see FIGS. 177-179). Instruments used include a 1.5 and 2.0 mm skived and non-slotted scalpet as described herein. The stop guide is configured for a depth approximately in a range of 2-4 mm. Suction is used and includes "wall suction" with the aspirator on a vacuum setting appropriate for evacuation of the skin plugs. The directed closure technique includes Flexzan/Optifoam with single or double mooring technique. The vector of directed closure is as indicated by Langer's Lines to reduce visible scarring, and the vector of closure is at right angles to the longitudinal deformation of the fractional skin defects.

Pre-op and intra-op considerations include generation of photo and video documentation perioperatively. A freehand resection of inked skin is employed where the margin of the tattoo includes non-tattooed skin. As most tattoos are created with impregnation of ink in the superficial dermis, an intradermal fractional resection will be performed (see FIGS. 178-179). Post-op considerations include removal of the Flexzan/Optifoam dressing approximately 7-10 days following the procedure. Photo documentation is obtained of removal of the Flexzan/Optifoam dressing.

With reference to FIGS. 176A-176C, the removal of indelible ink in a layered biological structure requires an anatomical determination of the depth that the material has been impregnated. For tattoos, the indelible ink is impregnated in a high concentration within the superficial (papillary) dermis to enhance the visibility of the tattoo. Key features in the determination of patient inclusion/exclusion criteria include the overall pattern and size of the tattoo, the anatomical area of tattoo, and the percent fractional resection capable within a single procedure.

Based upon these factors, the fractional resection of a tattoo of embodiments should be intradermal and should only extend to a depth immediately subjacent to the ink including a margin of non-inked dermis. The overall size and pattern of the tattoo determines the magnitude and setting of the procedure to be performed. For a small surface area tattoo, a smaller fractional resection of the entire area can be performed. For larger tattoos that involve a significant a significant surface area, either a more major fractional procedure in an operating room setting or a higher numbered sequence of smaller fractional procedures will be required. Transitioning into non-tattooed areas involving more complex patterns will be required.

Due to the enhanced risk of hypertrophic scarring, tattoos involving the deltoid shoulder and the sternal skin should be approached with caution. A different application of the four-to-one rule is not the overall surface area required to fractionally resect an aesthetic skin laxity deformity, but is instead the sequencing of procedures required to remove a deformity whether that deformity is a tattoo, port wine hemangioma or a large congenital nevus. As the percent density of fractional resection is between 20-25%, at least four procedures will be required for the resection of any type of skin surface deformity.

A fractional resection procedure of an embodiment comprises fundament factors including one or more of the dimensionality of the fractional field, the orientation of the fractional field, and the vector of directed closure. Each anatomical site (and each patient) involves a unique combination of these three factors for the proper conduct of an effective fractional resection procedure. The interaction of these three factors is used by a surgeon to create a reliable fractional procedure configured to produce uniformly-enhanced aesthetic clinical outcomes appropriate to the subject anatomical site.

The dimensionality of the fractional field conforms to the dimensions of the aesthetic deformity. FIG. 180 shows vertically and horizontally aligned example fractional fields and corresponding vertical and horizontal deformities, under an embodiment. The length and width of each procedure is determined by the unique metrics of the patient's deformity. For example, patients with more skin laxity will have larger factional fields that also will conform to the unique topography of the patient's deformity. For patients with more horizontal skin laxity, the fractional field is widened.

FIG. 181 shows a wider vertically aligned example fractional field with more severe skin laxity, under an embodiment. For patients with more vertical skin laxity, the fractional field is lengthened, but embodiments are not so limited. A unique topography of the field is marked preoperatively on the patient depending on the goal of the procedure and the unique patient metrics of the deformity itself.

The orientation of the fractional field is another factor in determining the amount and the direction of skin tightening. This factor is less patient-dependent as it is determined more by the anatomical region in which the procedure is being performed. FIG. 182 shows a horizontal dependant curvilinear deformity with a horizontally aligned example fractional field, under an embodiment. A horizontal orientation of the field provides more skin tightening in a horizontal dimension if the vector of directed closure is also horizontal. FIG. 183 shows a horizontal dependant curvilinear deformity with a horizontally aligned example vector of directed closure, under an embodiment.

In contrast, a vertical orientation of the field will not provide as much horizontal tightening if the vector of directed closure is horizontal. FIG. 184 shows an example fractional field vertically aligned with the vertical axis of the submental deformity, and having a horizontally aligned vector of directed closure at a right angle to the vertical axis of the fractional field, under an embodiment. Vectors of directed closure that are aligned with the longitudinal axis of the field provide maximum skin tightening but may hamper coaptation of the skin margins due to tension (see FIG. 4).

The vectors of directed closure are determined by the most effective direction of skin tightening to achieve a desired aesthetic goal. For some procedures, vectors of directed closure conform to established vectors employed in plastic surgery procedures. Combining a horizontally aligned vector of directed closure with a horizontally aligned fractional field provides maximum skin tightening but may hamper coaptation of skin margins and primary healing due to tension (see FIG. 4). Combining a horizontally aligned vector of directed closure with a vertically aligned fractional field provides less skin tightening but promotes coaptation of fractional skin margins and primary healing due to less tension (see FIG. 5). Further, vectors of directed closure that also conform to Langer's lines provide the least tension of closure and promote primary healing. However, the key factors affecting contouring and primary healing are dimensionality, orientation and the vector of directed closure.

Fractional resection comprises numerous principles as described herein. As one principle, alignment of the fractional field should correspond to the margins of the aesthetic deformity (see FIG. 1). An additional principle is that vectored closure at right angles to the longitudinal dimension of the field lengthens the longitudinal dimension of the field and tightens the horizontal dimension. For example, for enhanced contouring of the submentum, the longitudinal dimension is lengthened and the horizontal dimension is tightened to accentuate the cervical mandibular angle (see FIG. 5).

For patients with more skin laxity, a wider horizontal dimension of the fractional field produces more tightening in the horizontal dimension (see FIG. 2). Enhanced tightening also increases the tension that resists directed closure of the fractional skin defects in the horizontal dimension. A balance is met between enhanced tightening and primary healing by determining the appropriate width of the vertically oriented fractional field.

For vertically oriented aesthetic deformities, the fractional field is selected to be wide enough to account for the skin laxity of the aesthetic deformity. However, the fractional field should not be so wide as to prevent directed closure and coaptation of skin margins of the fractional skin defects within the field (see FIG. 2).

An additional principle includes enhanced contouring, and involves the use of focal lipectomy with fractional skin resection where lipodystrophy is present within the aesthetic deformity.

When planning a fractional resection procedure, the goal or desired outcome of the fractional procedure is first identified. When the procedure involves the submentum for example, enhanced definition of the cervical mandibular angle is the desired outcome. This goal is achieved using a vertically oriented fractional field that lengthens the vertical dimension. Further, the fractional field includes a width configured to adequately resect skin laxity. A horizontal vector of directed closure is used to achieve the clinical endpoint. FIG. 185 shows a vertical deformity of the submentum requiring lengthening in the vertical axis and tightening in the horizontal axis (left), and the desired goal of the cervical mandibular angle having enhanced definition (right), under an embodiment.

As another example involving the jowl, the desired goal is to straighten the curvilinear margin of the deformity to be in line with the jawline. A horizontally aligned fractional field encompassing the horizontally aligned deformity is used. To straighten the curvilinear margin of the deformity, the vector of directed closure is aligned horizontally with the jawline. FIG. 186 shows a horizontal dependent curvilinear deformity with horizontally aligned fractional field and horizontal vector of directed closure (left), and the desired goal following raising and straightening of the curvilinear deformity in line with the jaw margin (right), under an embodiment.

An additional example involves the bra line, where the goal is to straighten and raise the curvilinear margin of the deformity. The fractional procedure in this example includes use of a horizontally aligned fractional field that encompasses the horizontally aligned deformity. Further, the vector for directed closure is aligned horizontally to straighten and raise the curvilinear margin of the deformity. FIG. 187 shows the horizontally aligned fractional field (encompassing the horizontally aligned deformity) with a horizontal vector of directed closure (top), and the desired goal following raising and straightening of the margin of the curvilinear deformity (bottom), under an embodiment.

Another example involves the medial infragluteal fold. The goal in this region is to correct the right angle boxy contour of the deformity. An obliquely aligned fractional field is used that encompasses the margin of the obliquely aligned deformity. To straighten and raise the right angle margin of the deformity, the vector for directed closure is aligned obliquely along the longitudinal axis of the field. FIG. 188 shows an oblique fractional field (top), and the vector for directed closure is aligned obliquely (arrow) along the longitudinal axis of the field (bottom), under an embodiment.

In an example involving the upper arms, the goal is to raise the inferior margin of upper arm (when the arm is extended). Embodiments include use of an elliptical horizontally aligned fractional field that extends from the axilla to the elbow. A smaller fractional field can be used for smaller degrees of skin laxity. The vector of directed closure is aligned at right angles to the longitudinal axis of the fractional field in order to raise the inferior margin of the upper arm. As the vector of directed closure conforms to Langer's lines, enhanced primary healing also occurs. FIG. 189 shows an elliptical horizontally aligned fractional field that extends from the axilla to the elbow with a vector of directed closure aligned at right angles (arrow) to the longitudinal axis of the fractional field (top), and the resulting upper arm with the raised inferior margin (bottom), under an embodiment.

In yet another example directed to the proximal upper medial thighs, the goals are to straighten and raise the proximal horizontal curvilinear skin redundancy and, additionally, to tightening the distal vertical skin redundancy. A "T"-shaped fractional field comprising horizontal and vertical components is used to accomplish both goals. The vector of directed closure is aligned horizontally at right angles to both the horizontal and vertical components of the "T".

A further example includes the suprapatellar knee or the superior posterior elbow, and has the goal to tighten the vertically aligned skin redundancy. To achieve this goal, the fractional field is aligned vertically along the longitudinal aspect of the extremity. The vector of directed closure is employed horizontally at right angles to the longitudinal axis of the fractional field. This vertical alignment of the fractional field combined with a horizontal vector of directed closure has the additional benefit of obviating the need to splint across a joint.

Regardless of the anatomical region, fractional skin resection is a key component in the aesthetic restoration of the patient. Two-dimensional fractional skin tightening can provide significant three-dimensional contouring especially if the fractional field of the anatomical region is closed with the correct vector. Combined with fractional skin resection, additional aesthetic contouring is also provided with focal lipectomy in selected areas of lipodystrophy. These principles are especially evident in the submentum and jowl regions where a combination of skin laxity and lipodystrophy are major contributors to the aesthetic deformity. The successful perioperative conduct of an aesthetic fractional procedure depends on several factors as described herein that are to be accounted for in each procedure. These factors include, without limitation, skin laxity, skin thickness, lipodystrophy and gender.

Embodiments include a depth guide comprising small incremental changes in depth configured to fine-tune the depth of a transdermal fractional resection for a specific subject. The gender and age related variations of dermal thickness in a specific anatomical region determine the depth required for a transdermal fractional resection. FIG. 233 shows the tissue layers forming human skin. FIG. 234 shows a scalpet penetrating the epidermis and dermis of a subject during a fractional resection at an appropriate depth. FIG. 235 shows a scalpet penetrating the subdermal plexus of a subject during a deeper fractional resection. Deeper resections that involve the subdermal plexus of vessels may predispose the patient to a prolonged inflammatory wound healing response in subdermal (hypodermis) layer. This type of untoward postoperative response could lead to prolonged erythema due to neovascularization of the subdermal plexus and deep dermal reticular layers. Another untoward effect is the florid fibroblastic wound healing response that contracts the subdermal plane creating a corrugated texture ("skin corrugations") of the overlying skin surface. In contrast to deeper resections, superficial intradermal fractional resections may lead to inadequate aesthetic skin tightening due to recoil of the intact deep reticular dermis.

Another factor to be considered in determining an appropriate depth for a fractional resection procedure is the rigidity of the dermis that will resist deformation. This occurs in men in hirsute areas due to hair follicles stenting a thicker dermis. For Caucasian women with thinner non-hirsute skin, the complication of prolonged erythema and corrugated surface irregularities is more likely to occur. In contrast, women with actinic damage have stiffer skin due to colloid deposition within the dermis. These patients exhibit less textural changes and inflammation of the skin surface than patients without solar damage.

The fractional resection instrumentation of embodiments described herein therefore includes a depth guide comprising depth markings graduated in small increments configured to enable precise control of depth of a fractional resection. For example, an embodiment includes a depth stop calibrated to include a series of increments repeating at a regular interval, with the interval being in a range (e.g., 0.1 mm to 2 mm) of depths, but is not so limited.

A determination of skin dermal thickness is made in practice using a visual inspection of the fractionally resected defect, use of a digital metric gauge, and/or an ultrasound determination of skin dermal thickness in order to avoid the sequelae of a prolonged wound healing response in the subdermal layer. Using visual inspection, a practitioner observes the vacuum evacuation of the skin plugs. If the practitioner determines the depth is too superficial, an intradermal fractional resection occurs with compromised vacuum evacuation of the incised skin plugs, which causes many of the skin plugs to remain insitu. If the fractional resection is too deep, involvement of the subdermal vascular plexus occurs resulting in an increase in bleeding. The practitioner must choose the correct depth guide that is based on the patient's own histological layers that provides a transdermal resection that is neither too deep nor too superficial.

For a specific metric depth of a scalpel, the fractional resection of skin will involve different layers based on the variable thickness of the dermis. Although different anatomical regions will vary in skin thicknesses, variability of dermal thickness will also be observed in patients of different genders, ages, and ethnicities. Patients such as older Caucasian women will have a thinner dermis that will require a shorter depth stop to avoid broaching the subdermal plexus. In the same anatomical region, men will require a longer depth stop to provide a transdermal fractional resection.

The adaptation of the fractional resection procedure of embodiments for any anatomical region based on the specific physical findings of an individual patient subject of the procedure can also include adapting the preoperative marking of the fractional skin resection fields and the areas of lipodystrophy to the individual physical findings of the patient. For the submentum, for example, this corresponds to a vertical submental field that is marked as a wider region in patients with more skin laxity. This principle can be applied to any anatomical region where skin laxity is present.

Thus, the fractional resection of skin in a specific anatomical region, such as the submentum for example, is based on the histological features of the skin and not upon a metric that is applied for all genders, ethnicities and age. Avoidance of a prolonged wound healing response should reduce the period of postoperative erythema and skin surface irregularities. Limiting the depth of fractional resection also reduces depressed punctate surface irregularities caused by the unwarranted resection of subcutaneous fat.

Since the advent of bovine collagen injection filler, the use of non-biological injectables has taken a dominant role in the filler market. Embodiments described herein include a novel collagen injectable filler composition, the production and use of which comprises the novel aesthetic surgical discipline of fractional skin resection described in detail herein and in the Related Applications. The novel filler of embodiments herein is referred to as Live Autologous Dermal Matrix (LADMIX) Injectable Filler, or "LADMIX," but is not so limited. The LADMIX comprises a biological collagen injectable configured as a unique adjunct to the fractional resection of skin where the fractionally resected dermal plugs (also referred to herein as "pixels," "skin pixels," or "skin plugs") are used as a donor tissue to create a live autologous dermal injectable filler. Although dermal matrix is not "living" by itself, the presence of live fibroblasts in the injected filler continuously produces collagen as a live biological dermal filler. As the filler material is from the patient's own skin, resorption of the filler is minimized and the contour correction is more long-term than conventional artificial fillers. Further, immunological or foreign body rejection is also minimized or avoided.

FIG. 191 shows a face having target tissue that includes, for example, furrows and folds. The LADMIX injection provides a significant benefit to these commonly occurring aesthetic deformities. Under the embodiments herein, skin plugs of a fractional resection that might otherwise be discarded are harvested insitu from the skin surface. FIG. 192 shows a fractionally incised field (skin plugs insitu), under an embodiment. The combined procedure of fractional skin tightening and LADMIX filler injection is performed concurrently, but is not so limited.

The skin plugs are harvested insitu from the fractionally incised field with application of an adherent substrate, for example, doubly adherent dermatome tape, and/or as described in detail herein and in the Related Applications. FIG. 193 is a detailed view of fractional skin resection defect harvesting, under an embodiment. The external orientation of the epidermis is maintained during the harvesting process, as described in detail herein. The skin plugs can either be harvested with the membrane applied directly to a dermatome or the plugs can be separately harvested onto the membrane and then applied to the dermatome. FIG. 194 shows an example with skin plugs harvested using a membrane applied directly to a drum dermatome, under an embodiment, and as described in detail herein. FIG. 195 shows removal of the epidermal component by transecting the skin plugs generated by the dermatome with an outrigger blade of the dermatome, under an embodiment. FIG. 196 shows skin plugs separately harvested onto a membrane, and the membrane is then applied to a dermatome (e.g., drum), under an embodiment.

The harvested dermal plugs are collected for morselization into the LADMIX preparation or composition. The device used for morselization is configured to mechanically mince the dermal plugs into a viscous liquid that minimizes fibroblast cellular disruption. FIG. 197 shows a non-compressive moreselizer configured to mechanically mince the dermal plugs into a viscous liquid, under an embodiment.

The LADMIX preparation is loaded into a syringe with a large bore needle for injection. Prior to injection, a local anesthetic (e.g., 1% Xylocaine with epinephrine) is injected into the furrow of the wrinkle/fold deformity. The injection of a local anesthetic provides both anesthesia and lifting of the furrow that facilitates the injection of the LADMIX filler. The injection of the LADMIX filler is performed with a syringe and large bore needle with the needle tip down, for example. The needle tip is inserted into the longitudinal axis of the furrow but is not so limited. FIG. 198 shows injection of the LADMIX filler at a target tissue site, under an embodiment. Advancing the needle along the furrow of the deformity auto dissects the filler pocket while the LADMIX filler is being injected. The injected autologous filler is then manually massaged into a smooth surface contour. A steristrip is then applied over the injected furrow to stent and retain the corrected surface contour.

An example embodiment of the scalpet device includes a multi-scalpet array comprising a multi-functional chamber, and is configured for the simultaneous resection and collection of multiple pixels. The collection chamber, also referred to herein as the "chamber," is configured to preserve the viability and the volume of the autologous injectable filler and, further, is configured to serve one or more functions including, for example, acting as a collection chamber or receptacle for resected pixels, a mincing chamber for mincing the collected dermal plugs, a mixing chamber for mixing the minced tissue with hyaluronic acid or saline solution, and/or a transfer vessel or loading station for moving the minced pixel solution to a hypodermic, to name a few.

The multi-functional chamber, when configured or used for the collection chamber function, passively collects harvested dermal plugs by pushing the plugs into the chamber. At the end of this phase of duty cycle, a multifunctional port is configured for short periods of vacuum extraction of dermal plugs within the lumen of the scalpets. The chamber is otherwise kept at ambient atmospheric pressure to pressure the viability of the dermal plugs. An "O-ring" is included in a distal region of the central drive shaft (e.g., at the investing plate) to avoid retrograde gear particle contamination. A separate detachable (vacuum assisted) epidermal extraction chamber can be used first during the initial fractional resection pass, but embodiments are not so limited.

The multi-functional chamber, when configured or used for the mincing chamber function, receives a rotating mincing blade coupled or attached to the central drive shaft. During the harvest phase of the duty cycle, the central scalpet drive shaft and mincing blade are retracted proximally to avoid continuous mincing of the harvested dermal plugs. During the mincing phase of the duty cycle, the central drive shaft and mincing blade are advanced distally for a prescribed time period.

The multi-functional chamber, when configured or used for the mixing chamber function, receives a carrier fluid via syringe through a multifunctional chamber port. Carrier fluids can include one or more of saline, hyaluronic acid, hydrogels and bioactive factors such as dermal growth factor, for example.

The multi-functional chamber, when configured or used for the syringe loading chamber function, is configured for drawing or extracting the minced composition into a syringe via the multifunctional port for subsequent injection onto the target or recipient site.

More specifically, FIG. 199 shows an example of a scalpet device including a multi-functional chamber, under an embodiment. The multi-scalpet array of the scalpet device of this example embodiment includes a centerless 3×3 multi-scalpet array configured for the resection and collection of eight (8) pixels simultaneously, but is not so limited. The device includes a handpiece coupled to or including a central drive shaft or pinion coupled to a drive system (e.g., gears, etc.) and driving rotation of eight scalpets (no scalpet in center position of 3×3 array). A vacuum is applied through a vacuum port of the drive system housing (e.g., gearbox, etc.) to minimize and/or eliminate transfer of gear debris to the pixel chamber, but the embodiment is not so limited. The collection chamber or chamber is configured to serve one or more functions including, for example, acting as a collection receptacle for resected pixels, a mixing chamber for mincing and mixing the pixels with hyaluronic acid or saline solution, and/or a transfer vessel for moving the minced pixel solution to a hypodermic, to name a few. A size (e.g., diameter, etc.) of the collection chamber is selected based on, for example, the volume or number of pixels to be collected in the collection chamber.

The housing includes or is coupled to an end cap at the distal end of the scalpet device, and the end cap of an embodiment is detachable but is not so limited. A length of the end cap may vary depending on the depth of resection desired. Alternatively, the end cap is attached via an internal spring configured to extend the end cap over the scalpets when not in use. Once the end cap has been installed, vacuum tubing is connected to the vacuum port of the drive system housing. This assures the effective removal of any gear debris, and in combination with the mesh buffer plate assures the resected pixels are free from any unwanted materials. The scalpet device and/or the vacuum are configured to pull the resected pixels through the scalpets (e.g. lumen and proximal end region) and into the collection chamber, but are not so limited. FIG. 200 shows an example vacuum flow path through the scalpet device, under an embodiment.

FIG. 201 shows an example scalpet device following collection of pixels in the collection chamber, under an embodiment. Following completion of a portion of a harvesting procedure and/or collection in the chamber of sufficient dermal plugs or pixels, the handpiece with the attached scalpet array is inverted, allowing the pixels to collect at the proximal end of the collection chamber. The end cap is removed and the vacuum fitting and fastening screw are replaced with two plugs. FIG. 202 shows an inverted handpiece with pixels in the collection chamber, under an embodiment. The collection chamber is configured to receive or contain a saline and/or other desired solution or composition, which is added to the pixels. An alternative end cap with a Luer or similar fitting plug is attached, and the handpiece with the chamber is reverted back to its original orientation. FIG. 203 shows the inverted handpiece with the alternative end cap and fitting plug installed, under an embodiment.

The handpiece is then detached from the chamber, fitted with a mincing blade, and is then re-attached to the collection chamber. FIG. 204 shows the handpiece with mincing blade attached and positioned in the collection chamber with the pixel solution, under an embodiment. The pixel solution is minced to the desired consistency using the mincing blade, thereby forming the LADMIX filler. The mincer is then removed, and a syringe is attached to the end cap. The LADMIX filler is drawn into the syringe from the collection chamber, and the LADMIX filler is ready to be injected into a target tissue site using the needle attached to the syringe. FIG. 205 shows the LADMIX filler drawn into the syringe, under an embodiment. FIG. 206 shows the syringe and attached needle readied for injecting the LADMIX filler into the target tissue site, under an embodiment.

Harvesting tissue in an embodiment for use in preparing the LADMIX includes removal of the epidermis, which avoids the occurrence of epidermal inclusion cysts at the recipient injection site. The removal of the epidermis and the harvest of dermal plugs is accomplished using a method including, but not limited to, one or more of delamination of the epidermis, dermabrasion of the epidermis, vacuum assisted two-pass technique, and the two-pass technique with injection. Each of these methods is described in detail herein.

The delamination of the epidermis from the dermis comprises blistering the skin either within the entire fractional field or at individual fractional sites. FIG. 207 shows a skin blister formed within an entire fractional field, under an embodiment. FIG. 208 shows the fractional field following removal of the blistered tissue overlying the entire fractional field, under an embodiment. FIG. 209 shows formation of multiple skin blisters, under an embodiment. FIG. 210 shows multiple fractional fields following removal of the blistered tissue overlying the fractional fields, under an embodiment. The blistering of an embodiment is performed using vacuum-assisted mechanical vibratory shearing with heat. The blistering of an alternative embodiment is performed using vacuum-assisted mechanical vibratory shearing without heat. Yet another alternative embodiment for skin blister formation includes superficial injection of a local anesthetic or normal saline at the epidermal/dermal junction with the use of a short multiple needle injection manifold. Additional alternatives include vacuum assist and/or mechanical shearing and/or heat, but embodiments are not so limited.

Subsequent to the skin blistering, dermal plug harvesting is applied with a single pass of either a single scalpet system or with a multiple scalpet array as described in detail herein. FIG. 211 shows harvesting of dermal plugs within a blistered region using a single scalpet system or a multiple scalpet array, under an embodiment.

The removal of the epidermis and the harvest of dermal plugs of an alternative embodiment involves dermabrasion of the epidermis from the dermis. The entire fractional donor field is dermabraded with a standard dermabrasion system, but embodiments are not so limited. Alternatively, removal of the epidermis is accomplished by dermabrading each individual fractional site with a small rotatory burr powered by the single scalpet console described herein.

Another alternative embodiment for removal of the epidermis and the harvest of dermal plugs involves use of a vacuum assisted two-pass method or process. The first fractional resection pass is performed superficially to remove the epidermis and a small portion of the papillary dermis (inclusion of the papillary dermis into the harvested dermal plug is important as a higher density of fibroblasts are present in that portion of the dermal layer). The second fractional harvesting pass is performed full thickness through the dermis. The elastic recoil of the skin defect margins of the first fractional pass provides additional clearance of the fractional defect skin edges for the second harvest pass. As with other methods described herein, the incised dermal plug is then vacuum evacuated and collected into an inline scaled volumetric collection canister, for example.

An embodiment of the vacuum assisted two-pass method includes an additional method to provide epidermal margin clearance. This additional margin clearance method is used during the second fractional harvesting pass in which the scalpet/array is first inserted into the fractional defects without rotation. When fully inserted into the fractional defect of the first pass, the rotation of the console is then initiated for the second harvest pass.

An additional alternative embodiment for removal of the epidermis and the harvest of dermal plugs involves use of the vacuum assisted two-pass method with a superficial injection of a local anesthetic or normal saline. This method minimizes the unwanted resection of the papillary dermis during the first pass.

Other alternative embodiments hereunder include additional applications and procedures involving the autologous dermal filler, also referred to as the autologous injectable, and fractional skin grafting. More particularly, embodiments comprise fractional denuding of the epidermis of an autologous injectable donor site prior to the fractional harvesting of dermal plugs for mincing and composing to form the autologous injectable. The geometry and pattern of the fractionally denuded epidermis is the same as that of the fractional dermal plug harvest. The fractional denuding and fractional harvesting of dermal plugs includes use of single scalpet or multiple scalpet arrays as described herein, but is not so limited.

A procedure of an embodiment includes, at a donor site, harvesting a sheet of epidermis as a bleb, or blister, without removing the dermis. FIG. 227A shows harvesting of the epidermis at a donor site without removing the dermis, under an embodiment. The harvesting of epidermis of an embodiment comprises use of the Cellutome Epidermal Harvesting system, but is not so limited. This suction blister epidermal harvesting includes harvesting of the epidermal layer of the skin, which includes all epidermal cells, which have the potential to contain basal layer keratinocytes. These cells play a fundamental role in reepithelialization and wound healing. Also present in the harvested tissue are melanocytes, which produce melanin that is responsible for repigmentation of new skin. Therefore, the suction blister epidermal grafting technology of the Cellutome Epidermal Harvesting System isolates both keratinocytes and melanocytes within the microdomes (i.e. blisters), keeping the cellular structure of the epidermis intact and therefore viable for transplant.

Healing of the graft donor site of an embodiment is accelerated with minimal scarring as a result of harvesting the epidermal cell graft without sheet harvesting of the dermis as is commonly performed with a split thickness skin graft. Fractional harvesting of epidermal cell components will further accelerate healing of the donor site as the remainder of the donor site is not denuded.

The harvested epidermal tissue is then minced for application at a recipient site. In an embodiment the minced epidermal tissue is directly applied to a recipient site. Alternatively, a spray is formed from the epidermal tissue, and the spray comprising the epidermal cells is sprayed onto a graft recipient site. Embodiments include use of the RECELL Autologous Cell Harvesting System, for example, which is a device that enables production of a suspension of spray-on skin cells at a point of care using a small sample of a patient's own skin. This suspension includes the cells necessary to regenerate the outer layer of natural, healthy skin and is prepared and applied at the point-of-care.

Following generation of the denuded epidermis at the donor site, dermal plugs are fractionally harvested at the donor site while preserving the intermediary epidermis between the harvested epidermal plugs. The dermal plugs are harvested from regions having the denuded epidermis, but are not so limited. FIG. 227B shows fractional harvesting of the dermis at a donor site via the denuded regions of the epidermis, under an embodiment. The fractional resection or harvesting of the dermal plugs includes use of the fractional resection devices and/or methods described herein.

The harvested dermal tissue is then applied to a recipient skin defect site. In an embodiment, the dermal plugs are applied directly to the recipient skin defect site. FIG. 228A shows dermal plugs applied directly to the recipient skin defect site, under an embodiment. Following application of the dermal plugs at the defect site, the minced epidermal tissue is applied to the subjacent dermal grafted layer of dermal plugs. The minced epidermal tissue is directly applied to subjacent dermal grafted layer in an embodiment. In an alternative embodiment, a spray is formed from the epidermal tissue, and the epidermal cells are sprayed onto the subjacent dermal grafted layer, as described in detail herein.

As an alternatively to direct application of the dermal plugs, a minced dermal paste is generated using the harvested dermal plugs, and the minced dermal paste is applied directly to the recipient skin defect site. Minced epidermal tissue is then applied to the subjacent dermal grafted layer of dermal plugs. The minced epidermal tissue is directly applied to subjacent dermal grafted layer in an embodiment. In an alternative embodiment, a spray is formed from the epidermal tissue, and the epidermal cells are sprayed onto the subjacent dermal grafted layer. FIG. 228B shows the minced dermal paste applied directly to the recipient skin defect site, and the minced epidermal tissue or grafts applied to the subjacent dermal grafted layer, under an embodiment.

The fractional skin grafting of an embodiment realizes avoidance of erythema by limiting the evoked wound healing response from the subdermal layer through control of the scalpet insertion depth during a fraction harvesting procedure. FIG. 229 shows a scalpet inserted to an appropriate depth in tissue (left), and a scalpet inserted to an excessive depth in tissue (right). For men, this is less of an issue because their skin is thicker than women. With the same metric depth guide, women are more likely to have involvement of the subdermal plexus of vessels than men. For this reason, a shallower depth guide is employed for women when performing a fractional skin resection i.e., by comparison, a 4 mm depth guide should be used for men and a 3 mm depth guide should be used for women. Other remedies include exchanging the elastic adhesive membrane if saturated with blood to avoid contact inflammation of the fractional field. Treatment of the potential for prolonged erythema involves the early application of a topical steroid.

The fractional skin grafting of an embodiment realizes avoidance of surface contour irregularities in a similar manner as it realizes avoidance of prolonged erythema. A fractional resection that is so deep as to involve the subdermal layer evokes a subdermal plane of wound contraction resulting in the corrugation of the skin surface within the fractional field, as described herein. With the same metric depth guide, women are more likely to have involvement of the subdermal plexus of vessels than men due to gender differences in skin thickness. For this reason, a shallower depth guide should be employed in women when performing a fractional skin resection i.e., a 4 mm depth guide should be employed for men and a 3 mm depth guide should be employed in women. Another potential factor resulting in surface irregularities is the poor coaptation and overlapping of fractional skin margins of the fractional field secondary to excessive tension of vectored closure. FIG. 230 shows poor coaptation and overlapping of fractional skin margins of the fractional field. Tension of directed closure can be modified by reducing the dimension of the fractional field and by the more moderate regional application of manual tension that is applied to the elastic adhesive membrane.

The fractional skin grafting of an embodiment also realizes avoidance of follicular cysts. The principle etiology of follicular cysts is the entrapment of a hair follicle during the fractional resection of a hirsute area such as the anterior neck of a male patient. This complication occurs when a vertically applied single scalpet or a multiscalpet array transects the hair shaft distal to an obliquely coursing hair follicle. FIG. 231 shows a vertically applied scalpet transecting the hair shaft distal to an obliquely coursing hair follicle. If the angle of the hair shaft relative to the skin surface is decreased (obliqueness is increased), then more hair follicles may be entrapped. The entrapment of the hair follicle can evoke a foreign body reaction when the follicle enters an anagen phase. Avoidance of this complication under embodiments herein involves the tilting of the scalpet or MSA in line with the obliquely coursing hair shafts. FIG. 232 shows tilting of the scalpet in line with an obliquely coursing hair shafts during fractional skin grafting, under an embodiment. Furthermore, the depth of the fractional resection in a hirsute area must be deep enough to resect the terminal hair follicle i.e., the histologic depth of resection is in the immediate subjacent subdermal plane. In non-hirsute areas such as the submentum in women, entrapment of vellus hair follicles does not evoke a severe inflammatory condition. For this reason, an intradermal fractional resection can be performed in non-hirsute areas such as the submentum in women but should not be performed in hirsute areas such as the submentum in men.

The fractional skin grafting of an embodiment includes use in treatment of visible depigmented scarring within the fractional field. Depigmented scars are due to the inadequate coaptation of fractional skin margins within a fractional field. The etiology of this complication is associated with excessive resistance of closure due to excessive width of a fractional field for the amount of skin laxity. The visibility of the depigmentation is also associated with certain Fitzpatrick skin types such as #2-4. Revision of the depigmented scar involves the fractional resection within the borders of the scar i.e., the use of a 1 mm diameter scalpet within the margins of the depigmented scar, as described in detail herein. The vector of fractional closure is performed according to Langer's lines and is at right angles to the elongation of the fractional scar defect i.e., directed closure for the submentum is vertical, as described in detail herein.

Regardless of the method used for removal of the epidermis and harvest of the dermal plugs, the harvested dermal plugs are collected in a collection canister as described herein. FIG. 212 shows a collection vessel or canister including harvested dermal plugs, under an embodiment. Upon completion of harvesting, the dermal plugs are retrieved from the collection canister and inserted into a mincer container. FIG. 213 shows a mincer container or canister including harvested dermal plugs, under an embodiment. The mincer container is configured for use in mincing or cutting the dermal plugs into small pieces configured for injection, but is not so limited.

Mincing of an embodiment is performed with minimal trauma in order to preserve the viable fibroblasts. For this purpose, the mincer includes one or more of manual, rotary, oscillating, and reciprocating ultra-sharp blade(s) without compressive morselization. FIG. 214 shows a manual mincer including a blade device configured to be manipulated up/down and/or rotated, under an embodiment. FIG. 215 shows an electric mincer including a blade or cutting device configured to be rotated under power, under an embodiment. The rotation is imparted to the blade device with one or more of an electric motor, pneumatic motor, and a hand- or machine-operated device, but is not so limited.

The mincer container of an embodiment is also configured for use as a mixing chamber in which a carrier fluid/gel is added to the dermal tissue. The carrier fluid of embodiments includes one or more of hyaluronic acid, hydrogel, and normal saline, to name a few. To reduce surface loses and trauma to the injectable, the mincing container of an embodiment is configured as a loading chamber including a plunger and a port that directly loads the living autologous composition into the injection syringe. Prior to injection in the recipient site, the syringe may also be placed onto a centrifuge for separation of the liquefied fat from the dermal composition. A reduced friction syringe (e.g., glass, plastic, etc.) is used to further reduce trauma to the living autologous composition during injection.

The LADMIX harvest of an embodiment is configured to enable use of excised skin during plastic surgery procedures such as a facelift, abdominoplasty, mastopexy and/or breast reduction, to name a few. The combined procedure of an embodiment includes, but is not limited to, during the same plastic surgery procedure, placing (and adhering) the excised skin on a Padget dermatome using an adherent membrane tape. The skin is oriented down with epidermis in contact with the dermatome tape, but is not so limited. The epidermis is then removed by setting the dermatome on a superficial setting. The subcutaneous tissue can then be removed manually by instrumental defatting or with a second pass with the dermatome on a deep setting. The isolated dermal layer of the excised skin is then minced as described herein.

Injection of the LADMIX is performed in an embodiment at the time or during the same procedure as the fractional skin resection, but is not so limited. Combining these two procedures together as a single procedure provides a unique capability for aesthetic enhancement. The combined procedure also provides a unique capability for the treatment of depressed scar deformities where the living dermal composition is harvested from a fractional scar revision field. The procedure can also be applied for certain physiological disease states that can be identified, one example of which is the treatment of stress incontinence in women.

Procedures or methods using the LADMIX are configured for application to numerous different clinical methods or applications, including but not limited to one or more of aesthetic, reconstructive scar, and physiological disease states. Generally, the procedures include taking or obtaining detailed pre-operative photographs of the patient or subject. The patient is marked pre-operatively in either a standing or sitting position. The four-to-one rule is used, for example, to determine the overall size of the fractional resection field, but embodiments are not so limited. A smaller topographically-marked portion within the field may also be used to serve as the donor site for the harvest of the dermal plugs.

Preoperative sedation and prophylactic antibiotics are provided (e.g., intravenous, oral, etc.) as appropriate to a patient and/or procedure, and the patient is taken into the operating room where an anesthetic is administered as appropriate for the procedure to be performed. The operative area is prepped and draped in a sterile fashion. A local field or tumescent anesthetic is then injected into the operative site. A dilute solution of Xylocaine with epinephrine (e.g., 0.5% Xylocaine with 1 in 200,000 parts epinephrine for a field block, or 0.25% Xylocaine with 1 in 400,000 parts epinephrine for a tumescent anesthetic) is used to provide anesthesia (and vasoconstriction to reduce bleeding).

A marking system template or stencil is then applied to the operative site. The marking system template of an embodiment comprises a perforated and notched plate configured for use of corners of the plate to demarcate an adequate fractional density resection at the donor site. FIG. 216 is an example marking system template, under an embodiment. The peripheral notches are configured for orientation during application of the template, and the perforations indicate the density for the fractional resection where the surgeon "fills in" the intervening fractional resections freehand. Further, the marking template is configured for use in marking the operative site with ink, for example, or with a direct fractional marking resection through larger perforations within the template.

The fractional resection of an embodiment comprises a staggered technique of fractional resection in order to reduce the delineation of the rows and columns of the fractional resection field. Within the donor region of the field, a two-pass technique is used for the dermal harvest, as described in detail herein. The fractional field is then closed with Flexzan, or other elastic absorbent material, using a vector of directed closure that provides the maximum of aesthetic contouring. A sterile dressing is then applied to the combined fractional skin/fat resection/dermal donor site.

The harvested dermal plugs are then processed and injected into the previously marked recipient site during the same procedure to preserve the viability of the live autologous filler. After instillation of the local anesthetic, the recipient pocket for the injectable is created by first advancing the large bore needle of the syringe along the length of the previously marked depressed deformity. FIG. 217 shows creation of the recipient pocket for the injectable, under an embodiment. The large bore needle is then slowly retracted back while the autologous filler is injected along the entire length of the created pocket. FIG. 218 the recipient pocket with the injected filler, under an embodiment.

More particularly, an example procedure protocol involving the LADMIX injectable is described in detail. The donor and recipient sites are marked while the patient is in preoperative holding. The donor site in this example involves the non-hirsute right lower quadrant (RLQ) of the abdomen. The recipient sites will be the dorsum of the left hand and appendectomy scar in the RLQ.

With the patient in the operating room, a subdermal field block (e.g., 0.5% Xylocaine with 1 in 200,000 parts Epinephrine) is administered at the donor site of the RLQ of the abdomen. Another infiltration injected superficially at the dermal epidermal junction (without blistering) will also be administered throughout the demarcated area. Both recipient sites at the dorsum of the left hand and the depressed appendectomy scar receive a standard subdermal field block using the same local anesthetic. The donor and recipient sites are then prepped and draped in a sterile fashion.

The first pass of fractional resection at the donor site is performed with a depth stop/vacuum manifold (e.g., 1 mm depth stop/vacuum manifold) using a scalpet (e.g., 2 mm inside diameter) without an inline filter in the vacuum line. This initial pass is performed to remove the epidermis with as little papillary dermis as possible.

The second dermal harvest pass at the donor site is performed with an inline filter in place with a depth stop/vacuum manifold (e.g., 4-6 mm depth stop/vacuum manifold) using a scalpet (e.g., 1.5 mm inside diameter). The filter should be inserted as close to the manifold as possible. The scalpet/manifold is cleared periodically with normal saline in order to collect and hydrate all harvested dermal plugs into the filter.

The harvested dermal plugs are removed from the filter and placed into the mincer where a small volume of normal saline is added. The autologous composition is created by the mincing of the dermal plugs with normal saline but is not so limited. The composition is loaded (by aspiration) into a filler injection syringe using a short blunt-tip 17-gauge needle. A 22-gauge cannula is then used to inject the composition into the recipient sites.

A sample of the composition is first applied to a microscopic slide for viability staining to determine the viability of harvested fibroblasts. The first recipient site on the dorsum of the left hand is injected, for example, using a technique developed by Dr. Stephen Yoelin. To create the pocket, the cannula is first advanced without injection. The composition is then injected as the cannula is retracted in a retrograde fashion within the pocket.

The second recipient site of the depressed appendectomy scar is injected if an adequate amount of the injectable is available after injection of the first recipient site. Three months later the injected appendectomy scar will be excised for histologically evaluation to determine the long-term invivo structure and viability of the injected composition.

Determined by Langer's lines, for example, a directed closure of the RLQ donor site is performed with the application of Flexzan using the single mooring technique. Both recipient injection sites are manually manipulated to smooth contour. Steristrips (one-half inch) are then longitudinally applied to the recipient sites as a stent. A standard dressing of 4×4s and an ABD pad is applied over the Flexzan of the donor site.

Clinical applications of the LADMIX filler described herein include aesthetic applications, reconstructive applications, and physiologic applications, but embodiments are not so limited. The aesthetic applications include but are not limited to furrows, wrinkles, folds, and general aesthetic contouring. Furrows include aesthetic deformities caused by the attachment to facial muscle and are accentuated during animation of the anatomical region. The Glabellar furrows are the most frequently referenced aesthetic furrow deformity. The LADMIX composition is used to treat furrows by injecting the LADMIX subdermal, for example, between the skin and the muscle.

Wrinkles are for the most part caused by a linear atrophy of dermal collagen matrix. A superficial intradermal injection of LADMIX is effective for a long-term amelioration of the aesthetic deformities.

The prominence of folds, in particular the nasolabial fold, is due in part to progressive skin laxity of this structure. Injection of LADMIX along the margin of the nasolabial fold with the upper lip and alar groove provides a more youthful transition between these two structures.

Regarding general aesthetic contouring, for women, a prominent vermillion cutaneous junction and upper lip can be interpreted by society as aesthetically enhanced. LADMIX injections along the vermillion cutaneous junction of the upper lip provide a long term accentuation of this anatomical structure. The potential also exists for longer lasting lip augmentation.

The reconstructive applications of the LADMIX include but are not limited to applications involving scars and soft tissue contour deformities. Further, these applications require an understanding of the anatomical basis of the deformity. Depressed scar deformities, for example, have a scar attachment to a deeper tissue layer. In most cases, a release of the subjacent scar attachment is required during the same procedure involving the subdermal injection of the LADMIX composition.

Many depressed soft tissue contour deformities are due to a traumatic lipolysis of the subcutaneous fat layer. Following the release of the depressed deformity, the injection should be between the skin and the subjacent subcutaneous tissue.

The physiologic applications of the LADMIX include but are not limited to female incontinence, gastroesophageal reflux, and vocal cord voice modulation, for example. When being applied to treat female incontinence, the injection of a viable, autologous collagen filler provides a longer lasting physiologically support than a nonviable xenographic injectable. FIG. 219 shows treatment of female incontinence using injection of LADMIX, under an embodiment.

Patients with gastroesophageal reflux disease are resistant to pharmacological management that reduce gastric acidity. The injection of various sclerotic agents has been attempted with mixed results. The injection of LADMIX to the distal esophageal sphincter reduces the reflux of gastric contents. Combining the pharmacological management of gastric acidity with endoscopic LADMIX injection (as a physical impediment) would synergistically reduce the symptoms and incidence gastric-esophageal regurgitation.

The LADMIX described herein is used in clinical applications for vocal cord voice modulation. Poor or incomplete apposition of the vocal cords can lead to a variety of voice dysphonias. Submucosal injection of LADMIX into the vocal cords provides positive voice modulation in selected patients.

As described in detail herein, the fractionally harvested LADMIX composition comprising a living autologous injectable graft provides a novel new capability for regenerative medicine. Without limitation, this new medical discipline has great potential to correct the multiple aesthetic, physiological and anatomic maladies associated with congenital deformities, aging, trauma, and individual predilections to certain disease states. Employing both the bulk fill and inductive mechanisms of action, the continual synthesis and deposition of the patient's own neocollagen within the injected graft provides long-term clinical efficacy. In addition, the use of this autologous filler, which can be harvested repeatedly without visible scarring, also provides an ongoing treatment regimen for these disease states without the scarring associated with other graft harvest techniques.

Embodiments described herein include numerous mechanisms of action of a fractionally harvested LADMIX composition. More particularly, the mechanisms of action include biomechanical bulk fill mechanisms of action, and biologic mechanisms of action, each described in detail below.

The biomechanical bulk fill mechanisms of action include, for example, the volume expansion of a soft tissue depression that provides three-dimensional enhancement of an aesthetic contour. This mechanism of action also comprises continual neosynthesis of collagen within the LADMIX graft. The bulk fill mechanism of action can also be used for functional purposes to modify or enhance the function of other anatomical structures such as vocal cords, sphincters and orthopedic tissues such as tendons, ligaments and bone to name a few. Following are numerous examples involving the bulk fill mechanism of action, but the embodiments are not so limited.

The bulk fill mechanism of action includes a malar prominence procedure comprising a deep bulk fill technique of injection employed over the lateral periosteum of the Zygoma. The malar prominence procedure of an embodiment includes use of a blunt tip cannula to avoid intravascular injection, but is not so limited. FIG. 220A shows an example malar prominence procedure, under an embodiment.

Functional purposes also include notching of the alar rim, which comprises correction of unaesthetic notching or overall superior retrusion of the alar rim with subdermal injection of LADMIX along or adjacent the alar rim. FIG. 220B shows an example procedure involving notching of the alar rim, under an embodiment.

Functional purposes further include deviations and depressions of the nasal dorsum. The procedure of an embodiment comprises the injection of LADMIX into the concavity of the nasal dorsum deviation or into the depression of the nasal dorsum. For most procedures, the LADMIX composition is injected at the level of the nasal bone periosteum, but is not so limited. FIG. 220C shows an example procedure involving injecting of deviations and depressions of the nasal dorsum, under an embodiment.

Functional purposes also include projection of the nasal tip. Additional aesthetic definition and projection of the nasal tip is accomplished by the precise placement of subdermal injections of LADMIX that also highlight the light reflective surfaces of the nasal tip. FIG. 220D shows an example procedure involving projection of the nasal tip, under an embodiment.

Additional functional purposes of embodiments include the vermillion cutaneous junction. This procedure involves injecting a thin curvilinear bead of LADMIX sub-dermally along or adjacent the vermillion cutaneous junction. FIG. 220E shows an example procedure involving the vermillion cutaneous junction, under an embodiment.

Functional purposes of embodiments further include enhancement of the philtral columns of the upper lip. A key aesthetic feature of the upper lip is the central philtral columns. A precise subdermal augmentation within these columns is performed using LADMIX, for both aesthetic and reconstructive purposes. FIG. 220F shows an example procedure involving the philtral columns of the upper lip, under an embodiment.

Functional purposes also include the upper lip/columellar angle. An acute retrusive angle of the upper lip and columella is visually interpreted as an aesthetic deformity of the nose and upper lip. Embodiments include injection of LADMIX into or adjacent the base of the columellar to provide aesthetic enhancement by making this angle more obtuse. FIG. 220G shows an example procedure involving the upper lip/columellar angle, under an embodiment.

Embodiments include use of LADMIX for upper and lower lip augmentation. Depending on societal norms of aesthetics, augmentation of the upper and lower lips can be achieved with a reliably variable degree, due to minimal post injection absorption, with the injection of LADMIX subdermally and into or adjacent the orbicularis oris. FIG. 220H shows an example procedure involving upper and lower lip augmentation, under an embodiment.

Functional purposes further include the glabellar furrows. A LADMIX injection is more effective and longer lasting than a temporary neuromodulator induced neuropraxia of the procerus muscles. Embodiments correct this contour deformity using a minimally invasive surgical release of the furrow along with injection of LADMIX into or adjacent the dead-space produced by the release of the cleft. FIG. 220I shows an example procedure involving glabellar furrows, under an embodiment.

Functional purposes of embodiments include the nasolabial fold. The prominence of the nasolabial fold is reduced with the injection of LADMIX subcutaneously at or adjacent the border of the upper lip and nasolabial fold. FIG. 220J shows an example procedure involving the nasolabial fold, under an embodiment.

Functional purposes also include the nipple and nipple-areolar complex. The aesthetic features of the nipple areolar complex are determined more by contour than by size. Embodiments include selected injection of LADMIX for nipple projection. Additional LADMIX injection is used to establish or re-establish the conical contour of the areola, which can be reliably achieved on a patient-to-patient basis. FIG. 220K shows an example procedure involving the nipple and nipple-areolar complex, under an embodiment.

Functional purposes of embodiments include treatment of receded gums. The age related recession of the gingival is seen most prominently in the interdental papilla ("block") between teeth. This deformity has a very negative impact upon the overall aesthetic features of the smile and face. The interdental gingival injection of LADMIX restores this important aesthetic feature. From a functional standpoint for the treatment of gingival "pocket" formation, the gingival injection of LADMIX can also mitigate the occurrence of gingivitis. The bony (and fibrous) incorporation of dental implants can also be enhanced with the injection of LADMIX at or adjacent either the bony implant insertion pocket or the adjacent gingiva. FIG. 220L shows an example procedure involving the treatment of receded gums, under an embodiment.

Embodiments include additional examples of aesthetic bulk fill applications of LADMIX. FIG. 220M shows an example procedure involving the additional examples of aesthetic bulk fill applications, under an embodiment. These additional examples include, but are not limited to, one or more of forehead shaping, temple hollows enhancement, lateral brow enhancement, supra orbital hollow reflation, infra orbital hollow reflation, nasal bridge augmentation, nasal dorsum augmentation, canine fossa/pyriform aperture reflation, ear lobes enhancement, submalar reflation, preauricular fossa reflation, cupid's bow enhancement, oral commissure treatment, G-K point treatment, lateral mandible augmentation, post jowl sulcus treatment, pre-j owl sulcus treatment, mental crease effacement, marionette lines effacement, chin Augmentation, necklace line effacement, and reflation of superficial and deep fat pads of the face.

The bulk fill mechanisms of action of the fractionally harvested LADMIX composition also include numerous reconstructive bulk fill applications. The reconstructive bulk fill applications include, but are not limited to, glottic insufficiency, gastro-esophageal reflux, vesicoureteral reflux, urinary incontinence, projection of the reconstructed nipple-areolar complex, postpartum vaginal laxity, anal incontinence, joint laxity and subluxation, osteoarthritis, subtotal tendon tears, depressed scars and traumatic contour deformities, depressed skin graft deformities, depressed scar adhesions, acne scarring, subjacent soft tissue padding, hernias, aspiration pneumonitis, residual cleft lip deformity and residual cleft palate velopharyngeal incompetence, and congenital cleft palate.

Glottic insufficiency, which includes insufficient adduction of the vocal cords, is a primary biomechanical cause of inadequate phonation. The injection of LADMIX into vocal cords is used to assist laryngeal adduction and vocalization. FIG. 221A shows an example procedure involving the treatment of vocal cords, under an embodiment.

Gastro-esophageal reflux includes the continual regurgitation of gastric contents into the distal esophagus, which may continue to be symptomatic even with the use of histamine H2 and proton pump inhibitors. The circumferential injection of LADMIX into or adjacent the distal gastro-esophageal juncture provides a more effective and anatomically based treatment modality. FIG. 221B shows an example procedure involving the treatment of gastro-esophageal reflux, under an embodiment.

In the pediatric population, vesicoureteral reflux is a functional malady associated with recurrent bouts of pyelonephritis that may lead to a permanent reflux nephropathy. The injection of LADMIX into or adjacent the ureterovesical junction can improve the competence of this structure and decrease the incidence of pyelonephritis and damage to the kidneys. FIG. 221C shows an example procedure involving the treatment of vesicoureteral reflux, under an embodiment.

Embodiments include treatment of urinary (female and male) incontinence using LADMIX. Most commonly occurring in women, for example, as a postpartum injury to the birth canal, injection of LADMIX into or adjacent the functional internal sphincter (immediately distal to the neck of the bladder) can provide a longer lasting remedy for stress incontinence in women than other treatment modalities. FIG. 221D shows an example procedure involving the treatment of urinary incontinence, under an embodiment.

Embodiments include LADMIX-assisted projection of the reconstructed nipple-areolar complex as an adjunct to the neovascular bowtie nipple areolar reconstruction. Although the neovascular bowtie nipple-areolar reconstruction is an effective technique to restore the native contours of the nipple-areolar complex (without the need for skin grafting), additional contouring is obtained with LADMIX injection. Regardless of the nipple-areolar reconstruction technique used, enhanced projection of the reconstructed nipple-areolar complex can be obtained with the selected LADMIX injection of the nipple for projection, and the selected injection of the areola to enhance the conical contour of the entire nipple-areolar complex. FIG. 221E shows an example procedure involving projection of the reconstructed nipple-areolar complex, under an embodiment.

Embodiments include the use of LADMIX in the treatment of postpartum vaginal laxity. A circumferential submucosal injection of LADMIX at or adjacent to the vaginal introitus will buttress, when employed separately or as an adjunct to, the use of electromagnetic (EM) energy for vaginal tightening. FIG. 221F shows an example procedure involving treatment of postpartum vaginal laxity, under an embodiment.

Embodiments include LADMIX in the treatment of anal incontinence. There are multiple causes of anal incontinence, including peripartum injuries to the anal sphincter from midline tears and midline episiotomies, or from paraplegia, and from the surgical resection of lower rectal adenocarcinomas. Remedies that increase the biomechanical resistance of the anal sphincter lead to amelioration of symptoms, at least in part. Surgical procedures such as the gracilis muscle sling have been employed for severe cases of anal incontinence. Less severe cases benefit from the circumferential injection of LADMIX into or adjacent the anal sphincter, obviating the need for extensive surgical procedures. FIG. 221G shows an example procedure involving treatment of anal incontinence, under an embodiment.

Embodiments include treatment of joint laxity and subluxation. For small joint subluxation from trauma, the bulk fill buttressing of collateral ligaments from a LADMIX injection acts as an internal splint that stabilizes joint function, especially when the injection also evokes a delayed wound healing response. FIG. 221H shows an example procedure involving treatment of joint laxity and subluxation, under an embodiment.

Embodiments include treatment of osteoarthritis. The injection of LADMIX, a viable soft tissue bulk filler, between two eroded articular surfaces can significantly reduce pain symptoms of arthritic joints. FIG. 221I shows an example procedure involving treatment of osteoarthritis, under an embodiment.

Embodiments include treatment of subtotal tendon tears. The injection of LADMIX provides modest bulk fill effects, but the majority of the mechanism of action for the restoration of tendon function is the induction of a wound healing response. FIG. 221J shows an example procedure involving treatment of subtotal tendon tears, under an embodiment.

Embodiments include treatment of depressed scars and traumatic contour deformities. The bulk fill mechanism of action of the LADMIX is perhaps best suited for the leveling of depressed traumatic scars and soft tissue contour deformities. If the depressed scar or depressed contour deformity is not adherent to subjacent anatomical structures, then an injection without scar adhesion release can be performed. FIG. 221K shows an example procedure involving leveling of depressed traumatic scars, under an embodiment.

Embodiments include treatment of depressed skin graft deformities. This deformity is a subset of depressed scars and traumatic contour deformities in which the depressed deformity is due to the deficit of subdermal tissues. LADMIX is injected to raise the contour depression. FIG. 221L shows an example procedure involving leveling of soft tissue contour deformities, including depressed skin graft deformities, under an embodiment.

Embodiments include treatment of depressed scar adhesions. Any depressed scar deformity that is adherent to deeper (i.e., fascial) structures can include a surgical release as part of the LADMIX injection procedure. With this type of deformity, the scar release is performed as an initial procedure, immediately followed by the injection of the LADMIX composition into the dead space created by the surgical release of the adherent scar. Clinical examples of this technique are depressed adherent c-section and acne scars, but are not so limited. For the c-section scar, a linear release is performed by the surgical undermining (and incising) of the subjacent scar adhesion to the rectus fascia. LADMIX is then injected into the dead space void created by the surgical scar release. FIG. 221M shows an example procedure involving treatment of depressed scar adhesions, under an embodiment.

A technique similar to that used for treatment of depressed scar adhesions is used for the treatment or correction of acne scarring. The pit of the scar is released with a microtome beneath the surface of the adherent acne scar pit. The void created by the microtome release is then filled with the injection of LADMIX. Non-adherent acne scarring can be managed with LADMIX injection as the base of the depression with fractional skin resection of the topographical peaks adjacent the acne scarring.

Embodiments include treatment of subjacent soft tissue padding, such as the anterior aspect of the tibia. This bulk fill application of LADMIX provides a soft tissue cushion over weight bearing anatomical structures with inadequate soft tissue padding.

Embodiments include treatment of hernias. Another example of the initial therapeutic effect of a living bulk filler is the application of LADMIX over a fascial hernia defect. As an adjunct to LADMIX injection, a temporary supportive truss is used. However, the induction and active support of a delayed wound healing response is the key mechanism of action of this treatment protocol.

Embodiments include treatment of aspiration pneumonitis. The aspiration of gastric contents into the lungs is a serious insult both chemically and bacteriologically to the bronchial alveolar tree. Insufficient closure of the epiglottis onto the arytenoid fold is a primary pathophysiological mechanism of action for aspiration. Injection of LADMIX along the perimeter of the epiglottis significantly enhances closure of that structure onto the arytenoid fold. FIG. 221N shows an example procedure involving treatment of aspiration pneumonitis, under an embodiment.

Embodiments include treatment of residual cleft lip deformity and residual cleft palate velopharyngeal incompetence. For cleft lip, rotation and advancement of the cleft lip has for decades been the standard of repair for this congenital deformity. The principle limitation of this procedure however is the inadequate definition of the repaired philtral column. Injection of the philtral column and alar base with LADMIX can resolve this singular limitation of rotation and advancement. Additional correction of the nasal deformity associated with cleft tip can also be achieved with the injection of LADMIX into the alar rim and nasal tip. FIG. 221O shows an example procedure involving treatment of residual cleft lip deformity and residual cleft palate velopharyngeal incompetence, under an embodiment.

Congenital cleft palate repairs have improved significantly over several decades, but many of these patients still have residual hypernasality. This defect in phonation is especially evident with the pronouncement of consonants. Secondary procedures such as posterior pharyngeal flaps have been employed to correct these residual deficits of velopharyngeal competence. For less severe deficits of phonation, injection of LADMIX into the posterior border of the soft palate and the posterior pharynx can provide a permanent non-invasive alternate to the more invasive posterior pharyngeal flap procedures. FIG. 221P shows an example procedure involving congenital cleft palate repairs, under an embodiment.

The mechanisms of action of the fractionally harvested LADMIX composition also include biologic mechanisms of action as described herein. Biologic mechanisms of action comprise the induction of neocollagen dermal synthesis (and epidermal maturation) in skin adjacent to or directly in tissues injected with LADMIX. Biologic induction by LADMIX also stimulates the wound healing sequence and neocollagen synthesis in other non-cutaneous tissues, such as the mucosal soft tissue structures, and other non-epithelial structures such as tendons, ligaments, periosteum, and bone, for example. Further, the induction mechanism of action also involves the continual synthesis of neocollagen within the LADMIX graft where the neosynthesis is due to the induction of grafted living autologous fibroblasts. Examples of inductive clinical applications include, but are not limited to, aesthetic inductive applications, and reconstructive inductive applications, each of which is described in detail herein. Additional examples of inductive clinical applications include treatment of superficial lines of the face (using superficial needle/dermal injections), and improved skin quality across all surfaces of the body (superficial injections).

Aesthetic inductive applications include skin rejuvenation for wrinkling and dermal atrophy of the face. For the most part, wrinkling of the skin is due to focal intradermal linear and curvilinear defects within the superficial dermis. The injection of LADMIX either subdermally or intradermally can provide both an inductive and bulk fill effect to reduce visible wrinkling. More specifically, induced neocollagen synthesis within the dermis, and with induced maturation of the epidermis, will reduce visible wrinkling. The translation of intrinsic polarizing factors from fractionally harvested and grafted dermal papillae stem cells (e.g., LGR4, LGR5, LGR6) may also have a contributory effect to the restoration of the histologic architecture of the skin and other tissues. FIG. 222 shows an example aesthetic inductive application including skin rejuvenation, under an embodiment.

Aesthetic inductive applications further include skin rejuvenation for generalized age related dermal atrophy such as the dorsum of the hand. Similar to the description of the inductive mechanism of action in skin, the injection of LADMIX can also be applied to a broader age related atrophy of the skin such the dorsum of the hand and the anterior tibial aspect of the lower leg (e.g., see FIG. 222).

Reconstructive inductive applications include, but are not limited to, enhanced healing of surgical incisions, enhanced healing of skeletal fractures, enhanced healing of the partial disruption of tendon and muscle tears, treatment of established ligament laxity, and post-repair enhanced healing of fascial structures, each of which is described in detail herein.

Regarding enhancement of healing of surgical incisions, two major concerns exist about the healing of surgical incisions. The first concern is the length of time that sutures are required to support closure of the incision. Prolonged periods of surface suture retention may result in unsightly cross-hatching scarring. The second major concern is the subsequent spreading of a healed incision due the reduced tensile strength of the incision. As a result, the incisional scar is wider and more visibly apparent. By evoking the wound healing response, the perioperative use of LADMIX along the incisional margins can reduce the length of time for suture retention and the subsequent spreading of an early-healed incision.

An example includes the use of LADMIX to further buttress wound closures in Moh's Chemosurgical resections. Combined with fractional resection of dog-ear skin redundancies at either end of the Moh's closure, a significant reduction in both the length and visibility of the post resectional scar occurs. LADMIX injection can also be used in conjunction with tissue glues such as cyanoacrylate to enhance the strength of wound and incisional closure healing without surface sutures.

Reconstructive inductive applications include enhanced healing of skeletal fractures. In the course of healing of a skeletal fracture, biomechanically competent fusion across the fracture site may take many months (e.g., 3-4 months). During this initial period, the patient must be casted. Although internal fixation with the surgical application of an AO fixation plate or with the insertion of an intramedullary rod may shorten this period, the use of LADMIX can also lead to a significant shortening the period of the biomechanically rigid fusion across a fracture.

Reconstructive inductive applications also include enhanced healing of the partial disruption of tendon and muscle tears such as the Achilles tendon and calf muscles. The injection of LADMIX can provoke a florid wound healing response that promotes early healing with a predicted long-term increase in the tensile strength of the damaged tendons and muscles. The injection of LADMIX can also be used as an adjunct for the surgical repairs of tendons for the same reasons (e.g., see FIG. 221J).

Reconstructive inductive applications further include treatment of established ligament laxity and the promotion of enhanced healing involving subtotal disruptions of ligaments. This non-surgical treatment algorithm involves the injection of LADMIX into the lax collateral ligament with external splinting. Acute partial tears of collateral ligaments will also benefit from the enhanced wound healing response from a LADMIX injection and splinting. Furthermore, this approach can also be applied as an adjunct to the surgical repairs of disrupted ligaments (e.g., see FIGS. 221H and 221I).

Embodiments of reconstructive inductive applications include post-repair enhanced healing of fascial structures such as hernia. Inguinal hernia is a common structural defect of fascia that is typically managed by surgical herniorrhaphy. For more severe cases, a prosthetic mesh onlay is also required to further buttress the repair. For minor hernias such as in the inguinal and umbilical regions, the use of a LADMIX injection with a supportive truss can obviate the need for surgery. For surgical repairs, the use of LADMIX can obviate the need of prosthetic mesh membrane.

Embodiments involving LADMIX generally comprise the fractional harvest of tissue, preparation of the LADMIX composition, and injection of the LADMIX at target or treatment site(s) on a subject, as described in detail herein. The fractional harvest comprises resection of epidermis but is not so limited. More particularly, for the dermal harvest of LADMIX, the removal of the epidermis is performed so as not to include the epidermal cells within the LADMIX composition. While the inclusion of epidermal (and hair follicle) cells within the LADMIX composition may not create any deleterious clinical effects at the recipient injection site, removal of the epidermis avoids development of epidermal inclusion cysts within the injection site that could result from retainment of epidermal cells within the LADMIX composition. A number of procedural options are available hereunder for removal of the epidermis as described in detail herein.

The fractional harvest of an example embodiment includes a double pass technique with either a single scalpel or multi-scalpel array as described in detail herein. Using this technique, a first superficial pass is performed at the fractional harvest field where the epidermis and a thin border of superficial papillary dermis is fractionally resected. A second pass is then performed either intradermally or full thickness where the dermal plug is harvested. Another development of this technique is the inclusion of the dermal papillae of the hair follicle. The dermal papilla contains stem cells that have the post injection potential of transcribing insitu growth factors and other agents (e.g., LGR4, LGR5, LGR6) that "polarize" or induce a normal skin architecture of the injected composition and/or overlying skin. Another corollary of the double pass technique is that a fractional dermabrasion can be employed to remove the epidermis on a first pass.

Other techniques for the removal of the epidermis include the area delamination (blistering) of the epidermis within the fractional harvest field. Further, the epidermal delamination includes, but is not limited to, fluid injection delamination, thermal delamination, and chemical delamination. Removal of the epidermal components of embodiments can also be performed after fractional harvest of the skin plugs. Prior to or subsequent to forming the composition, mechanical and chemical means can be used to isolate the dermal components from the epidermal components of the fractional harvest. These isolation techniques include without limitation, centrifugation, aspiration and the use of keratolytic agents.

The LADMIX instrumentation and composition components include a single multifunctional canister configured or used to reduce composition loses from the use of multiple surface containers. FIG. 223 is an example multifunctional canister, under an embodiment. For this purpose, a single multifunctional container or housing is described that is configured as in-series with the single or multi-scalpet array systems. The multiple functions of the canister include harvest hydration, mincing, and mixing with carrier fluid (e.g., saline, bioactive substances such as growth factors and other commercially available injectable compositions such as Hyaluronic Acid (HA), Polylactic Acid (PLLA), and Calcium Hydroxylapatite (Radiesse), etc.) that can be added electively by the clinician. The multifunctional canister of an embodiment is also configured for syringe loading using, for example, a separate port at the base of the canister through which the composition is drawn into the injection syringe. In addition to reducing the surface losses of multiple containers, this multifunctional canister is also configured to provide a sterile environment that reduces inadvertent bacterial and chemical contamination of the injectable.

Inductive applications of LADMIX comprise injections administered to tissues either adjacent or within pre-existing tissues (e.g., FIG. 223). For the treatment of wrinkling or generalized dermal atrophy of thin skin, the injections are performed more broadly at either the subdermal or intradermal levels.

Most aesthetic bulk fill injections of the LADMIX composition are performed or delivered relatively deeper than inductive injections. To provide a smoother bulk fill clinical end result that avoids visible surface irregularities and the potential for intravascular injection, the bulk fill injection is performed using a blunt tip cannula. An example of a deep bulk fill injection is the augmentation of the zygomatic prominence where the LADMIX injection is performed deeply over the periosteum of the Zygoma. However some bulk fill applications that are more superficial include the aesthetic delineation of the vermillion-cutaneous junction and philtral columns. Examples of a relatively intermediate depth of injection are aesthetic bulk fill injections for upper and lower lip augmentation. FIG. 224 shows an example intermediate depth aesthetic bulk fill injection, under an embodiment.

Reconstructive applications of LADMIX, such as glottic insufficiency, female incontinence and gastro-esophageal reflux, comprise a submucosal LADMIX injection performed in conjunction with the use of various medical scope instrumentation such as the fiberoptic laryngoscope, cystoscope and upper gastrointestinal endoscope.

The LADMIX procedures of an embodiment may involve administration of local anesthesia, for example. Embodiments therefore include a multi-needle manifold configured for injection of a local anesthetic field block, as described in the Related Applications. The multi-needle manifold of embodiments herein includes numerous injection needles having different lengths. In addition to injection needles of different lengths, each length needle comprises a separate container manifold for a different tissue level of injection such as the subdermal/intradermal field blocks for fractional resection and harvesting. Further, a longer injection needle manifold is used for the subcutaneous anesthetic infusion of a fractional lipectomy procedure.

More particularly, FIGS. 225A-225C show different views of a drug delivery device 300 including a flat array of fine needles 312 of differing lengths positioned on manifold 310, under an embodiment. The needle array of an embodiment includes numerous sets or groups of needles, with each set or group including needles of equivalent lengths, such that the needle length of each set is different from the needle length of one or more other sets. The needle array of an alternative embodiment includes needles of different lengths randomly placed on the manifold.

In an embodiment, each needle length corresponds to a different tissue level of injection (e.g., subdermal/intradermal field blocks for fractional resection and harvesting), and is coupled or connected to a separate container manifold (not shown) or manifold compartment. This configuration enables delivery of different compositions to various different tissue levels via different sets or groups of needles. For example, a first set of needles having a first length are configured to deliver a first composition from a first container manifold, while a second set of needles having a second length are configured to deliver a second composition from a second container manifold.

In this example embodiment, syringe 302 can be plugged into a disposable adaptor 306 with handles, and a seal 308 can be utilized to ensure that the syringe 302 and the disposable adaptor 306 are securely coupled to each other. When the syringe plunger 304 is pushed, any drug(s) carried or contained in syringe 302 or compartmentalized manifold 310 is delivered into the patient's skin through the corresponding needle group or array when the needle group or array is pushed into a subject's skin at a target site.

The syringe plunger in alternative embodiments of the drug delivery device can be powered by an electric motor, for example. In some embodiments, a fluid pump (not shown) attached to an intravenous bag and tubing can be coupled or connected to the injection chamber and/or the manifold for continuous injection. In some embodiments, the volume of the syringe plunger and/or the manifold is calibrated and programmable.

The use of the drug delivery device 300 may have as many clinical applications as the number of pharmacological agents requiring transcutaneous injection or absorption. For example, potential applications include the injection of local anesthetics, the injection of neuromodulators such as Botulinum toxin (Botox), the injection of insulin, and the injection of replacement estrogens and corticosteroids, to name a few.

Embodiments of three-dimensional aesthetic contouring by fractional resection described herein include the directed closure of a fractionally resected field using specific anatomically-based vectors of closure for fractionally created skin defects within a fractional field. Each separate anatomical region has specific vectors that are most effective in creating a three-dimensional aesthetic contour. An example of this is fractional resection of the submentum where fractional skin and fat resection is combined with directed closure using a more horizontally aligned vector for the lower portion of the field at the cervical mental angle and a more obliquely upward vector for the region immediately below the chin.

Techniques have described the use of a two-person manual unidirectional technique for wound closure that made it difficult to reliably replicate the optimal vectors of closure. Embodiments include an application of the adherent membrane, for use by a single person, which reliably provides reproducible vectors of directed closure. This embodiment employs, for a single constituent vector, a bidirectional application within a single vector. Each opposing application is assisted with placement of a bulldog clamp having the same width as the membrane. The clamp is placed at the medial end of the membrane to avoid distortion of the elastic membrane.

During the membrane application process, the membrane is first moored (e.g., using manual compression) on the outside of the lateral aspect of the field. With the mooring point secured, the practitioner's opposite hand (holding the clamp) is pulled over the fractional field. Under tension with the opposite hand, the mooring hand is then advanced over the membrane to adhere the membrane and secure the closure. The medial end of the elastic membrane is adhered to the medial aspect of the fractional field following removal of the clamp. The technique of vectored application of the adherent membrane is then repeated for the opposite side, pulling the membrane from the opposite direction but along the same vector of closure where both component membranes are joined in the midline. For clinical applications such as the submentum in which two vectors of closure are employed, the procedure is repeated for each vector.

Intradermal fractional skin resection described herein has a decreased potential for scarring, especially for patients with more deeply pigmented skin (Fitzpatrick 4-6), or in anatomical regions with thicker skin (e.g., bra line, back, etc.). Further, a reduction in bleeding is realized as the subdermal vascular plexus remains intact. This technique preserves the vascular supply of the skin as the subdermal plexus remains intact, which is most important when fractional resection of skin is used as an adjunct with liposuction. Additionally, this technique preserves the skins sensory innervation as the subdermal sensory plexus remains intact. FIG. 226 depicts preservation of subdermal structures during intradermal fractional resection, under an embodiment.

Embodiments include a system comprising a cannula assembly configured for rotational fractional resection (RFR). The cannula assembly includes at least one cannula configured for rotational operation and enclosed in a depth guide configured to control an insertion depth of the at least one cannula. The depth guide includes a vacuum chamber configured to maintain vacuum to evacuate resected tissue generated by the RFR.

Embodiments include a system comprising a cannula assembly configured for rotational fractional resection (RFR), wherein the cannula assembly includes at least one cannula configured for rotational operation and enclosed in a depth guide configured to control an insertion depth of the at least one cannula, wherein the depth guide includes a vacuum chamber configured to maintain vacuum to evacuate resected tissue generated by the RFR.

A proximal end of the cannula assembly is configured to removeably couple to a carrier comprising a proximal end and a distal end, wherein the proximal end of the carrier is configured to removeably couple to a remote console.

The carrier includes a drive shaft, and a distal end of the drive shaft is coupled to a chuck, wherein a proximal end of the drive shaft is configured to removeably couple to the remote console, wherein the cannula assembly is configured to removeably couple to the distal end of the carrier via the chuck.

The proximal end of the drive shaft is configured to removeably couple to a motor of the remote console, and couple rotational force from the motor to the cannula assembly, wherein the at least one cannula is configured to rotate around a central axis of the at least one cannula.

The remote console comprises an electro-mechanical device configured to provide services to the cannula assembly.

The remote console comprises the motor configured to couple to the carrier, wherein the motor configures the at least one cannula of the cannula assembly to be rotated at controlled speeds.

The carrier is configured for control by the motor.

The carrier is configured for rotational speed control of the motor.

The remote console comprises a vacuum source configured to couple to the vacuum chamber, wherein the vacuum source configures the cannula assembly to evacuate resected tissue of a fractional resection procedure away from a target site via the vacuum chamber.

The at least one cannula comprises at least one scalpet including a tube comprising a lumen, and a distal end sharpened around a circumference of the tube and forming a cutting edge.

The distal end and the lumen of the at least one scalpet are configured to pass the resected tissue from a target site.

The at least one scalpet includes at least one aperture positioned axially in the scalpet adjacent the lumen, wherein the at least one aperture is configured to pass the tissue.

A diameter of the cutting edge is approximately 1.5 millimeters.

The vacuum chamber is configured to couple vacuum to the lumen via the aperture, wherein the vacuum is configured to evacuate the resected tissue of a fractional resection procedure via the lumen and the vacuum chamber.

The vacuum chamber is configured to couple to a remote vacuum source.

The depth guide includes at least one vacuum seal configured to form the vacuum chamber.

The at least one vacuum seal is configured for application of vacuum during rotation of the at least one scalpet, wherein the vacuum is configured to maintain an approximately constant vacuum level.

The insertion depth is variable in a range of approximately 0.1 millimeters to eight (8) millimeters.

The system includes a plurality of depth guides, wherein each depth guide of the plurality of depth guides corresponds to a different insertion depth, wherein the depth guide is selected based on the insertion depth of the RFR.

The cannula assembly comprises a multi-scalpet array (MSA).

The at least one cannula includes a plurality of scalpets, and each scalpet of the plurality of scalpets comprises a tube comprising a lumen, and a distal end sharpened around a circumference of the tube and forming a cutting edge.

A diameter of the cutting edge is approximately 1.5 millimeters.

The MSA includes the plurality of scalpets configured in a rectangular array.

The MSA includes the plurality of scalpets configured in one of a 3-by-3 array including nine (9) scalpets, and a 5-by-5 array including twenty-five (25) scalpets.

The MSA includes a drive shaft coupled to a proximal region of a central scalpet of the scalpet array, wherein the drive shaft is configured to couple rotational force from a remote source to the plurality of scalpets.

A rotational speed of the plurality of scalpets is in a range of approximately 75 revolutions per minute to 2000 revolutions per minute.

A rotational speed of the plurality of scalpets is approximately 1400 revolutions per minute.

The drive shaft includes at least one aperture positioned axially in a distal region, wherein the at least one aperture is configured to couple the vacuum chamber to a lumen of the central scalpet via the proximal end of the central scalpet.

The aperture is configured to evacuate resected tissue of a fractional resection procedure via the lumen of the central scalpet and the vacuum chamber.

Each scalpet of the scalpet array includes a gear in a proximal region of the scalpet, wherein the gears of the plurality of scalpets intermesh.

The gears comprise at least one of polymer and metal.

Each gear is secured to the corresponding scalpet via direct molding, adhesive, and press fitting.

Each scalpet of the scalpet array includes a spacer adjacent the corresponding gear, wherein each spacer is configured to align the corresponding gear.

The plurality of scalpets operates in unison.

Each scalpet rotates in a direction opposite a rotation direction of at least one adjacent scalpet.

Each scalpet of the plurality of scalpets includes a tube comprising a lumen, and a distal end sharpened around a circumference of the tube and forming a cutting edge.

The distal end, the lumen, and a proximal end of each scalpet of the plurality of scalpets is configured to pass resected tissue from a target site.

The vacuum chamber is configured to couple to a remote vacuum source.

The vacuum chamber is configured to couple vacuum to lumens of the plurality of scalpets.

The vacuum is configured to assist removal of the resected tissue from a target site by drawing the resected tissue away from the target site via the vacuum chamber and the distal end, the lumen, and the proximal end of the plurality of scalpets.

The system includes a seal located along a proximal region of the driveshaft, wherein the seal is configured to maintain vacuum pressure in the vacuum chamber.

The system includes a gearbox configured to house the gears and the proximal region of each scalpet of the plurality of scalpets.

The gearbox includes a gearbox housing and a gearbox cover.

The gearbox housing and the gearbox cover are configured as bearing plates for the gears.

The gearbox housing is configured as an interface to the vacuum chamber.

The system includes a depth slider configured to control selection of the insertion depth of the plurality of scalpets.

The depth slider is integrated with the vacuum chamber.

A distal end of the plurality of scalpets extends beyond a distal end of the depth slider, and a longitudinal position of the depth slider along the MSA controls the insertion depth by controlling a length of the plurality of scalpets extending beyond the distal end of the depth slider.

The insertion depth of the plurality of scalpets is variable in a range of approximately two (2) millimeters to ten (10) millimeters.

The depth slider is coupled to a lock collar configured to secure the depth slider in a selected position.

The lock collar is configured to slide along an external region of the MSA to control a state of the depth slider between a locked state and an unlocked state.

In the unlocked state the depth slider is free to be moved to a position corresponding to a selected insertion depth of the plurality of scalpets, and in the locked state the depth slider is secured in a selected position.

The at least one cannula includes a focal lipectomy cannula.

The focal lipectomy cannula includes a tube comprising a lumen and a distal end that is blunt around a circumference of the tube.

The focal lipectomy cannula includes at least one aperture positioned axially in a proximal region of the cannula adjacent the lumen, wherein the focal lipectomy cannula is configured to pass resected tissue from a target site via the lumen and the at least one aperture.

The focal lipectomy cannula comprises an inside diameter of approximately two (2) millimeters.

The focal lipectomy cannula comprises a length of approximately four (4) centimeters.

Embodiments include a system comprising a carrier comprising a proximal end and a distal end. The proximal end is configured to removeably couple to a remote console. The system includes a cannula assembly configured to removeably couple to the distal end of the carrier. The cannula assembly is configured for rotational fractional resection (RFR) and includes at least one cannula rotatably coupled to the carrier and enclosed in a depth guide configured to control an insertion depth of the at least one cannula. The depth guide includes a vacuum chamber configured to form vacuum to evacuate resected tissue generated by the RFR.

Embodiments include a system comprising: a carrier comprising a proximal end and a distal end, wherein the proximal end is configured to removeably couple to a remote console; a cannula assembly configured to removeably couple to the distal end of the carrier, wherein the cannula assembly is configured for rotational fractional resection (RFR) and includes at least one cannula rotatably coupled to the carrier and enclosed in a depth guide configured to control an insertion depth of the at least one cannula, wherein the depth guide includes a vacuum chamber configured to form vacuum to evacuate resected tissue generated by the RFR.

The carrier includes a drive shaft, and a distal end of the drive shaft is coupled to a chuck, wherein a proximal end of the drive shaft is configured to removeably couple to the remote console, wherein the cannula assembly is configured to removeably couple to the distal end of the carrier via the chuck.

The proximal end of the drive shaft is configured to removeably couple to a motor of the remote console, and couple rotational force from the motor to the cannula assembly, wherein the at least one cannula is configured to rotate around a central axis of the at least one cannula.

The at least one cannula comprises at least one scalpet including a tube comprising a lumen, and a distal end sharpened around a circumference of the tube and forming a cutting edge.

The distal end and the lumen of the at least one scalpet are configured to pass the resected tissue from a target site.

The at least one scalpet includes at least one aperture positioned axially in the scalpet adjacent the lumen, wherein the at least one aperture is configured to pass the tissue.

A diameter of the cutting edge is approximately 1.5 millimeters.

The vacuum chamber is configured to couple vacuum to the lumen via the aperture, wherein the vacuum is configured to evacuate the resected tissue of a fractional resection procedure via the lumen and the vacuum chamber.

The vacuum chamber is configured to couple to the remote console, wherein the remote console includes a vacuum source.

The depth guide includes at least one vacuum seal configured to form the vacuum chamber.

The at least one vacuum seal is configured for application of vacuum during rotation of the at least one scalpet, wherein the vacuum is configured to maintain an approximately constant vacuum level.

The insertion depth is variable in a range of approximately 0.1 millimeters to eight (8) millimeters.

The system includes a plurality of depth guides, wherein each depth guide of the plurality of depth guides corresponds to a different insertion depth, wherein the depth guide is selected based on the insertion depth of the RFR.

The cannula assembly comprises a multi-scalpet array (MSA).

The at least one cannula includes a plurality of scalpets, and each scalpet of the plurality of scalpets comprises a tube comprising a lumen, and a distal end sharpened around a circumference of the tube and forming a cutting edge.

A diameter of the cutting edge is approximately 1.5 millimeters.

The MSA includes the plurality of scalpets configured in a rectangular array.

The MSA includes the plurality of scalpets configured in one of a 3-by-3 array including nine (9) scalpets, and a 5-by-5 array including twenty-five (25) scalpets.

The MSA includes a drive shaft coupled to a proximal region of a central scalpet of the scalpet array, wherein the drive shaft is configured to couple rotational force from the carrier to the plurality of scalpets.

A rotational speed of the plurality of scalpets is in a range of approximately 75 revolutions per minute to 2000 revolutions per minute.

A rotational speed of the plurality of scalpets is approximately 1400 revolutions per minute.

The drive shaft includes at least one aperture positioned axially in a distal region, wherein the at least one aperture is configured to couple the vacuum chamber to a lumen of the central scalpet via the proximal end of the central scalpet.

The aperture is configured to evacuate resected tissue of a fractional resection procedure via the lumen of the central scalpet and the vacuum chamber.

Each scalpet of the scalpet array includes a gear in a proximal region of the scalpet, wherein the gears of the plurality of scalpets intermesh.

The gears comprise at least one of polymer and metal.

Each gear is secured to the corresponding scalpet via direct molding, adhesive, and press fitting.

Each scalpet of the scalpet array includes a spacer adjacent the corresponding gear, wherein each spacer is configured to align the corresponding gear.

The plurality of scalpets operates in unison.

Each scalpet rotates in a direction opposite a rotation direction of at least one adjacent scalpet.

Each scalpet of the plurality of scalpets includes a tube comprising a lumen, and a distal end sharpened around a circumference of the tube and forming a cutting edge.

The distal end, the lumen, and a proximal end of each scalpet of the plurality of scalpets is configured to pass resected tissue from a target site.

The vacuum chamber is configured to couple to the remote console, wherein the remote console includes a vacuum source.

An operating vacuum pressure is up to approximately 25 inches of mercury.

The vacuum chamber is configured to couple vacuum to lumens of the plurality of scalpets.

The vacuum is configured to assist removal of the resected tissue from a target site by drawing the resected tissue away from the target site via the vacuum chamber and the distal end, the lumen, and the proximal end of the plurality of scalpets.

The system includes a seal located along a proximal region of the driveshaft, wherein the seal is configured to maintain vacuum pressure in the vacuum chamber.

The system includes a gearbox configured to house the gears and the proximal region of each scalpet of the plurality of scalpets.

The gearbox includes a gearbox housing and a gearbox cover.

The gearbox housing and the gearbox cover are configured as bearing plates for the gears.

The gearbox housing is configured as an interface to the vacuum chamber.

The system includes a depth slider configured to control selection of the insertion depth of the plurality of scalpets.

The depth slider is integrated with the vacuum chamber.

A distal end of the plurality of scalpets extends beyond a distal end of the depth slider, and a longitudinal position of the depth slider along the MSA controls the insertion depth by controlling a length of the plurality of scalpets extending beyond the distal end of the depth slider.

The insertion depth of the plurality of scalpets is variable in a range of approximately two (2) millimeters to ten (10) millimeters.

The depth slider is coupled to a lock collar configured to secure the depth slider in a selected position.

The lock collar is configured to slide along an external region of the MSA to control a state of the depth slider between a locked state and an unlocked state.

In the unlocked state the depth slider is free to be moved to a position corresponding to a selected insertion depth of the plurality of scalpets, and in the locked state the depth slider is secured in a selected position.

The at least one cannula includes a focal lipectomy cannula.

The focal lipectomy cannula includes a tube comprising a lumen and a distal end that is blunt around a circumference of the tube.

The focal lipectomy cannula includes at least one aperture positioned axially in a proximal region of the cannula adjacent the lumen, wherein the focal lipectomy cannula is configured to pass resected tissue from a target site via the lumen and the at least one aperture.

The focal lipectomy cannula comprises an inside diameter of approximately two (2) millimeters.

The focal lipectomy cannula comprises a length of approximately four (4) centimeters.

The remote console comprises an electro-mechanical device configured to provide services to the cannula assembly.

The remote console comprises a motor configured to couple to the carrier, wherein the motor configures the at least one cannula of the cannula assembly to be rotated at controlled speeds.

The remote console comprises a vacuum source configured to couple to the vacuum chamber, wherein the vacuum source configures the cannula assembly to evacuate resected tissue of a fractional resection procedure away from a target site via the vacuum chamber.

The carrier is configured as a handpiece.

The carrier is configured for control by the remote console.

The carrier is configured for control by a motor of the remote console.

The carrier is configured for rotational speed control of the motor.

Embodiments include a method comprising determining histological factors at a target site of a subject. The method includes determining parameters of a fractional resection based on the histological factors. The parameters include dimensionality of a fractional field, orientation of the fractional field, resection depth, and a vector of directed closure. The method includes configuring a cannula assembly for the fractional resection. The fractional resection includes a procedure to generate a fractional field at the target site by fractionally resecting tissue according to the parameters.

The fractional resection includes applying a cannula array of the cannula assembly to the target site, and rotating at least one cannula of the cannula array to circumferentially incise and remove a plurality of skin plugs in the fractional field.

Embodiments include a method comprising: determining histological factors at a target site of a subject; determining parameters of a fractional resection based on the histological factors, wherein the parameters include dimensionality of a fractional field, orientation of the fractional field, resection depth, and a vector of directed closure; and configuring a cannula assembly for the fractional resection, wherein the fractional resection includes a procedure to generate a fractional field at the target site by fractionally resecting tissue according to the parameters, wherein the fractional resection includes applying a cannula array of the cannula assembly to the target site, and rotating at least one cannula of the cannula array to circumferentially incise and remove a plurality of skin plugs in the fractional field.

Histological factors include at least one of skin laxity and skin thickness.

The dimensionality conforms to at least one dimension of an aesthetic deformity of the target site.

A width and a length of the fractional field is determined according to the physiological factors.

A width of the fractional field is increased in proportion to an increase in horizontal skin laxity.

A length of the fractional field is increased in proportion to an increase in vertical skin laxity.

A horizontal orientation of the fractional field provides increased skin tightening in a horizontal dimension relative to a vertical orientation of the fractional field if the vector of directed closure is horizontal.

An alignment of the fractional field corresponds to margins of the aesthetic deformity.

Directed closure at right angles to a longitudinal dimension of the fractional field lengthens a longitudinal dimension of the fractional field and tightens a horizontal dimension of the fractional field.

The procedure comprises selectively controlling a depth of the fractional resection based on topographic features of a convex contour deformity of the target site.

A depth of the fractional resection is variable.

The depth is approximately in a range of 0.1 millimeters to eight (8) millimeters.

The directed closure comprises closure substantially in at least one of a first direction, a horizontal direction, a vertical direction, and a plurality of directions.

When the target site includes a submentum, the procedure comprises a fractional field with a vertical orientation, and a horizontal vector of directed closure.

When the target site includes a jowl, the procedure comprises a fractional field with a horizontal orientation, and a horizontal vector of directed closure.

When the target site includes a bra line, the procedure comprises a fractional field with a horizontal orientation, and a horizontal vector of directed closure.

When the target site includes a medial infragluteal fold, the procedure comprises an obliquely aligned fractional field that encompasses a margin of an aesthetic deformity, and a vector of directed closure aligned obliquely along a longitudinal axis of the fractional field.

When the target site includes an upper arm, the procedure comprises a horizontally aligned fractional field, and a vector of directed closure aligned at right angles to a longitudinal axis of the fractional field.

When the target site includes a proximal upper medial thigh, the procedure comprises a T-shaped fractional field, and a vector of directed closure aligned horizontally at right angles to each of vertical and horizontal components forming the T-shaped field.

When the target site includes at least one of a suprapatellar knee and a superior posterior elbow, the procedure comprises a fractional field aligned vertically along a longitudinal aspect of the extremity, and a vector of directed closure at approximately right angles to a longitudinal axis of the fractional field.

When the target site includes a dependent curvilinear aesthetic deformity, the procedure comprises a horizontally aligned fractional field, and a vector of directed closure along an elongated horizontal axis of the fractional field.

When an aesthetic deformity of the target site includes lipodystrophy, the procedure includes focal lipectomy with the fractional resection.

The removing the plurality of skin plugs includes evacuating the plurality of skin plugs from the target site using vacuum force delivered via the cannula array.

The removing a plurality of skin plugs includes selectively controlling evacuation of an amount of at least one of skin tissue and fat tissue as appropriate to the selected at least one fractional resection type.

The controlling comprises controlling the evacuation to include the skin tissue while minimizing the fat tissue.

The controlling comprises controlling the evacuation to include the skin tissue and the fat tissue.

The method includes use of a system comprising the cannula assembly configured for rotational fractional resection (RFR), wherein the cannula assembly includes the at least one cannula configured for rotational operation and enclosed in a depth guide configured to control an insertion depth of the at least one cannula, wherein the depth guide includes a vacuum chamber configured to maintain vacuum to evacuate resected tissue generated by the RFR.

A proximal end of the cannula assembly is configured to removeably couple to a carrier comprising a proximal end and a distal end, wherein the proximal end of the carrier is configured to removeably couple to a motor of a remote console, and couple rotational force from the motor to the cannula assembly, wherein the at least one cannula is configured to rotate at controlled speeds around a central axis of the at least one cannula.

The remote console comprises a vacuum source configured to couple to the vacuum chamber, wherein the vacuum source configures the cannula assembly to evacuate resected tissue of a fractional resection procedure away from a target site via the vacuum chamber.

The at least one cannula comprises at least one scalpet including a tube comprising a lumen, and a distal end sharpened around a circumference of the tube and forming a cutting edge.

The at least one scalpet includes at least one aperture positioned axially in the scalpet adjacent the lumen, wherein the lumen and the at least one aperture are configured to pass the tissue.

The vacuum chamber is configured to couple vacuum to the lumen via the aperture, wherein the vacuum is configured to evacuate the resected tissue of a fractional resection procedure via the lumen and the vacuum chamber.

The method includes a plurality of depth guides, wherein each depth guide of the plurality of depth guides corresponds to a different insertion depth, wherein the insertion depth is variable in a range of approximately 0.1 millimeters to eight (8) millimeters, wherein the depth guide is selected based on the insertion depth of the RFR.

The cannula assembly comprises a multi-scalpet array (MSA).

The at least one cannula includes a plurality of scalpets, and each scalpet of the plurality of scalpets comprises a tube comprising a lumen, and a distal end sharpened around a circumference of the tube and forming a cutting edge.

The MSA includes a drive shaft coupled to a proximal region of a central scalpet of the scalpet array, wherein the drive shaft is configured to couple rotational force from a remote source to the plurality of scalpets.

The drive shaft includes at least one aperture positioned axially in a distal region, wherein the at least one aperture is configured to couple the vacuum chamber to a lumen of the central scalpet via the proximal end of the central scalpet, wherein the aperture is configured to evacuate resected tissue of a fractional resection procedure via the lumen of the central scalpet and the vacuum chamber.

Each scalpet of the scalpet array includes a gear in a proximal region of the scalpet, wherein the gears of the plurality of scalpets intermesh and the plurality of scalpets operates in unison.

The method includes a gearbox configured to house the gears and the proximal region of each scalpet of the plurality of scalpets.

Each scalpet of the plurality of scalpets includes a tube comprising a lumen, and a distal end sharpened around a circumference of the tube and forming a cutting edge.

The distal end, the lumen, and a proximal end of each scalpet of the plurality of scalpets is configured to pass resected tissue from a target site.

The vacuum chamber is configured to couple to a remote vacuum source to couple vacuum to lumens of the plurality of scalpets.

The vacuum is configured to assist removal of the resected tissue from a target site by drawing the resected tissue away from the target site via the vacuum chamber and the distal end, the lumen, and the proximal end of the plurality of scalpets.

A depth slider is configured to control selection of the insertion depth of the plurality of scalpets, wherein a distal end of the plurality of scalpets extends beyond a distal end of the depth slider, and a longitudinal position of the depth slider along the MSA controls the insertion depth by controlling a length of the plurality of scalpets extending beyond the distal end of the depth slider.

The depth slider is coupled to a lock collar configured to secure the depth slider in a selected position, wherein the lock collar is configured to slide along an external region of the MSA to control a state of the depth slider between a locked state and an unlocked state, wherein in the unlocked state the depth slider is free to be moved to a position corresponding to a selected insertion depth of the plurality of scalpets, and in the locked state the depth slider is secured in a selected position.

The at least one cannula includes a focal lipectomy cannula, wherein the focal lipectomy cannula includes a tube comprising a lumen and a distal end that is blunt around a circumference of the tube.

The focal lipectomy cannula includes at least one aperture positioned axially in a proximal region of the cannula adjacent the lumen, wherein the focal lipectomy cannula is configured to pass resected tissue from a target site via the lumen and the at least one aperture.

Embodiments include a system comprising a plurality of cannula assemblies configured for rotational fractional resection (RFR). The plurality of cannula assemblies includes a first cannula assembly comprising a cannula configured for rotational operation and enclosed in a depth guide configured to control an insertion depth of the cannula. The depth guide includes a first vacuum chamber configured to maintain vacuum to evacuate resected tissue generated by the RFR. The plurality of cannula assemblies includes a second cannula assembly comprising a plurality of cannulas configured for rotational operation and enclosed in a depth slider integrated with a second vacuum chamber. The depth slider is configured to control selection of the insertion depth of the plurality of cannulas. The plurality of cannula assemblies includes a third cannula assembly comprising a focal lipectomy cannula integrated with a third vacuum chamber.

Embodiments include a system comprising a plurality of cannula assemblies configured for rotational fractional resection (RFR), wherein the plurality of cannula assemblies includes: a first cannula assembly comprising a cannula configured for rotational operation and enclosed in a depth guide configured to control an insertion depth of the cannula, wherein the depth guide includes a first vacuum chamber configured to maintain vacuum to evacuate resected tissue generated by the RFR; a second cannula assembly comprising a plurality of cannulas configured for rotational operation and enclosed in a depth slider integrated with a second vacuum chamber, wherein the depth slider is configured to control selection of the insertion depth of the plurality of cannulas; and a third cannula assembly comprising a focal lipectomy cannula integrated with a third vacuum chamber.

A proximal end of the each cannula assembly of the plurality of cannula assemblies is configured to removeably couple to a carrier comprising a proximal end and a distal end, wherein the proximal end of the carrier is configured to removeably couple to a remote console.

The carrier includes a drive shaft, and a distal end of the drive shaft is coupled to a chuck, wherein a proximal end of the drive shaft is configured to removeably couple to the remote console, wherein each cannula assembly is configured to removeably couple to the distal end of the carrier via the chuck.

The proximal end of the drive shaft is configured to removeably couple to a motor of the remote console, and couple rotational force from the motor to each cannula assembly, wherein each cannula of each cannula assembly is configured to rotate around a central axis of the cannula.

The remote console comprises an electro-mechanical device configured to provide services to the cannula assembly.

The remote console comprises the motor configured to couple to the carrier, wherein the motor configures each cannula of each cannula assembly to be rotated at controlled speeds.

The carrier is configured for control by the motor.

The carrier is configured for rotational speed control of the motor.

The remote console comprises a vacuum source configured to couple to the vacuum chamber, wherein the vacuum source configures each cannula assembly of the plurality of cannula assemblies to evacuate resected tissue of a fractional resection procedure away from a target site via the vacuum chamber.

The cannula of the first cannula assembly comprises a scalpet including a tube comprising a lumen, and a distal end sharpened around a circumference of the tube and forming a cutting edge.

The distal end and the lumen of the scalpet is configured to pass the resected tissue from a target site.

The scalpet includes at least one aperture positioned axially in the scalpet adjacent the lumen, wherein the at least one aperture is configured to pass the tissue.

A diameter of the cutting edge is approximately 1.5 millimeters.

The vacuum chamber is configured to couple vacuum to the lumen via the aperture, wherein the vacuum is configured to evacuate the resected tissue of a fractional resection procedure via the lumen and the vacuum chamber.

The vacuum chamber is configured to couple to a remote vacuum source.

The depth guide includes at least one vacuum seal configured to form the vacuum chamber.

The at least one vacuum seal is configured for application of vacuum during rotation of the at least one scalpet, wherein the vacuum is configured to maintain an approximately constant vacuum level.

The insertion depth is variable in a range of approximately 0.1 millimeters to eight (8) millimeters.

The system includes a plurality of depth guides, wherein each depth guide of the plurality of depth guides corresponds to a different insertion depth, wherein the depth guide is selected based on the insertion depth of the RFR.

The second cannula assembly comprises a multi-scalpet array (MSA).

The plurality of cannulas includes a plurality of scalpets, and each scalpet of the plurality of scalpets comprises a tube comprising a lumen, and a distal end sharpened around a circumference of the tube and forming a cutting edge.

A diameter of the cutting edge is approximately 1.5 millimeters.

The MSA includes the plurality of scalpets configured in a rectangular array.

The MSA includes the plurality of scalpets configured in one of a 3-by-3 array including nine (9) scalpets, and a 5-by-5 array including twenty-five (25) scalpets.

The MSA includes a drive shaft coupled to a proximal region of a central scalpet of the scalpet array, wherein the drive shaft is configured to couple rotational force from a remote source to the plurality of scalpets.

A rotational speed of the plurality of scalpets is in a range of approximately 75 revolutions per minute to 2000 revolutions per minute.

A rotational speed of the plurality of scalpets is approximately 1400 revolutions per minute.

The drive shaft includes at least one aperture positioned axially in a distal region, wherein the at least one aperture is configured to couple the second vacuum chamber to a lumen of the central scalpet via the proximal end of the central scalpet.

The aperture is configured to evacuate resected tissue of a fractional resection procedure via the lumen of the central scalpet and the second vacuum chamber.

Each scalpet of the scalpet array includes a gear in a proximal region of the scalpet, wherein the gears of the plurality of scalpets intermesh.

The gears comprise at least one of polymer and metal.

Each gear is secured to the corresponding scalpet via direct molding, adhesive, and press fitting.

Each scalpet of the scalpet array includes a spacer adjacent the corresponding gear, wherein each spacer is configured to align the corresponding gear.

The plurality of scalpets operates in unison.

Each scalpet rotates in a direction opposite a rotation direction of at least one adjacent scalpet.

Each scalpet of the plurality of scalpets includes a tube comprising a lumen, and a distal end sharpened around a circumference of the tube and forming a cutting edge.

The distal end, the lumen, and a proximal end of each scalpet of the plurality of scalpets is configured to pass resected tissue from a target site.

The second vacuum chamber is configured to couple to a remote vacuum source.

The second vacuum chamber is configured to couple vacuum to lumens of the plurality of scalpets.

The vacuum is configured to assist removal of the resected tissue from a target site by drawing the resected tissue away from the target site via the second vacuum chamber and the distal end, the lumen, and the proximal end of the plurality of scalpets.

The system includes a seal located along a proximal region of the driveshaft, wherein the seal is configured to maintain vacuum pressure in the second vacuum chamber.

The system includes a gearbox configured to house the gears and the proximal region of each scalpet of the plurality of scalpets.

The gearbox includes a gearbox housing and a gearbox cover.

The gearbox housing and the gearbox cover are configured as bearing plates for the gears.

The gearbox housing is configured as an interface to the second vacuum chamber.

A distal end of the plurality of scalpets extends beyond a distal end of the depth slider, and a longitudinal position of the depth slider along the MSA controls the insertion depth by controlling a length of the plurality of scalpets extending beyond the distal end of the depth slider.

The insertion depth of the plurality of scalpets is variable in a range of approximately two (2) millimeters to ten (10) millimeters.

The depth slider is coupled to a lock collar configured to secure the depth slider in a selected position.

The lock collar is configured to slide along an external region of the MSA to control a state of the depth slider between a locked state and an unlocked state.

In the unlocked state the depth slider is free to be moved to a position corresponding to a selected insertion depth of the plurality of scalpets, and in the locked state the depth slider is secured in a selected position.

The focal lipectomy cannula includes a tube comprising a lumen and a distal end that is blunt around a circumference of the tube.

The focal lipectomy cannula includes at least one aperture positioned axially in a proximal region of the cannula adjacent the lumen, wherein the focal lipectomy cannula is configured to pass resected tissue from a target site via the lumen and the at least one aperture.

The focal lipectomy cannula comprises an inside diameter of approximately two (2) millimeters.

The focal lipectomy cannula comprises a length of approximately four (4) centimeters.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments is not intended to be exhaustive or to limit the systems and methods to the precise forms disclosed. While specific embodiments of, and examples for, the medical devices and methods are described herein for illustrative purposes, various equivalent modifications are possible within the scope of the systems and methods, as those skilled in the relevant art will recognize. The teachings of the medical devices and methods provided herein can be applied to other systems and methods, not only for the systems and methods described above.

The elements and acts of the various embodiments described above can be combined to provide further embodiments. These and other changes can be made to the medical devices and methods in light of the above detailed description.

In general, in the following claims, the terms used should not be construed to limit the medical devices and methods and corresponding systems and methods to the specific embodiments disclosed in the specification and the claims, but should be construed to include all systems that operate under the claims. Accordingly, the medical devices and methods and corresponding systems and methods are not limited by the disclosure, but instead the scope is to be determined entirely by the claims.

While certain aspects of the medical devices and methods and corresponding systems and methods are presented below in certain claim forms, the inventors contemplate the various aspects of the medical devices and methods and corresponding systems and methods in any number of claim forms. Accordingly, the inventors reserve the right to add additional claims after filing the application to pursue such additional claim forms for other aspects of the medical devices and methods and corresponding systems and methods.

What is claimed is:

1. A method comprising:
   determining histological factors at a target site of a subject;
   determining parameters of a fractional resection based on the histological factors, wherein the parameters include dimensionality of a fractional field, orientation of the fractional field, resection depth, and a vector of directed closure; and
   configuring a cannula assembly for the fractional resection, wherein the fractional resection includes a procedure to generate a fractional field at the target site by fractionally resecting tissue according to the parameters, wherein the fractional resection includes applying a cannula array of the cannula assembly to the target site, and rotating at least one cannula of the cannula array to circumferentially incise and remove a plurality of skin plugs in the fractional field by selectively controlling evacuation of an amount of at least one of skin tissue and fat tissue as appropriate to the selected at least one fractional resection type, wherein the controlling comprises controlling the evacuation to include the skin tissue while minimizing the fat tissue.

2. The method of claim 1, wherein histological factors include at least one of skin laxity and skin thickness.

3. The method of claim 1, wherein the dimensionality conforms to at least one dimension of an aesthetic deformity of the target site.

4. The method of claim 3, wherein a width and a length of the fractional field is determined according to the physiological factors.

5. The method of claim 4, wherein a width of the fractional field is increased in proportion to an increase in horizontal skin laxity.

6. The method of claim 4, wherein a length of the fractional field is increased in proportion to an increase in vertical skin laxity.

7. The method of claim 3, wherein a horizontal orientation of the fractional field provides increased skin tightening in a horizontal dimension relative to a vertical orientation of the fractional field if the vector of directed closure is horizontal.

8. The method of claim 3, wherein an alignment of the fractional field corresponds to margins of the, aesthetic deformity.

9. The method of claim 3, wherein directed closure at right angles to a longitudinal dimension of the fractional field lengthens a longitudinal dimension of the fractional field and tightens a horizontal dimension of the fractional field.

10. The method of claim 3, wherein the procedure comprises selectively controlling a depth of the fractional resection based on topographic features of a convex contour deformity of the target site.

11. The method of claim 10, wherein a depth of the fractional resection is variable.

12. The method of claim 11, wherein the depth is approximately in a range of 0.1 millimeters to eight (8) millimeters.

13. The method of claim 3, wherein the directed closure comprises closure substantially in at least one of a first direction, a horizontal direction, a vertical direction, and a plurality of directions.

14. The method of claim 1, wherein, when the target site includes a submentum, the procedure comprises a fractional field with a vertical orientation, and a horizontal vector of directed closure.

15. The method of claim 1, wherein, when the target site includes a jowl, the procedure comprises a fractional field with a horizontal orientation, and a horizontal vector of directed closure.

16. The method of claim 1, wherein, when the target site includes a bra line, the procedure comprises a fractional field with a horizontal orientation, and a horizontal vector of directed closure.

17. The method of claim 1, wherein, when the target site includes a medial infragluteal fold, the procedure comprises an obliquely aligned fractional field that encompasses a margin of an aesthetic deformity, and a vector of directed closure aligned obliquely along a longitudinal axis of the fractional field.

18. The method of claim 1, wherein, when the target site includes an upper arm, the procedure comprises a horizontally aligned fractional field, and a vector of directed closure aligned at right angles to a longitudinal axis of the fractional field.

19. The method of claim 1, wherein, when the target site includes a proximal upper medial thigh, the procedure comprises a T-shaped fractional field, and a vector of directed closure aligned horizontally at right angles to each of vertical and horizontal components forming the T-shaped field.

20. The method of claim 1, wherein, when the target site includes at least one of a suprapatellar knee and a superior posterior elbow, the procedure comprises a fractional field aligned vertically along a longitudinal aspect of the extremity, and a vector of directed closure at approximately right angles to a longitudinal axis of the fractional field.

21. The method of claim 1, wherein, when the target site includes a dependent curvilinear aesthetic deformity, the procedure comprises a horizontally aligned fractional field, and a vector of directed closure along an elongated horizontal axis of the fractional field.

22. The method of claim 1, wherein, when an aesthetic deformity of the target site includes lipodystrophy, the procedure includes focal lipectomy with the fractional resection.

23. The method of claim 1, wherein the removing the plurality of skin plugs includes evacuating the plurality of skin plugs from the target site using vacuum force delivered via the cannula array.

24. The method of claim 1, wherein the controlling comprises controlling the evacuation to include the skin tissue and the fat tissue.

25. The method of claim 1, wherein the method includes use of a system comprising the cannula assembly configured for rotational fractional resection (RFR), wherein the cannula assembly includes the at least one cannula configured for rotational operation and enclosed in a depth guide configured to control an insertion depth of the at least one cannula, wherein the depth guide includes a vacuum chamber configured to maintain vacuum to evacuate resected tissue generated by the RFR.

26. The method of claim 25, wherein a proximal end of the cannula assembly is configured to removeably couple to a carrier comprising a proximal end and a distal end, wherein the proximal end of the carrier is configured to removeably couple to a motor of a remote console, and couple rotational force from the motor to the cannula assembly, wherein the at least one cannula is configured to rotate at controlled speeds around a central axis of the at least one cannula.

27. The method of claim 26, wherein the remote console comprises a vacuum source configured to couple to the vacuum chamber, wherein the vacuum source configures the cannula assembly to evacuate resected tissue of a fractional resection procedure away from a target site via the vacuum chamber.

28. The method of claim 25, wherein the at least one cannula comprises at least one scalpet including a tube comprising a lumen, and a distal end sharpened around a circumference of the tube and forming a cutting edge.

29. The method of claim 28, wherein the at least one scalpet includes at least one aperture positioned axially in the scalpet adjacent the lumen, wherein the lumen and the at least one aperture are configured to pass the tissue.

30. The method of claim 29, wherein the vacuum chamber is configured to couple vacuum to the lumen via the aperture, wherein the vacuum is configured to evacuate the resected tissue of a fractional resection procedure via the lumen and the vacuum chamber.

31. The method of claim 30, comprising a plurality of depth guides, wherein each depth guide of the plurality of depth guides corresponds to a different insertion depth, wherein the insertion depth is variable in a range of approximately 0.1 millimeters to eight (8) millimeters, wherein the depth guide is selected based on the insertion depth of the RFR.

32. The method of claim 25, wherein the cannula assembly comprises a multi-scalpet array (MSA).

33. The method of claim 32, wherein the at least one cannula includes a plurality of scalpets, and each scalpet of the plurality of scalpets comprises a tube comprising a lumen, and a distal end sharpened around a circumference of the tube and forming a cutting edge.

34. The method of claim 32, wherein the MSA includes a drive shaft coupled to a proximal region of a central scalpet of the scalpet array, wherein the drive shaft is configured to couple rotational force from a remote source to the plurality of scalpets.

35. The method of claim 34, wherein the drive shaft includes at least one aperture positioned axially in a distal region, wherein the at least, one aperture is configured to couple the vacuum chamber to a lumen of the central scalpet via the proximal end of the central scalpet, wherein the aperture is configured to evacuate resected tissue of a fractional resection procedure via the lumen of the central scalpet and the vacuum chamber.

36. The method of claim 34, wherein each scalpet of the scalpet array includes a gear in a proximal region of the scalpet, wherein the gears of the plurality of scalpets intermesh and the plurality of scalpets operates in unison.

37. The method of claim 36, comprising a gearbox configured to house the gears and the proximal region of each scalpet of the plurality of scalpets.

38. The method of claim 36, wherein each scalpet of the plurality of scalpets includes a tube comprising a lumen, and a distal end sharpened around a circumference of the tube and forming a cutting edge.

39. The method of claim 38, wherein the distal end, the lumen, and a proximal end of each scalpet of the plurality of scalpets is configured to pass resected tissue from a target site.

40. The method of claim 39, wherein the vacuum chamber is configured to couple to a remote vacuum source to couple vacuum to lumens of the plurality of scalpets.

41. The method of claim 40, wherein the vacuum is configured to assist removal of the resected tissue from a target site by drawing the resected tissue away from the target site via the vacuum chamber and the distal end, the lumen, and the proximal end of the plurality of scalpets.

42. The method of claim 32, comprising a depth slider configured to control selection of the insertion depth of the plurality of scalpets, wherein a distal end of the plurality of scalpets extends beyond a distal end of the depth slider, and a longitudinal position of the depth slider along the MSA controls the insertion depth by controlling a length of the plurality of scalpets extending beyond the distal end of the depth slider.

43. The method of claim 42, wherein the depth slider is coupled to a lock collar configured to secure the depth slider in a selected position, wherein the lock collar is configured to slide along an external region of the MSA to control a state of the depth slider between a locked state and an unlocked state, wherein in the unlocked state the depth slider is free to be moved to a position corresponding to a selected insertion depth of the plurality of scalpets, and in the locked state the depth slider is secured in a selected position.

44. The method of claim 25, wherein the at least one cannula includes a focal lipectomy cannula, wherein the focal lipectomy cannula includes a tube comprising a lumen and a distal end that is blunt around a circumference of the tube.

45. The method of claim 44, wherein the focal lipectomy cannula includes at least one aperture positioned axially in a proximal region of the cannula adjacent the lumen, wherein the focal lipectomy cannula is configured to pass resected tissue from a target site via the lumen and the at least one aperture.

\* \* \* \* \*